(12) United States Patent
Lyssikatos et al.

(10) Patent No.: US 12,240,846 B2
(45) Date of Patent: *Mar. 4, 2025

(54) 5- AND 6-AZAINDOLE COMPOUNDS FOR INHIBITION OF Bcr-Abl TYROSINE KINASES

(71) Applicant: Enliven Inc., Boulder, CO (US)

(72) Inventors: Joseph P. Lyssikatos, Boulder, CO (US); Samuel Kintz, Boulder, CO (US); Li Ren, Superior, CO (US)

(73) Assignee: Enliven Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/233,259

(22) Filed: Aug. 11, 2023

(65) Prior Publication Data

US 2023/0382907 A1    Nov. 30, 2023

Related U.S. Application Data

(63) Continuation of application No. 18/080,641, filed on Dec. 13, 2022, now Pat. No. 11,807,638, which is a continuation of application No. 17/493,380, filed on Oct. 4, 2021, now Pat. No. 11,767,321.

(60) Provisional application No. 63/224,236, filed on Jul. 21, 2021, provisional application No. 63/087,763, filed on Oct. 5, 2020.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................. C07D 471/04
USPC ........................................................ 514/247
See application file for complete search history.

(56) References Cited

U.S. PATENT DOCUMENTS

| | | |
|---|---|---|
| 6,469,026 B2 | 10/2002 | Marlowe et al. |
| 7,256,287 B2 | 8/2007 | Sircar et al. |
| 8,263,612 B2 | 9/2012 | Bondy et al. |
| 8,450,340 B2 | 5/2013 | Hood et al. |
| 8,648,201 B2 | 2/2014 | Calderini et al. |
| 8,815,897 B2 | 8/2014 | Hood et al. |
| 8,846,714 B2 | 9/2014 | Hood et al. |
| 9,102,672 B2 | 8/2015 | Hadida-Ruah et al. |
| 9,518,015 B2 | 12/2016 | Torrens Jover et al. |
| 9,732,080 B2 | 8/2017 | Hadida-Ruah et al. |
| 10,167,286 B2 | 1/2019 | Roulet et al. |
| 10,292,395 B2 | 5/2019 | Yonemura et al. |
| 10,323,023 B2 | 6/2019 | Zhao et al. |
| 11,767,321 B2 | 9/2023 | Lyssikatos et al. |
| 11,807,638 B2 | 11/2023 | Lyssikatos et al. |
| 2002/0061892 A1 | 5/2002 | Wang et al. |
| 2003/0004165 A1 | 1/2003 | Iino et al. |
| 2003/0186972 A1 | 10/2003 | Marlowe et al. |
| 2003/0187261 A1 | 10/2003 | Havlicek et al. |
| 2004/0116328 A1 | 6/2004 | Yoshikawa et al. |
| 2005/0026853 A1 | 2/2005 | Mekouar et al. |
| 2005/0124604 A1 | 6/2005 | Sircar et al. |
| 2005/0130977 A1 | 6/2005 | Lindsley et al. |
| 2005/0256179 A1 | 11/2005 | Sircar et al. |
| 2006/0063787 A1 | 3/2006 | Yoshikawa et al. |
| 2006/0094722 A1 | 5/2006 | Yasuda et al. |
| 2006/0100199 A1 | 5/2006 | Yoshikawa et al. |
| 2007/0015758 A1 | 1/2007 | Baruah et al. |
| 2007/0032493 A1 | 2/2007 | Foley et al. |
| 2007/0054916 A1 | 3/2007 | Patel et al. |
| 2007/0219178 A1 | 9/2007 | Muramoto |
| 2007/0275984 A1 | 11/2007 | Imogai et al. |
| 2008/0021026 A1 | 1/2008 | Kahraman et al. |
| 2008/0021217 A1 | 1/2008 | Borchardt et al. |
| 2009/0042928 A1 | 2/2009 | Grootenhuis et al. |
| 2009/0176778 A1 | 7/2009 | Schmitz et al. |
| 2009/0246198 A1 | 10/2009 | Dong et al. |
| 2009/0312321 A1 | 12/2009 | Ren et al. |
| 2010/0010217 A1 | 1/2010 | Valiante et al. |
| 2010/0204265 A1 | 8/2010 | Baskaran et al. |
| 2010/0210476 A1 | 8/2010 | Salom et al. |
| 2011/0098267 A1 | 4/2011 | Babu et al. |
| 2011/0118271 A1 | 5/2011 | Flynn et al. |
| 2011/0160232 A1 | 6/2011 | Ren et al. |
| 2011/0312959 A1 | 12/2011 | Yasri et al. |
| 2012/0021434 A1 | 1/2012 | Foley et al. |
| 2012/0035194 A1 | 2/2012 | Huang et al. |
| 2012/0121540 A1 | 5/2012 | Schmitz et al. |
| 2012/0178180 A1 | 7/2012 | Kruse et al. |
| 2012/0214684 A1 | 8/2012 | Vieweg et al. |
| 2012/0289540 A1 | 11/2012 | Flynn et al. |

(Continued)

FOREIGN PATENT DOCUMENTS

| | | |
|---|---|---|
| CN | 109721620 A | 5/2019 |
| CN | 112239473 A | 1/2021 |

(Continued)

OTHER PUBLICATIONS

Liang et al., Bioorganic & Medicinal Chemistry Letters (2017), 27(18), 4370-4376.*

Menzer et al., Journal of Chemical Theory and Computation (2018), 14(11), 6035-6049.*

International Preliminary Report on Patentability mailed on Apr. 20, 2023, for PCT Application No. PCT/US2021/071695, filed on Oct. 4, 2021, 7 pages.

(Continued)

*Primary Examiner* — Niloofar Rahmani

(74) *Attorney, Agent, or Firm* — Morrison & Foerster LLP

(57) ABSTRACT

The present disclosure relates to compounds and compositions for inhibition of Bcr-Abl tyrosine kinases, methods of preparing said compounds and compositions, and their use in the treatment of various cancers, such as chronic myeloid leukemia (CML).

14 Claims, No Drawings

(56) References Cited

U.S. PATENT DOCUMENTS

| | | |
|---|---|---|
| 2013/0072473 A1 | 3/2013 | Tait et al. |
| 2014/0155398 A1 | 6/2014 | Verma et al. |
| 2014/0243324 A1 | 8/2014 | Bissonnette et al. |
| 2014/0350248 A1 | 11/2014 | Ren et al. |
| 2014/0358198 A1 | 12/2014 | Buchholz et al. |
| 2015/0150852 A1 | 6/2015 | Byrd et al. |
| 2015/0320759 A1 | 11/2015 | Flynn et al. |
| 2015/0353539 A1 | 12/2015 | Cheve et al. |
| 2015/0376219 A1 | 12/2015 | Zhong |
| 2016/0016951 A1 | 1/2016 | Schiemann et al. |
| 2016/0060262 A1 | 3/2016 | Lyssikatos et al. |
| 2017/0145025 A1 | 5/2017 | Li et al. |
| 2018/0208605 A1 | 7/2018 | Gummadi et al. |
| 2019/0055265 A1 | 2/2019 | Clark et al. |
| 2019/0106425 A1 | 4/2019 | Jordan et al. |
| 2019/0194207 A1 | 6/2019 | De Roulet et al. |
| 2019/0263819 A1 | 8/2019 | Jordan et al. |
| 2021/0171499 A1 | 6/2021 | Ammann et al. |
| 2021/0218575 A1 | 7/2021 | Wright |
| 2023/0065635 A1 | 3/2023 | Lyssikatos et al. |
| 2023/0130724 A1 | 4/2023 | Lyssikatos et al. |
| 2024/0043420 A1 | 2/2024 | Lyssikatos |
| 2024/0287062 A1 | 8/2024 | Lyssikatos |

FOREIGN PATENT DOCUMENTS

| | | |
|---|---|---|
| CN | 112341477 A | 2/2021 |
| CN | 112654622 A | 4/2021 |
| EP | 1914234 A1 | 4/2008 |
| EP | 2570125 A1 | 3/2013 |
| EP | 2669270 A1 | 12/2013 |
| EP | 2818472 A1 | 12/2014 |
| EP | 2515655 B1 | 8/2015 |
| EP | 2094702 B1 | 9/2015 |
| EP | 3001903 A1 | 4/2016 |
| EP | 3385261 A1 | 10/2018 |
| EP | 3421464 A1 | 1/2019 |
| EP | 3421465 A1 | 1/2019 |
| JP | 2012505916 | 3/2012 |
| JP | 2012517465 A | 8/2012 |
| JP | 2014502601 A | 2/2014 |
| JP | 2016507508 A | 3/2016 |
| WO | 199909030 A1 | 2/1999 |
| WO | 200051379 A1 | 8/2000 |
| WO | 200053181 A1 | 9/2000 |
| WO | 200053602 A1 | 9/2000 |
| WO | 200172708 A2 | 10/2001 |
| WO | 200172712 A1 | 10/2001 |
| WO | 2005063720 A1 | 7/2005 |
| WO | 2006004984 A1 | 1/2006 |
| WO | 2006030031 A1 | 3/2006 |
| WO | 2006128129 A2 | 11/2006 |
| WO | 2006128172 A2 | 11/2006 |
| WO | 2007042784 A2 | 4/2007 |
| WO | 2007092531 A2 | 8/2007 |
| WO | 2007125405 A2 | 11/2007 |
| WO | 2007136465 A2 | 11/2007 |
| WO | 2008034008 A2 | 3/2008 |
| WO | 2008042639 A1 | 4/2008 |
| WO | 2008133669 A2 | 11/2008 |
| WO | 2009100406 A2 | 8/2009 |
| WO | 2010045542 A2 | 4/2010 |
| WO | 2010092489 A1 | 8/2010 |
| WO | 2011046954 A1 | 4/2011 |
| WO | 2011084486 A1 | 7/2011 |
| WO | 2011094890 A1 | 8/2011 |
| WO | 2011097300 A1 | 8/2011 |
| WO | 2012068406 A2 | 5/2012 |
| WO | 2012080284 A2 | 6/2012 |
| WO | 2012102405 A1 | 8/2012 |
| WO | 2013037960 A1 | 3/2013 |
| WO | 2013078254 A1 | 5/2013 |
| WO | 2014043296 A1 | 3/2014 |
| WO | 2014102377 A1 | 7/2014 |
| WO | 2014207260 A1 | 12/2014 |
| WO | 2015023958 A1 | 2/2015 |
| WO | 2015123365 A1 | 8/2015 |
| WO | 2015247076 A1 | 11/2015 |
| WO | 2015193167 A1 | 12/2015 |
| WO | 2016009076 A1 | 1/2016 |
| WO | 2016014674 A1 | 1/2016 |
| WO | 2016144351 A1 | 9/2016 |
| WO | 2016144706 A2 | 9/2016 |
| WO | 2016202755 A1 | 12/2016 |
| WO | 2017009806 A1 | 1/2017 |
| WO | 2017021348 A1 | 2/2017 |
| WO | 2017028314 A1 | 2/2017 |
| WO | 2017031427 A1 | 2/2017 |
| WO | 2017049165 A1 | 3/2017 |
| WO | 2017093727 A1 | 6/2017 |
| WO | 2017178844 A1 | 10/2017 |
| WO | 2017178845 A1 | 10/2017 |
| WO | 2019000683 A1 | 1/2019 |
| WO | 2019001572 A1 | 1/2019 |
| WO | 2019113523 A1 | 6/2019 |
| WO | 2019126082 A1 | 6/2019 |
| WO | 2019175897 A1 | 9/2019 |
| WO | 2019191227 A1 | 10/2019 |
| WO | 2020021024 A1 | 1/2020 |
| WO | 2020093905 A1 | 5/2020 |
| WO | 2020103896 A1 | 5/2020 |
| WO | 2020181050 A1 | 9/2020 |
| WO | 2020249957 A1 | 12/2020 |
| WO | 2021007350 A1 | 1/2021 |
| WO | 2021013083 A1 | 1/2021 |
| WO | 2021081207 A1 | 4/2021 |
| WO | 2022076973 A1 | 4/2022 |
| WO | 2022076975 A1 | 4/2022 |
| WO | 2022118263 A1 | 6/2022 |
| WO | 2022236319 A1 | 11/2022 |
| WO | 2023052019 A1 | 4/2023 |
| WO | 2024097953 A1 | 5/2024 |
| WO | 2024098001 A1 | 5/2024 |
| WO | 2024159094 A1 | 8/2024 |

OTHER PUBLICATIONS

International Search Report and Written Opinion mailed on Feb. 23, 2022, for PCT Application No. PCT/US21/71695, filed on Oct. 4, 2021, 14 pages.

Liang, J. et al. (2017, e-pub. Aug. 12, 2017). "Identification of an Imidazopyridine Scaffold to Generate Potent and Selective TYK2 Inhibitors that Demonstrate Activity in an in Vivo Psoriasis Model," Bioorganic & Medicinal Chemistry Letters 27(18):4370-4376.

Menzer, W.M. et al. (2018). "Simple Entropy Terms for End-Point Binding Free Energy Calculations," Journal of Chemical Theory arid Computation 14(11):6035-6049.

PubChem. (Create Date May 18, 2017, Date Accessed Jan. 26, 2022). "N-[2-{2-chlorophenyl)-1-methylpyrrolo [3,2-c] pyridin-6-yl] cyclopropanecarboxamide," PubChem CID 126962388, 6 pages.

Berge, S.M. et al. (Jan. 1977). "Pharmaceutical Salts," Journal of Pharmaceutical Sciences 66(1):1-19.

Extended European Search Report mailed on Oct. 7, 2024, for European Patent Application No. 21878713.3, filed on Oct. 4, 2021, 6 pages.

PubChem. (Create Date Aug. 13, 2022). "1-[3-(1-benzothiophen-3-yl)-1H-pyrrolo{2,3-b]pyridin-6-yl]-3-ethyluurea," PubChem CID 152209919, 7 pages.

Ren, L. et al. (Apr. 3, 2012, e-pub. Apr. 10, 2012). "The Discovery of Potent and Selective Pyridopyrimidine-7-One Based Inhibitors of B-RafV600E Kinase," Bioorganic & Medicinal Chemistry Letters 22(10):3387-3391.

* cited by examiner

5- AND 6-AZAINDOLE COMPOUNDS FOR INHIBITION OF Bcr-Abl TYROSINE KINASES

CROSS-REFERENCE TO RELATED APPLICATIONS

This application is a continuation of U.S. application Ser. No. 18/080,641, filed Dec. 13, 2022, which is a continuation of U.S. application Ser. No. 17/493,380, filed Oct. 4, 2021, which claims priority to and the benefit of U.S. Provisional Application No. 63/087,763, filed on Oct. 5, 2020, and U.S. Provisional Application No. 63/224,236, filed on Jul. 21, 2021, the disclosures of each of which are incorporated herein by reference in their entireties.

FIELD OF THE INVENTION

Provided herein are compounds and compositions for inhibition of Bcr-Abl tyrosine kinases, methods of preparing said compounds and compositions, and their use in the treatment of various cancers, such as chronic myeloid leukemia (CML).

BACKGROUND

The cytogenetic abnormality known as the Philadelphia chromosome is highly associated with the occurrence of a number of hematological malignancies, including a majority of chronic myeloid leukemias (CML) and a subset of acute lymphoblastic leukemias (Ph+ ALL). The Philadelphia chromosome is a product of a translocation between the breakpoint cluster region (BCR) gene on chromosome 22 and the Abelson (ABL) tyrosine kinase gene on chromosome 9, resulting in the oncogenic fusion gene product Bcr-Abl. The resultant fusion protein is both overexpressed and harbors constitutive kinase activity that then drives the activation of a number of intracellular signaling cascades to induce the uncontrolled cell growth, division and survival associated with oncogenic transformation. Accordingly, therapeutic intervention employing inhibitors of the Bcr-Abl tyrosine kinase represents a cornerstone of the current treatment paradigm for patients with Philadelphia-positive neoplastic disorders.

Imatinib (STI-571), a small molecule Bcr-Abl tyrosine kinase inhibitor (Bcr-Abl TKI), was developed as a highly effective treatment for CML in the early 1990s and is still employed today as a first line treatment for CML. However, in more aggressive cases of CML, patients often relapse due to the emergence of resistance. The primary mechanism of this resistance derives from a variety of on-target genetic alterations that drives either aberrant overexpression of the Bcr-Abl fusion or, more commonly, introduce amino acid mutations within the Abl kinase domain that reduce imatinib's binding affinity for the active site thereby markedly reducing its inhibitory activity. These alterations can either appear stochastically and represent a sub-population within the initial tumor cell population or arise under the selective pressure of inhibitor treatment. One of the predominant on-target Bcr-Abl resistance mutations derives from point mutations that introduce an isoleucine residue for a threonine at position 315 within the Abl kinase domain (T315I) also known as the 'gatekeeper' position. In addition to imatinib, this mutant form of BCR-Abl is profoundly resistant to all second generation Bcr-Abl TKIs (Nilotinib, Dasatinib, Bosutinib, Radotinib). Currently, there exists only one therapeutic option for patients harboring a T315I mutation—the third line Bcr-Abl TKI, Ponatinib. While effective at treating patients with T315I CML, ponatinib suffers from poor selectivity for Bcr-Abl versus a number of other protein kinases. Accordingly, ponatinib has been reported to elicit significant dose-limiting toxicities, which then limits its ability to effectively engage the target to achieve clinical efficacy.

Besides on- or off-target resistance, intolerance to Bcr-Abl TKIs also represents a major clinical challenge. The doses of more than 50% of Ph+ leukemia patients require modification due to adverse events. In fact, approximately 30% of patients are compelled to dose reduce within the first 6 months of treatment. These drug-related side effects appear early in the course of treatment and, while manageable in most cases, toxicities persist, significantly impacting the patients' quality of life, resulting in decreased compliance. Accordingly, around 40% of patients discontinue first and second generation Bcr-Abl TKIs within the first 5 years of treatment. All of the currently approved Bcr-Abl targeted therapies inhibit other tyrosine kinases, which can lead to potentially debilitating side effects. Specifically, potent inhibition of VEGFRs, PDGFRs, c-Kit and/or the c-Src family can lead to dose-limiting side effects in patients. To address these adverse effects, dose reductions, dose interruptions, and even dose discontinuations are often required during the course of therapy, however such treatment regimens ultimately result in suboptimal therapeutic benefit.

Accordingly, there remains a substantial unmet medical need for Bcr-Abl TKIs with improved selectivity to improve tolerability and enhanced potency against the wide array of resistance mechanisms in Philadelphia-positive disorders.

SUMMARY OF THE INVENTION

Provided herein are compounds and compositions that selectively inhibit Bcr-Abl tyrosine kinases and that are useful for treating disorders mediated by Bcr-Abl tyrosine kinases.

In one aspect, provided herein is a compound of formula (I),

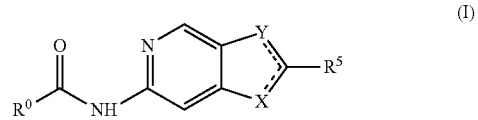

or a pharmaceutically acceptable salt, solvate, hydrate, or co-crystal thereof, or a mixture of any of the foregoing, wherein:

X is $NR^{3'}$ or $CR^3$,

Y is $NR^2$ or $CR^4$, wherein when X is $NR^{3'}$ then Y is $CR^4$, Y has a double bond to $CR^5$, and X has a single bond to $CR^5$; or when X is $CR^3$ then Y is $NR^2$, Y has a single bond to $CR^5$, and X has a double bond to $CR^5$;

$R^0$ is a group

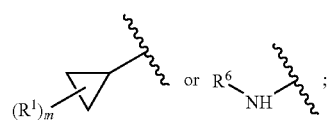

m is an integer from 0 to 3;

each $R^1$ is independently -D, —F, $C_1$-$C_3$ alkyl, $C_1$-$C_3$ alkylene-$NR^7R^8$, $C_1$-$C_3$ alkylene-$NR^7R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^7R^{8'}$, $C_1$-$C_2$ alkylene-($C_3$-$C_6$ cycloalkylene)-($C_0$-$C_2$ alkylene)-OH, $C_1$-$C_2$ alkylene-(4- to 8-membered heterocycloalkylene)-($C_0$-$C_2$ alkylene)-$NR^7R^{8'}$, $C_1$-$C_2$ alkylene-(4- to 8-membered heterocycloalkylene)-($C_0$-$C_2$ alkylene)-$NR^7R^{8'}$, $C_1$-$C_2$ alkylene-($C_3$-$C_7$ heterocycloalkylene)-($C_0$-$C_2$ alkylene)-$NR^7R^8$, or $C_1$-$C_2$ alkylene-($C_3$-$C_7$ heterocycloalkylene)-($C_0$-$C_2$ alkylene)-$NR^7R^{8'}$, wherein the alkyl, alkylene, cycloalkylene, and heterocycloalkylene moieties in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

$R^2$ is —H, $C_1$-$C_3$ alkyl, or $C_3$-$C_6$ cycloalkyl, wherein said $C_1$-$C_3$ alkyl is optionally substituted with 1-3 fluorine atoms and/or 1-6 deuterium atoms;

$R^3$ is —H, $C_1$-$C_3$ alkyl, $C_3$-$C_4$ cycloalkyl, halogen, or —CN;

$R^{3'}$ is —H, $C_1$-$C_3$ alkyl, —$C_3$-$C_4$ cycloalkyl, or —CN;

$R^4$ is —H, $C_1$-$C_3$ alkyl, or halogen, wherein said $C_1$-$C_3$ alkyl is optionally substituted with 1-3 fluorine atoms and/or 1-6 deuterium atoms;

$R^5$ is $C_6$-$C_{14}$ aryl or 5-to-10-membered heteroaryl, wherein said $C_6$-$C_{14}$ aryl or said 5-to-10-membered heteroaryl is optionally substituted with 1-5 $R^9$ groups;

$R^6$ is —H, $C_1$-$C_6$ alkyl, $C_3$-$C_6$ cycloalkyl, $C_1$-$C_6$ alkylene-$NR^7R^8$, $C_1$-$C_6$ alkylene-$NR^7R^{8'}$, $C_1$-$C_6$ alkylene-OH, $C_1$-$C_6$ alkylene-CN, $C_1$-$C_2$ alkylene-($C_3$-$C_6$cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^7R^{8'}$, $C_1$-$C_2$ alkylene-($C_3$-$C_6$cycloalkylene)-($C_0$-$C_2$ alkylene)-OH, $C_1$-$C_2$ alkylene-(4- to 8-membered heterocycloalkylene)-($C_0$-$C_2$ alkylene)-$NR^7R^8$, $C_1$-$C_2$ alkylene-(4- to 8-membered heterocycloalkylene)-($C_0$-$C_2$ alkylene)-$NR^7R^{8'}$, $C_1$-$C_2$ alkylene-($C_3$-$C_7$ heterocycloalkylene)-($C_0$-$C_2$alkylene)-$NR^7R^8$, or $C_1$-$C_2$ alkylene-($C_3$-$C_7$ heterocycloalkylene)-($C_0$-$C_2$alkylene)-$NR^7R^{8'}$, wherein the alkyl, alkylene, cycloalkyl, cycloalkylene, and heterocycloalkylene moieties in $R^6$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^7$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl;

each $R^8$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl;

each pair of $R^{7'}$ and $R^{8'}$ taken together with the nitrogen atom to which they are attached independently form a 3- to 8-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —$OR^{10}$, —$NR^7R^8$, $C_1$-$C_3$ alkyl, $C_1$-$C_3$ haloalkyl, $C_3$-$C_6$ cycloalkyl, —CN, $S(O)_nC_1$-$C_3$ alkyl, or $S(O)_nC_3$-$C_6$ cycloalkyl, wherein n is an integer from 0 to 2; and each $R^{10}$ is independently —H, $C_1$-$C_3$ alkyl, $C_1$-$C_3$ haloalkyl, or $C_3$-$C_6$ cycloalkyl, wherein said $C_1$-$C_3$ alkyl is optionally substituted with hydroxyl, $C_1$-$C_3$ alkoxy, and/or 1-6 deuterium atoms.

In another aspect, provided herein is a compound of formula (I),

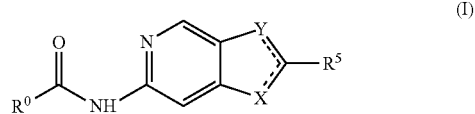

(I)

or a pharmaceutically acceptable salt, solvate, hydrate, or co-crystal thereof, or a mixture of any of the foregoing, wherein:

X is $NR^{3'}$ or $CR^3$,

Y is $NR^2$ or $CR^4$, wherein when X is $NR^{3'}$ then Y is $CR^4$, Y has a double bond to $CR^5$, and X has a single bond to $CR^5$; or when X is $CR^3$ then Y is $NR^2$. Y has a single bond to $CR^5$, and X has a double bond to $CR^5$;

$R^0$ is a group

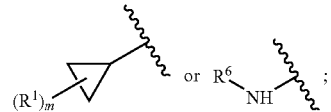

m is an integer from 0 to 3;

each $R^1$ is independently -D, —F, $C_1$-$C_3$ alkyl, $C_1$-$C_3$ alkylene-$NR^7R^8$, $C_1$-$C_3$ alkylene-$NR^7R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^7R^{8'}$, $C_1$-$C_2$ alkylene-($C_3$-$C_6$cycloalkylene)-($C_0$-$C_2$ alkylene)-OH, $C_1$-$C_2$ alkylene-($C_4$-$C_6$ heterocycloalkylene)-($C_0$-$C_2$ alkylene)-$NR^7R^{8'}$, or $C_1$-$C_2$ alkylene-($C_4$-$C_6$ heterocycloalkylene)-($C_0$-$C_2$ alkylene)-$NR^7R^{8'}$, wherein the alkyl, alkylene, cycloalkylene, and heterocycloalkylene moieties in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

$R^2$ is —H, $C_1$-$C_3$ alkyl, or $C_3$-$C_6$ cycloalkyl, wherein said $C_1$-$C_3$ alkyl is optionally substituted with 1-3 fluorine atoms and/or 1-6 deuterium atoms;

$R^3$ is —H, $C_1$-$C_3$ alkyl, $C_3$-$C_6$ cycloalkyl, halogen, or —CN;

$R^{3'}$ is —H, $C_1$-$C_3$ alkyl, —$C_3$-$C_6$ cycloalkyl, or —CN;

$R^4$ is —H, $C_1$-$C_3$ alkyl, or halogen, wherein said $C_1$-$C_3$ alkyl is optionally substituted with 1-3 fluorine atoms and/or 1-6 deuterium atoms;

$R^5$ is $C_6$-$C_{14}$ aryl or 5-to-10-membered heteroaryl, wherein said $C_6$-$C_{14}$ aryl or said 5-to-10-membered heteroaryl is optionally substituted with 1-5 $R^9$ groups;

$R^6$ is —H, $C_1$-$C_6$ alkyl, $C_3$-$C_6$ cycloalkyl, $C_1$-$C_6$ alkylene-$NR^7R^8$, $C_1$-$C_6$ alkylene-$NR^7R^{8'}$, $C_1$-$C_6$ alkylene-OH, $C_1$-$C_6$ alkylene-CN, $C_1$-$C_2$ alkylene-($C_3$-$C_6$ cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-($C_3$—C cycloalkylene)-($C_0$-$C_2$ alkylene)-OH, $C_1$-$C_2$ alkylene-($C_4$-$C_6$ heterocycloalkylene)-($C_0$-$C_2$ alkylene)-$NR^7R^8$, or $C_1$-$C_2$ alkylene-($C_4$-$C_6$ heterocycloalkylene)-($C_0$-$C_2$ alkylene)-$NR^{7'}R^{8'}$, wherein the alkyl, alkylene, cycloalkyl, cycloalkylene, and heterocycloalkylene moieties in $R^6$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^7$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl;

each $R^8$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl;

each pair of $R^{7'}$ and $R^{8'}$ taken together with the nitrogen atom to which they are attached independently form a 4-to-6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —$OR^{10}$, —$NR^7R^8$, $C_1$-$C_3$ alkyl, $C_1$-$C_3$ haloalkyl, $C_3$-$C_6$ cycloalkyl, —CN, $S(O)_nC_1$-$C_3$ alkyl, or $S(O)_nC_3$-$C_6$ cycloalkyl, wherein n is an integer from 0 to 2; and each $R^{10}$ is independently —H, $C_1$-$C_3$ alkyl, $C_1$-$C_3$ haloalkyl, or $C_3$-$C_6$ cycloalkyl, wherein said $C_1$-$C_3$ alkyl is optionally substituted with hydroxyl, $C_1$-$C_3$ alkoxy, and/or 1-6 deuterium atoms.

In some embodiments, the compound of formula (I) is a compound of formula (I-A):

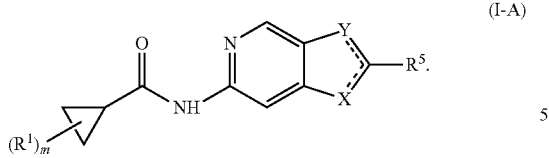
(I-A)

In some embodiments, the compound of formula (I) is a compound of formula (I-A-i) or formula (I-A-ii):

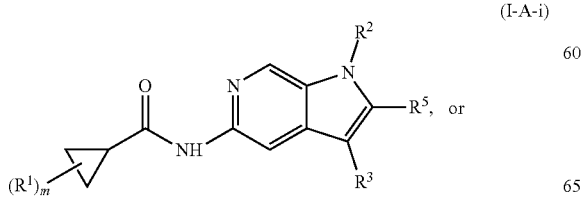
(I-A-i)

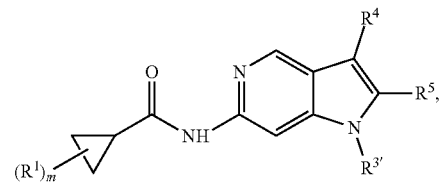
(I-A-ii)

wherein
m is an integer 0 or 2;
each $R^1$ is independently —F, $C_1$-$C_3$ alkyl, $C_1$-$C_3$ alkylene-$NR^7R^8$, $C_1$-$C_3$ alkylene-$NR^{7'}R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$ alkylene)-$NR^7R^8$, $C_1$-$C_3$ alkylene-CN, $C_1$-$C_2$ alkylene-($C_3$-$C_6$cycloalkylene)-($C_0$-$C_2$ alkylene)-$NR^{7'}R^{8'}$, $C_1$-$C_2$ alkylene-($C_3$-$C_6$ cycloalkylene)-($C_0$-$C_2$ alkylene)-OH, $C_1$-$C_2$ alkylene-($C_4$-$C_6$ heterocycloalkylene)-($C_0$-$C_2$ alkylene)-$NR^7R^8$, or $C_1$-$C_2$ alkylene-($C_4$-$C_6$ heterocycloalkylene)-($C_0$-$C_2$ alkylene)-$NR^{7'}R^{8'}$, wherein the alkyl, alkylene, cycloalkylene, and heterocycloalkylene in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;
$R^2$ is —H, —$CH_3$, $CD_3$, —$CHF_2$, or —$CH_2CH_3$;
$R^3$ is —H, $C_1$-$C_3$ alkyl, $C_3$-cycloalkyl, halogen, or —CN;
$R^{3'}$ is —H, $C_1$-$C_3$ alkyl, $C_3$-cycloalkyl, or —CN;
$R^4$ is —H, —$CH_3$, —$CD_3$, —$CHF_2$, —$CH_2CH_3$, or halogen;
$R^5$ is $C_6$-$C_{14}$ aryl or 5-to-10-membered heteroaryl, wherein said 5-to-10-membered heteroaryl is selected from the group consisting of:

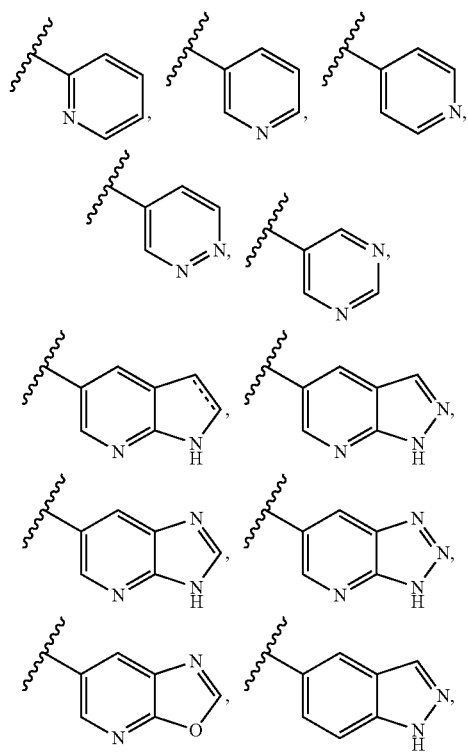

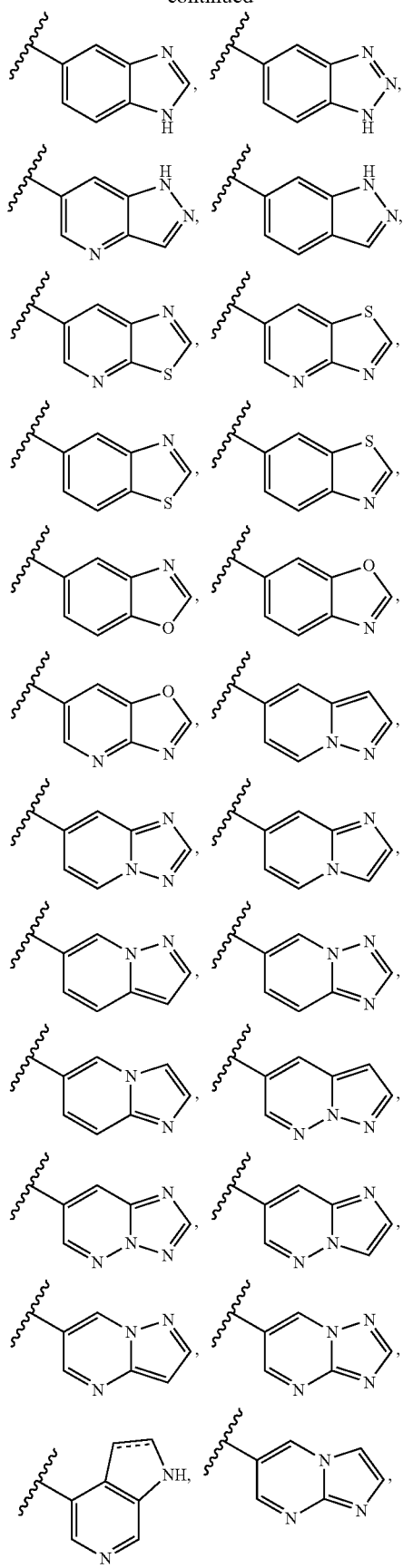

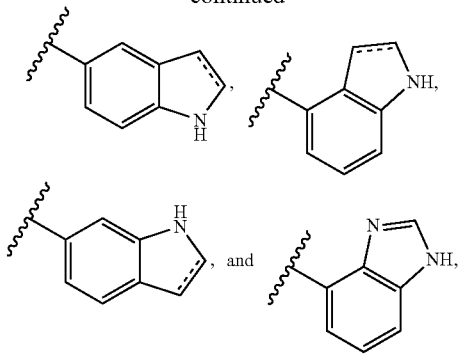

wherein ⸗ indicates a single or double bond, and wherein said $C_6$-$C_{14}$ aryl or said 5-to-10-membered heteroaryl is optionally substituted with 1-5 $R^9$ groups;

each $R^{7'}$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;

each $R^{8'}$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;

each pair of $R^{7'}$ and $R^{8'}$ taken together with the nitrogen atom to which they are attached independently form a 4-to-6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —OR$^{10}$, $C_1$-$C_3$ alkyl, —CF$_2$H, —CF$_3$, $C_3$-$C_6$ cycloalkyl, or —CN, and each $R^{10}$ is independently —H, $C_1$-$C_3$ alkyl, —CD$_3$, —CF$_2$H, —CF$_3$, or $C_3$-$C_6$ cycloalkyl, wherein said $C_1$-$C_3$ alkyl is optionally substituted with hydroxyl and/or $C_1$-$C_3$ alkoxy and/or 1-6 deuterium atoms.

In some embodiments, which may be combined with any of the preceding embodiments, each $R^1$ is independently —F, $C_1$-$C_3$ alkylene-NR$^{7'}$R$^{8'}$, or $C_1$-$C_3$ alkylene-OH; and wherein each pair of R$^{7'}$ and R$^{8'}$ of R$^1$ taken together with the nitrogen atom to which they are attached independently form a 4-to-6-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by H, or $C_1$-$C_3$ alkyl. In other embodiments, which may be combined with any of the preceding embodiments, $R^5$ is phenyl or 5-to-10-membered heteroaryl, wherein said 5-to-10-membered heteroaryl is selected from the group consisting of:

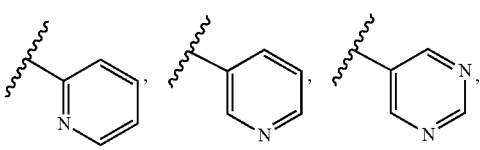

-continued

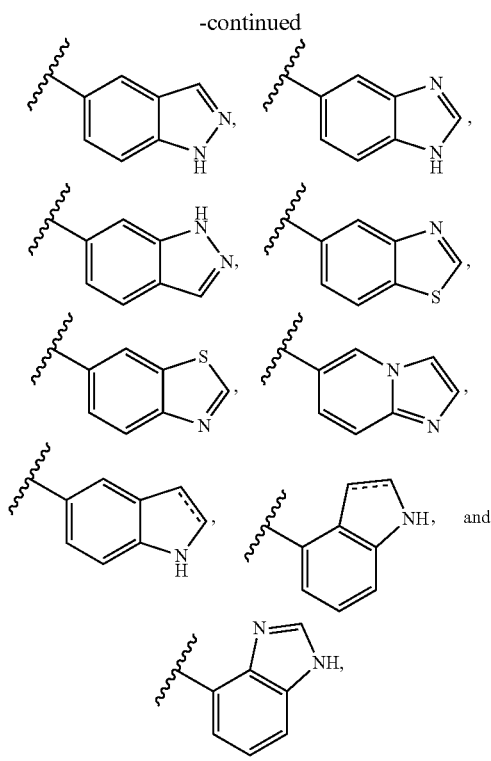

wherein ⸺ indicates a single or double bond, and wherein said phenyl or said 5-to-10-membered heteroaryl is optionally substituted with 1-3 R⁹ groups. In still other embodiments, which may be combined with any of the preceding embodiments, R² is —CH₃, CD₃, or —CH₂CH₃; R³ is —H, —F, —CH₃, or —CN; R³' is —H or —CH₃; and R⁴ is —H, —F or —CH₃. In yet further embodiments, which may be combined with any of the preceding embodiments, each R⁹ is independently —F, —Cl, —OR¹⁰, —CH₃, or —CN, and each R¹⁰ is independently —H, —CH₃, —CD₃, or —CH₂CH₃, wherein said —CH₃ or said —CH₂CH₃ is optionally substituted with hydroxyl and/or —OCH₃.

In yet other embodiments, which may be combined with any of the preceding embodiments, the compound of formula (I) is a compound of formula (I-A-i) or formula (I-A-ii):

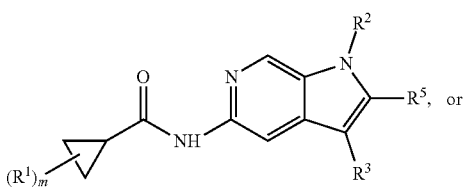
(I-A-i)

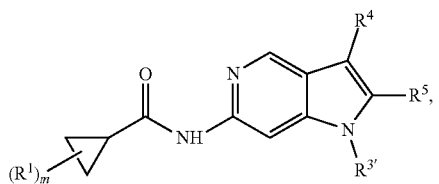
(I-A-ii)

wherein
m is an integer 0 or 1;
R¹ is —F, C₁-C₃ alkylene-NR⁷'R⁸', or C₁-C₃ alkylene-OH;
R² is —CH₃, CD₃, or —CH₂CH₃;
R³ is —H, —F, —CH₃, or —CN;
R³' is —H or —CH₃;
R⁴ is —H, —F or —CH₃;
R⁵ is phenyl or 5-to-10-membered heteroaryl, wherein said 5-to-10-membered heteroaryl is selected from the group consisting of:

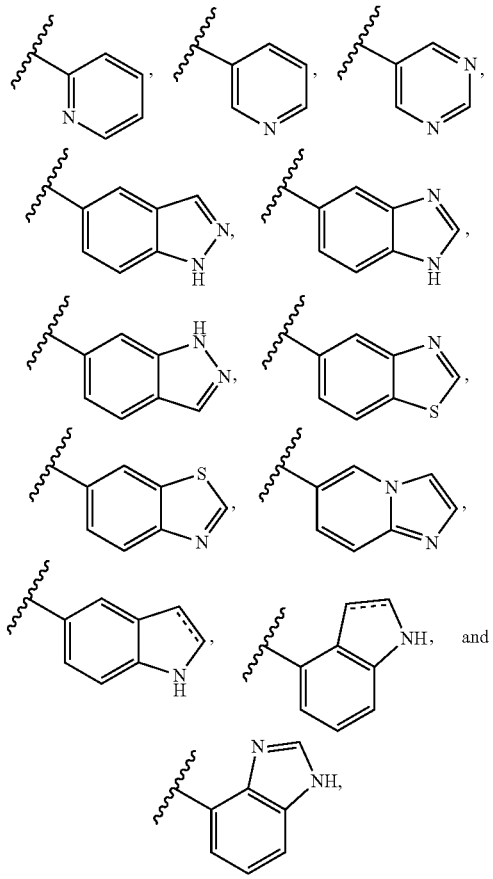

wherein ⸺ indicates a single or double bond, and wherein said phenyl or said 5-to-10-membered heteroaryl is optionally substituted with 1-3 R⁹ groups;
each pair of R⁷' and R⁸' taken together with the nitrogen atom to which they are attached independently form a 4-to-6-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by H, or C₁-C₃ alkyl;
each R⁹ is independently —F, —Cl, —OR¹⁰, —CH₃, or —CN, and
each R¹⁰ is independently —H, —CH₃, —CD₃, or —CH₂CH₃, wherein said —CH₃ or said —CH₂CH₃ is optionally substituted with hydroxyl and/or —OCH₃.
In still yet other embodiments, which may be combined with any of the preceding embodiments, the compound of formula (I) is a compound of formula (I-A-i) or formula (I-A-ii):

(I-A-i)

[Structure of formula (I-A-i)]

or (I-A-ii)

[Structure of formula (I-A-ii)]

wherein m is an integer 0 or 1;

$R^1$ is —F;

$R^2$ is —CH$_3$;

$R^3$ is —H or —CH$_3$;

$R^{3'}$ is —H or —CH$_3$;

$R^4$ is —CH$_3$;

$R^5$ is a 5-to-10-membered heteroaryl, wherein said 5-to-10-membered heteroaryl is selected from the group consisting of:

[Two heteroaryl structures: pyridine and pyrimidine] and wherein said 5-to-10-membered heteroaryl is optionally substituted with 1-3 $R^9$ groups;

each $R^9$ is independently —F or —OR$^{10}$, and each $R^{10}$ is independently —H or —CH$_3$.

In other embodiments of the present aspect, the compound of formula (I) is a compound of formula (I-B):

(I-B)

[Structure of formula (I-B)]

In some embodiments of the foregoing, the compound of formula (I) is a compound of formula (I-B-i) or formula (I-B-ii):

(I-B-i)

[Structure of formula (I-B-i)]

or

-continued (I-B-ii)

[Structure of formula (I-B-ii)]

wherein $R^2$ is —H, —CH$_3$, CD$_3$, —CHF$_2$, or —CH$_2$CH$_3$;

$R^3$ is —H, C$_1$-C$_3$ alkyl, C$_3$-cycloalkyl, halogen, or —CN;

$R^{3'}$ is —H, C$_1$-C$_3$ alkyl, C$_3$-cycloalkyl, or —CN;

$R^4$ is —H, —CH$_3$, —CD$_3$, —CHF$_2$, —CH$_2$CH$_3$, or halogen;

$R^5$ is C$_6$-C$_{14}$ aryl or 5-to-10-membered heteroaryl, wherein said 5-to-10-membered heteroaryl is selected from the group consisting of:

[Multiple heteroaryl structures shown]

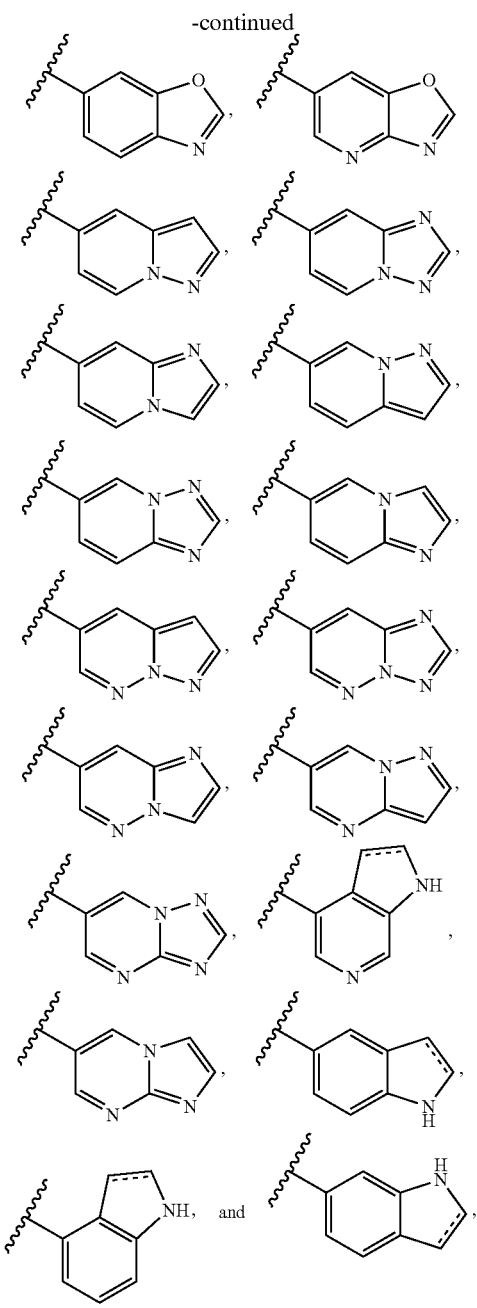

wherein ⁼⁼⁼ indicates a single or double bond, and wherein said $C_6$-$C_{14}$ aryl or said 5-to-10-membered heteroaryl is optionally substituted with 1-5 $R^9$ groups; $R^6$ is $C_1$-$C_3$ alkyl, $C_3$-$C_6$ cycloalkyl, $C_1$-$C_3$ alkylene-$NR^7R^8$, $C_1$-$C_3$ alkylene-$NR^{7'}R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$alkylene)-$NR^7R^8$, $C_1$-$C_2$ alkylene-($C_3$-$C_6$ cycloalkylene)-($C_0$-$C_2$alkylene)-$NR^{7'}R^{8'}$, $C_1$-$C_2$ alkylene-($C_3$-$C_6$ cycloalkylene)-($C_0$-$C_2$ alkylene)-OH, $C_1$-$C_2$ alkylene-($C_4$-$C_6$ heterocycloalkylene)-($C_0$-$C_2$ alkylene)-$NR^7R^8$, or $C_1$-$C_2$ alkylene-($C_4$-$C_6$ heterocycloalkylene)-($C_0$-$C_2$alkylene)-$NR^{7'}R^{8'}$, wherein the alkyl, alkylene, cycloalkyl, cycloalkylene, and heterocycloalkylene moieties in $R^6$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^7$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;

each $R^8$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;

each pair of $R^{7'}$ and $R^{8'}$ taken together with the nitrogen atom to which they are attached independently form a 4-to-6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —$OR^{10}$, $C_1$-$C_3$ alkyl, —$CF_2H$, —$CF_3$, $C_3$-$C_6$cycloalkyl, or —CN, and each $R^{10}$ is independently —H, $C_1$-$C_3$ alkyl, —$CD_3$, —$CF_2H$, —$CF_3$, or $C_3$-$C_6$ cycloalkyl, wherein said $C_1$-$C_3$ alkyl is optionally substituted with hydroxyl and/or $C_1$-$C_3$ alkoxy.

In some embodiments, which may be combined with any of the preceding embodiments, $R^6$ is $C_1$-$C_3$ alkyl or $C_1$-$C_3$ alkylene-$NR^{7'}R^{8'}$; and wherein each pair of $R^{7'}$ and $R^{8'}$ of $R^6$ taken together with the nitrogen atom to which they are attached independently form a 4-to-6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl. In other embodiments, which may be combined with any of the preceding embodiments, $R^5$ is phenyl or 5-to-10-membered heteroaryl, wherein said 5-to-10-membered heteroaryl is selected from the group consisting of:

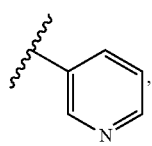

wherein said phenyl or said 5-to-10-membered heteroaryl is optionally substituted with 1-3 $R^9$ groups. In still other embodiments, which may be combined with any of the preceding embodiments, each $R^9$ is independently —F, —$OR^{10}$, —$CH_3$, and each $R^{10}$ is independently —H, —$CH_3$, —$CD_3$, —$CF_2H$, or —$CF_3$. In yet other embodiments, which may be combined with any of the preceding embodiments, $R^2$ is —H or —$CH_3$; $R^3$ is —H; $R^3$ is —H; and $R^4$ is —H or —$CH_3$.

In some embodiments, which may be combined with any of the preceding embodiments, the compound of formula (I) is a compound of formula (I-B-i) or formula (I-B-ii):

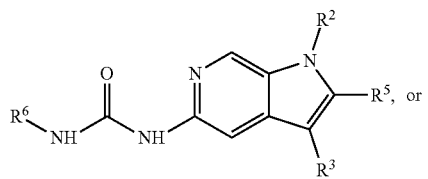
(I-B-i)

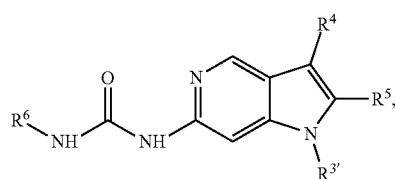
(I-B-ii)

wherein
R² is —H or —CH₃;
R³ is —H;
R³' is —H;
R⁴ is —H or —CH₃;
R⁵ is phenyl or 5-to-10-membered heteroaryl, wherein said 5-to-10-membered heteroaryl is selected from the group consisting of:

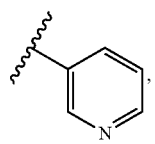 [SMILES: *c1cccnc1]

wherein said phenyl or said 5-to-10-membered heteroaryl is optionally substituted with 1-3 R⁹ groups;
R⁶ is C₁-C₃ alkyl or C₁-C₃ alkylene-NR⁷'R⁸';
each pair of R⁷' and R⁸' taken together with the nitrogen atom to which they are attached independently form a 4-to-6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with C₁-C₃ alkyl, C₃-C₆ cycloalkyl, C₂-C₃ haloalkyl, C₂-C₃ alkylene-CN, or C₂-C₃ heteroalkyl;
each R⁹ is independently —F, —OR¹⁰, —CH₃, and
each R¹⁰ is independently —H, —CH₃, —CD₃, —CF₂H, or —CF₃.

Also provided herein is a compound which is selected from the group consisting of:

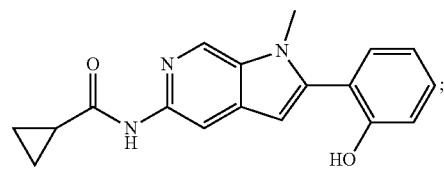

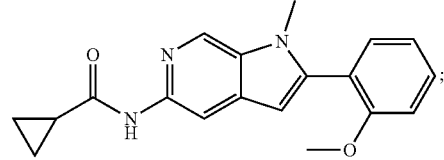

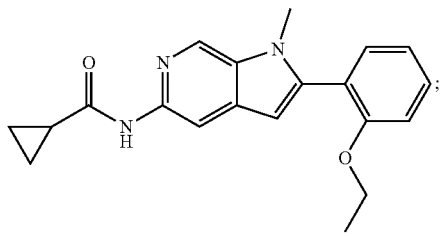

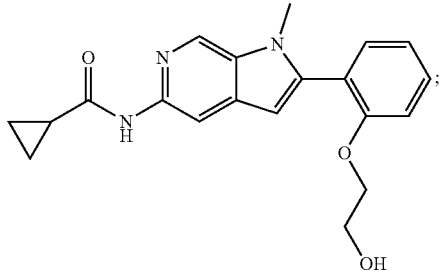

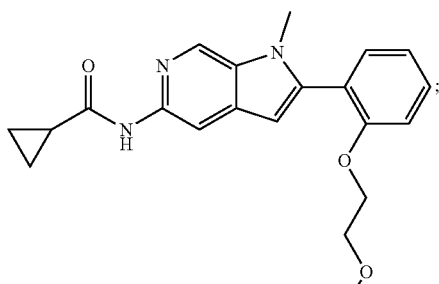

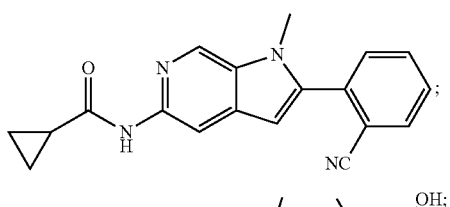

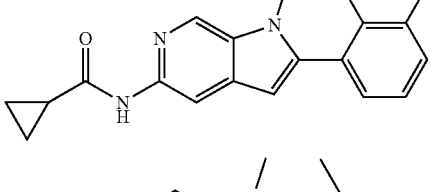

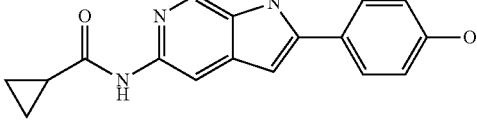

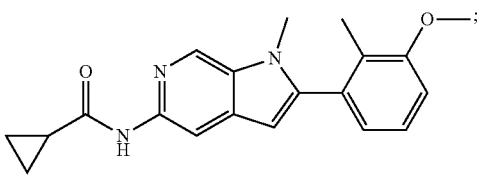

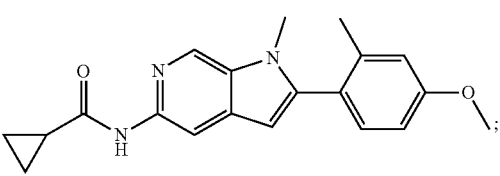

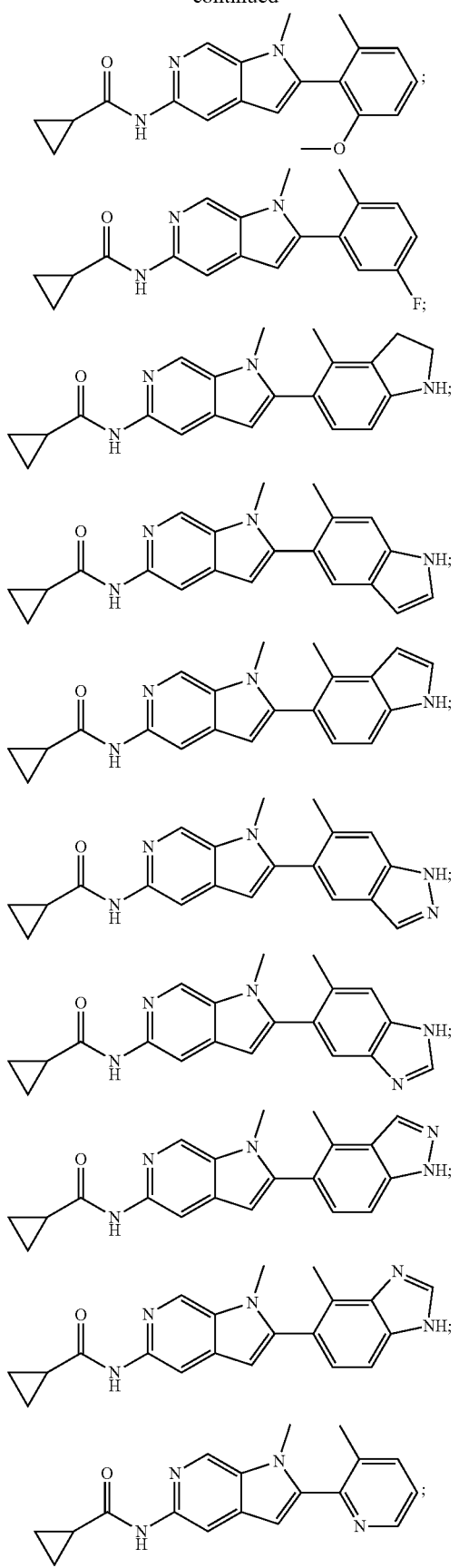
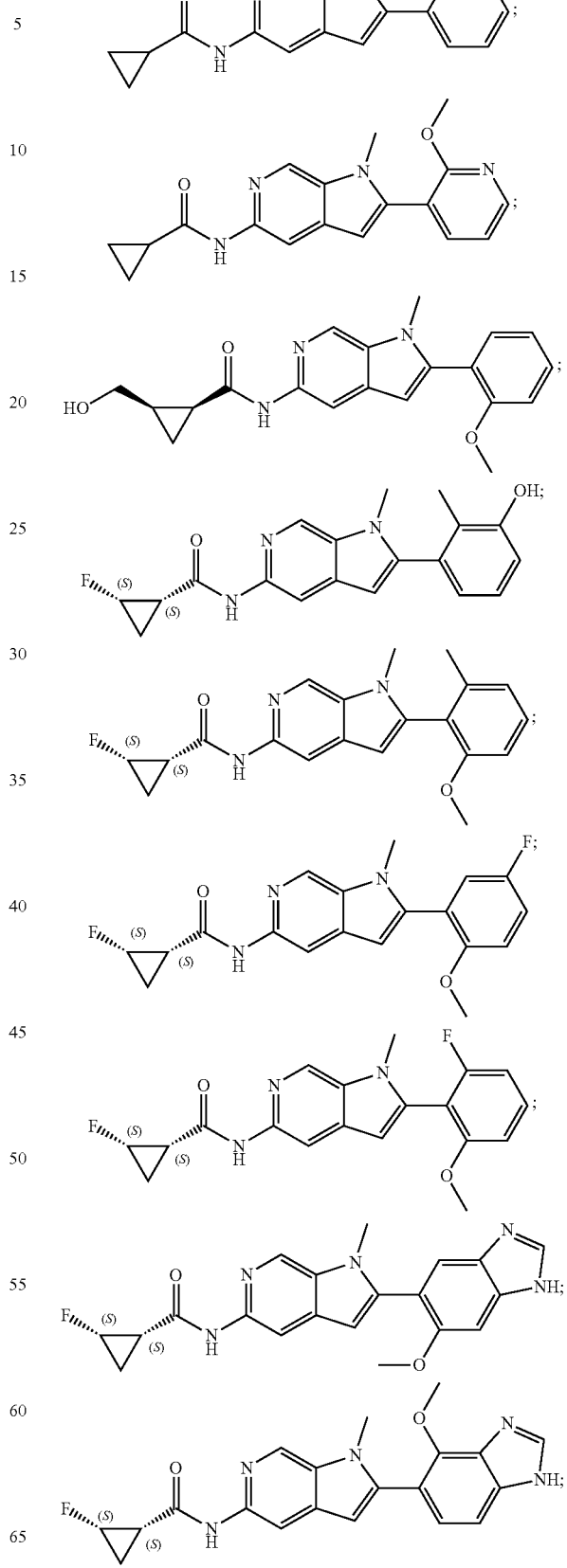

-continued
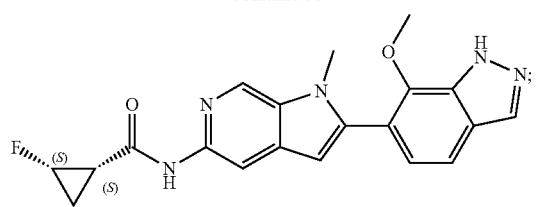
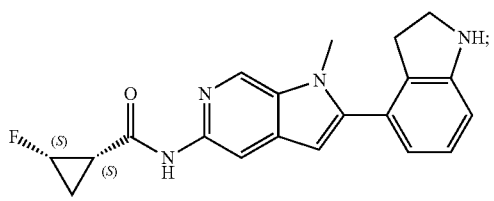
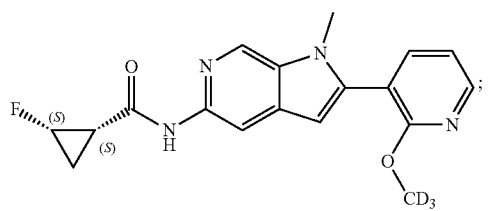
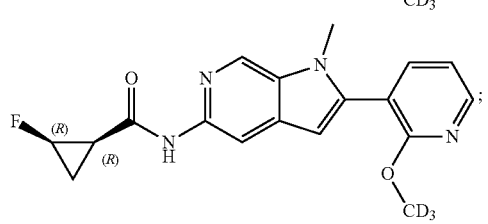
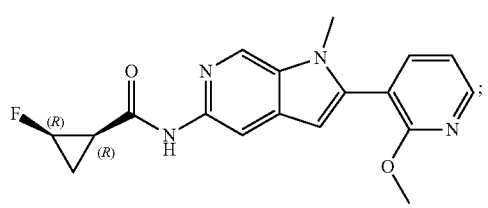
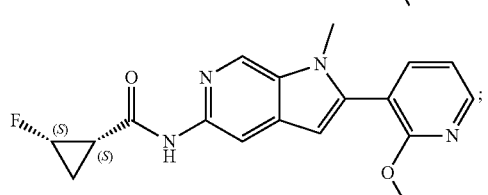
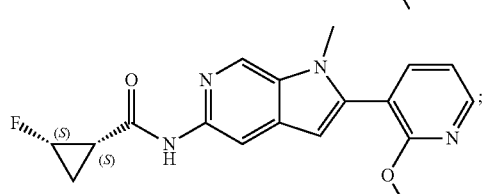
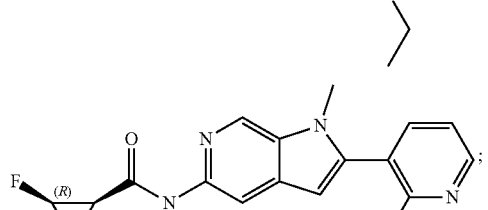
-continued

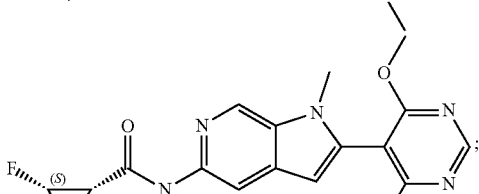
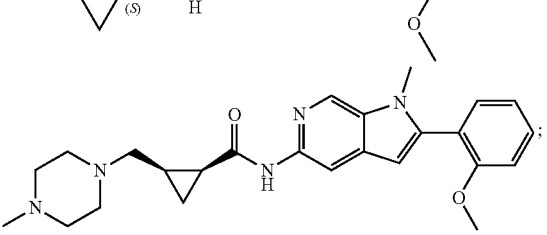
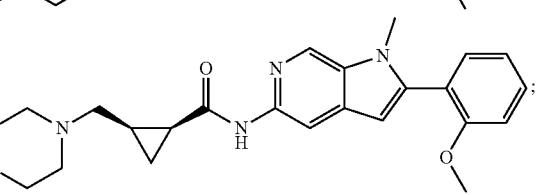
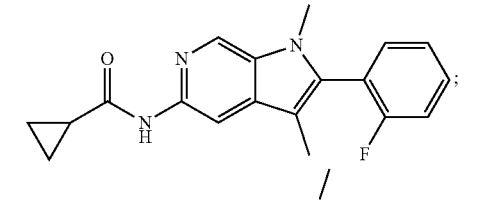
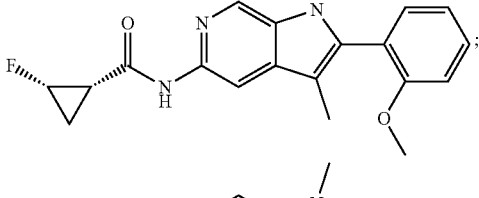
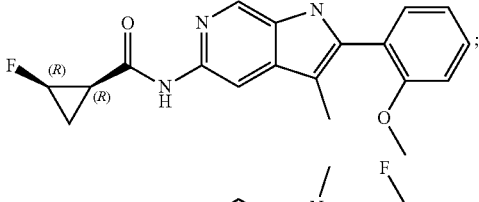
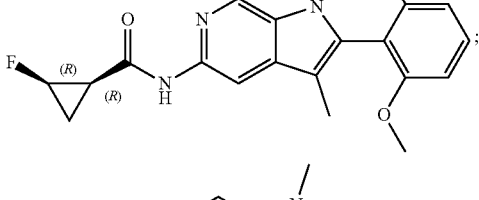
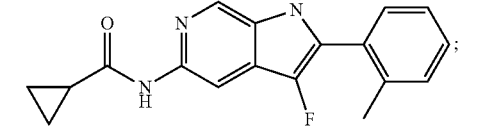

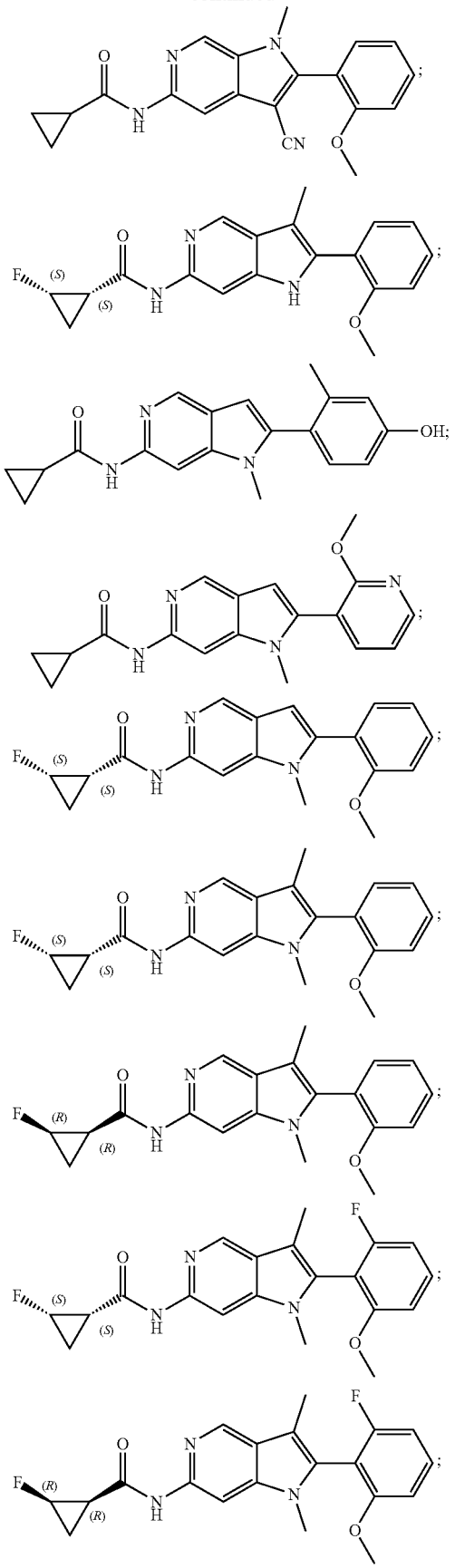
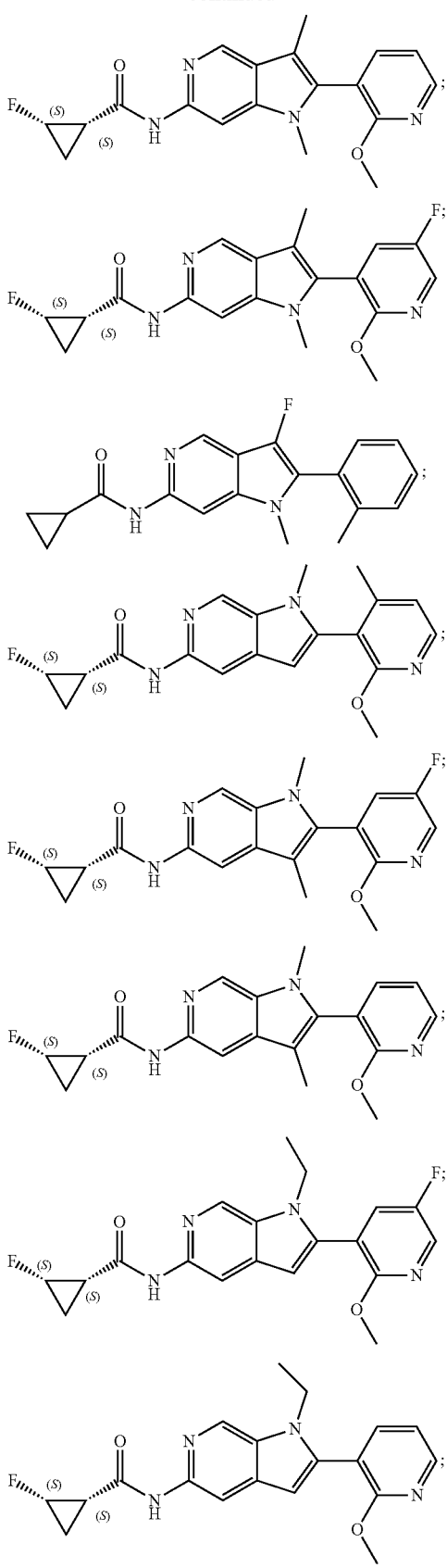

-continued
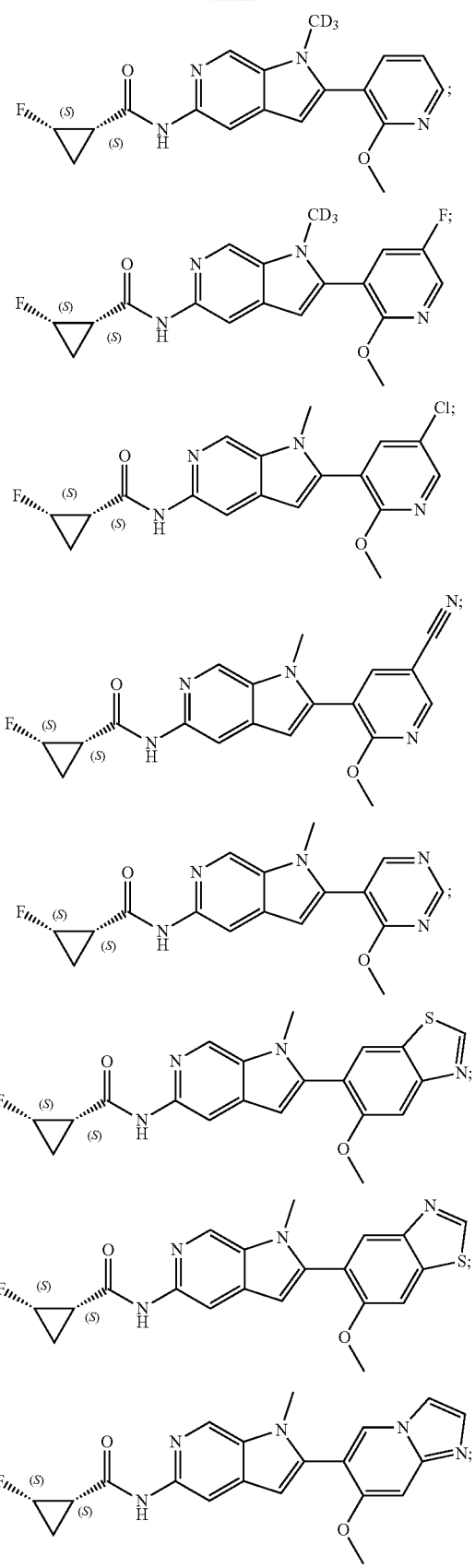
-continued
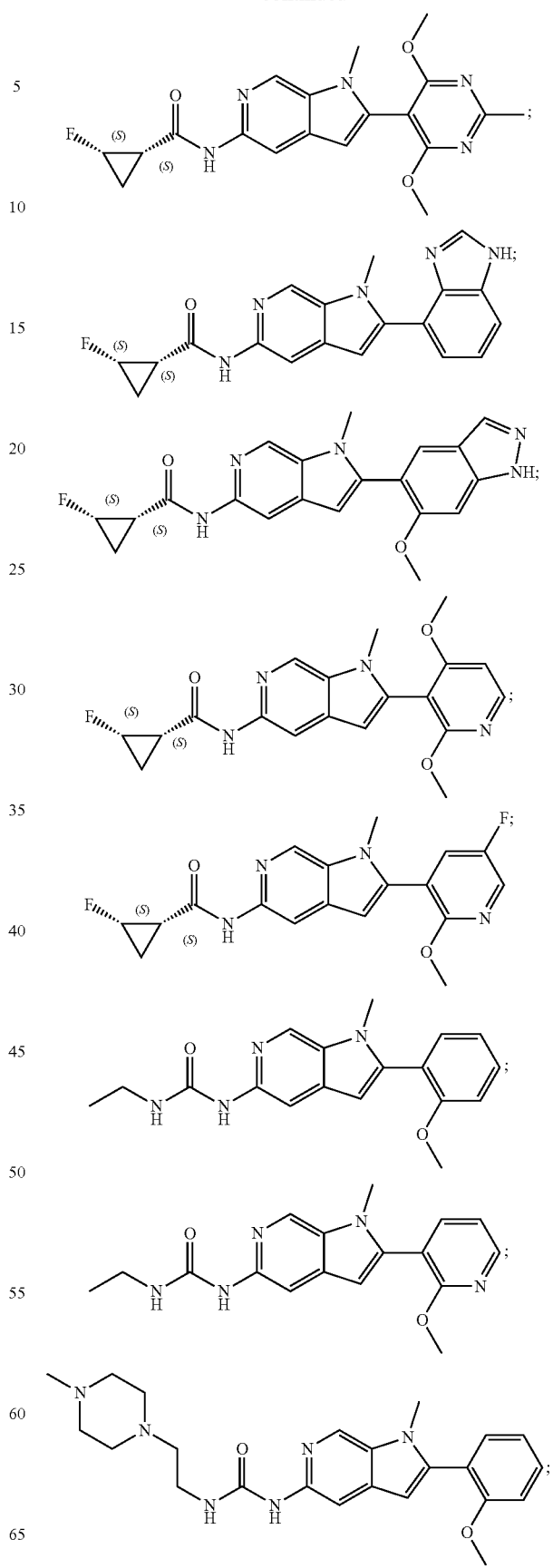

25
-continued
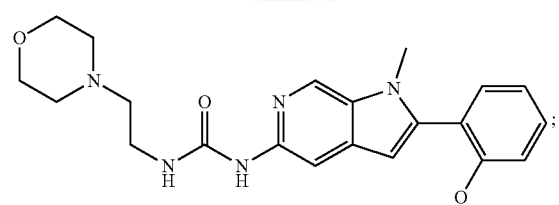
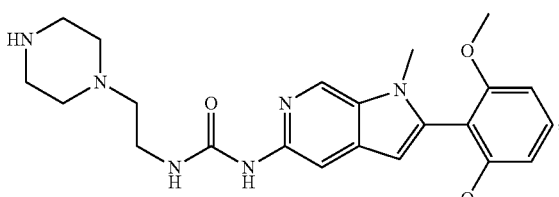
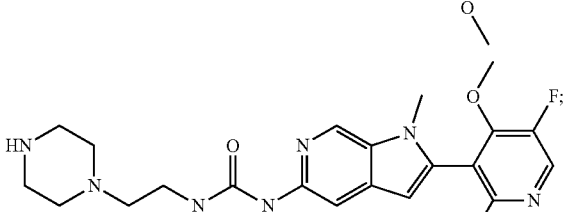
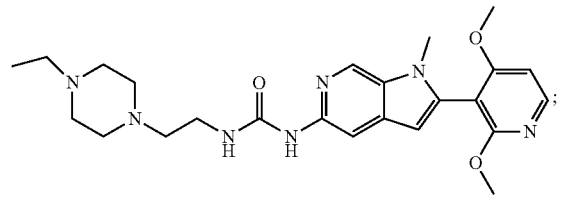
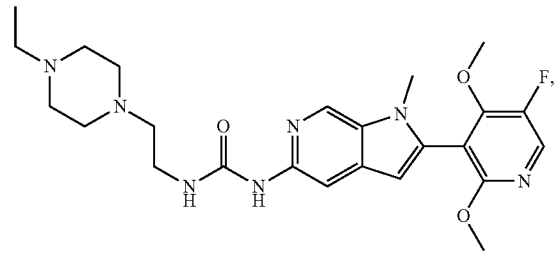
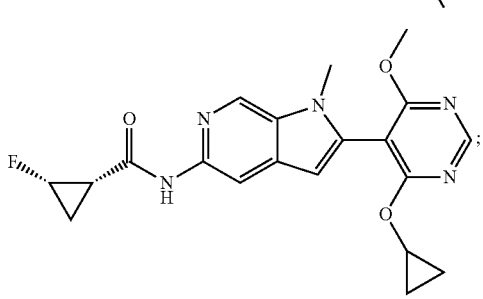
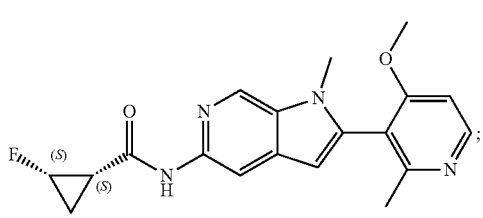
26
-continued
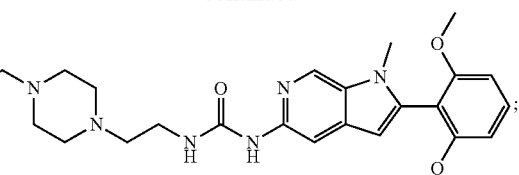
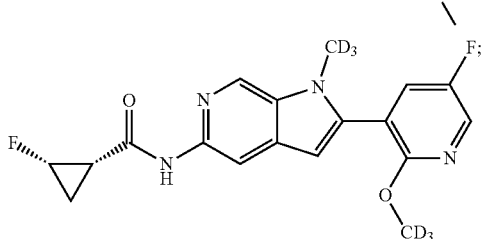
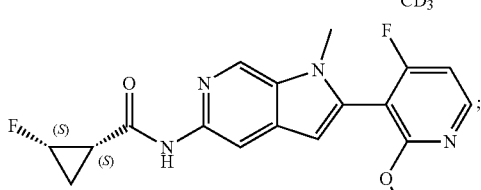
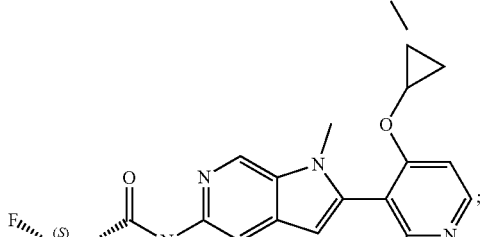
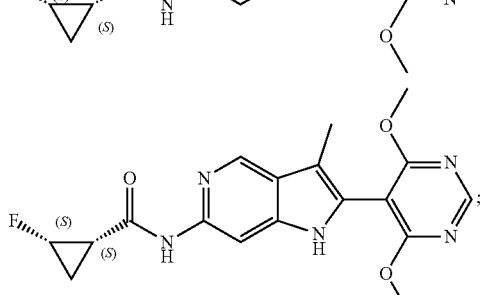
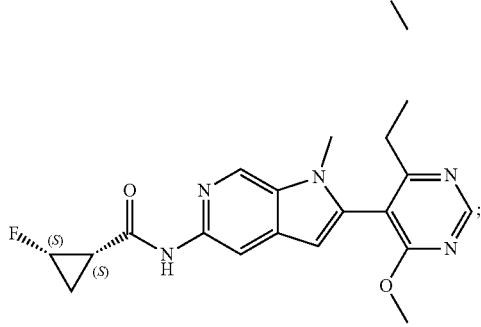
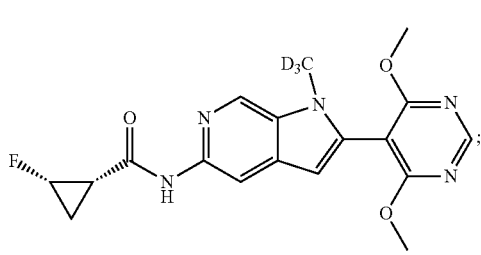

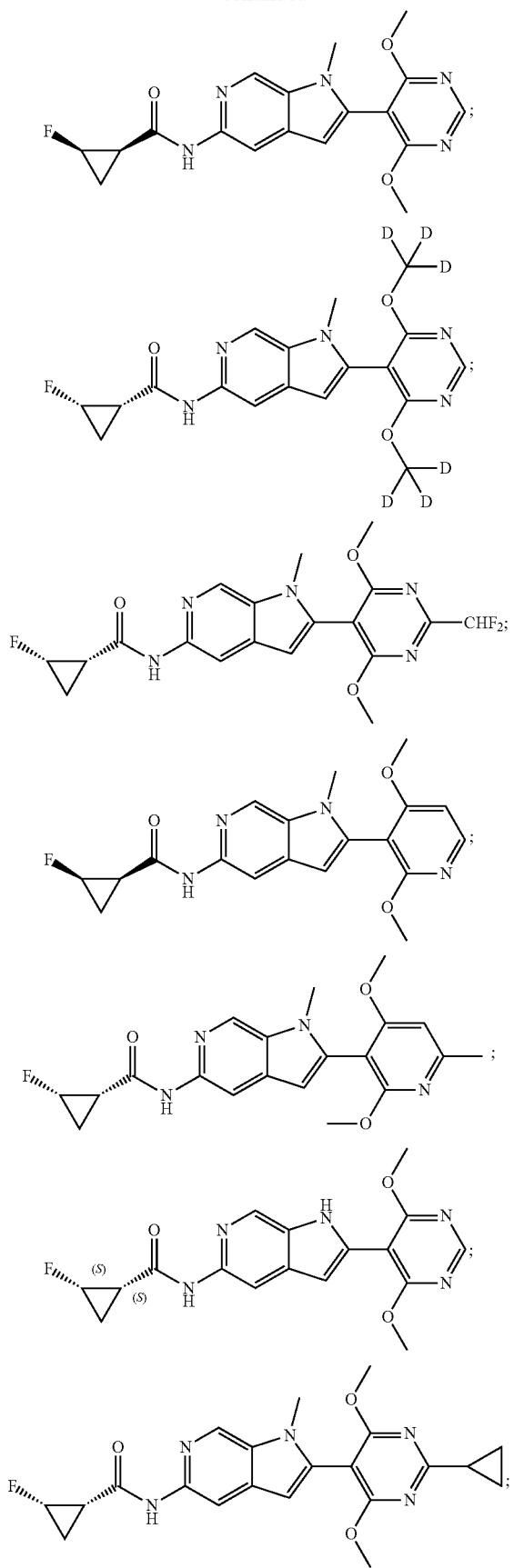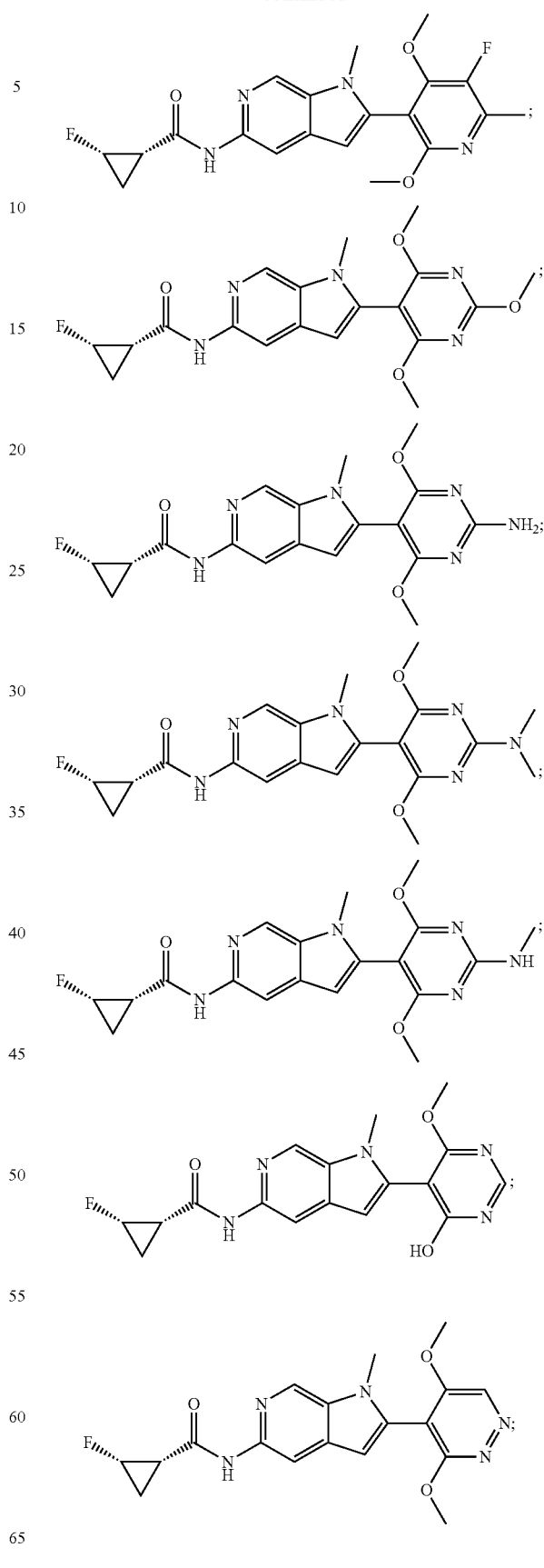

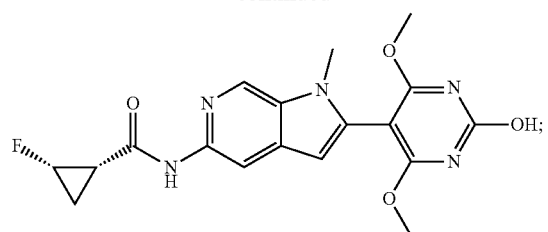
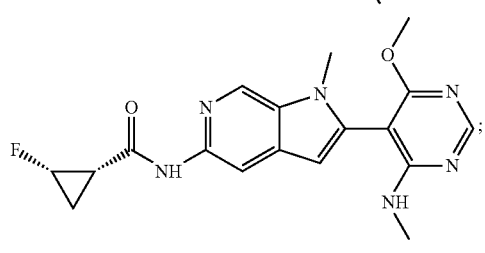
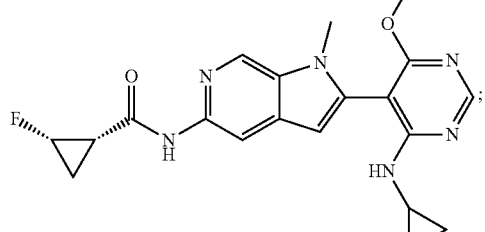
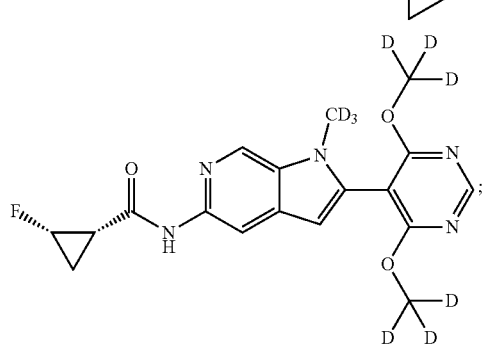
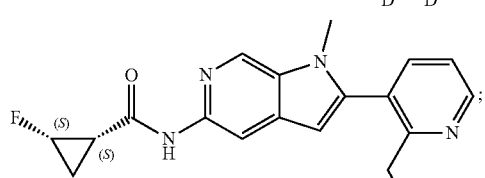
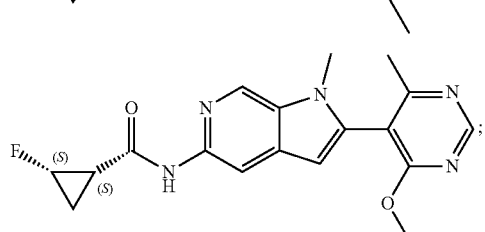
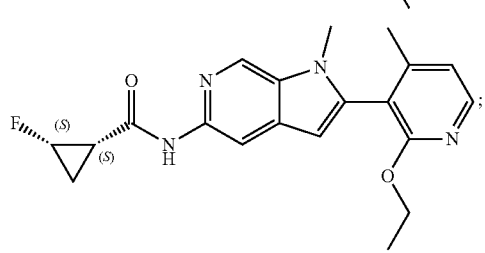
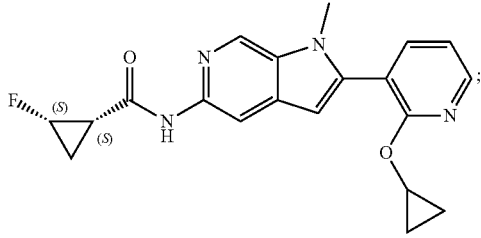
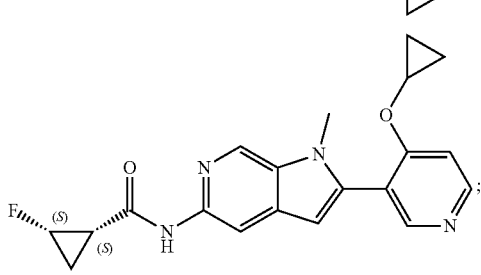
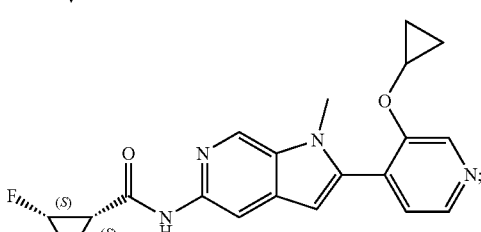
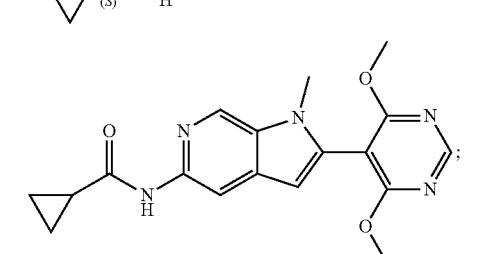
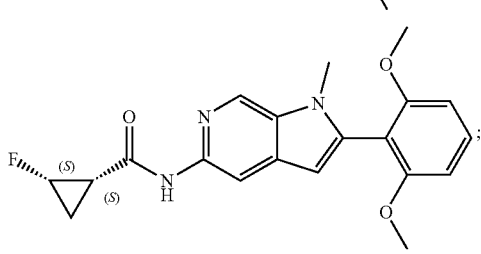
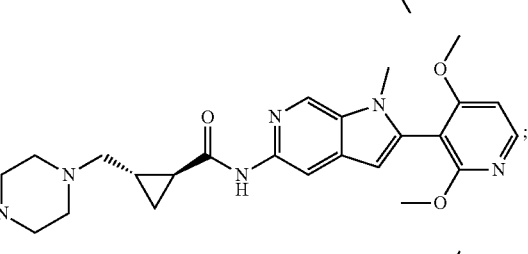
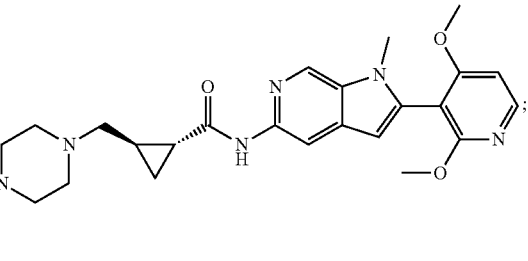

31
-continued
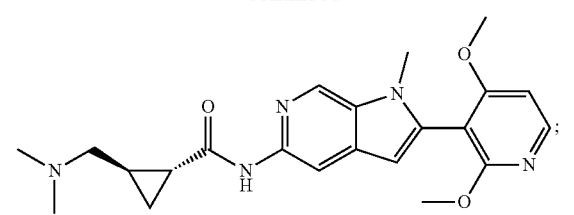
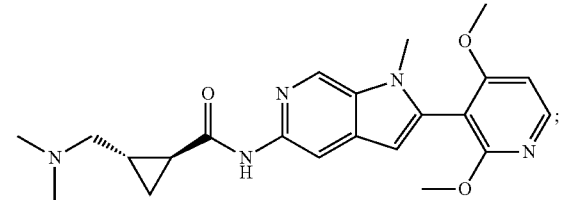
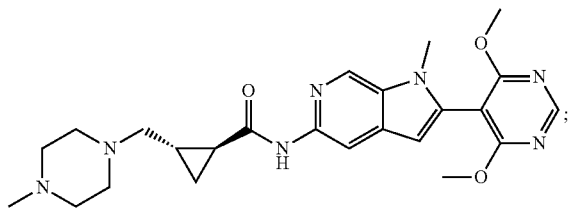
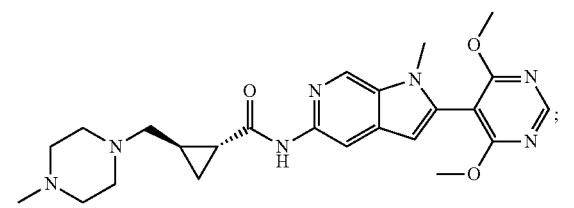
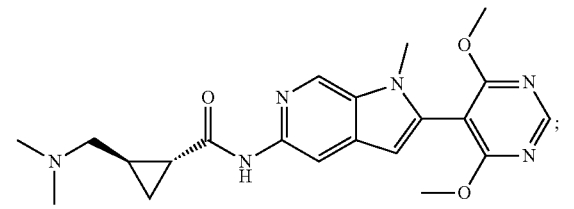
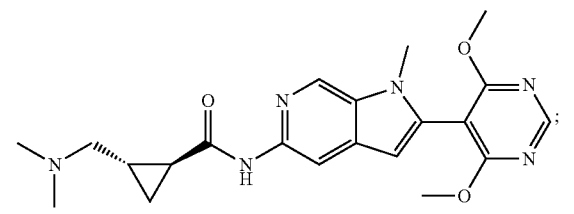
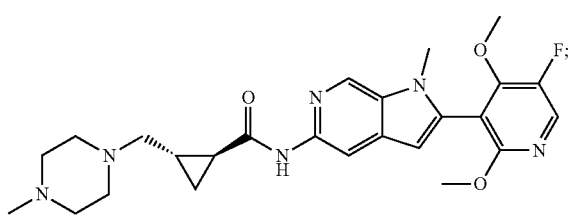
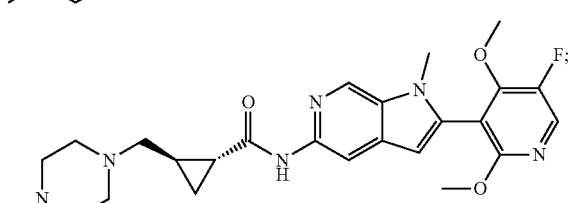
32
-continued
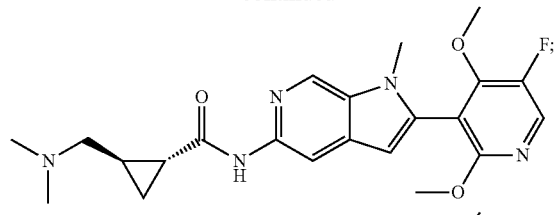
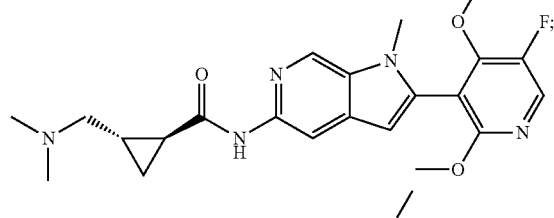
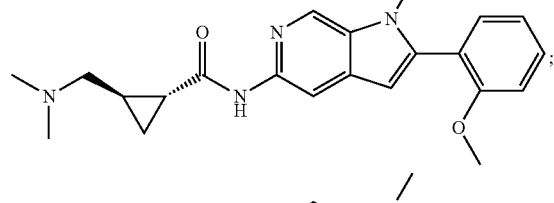

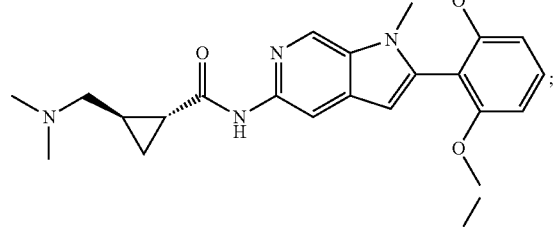
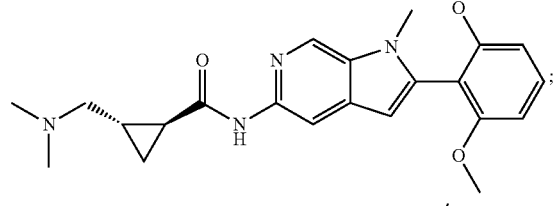
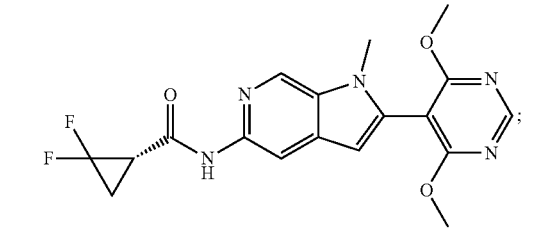
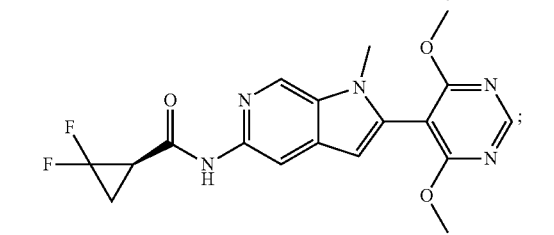

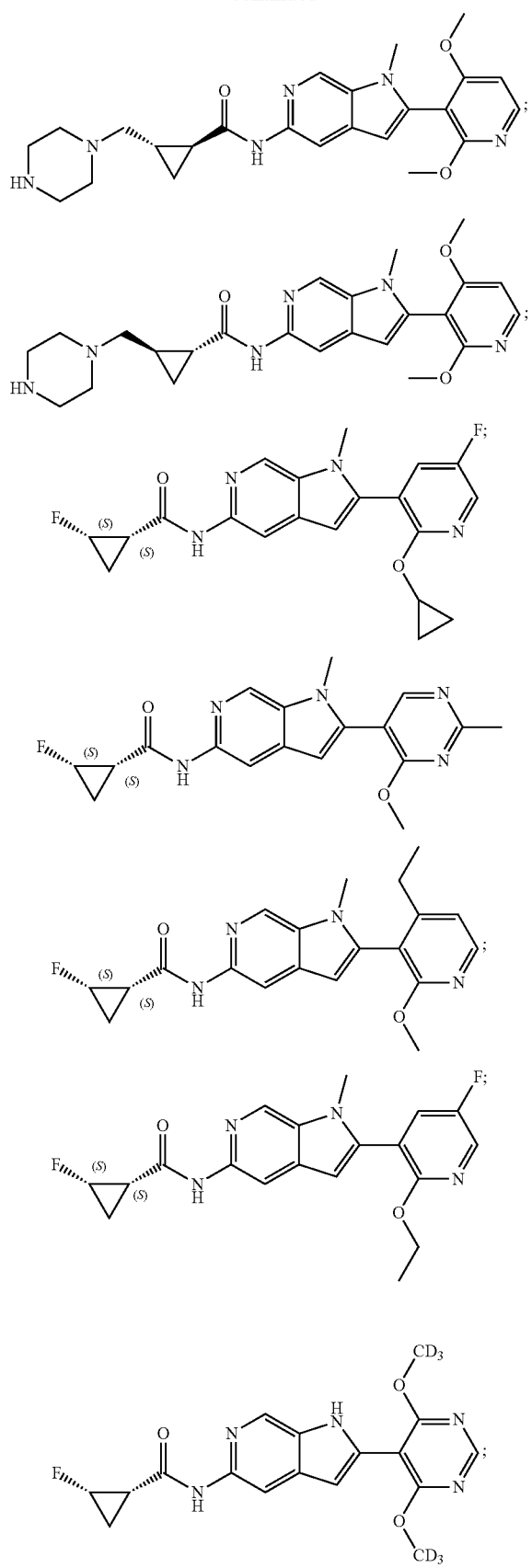

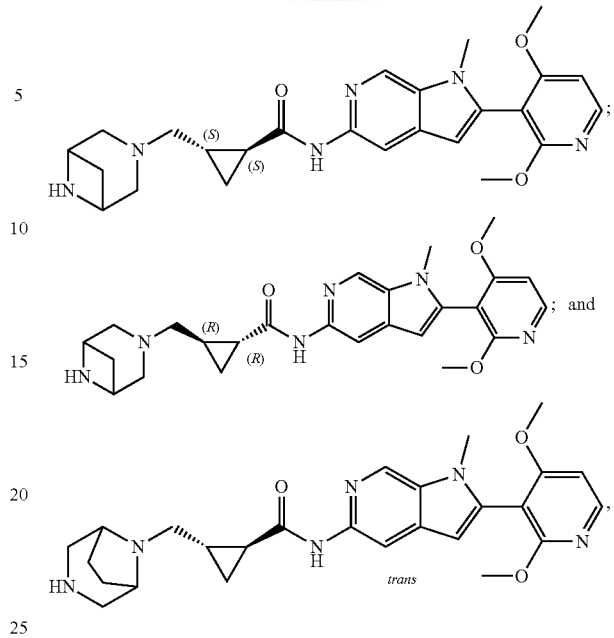

or a pharmaceutically acceptable salt, solvate, hydrate, or co-crystal thereof, or a mixture of any of the foregoing.

In another aspect, provided herein is a pharmaceutical composition comprising a compound of formula (I) as described herein, or a pharmaceutically acceptable salt, solvate, hydrate, or co-crystal thereof, or a mixture of any of the foregoing, and one or more pharmaceutically acceptable excipients.

In yet another aspect, the present disclosure provides a method of inhibiting Bcr-Abl enzymatic activity in a cell, comprising exposing the cell with an effective amount of a compound of formula (I) as described herein, or a pharmaceutically acceptable salt, solvate, hydrate, or co-crystal thereof, or a mixture of any of the foregoing, or a pharmaceutical composition comprising a compound of formula (I) as described herein, or a pharmaceutically acceptable salt, solvate, hydrate, or co-crystal thereof, or a mixture of any of the foregoing.

In still yet another aspect, provided herein is a method of treating chronic myeloid leukemia (CML), acute myeloid leukemia (AML), acute lymphoblastic leukemia (ALL), or a mixed phenotype acute leukemia, in a human in need thereof, comprising administering to the human a compound of formula (I) as described herein, or a pharmaceutically acceptable salt, solvate, hydrate, or co-crystal thereof, or a mixture of any of the foregoing, or a pharmaceutical composition comprising a compound of formula (I) as described herein, or a pharmaceutically acceptable salt, solvate, hydrate, or co-crystal thereof, or a mixture of any of the foregoing.

In some embodiments of the present aspect, the leukemia is refractory leukemia. In certain embodiments of the foregoing, the refractory leukemia is associated with a mutation in the Bcr-Abl tyrosine kinase gene resulting in specific amino acid substitutions selected from the group consisting of M244V, L248V, G250E, G250A, Q252H, Q252R, Y253F, Y253H, E255K, E255V, D276G, F311L, T315N, T315A, F317V, F317L, M343T, M351T, E355G, F359A, F359V, V379I, F382L, L387M, H396P, H396R, S417Y, E459K, F486S, and T315I. In still further embodiments of the foregoing, the refractory leukemia is associated with a mutation in the Bcr-Abl tyrosine kinase gene resulting in specific amino acid substitution T315I. In yet other embodiments, which may be combined with any preceding embodiments of the present aspect, the method further comprises administering one or more pharmaceutical agents including anti-microtubular therapies, topoisomerase inhibitors, alkylating agents, nucleotide synthesis inhibitors, DNA synthesis inhibitors, protein synthesis inhibitors, developmental signaling pathway inhibitors, pro-apoptotic agents, Abl myristoyl-pocket binding inhibitors, MEK1/2 inhibitors, AKT inhibitors, PI3K inhibitors and/or radiation.

DETAILED DESCRIPTION

The following description sets forth exemplary methods, parameters, and the like. It should be recognized, however, that such description is not intended as a limitation on the scope of the present disclosure but is instead provided as a description of exemplary embodiments.

I. Definitions

As used herein, the following definitions shall apply unless otherwise indicated. Further, if any term or symbol used herein is not defined as set forth below, it shall have its ordinary meaning in the art.

The term "excipient" as used herein means an inert or inactive substance that may be used in the production of a drug or pharmaceutical, such as a tablet containing a compound of the present disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey de, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The terms "individual", "subject" and "patient" refer to mammals and includes humans and non-human mammals. Examples of patients include, but are not limited to, mice, rats, hamsters, guinea pigs, pigs, rabbits, cats, dogs, goats, sheep, cows, and humans. In some embodiments, patient refers to a human.

As used herein, the term "mammal" includes, but is not limited to, humans, mice, rats, guinea pigs, monkeys, dogs, cats, horses, cows, pigs, and sheep.

"Pharmaceutically acceptable" refers to safe and non-toxic, and suitable for in vivo or for human administration.

As used herein, the term "alkyl", by itself or as part of another substituent, means, unless otherwise stated, a straight or branched chain hydrocarbon radical, having the number of carbon atoms designated (e.g., $C_1$-$C_6$ means one to six carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. In some embodiments, the term "alkyl" may encompass $C_1$-$C_6$ alkyl, $C_2$-$C_6$ alkyl, $C_3$-$C_6$ alkyl, $C_4$-$C_6$ alkyl, $C_5$-$C_6$ alkyl, $C_1$-$C_5$ alkyl, $C_2$-$C_5$ alkyl, $C_3$-$C_5$ alkyl, $C_4$-$C_5$ alkyl, $C_1$-$C_4$ alkyl, $C_2$-$C_4$ alkyl, $C_3$-$C_4$ alkyl, $C_1$-$C_3$ alkyl, $C_2$-$C_3$ alkyl, or $C_1$-$C_2$ alkyl.

The term "cycloalkyl," "carbocyclic," or "carbocycle" refers to hydrocarbon rings having the indicated number of ring atoms (e.g., $C_3$-$C_6$ cycloalkyl means 3-6 carbons) and being fully saturated or having no more than one double bond between ring vertices. As used herein, "cycloalkyl," "carbocyclic," or "carbocycle" is also meant to refer to bicyclic, polycyclic and spirocyclic hydrocarbon rings such as, for example, bicyclo[2.2.1]heptane, pinane, bicyclo[2.2.2]octane, adamantane, norborene, spirocyclic $C_5$-$C_{12}$ alkane, etc. In some embodiments, "cycloalkyl" encompasses $C_3$-$C_7$ cycloalkyl, $C_4$-$C_7$ cycloalkyl, $C_5$-$C_7$ cycloalkyl, $C_5$-$C_7$ cycloalkyl, $C_3$-$C_6$ cycloalkyl, $C_4$-$C_6$ cycloalkyl, $C_5$-$C_6$ cycloalkyl, $C_3$-$C_5$ cycloalkyl, $C_4$-$C_5$ cycloalkyl, or $C_3$-$C_4$ cycloalkyl. In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH=N($CH_3$)—$CH_3$. Up to two heteroatoms can be consecutive, such as, for example, —$CH_2$—NH—$OCH_3$ and —$CH_2$—O—Si($CH_3$)$_3$.

The term "heterocycloalkyl," "heterocyclic," or "heterocycle" refers to a cycloalkyl radical group having the indicated number of ring atoms (e.g., 5-6 membered heterocycloalkyl) that contain from one to five heteroatoms selected from the group consisting of N, O, and S, wherein the nitrogen and sulfur atoms are optionally oxidized, nitrogen atom(s) are optionally quaternized, as ring atoms. Unless otherwise stated, a "heterocycloalkyl," "heterocyclic," or "heterocycle" ring can be a monocyclic, a bicyclic, bridged or fused ring system, spirocyclic or a polycyclic ring system. Non-limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-5-oxide, thiomorpholine-S,S-oxide, piperazine, pyran, pyridone, 3-pyrroline, thiopyran, pyrone, tetrahydrofuran, tetrhydrothiophene, quinuclidine, tropane and the like. A "heterocycloalkyl," "heterocyclic," or "heterocycle" group can be attached to the remainder of the molecule through one or more ring carbons or heteroatoms. In some embodiments, "heterocycloalkyl" encompasses 3- to 10-membered heterocycloalkyl, 4- to 10-membered heterocycloalkyl, 5- to 10-membered heterocycloalkyl, 6- to 10-membered heterocycloalkyl, 7- to 10-membered heterocycloalkyl, 8- to 10-membered heterocycloalkyl, 9- to 10-membered heterocycloalkyl, 3- to 9-membered heterocycloalkyl, 4- to 9-membered heterocycloalkyl, 5- to 9-membered heterocycloalkyl, 6 to 9-membered heterocycloalkyl, 7- to 9-membered heterocycloalkyl, 8- to 9-membered heterocycloalkyl, 3- to 8-membered heterocycloalkyl, 4- to 8-membered heterocycloalkyl, 5 to 8-membered heterocycloalkyl, 6- to 8-membered heterocycloalkyl, 7- to 8-membered heterocycloalkyl, 3- to 7-membered heterocycloalkyl, 4- to 7-membered heterocycloalkyl, 5 to 7-membered heterocycloalkyl, 6- to 7-membered heterocycloalkyl, 3- to 6-membered heterocycloalkyl, 4- to 6-membered heterocycloalkyl, 5- to 6-membered heterocycloalkyl, 3 to 10-membered heterocycloalkyl, 4- to 5-membered heterocycloalkyl, or 3- to 4-membered heterocycloalkyl. In other embodiments, "heterocycloalkyl" may be characterized by the number of carbon atoms in the ring, provided that the ring contains at least one heteroatom. For example, in some embodiments, "heterocycloalkyl" encompasses $C_3$-$C_9$ heterocycloalkyl, $C_3$-$C_8$ heterocycloalkyl, $C_3$-$C_7$ heterocycloalkyl, $C_3$-$C_6$ heterocycloalkyl, $C_3$-$C_5$ heterocycloalkyl, $C_3$-$C_4$ heterocycloalkyl, $C_4$-$C_9$ heterocycloalkyl, $C_4$-$C_8$ heterocycloalkyl, $C_4$-$C_7$ heterocycloalkyl, $C_4$-$C_6$ heterocycloalkyl, $C_4$-$C_5$ heterocycloalkyl, $C_5$-$C_9$ heterocycloalkyl, $C_5$-$C_8$ heterocycloalkyl, $C_5$-$C_7$ heterocycloalkyl, $C_5$-$C_6$ heterocycloalkyl, $C_6$-$C_9$ heterocycloalkyl, $C_6$-$C_5$ heterocycloalkyl, $C_6$-$C_7$ heterocycloalkyl, $C_7$-$C_9$ heterocycloalkyl, $C_7$-$C_8$ heterocycloalkyl, or $C_8$-$C_9$ heterocycloalkyl. It should be recognized that "heterocycloalkyl" as described by the number of ring atoms may also be described by number of carbon atoms in the ring. For example, a piperazinyl ring may be described as a $C_4$ heterocycloalkyl ring or a 6-membered heterocycloalkyl ring; an azetidinyl or oxetanyl ring may each be described as a $C_3$ heterocycloalkyl ring or a 4-membered heterocycloalkyl ring.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms. In some embodiments, an alkyl (or alkylene) group will have 10 or fewer carbon atoms.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$—, —$CH_2$—S—$CH_2$—$CH_2$—NH—$CH_2$—, —O—$CH_2$—CH═CH—, —$CH_2$—CH═C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The term "heterocycloalkylene" by itself or as part of another substituent means a divalent radical, saturated or unsaturated or polyunsaturated, derived from heterocycloalkyl. For heterocycloalkylene groups, heteroatoms can also occupy either or both of the chain termini.

The terms "alkoxy" and "alkylamino" are used in their conventional sense, and refer to those alkyl groups attached to the remainder of the molecule via an oxygen atom or an amino group, respectively.

The term "heterocycloalkoxy" refers to a heterocycloalkyl-O— group in which the heterocycloalkyl group is as previously described herein.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "$C_1$-$C_4$ haloalkyl" is mean to include trifluoromethyl, 2,2,2-trifluoroethyl, 4-chlorobutyl, 3-bromopropyl, difluoromethyl, and the like.

The term "haloalkyl-OH" refers to a haloalkyl group as described above which is also substituted by one or more hydroxyl groups. The term "haloalkyl-OH" is meant to include haloalkyl substituted by one hydroxyl group, as well as haloalkyl substituted by multiple hydroxyl groups. For example, the term "haloalkyl-OH" includes —CH(F)OH, —$CH_2$CFHCH$_2$OH, —CH(OH)CF$_3$, and the like.

The term "alkyl-OH" refers to an alkyl substituted by one or more hydroxyl groups. The term "alkyl-OH" is meant to include alkyl substituted by one hydroxyl group, as well as alkyl substituted by multiple hydroxyl groups. For example, the term "alkyl-OH" includes
—$CH_2$OH, —CH(OH)CH$_3$, —$CH_2$CH$_2$OH, —C(CH$_3$)$_2$OH, and the like.

The term "alkyl-CN" refers to an alkyl substituted by one or more cyano groups. The term "alkyl-CN" is meant to include alkyl substituted by one cyano group, as well as alkyl substituted by multiple cyano groups. For example, the term "alkyl-CN" includes —$CH_2$CN, —$CH_2CH_2$CN, —CH(CN)CH$_3$, and the like.

The term "aryl" means, unless otherwise stated, a polyunsaturated, typically aromatic, hydrocarbon group, which can be a single ring or multiple rings (up to three rings) which are fused together. In some embodiments, "aryl" encompasses $C_6$-$C_{14}$ aryl, $C_8$-$C_{14}$ aryl, $C_{10}$-$C_{14}$ aryl, $C_{12}$-$C_{14}$ aryl, $C_6$-$C_{12}$ aryl, $C_8$-$C_{12}$ aryl, $C_{10}$-$C_{12}$ aryl, $C_6$-$C_{10}$ aryl, $C_8$-$C_{10}$ aryl, or $C_6$-$C_8$ aryl. In some embodiments, both rings of a polycyclic aryl group are aromatic (e.g., naphthyl). In other embodiments, polycyclic aryl groups may include a non-aromatic ring fused to an aromatic ring, provided the polycyclic aryl group is bound to the parent structure via an atom in the aromatic ring. Thus, in some embodiments, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, in some embodiments, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups). In some embodiments, aryl is phenyl or naphthyl. In certain embodiments, aryl is phenyl.

The term "heteroaryl" refers to aryl groups (or rings) that contain from one to five heteroatoms selected from the group consisting of N, O, and S, wherein the nitrogen and sulfur atoms are optionally oxidized, and the nitrogen atom(s) are optionally quaternized. A heteroaryl group can be attached to the remainder of the molecule through a carbon atom or a heteroatom as valency permits. In some embodiments, both rings of a polycyclic heteroaryl group are aromatic. In other embodiments, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, in some embodiments, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. In some embodiments, the term "heteroaryl" encompasses 5- to 10-membered heteroaryl, 6- to 10-membered heteroaryl, 7- to 10-membered heteroaryl, 8- to 10-membered heteroaryl, 9- to 10-membered heteroaryl, 5- to 9-membered heteroaryl, 6- to 9-membered heteroaryl, 7- to 9-membered heteroaryl, 8- to 9-membered heteroaryl, 5- to 8-membered heteroaryl, 6- to 8-membered heteroaryl, 7- to 8-membered heteroaryl, 5- to 7-membered heteroaryl, 6- to 7-membered heteroaryl, or 5- to 6-membered heteroaryl.

The above terms (e.g., "alkyl," "aryl" and "heteroaryl"), in some embodiments, will include both substituted and unsubstituted forms of the indicated radical. The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocycloalkyl, heterocycloalkenyl, aralkyl, aminosulfonyl, sulfonylamino, sulfonyl, oxo and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein, a wavy line "⌇" that intersects a bond in a chemical structure indicates the point of attachment of the atom to which the wavy bond is connected in the chemical structure to the remainder of a molecule, or to the remainder of a fragment of a molecule.

As used herein, the representation of a group (e.g., $X^a$) in parenthesis followed by a subscript integer range (e.g., $(X^a)_{0-1}$) means that the group can have the number of occurrences as designated by the integer range. For example, $(X^a)_{0-1}$ means the group $X^a$ can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker. Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the present disclosure can contain asymmetric or chiral centers, and therefore exist in different stereoisomeric forms. It is intended that all stereoisomeric forms of the compounds of the present disclosure, including but not limited to, diastereomers, enantiomers and atropisomers, as well as mixtures thereof such as racemic mixtures, form part of the present disclosure. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the present disclosure. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water. Certain compounds of the present disclosure can exist in unsolvated forms as well as solvated forms, including hydrated forms. In general, the solvated forms are equivalent to unsolvated forms and are intended to be encompassed within the scope of the present disclosure.

The term "co-crystal" as used herein refers to a solid that is a crystalline single phase material composed of two or more different molecular or ionic compounds generally in a stoichiometric ratio which are neither solvates nor simple salts. A co-crystal consists of two or more components that form a unique crystalline structure having unique properties. $C_0$-crystals are typically characterized by a crystalline structure, which is generally held together by freely reversible, non-covalent interactions. As used herein, a co-crystal refers to a compound of the present disclosure and at least one other component in a defined stoichiometric ratio that form a crystalline structure.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience. New York, 2006.

As used herein, the term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure.

The compounds of the present disclosure can also contain unnatural proportions of atomic isotopes at one or more of the atoms that constitute such compounds. For example, the present disclosure also embraces isotopically-labeled variants of the present disclosure which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the present disclosure and include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present disclosure (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present disclosure can generally be prepared by following procedures analogous to those disclosed in the Schemes and/or in the Examples herein below, by substituting an isotopically labeled reagent for a non-isotopically labeled reagent.

"Treating" or "treatment" of a disease in a patient refers to inhibiting the disease or arresting its development; or ameliorating or causing regression of the disease. As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delay or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the present disclosure contemplate any one or more of these aspects of treatment.

"Preventing", "prevention", or "prophylaxis" of a disease in a patient refers to preventing the disease from occurring in a patient that is predisposed or does not yet display symptoms of the disease.

The phrase "therapeutically effective amount" means an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "cancer" and "cancerous" refer to or describe the physiological condition in mammals that is typically characterized by unregulated cell growth.

It is appreciated that certain features of the present disclosure, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

II. Compounds

In one aspect, provided herein is a compound of formula (I),

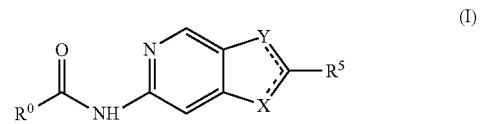

or a pharmaceutically acceptable salt, solvate, hydrate, or co-crystal thereof, or a mixture of any of the foregoing, wherein:

X is $NR^{3'}$ or $CR^3$,

Y is $NR^2$ or $CR^4$, wherein when X is $NR^{3'}$ then Y is $CR^4$, Y has a double bond to $CR^5$, and X has a single bond to $CR^5$; or when X is $CR^3$ then Y is $NR^2$, Y has a single bond to $CR^5$, and X has a double bond to $CR^5$;

$R^0$ is a group

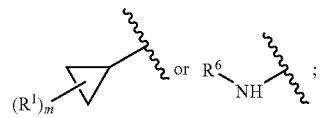

m is an integer from 0 to 3;

each $R^1$ is independently -D, —F, $C_1$-$C_3$ alkyl, $C_1$-$C_3$ alkylene-$NR^7R^8$, $C_1$-$C_3$ alkylene-$NR^7R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^7R^{8'}$, $C_1$-$C_2$ alkylene-($C_3$-$C_6$cycloalkylene)-($C_0$-$C_2$ alkylene)-OH, $C_1$-$C_2$ alkylene-(4- to 8-membered heterocycloalkylene)-($C_0$-$C_2$ alkylene)-$NR^7R^8$, $C_1$-$C_2$ alkylene-(4- to 8-membered heterocycloalkylene)-($C_0$-$C_2$ alkylene)-$NR^7R^{8'}$, $C_1$-$C_2$ alkylene-($C_3$-$C_7$ heterocycloalkylene)-($C_0$-$C_2$ alkylene)-$NR^7R^8$, or $C_1$-$C_2$ alkylene-($C_3$-$C_7$ heterocycloalkylene)-($C_0$-$C_2$ alkylene)-$NR^7R^{8'}$, wherein the alkyl, alkylene, cycloalkylene, and heterocycloalkylene moieties in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

$R^2$ is —H, $C_1$-$C_3$ alkyl, or $C_3$-$C_6$ cycloalkyl, wherein said $C_1$-$C_3$ alkyl is optionally substituted with 1-3 fluorine atoms and/or 1-6 deuterium atoms;

$R^3$ is —H, $C_1$-$C_3$ alkyl, $C_3$-$C_6$ cycloalkyl, halogen, or —CN;

$R^{3'}$ is —H, $C_1$-$C_3$ alkyl, —$C_3$-$C_6$ cycloalkyl, or —CN;

$R^4$ is —H, $C_1$-$C_3$ alkyl, or halogen, wherein said $C_1$-$C_3$ alkyl is optionally substituted with 1-3 fluorine atoms and/or 1-6 deuterium atoms;

$R^5$ is $C_6$-$C_{14}$ aryl or 5-to-10-membered heteroaryl, wherein said $C_6$-$C_{14}$ aryl or said 5-to-10-membered heteroaryl is optionally substituted with 1-5 $R^9$ groups;

$R^6$ is —H, $C_1$-$C_6$ alkyl, $C_3$-$C_6$ cycloalkyl, $C_1$-$C_6$ alkylene-$NR^7R^8$, $C_1$-$C_6$ alkylene-$NR^{7'}R^{8'}$, $C_1$-$C_6$ alkylene-OH, $C_1$-$C_6$ alkylene-CN, $C_1$-$C_2$ alkylene-($C_3$-$C_6$cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-($C_3$-$C_6$cycloalkylene)-($C_0$-$C_2$ alkylene)-OH, $C_1$-$C_2$ alkylene-(4- to 8-membered heterocycloalkylene)-($C_0$-$C_2$ alkylene)-$NR^7R^8$, $C_1$-$C_2$ alkylene-(4- to 8-membered heterocycloalkylene)-($C_0$-$C_2$ alkylene)-$NR^7R^8$, $C_1$-$C_2$ alkylene-($C_3$—C heterocycloalkylene)-($C_0$-$C_2$alkylene)-$NR^{7'}R^{8'}$, or $C_1$-$C_2$ alkylene-($C_3$-$C_7$ heterocycloalkylene)-($C_0$-$C_2$alkylene)-$NR^{7'}R^{8'}$, wherein the alkyl, alkylene, cycloalkyl, cycloalkylene, and heterocycloalkylene moieties in $R^6$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^7$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl;

each $R^8$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl;

each pair of $R^{7'}$ and $R^{8'}$ taken together with the nitrogen atom to which they are attached independently form a 3- to 8-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —$OR^{10}$, —$NR^7R^8$, $C_1$-$C_3$ alkyl, $C_1$-$C_3$ haloalkyl, $C_3$-$C_6$ cycloalkyl, —CN, $S(O)_nC_1$-$C_3$ alkyl, or $S(O)_nC_3$-$C_6$ cycloalkyl, wherein n is an integer from 0 to 2; and each $R^{10}$ is independently —H, $C_1$-$C_3$ alkyl, $C_1$-$C_3$ haloalkyl, or $C_3$-$C_6$ cycloalkyl, wherein said $C_1$-$C_3$ alkyl is optionally substituted with hydroxyl, $C_1$-$C_3$ alkoxy, and/or 1-6 deuterium atoms.

In one aspect, provided herein is a compound of formula (I)

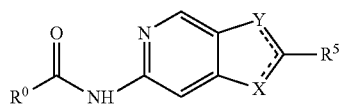

(I)

or a pharmaceutically acceptable salt, solvate, hydrate, or co-crystal thereof, or a mixture of any of the foregoing, wherein:

X is $NR^{3'}$ or $CR^3$,

Y is $NR^2$ or $CR^4$, wherein when X is $NR^{3'}$ then Y is $CR^4$, Y has a double bond to $CR^5$, and X has a single bond to $CR^5$; or when X is $CR^3$ then Y is $NR^2$. Y has a single bond to $CR^5$, and X has a double bond to $CR^5$;

$R^0$ is a group

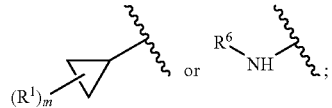

m is an integer from 0 to 3;

each $R^1$ is independently -D, —F, $C_1$-$C_3$ alkyl, $C_1$-$C_3$ alkylene-$NR^7R^8$, $C_1$-$C_3$ alkylene-$NR^{7'}R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-($C_3$-$C_6$cycloalkylene)-($C_0$-$C_2$ alkylene)-OH, $C_1$-$C_2$ alkylene-($C_4$-$C_6$ heterocycloalkylene)-($C_0$-$C_2$ alkylene)-$NR^7R^8$, or $C_1$-$C_2$ alkylene-($C_4$-$C_6$ heterocycloalkylene)-($C_0$-$C_2$ alkylene)-$NR^{7'}R^{8'}$, wherein the alkyl, alkylene, cycloalkylene, and heterocycloalkylene moieties in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

$R^2$ is —H, $C_1$-$C_3$ alkyl, or $C_3$-$C_6$ cycloalkyl, wherein said $C_1$-$C_3$ alkyl is optionally substituted with 1-3 fluorine atoms and/or 1-6 deuterium atoms;

$R^3$ is —H, $C_1$-$C_3$ alkyl, $C_3$-$C_6$ cycloalkyl, halogen, or —CN;

$R^{3'}$ is —H, $C_1$-$C_3$ alkyl, —$C_3$-$C_6$ cycloalkyl, or —CN;

$R^4$ is —H, $C_1$-$C_3$ alkyl, or halogen, wherein said $C_1$-$C_3$ alkyl is optionally substituted with 1-3 fluorine atoms and/or 1-6 deuterium atoms;

$R^5$ is $C_6$-$C_{14}$ aryl or 5-to-10-membered heteroaryl, wherein said $C_6$-$C_{14}$ aryl or said 5-to-10-membered heteroaryl is optionally substituted with 1-5 $R^9$ groups;

$R^6$ is —H, $C_1$-$C_6$ alkyl, $C_3$-$C_6$ cycloalkyl, $C_1$-$C_6$ alkylene-$NR^7R^8$, $C_1$-$C_6$ alkylene-$NR^{7'}R^{8'}$, $C_1$-$C_6$ alkylene-OH, $C_1$-$C_6$ alkylene-CN, $C_1$-$C_2$ alkylene-($C_3$-$C_6$ cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-($C_3$—C cycloalkylene)-($C_0$-$C_2$ alkylene)-OH, $C_1$-$C_2$ alkylene-($C_4$-$C_6$ heterocycloalkylene)-($C_0$-$C_2$ alkylene)-$NR^7R^8$, or $C_1$-$C_2$ alkylene-($C_4$-$C_6$ heterocycloalkylene)-($C_0$-$C_2$ alkylene)-$NR^{7'}R^{8'}$, wherein the alkyl, alkylene, cycloalkyl, cycloalkylene, and heterocycloalkylene moieties in $R^6$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^7$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl;

each $R^8$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl;

each pair of $R^7$ and $R^8$ taken together with the nitrogen atom to which they are attached independently form a 4-to-6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —$OR^{10}$, —$NR^7R^8$, $C_1$-$C_3$ alkyl, $C_1$-$C_3$ haloalkyl, $C_3$-$C_6$ cycloalkyl, —CN, $S(O)_nC_1$-$C_3$ alkyl, or $S(O)_nC_3$-$C_6$ cycloalkyl, wherein n is an integer from 0 to 2; and each $R^{10}$ is independently —H, $C_1$-$C_3$ alkyl, $C_1$-$C_3$ haloalkyl, or $C_3$-$C_6$ cycloalkyl, wherein said $C_1$-$C_3$ alkyl is optionally substituted with hydroxyl, $C_1$-$C_3$ alkoxy, and/or 1-6 deuterium atoms.

In some embodiments of the present aspect, $R^0$ is

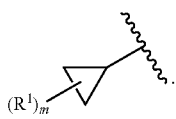

In some embodiments wherein $R^0$ is

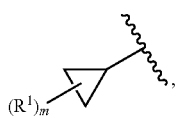

m is an integer 0, 1, 2 or 3. In some embodiments, m is 0. In other embodiments, m is 1. In yet other embodiments, m is 2. In still yet other embodiments, m is 3. In other embodiments of the present aspect, $R^0$ is

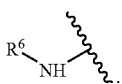

In some embodiments, the compound of formula (I) is a compound of formula (I-A) or formula (I-B):

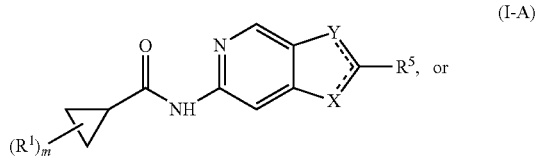

(I-A)

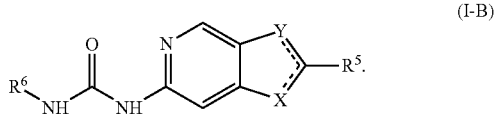

(I-B)

In some embodiments, each $R^1$ is independently -D, —F, $C_1$-$C_3$ alkyl, $C_1$-$C_3$ alkylene-$NR^7R^8$, $C_1$-$C_3$ alkylene-$NR^{7'}R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$alkylene)-$NR^7R^8$, $C_1$-$C_2$ alkylene-($C_3$-$C_6$ cycloalkylene)-($C_0$-$C_2$alkylene)-$NR^{7'}R^{8'}$, $C_1$-$C_2$ alkylene-($C_3$-$C_6$cycloalkylene)-($C_0$-$C_2$ alkylene)-OH, $C_1$-$C_2$ alkylene-(4- to 8-membered heterocycloalkylene)-($C_0$-$C_2$ alkylene)-$NR^7R^8$, $C_1$-$C_2$ alkylene-(4- to 8-membered heterocycloalkylene)-($C_0$-$C_2$ alkylene)-$NR^{7'}R^{8'}$, $C_1$-$C_2$ alkylene-($C_3$-$C_7$ heterocycloalkylene)-($C_0$-$C_2$ alkylene)-$NR^7R^8$, or $C_1$-$C_2$ alkylene-($C_3$-$C_7$ heterocycloalkylene)-($C_0$-$C_2$ alkylene)-$NR^{7'}R^{8'}$, wherein the alkyl, alkylene, cycloalkylene, and heterocycloalkylene moieties in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl.

In some embodiments, each $R^1$ is independently -D, —F, $C_1$-$C_3$ alkyl, $C_1$-$C_3$ alkylene-$NR^7R^8$, $C_1$-$C_3$ alkylene-$NR^{7'}R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$alkylene)-$NR^7R^8$, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-($C_3$-$C_6$ cycloalkylene)-($C_0$-$C_2$ alkylene)-OH, $C_1$-$C_2$ alkylene-($C_4$-$C_6$ heterocycloalkylene)-($C_0$-$C_2$alkylene)-$NR^7R^8$, or $C_1$-$C_2$ alkylene-($C_4$-$C_6$ heterocycloalkylene)-($C_0$-$C_2$ alkylene)-$NR^{7'}R^{8'}$, wherein the alkyl, alkylene, cycloalkylene, and heterocycloalkylene moieties in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl. In some embodiments, each $R^1$ is independently —F, $C_1$-$C_3$ alkyl, $C_1$-$C_3$ alkylene-$NR^7R^8$, $C_1$-$C_3$ alkylene-$NR^{7'}R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$alkylene)-$NR^7R^8$, $C_1$-$C_3$ alkylene-CN, $C_1$-$C_2$ alkylene-($C_3$-$C_6$cycloalkylene)-($C_0$-$C_2$alkylene)-$NR^{7'}R^{8'}$, $C_1$-$C_2$ alkylene-($C_3$-$C_6$ cycloalkylene)-($C_0$-$C_2$ alkylene)-OH, $C_1$-$C_2$ alkylene-($C_4$-$C_6$ heterocycloalkylene)-($C_0$-$C_2$alkylene)-$NR^7R^8$, or $C_1$-$C_2$ alkylene-($C_4$-$C_6$ heterocycloalkylene)-($C_0$-$C_2$ alkylene)-$NR^{7'}R^{8'}$, wherein the alkyl, alkylene, cycloalkylene, and heterocycloalkylene in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl. In some embodiments, each $R^1$ is independently -D, —F, $C_1$-$C_3$ alkyl. In some embodiments, each $R^1$ is independently $C_1$-$C_3$ alkyl, $C_1$-$C_3$ alkylene-$NR^7R^8$, $C_1$-$C_3$ alkylene-$NR^{7'}R^{8'}$, $C_1$-$C_3$ alkylene-OH, or $C_1$-$C_3$ alkylene-CN. In some embodiments, each $R^1$ is independently $C_1$-$C_3$ alkylene-$NR^7R^8$. $C_1$-$C_3$ alkylene-$NR^{7'}R^{8'}$, $C_1$-$C_2$ alkylene-($C_3$-$C_6$ cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-(4- to 8-membered heterocycloalkylene)-($C_0$-$C_2$ alkylene)-$NR^7R^8$, $C_1$-$C_2$ alkylene-(4- to 8-membered heterocycloalkylene)-($C_0$-$C_2$alkylene)-$NR^{7'}R^{8'}$, $C_1$-$C_2$ alkylene-($C_3$-$C_7$ heterocycloalkylene)-($C_0$-$C_2$ alkylene)-$NR^7R^8$, or $C_1$-$C_2$ alkylene-($C_3$-$C_7$ heterocycloalkylene)-($C_0$-$C_2$ alkylene)-$NR^{7'}R^{8'}$. In some embodiments, each $R^1$ is independently $C_1$-$C_3$ alkylene-$NR^7R^8$, $C_1$-$C_3$ alkylene-$NR^{7'}R^{8'}$, $C_1$-$C_2$ alkylene-($C_3$-$C_6$ cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-($C_4$-$C_6$ heterocycloalkylene)-($C_0$-$C_2$alkylene)-$NR^7R^8$, or $C_1$-$C_2$ alkylene-($C_4$-$C_6$ heterocycloalkylene)-($C_0$-$C_2$alkylene)-$NR^{7'}R^{8'}$ In some embodiments, each $R^1$ is independently $C_1$-$C_3$ alkylene-OH, $C_1$-$C_3$ alkylene-CN, or $C_1$-$C_2$ alkylene-($C_3$-$C_6$ cycloalkylene)-($C_0$-$C_2$ alkylene)-

OH. In some embodiments, each $R^1$ is independently —F, $C_1$-$C_3$alkylene-$NR^{7'}R^{8'}$, or $C_1$-$C_3$ alkylene-OH, wherein each pair of $R^{7'}$ and $R^{8'}$ of $R^1$ taken together with the nitrogen atom to which they are attached independently form 3- to 8-membered heterocyclic ring, wherein the heterocyclic ring optionally contains an additional 1-2 heteroatoms selected from the group consisting of N, O, and S. and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl. In some embodiments, each $R^1$ is independently —F, $C_1$-$C_3$ alkylene-$NR^{7'}R^{8'}$, or $C_1$-$C_3$ alkylene-OH, wherein each pair of $R^{7'}$ and $R^{8'}$ of $R^1$ taken together with the nitrogen atom to which they are attached independently form a 4-to-6-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by H or $C_1$-$C_3$ alkyl. In some embodiments, each $R^1$ is independently —F, $C_1$-$C_3$ alkylene-$NR^{7'}R^{8'}$, or $C_1$-$C_3$ alkylene-OH. In certain embodiments, each $R^1$ is —F. In some embodiments, each $R^1$ is independently $C_1$-$C_3$ alkylene-$NR^{7'}R^{8'}$. In certain embodiments, each $R^1$ is independently optionally substituted —$C_1$-$C_2$ alkylene-N-morpholinyl or optionally substituted —$C_1$-$C_2$ alkylene-N-piperazinyl. In some embodiments, each $R^1$ is independently optionally substituted

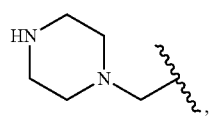

optionally substituted

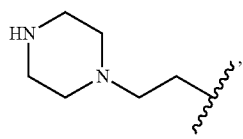

optionally substituted

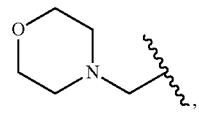

optionally substituted

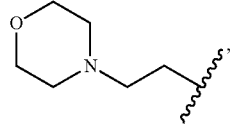 [SMILES: *CCN1CCOCC1]

optionally substituted,

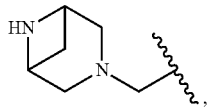

or optionally substituted

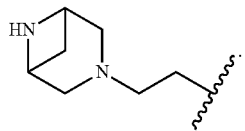 [SMILES: *CCN1CC2CC(C1)N2]

In certain embodiments, each $R^1$ is independently optionally substituted

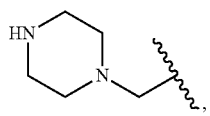

optionally substituted

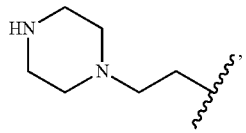

optionally substituted

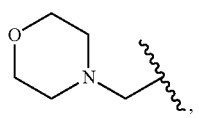

or optionally substituted

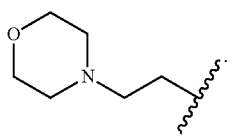

In some embodiments, each $R^1$ is independently

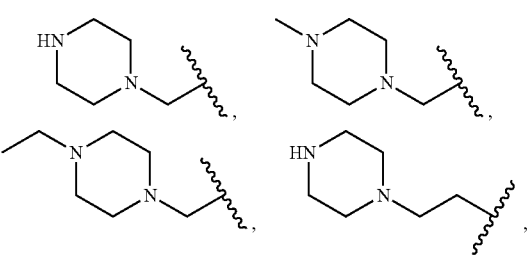

-continued

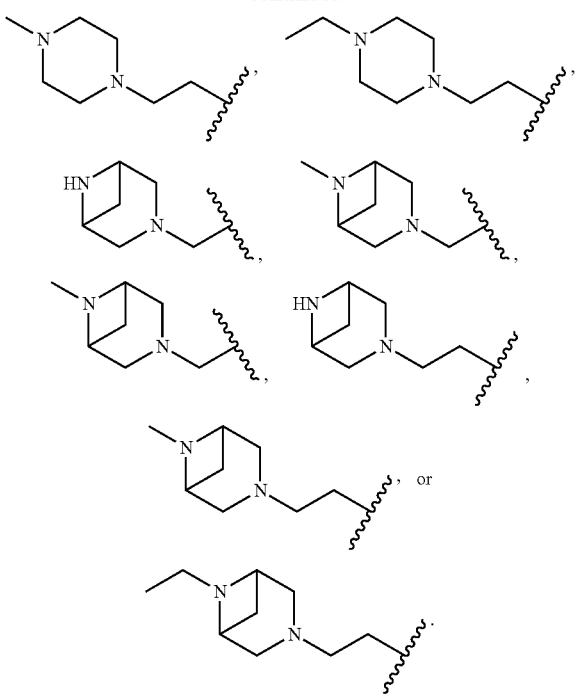

In certain embodiments, each $R^1$ is independently

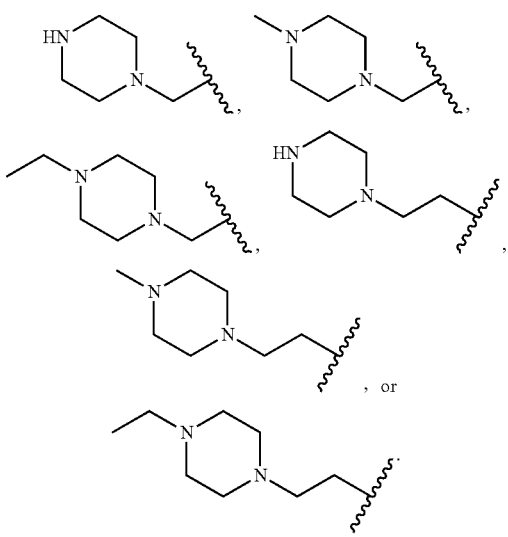

In certain other embodiments, each $R^1$ is independently

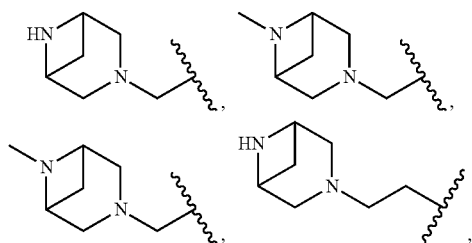

-continued

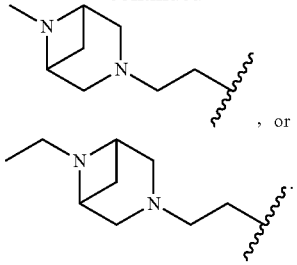

In still other embodiments, each $R^1$ is independently

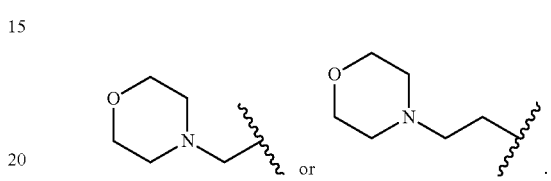

In some embodiments, each $R^1$ is independently $C_1$-$C_3$ alkylene-OH. In certain other embodiments, each $R^1$ is independently —$C_1$-$C_2$ alkylene-OH. In certain embodiments, each $R^1$ is independently —$CH_2OH$, —$CH_2CH_2OH$, —$CH(OH)CH_3$, —$CH_2CH_2CH_2OH$, —$CH_2CH(OH)CH_3$, or —$CH(CN)CH_2CH_3$. In certain other embodiments, each $R^1$ is independently —$CH_2OH$ or —$CH_2CH_2OH$.

In some embodiments of the present aspect, X is $CR^3$ and Y is $NR^2$. In some embodiments wherein X is $CR^3$ and Y is $NR^2$, $R^2$ is —H, $C_1$-$C_3$ alkyl, or $C_3$-$C_6$ cycloalkyl, wherein said $C_1$-$C_3$ alkyl is optionally substituted with 1-3 fluorine atoms and/or 1-6 deuterium atoms, and $R^3$ is —H, $C_1$-$C_3$ alkyl, $C_3$-$C_6$ cycloalkyl, halogen, or —CN.

In some embodiments, $R^2$ is —H, $C_1$-$C_3$ alkyl, or $C_3$-$C_6$ cycloalkyl, wherein said $C_1$-$C_3$ alkyl is optionally substituted with 1-3 fluorine atoms and/or 1-6 deuterium atoms. In some embodiments, $R^2$ is —H or $C_1$-$C_3$ alkyl, wherein said $C_1$-$C_3$ alkyl is optionally substituted with 1-3 fluorine atoms and/or 1-6 deuterium atoms. In some embodiments, $R^2$ is —H or $C_3$-$C_6$ cycloalkyl. In some embodiments, $R^2$ is $C_1$-$C_3$ alkyl or $C_3$-$C_6$ cycloalkyl, wherein said $C_1$-$C_3$ alkyl is optionally substituted with 1-3 fluorine atoms and/or 1-6 deuterium atoms. In some embodiments, $R^2$ is —H. In some embodiments, $R^2$ is $C_1$-$C_3$ alkyl, wherein said $C_1$-$C_3$ alkyl is optionally substituted with 1-3 fluorine atoms and/or 1-6 deuterium atoms. In certain embodiments, $R^2$ is —$CH_3$, —$CH_2CH_3$, —$CH_2CH_2CH_3$, or —$CH(CH_3)_2$, wherein said —$CH_3$, —$CH_2CH_3$, —$CH_2CH_2CH_3$, or —$CH(CH_3)_2$ is optionally substituted with 1-3 fluorine atoms and/or 1-6 deuterium atoms. In some embodiments. $R^2$ is $C_3$-$C_6$ cycloalkyl. In certain embodiments, $R^2$ is cyclopropyl, cyclobutyl, cyclopentyl or cyclohexyl.

In some embodiments, $R^2$ is —H, —$CH_3$, —$CD_3$, —$CHF_2$, or —$CH_2CH_3$. In some embodiments, $R^2$ is —$CH_3$, —$CD_3$, —$CHF_2$, or —$CH_2CH_3$. In some embodiments, $R^2$ is —H, —$CD_3$, —$CHF_2$, or —$CH_2CH_3$. In some embodiments, $R^2$ is —H, —$CH_3$, —$CHF_2$, or —$CH_2CH_3$. In some embodiments, $R^2$ is —H, —$CH_3$, —$CD_3$, or —$CH_2CH_3$. In some embodiments, $R^2$ is —H, —$CH_3$, —$CD_3$, or —$CHF_2$. In some embodiments, $R^2$ is —$CH_3$, —$CD_3$, or —$CHF_2$. In some embodiments, $R^2$ is —$CH_3$ or —$CH_2CH_3$. In some embodiments, $R^2$ is —H or —$CH_3$.

In some embodiments, $R^3$ is —H, $C_1$-$C_3$ alkyl, $C_3$-cycloalkyl, halogen, or —CN. In some embodiments, $R^3$ is —H, $C_1$-$C_3$ alkyl, $C_3$-$C_6$ cycloalkyl, or halogen. In some embodiments, $R^3$ is —H, $C_1$-$C_3$ alkyl, $C_3$-$C_6$ cycloalkyl, or —CN. In some embodiments, $R^3$ is —H, $C_1$-$C_3$ alkyl, halogen, or —CN. In some embodiments, $R^3$ is —H, $C_3$-$C_6$ cycloalkyl, halogen, or —CN. In some embodiments, $R^3$ is $C_1$-$C_3$ alkyl, $C_3$-$C_6$ cycloalkyl, halogen, or —CN. In some embodiments, $R^3$ is —H, $C_1$-$C_3$ alkyl, $C_3$-$C_6$ cycloalkyl, halogen, or —CN. In some embodiments, $R^3$ is —H, —F, —CH$_3$, or —CN. In some embodiments, $R^3$ is —H, —F, or —CH$_3$. In some embodiments, $R^3$ is —H, —F, or —CN. In some embodiments, $R^3$ is —H, —CH$_3$, or —CN. In some embodiments, $R^3$ is —F, —CH$_3$, or —CN. In some embodiments, $R^3$ is —H or —F. In some embodiments, $R^3$ is —H or —CH$_3$. In some embodiments, $R^3$ is —H or —CN. In some embodiments, $R^3$ is —F or —CH$_3$. In some embodiments, $R^3$ is —F or —CN. In some embodiments, $R^3$ is —CH$_3$ or —CN. In some embodiments, $R^3$ is —H. In some embodiments, $R^3$ is —F. In some embodiments, $R^3$ is —CH$_3$. In some embodiments, $R^3$ is —CN.

In some embodiments, $R^2$ is —CH$_3$, —CD$_3$, or —CH$_2$CH$_3$, and $R^3$ is —H, —F, —CH$_3$, or —CN. In some embodiments, $R^2$ is —CH$_3$, C and $R^3$ is —H, —F, —CH$_3$, or —CN. In some embodiments, $R^2$ is —CD$_3$, and $R^3$ is —H, —F, —CH$_3$, or —CN. In some embodiments, $R^2$ is —CH$_2$CH$_3$, and $R^3$ is —H, —F, —CH$_3$, or —CN. In some embodiments, $R^2$ is —CH$_3$, —CD$_3$, or —CH$_2$CH$_3$, and $R^3$ is —H. In some embodiments, $R^2$ is —CH$_3$, —CD$_3$, or —CH$_2$CH$_3$, and $R^3$ is —F. In some embodiments, $R^2$ is —CH$_3$, —CD$_3$, or —CH$_2$CH$_3$, and $R^3$ is —CH$_3$. In some embodiments. $R^2$ is —CH$_3$, —CD$_3$, or —CH$_2$CH$_3$, and $R^3$ is —CN. In some embodiments, $R^2$ is —CH$_3$, —CD$_3$, or —CH$_2$CH$_3$, and $R^3$ is —H, —F, —CH$_3$, or —CN. In some embodiments, $R^2$ is —CH$_3$, and $R^3$ is —H or —CH$_3$. In some embodiments, $R^2$ is —CH$_3$, and $R^3$ is —H. In some embodiments, $R^2$ is —CH$_3$, and $R^3$ is —CH$_3$. In some embodiments, $R^2$ is —H or —CH$_3$, and $R^3$ is —H. In some embodiments, $R^2$ is —H and $R^3$ is —H. In some embodiments, $R^2$ is —CH$_3$, and $R^3$ is —H.

In other embodiments of the present aspect, X is NR$^{3'}$ and Y is CR$^4$. In some embodiments wherein X is NR$^{3'}$ and Y is CR$^4$, R$^{3'}$ is —H, $C_1$-$C_3$ alkyl, —$C_3$-$C_6$ cycloalkyl, or —CN, and $R^4$ is —H, $C_1$-$C_3$ alkyl, or halogen, wherein said $C_1$-$C_3$ alkyl is optionally substituted with 1-3 fluorine atoms and/or 1-6 deuterium atoms.

In some embodiments, $R^{3'}$ is —H, $C_1$-$C_3$ alkyl, or $C_3$-cycloalkyl. In some embodiments, $R^{3'}$ is —H, $C_1$-$C_3$ alkyl, or —CN. In some embodiments, $R^{3'}$ is —H, $C_3$-cycloalkyl, or —CN. In some embodiments, $R^{3'}$ is $C_1$-$C_3$ alkyl, $C_3$-cycloalkyl, or —CN. In some embodiments, $R^{3'}$ is —H or $C_1$-$C_3$ alkyl. In certain embodiments, $R^{3'}$ is —H or —CH$_3$. In some embodiments, $R^{3'}$ is —H or $C_3$-cycloalkyl. In some embodiments, $R^{3'}$ is —H or —CN. In some embodiments, $R^{3'}$ is $C_1$-$C_3$ alkyl or $C_3$-cycloalkyl. In some embodiments, $R^{3'}$ is $C_1$-$C_3$ alkyl or —CN. In some embodiments, $R^{3'}$ is $C_3$-cycloalkyl, or —CN. In some embodiments, $R^{3'}$ is —H. In some embodiments, $R^{3'}$ is $C_1$-$C_3$ alkyl. In certain embodiments, $R^{3'}$ is —CH$_3$, —CH$_2$CH$_3$, —CH$_2$CH$_2$CH$_3$, or —CH(CH$_3$)$_2$. In certain embodiments, $R^{3'}$ is —CH$_3$. In some embodiments, $R^{3'}$ is $C_3$-cycloalkyl. In some embodiments, $R^{3'}$ is —CN.

In some embodiments, $R^4$ is —H or $C_1$-$C_3$ alkyl, wherein said $C_1$-$C_3$ alkyl is optionally substituted with 1-3 fluorine atoms and/or 1-6 deuterium atoms. In some embodiments, $R^4$ is —H, or halogen. In some embodiments, $R^4$ is $C_1$-$C_3$ alkyl or halogen, wherein said $C_1$-$C_3$ alkyl is optionally substituted with 1-3 fluorine atoms and/or 1-6 deuterium atoms. In some embodiments, $R^4$ is —H. In some embodiments, $R^4$ is $C_1$-$C_3$ alkyl, wherein said $C_1$-$C_3$ alkyl is optionally substituted with 1-3 fluorine atoms and/or 1-6 deuterium atoms. In some embodiments, $R^4$ is —CH$_3$, —CH$_2$CH$_3$, —CH$_2$CH$_2$CH$_3$, or —CH(CH$_3$)$_2$, wherein said —CH$_3$, —CH$_2$CH$_3$, —CH$_2$CH$_2$CH$_3$, or —CH(CH$_3$)$_2$ is optionally substituted with 1-3 fluorine atoms and/or 1-6 deuterium atoms. In certain embodiments, $R^4$ is CH$_3$. In some embodiments, $R^4$ is halogen. In certain embodiments, $R^4$ is —F, —Cl, or —Br. In certain other embodiments, $R^4$ is —F. In some embodiments, $R^4$ is —H, —F or —CH$_3$. In some embodiments, $R^4$ is —H, —CH$_3$, —CD$_3$, —CHF$_2$, —CH$_2$CH$_3$, or halogen. In some embodiments, $R^4$ is —H, —CH$_3$, —CD$_3$, —CH—F$_2$, or —CH$_2$CH$_3$. In some embodiments, $R^4$ is —H, —CH$_3$, —CD$_3$, —CHF$_2$, or halogen. In some embodiments, $R^4$ is —H, —CH$_3$, —CD$_3$, —CH$_2$CH$_3$, or halogen. In some embodiments, $R^4$ is —H, —CH$_3$, —CHF$_2$, —CH$_2$CH$_3$, or halogen. In some embodiments, $R^4$ is —H, —CD$_3$, —CHF$_2$, —CH$_2$CH$_3$, or halogen. In some embodiments, $R^4$ is —CH$_3$, —CD$_3$, —CHF$_2$, —CH$_2$CH$_3$, or halogen. In some embodiments, $R^4$ is —H or halogen. In some embodiments, $R^4$ is —CH$_3$ or —CH$_2$CH$_3$. In some embodiments, $R^4$ is —CH$_3$, —CD$_3$, or —CHF$_2$.

In some embodiments. $R^{3'}$ is —H or —CH$_3$, and $R^4$ is —H, —F or —CH$_3$. In some embodiments, $R^{3'}$ is —H. and $R^4$ is —H. —F or —CH$_3$. In some embodiments, $R^1$ is —CH$_3$, and $R^4$ is —H, —F or —CH$_3$. In some embodiments, $R^3$ is —H or —CH$_3$, and $R^4$ is —H. In some embodiments, $R^{3'}$ is —H or —CH$_3$, and $R^4$ is —F. In some embodiments, $R^{3'}$ is —H or —CH$_3$, and $R^4$ is —CH$_3$. In certain embodiments. $R^{3'}$ is —H, and $R^4$ is —H. In certain embodiments, $R^{3'}$ is —H, and $R^4$ is —F. In certain embodiments, $R^{3'}$ is —H, and $R^4$ is —CH$_3$. In certain embodiments, $R^{3'}$ is —CH$_3$, and $R^4$ is —H. In certain embodiments, $R^{3'}$ is —CH$_3$, and $R^4$ is —F. In certain other embodiments, $R^{3'}$ is —CH$_3$, and $R^4$ is —CH$_3$.

In some embodiments, $R^5$ is $C_6$-$C_{14}$ aryl or 5- to 10-membered heteroaryl, wherein said $C_6$-$C_{14}$ aryl or said 5-to-10-membered heteroaryl is optionally substituted with 1-5 $R^9$ groups. In some embodiments, $R^5$ is a $C_6$-$C_{14}$ aryl, wherein said $C_6$-$C_{14}$ aryl is optionally substituted with 1-5 $R^9$ groups. In some embodiments. $R^5$ is phenyl, wherein said phenyl is optionally substituted with 1-5 $R^9$ groups. In some embodiments, $R^5$ is 5- to 10-membered heteroaryl, wherein said 5-to-10-membered heteroaryl is optionally substituted with 1-5 $R^9$ groups. In some embodiments, $R^5$ is a 5-to-10-membered heteroaryl selected from the group consisting of:

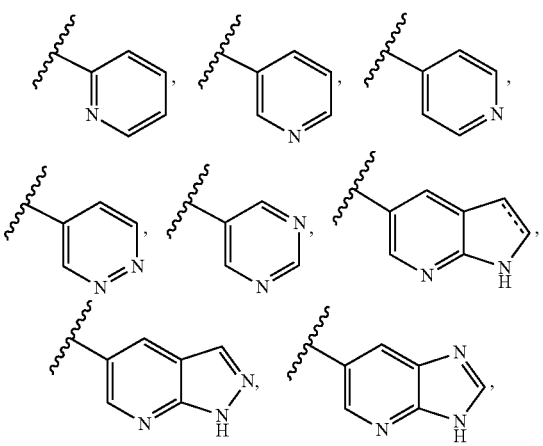

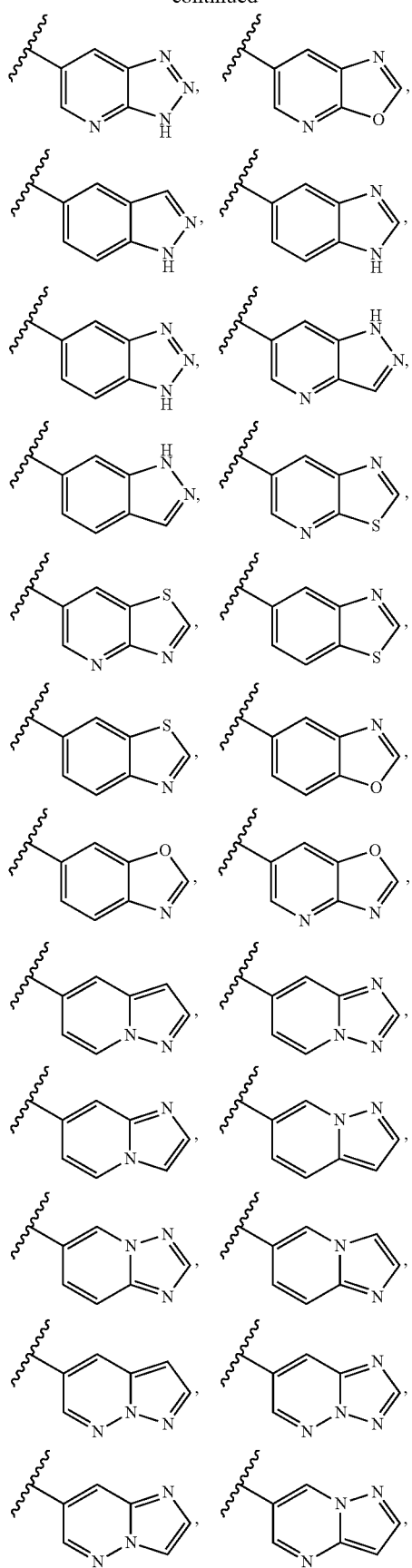
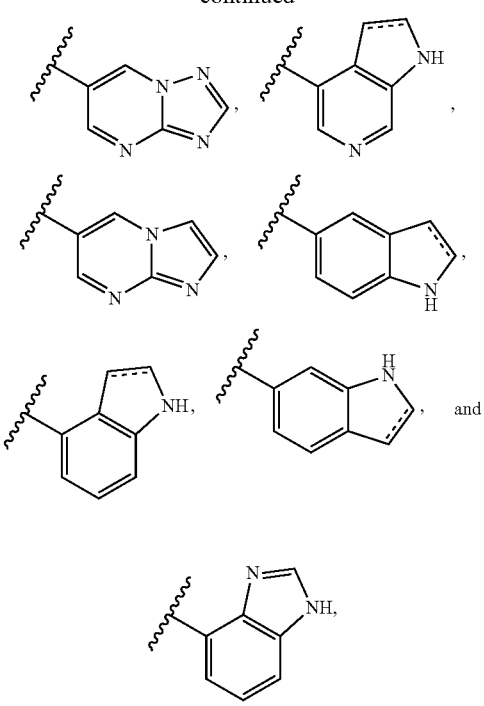
wherein --- indicates a single or double bond, and wherein said $C_6$-$C_{14}$ aryl or said 5-to-10-membered heteroaryl is optionally substituted with 1-5 $R^9$ groups. In some embodiments, $R^5$ is a 5-to-10-membered heteroaryl selected from the group consisting of:
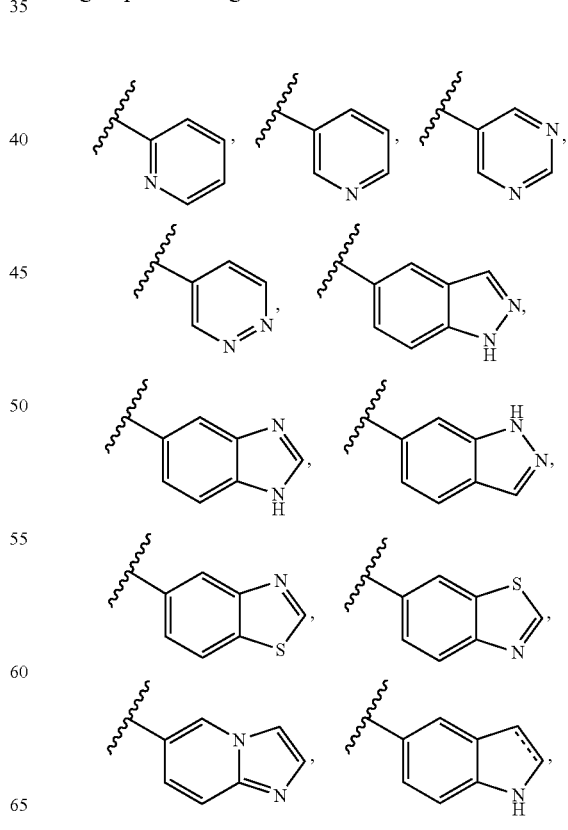

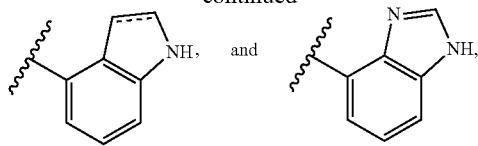 and 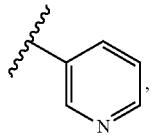

wherein --- indicates a single or double bond, and wherein said phenyl or said 5-to-10-membered heteroaryl is optionally substituted with 1-3 $R^9$ groups. In some embodiments, $R^5$ is a 5-to-10-membered heteroaryl selected from the group consisting of:

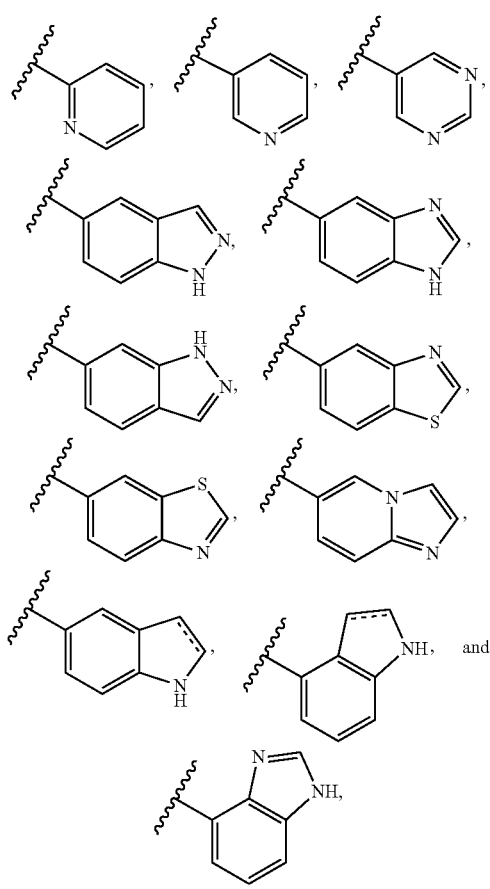

wherein --- indicates a single or double bond, and wherein said phenyl or said 5-to-10-membered heteroaryl is optionally substituted with 1-3 $R^9$ groups. In some embodiments, $R^5$ is a 5-to-10-membered heteroaryl selected from the group consisting of:

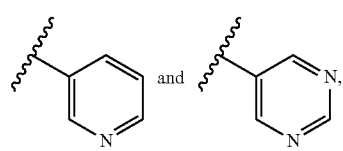

wherein said 5-to-10-membered heteroaryl is optionally substituted with 1-3 $R^9$ groups. In some embodiments, $R^5$ is a 5-to-10-membered heteroaryl selected from the group consisting of:

wherein said phenyl or said 5-to-10-membered heteroaryl is optionally substituted with 1-3 $R^9$ groups.

In some embodiments, $R^5$ is a 5-to-10-membered heteroaryl selected from the group consisting of:

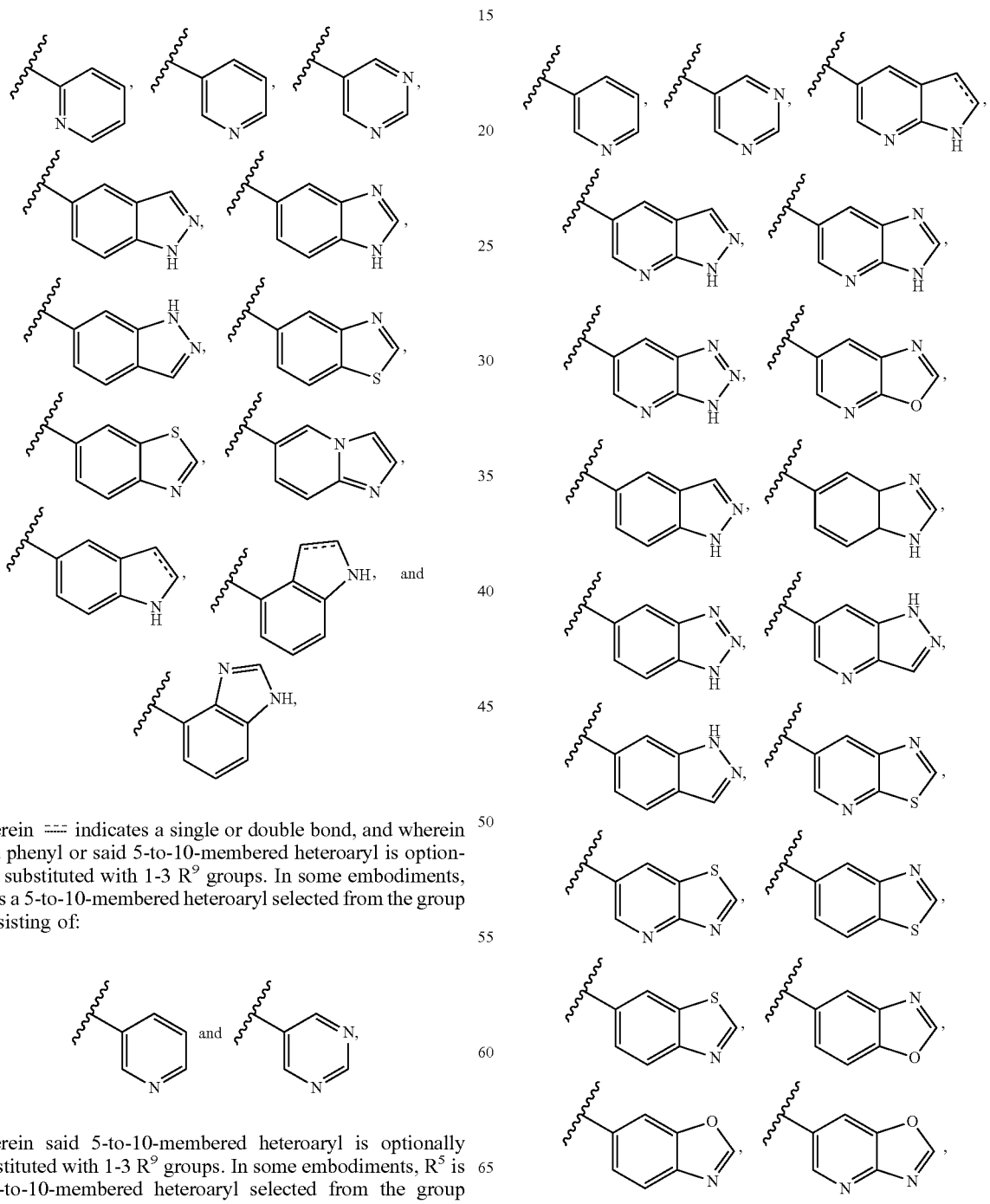

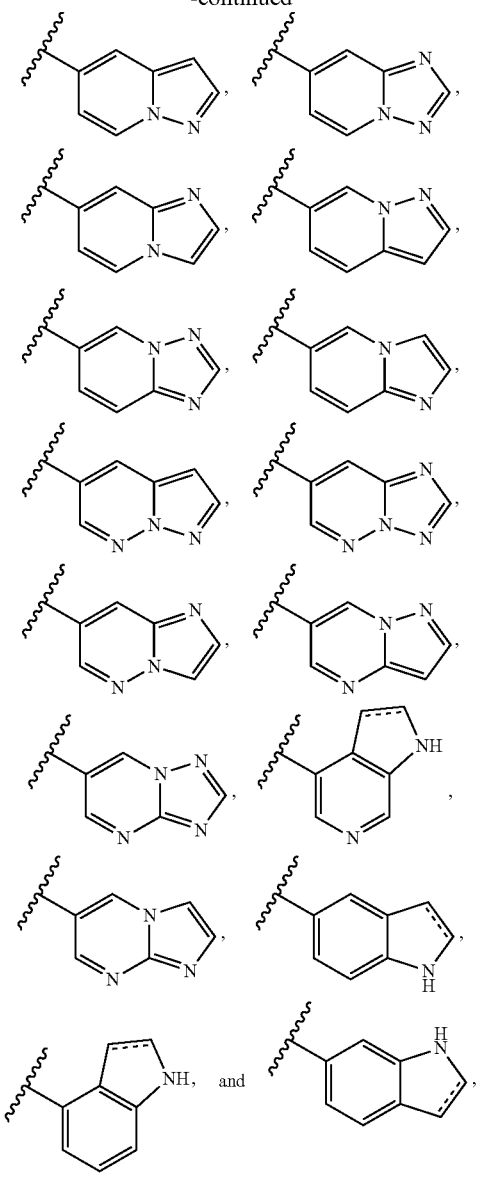

wherein ⚌ indicates a single or double bond, and wherein said $C_6$-$C_{14}$ aryl or said 5-to-10-membered heteroaryl is optionally substituted with 1-5 $R^9$ groups. In some embodiments, $R^5$ is phenyl or 5-to-10-membered heteroaryl, wherein said 5-to-10-membered heteroaryl is selected from the group consisting of:

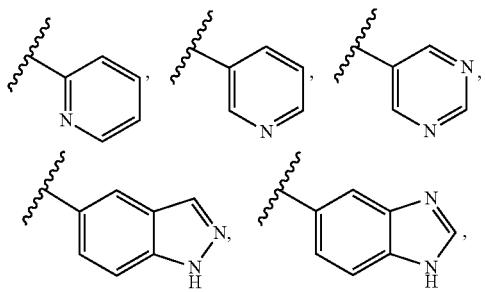

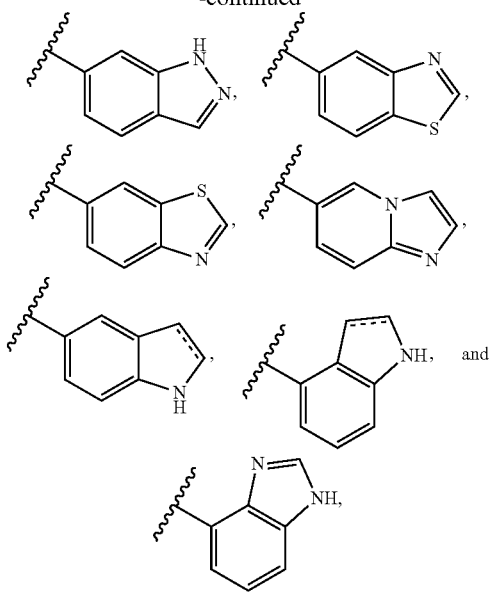

wherein ⚌ indicates a single or double bond, and wherein said phenyl or said 5-to-10-membered heteroaryl is optionally substituted with 1-3 $R^9$ groups. In some embodiments, $R^5$ is phenyl or 5-to-10-membered heteroaryl, wherein said 5-to-10-membered heteroaryl is selected from the group consisting of:

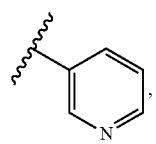

wherein said phenyl or said 5-to-10-membered heteroaryl is optionally substituted with 1-3 $R^9$ groups.

In some embodiments. $R^6$ is —H, $C_1$-$C_6$ alkyl, $C_3$-$C_6$ cycloalkyl, $C_1$-$C_6$ alkylene-$NR^7R^8$, $C_1$-$C_6$ alkylene-$NR^{7'}R^{8'}$, $C_1$-$C_6$ alkylene-OH, $C_1$-$C_6$ alkylene-CN, $C_1$-$C_2$ alkylene-($C_3$-$C_6$ cycloalkylene)-($C_0$-$C_2$ alkylene)-$NR^7R^8$, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-($C_3$-$C_6$ cycloalkylene)-($C_0$-$C_2$ alkylene)-OH, $C_1$-$C_2$ alkylene-(4- to 8-membered heterocycloalkylene)-($C_0$-$C_2$ alkylene)-$NR^7R^8$, $C_1$-$C_2$ alkylene-(4- to 8-membered heterocycloalkylene)-($C_0$-$C_2$ alkylene)-$NR^{7'}R^{8'}$. $C_1$-$C_2$ alkylene-($C_3$-$C_7$ heterocycloalkylene)-($C_0$-$C_2$ alkylene)-$NR^7R^8$, or $C_1$-$C_2$ alkylene-($C_3$-$C_7$ heterocycloalkylene)-($C_0$-$C_2$ alkylene)-$NR^{7'}R^{8'}$, wherein the alkyl, alkylene, cycloalkyl, cycloalkylene, and heterocycloalkylene moieties in $R^6$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl.

In some embodiments, $R^6$ is —H, $C_1$-$C_6$ alkyl, $C_3$-$C_6$ cycloalkyl, $C_1$-$C_6$ alkylene-$NR^7R^8$, $C_1$-$C_6$ alkylene-$NR^{7'}R^{8'}$, $C_1$-$C_6$ alkylene-OH, $C_1$-$C_6$ alkylene-CN, $C_1$-$C_2$ alkylene-($C_3$-$C_6$cycloalkylene)-($C_0$-$C_2$ alkylene)-$NR^7R^8$, $C_1$-$C_2$ alkylene-($C_3$-$C_6$cycloalkylene)-($C_0$-$C_2$ alkylene)-$NR^{7'}R^{8'}$, $C_1$-$C_2$ alkylene-($C_3$-$C_6$ cycloalkylene)-($C_0$-$C_2$alkylene)-OH, $C_1$-$C_2$ alkylene-($C_4$-$C_6$ heterocycloalkylene)-($C_0$-$C_2$ alkylene)-NR$^7$R$^8$, or C$_1$-C$_2$ alkylene-(C$_4$-C$_6$ heterocycloalkylene)-(C$_0$-C$_2$ alkylene)-NR$^{7'}$R$^{8'}$, wherein the alkyl, alkylene, cycloalkyl, cycloalkylene, and heterocycloalkylene moieties in R$^6$ are optionally substituted with 1-3 fluorine atoms and/or 1-6 deuterium atoms, and wherein each heterocyclic nitrogen atom, if present, is independently optionally substituted with C$_1$-C$_3$ alkyl, C$_3$-C$_6$ cycloalkyl, C$_2$-C$_3$ haloalkyl, C$_2$-C$_3$ alkylene-CN, or C$_2$-C$_3$ heteroalkyl.

In some embodiments, R$^6$ is C$_1$-C$_3$ alkyl, C$_3$-C$_6$ cycloalkyl, C$_1$-C$_3$ alkylene-NR$^7$R$^8$, C$_1$-C$_3$ alkylene-NR$^{7'}$R$^{8'}$, C$_1$-C$_3$ alkylene-OH, C$_1$-C$_3$ alkylene-CN, C$_1$-C$_2$ alkylene-(C$_3$-C$_6$ cycloalkylene)-(C$_0$-C$_2$alkylene)-NR$^7$R$^8$, C$_1$-C$_2$ alkylene-(C$_3$-C$_6$ cycloalkylene)-(C$_0$-C$_2$ alkylene)-NR$^{7'}$R$^{8'}$, C$_1$-C$_2$ alkylene-(C$_3$-C$_6$ cycloalkylene)-(C$_0$-C$_2$ alkylene)-OH, C$_1$-C$_2$ alkylene-(4- to 8-membered heterocycloalkylene)-(C$_0$-C$_2$ alkylene)-NR$^7$R$^8$, C$_1$-C$_2$ alkylene-(4- to 8-membered heterocycloalkylene)-(C$_0$-C$_2$ alkylene)-NR$^{7'}$R$^{8'}$, C$_1$-C$_2$ alkylene-(C$_3$-C$_7$ heterocycloalkylene)-(C$_0$-C$_2$ alkylene)-NR$^7$R$^8$, or C$_1$-C$_2$ alkylene-(C$_3$-C$_7$ heterocycloalkylene)-(C$_0$-C$_2$alkylene)-NR$^{7'}$R$^{8'}$, wherein the alkyl, alkylene, cycloalkyl, cycloalkylene, and heterocycloalkylene moieties in R$^6$ are optionally substituted with 1-3 fluorine atoms and/or 1-6 deuterium atoms, and wherein each heterocyclic nitrogen atom, if present, is independently optionally substituted with C$_1$-C$_3$ alkyl, C$_3$-C$_6$ cycloalkyl, C$_2$-C$_3$ haloalkyl, C$_2$-C$_3$ alkylene-CN, or C$_2$-C$_3$ heteroalkyl. In some embodiments, R$^6$ is C$_1$-C$_3$ alkyl, C$_3$-C$_6$ cycloalkyl, C$_1$-C$_3$ alkylene-NR$^7$R$^8$, C$_1$-C$_3$ alkylene-NR$^{7'}$R$^{8'}$, C$_1$-C$_3$ alkylene-OH, C$_1$-C$_3$ alkylene-CN, C$_1$-C$_2$ alkylene-(C$_3$-C$_6$cycloalkylene)-(C$_0$-C$_2$alkylene)-NR$^7$R$^8$, C$_1$-C$_2$ alkylene-(C$_3$-C$_6$cycloalkylene)-(C$_0$-C$_2$ alkylene)-NR$^{7'}$R$^{8'}$, C$_1$-C$_2$ alkylene-(C$_3$-C$_6$ cycloalkylene)-(C$_0$-C$_2$ alkylene)-OH, C$_1$-C$_2$ alkylene-(C$_4$-C$_6$ heterocycloalkylene)-(C$_0$-C$_2$ alkylene)-NR$^7$R$^8$, or C$_1$-C$_2$ alkylene-(C$_4$-C$_6$ heterocycloalkylene)-(C$_0$-C$_2$ alkylene)-NR$^{7'}$R$^{8'}$, wherein the alkyl, alkylene, cycloalkyl, cycloalkylene, and heterocycloalkylene moieties in R$^6$ are optionally substituted with 1-3 fluorine atoms and/or 1-6 deuterium atoms, and wherein each heterocyclic nitrogen atom, if present, is independently optionally substituted with C$_1$-C$_3$ alkyl, C$_3$-C$_6$ cycloalkyl, C$_2$-C$_3$ haloalkyl, C$_2$-C$_3$ alkylene-CN, or C$_2$-C$_3$ heteroalkyl. In some embodiments, C$_1$-C$_6$ alkyl, C$_3$-C$_6$ cycloalkyl, C$_1$-C$_6$ alkylene-NR$^7$R$^8$, C$_1$-C$_6$ alkylene-NR$^{7'}$R$^{8'}$, C$_1$-C$_6$ alkylene-OH, or C$_1$-C$_6$ alkylene-CN. In some embodiments, R$^6$ is C$_1$-C$_6$ alkyl, C$_3$-C$_6$ cycloalkyl, C$_1$-C$_2$ alkylene-(C$_3$-C$_6$ cycloalkylene)-(C$_0$-C$_2$ alkylene)-NR$^7$R$^8$, C$_1$-C$_2$ alkylene-(C$_3$-C$_4$cycloalkylene)-(C$_0$-C$_2$ alkylene)-NR$^{7'}$R$^{8'}$, C$_1$-C$_2$ alkylene-(C$_3$-C$_6$ cycloalkylene)-(C$_0$-C$_2$ alkylene)-OH, C$_1$-C$_2$ alkylene-(4- to 8-membered heterocycloalkylene)-(C$_0$-C$_2$ alkylene)-NR$^7$R$^8$, C$_1$-C$_2$ alkylene-(4- to 8-membered heterocycloalkylene)-(C$_0$-C$_2$ alkylene)-NR$^{7'}$R$^{8'}$, C$_1$-C$_2$ alkylene-(C$_3$-C$_7$ heterocycloalkylene)-(C$_0$-C$_2$ alkylene)-NR$^7$R$^8$, or C$_1$-C$_2$ alkylene-(C$_3$-C$_7$ heterocycloalkylene)-(C$_0$-C$_2$ alkylene)-NR$^{7'}$R$^{8'}$. In some embodiments, R$^6$ is C$_1$-C$_6$ alkyl, C$_3$-C$_6$ cycloalkyl, C$_1$-C$_2$ alkylene-(C$_3$-C$_6$cycloalkylene)-(C$_0$-C$_2$ alkylene)-NR$^7$R$^8$, C$_1$-C$_2$ alkylene-(C$_3$-C$_6$ cycloalkylene)-(C$_0$-C$_2$alkylene)-NR$^{7'}$R$^{8'}$, C$_1$-C$_2$ alkylene-(C$_3$-C$_6$ cycloalkylene)-(C$_0$-C$_2$ alkylene)-OH, C$_1$-C$_2$ alkylene-(C$_4$-C$_6$ heterocycloalkylene)-(C$_0$-C$_2$ alkylene)-NR$^7$R$^8$, or C$_1$-C$_2$ alkylene-(C$_4$-C$_6$ heterocycloalkylene)-(C$_0$-C$_2$ alkylene)-NR$^{7'}$R$^{8'}$. In some embodiments, R$^6$ is C$_1$-C$_6$ alkylene-NR$^7$R$^8$, C$_1$-C$_6$ alkylene-NR$^{7'}$R$^{8'}$, C$_1$-C$_6$ alkylene-OH, or C$_1$-C$_6$ alkylene-CN. In some embodiments, R$^6$ is C$_1$-C$_6$ alkylene-NR$^7$R$^8$, C$_1$-C$_6$ alkylene-NR$^{7'}$R$^{8'}$, C$_1$-C$_2$ alkylene-(C$_3$-C$_6$ cycloalkylene)-(C$_0$-C$_2$ alkylene)-NR$^7$R$^8$, C$_1$-C$_2$ alkylene-(C$_3$-C$_6$ cycloalkylene)-(C$_0$-C$_2$ alkylene)-NR$^{7'}$R$^{8'}$, C$_1$-C$_2$ alkylene-(4- to 8-membered heterocycloalkylene)-(C$_0$-C$_2$ alkylene)-NR$^7$R$^8$, C$_1$-C$_2$ alkylene-(4- to 8-membered heterocycloalkylene)-(C$_0$-C$_2$ alkylene)-NR$^{7'}$R$^{8'}$. C$_1$-C$_2$ alkylene-(C$_3$-C$_7$ heterocycloalkylene)-(C$_0$-C$_2$ alkylene)-NR$^7$R$^8$, or C$_1$-C$_2$ alkylene-(C$_3$-C$_7$ heterocycloalkylene)-(C$_0$-C$_2$ alkylene)-NR$^{7'}$R$^{8'}$. In some embodiments, R$^6$ is C$_1$-C$_6$ alkylene-NR$^7$R$^8$, C$_1$-C$_6$ alkylene-NR$^{7'}$R$^{8'}$, C$_1$-C$_2$ alkylene-(C$_3$-C$_6$cycloalkylene)-(C$_0$-C$_2$alkylene)-NR$^7$R$^8$, C$_1$-C$_2$ alkylene-(C$_3$-C$_6$ cycloalkylene)-(C$_0$-C$_2$ alkylene)-NR$^{7'}$R$^{8'}$, C$_1$-C$_2$ alkylene-(C$_4$-C$_6$ heterocycloalkylene)-(C$_0$-C$_2$ alkylene)-NR$^7$R$^8$, or C$_1$-C$_2$ alkylene-(C$_4$-C$_6$ heterocycloalkylene)-(C$_0$-C$_2$ alkylene)-NR$^{7'}$R$^{8'}$ In other embodiments, R$^6$ is C$_1$-C$_6$ alkylene-OH or C$_1$-C$_6$ alkylene-CN. In some embodiments, R$^6$ is C$_1$-C$_3$ alkyl or C$_1$-C$_3$ alkylene-NR$^7$R$^8$. In certain embodiments, R$^6$ is C$_1$-C$_3$ alkyl or C$_1$-C$_3$ alkylene-NR$^7$R$^8$, wherein each pair of R$^{7'}$ and R$^{8'}$ of R$^6$ taken together with the nitrogen atom to which they are attached independently form a 3- to 8-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with C$_1$-C$_3$ alkyl, C$_3$-C$_6$ cycloalkyl, C$_2$-C$_3$ haloalkyl, C$_2$-C$_3$ alkylene-CN, or C$_2$-C$_3$ heteroalkyl. In certain other embodiments, R$^6$ is C$_1$-C$_3$ alkyl or C$_1$-C$_3$ alkylene-NR$^{7'}$R$^{8'}$, wherein each pair of R$^{7'}$ and R$^{8'}$ of R$^6$ taken together with the nitrogen atom to which they are attached independently form a 4- to 6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with C$_1$-C$_3$ alkyl, C$_3$-C$_6$ cycloalkyl, C$_2$-C$_3$ haloalkyl, C$_2$-C$_3$ alkylene-CN, or C$_2$-C$_3$ heteroalkyl. In some embodiments, R$^6$ is C$_1$-C$_3$ alkyl. In certain embodiments, R$^6$ is —CH$_3$, —CH$_2$CH$_3$, —CH$_2$CH$_2$CH$_3$, or —CH(CH$_3$)$_2$. In certain other embodiments, R$^6$ is —CH$_2$CH$_3$. In some embodiments, R$^6$ is C$_1$-C$_3$ alkylene-NR$^{7'}$R$^{8'}$. In certain embodiments, each R$^6$ is independently optionally substituted —C$_1$-C$_2$ alkylene-N-morpholinyl or optionally substituted —C$_1$-C$_2$ alkylene-N-piperazinyl. In some embodiments, each R$^6$ is independently optionally substituted

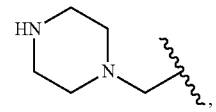

optionally substituted

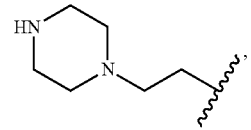 [SMILES: *CCN1CCNCC1]

optionally substituted

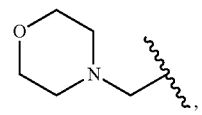

optionally substituted
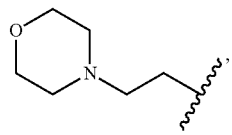 [SMILES: *CCN1CCOCC1]
optionally substituted
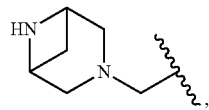
or optionally substituted
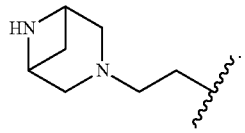
In certain embodiments, each $R^6$ is independently optionally substituted
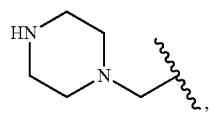
optionally substituted
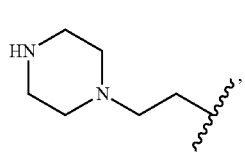
optionally substituted
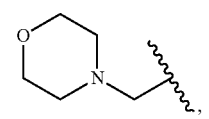
or optionally substituted
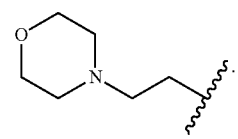 [SMILES: *CCN1CCOCC1]
In some embodiments, each $R^6$ is independently
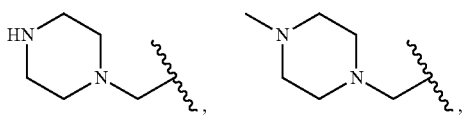
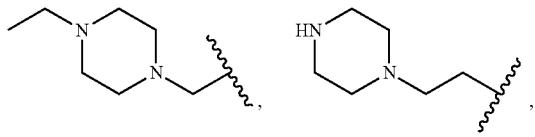
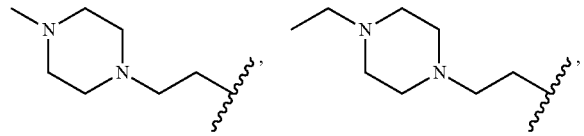
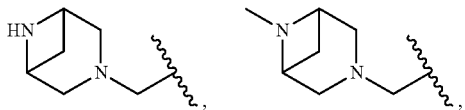
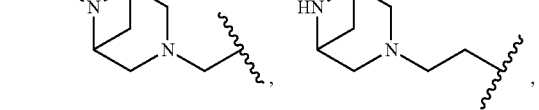
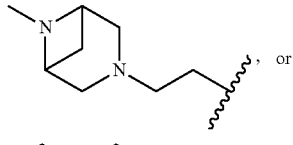
, or
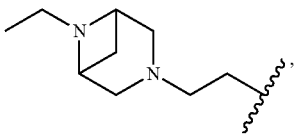
In certain embodiments, each $R^6$ is independently
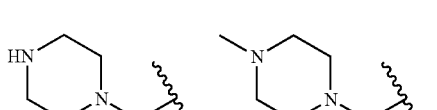
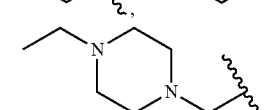
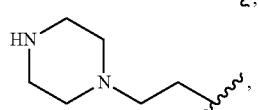
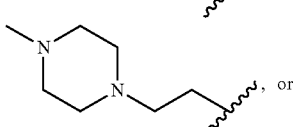
, or
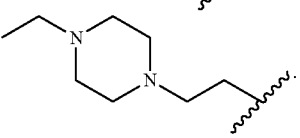

In certain other embodiments, each $R^6$ is independently

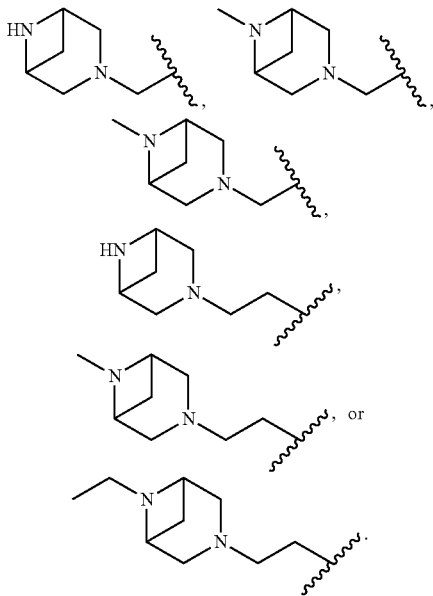

In still other embodiments, each $R^6$ is independently

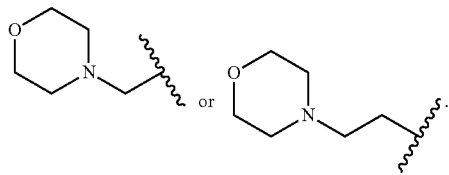 [SMILES: *CN1CCOCC1 ; *CCN1CCOCC1]

In some embodiments, each $R^1$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl. In some embodiments, each $R^7$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl. In some embodiments, each $R^7$ is independently —H. In some embodiments, each $R^7$ is independently $C_1$-$C_3$ alkyl. In certain embodiments, each $R^7$ is independently —CH$_3$, —CH$_2$CH$_3$, —CH$_2$CH$_2$CH$_3$, or —CH(CH$_3$)$_2$. In some embodiments, each $R^7$ is independently $C_3$-$C_6$ cycloalkyl. In certain embodiments, $R^7$ is cyclopropyl, cyclobutyl, cyclopentyl or cyclohexyl. In some embodiments, each $R^7$ is independently $C_2$-$C_3$ haloalkyl. In certain embodiment, each $R^7$ is independently $C_2$-$C_3$ haloalkyl, wherein the each halogen atom of each $C_2$-$C_3$ haloalkyl is independently —F, —Cl, or —Br. In some embodiments, each $R^7$ is independently $C_2$-$C_3$ alkylene-CN. In certain embodiments, each $R^7$ is independently —CH$_2$CH$_2$CN, —CH(CN)CH$_3$, —CH$_2$CH$_2$CH$_2$CN, —CH$_2$CH(CN)CH$_3$, —CH(CN)CH$_2$CH$_3$, or —CH(CH$_2$CN)CH$_3$. In some embodiments, each $R^7$ is independently $C_2$-$C_3$ heteroalkyl. In certain embodiments, each $R^1$ is independently —CH$_2$CH$_2$OH, —CH(OH)CH$_3$, —CH$_2$CH$_2$CH$_2$OH, —CH$_2$CH(OH)CH$_3$, or —CH(OH)CH$_2$CH$_3$, —CH$_2$OCH$_3$, —CH$_2$OCH$_2$CH$_3$, —CH$_2$CH$_2$OCH$_3$, —CH(OCH$_3$)CH$_3$, —CH(CH$_2$OH)CH$_3$, —CH$_2$CH$_2$NH$_2$, —CH(NH$_2$)CH$_3$, —CH$_2$CH$_2$CH$_2$NH$_2$, —CH$_2$CH(NH$_2$)CH$_3$, or —CH(NH$_2$)CH$_2$CH$_3$, —CH$_2$NHCH$_3$, —CH$_2$NHCH$_2$CH$_3$. —CH$_2$CH$_2$NHCH$_3$, —CH(NHCH$_3$)CH$_3$, —CH(CH$_2$NH$_2$CH$_3$, —CH$_2$CH$_2$SH, —CH(SH)CH$_3$, —CH$_2$CH$_2$CH$_2$SH, —CH$_2$CH(SH)CH$_3$, or —CH(SH)CH$_2$CH$_3$, —CH$_2$SCH$_3$, —CH$_2$SCH$_2$CH$_3$, —CH$_2$CH$_2$SCH$_3$, —CH(SCH$_3$)CH$_3$, or —CH(CH$_2$SH)CH$_3$.

In some embodiments, each $R^8$ is independently —H, $C_1$-$C_6$ alkyl, $C_3$-$C_6$ cycloalkyl, $C_1$-$C_6$ haloalkyl, $C_1$-$C_6$ alkylene-CN, or $C_1$-$C_6$ heteroalkyl. In some embodiments, each $R^8$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl. In some embodiments, each $R^8$ is independently —H. In some embodiments, each $R^8$ is independently $C_1$-$C_3$ alkyl. In certain embodiments, each $R^8$ is independently —CH$_3$, —CH$_2$CH$_3$, —CH$_2$CH$_2$CH$_3$, or —CH(CH$_3$)$_2$. In some embodiments, each $R^8$ is independently $C_3$-$C_6$ cycloalkyl. In certain embodiments. $R^8$ is cyclopropyl, cyclobutyl, cyclopentyl or cyclohexyl. In some embodiments, each $R^8$ is independently $C_2$-$C_3$ haloalkyl. In certain embodiment, each $R^8$ is independently $C_2$-$C_3$ haloalkyl, wherein the each halogen atom of each $C_2$-$C_3$ haloalkyl is independently —F, —Cl, or —Br. In some embodiments, each $R^8$ is independently $C_2$-$C_3$ alkylene-CN. In certain embodiments, each $R^8$ is independently —CH$_2$CH$_2$CN, —CH(CN)CH$_3$, —CH$_2$CH$_2$CH$_2$CN, —CH$_2$CH(CN)CH$_3$, —CH(CN)CH$_2$CH$_3$, or —CH(CH$_2$CN)CH$_3$. In some embodiments, each $R^8$ is independently $C_2$-$C_3$ heteroalkyl. In certain embodiments, each $R^8$ is independently —CH$_2$CH$_2$OH, —CH(OH)CH$_3$, —CH$_2$CH$_2$CH$_2$OH, —CH$_2$CH(OH)CH$_3$, or —CH(OH)CH$_2$CH$_3$—CH$_2$OCH$_3$, —CH$_2$OCH$_2$CH$_3$, —CH$_2$CH$_2$OCH$_3$, —CH(OCH$_3$)CH$_3$, —CH(CH$_2$OH)CH$_3$, —CH$_2$CH$_2$NH$_2$, —CH(NH$_2$)CH$_3$, —CH$_2$CH$_2$CH$_2$NH$_2$, —CH$_2$CH(NH$_2$)CH$_3$, or —CH(NH$_2$)CH$_2$CH$_3$, —CH$_2$NHCH$_3$, —CH$_2$NHCH$_2$CH$_3$. —CH$_2$CH$_2$NHCH$_3$, —CH(NHCH$_3$)CH$_3$, —CH(CH$_2$NH$_2$CH$_3$, —CH$_2$CH$_2$SH, —CH(SH)CH$_3$, —CH$_2$CH$_2$CH$_2$SH, —CH$_2$CH(SH)CH$_3$, or —CH(SH)CH$_2$CH$_3$, —CH$_2$SCH$_3$, —CH$_2$SCH$_2$CH$_3$. —CH$_2$CH$_2$SCH$_3$, —CH(SCH$_3$)CH$_3$, or —CH(CH$_2$SH)CH$_3$.

In some embodiments, each pair of $R^{7'}$ and $R^{8'}$ taken together with the nitrogen atom to which they are attached independently form a 3- to 8-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl. In some embodiments, each pair of $R^{7'}$ and $R^{8'}$ of $R^1$ taken together with the nitrogen atom to which they are attached independently form a 3 to 8-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by —H or $C_1$-$C_3$ alkyl. In some embodiments, each pair of $R^{7'}$ and $R^{8'}$ taken together with the nitrogen atom to which they are attached independently form a 4-to-6-membered heterocyclic ring, wherein the heterocyclic ring optionally contains an additional 1-2 heteroatoms selected from the group consisting of N, O, and S. and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl. In some embodiments, each pair of $R^{7'}$ and $R^{8'}$ of $R^1$ taken together with the nitrogen atom to which they are attached independently form a 4-to-6-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by —H or $C_1$-$C_3$ alkyl.

In some embodiments, each $R^9$ is independently halogen, —$OR^{10}$, —$NR^7R^{8'}$, $C_1$-$C_3$ alkyl, $C_1$-$C_3$ haloalkyl, $C_3$-$C_6$cycloalkyl, —CN, $S(O)_nC_1$-$C_3$ alkyl, or $S(O)_nC_3$-$C_6$ cycloalkyl, wherein n is an integer from 0 to 2. In some embodiments, each $R^9$ is independently halogen, —$OR^{10}$, $C_1$-$C_3$ alkyl, —$CF_2H$, —$CF_3$, $C_3$-$C_6$ cycloalkyl, or —CN. In some embodiments, each $R^9$ is independently —F, —Cl, —$OR^{10}$, —$CH_3$, or —CN. In some embodiments, each $R^9$ is independently —F, —$OR^{10}$, or —$CH_3$. In some embodiments, each $R^9$ is independently —F or —$OR^{10}$. In certain embodiments, each $R^9$ is independently, —F, —OH, —$OCH_3$, or —$OCD_3$.

In some embodiments, each $R^{10}$ is independently —H, $C_1$-$C_3$ alkyl, $C_1$-$C_3$ haloalkyl, or $C_3$-$C_6$ cycloalkyl, wherein said $C_1$-$C_3$ alkyl is optionally substituted with hydroxyl, $C_1$-$C_3$ alkoxy, and/or 1-6 deuterium atoms. In some embodiments, each $R^{10}$ is independently —H, $C_1$-$C_3$ alkyl, —$CD_3$, —$CF_2H$, —$CF_3$, or $C_3$-$C_6$ cycloalkyl, wherein said $C_1$-$C_3$ alkyl is optionally substituted with hydroxyl and/or $C_1$-$C_3$ alkoxy and/or 1-6 deuterium atoms. In some embodiments, each $R^{10}$ is independently —H, —$CH_3$, —$CD_3$, —$CH_2CH_3$, or cyclopropyl, wherein said —$CH_3$ or said —$CH_2CH_3$ is optionally substituted with hydroxyl and/or —$OCH_3$. In some embodiments, each $R^{10}$ is independently —H, —$CH_3$, —$CD_3$, or —$CH_2CH_3$, wherein said —$CH_3$ or said —$CH_2CH_3$ is optionally substituted with hydroxyl and/or —$OCH_3$. In some embodiments, each $R^{10}$ is independently —H, —$CH_3$, —$CD_3$, —$CF_2H$, or —$CF_3$. In some embodiments, each $R^{10}$ is independently —H or —$CH_3$.

In some embodiments, the compound of formula (I) is a compound of formula (I-A), or a pharmaceutically acceptable salt, solvate, hydrate, or co-crystal thereof, or a mixture of any of the foregoing:

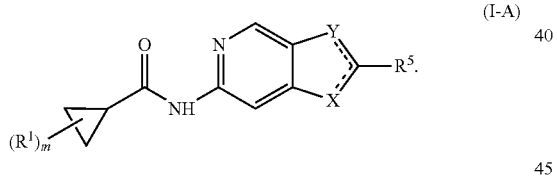
(I-A)

In some embodiments, the compound of formula (I) or formula (I-A) is a compound of formula (I-A-i) or (I-A-ii):

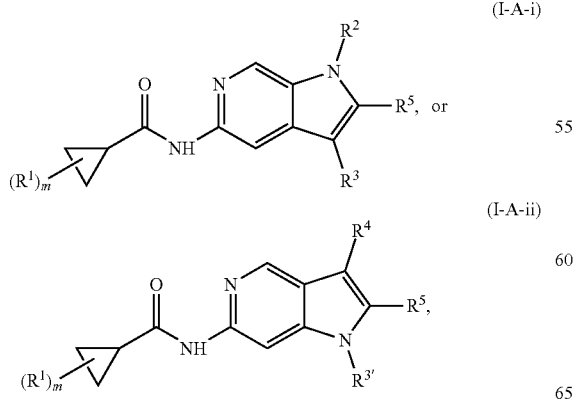
(I-A-i), or (I-A-ii)

wherein m is an integer 0 or 2;

each $R^1$ is independently —F, $C_1$-$C_3$ alkyl, $C_1$-$C_3$ alkylene-$NR^7R^8$, $C_1$-$C_3$ alkylene-$NR^7R^{8'}$, $C_1$-$C_3$ alkylene-OH, $C_1$-$C_3$ alkylene-CN, $C_1$-$C_2$ alkylene-($C_3$-$C_6$ cycloalkylene)-($C_0$-$C_2$ alkylene)-$NR^7R^8$, $C_1$-$C_3$ alkylene-CN, $C_1$-$C_2$ alkylene-($C_3$-$C_6$ cycloalkylene)-($C_0$-$C_2$ alkylene)-$NR^7R^{8'}$, $C_1$-$C_2$ alkylene-($C_3$-$C_6$ cycloalkylene)-($C_0$-$C_2$alkylene)-OH, $C_1$-$C_2$ alkylene-($C_4$-$C_6$ heterocycloalkylene)-($C_0$-$C_2$ alkylene)-$NR^7R^8$, or $C_1$-$C_2$ alkylene-($C_4$-$C_4$ heterocycloalkylene)-($C_0$-$C_2$ alkylene)-$NR^7R^{8'}$, wherein the alkyl, alkylene, cycloalkylene, and heterocycloalkylene in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

$R^2$ is —H, —$CH_3$, $CD_3$, —$CHF_2$, or —$CH_2CH_3$;

$R^3$ is —H, $C_1$-$C_3$ alkyl, $C_3$-cycloalkyl, halogen, or —CN;

$R^{3'}$ is —H, $C_1$-$C_3$ alkyl, $C_3$-cycloalkyl, or —CN;

$R^4$ is —H, —$CH_3$, —$CD_3$, —$CHF_2$, —$CH_2CH_3$, or halogen;

$R^5$ is $C_6$-$C_{14}$ aryl or 5-to-10-membered heteroaryl, wherein said 5-to-10-membered heteroaryl is selected from the group consisting of:

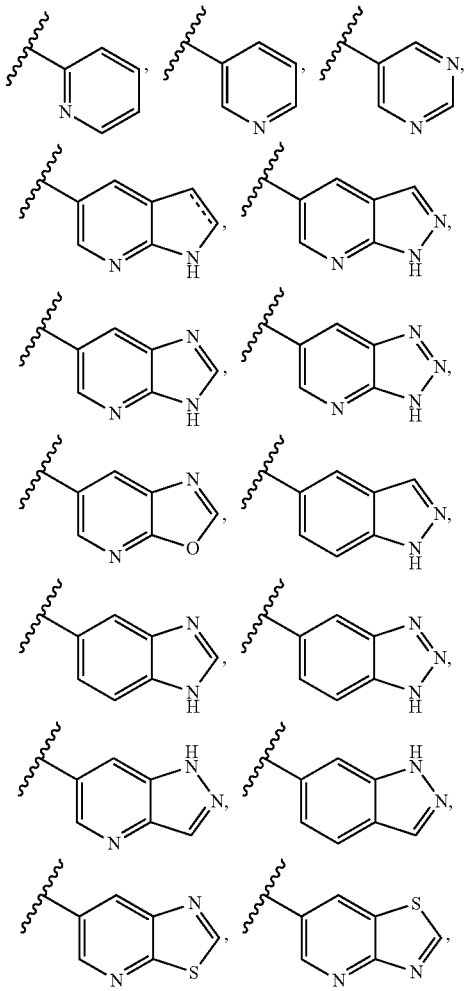

-continued

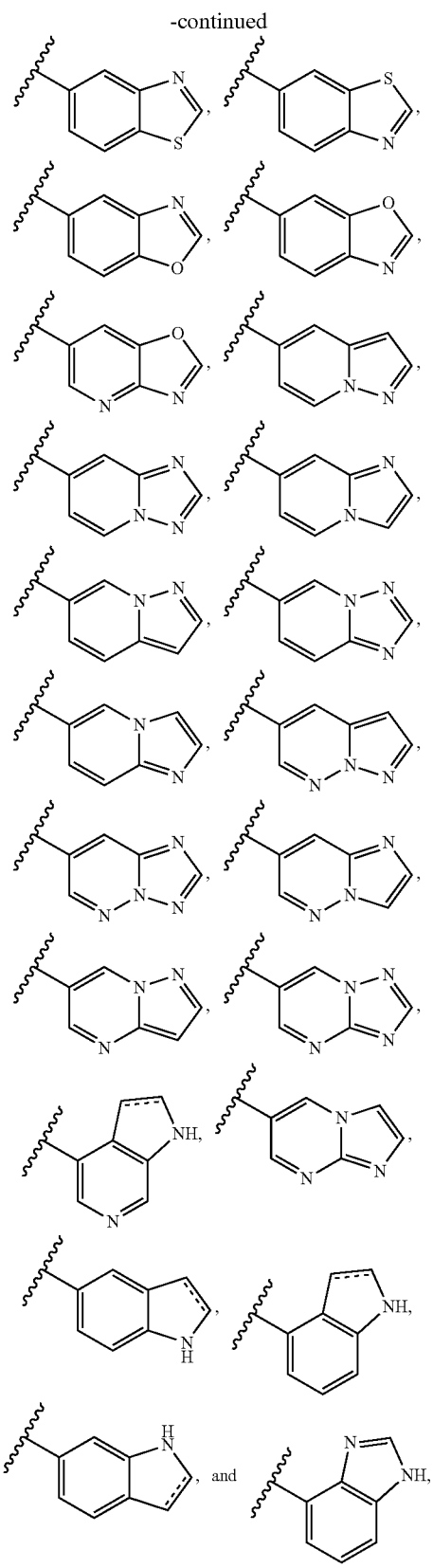

wherein === indicates a single or double bond, and wherein said $C_6$-$C_{14}$ aryl or said 5-to-10-membered heteroaryl is optionally substituted with 1-5 $R^9$ groups;

each $R^7$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;

each $R^8$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;

each pair of $R^{7'}$ and $R^{8'}$ taken together with the nitrogen atom to which they are attached independently form a 4-to-6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —OR$^{10}$, $C_1$-$C_3$ alkyl, —CF$_2$H, —CF$_3$, $C_3$-$C_6$ cycloalkyl, or —CN, and each $R^{10}$ is independently —H, $C_1$-$C_3$ alkyl, —CD$_3$, —CF$_2$H, —CF$_3$, or $C_3$-$C_6$ cycloalkyl, wherein said $C_1$-$C_3$ alkyl is optionally substituted with hydroxyl and/or $C_1$-$C_3$ alkoxy and/or 1-6 deuterium atoms.

In some embodiments, each $R^1$ is independently —F, $C_1$-$C_3$ alkylene-NR$^{7'}$R$^{8'}$, or $C_1$-$C_3$ alkylene-OH; and wherein each pair of R$^{7'}$ and R$^{8'}$ of R$^1$ taken together with the nitrogen atom to which they are attached independently form a 4-to-6-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by H or $C_1$-$C_3$ alkyl.

In some embodiments, $R^5$ is phenyl or 5-to-10-membered heteroaryl, wherein said 5-to-10-membered heteroaryl is selected from the group consisting of:

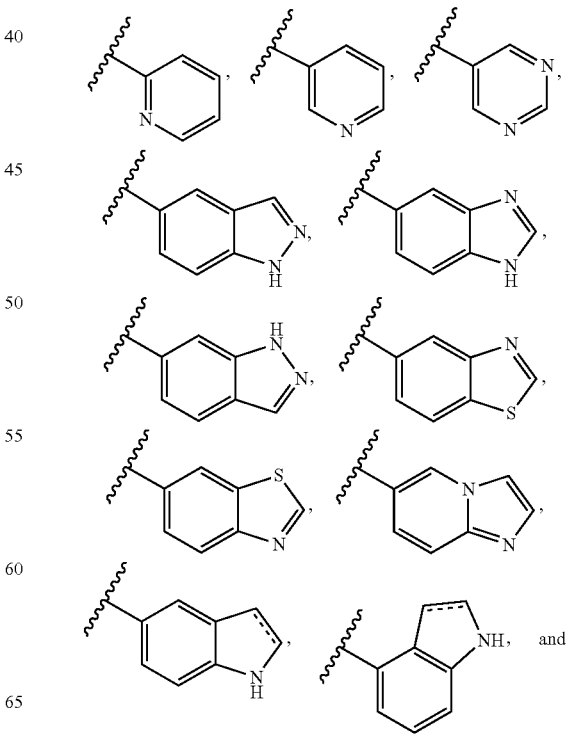

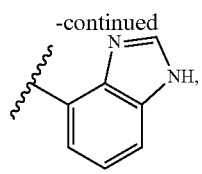

wherein ⚌ indicates a single or double bond, and wherein said phenyl or said 5-to-10-membered heteroaryl is optionally substituted with 1-3 $R^9$ groups.

In some embodiments, $R^2$ is —$CH_3$, $CD_3$, or —$CH_2CH_3$; $R^3$ is —H, —F, —$CH_3$, or —CN; $R^{3'}$ is —H or —$CH_3$; and $R^4$ is —H, —F or —$CH_3$.

In some embodiments, each $R^9$ is independently —F, —Cl, —$OR^{10}$, —$CH_3$, or —CN, and each $R^{10}$ is independently —H, —$CH_3$, —$CD_3$, or —$CH_2CH_3$, wherein said —$CH_3$ or said —$CH_2CH_3$ is optionally substituted with hydroxyl and/or —$OCH_3$.

In some embodiments, the compound of formula (I) is a compound of formula (I-A-i) or formula (I-A-ii), wherein m is an integer 0 or 1; $R^1$ is —F, $C_1$-$C_3$ alkylene-$NR^7R^{8'}$, or $C_1$-$C_3$ alkylene-OH; $R^2$ is —$CH_3$, $CD_3$, or —$CH_2CH_3$; $R^3$ is —H, —F, —$CH_3$, or —CN; $R^{3'}$ is —H or —$CH_3$; $R^4$ is —H, —F or —$CH_3$; $R^5$ is phenyl or 5-to-10-membered heteroaryl, wherein said 5-to-10-membered heteroaryl is selected from the group consisting of:

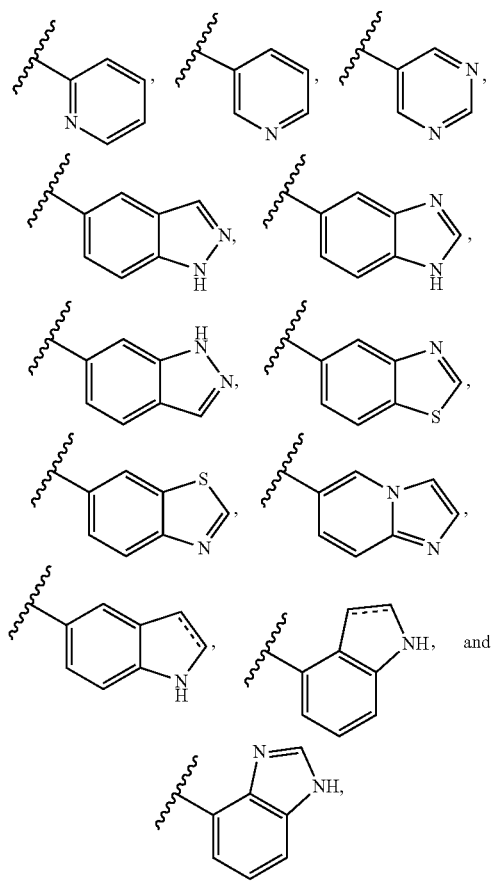

wherein ⚌ indicates a single or double bond, and wherein said phenyl or said 5-to-10-membered heteroaryl is optionally substituted with 1-3 $R^9$ groups; each pair of $R^7$ and $R^{8'}$ taken together with the nitrogen atom to which they are attached independently form a 4-to-6-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by H, or $C_1$-$C_3$ alkyl; each $R^9$ is independently —F, —Cl, —$OR^{10}$, —$CH_3$, or —CN, and each $R^{10}$ is independently —H, —$CH_3$, —$CD_3$, or —$CH_2CH_3$, wherein said —$CH_3$ or said —$CH_2CH_3$ is optionally substituted with hydroxyl and/or —$OCH_3$.

In some embodiments, the compound of formula (I) is a compound of formula (I-A-i) or formula (I-A-ii), wherein m is an integer 0 or 1; $R^7$ is —F; $R^2$ is —$CH_3$; $R^3$ is —H or —$CH_3$; $R^{3'}$ is —H or —$CH_3$; $R^4$ is —$CH_3$; $R^5$ is a 5-to-10-membered heteroaryl, wherein said 5-to-10-membered heteroaryl is selected from the group consisting of:

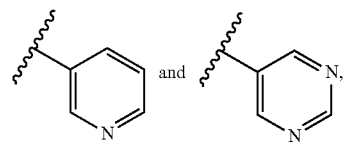 [SMILES: *c1cccnc1 ; *c1cncnc1]

wherein said 5-to-10-membered heteroaryl is optionally substituted with 1-3 $R^9$ groups; each $R^9$ is independently —F or —$OR^{10}$, and each $R^{10}$ is independently —H or —$CH_3$.

In some embodiments, the compound of formula (I) is a compound of formula (I-B), or a pharmaceutically acceptable salt, solvate, hydrate, or co-crystal thereof, or a mixture of any of the foregoing:

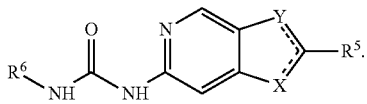

(I-B)

In some embodiments, the compound of formula (I) or formula (I-B) is a compound of formula (I-B-i) or (I-B-ii):

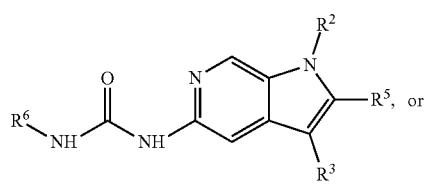

(I-B-i)

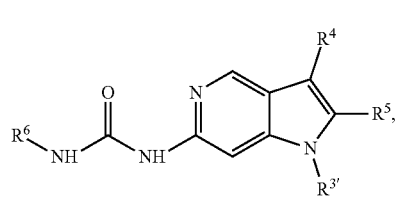

(I-B-ii)

wherein
$R^2$ is —H, —$CH_3$, $CD_3$, —$CHF_2$, or —$CH_2CH_3$;
$R^3$ is —H, $C_1$-$C_3$ alkyl, $C_3$-cycloalkyl, halogen, or —CN;
$R^{3'}$ is —H, $C_1$-$C_3$ alkyl, $C_3$-cycloalkyl, or —CN;
$R^4$ is —H, —$CH_3$, —$CD_3$, —$CHF_2$, —$CH_2CH_3$, or halogen;

R[5] is C_6-C_14 aryl or 5-to-10-membered heteroaryl, wherein said 5-to-10-membered heteroaryl is selected from the group consisting of:

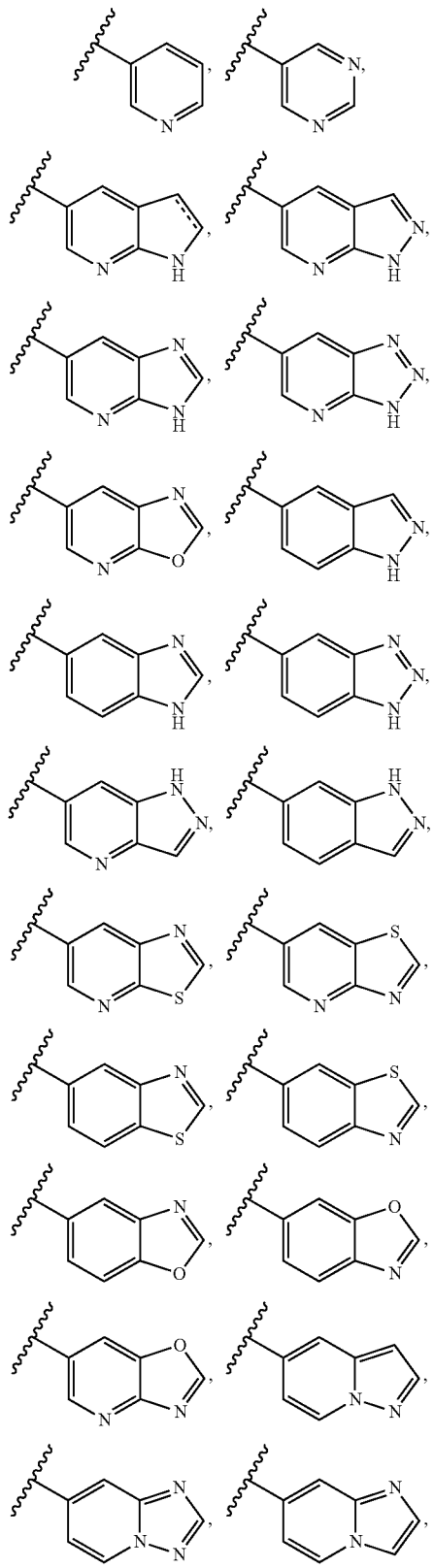

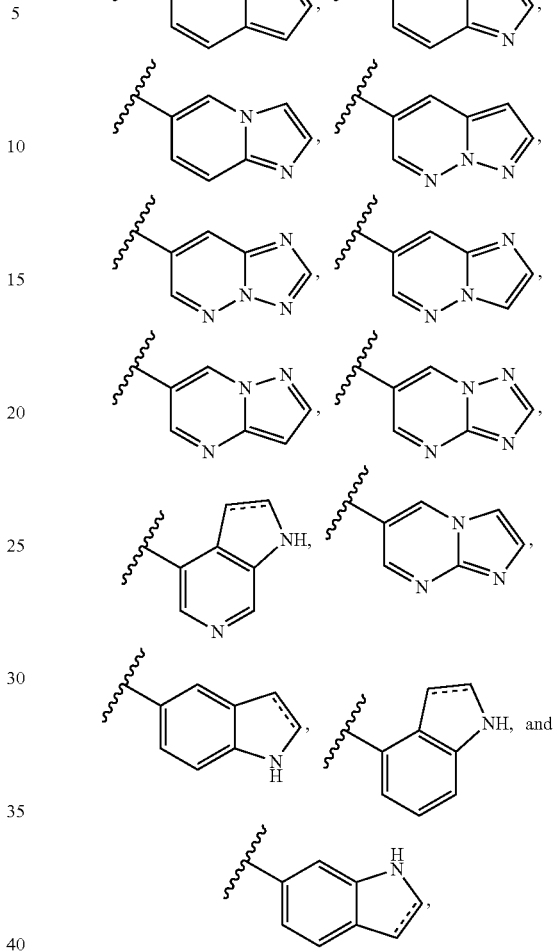

wherein ≈ indicates a single or double bond, and wherein said $C_6$-$C_{14}$ aryl or said 5-to-10-membered heteroaryl is optionally substituted with 1-5 $R^9$ groups; $R^6$ is $C_1$-$C_3$ alkyl, $C_3$-$C_6$ cycloalkyl, $C_1$-$C_3$ alkylene-$NR^7R^8$, $C_1$-$C_3$ alkylene-$NR^{1'}R^{8'}$, $C_1$-$C_3$ alkylene-OH, $C_1$-$C_3$ alkylene-CN, $C_1$-$C_2$ alkylene-($C_3$-$C_6$cycloalkylene)-($C_0$-$C_2$alkylene)-$NR^7R^8$, $C_1$-$C_2$ alkylene-($C_3$-$C_6$cycloalkylene)-($C_0$-$C_2$alkylene)-$NR^7R^{8'}$, $C_1$-$C_2$ alkylene-($C_3$-$C_6$cycloalkylene)-($C_0$-$C_2$ alkylene)-OH, $C_1$-$C_2$ alkylene-($C_4$-$C_6$ heterocycloalkylene)-($C_0$-$C_2$ alkylene)-$NR^7R^8$, or $C_1$-$C_2$ alkylene-($C_4$-$C_6$ heterocycloalkylene)-($C_0$-$C_2$alkylene)-$NR^{7'}R^{8'}$, wherein the alkyl, alkylene, cycloalkyl, cycloalkylene, and heterocycloalkylene moieties in $R^6$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^7$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;

each $R^8$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;

each pair of $R^{7'}$ and $R^{8'}$ taken together with the nitrogen atom to which they are attached independently form a 4- to 6-membered heterocyclic ring, wherein the heterocyclic ring optionally contains an additional 1-2 heteroatoms selected from the group consisting of N, O, and S. and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —$OR^{10}$, $C_1$-$C_3$ alkyl, —$CF_2H$, —$CF_3$, $C_3$-$C_6$cycloalkyl, or —CN, and each $R^{10}$ is independently —H, $C_1$-$C_3$ alkyl, —$CD_3$, —$CF_2H$, —$CF_3$, or $C_3$-$C_6$ cycloalkyl, wherein said $C_1$-$C_3$ alkyl is optionally substituted with hydroxyl and/or $C_1$-$C_3$ alkoxy.

In some embodiments, $R^6$ is $C_1$-$C_3$ alkyl or $C_1$-$C_3$ alkylene-$NR^{7'}R^{8'}$; and wherein each pair of $R^{7'}$ and $R^{8'}$ of $R^6$ taken together with the nitrogen atom to which they are attached independently form a 4- to 6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl.

In some embodiments, $R^5$ is phenyl or 5-to-10-membered heteroaryl, wherein said 5-to-10-membered heteroaryl is selected from the group consisting of:

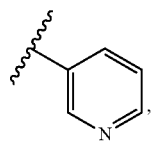 [SMILES: *c1cccnc1]

wherein said phenyl or said 5-to-10-membered heteroaryl is optionally substituted with 1-3 $R^9$ groups.

In some embodiments, each $R^9$ is independently —F, —$OR^{10}$, —$CH_3$, and each $R^{10}$ is independently —H, —$CH_3$, —$CD_3$, —$CF_2H$, or —$CF_3$.

In some embodiments. $R^2$ is —H or —$CH_3$; $R^3$ is —H; $R^{3'}$ is —H; and $R^4$ is —H or —$CH_3$.

In some embodiments, the compound of formula (I) is a compound of formula (i-B-i) or formula (I-B-ii), wherein $R^2$ is —H or —$CH_3$; $R^3$ is —H; $R^{3'}$ is —H; $R^4$ is —H or —$CH_3$; $R^5$ is phenyl or 5-to-10-membered heteroaryl, wherein said 5-to-10-membered heteroaryl is selected from the group consisting of:

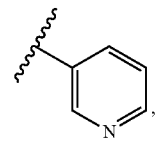

wherein said phenyl or said 5-to-10-membered heteroaryl is optionally substituted with 1-3 $R^9$ groups; $R^6$ is $C_1$-$C_3$ alkyl or $C_1$-$C_3$ alkylene-$NR^{7'}R^{8'}$; each pair of $R^{7'}$ and $R^{8'}$ taken together with the nitrogen atom to which they are attached independently form a 4- to 6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl; each $R^9$ is independently —F, —$OR^{10}$, —$CH_3$, and each $R^{10}$ is independently —H, —$CH_3$, —$CD_3$, —$CF_2H$, or —$CF_3$.

In some embodiments, provided is a compound selected from the compounds in Table 1, or a pharmaceutically acceptable salt, solvate, hydrate, or co-crystal thereof, or a mixture of any of the foregoing.

TABLE 1

| Cmpd No. | Compound Structure | Cmpd No. | Compound Structure |
|---|---|---|---|
| 1 | 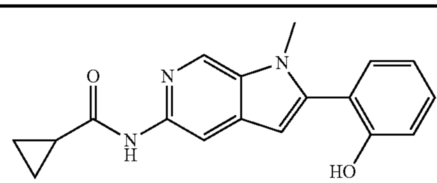 | | |
| 2 | 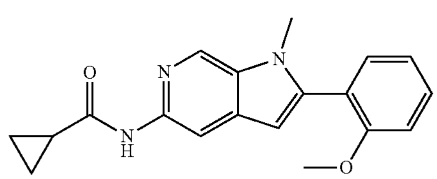 [SMILES: COc1ccccc1-c1cc2cc(NC(=O)C3CC3)ncc2n1C] | | |
| 3 | 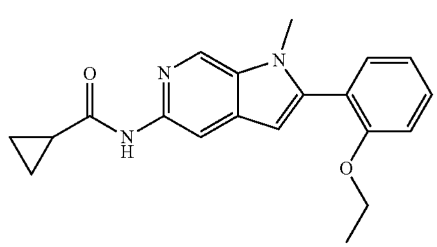 [SMILES: CCOc1ccccc1-c1cc2cc(NC(=O)C3CC3)ncc2n1C] | | |

TABLE 1-continued

| Cmpd No. | Compound Structure | Cmpd No. | Compound Structure |
|---|---|---|---|
| 4 | *cyclopropanecarboxamide-N-linked to 1-methyl-6-azaindole, 2-substituted with 2-(2-hydroxyethoxy)phenyl* | | |
| 5 | *cyclopropanecarboxamide-N-linked to 1-methyl-6-azaindole, 2-substituted with 2-(2-methoxyethoxy)phenyl* | | |
| 6 | *cyclopropanecarboxamide-N-linked to 1-methyl-6-azaindole, 2-substituted with 2-cyanophenyl* | | |
| 7 | *cyclopropanecarboxamide-N-linked to 1-methyl-6-azaindole, 2-substituted with 3-hydroxy-2-methylphenyl* | | |
| 8 | *cyclopropanecarboxamide-N-linked to 1-methyl-6-azaindole, 2-substituted with 4-hydroxy-2-methylphenyl* | | |
| 9 | *cyclopropanecarboxamide-N-linked to 1-methyl-6-azaindole, 2-substituted with 3-methoxy-2-methylphenyl* | | |
| 10 | *cyclopropanecarboxamide-N-linked to 1-methyl-6-azaindole, 2-substituted with 4-methoxy-2-methylphenyl* | | |

TABLE 1-continued
| Cmpd No. | Compound Structure | Cmpd No. | Compound Structure |
|---|---|---|---|
| 11 | 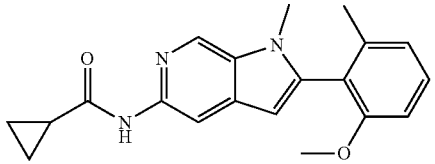 [SMILES: COc1cccc(C)c1-c1cc2cc(NC(=O)C3CC3)ncc2n1C] | | |
| 12 | 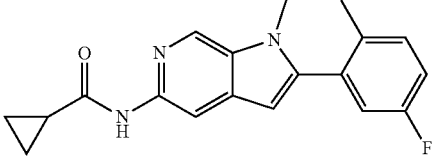 | | |
| 13 | 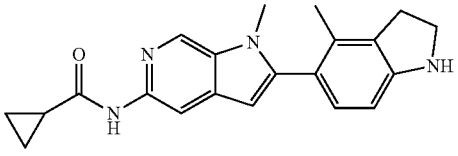 [SMILES: Cc1c(-c2cc3cc(NC(=O)C4CC4)ncc3n2C)ccc2c1CCN2] | | |
| 14 | 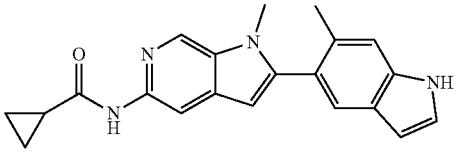 [SMILES: Cc1cc2[nH]ccc2cc1-c1cc2cc(NC(=O)C3CC3)ncc2n1C] | | |
| 15 | 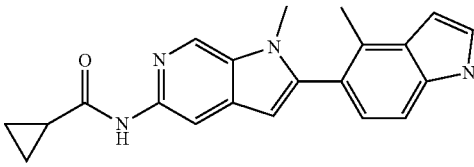 | | |
| 16 | 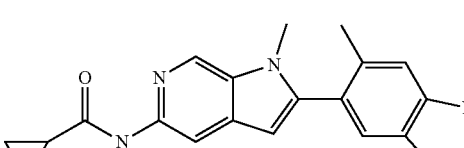 | | |
| 17 | 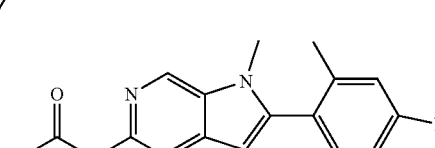 | | |
| 18 | 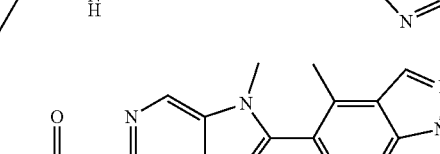 | | |
| 19 | 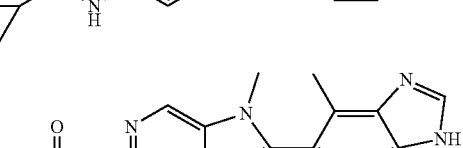 | | |

TABLE 1-continued

| Cmpd No. | Compound Structure | Cmpd No. | Compound Structure |
|---|---|---|---|
| 20 | 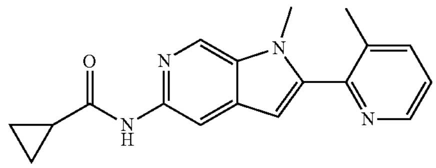 [SMILES: Cc1cccnc1-c1cc2cc(NC(=O)C3CC3)ncc2n1C] | | |
| 21 | 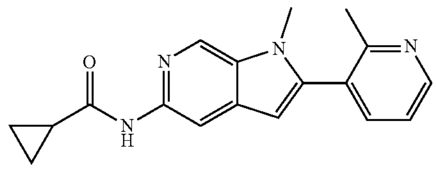 [SMILES: Cc1ncccc1-c1cc2cc(NC(=O)C3CC3)ncc2n1C] | | |
| 22 | 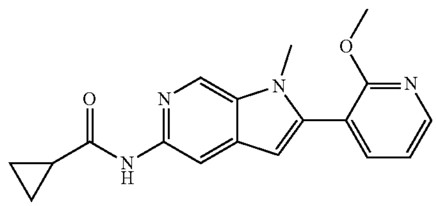 [SMILES: COc1ncccc1-c1cc2cc(NC(=O)C3CC3)ncc2n1C] | | |
| 23 | 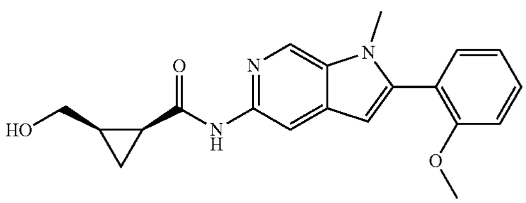 [SMILES: COc1ccccc1-c1cc2cc(NC(=O)[C@H]3C[C@H]3CO)ncc2n1C] | 23-1 | 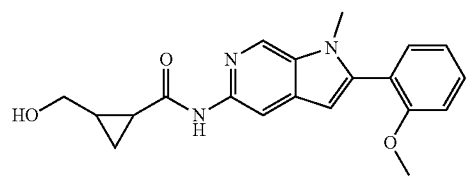 [SMILES: COc1ccccc1-c1cc2cc(NC(=O)C3CC3CO)ncc2n1C] |
| 24 | 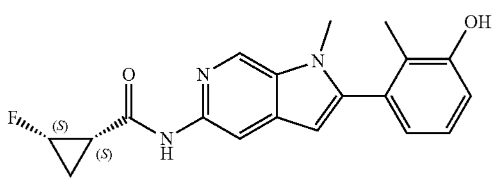 | 24-1 | 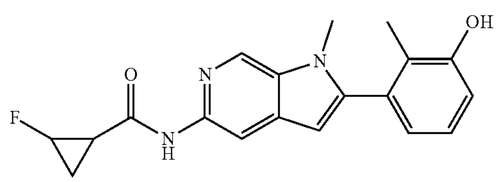 [SMILES: Cc1c(O)cccc1-c1cc2cc(NC(=O)C3CC3F)ncc2n1C] |
| 25 | 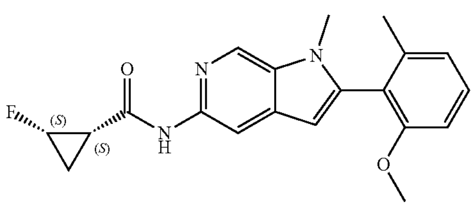 | 25-1 | 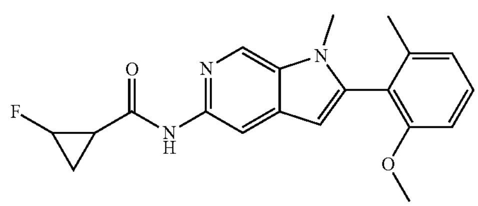 [SMILES: COc1cccc(C)c1-c1cc2cc(NC(=O)C3CC3F)ncc2n1C] |
| 26 | 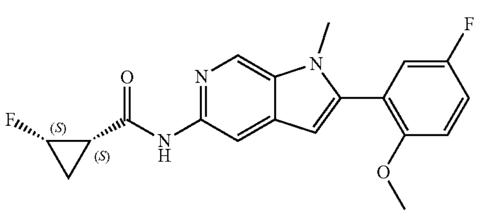 | 26-1 | 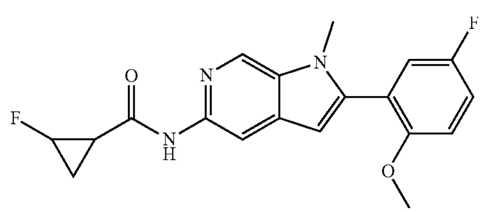 [SMILES: COc1ccc(F)cc1-c1cc2cc(NC(=O)C3CC3F)ncc2n1C] |
| 27 | 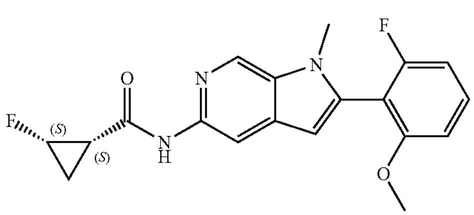 | 27-1 | 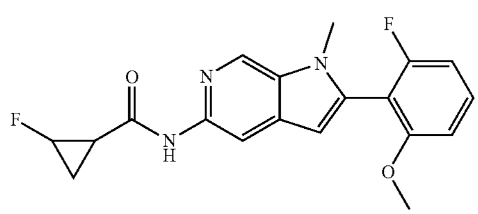 [SMILES: COc1cccc(F)c1-c1cc2cc(NC(=O)C3CC3F)ncc2n1C] |

TABLE 1-continued

| Cmpd No. | Compound Structure | Cmpd No. | Compound Structure |
|---|---|---|---|
| 28 | 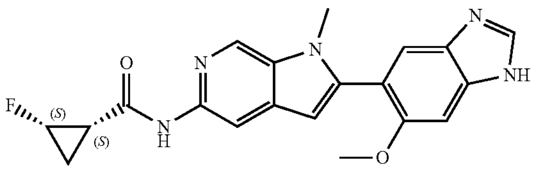 | 28-1 | 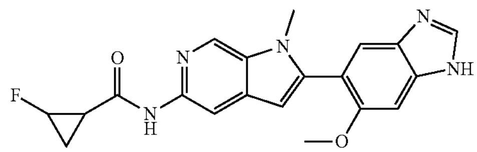 [SMILES: COc1cc2[nH]cnc2cc1-c1cc2cc(NC(=O)C3CC3F)ncc2n1C] |
| 29 | 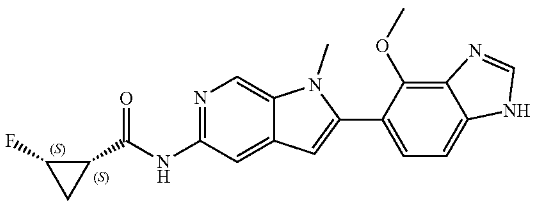 | 29-1 | 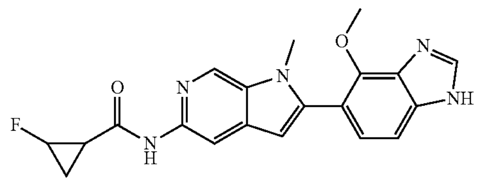 [SMILES: COc1c(-c2cc3cc(NC(=O)C4CC4F)ncc3n2C)ccc2[nH]cnc12] |
| 30 | 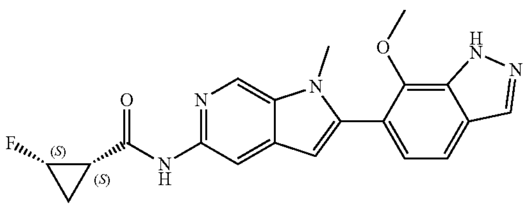 | 30-1 | 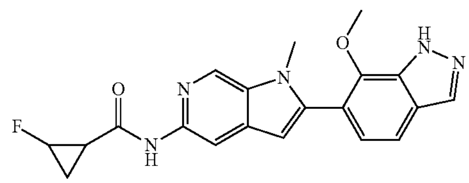 [SMILES: COc1c(-c2cc3cc(NC(=O)C4CC4F)ncc3n2C)ccc2cn[nH]c12] |
| 31 | 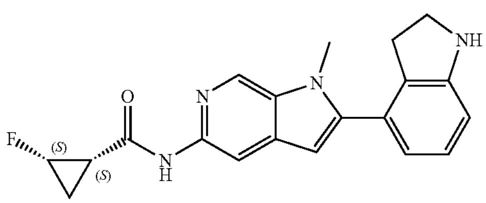 | 31-1 | 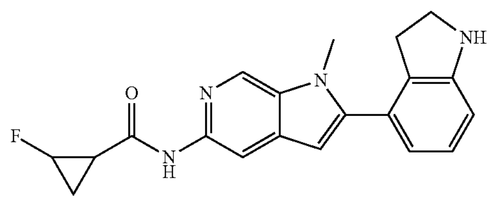 |
| 32 | 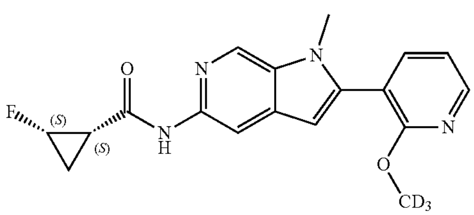 | 32-1 | 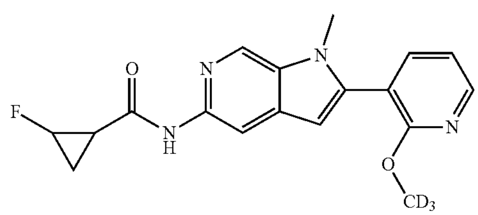 |
| 33 | 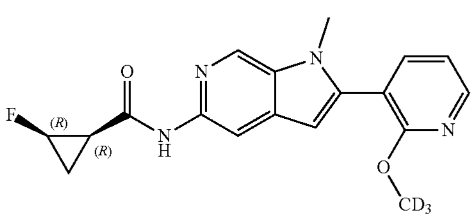 | 32-1 | 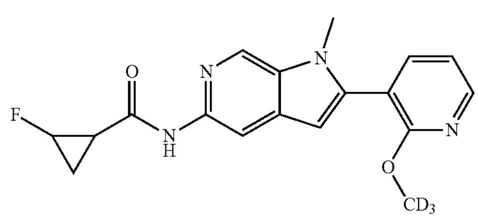 [SMILES: [2H]C([2H])([2H])Oc1ncccc1-c1cc2cc(NC(=O)C3CC3F)ncc2n1C] |
| 34 | 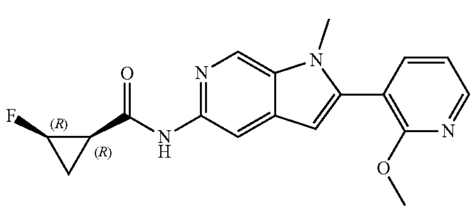 | 34-1 | 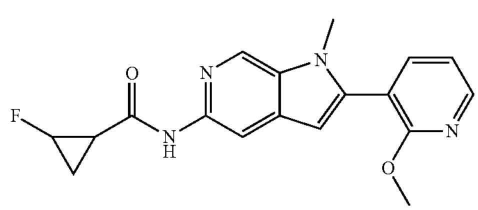 [SMILES: COc1ncccc1-c1cc2cc(NC(=O)C3CC3F)ncc2n1C] |

TABLE 1-continued

| Cmpd No. | Compound Structure | Cmpd No. | Compound Structure |
|---|---|---|---|
| 35 | 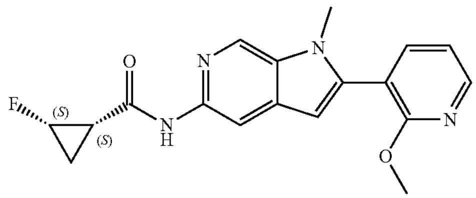 | 34-1 | 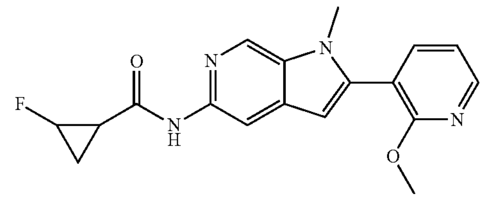 [SMILES: COc1ncccc1-c1cc2cc(NC(=O)C3CC3F)ncc2n1C] |
| 36 | 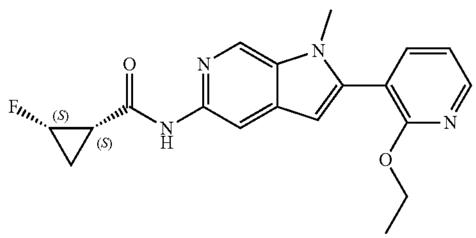 | 36-1 | 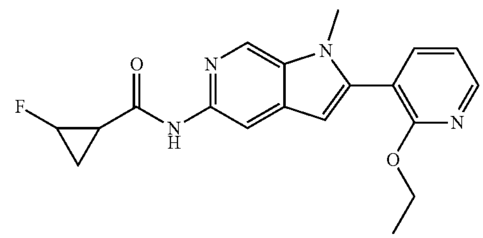 [SMILES: CCOc1ncccc1-c1cc2cc(NC(=O)C3CC3F)ncc2n1C] |
| 37 | 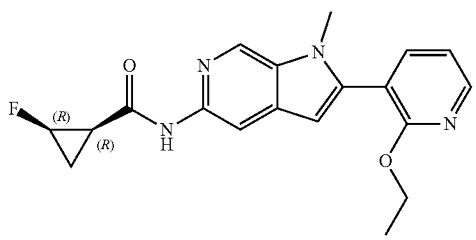 | 36-1 | 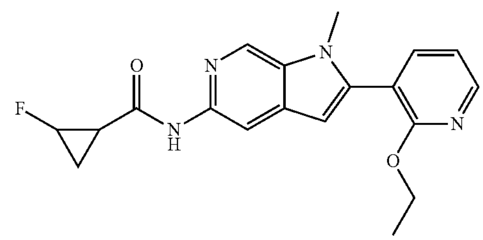 [SMILES: CCOc1ncccc1-c1cc2cc(NC(=O)C3CC3F)ncc2n1C] |
| 38 | 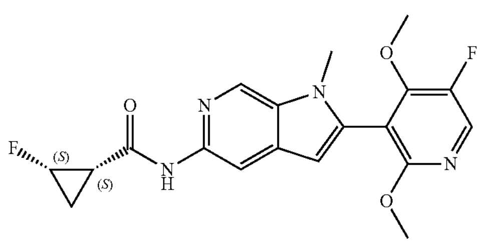 | 38-1 | 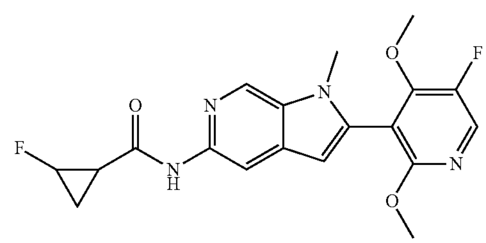 [SMILES: COc1ncc(F)c(OC)c1-c1cc2cc(NC(=O)C3CC3F)ncc2n1C] |
| 39 | 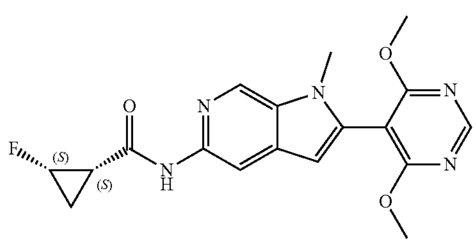 | 39-1 | 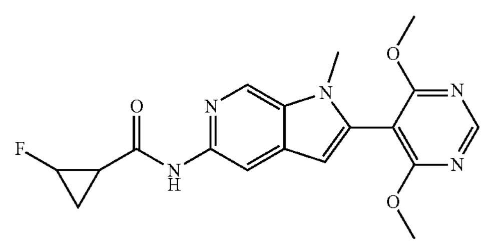 [SMILES: COc1ncnc(OC)c1-c1cc2cc(NC(=O)C3CC3F)ncc2n1C] |
| 40 | 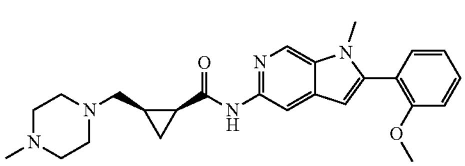 [SMILES: COc1ccccc1-c1cc2cc(NC(=O)[C@H]3C[C@H]3CN3CCN(C)CC3)ncc2n1C] | 40-1 | 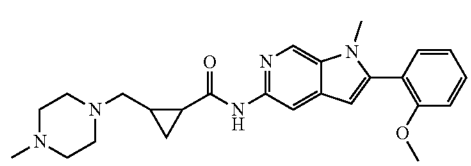 [SMILES: COc1ccccc1-c1cc2cc(NC(=O)C3CC3CN3CCN(C)CC3)ncc2n1C] |
| 41 | 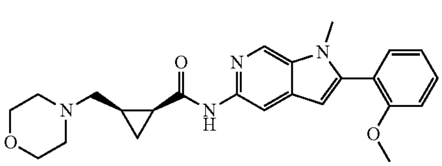 [SMILES: COc1ccccc1-c1cc2cc(NC(=O)[C@H]3C[C@H]3CN3CCOCC3)ncc2n1C] | 41-1 | 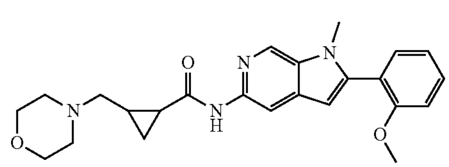 [SMILES: COc1ccccc1-c1cc2cc(NC(=O)C3CC3CN3CCOCC3)ncc2n1C] |

TABLE 1-continued

| Cmpd No. | Compound Structure | Cmpd No. | Compound Structure |
|---|---|---|---|
| 42 | 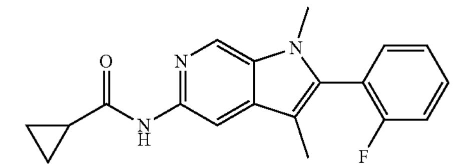 [SMILES: Cc1c(-c2ccccc2F)n(C)c2cnc(NC(=O)C3CC3)cc12] | | |
| 43 | 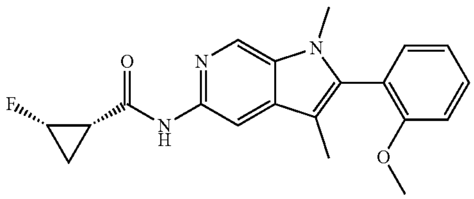 [SMILES: COc1ccccc1-c1c(C)c2cc(NC(=O)[C@@H]3C[C@@H]3F)ncc2n1C] | 43-1 | 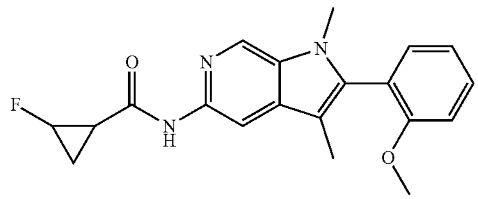 [SMILES: COc1ccccc1-c1c(C)c2cc(NC(=O)C3CC3F)ncc2n1C] |
| 44 | 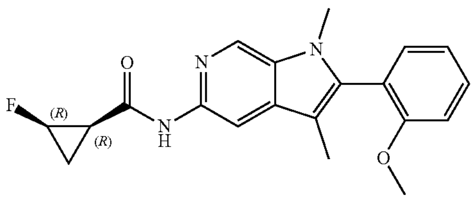 | 43-1 | 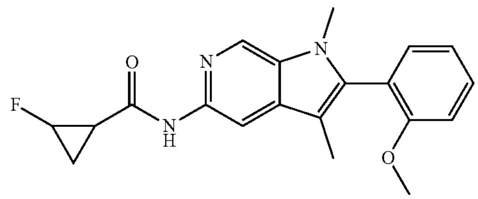 [SMILES: COc1ccccc1-c1c(C)c2cc(NC(=O)C3CC3F)ncc2n1C] |
| 45 | 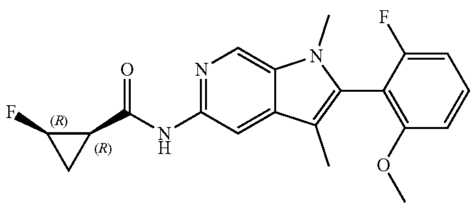 | 45-1 | 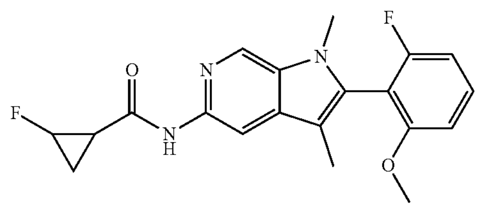 [SMILES: COc1cccc(F)c1-c1c(C)c2cc(NC(=O)C3CC3F)ncc2n1C] |
| 46 | 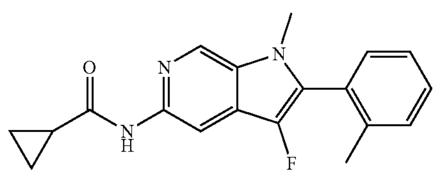 [SMILES: Cc1ccccc1-c1c(F)c2cc(NC(=O)C3CC3)ncc2n1C] | | |
| 47 | 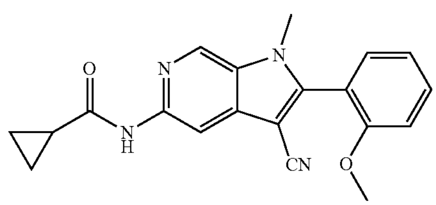 [SMILES: COc1ccccc1-c1c(C#N)c2cc(NC(=O)C3CC3)ncc2n1C] | | |
| 48 | 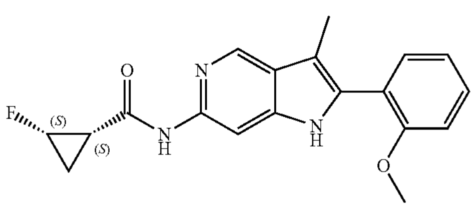 | 48-1 | 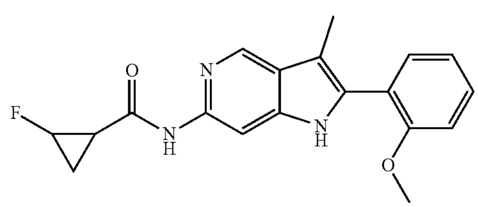 [SMILES: COc1ccccc1-c1[nH]c2cc(NC(=O)C3CC3F)ncc2c1C] |
| 49 | 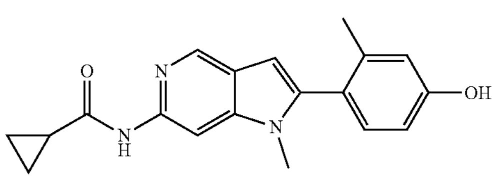 [SMILES: Cc1cc(O)ccc1-c1cc2cnc(NC(=O)C3CC3)cc2n1C] | | |

TABLE 1-continued

| Cmpd No. | Compound Structure | Cmpd No. | Compound Structure |
|---|---|---|---|
| 50 | 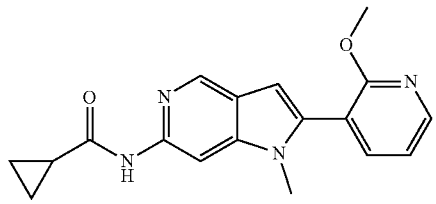 [SMILES: COc1ncccc1-c1cc2cnc(NC(=O)C3CC3)cc2n1C] | | |
| 51 | 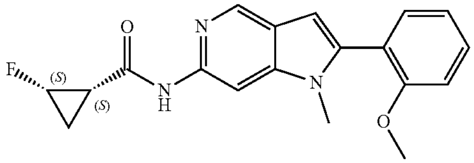 | 51-1 | 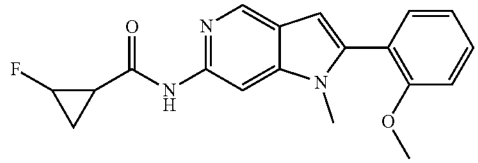 [SMILES: COc1ccccc1-c1cc2cnc(NC(=O)C3CC3F)cc2n1C] |
| 52 | 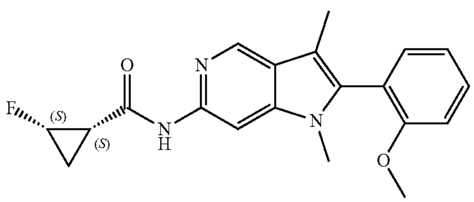 | 52-1 | 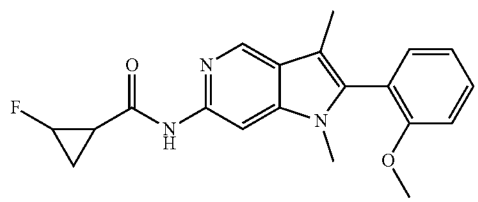 [SMILES: COc1ccccc1-c1c(C)c2cnc(NC(=O)C3CC3F)cc2n1C] |
| 53 | 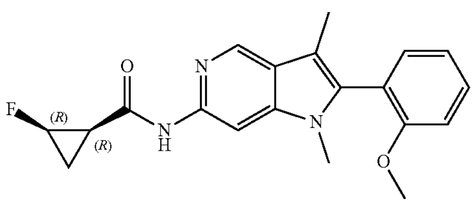 | 52-1 | 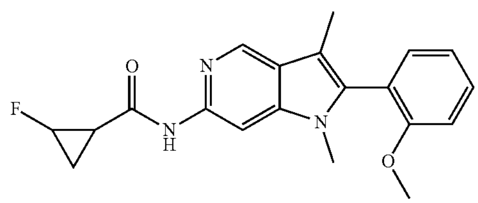 [SMILES: COc1ccccc1-c1c(C)c2cnc(NC(=O)C3CC3F)cc2n1C] |
| 54 | 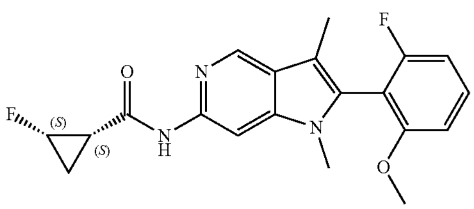 | 54-1 | 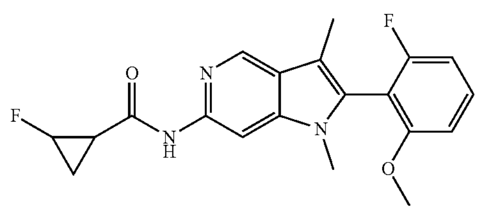 [SMILES: COc1cccc(F)c1-c1c(C)c2cnc(NC(=O)C3CC3F)cc2n1C] |
| 55 | 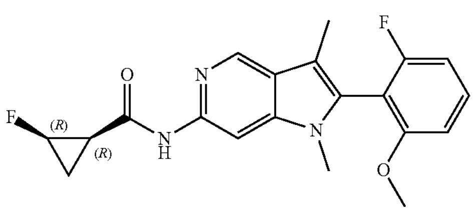 | 54-1 | 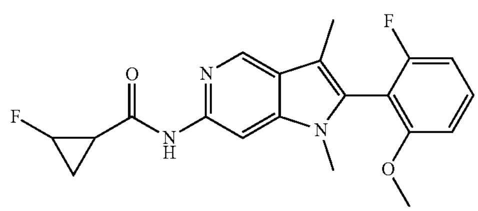 [SMILES: COc1cccc(F)c1-c1c(C)c2cnc(NC(=O)C3CC3F)cc2n1C] |
| 56 | 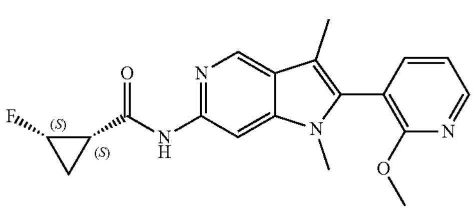 | 56-1 | 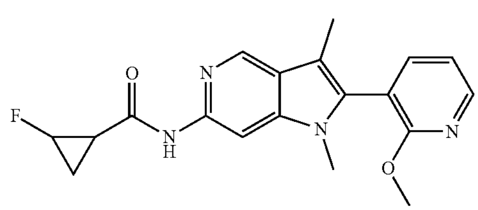 [SMILES: COc1ncccc1-c1c(C)c2cnc(NC(=O)C3CC3F)cc2n1C] |

TABLE 1-continued

| Cmpd No. | Compound Structure | Cmpd No. | Compound Structure |
|---|---|---|---|
| 57 | 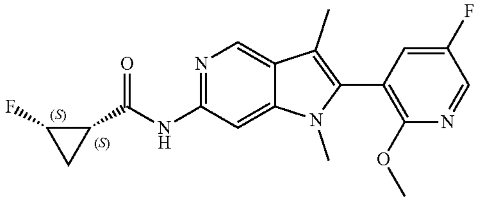 | 57-1 | 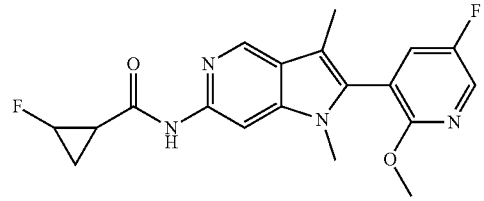 [SMILES: COc1ncc(F)cc1-c1c(C)c2cnc(NC(=O)C3CC3F)cc2n1C] |
| 58 | 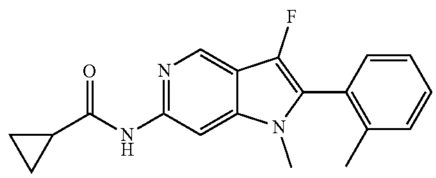 [SMILES: Cc1ccccc1-c1c(F)c2cnc(NC(=O)C3CC3)cc2n1C] | | |
| 59 | 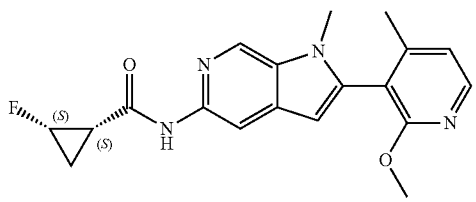 | 59-1 | 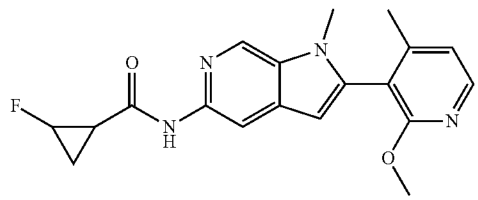 [SMILES: COc1nccc(C)c1-c1cc2cc(NC(=O)C3CC3F)ncc2n1C] |
| 60 | 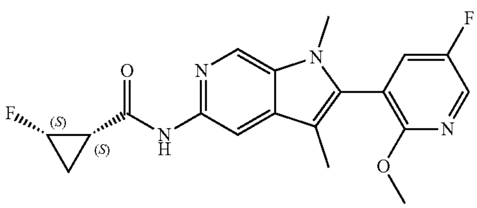 | 60-1 | 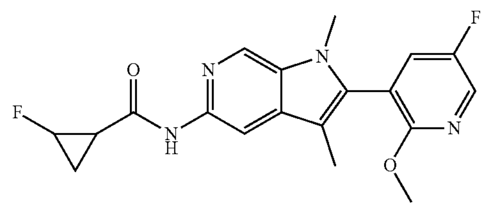 [SMILES: COc1ncc(F)cc1-c1c(C)c2cc(NC(=O)C3CC3F)ncc2n1C] |
| 61 | 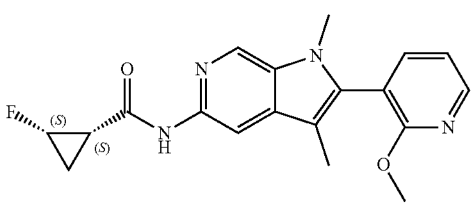 | 61-1 | 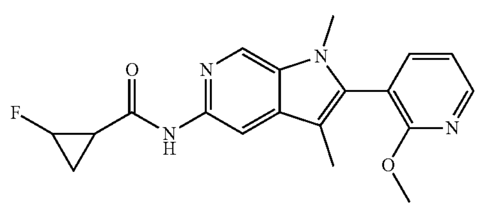 |
| 62 | 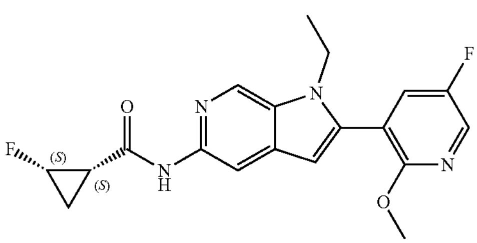 | 62-1 | 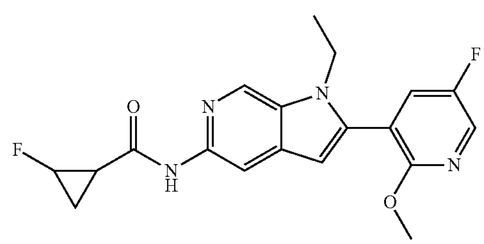 [SMILES: CCn1c(-c2cc(F)cnc2OC)cc2cc(NC(=O)C3CC3F)ncc21] |
| 63 | 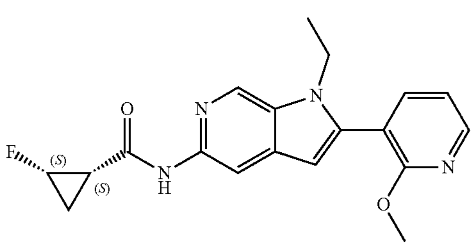 | 63-1 | 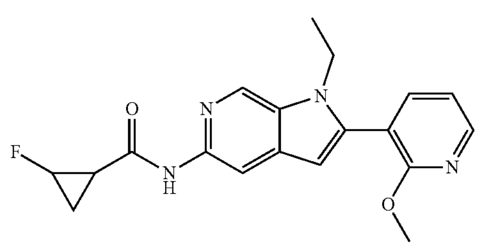 [SMILES: CCn1c(-c2cccnc2OC)cc2cc(NC(=O)C3CC3F)ncc21] |

TABLE 1-continued

| Cmpd No. | Compound Structure | Cmpd No. | Compound Structure |
|---|---|---|---|
| 64 | (structure) | 64-1 | (structure) |
| 65 | (structure) | 65-1 | (structure) |
| 66 | (structure) | 66-1 | (structure) |
| 67 | (structure) | 67-1 | (structure) |
| 68 | (structure) | 68-1 | (structure) |
| 69 | (structure) | 69-1 | (structure) |
| 70 | (structure) | 70-1 | (structure) |

TABLE 1-continued

| Cmpd No. | Compound Structure | Cmpd No. | Compound Structure |
|---|---|---|---|
| 71 | 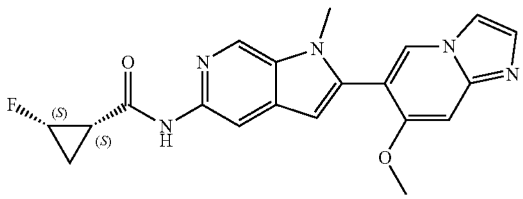 | 71-1 | 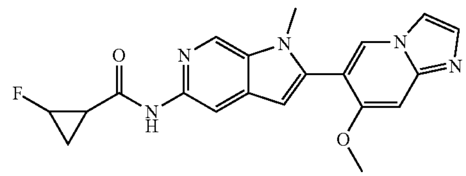 [SMILES: COc1cc2nccn2cc1-c1cc2cc(NC(=O)C3CC3F)ncc2n1C] |
| 72 | 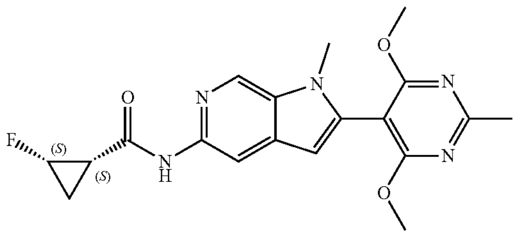 | 72-1 | 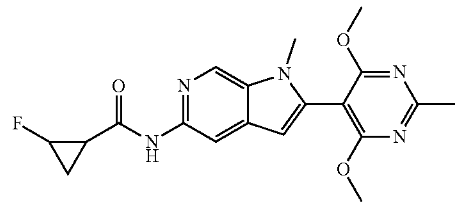 [SMILES: COc1nc(C)nc(OC)c1-c1cc2cc(NC(=O)C3CC3F)ncc2n1C] |
| 73 | 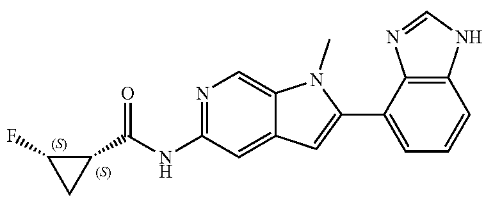 | 73-1 | 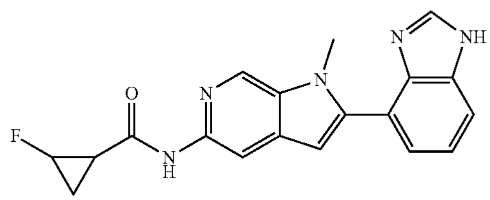 [SMILES: Cn1c(-c2cccc3[nH]cnc23)cc2cc(NC(=O)C3CC3F)ncc21] |
| 74 | 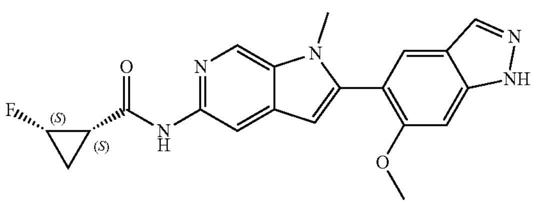 | 74-1 | 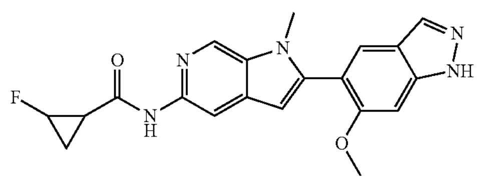 [SMILES: COc1cc2[nH]ncc2cc1-c1cc2cc(NC(=O)C3CC3F)ncc2n1C] |
| 75 | 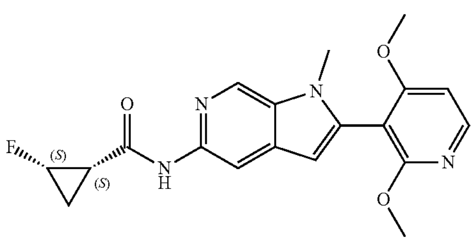 | 75-1 | 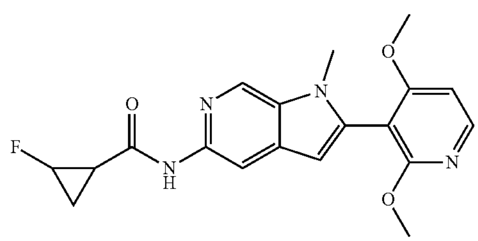 |
| 76 | 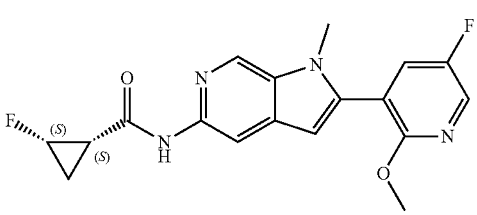 | 76-1 | 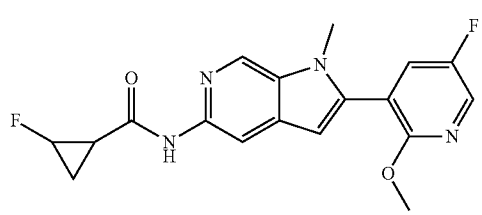 [SMILES: COc1ncc(F)cc1-c1cc2cc(NC(=O)C3CC3F)ncc2n1C] |
| 77 | 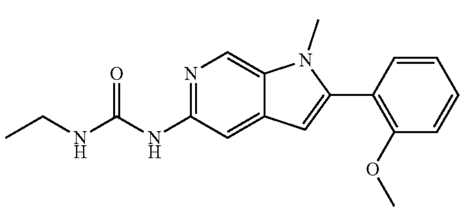 [SMILES: CCNC(=O)Nc1cc2cc(-c3ccccc3OC)n(C)c2cn1] | | |

TABLE 1-continued

| Cmpd No. | Compound Structure | Cmpd No. | Compound Structure |
| --- | --- | --- | --- |
| 78 | 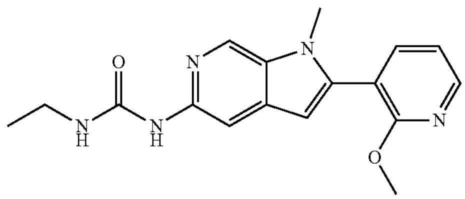 [SMILES: CCNC(=O)Nc1cc2cc(-c3cccnc3OC)n(C)c2cn1] | | |
| 79 | 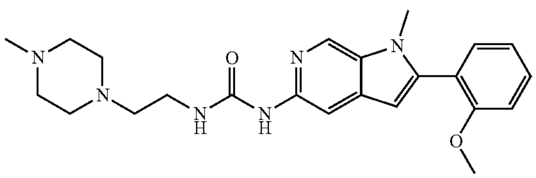 [SMILES: COc1ccccc1-c1cc2cc(NC(=O)NCCN3CCN(C)CC3)ncc2n1C] | | |
| 80 | 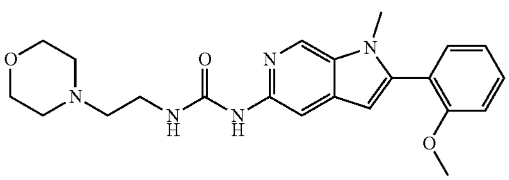 [SMILES: COc1ccccc1-c1cc2cc(NC(=O)NCCN3CCOCC3)ncc2n1C] | | |
| 81 | 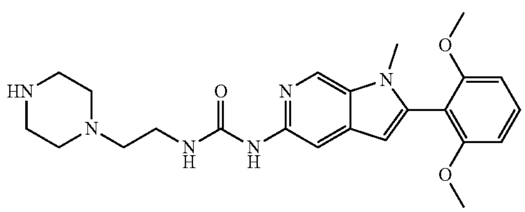 [SMILES: COc1cccc(OC)c1-c1cc2cc(NC(=O)NCCN3CCNCC3)ncc2n1C] | | |
| 82 | 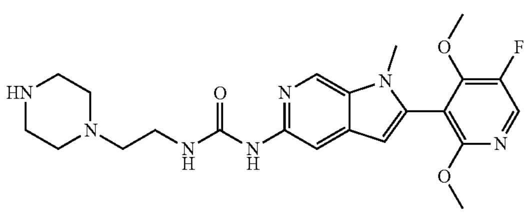 [SMILES: COc1ncc(F)c(OC)c1-c1cc2cc(NC(=O)NCCN3CCNCC3)ncc2n1C] | | |
| 83 | 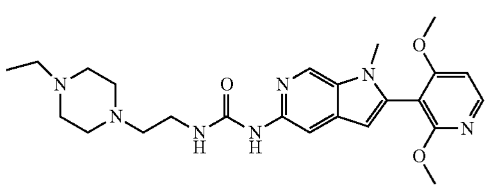 [SMILES: CCN1CCN(CCNC(=O)Nc2cc3cc(-c4c(OC)ccnc4OC)n(C)c3cn2)CC1] | | |
| 84 | 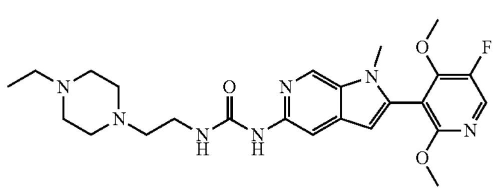 [SMILES: CCN1CCN(CCNC(=O)Nc2cc3cc(-c4c(OC)ncc(F)c4OC)n(C)c3cn2)CC1] | | |

TABLE 1-continued

| Cmpd No. | Compound Structure | Cmpd No. | Compound Structure |
|---|---|---|---|
| 85 | 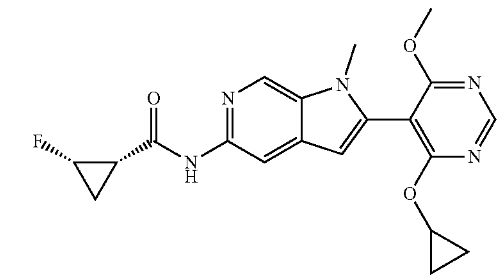 [SMILES: COc1ncnc(OC2CC2)c1-c1cc2cc(NC(=O)[C@@H]3C[C@@H]3F)ncc2n1C] | 85-1 | 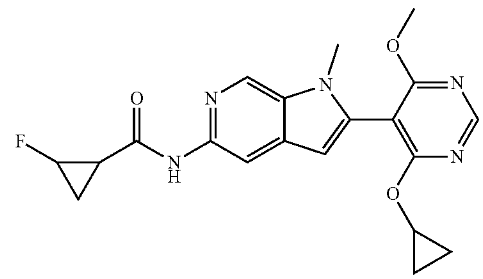 [SMILES: COc1ncnc(OC2CC2)c1-c1cc2cc(NC(=O)C3CC3F)ncc2n1C] |
| 86 | 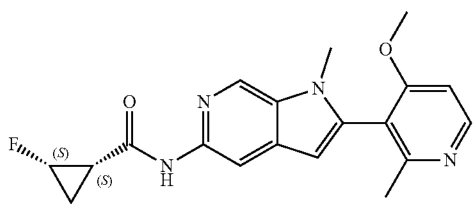 | 86-1 | 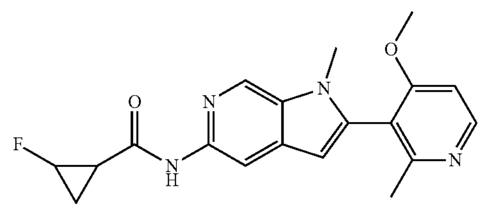 [SMILES: COc1ccnc(C)c1-c1cc2cc(NC(=O)C3CC3F)ncc2n1C] |
| 87 | 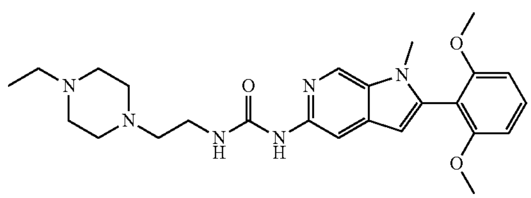 [SMILES: CCN1CCN(CCNC(=O)Nc2cc3cc(-c4c(OC)cccc4OC)n(C)c3cn2)CC1] | | |
| 88 | 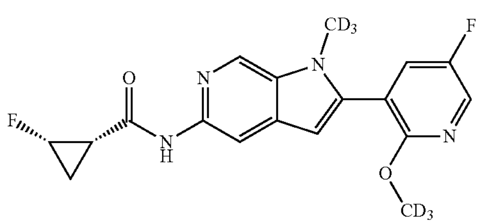 [SMILES: [2H]C([2H])([2H])Oc1ncc(F)cc1-c1cc2cc(NC(=O)[C@@H]3C[C@@H]3F)ncc2n1C([2H])([2H])[2H]] | 88-1 | 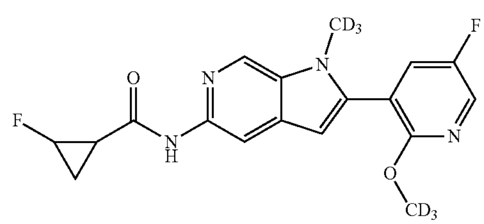 [SMILES: [2H]C([2H])([2H])Oc1ncc(F)cc1-c1cc2cc(NC(=O)C3CC3F)ncc2n1C([2H])([2H])[2H]] |
| 89 | 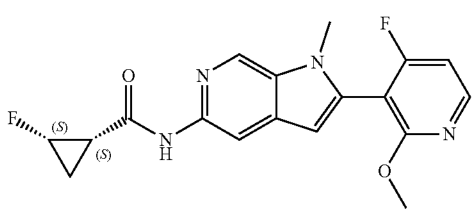 | 89-1 | 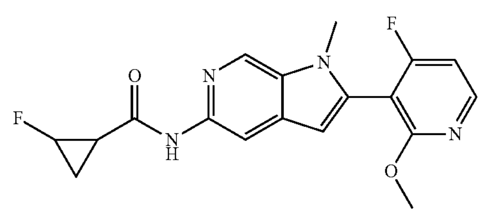 [SMILES: COc1nccc(F)c1-c1cc2cc(NC(=O)C3CC3F)ncc2n1C] |
| 90 | 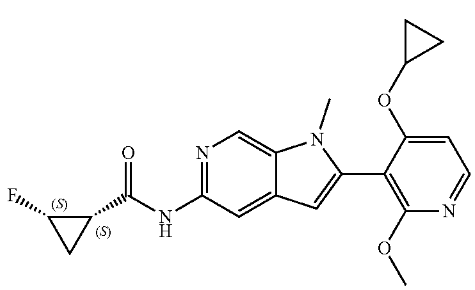 | 90-1 | 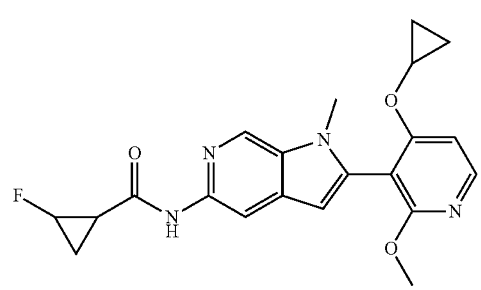 [SMILES: COc1nccc(OC2CC2)c1-c1cc2cc(NC(=O)C3CC3F)ncc2n1C] |

TABLE 1-continued

| Cmpd No. | Compound Structure | Cmpd No. | Compound Structure |
|---|---|---|---|
| 91 | 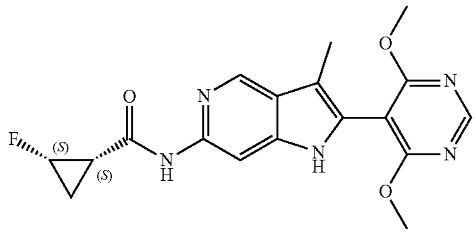 | 91-1 | 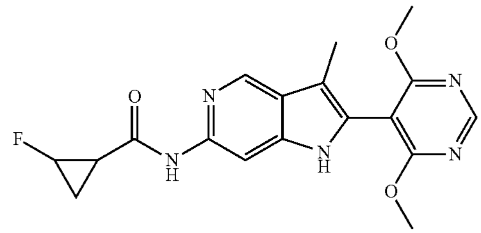 [SMILES: COc1ncnc(OC)c1-c1[nH]c2cc(NC(=O)C3CC3F)ncc2c1C] |
| 92 | 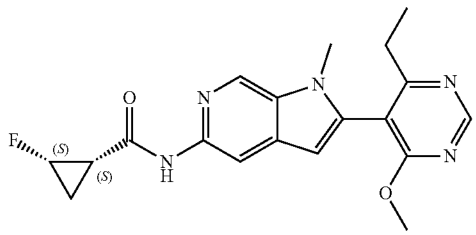 | 92-1 | 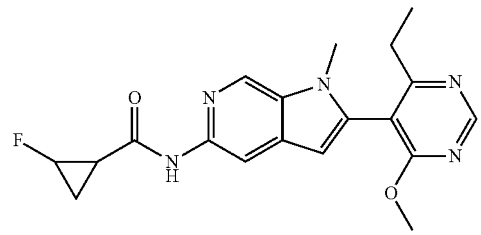 |
| 93 | 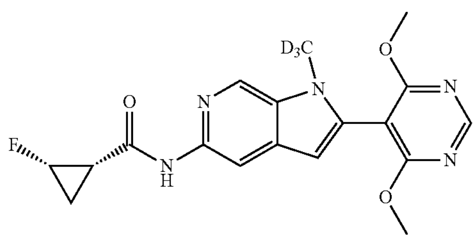 [SMILES: [2H]C([2H])([2H])n1c(-c2c(OC)ncnc2OC)cc2cc(NC(=O)[C@@H]3C[C@@H]3F)ncc21] | 93-1 | 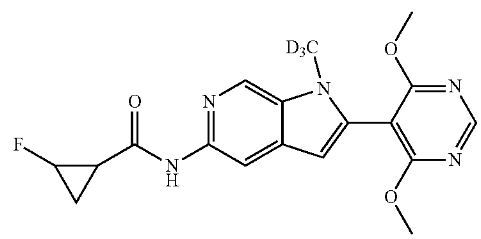 [SMILES: [2H]C([2H])([2H])n1c(-c2c(OC)ncnc2OC)cc2cc(NC(=O)C3CC3F)ncc21] |
| 94 | 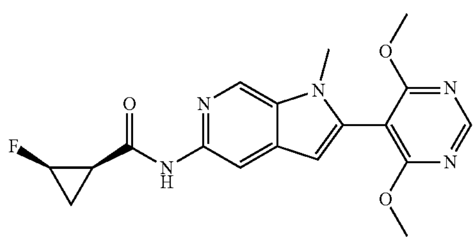 [SMILES: COc1ncnc(OC)c1-c1cc2cc(NC(=O)[C@H]3C[C@H]3F)ncc2n1C] | 39-1 | 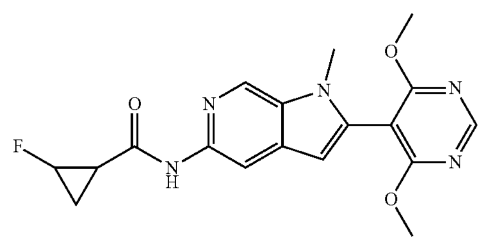 [SMILES: COc1ncnc(OC)c1-c1cc2cc(NC(=O)C3CC3F)ncc2n1C] |
| 95 | 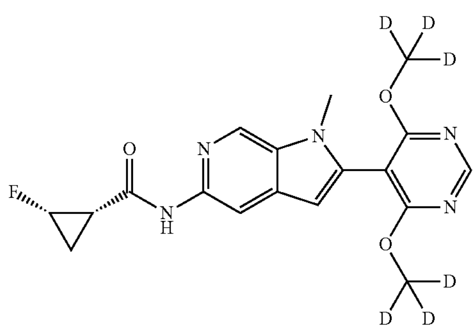 [SMILES: [2H]C([2H])([2H])Oc1ncnc(OC([2H])([2H])[2H])c1-c1cc2cc(NC(=O)[C@@H]3C[C@@H]3F)ncc2n1C] | 95-1 | 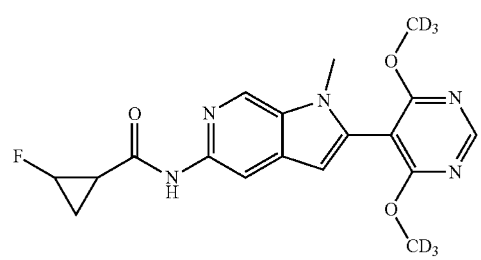 |
| 96 | 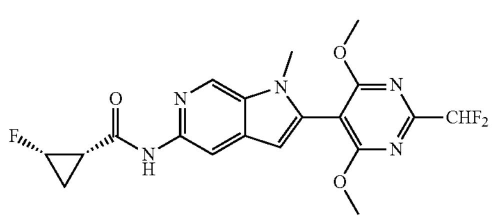 [SMILES: COc1nc(C(F)F)nc(OC)c1-c1cc2cc(NC(=O)C3CC3F)ncc2n1C] | 96-1 | 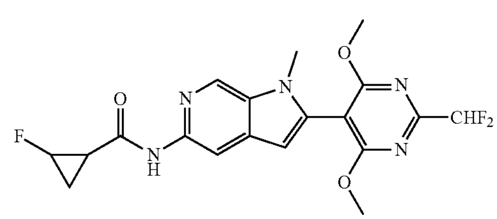 |

TABLE 1-continued

| Cmpd No. | Compound Structure | Cmpd No. | Compound Structure |
|---|---|---|---|
| 97 | 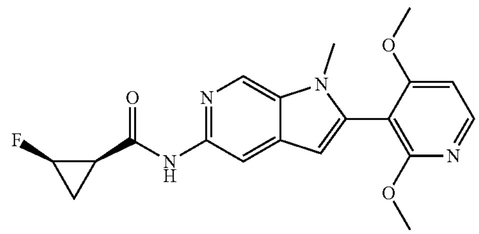 [SMILES: COc1ccnc(OC)c1-c1cc2cc(NC(=O)[C@H]3C[C@H]3F)ncc2n1C] | 75-1 | 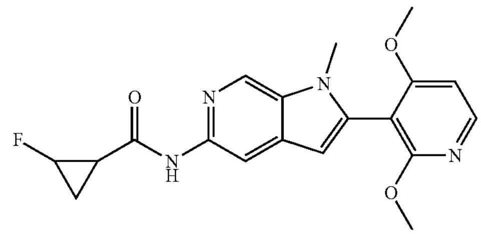 [SMILES: COc1ccnc(OC)c1-c1cc2cc(NC(=O)C3CC3F)ncc2n1C] |
| 98 | 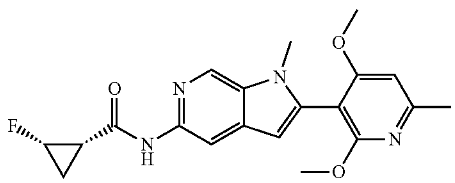 [SMILES: COc1cc(C)nc(OC)c1-c1cc2cc(NC(=O)[C@@H]3C[C@@H]3F)ncc2n1C] | 98-1 | 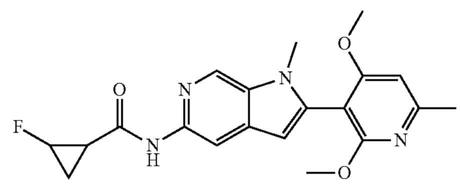 |
| 99 | 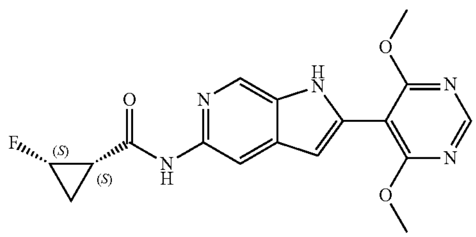 | 99-1 | 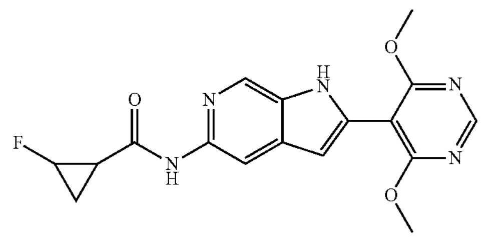 [SMILES: COc1ncnc(OC)c1-c1cc2cc(NC(=O)C3CC3F)ncc2[nH]1] |
| 100 | 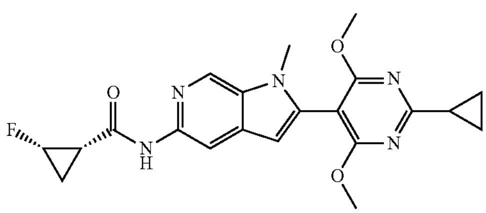 [SMILES: COc1nc(C2CC2)nc(OC)c1-c1cc2cc(NC(=O)[C@@H]3C[C@@H]3F)ncc2n1C] | 100-1 | 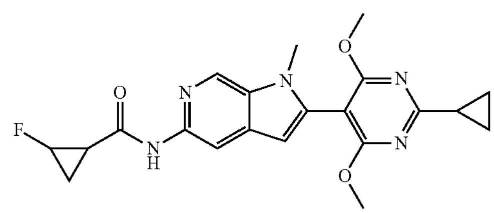 [SMILES: COc1nc(C2CC2)nc(OC)c1-c1cc2cc(NC(=O)C3CC3F)ncc2n1C] |
| 101 | 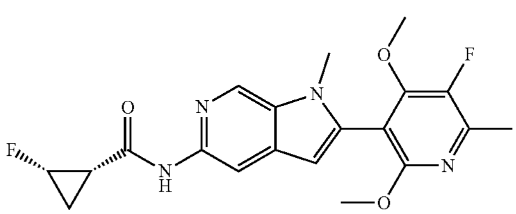 [SMILES: COc1nc(C)c(F)c(OC)c1-c1cc2cc(NC(=O)[C@@H]3C[C@@H]3F)ncc2n1C] | 101-1 | 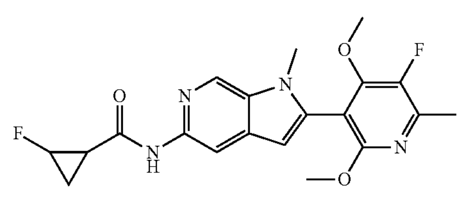 [SMILES: COc1nc(C)c(F)c(OC)c1-c1cc2cc(NC(=O)C3CC3F)ncc2n1C] |
| 102 | 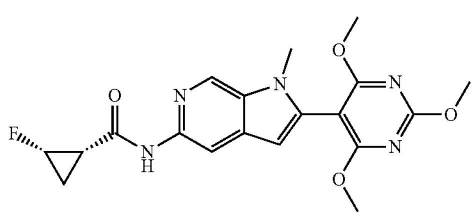 | 102-1 | 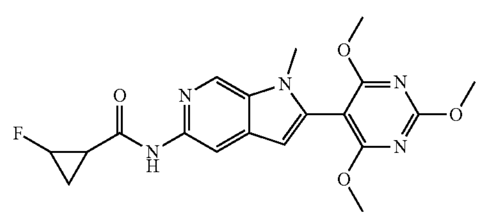 [SMILES: COc1nc(OC)c(-c2cc3cc(NC(=O)C4CC4F)ncc3n2C)c(OC)n1] |
| 103 | 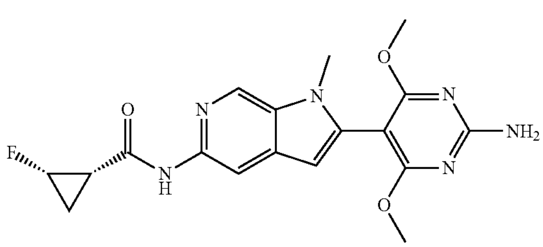 [SMILES: COc1nc(N)nc(OC)c1-c1cc2cc(NC(=O)[C@@H]3C[C@@H]3F)ncc2n1C] | 103-1 | 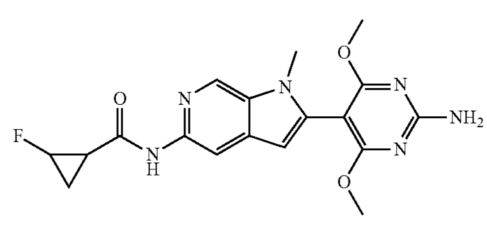 [SMILES: COc1nc(N)nc(OC)c1-c1cc2cc(NC(=O)C3CC3F)ncc2n1C] |

TABLE 1-continued

| Cmpd No. | Compound Structure | Cmpd No. | Compound Structure |
| --- | --- | --- | --- |
| 104 | 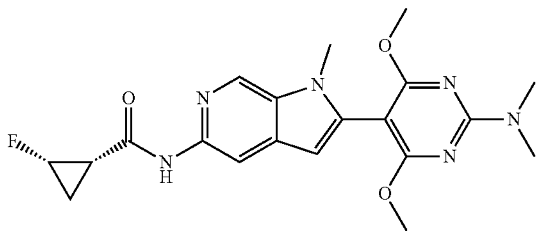 [SMILES: COc1nc(N(C)C)nc(OC)c1-c1cc2cc(NC(=O)[C@@H]3C[C@@H]3F)ncc2n1C] | 104-1 | 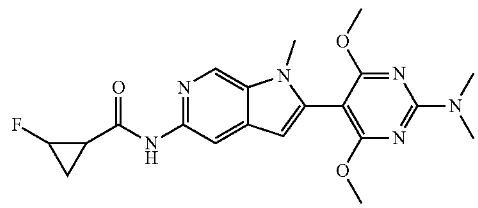 [SMILES: COc1nc(N(C)C)nc(OC)c1-c1cc2cc(NC(=O)C3CC3F)ncc2n1C] |
| 105 | 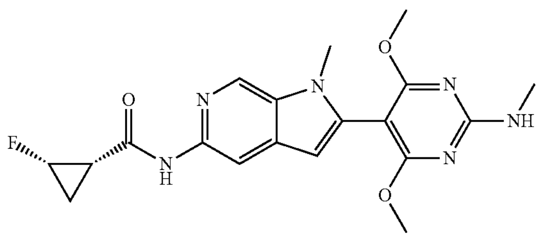 [SMILES: CNc1nc(OC)c(-c2cc3cc(NC(=O)[C@@H]4C[C@@H]4F)ncc3n2C)c(OC)n1] | 105-1 | 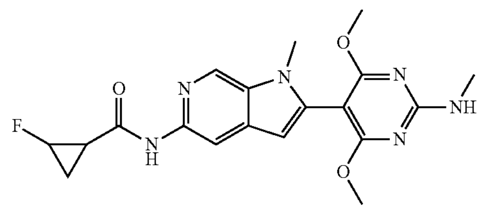 [SMILES: CNc1nc(OC)c(-c2cc3cc(NC(=O)C4CC4F)ncc3n2C)c(OC)n1] |
| 106 | 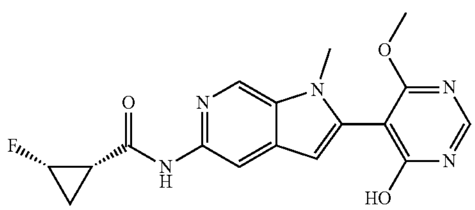 [SMILES: COc1ncnc(O)c1-c1cc2cc(NC(=O)[C@@H]3C[C@@H]3F)ncc2n1C] | 106-1 | 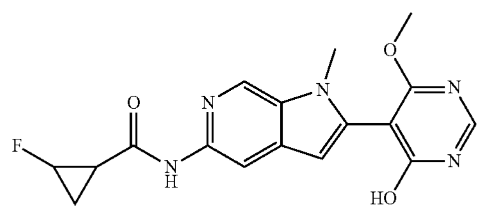 [SMILES: COc1ncnc(O)c1-c1cc2cc(NC(=O)C3CC3F)ncc2n1C] |
| 107 | 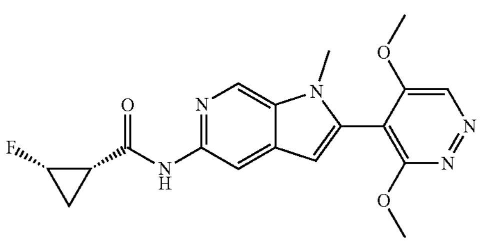 [SMILES: COc1cnnc(OC)c1-c1cc2cc(NC(=O)[C@@H]3C[C@@H]3F)ncc2n1C] | 107-1 | 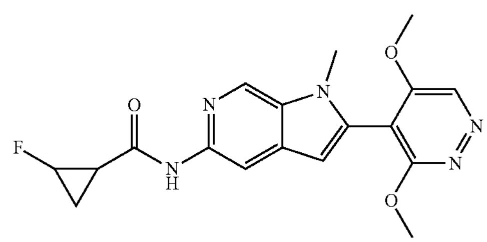 [SMILES: COc1cnnc(OC)c1-c1cc2cc(NC(=O)C3CC3F)ncc2n1C] |
| 108 | 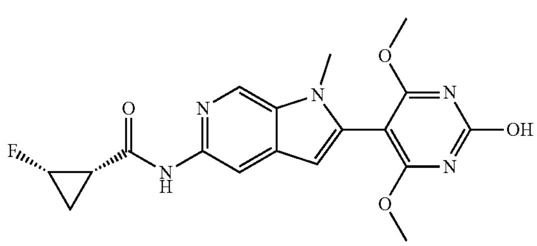 [SMILES: COc1nc(O)nc(OC)c1-c1cc2cc(NC(=O)[C@@H]3C[C@@H]3F)ncc2n1C] | 108-1 | 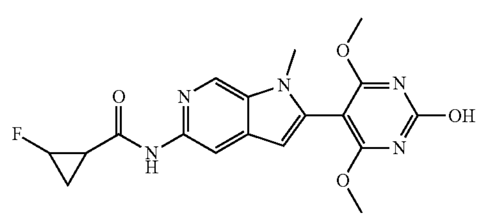 [SMILES: COc1nc(O)nc(OC)c1-c1cc2cc(NC(=O)C3CC3F)ncc2n1C] |
| 109 | 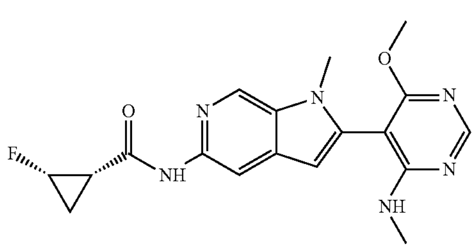 [SMILES: CNc1ncnc(OC)c1-c1cc2cc(NC(=O)[C@@H]3C[C@@H]3F)ncc2n1C] | 109-1 | 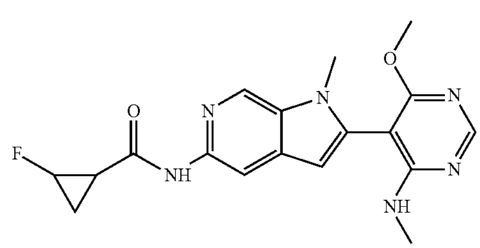 [SMILES: CNc1ncnc(OC)c1-c1cc2cc(NC(=O)C3CC3F)ncc2n1C] |

TABLE 1-continued

| Cmpd No. | Compound Structure | Cmpd No. | Compound Structure |
|---|---|---|---|
| 110 | 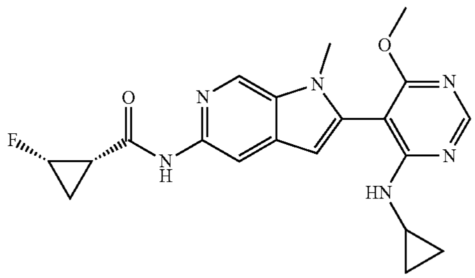 [SMILES: COc1ncnc(NC2CC2)c1-c1cc2cc(NC(=O)[C@@H]3C[C@@H]3F)ncc2n1C] | 110-1 | 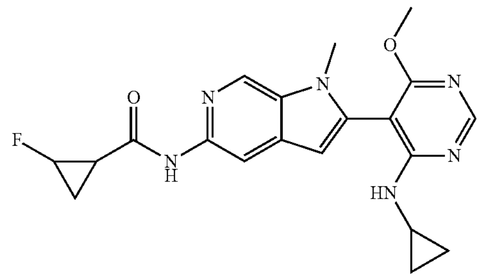 [SMILES: COc1ncnc(NC2CC2)c1-c1cc2cc(NC(=O)C3CC3F)ncc2n1C] |
| 111 | 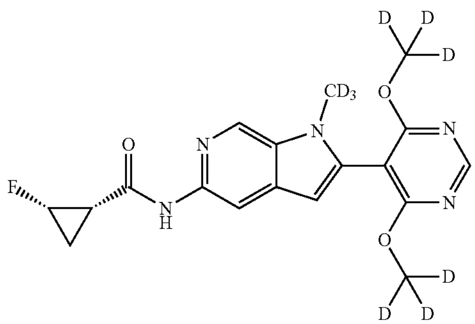 | 111-1 | 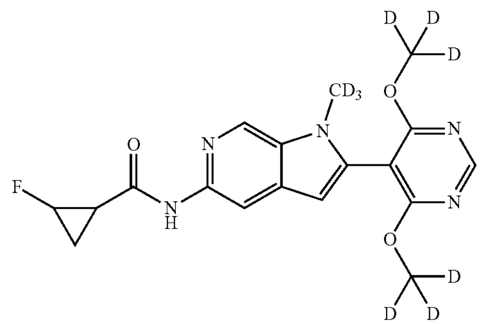 [SMILES: [2H]C([2H])([2H])Oc1ncnc(OC([2H])([2H])[2H])c1-c1cc2cc(NC(=O)[C@@H]3C[C@@H]3F)ncc2n1C([2H])([2H])[2H]] |
| 112 | 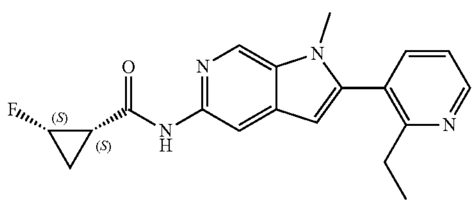 | 112-1 | 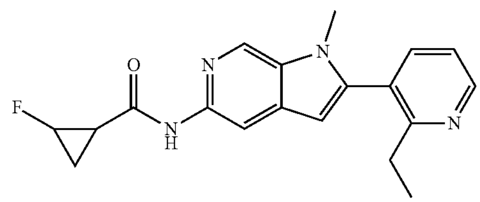 [SMILES: CCc1ncccc1-c1cc2cc(NC(=O)C3CC3F)ncc2n1C] |
| 113 | 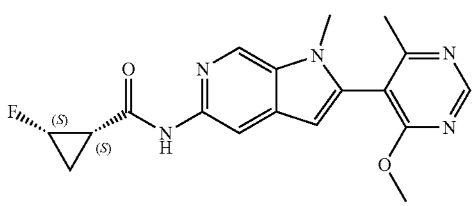 | 113-1 | 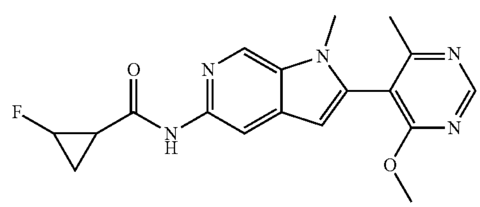 [SMILES: COc1ncnc(C)c1-c1cc2cc(NC(=O)C3CC3F)ncc2n1C] |
| 114 | 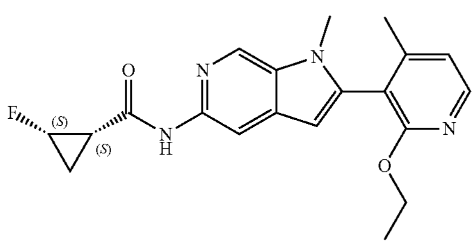 | 114-1 | 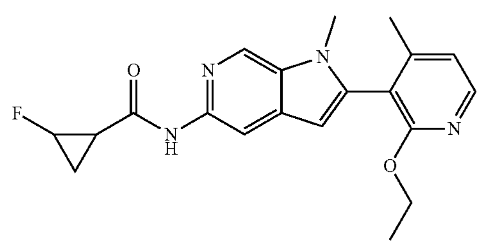 [SMILES: CCOc1nccc(C)c1-c1cc2cc(NC(=O)C3CC3F)ncc2n1C] |
| 115 | 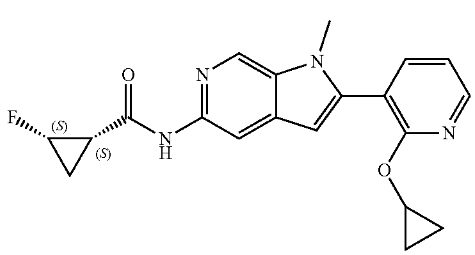 | 115-1 | 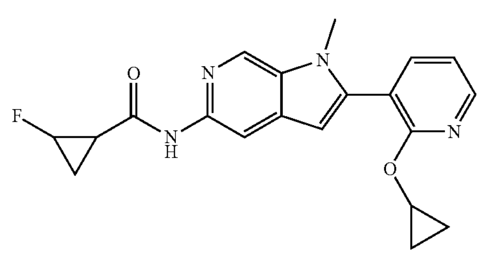 [SMILES: Cn1c(-c2cccnc2OC2CC2)cc2cc(NC(=O)C3CC3F)ncc21] |

TABLE 1-continued
| Cmpd No. | Compound Structure | Cmpd No. | Compound Structure |
|---|---|---|---|
| 116 | 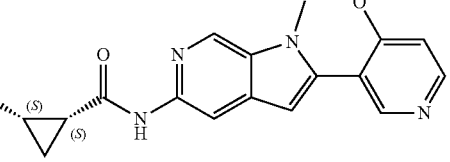 | 116-1 | 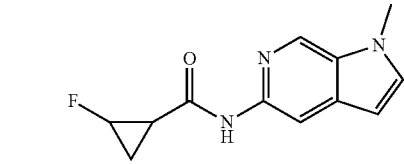 |
| 117 | 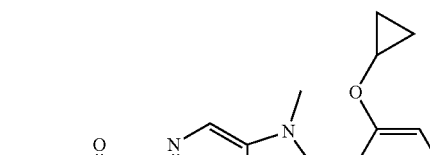 | 117-1 | 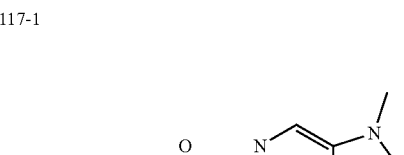 |
| 118 | 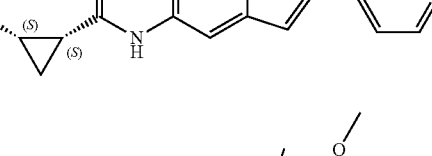 | | |
| 119 | 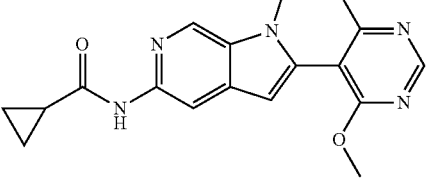 | 119-1 | 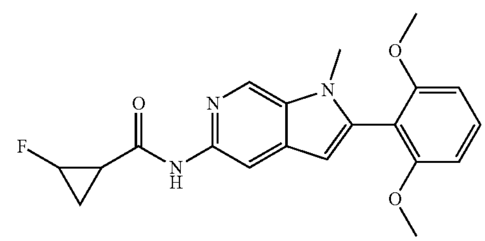 [SMILES: COc1cccc(OC)c1-c1cc2cc(NC(=O)C3CC3F)ncc2n1C] |
| 120 | 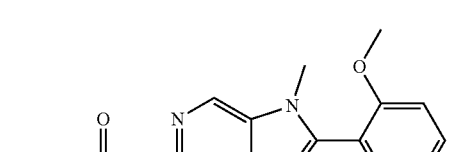 | 120-1 | 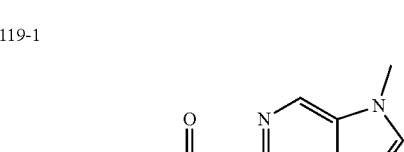 |
| 121 | 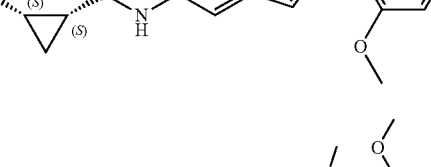 | 120-1 | 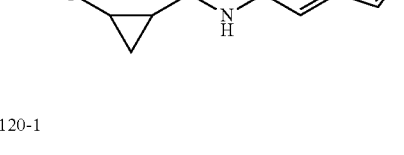 |
| 122 | 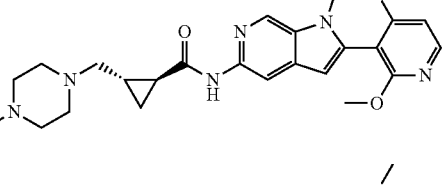 | 122-1 | 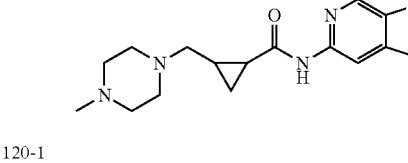 |

TABLE 1-continued

| Cmpd No. | Compound Structure | Cmpd No. | Compound Structure |
|---|---|---|---|
| 123 | 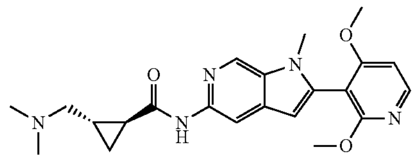 [SMILES: COc1ccnc(OC)c1-c1cc2cc(NC(=O)[C@H]3C[C@@H]3CN(C)C)ncc2n1C] | 122-1 | 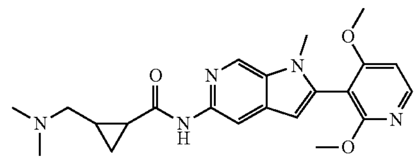 [SMILES: COc1ccnc(OC)c1-c1cc2cc(NC(=O)C3CC3CN(C)C)ncc2n1C] |
| 124 | 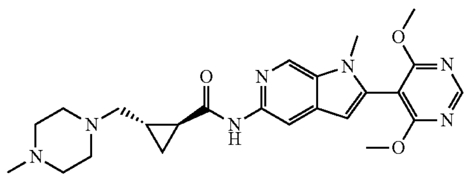 [SMILES: COc1ncnc(OC)c1-c1cc2cc(NC(=O)[C@H]3C[C@@H]3CN3CCN(C)CC3)ncc2n1C] | 124-1 | 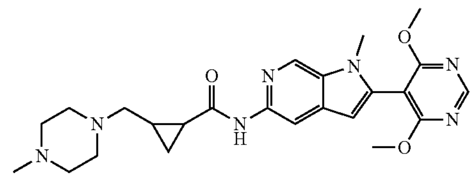 [SMILES: COc1ncnc(OC)c1-c1cc2cc(NC(=O)C3CC3CN3CCN(C)CC3)ncc2n1C] |
| 125 | 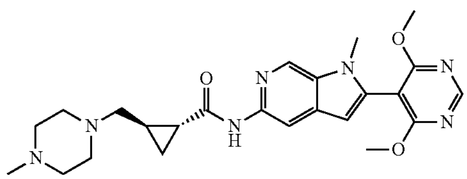 [SMILES: COc1ncnc(OC)c1-c1cc2cc(NC(=O)[C@@H]3C[C@H]3CN3CCN(C)CC3)ncc2n1C] | 124-1 | 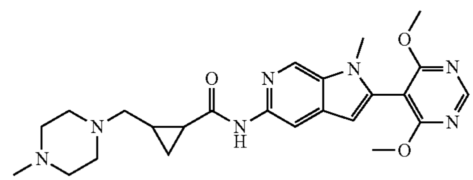 |
| 126 | 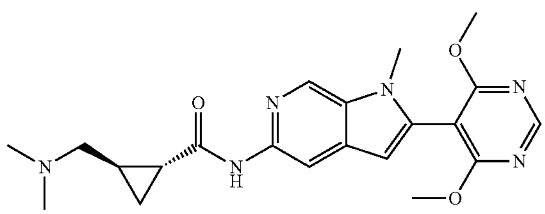 [SMILES: COc1ncnc(OC)c1-c1cc2cc(NC(=O)[C@@H]3C[C@H]3CN(C)C)ncc2n1C] | 126-1 | 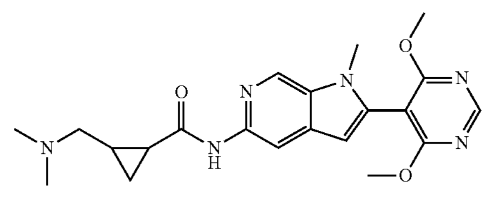 [SMILES: COc1ncnc(OC)c1-c1cc2cc(NC(=O)C3CC3CN(C)C)ncc2n1C] |
| 127 | 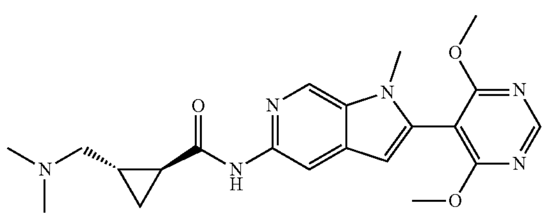 [SMILES: COc1ncnc(OC)c1-c1cc2cc(NC(=O)[C@H]3C[C@@H]3CN(C)C)ncc2n1C] | 126-1 | 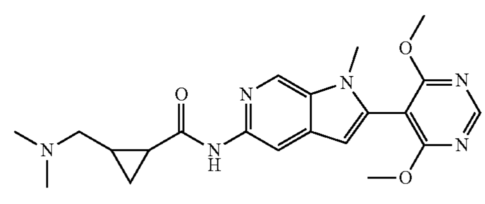 [SMILES: COc1ncnc(OC)c1-c1cc2cc(NC(=O)C3CC3CN(C)C)ncc2n1C] |
| 128 | 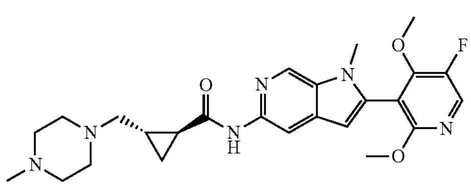 [SMILES: COc1ncc(F)c(OC)c1-c1cc2cc(NC(=O)[C@H]3C[C@@H]3CN3CCN(C)CC3)ncc2n1C] | 128-1 | 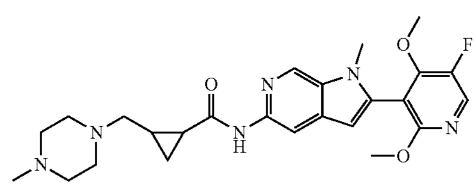 [SMILES: COc1ncc(F)c(OC)c1-c1cc2cc(NC(=O)C3CC3CN3CCN(C)CC3)ncc2n1C] |
| 129 | 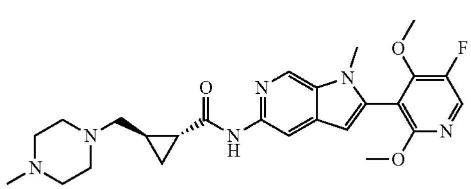 [SMILES: COc1ncc(F)c(OC)c1-c1cc2cc(NC(=O)[C@@H]3C[C@H]3CN3CCN(C)CC3)ncc2n1C] | 128-1 | 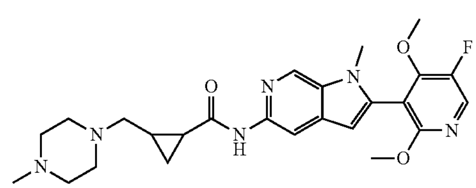 [SMILES: COc1ncc(F)c(OC)c1-c1cc2cc(NC(=O)C3CC3CN3CCN(C)CC3)ncc2n1C] |
| 130 | 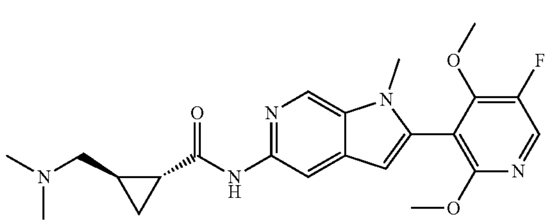 [SMILES: COc1ncc(F)c(OC)c1-c1cc2cc(NC(=O)[C@@H]3C[C@H]3CN(C)C)ncc2n1C] | 130-1 | 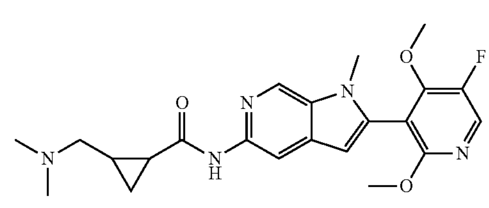 [SMILES: COc1ncc(F)c(OC)c1-c1cc2cc(NC(=O)C3CC3CN(C)C)ncc2n1C] |

TABLE 1-continued

| Cmpd No. | Compound Structure | Cmpd No. | Compound Structure |
|---|---|---|---|
| 131 | 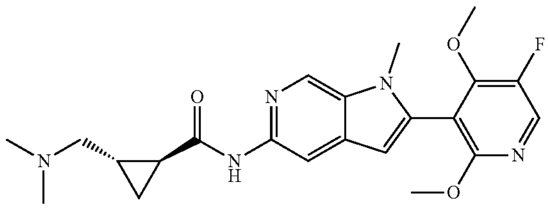 [SMILES: COc1ncc(F)c(OC)c1-c1cc2cc(NC(=O)[C@H]3C[C@@H]3CN(C)C)ncc2n1C] | 130-1 | 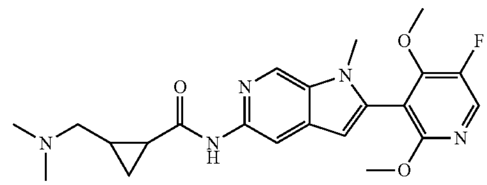 [SMILES: COc1ncc(F)c(OC)c1-c1cc2cc(NC(=O)C3CC3CN(C)C)ncc2n1C] |
| 132 | 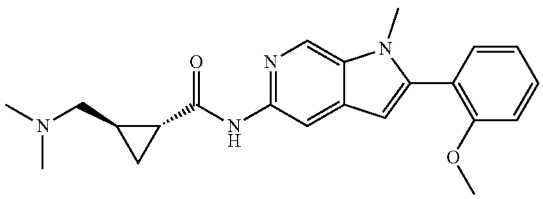 [SMILES: COc1ccccc1-c1cc2cc(NC(=O)[C@@H]3C[C@H]3CN(C)C)ncc2n1C] | 132-1 | 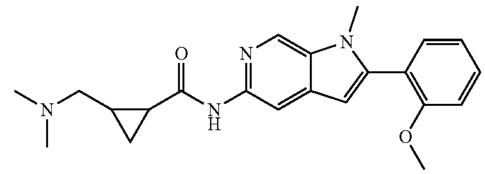 [SMILES: COc1ccccc1-c1cc2cc(NC(=O)C3CC3CN(C)C)ncc2n1C] |
| 133 | 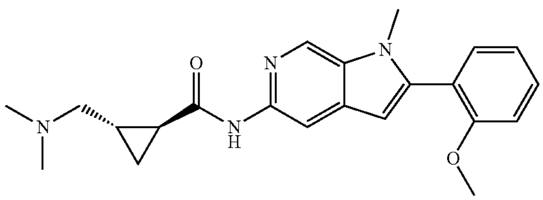 [SMILES: COc1ccccc1-c1cc2cc(NC(=O)[C@H]3C[C@@H]3CN(C)C)ncc2n1C] | 132-1 | 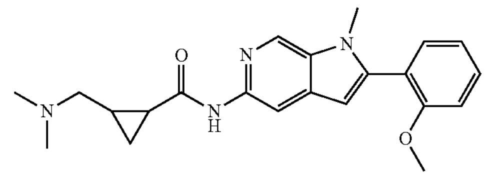 [SMILES: COc1ccccc1-c1cc2cc(NC(=O)C3CC3CN(C)C)ncc2n1C] |
| 134 | 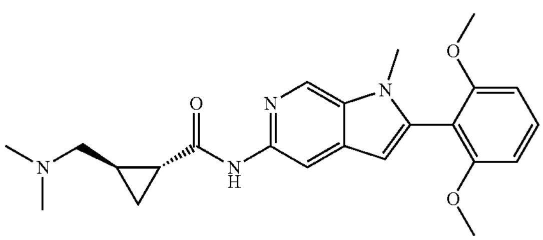 [SMILES: COc1cccc(OC)c1-c1cc2cc(NC(=O)[C@@H]3C[C@H]3CN(C)C)ncc2n1C] | 134-1 | 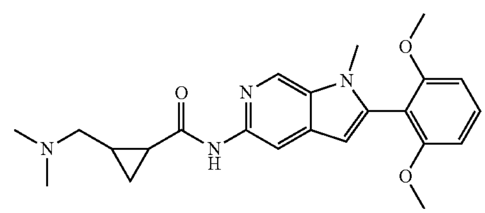 [SMILES: COc1cccc(OC)c1-c1cc2cc(NC(=O)C3CC3CN(C)C)ncc2n1C] |
| 135 | 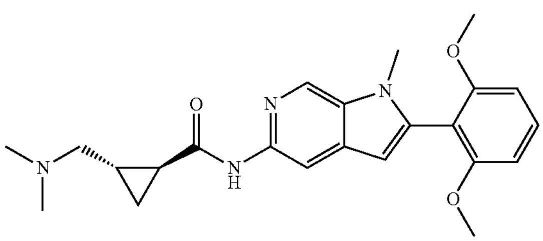 [SMILES: COc1cccc(OC)c1-c1cc2cc(NC(=O)[C@H]3C[C@@H]3CN(C)C)ncc2n1C] | 134-1 | 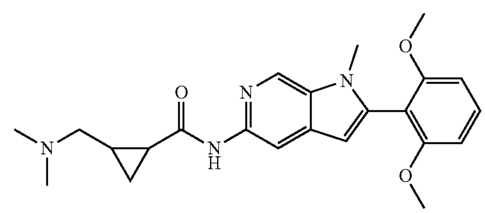 [SMILES: COc1cccc(OC)c1-c1cc2cc(NC(=O)C3CC3CN(C)C)ncc2n1C] |
| 136 | 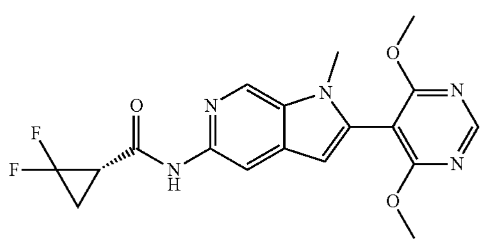 [SMILES: COc1ncnc(OC)c1-c1cc2cc(NC(=O)[C@@H]3CC3(F)F)ncc2n1C] | 136-1 | 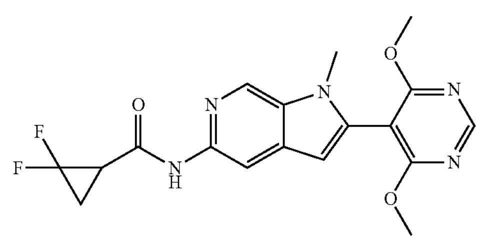 [SMILES: COc1ncnc(OC)c1-c1cc2cc(NC(=O)C3CC3(F)F)ncc2n1C] |
| 137 | 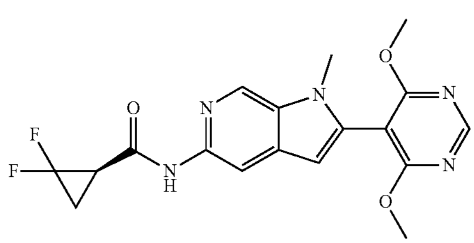 [SMILES: COc1ncnc(OC)c1-c1cc2cc(NC(=O)[C@H]3CC3(F)F)ncc2n1C] | 136-1 | 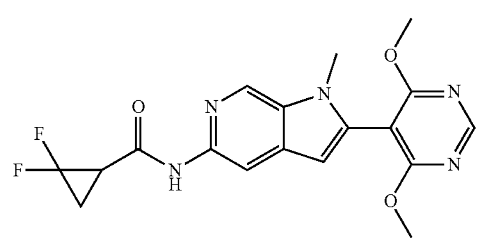 [SMILES: COc1ncnc(OC)c1-c1cc2cc(NC(=O)C3CC3(F)F)ncc2n1C] |

| Cmpd No. | Compound Structure | Cmpd No. | Compound Structure |
|---|---|---|---|
| 138 | 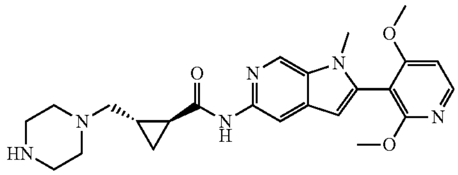 [SMILES: COc1ccnc(OC)c1-c1cc2cc(NC(=O)[C@H]3C[C@@H]3CN3CCNCC3)ncc2n1C] | 138-1 | 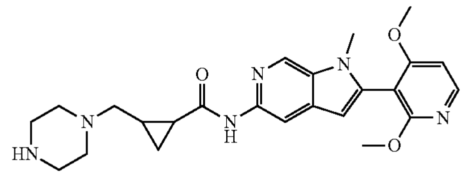 [SMILES: COc1ccnc(OC)c1-c1cc2cc(NC(=O)C3CC3CN3CCNCC3)ncc2n1C] |
| 139 | 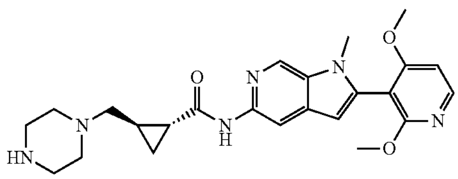 [SMILES: COc1ccnc(OC)c1-c1cc2cc(NC(=O)[C@@H]3C[C@H]3CN3CCNCC3)ncc2n1C] | 138-1 | 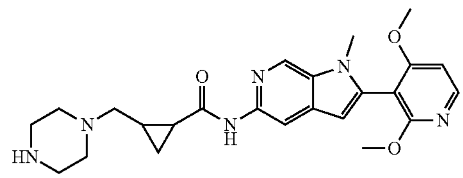 [SMILES: COc1ccnc(OC)c1-c1cc2cc(NC(=O)C3CC3CN3CCNCC3)ncc2n1C] |
| 140 | 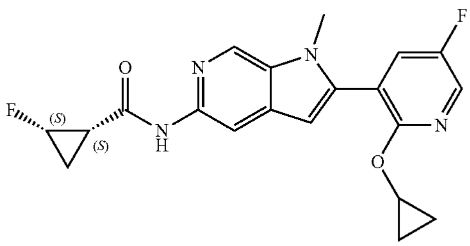 | 140-1 | 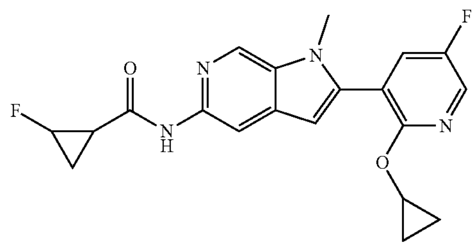 [SMILES: Cn1c(-c2cc(F)cnc2OC2CC2)cc2cc(NC(=O)C3CC3F)ncc21] |
| 141 | 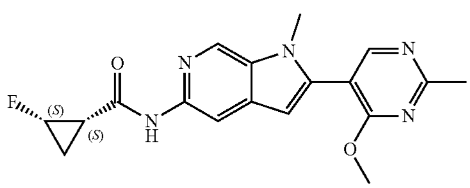 | 141-1 | 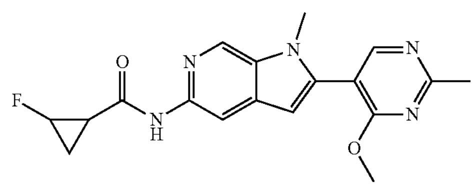 [SMILES: COc1nc(C)ncc1-c1cc2cc(NC(=O)C3CC3F)ncc2n1C] |
| 142 | 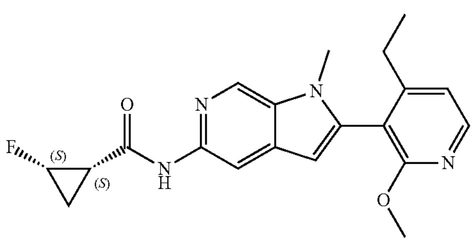 | 142-1 | 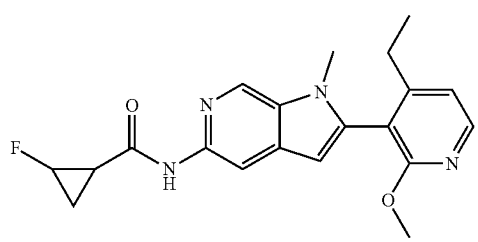 |
| 143 | 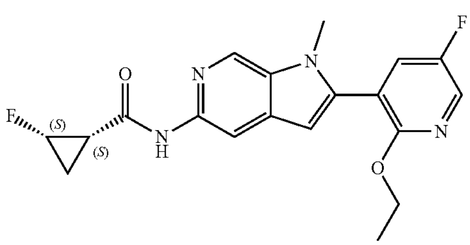 | 143-1 | 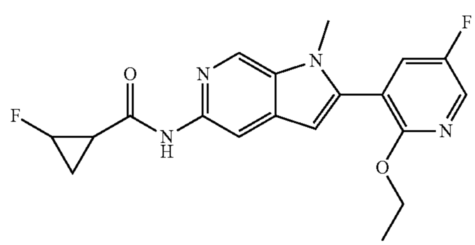 [SMILES: CCOc1ncc(F)cc1-c1cc2cc(NC(=O)C3CC3F)ncc2n1C] |
| 144 | 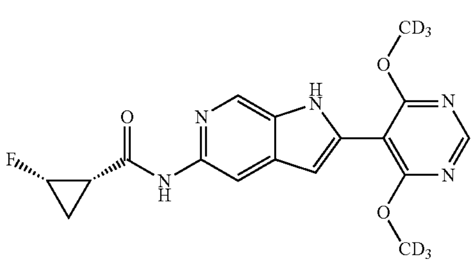 | 144-1 | 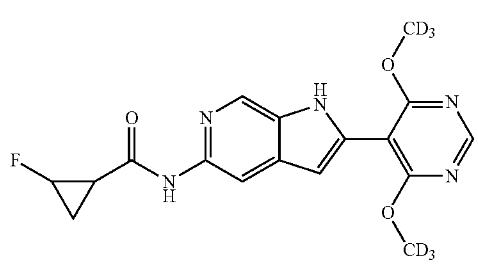 [SMILES: [2H]C([2H])([2H])Oc1ncnc(OC([2H])([2H])[2H])c1-c1cc2cc(NC(=O)C3CC3F)ncc2[nH]1] |

TABLE 1-continued

| Cmpd No. | Compound Structure | Cmpd No. | Compound Structure |
|---|---|---|---|
| 145 | 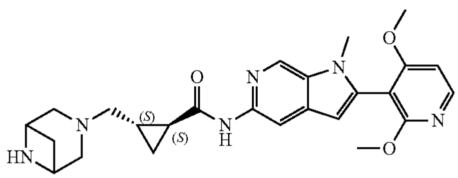 | 145-1 | 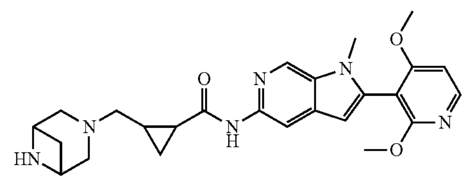 [SMILES: COc1ccnc(OC)c1-c1cc2cc(NC(=O)C3CC3CN3CC4CC(C3)N4)ncc2n1C] |
| 146 | 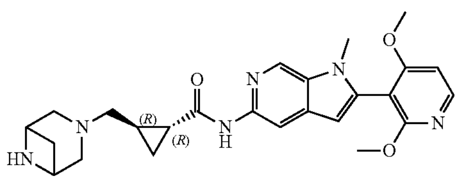 | 145-1 | 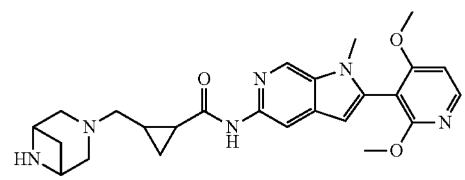 [SMILES: COc1ccnc(OC)c1-c1cc2cc(NC(=O)C3CC3CN3CC4CC(C3)N4)ncc2n1C] |
| 147 | (trans) | 147-1 | 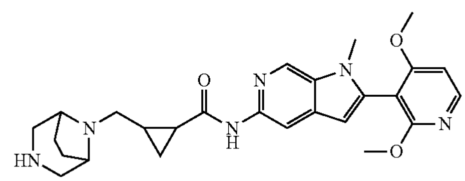 [SMILES: COc1ccnc(OC)c1-c1cc2cc(NC(=O)C3CC3CN3C4CCC3CNC4)ncc2n1C] |

Although certain compounds described in Table 1 are presented as specific stereoisomers and/or in a non-stereochemical form, it is understood that any or all non-stereochemical forms and any or all stereochemical forms, including any enantiomeric or diastereomeric forms, and any tautomers or other forms of any of the compounds of Table 1 are herein described. In some embodiments, the compound described herein is selected from Compound Nos, 1-147.

This disclosure also includes all salts, such as pharmaceutically acceptable salts, of compounds referred to herein. This disclosure also includes any or all of the stereochemical forms, including any enantiomeric or diastereomeric forms, and any tautomers or other forms, such as N-oxides, solvates, hydrates, or isotopomers, of the compounds described. The present disclosure also includes co-crystals of the compounds described herein. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

In the descriptions herein, it is understood that every description, variation, embodiment, or aspect of a moiety can be combined with every description, variation, embodiment, or aspect of other moieties the same as if each and every combination of descriptions is specifically and individually listed. For example, every description, variation, embodiment, or aspect provided herein with respect to $R^0$ of formula (I) may be combined with every description, variation, embodiment, or aspect of X, Y, m, $R^1$, $R^2$, $R^3$, $R^{3'}$, $R^4$, $R^5$, $R^6$, $R^7$, $R^{7'}$, $R^8$, $R^{8'}$, $R^9$, and/or $R^{10}$ the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments, or aspects of formula (I), where applicable, apply equally to any of formulae (I-A), (I-A-i), (I-B), (I-B-i) and (I-B-ii) detailed herein, and are equally described, the same as if each and every description, variation, embodiment or aspect were separately and individually listed for all formulae.

III. General Synthetic Methods

The compounds of the present disclosure may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

The intermediates described in the following preparations may contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See e.g., Greene and Wuts, *Protective Groups in Organic Synthesis*, (T. Greene and P. Wuts, eds., 2d ed. 1991).

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See e.g., J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994).

The compounds of the present invention, or a pharmaceutically acceptable salt, solvate, hydrate, or co-crystal thereof, or a mixture of any of the foregoing, may be prepared by a variety of procedures known in the art, some of which are illustrated in the Examples below. The specific synthetic steps for each of the routes described may be combined in different ways, to prepare compounds of the present disclosure, or salts thereof. The products of each step can be recovered by conventional methods well known in the art, including extraction, evaporation, precipitation, chromatography, filtration, trituration, and crystallization. The reagents and starting materials are readily available to one of ordinary skill in the art. Others may be made by standard techniques of organic and heterocyclic chemistry which are analogous to the syntheses of known structurally-similar compounds and the procedures described in the Examples which follow including any novel procedures.

Compounds of formula (I) can be prepared according to Scheme A, Scheme B, Scheme C, Scheme D, Scheme E, Scheme F, Scheme G, Scheme H, Scheme I, and Scheme J, wherein the $R^1$, $R^2$, $R^3$, $R^{3'}$, $R^4$, $R^5$, $R^6$, and m are as defined for formula (I) or any applicable variation thereof as detailed herein. More specifically, compounds of formula (I-A), (I-A-i) and (I-A-ii) may be prepared as described in Scheme A, Scheme B, Scheme E, Scheme F, Scheme I, and Scheme J; compounds of formula (I-B), (I-B-i) and (I-B-ii) may be prepared as described in Scheme A, Scheme B, Scheme C, Scheme D, Scheme E, Scheme F, Scheme G, Scheme H, Scheme I, and Scheme J.

Scheme A-Part I.

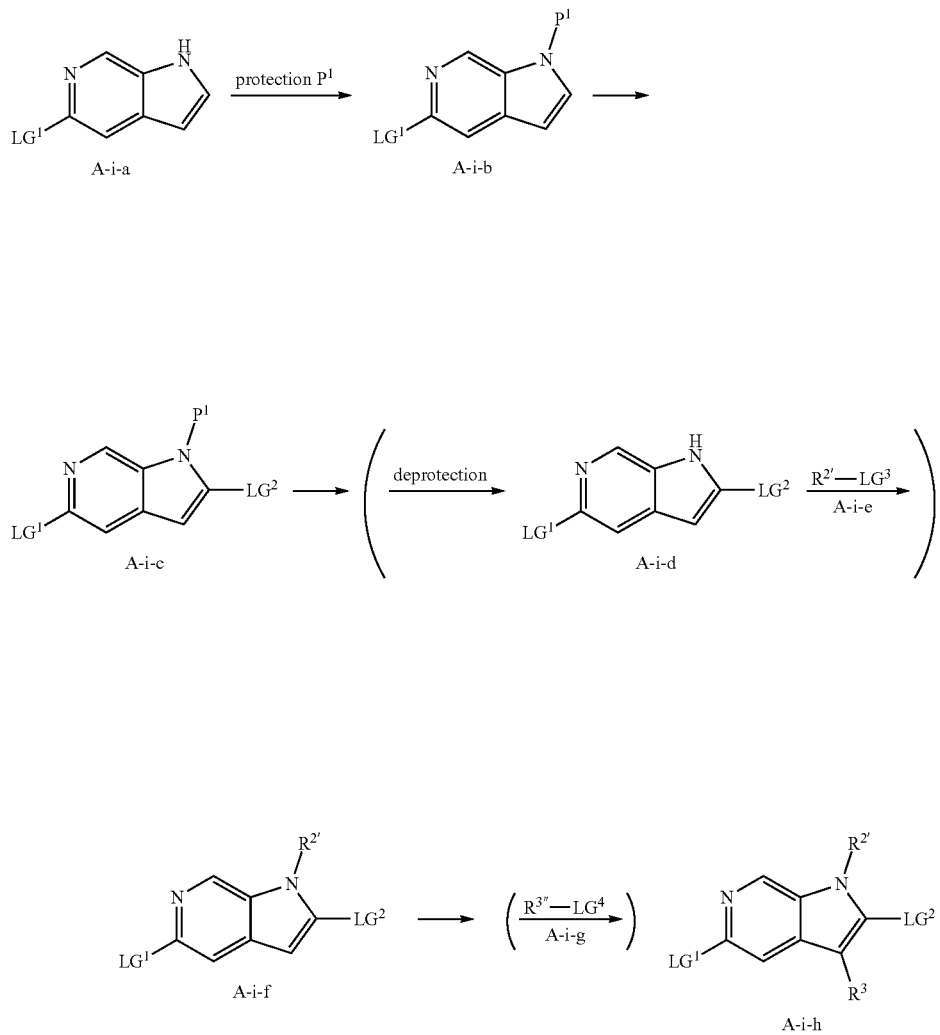

Scheme A-Part II.

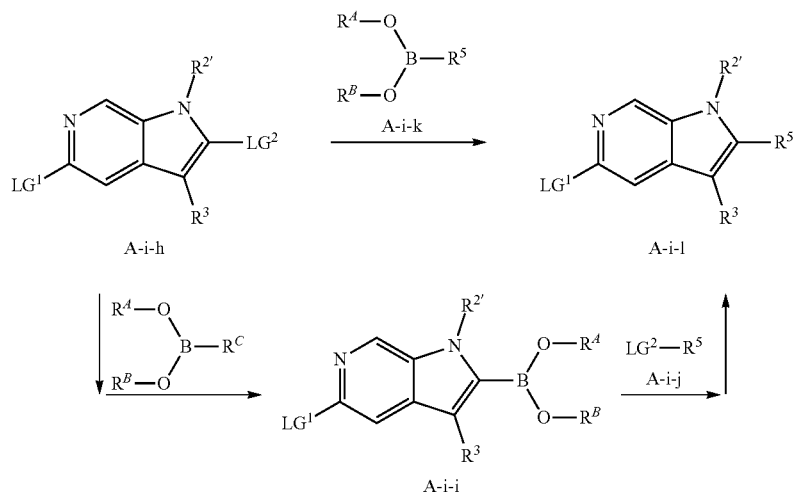

Scheme A-Part III.

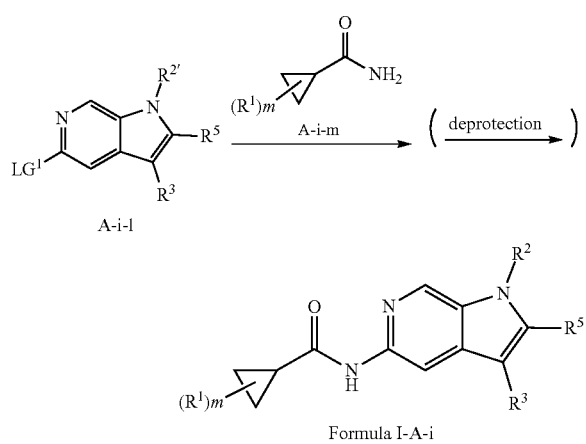

Compounds of formula (I-A-i) may be prepared according to the general synthetic scheme shown in Scheme A, Parts I-II. In Scheme A, Part I, 6-azaindole compounds of general formula A-i-a, wherein $LG^1$ is a leaving group (such as chloro or bromo), are protected at the imidazolyl nitrogen with a protecting group $P^1$ (e.g., with a Boc- or SEM-group) to give the compounds of general formula A-i-b. A suitable leaving group $LG^2$ (such as iodo) is added to the protected compounds of general formula A-i-b in preparation for the installation of the $R^5$ moiety. The resulting compounds of general formula A-i-c are further subjected to reactions to introduce substituents $R^{2'}$ and $R^3$ onto the 6-azaindole core as required to produce the intermediate compounds of general formula A-i-h. As shown in Scheme A, $R^{2'}$ has the same definition as $R^2$ as described herein, unless $R^2$ is hydrogen, in which instance, $R^{2'}$ is a protecting group $P^1$. Similarly, the substituent $R^{3''}$ has the same definition as $R^3$, except that $R^{3''}$ does not include hydrogen. $LG^3$ and $LG^4$ are leaving groups such as chloro, bromo, or iodo.

In Part II of Scheme A, the $R^5$ aryl or heteroaryl moiety is added to the compounds of general formula A-i-h, at the position occupied by $LG^2$, to yield the further intermediate compounds of general formula A-i-l. The installation of the $R^5$ moiety may be achieved, for example, by two routes as shown above. In the first route, the compounds of general formula A-i-h are reacted with a suitable boronic acid derivative comprising the desired $R^5$ group A-i-k, wherein $R^A$ and $R^B$ are independently selected from the group consisting of halogen, OH, and O—($C_1$-$C_6$ alkyl), or $R^A$ and $R^B$ are taken together with the boron atom to which they are attached to form a 5-10 membered heterocycle, to give the intermediate compounds of formula A-i-l. In the second route, the compounds of formula A-i-h are directly reacted with boronic acid or a derivative thereof, wherein $R^c$ is a suitable leaving group (such as O—$C_1$-$C_3$ alkyl, or another boronic acid or derivative thereof, i.e., in a diboron compound), to give the 6-azaindolyl-boronate compounds of formula A-i-i. The resulting boronate compounds are further reacted with an $R^5$-containing substrate (A-i-j) to give compounds of formula A-i-l.

In Part III of Scheme A, the compounds of formula A-i-l are reacted with suitable cyclopropanecarboxamides of formula A-i-m to provide compounds of formula I-A-i.

Scheme B-Part I.

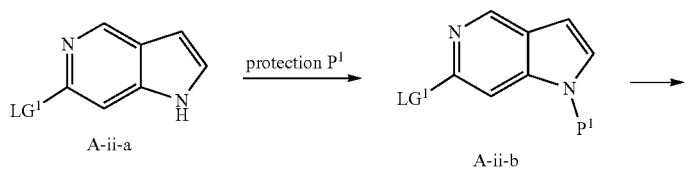

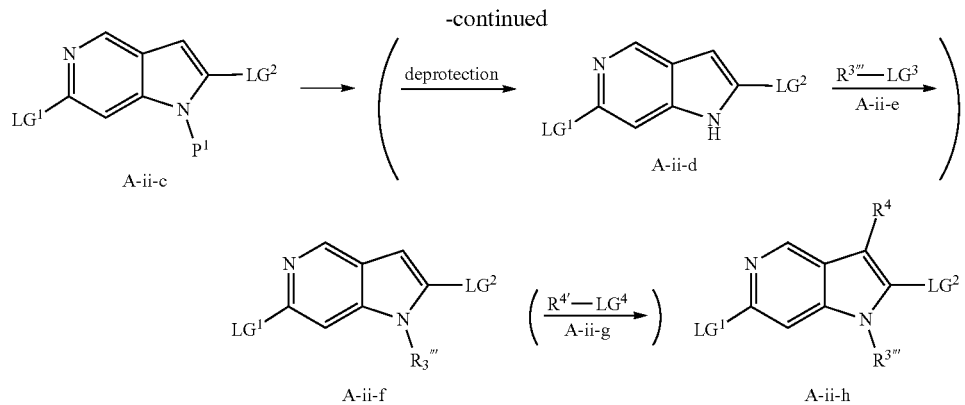

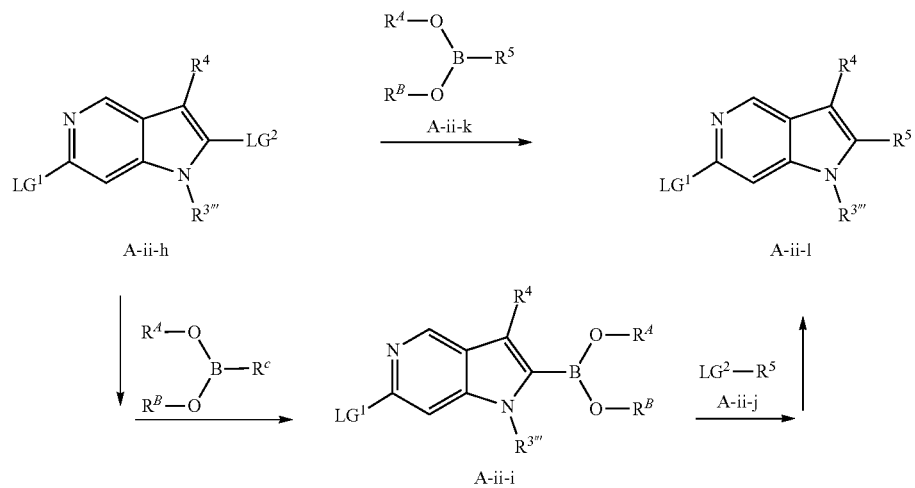

Scheme B- Part II.

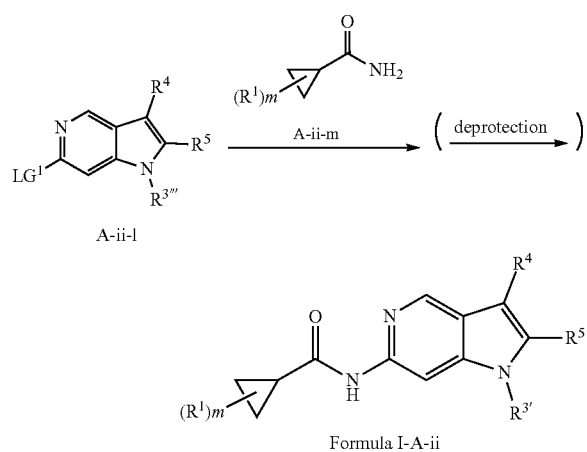

Scheme B- Part III.

Similar to Scheme A, Scheme B describes the preparation of compounds of formula (I-A-ii) having a 5-azaindolyl core. Compounds of formula (I-A-ii) may be prepared according to the general synthetic scheme shown in Scheme B, Parts I-III. In Scheme B. Part I, 5-azaindole compounds of general formula A-ii-a, wherein $LG^1$ is a leaving group (such as chloro or bromo), are protected at the imidazolyl nitrogen with a protecting group $P^1$ (e.g., with a Boc- or SEM-group) to give the compounds of general formula A-ii-b. A suitable leaving group $LG^2$ (such as iodo) is added to the protected compounds of general formula A-ii-b in preparation for the installation of the $R^5$ moiety. The resulting compounds of general formula A-ii-c are further subjected to reactions to introduce substituents $R^{4'}$ and $R^{3'''}$ onto the 5-azaindole core as required to produce the intermediate compounds of general formula A-ii-h. As shown in Scheme B, the substituent $R^{3'''}$ has the same definition as $R^3$, unless $R^{3'''}$ is hydrogen, in which instance, $R^{3'''}$ is a protecting group $P^1$. Similarly, $R^{4'}$ has the same definition as $R^4$ as described herein, except that $R^{4'}$ does not include hydrogen. $LG^3$ and $LG^4$ are leaving groups such as chloro, bromo, or iodo.

In Part II of Scheme B, the $R^5$ aryl or heteroaryl moiety is added to the compounds of general formula A-ii-h, at the position occupied by $LG^2$, to yield the further intermediate compounds of general formula A-ii-l. The installation of the $R^5$ moiety may be achieved, for example, by two routes as shown above. In the first route, the compounds of general formula A-ii-h are reacted with a suitable boronic acid derivative comprising the desired $R^5$ group A-ii-k, wherein $R^A$ and $R^B$ are independently selected from the group consisting of halogen, OH, and O—($C_1$-$C_6$ alkyl), or $R^A$ and $R^B$ are taken together with the boron atom to which they are attached to form a 5-10 membered heterocycle, to give the intermediate compounds of formula A-ii-l. In the second route, the compounds of formula A-ii-h are directly reacted with boronic acid or a derivative thereof, wherein $R^c$ is a suitable leaving group (such as O—$C_1$-$C_3$ alkyl, or another boronic acid or derivative thereof, i.e., in a diboron compound), to give the 5-azaindolyl-boronate compounds of formula A-ii-i. The resulting boronate compounds are further reacted with an $R^5$-containing substrate (A-ii-j) to give compounds of formula A-ii-l.

In Part III of Scheme B, the compounds of formula A-ii-l are reacted with suitable cyclopropanecarboxamides of formula A-ii-m to provide compounds of formula I-A-ii.

Compounds of formula (I-B) may also be prepared according to the general synthetic schemes shown in Scheme C and Scheme D. In Scheme C, the 6-azaindolyl compounds of formula A-i-l obtained from Scheme A (Parts I and II) are reacted with suitable urea compounds of formula B-i-m to provide compounds of formula I-B-i. In Scheme D, the 5-azaindolyl compounds of formula A-ii-l obtained from Scheme B (Parts I and II) are reacted with suitable urea compounds of formula B-ii-m to provide compounds of formula I-B-ii.

Alternatively, the addition of the cyclopropylcarboxamidyl or urea moiety as described in Scheme A (Part III), Scheme B (Part II), Scheme C and Scheme D may be substituted with the methods as described in Scheme E, Scheme F, Scheme G and Scheme H, respectively.

Scheme E.

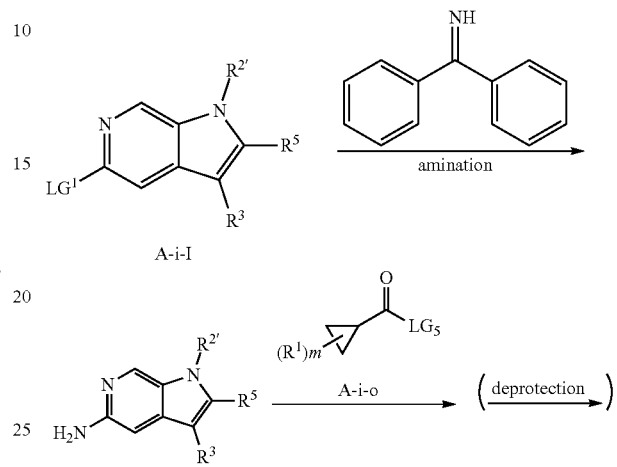

Scheme C.

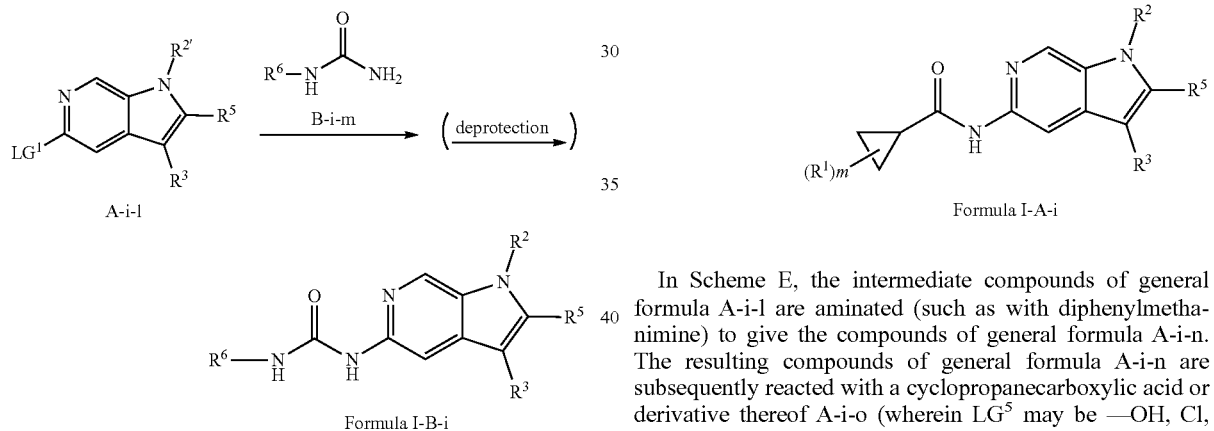

In Scheme E, the intermediate compounds of general formula A-i-l are aminated (such as with diphenylmethanimine) to give the compounds of general formula A-i-n. The resulting compounds of general formula A-i-n are subsequently reacted with a cyclopropanecarboxylic acid or derivative thereof A-i-o (wherein $LG^5$ may be —OH, Cl, —O—$C_1$-$C_6$ alkyl, etc.) to give the desired compounds of formula (I-A-i). Similarly, in Scheme F, the intermediate compounds of general formula A-ii-l are aminated (such as with diphenylmethanimine) to give the compounds of general formula A-ii-n. The resulting compounds of general formula A-ii-n are subsequently reacted with a cyclopropanecarboxylic acid or derivative thereof A-ii-o (wherein $LG^5$ may be —OH, Cl, —O—$C_1$-$C_6$ alkyl, etc.) to give the desired compounds of formula (I-A-ii).

Scheme D.

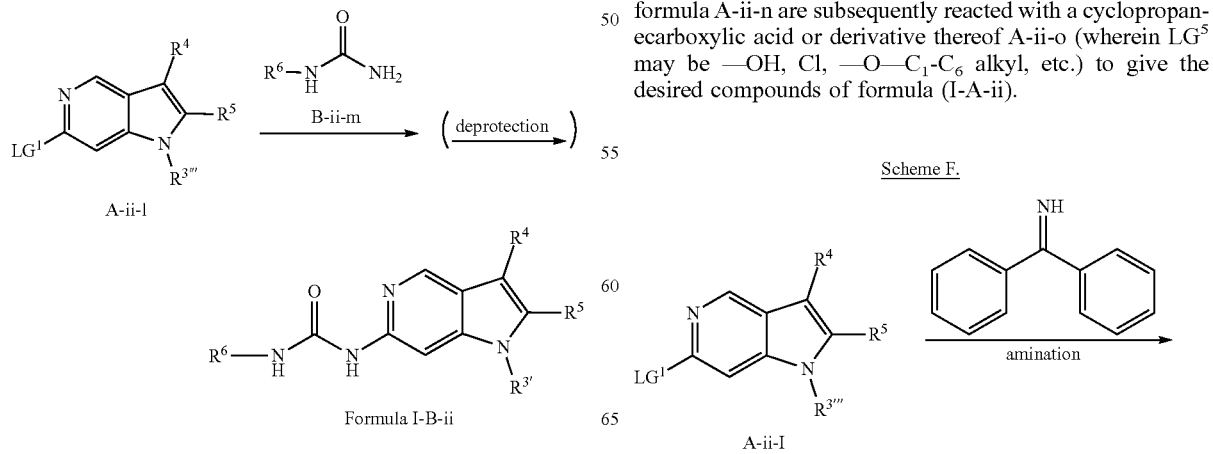

Scheme F.

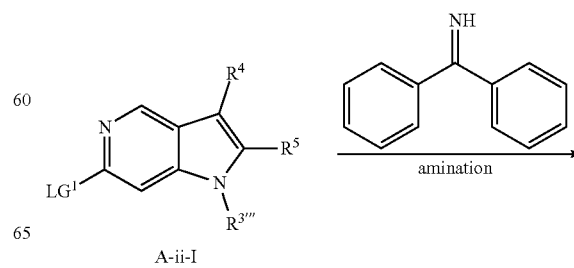

-continued

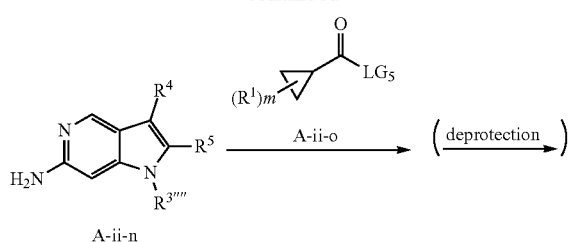

A-ii-n

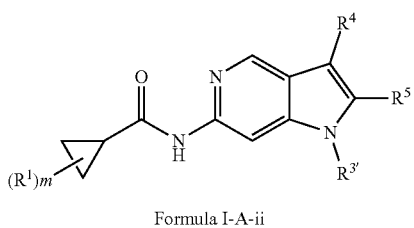

Formula I-A-ii

Compounds of general formula (I-B) may also be prepared from the compounds of general formulae A-i-n and A-ii-n described in Schemes G and H. In Scheme G, the compounds of general formula A-i-n are reacted with carboxylic acid derivatives (e.g., phenyl carbonylchloridate and $R^6$-containing free amines B-i-o in successive steps to give the desired urea compounds of general formula I-B-i. Similarly, in Scheme H, the compounds of general formula A-ii-n are reacted with carboxylic acid derivatives and $R^6$-containing free amines B-ii-o in successive steps to give the desired urea compounds of general formula I-B-ii.

Scheme G.

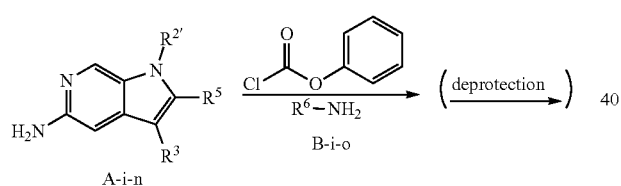

Formula I-B-i

Scheme H.

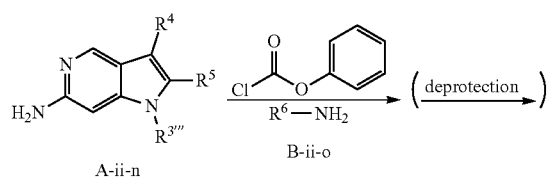

-continued

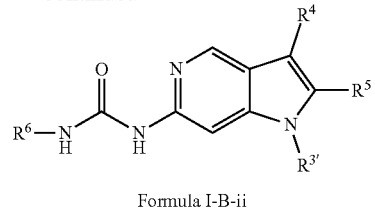

Formula I-B-ii

Scheme I and Scheme J below describe further alternatives for the preparation of 5- and 6-azaindole intermediates compounds in the synthesis of compounds of general formula (I). In Scheme 1,3-aminopyridine compounds of formula A-i-p, wherein $LG^6$ is a leaving group (e.g., iodo), are reacted with $R^3$— and $R^5$-containing ethyne compounds of formula A-i-q, thereby providing intermediate compounds of formula A-i-r. In Scheme J, 4-aminopyridine compounds of formula A-ii-p are reacted with $R^4$— and $R^5$-containing ethyne compounds of formula A-ii-q, thereby providing intermediate compounds of formula A-ii-r.

Scheme I.

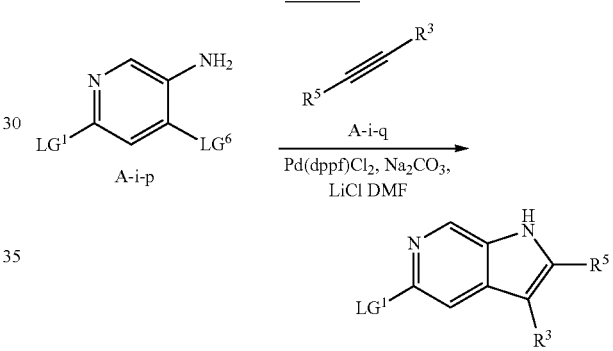

Scheme J.

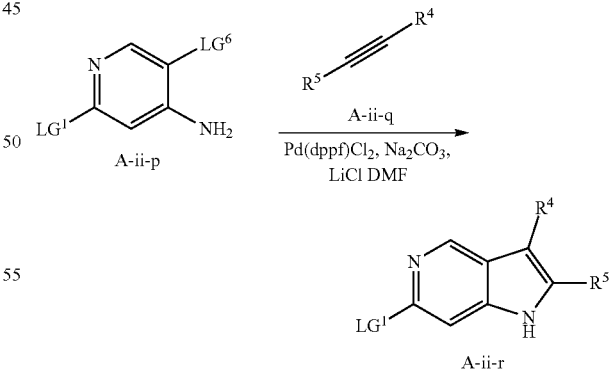

The intermediate compounds of formula A-i-r and A-ii-r may be further reacted, for example, to append or remove any protecting groups or to introduce substituents $R^2$ or $R^3$, prior to coupling to give the final cyclopropylcarboxamido compounds of formula (I-A-i) and (I-A-ii) or the ureido compounds of formula (I-B-i) and (I-B-ii) as shown in Schemes A through H.

IV. Pharmaceutical Compositions and Formulations

Any of the compounds described herein may be formulated as a pharmaceutically acceptable composition.

Pharmaceutical compositions of any of the compounds detailed herein are embraced by this disclosure. Thus, the present disclosure includes pharmaceutical compositions comprising a compound as detailed herein, or a pharmaceutically acceptable salt, solvate, hydrate, or co-crystal thereof, or a mixture of any of the foregoing, and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound, or a pharmaceutically acceptable salt, solvate, hydrate, or co-crystal thereof, or a mixture of any of the foregoing, as detailed herein are provided, such as compositions of substantially pure compounds. In some embodiments, a composition containing a compound, or a pharmaceutically acceptable salt, solvate, hydrate, or co-crystal thereof, or a mixture of any of the foregoing, as detailed herein is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 intends a composition that contains no more than 35% impurity, wherein the impurity denotes a compound other than the compound of Table 1. In one variation, a composition of substantially pure compound, or a pharmaceutically acceptable salt, solvate, hydrate, or co-crystal thereof, or a mixture of any of the foregoing, is provided wherein the composition contains no more than 25% impurity. In another variation, a composition of substantially pure compound, or a pharmaceutically acceptable salt, solvate, hydrate, or co-crystal thereof, or a mixture of any of the foregoing, is provided wherein the composition contains or no more than 20% impurity. In still another variation, a composition of substantially pure compound, or a pharmaceutically acceptable salt, solvate, hydrate, or co-crystal thereof, or a mixture of any of the foregoing, is provided wherein the composition contains or no more than 10% impurity. In a further variation, a composition of substantially pure compound, or a pharmaceutically acceptable salt, solvate, hydrate, or co-crystal thereof, or a mixture of any of the foregoing, is provided wherein the composition contains no more than 5% impurity. In another variation, a composition of substantially pure compound, or a pharmaceutically acceptable salt, solvate, hydrate, or co-crystal thereof, or a mixture of any of the foregoing, is provided wherein the composition contains no more than 3% impurity. In still another variation, a composition of substantially pure compound, or a pharmaceutically acceptable salt, solvate, hydrate, or co-crystal thereof, or a mixture of any of the foregoing, is provided wherein the composition contains no more than 1% impurity. In a further variation, a composition of substantially pure compound, or a pharmaceutically acceptable salt, solvate, hydrate, or co-crystal thereof, or a mixture of any of the foregoing, is provided wherein the composition contains no more than 0.5% impurity. In yet other variations, a composition of substantially pure compound means that the composition contains no more than 15%, no more than 10%, no more than 5%, no more than 3%, or no more than 1% impurity, which impurity may be the compound in a different stereochemical form. For instance, and without limitation, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein. In some embodiments, the compounds and compositions as provided herein are sterile. Methods for sterilization known in the art may be suitable for any compounds or form thereof and compositions thereof as detailed herein.

A compound detailed herein, or a pharmaceutically acceptable salt, solvate, hydrate, or co-crystal thereof, or a mixture of any of the foregoing, may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound, or a pharmaceutically acceptable salt, solvate, hydrate, or co-crystal thereof, or a mixture of any of the foregoing, may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A compound detailed herein, or a pharmaceutically acceptable salt, solvate, hydrate, or co-crystal thereof, or a mixture of any of the foregoing, can be used in the preparation of a formulation, such as a pharmaceutical formulation, by combining the compound or compounds, or a pharmaceutically acceptable salt, solvate, hydrate, or co-crystal thereof, or a mixture of any of the foregoing, with a pharmaceutically acceptable carrier. Depending on the therapeutic form of the system (e.g., transdermal patch vs, oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington's Pharmaceutical Sciences, Mack Publishing Company, Philadelphia, PA, 20th ed. (2000), which is incorporated herein by reference.

A compound detailed herein, or a pharmaceutically acceptable salt, solvate, hydrate, or co-crystal thereof, or a mixture of any of the foregoing, may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds, or a pharmaceutically acceptable salt, solvate, hydrate, or co-crystal thereof, or a mixture of any of the foregoing, described herein can be formulated in a tablet in any dosage form described, for example, a compound as described herein, or a pharmaceutically acceptable salt, solvate, hydrate, or co-crystal thereof, or a mixture of any of the foregoing, can be formulated as a 10 mg tablet.

Compositions comprising a compound, or a pharmaceutically acceptable salt, solvate, hydrate, or co-crystal thereof, or a mixture of any of the foregoing, provided herein are also described. In one variation, the composition comprises a compound, or a pharmaceutically acceptable salt, solvate, hydrate, or co-crystal thereof, or a mixture of any of the foregoing, and a pharmaceutically acceptable carrier or excipient. In another variation, a composition of substantially pure compound, or a pharmaceutically acceptable salt, solvate, hydrate, or co-crystal thereof, or a mixture of any of the foregoing, is provided. In some embodiments, the composition is for use as a human or veterinary medicament. In some embodiments, the composition is for use in a method described herein. In some embodiments, the composition is for use in the treatment of a disease or disorder described herein.

Compositions formulated for co-administration of a compound provided herein and one or more additional pharmaceutical agents are also described. The co-administration can be simultaneous or sequential in any order. A compound provided herein may be formulated for co-administration with the one or more additional pharmaceutical agents in the same dosage form (e.g., single tablet or single i.v.) or separate dosage forms (e.g., two separate tablets, two separate i.v., or one tablet and one i.v.). Furthermore, co-administration can be, for example, 1) concurrent delivery, through the same route of delivery (e.g., tablet or i.v.), 2) sequential delivery on the same day, through the same route or different routes of delivery, or 3) delivery on different days, through the same route or different routes of delivery.

V. Methods of Use

Compounds and compositions detailed herein, such as a pharmaceutical composition containing a compound of formula (I) or any variation thereof provided herein, or a pharmaceutically acceptable salt, solvate, hydrate, or co-crystal thereof, or a mixture of any of the foregoing, and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided herein is a method of inhibiting Bcr-Abl tyrosine kinase enzymatic activity, comprising contacting an effective amount of a compound or composition provided herein, to the Bcr-Abl tyrosine kinase. In some embodiments, provided herein is a method of inhibiting Bcr-Abl tyrosine kinase in a cell, comprising administering an effective amount of a compound or composition of the disclosure to the cell. In some embodiments, provided herein is a method of inhibiting Bcr-Abl tyrosine kinase in an individual in need thereof, comprising administering an effective amount of a compound or composition of the disclosure to the individual. In some variations, the compounds provided herein are selective for inhibiting Bcr-Abl tyrosine kinase. As such, in some embodiments, provided herein is a method of selectively inhibiting Bcr-Abl tyrosine kinase, as compared to other tyrosine kinases, including but not limited to c-KIT, FGFR, PDGFR, SRC, CSFR1, or VEGFR.

The compounds and compositions described herein may be used in a method of treating a disease or disorder mediated by Bcr-Abl tyrosine kinase activity. In some embodiments, the compound or composition is administered according to a dosage described herein.

In some embodiments, provided herein is a method for treating a disease or disorder mediated by Bcr-Abl tyrosine kinase activity comprising administering to an individual in need of treatment an effective amount of a compound of formula (I) or any variation thereof, or a pharmaceutically acceptable salt, solvate, hydrate, or co-crystal thereof, or a mixture of any of the foregoing. In some embodiments, the disease or disorder is a cancer mediated by Bcr-Abl tyrosine kinase activity. In some embodiments, the disease or disorder is chronic myeloid leukemia (CML), acute myeloid leukemia (AML), or acute lymphoblastic leukemia (ALL). In some embodiments, the disease or disorder is a cancer, such as leukemia. In some variations, the cancer is chronic myeloid leukemia (CML), Philadelphia-positive acute lymphoblastic leukemia (Ph+ ALL), acute myelogenous leukemia (AML), or mixed phenotype acute leukemia.

In certain embodiments, the leukemia is chronic myeloid leukemia. Chronic myeloid leukemia may be characterized by the state of disease progression, as determined by blast cells. In still further embodiments, the chronic myeloid leukemia is chronic phase CML, accelerated phase CML, or blastic phase CML. In some embodiments, the chronic myeloid leukemia is refractory chronic myeloid leukemia.

In some embodiments, the disease or disorder mediated by Bcr-Abl tyrosine kinase activity is refractory or resistant to first-line treatment, second-line treatment, and/or third-line treatment. In certain embodiments, the condition mediated by Bcr-Abl tyrosine kinase activity is refractory or resistant to treatment with one or more Bcr-Abl tyrosine kinase inhibitors selected from the group consisting of imatinib, nilotinib, dasatinib, bafetinib, bosutinib, radotinib, asciminib, and ponatinib. First-line treatment as described herein includes the use of imatinib; second- and third-line treatments as described herein include the use of nilotinib, dasatinib, bafetinib, bosutinib, radotinib, asciminib, and/or ponatinib. In some variations of the foregoing, the chronic myeloid leukemia is refractory chronic myeloid leukemia.

Resistant subtypes of Bcr-Abl tyrosine kinase-mediated diseases or disorders may be associated with any number of Bcr-Abl dependent or Bcr-Abl independent resistance mechanisms. In some embodiments wherein the disease or disorder mediated by Bcr-Abl tyrosine kinase activity is refractory to treatment, the disease or disorder is characterized as being associated with one or more Bcr-Abl dependent resistance mechanisms. Bcr-Abl dependent resistance mechanisms include, but are not limited to, one or more point mutations that result in amino acid substitutions at the following positions within Bcr-Abl: M244, L248, G250, G250, Q252, Q252, Y253, Y253, E255, E255, D276, F311, T315, F317, F317, M343, M351, E355, F359, F359, V379, F382, L387, H396, H396, S417, E459, or F486 in the Bcr-Abl tyrosine kinase. In certain variations, the refractory disease or disorder mediated by Bcr-Abl tyrosine kinase is associated with one or more specific point mutations in the Bcr-Abl tyrosine kinase gene resulting in specific amino acid substitutions selected from the group consisting of: M244V, L248V, G250E, G250A, Q252H, Q252R, Y253F, Y253H, E255K, E255V, D276G, F311L, T315N, T315A, F317V, F317L, M343T, M351T, E355G, F359A, F359V, V379I, F382L, L387M, H396P, H396R, S417Y, E459K, F486S, and T315I. In certain embodiments, the refractory disease or disorder mediated by Bcr-Abl tyrosine kinase is associated with a mutation resulting in the T315I substitution. In still further embodiments, the refractory disease or disorder mediated by Bcr-Abl tyrosine kinase is associated with a T315I mutation at the onset of treatment and 1315M mutation following ponatinib. In other embodiments, the refractory disease or disorder mediated by Bcr-Abl tyrosine kinase is associated with one or more mutations leading to amino acid substitutions within the P-loop (M244V, G250E, Q252H, Y253H/F, E255K/V).

In some embodiments, provided is a method for treating cancer in an individual in need thereof, comprising administering to the individual an effective amount of a compound of formula (I), or any variation thereof as described herein. In some embodiments, the cancer is leukemia. In some embodiments, the cancer is chronic myeloid leukemia (CML), Philadelphia-positive acute lymphoblastic leukemia (Ph+ ALL), acute myelogenous leukemia (AML), or mixed phenotype acute leukemia. In some embodiments, the cancer is chronic myeloid leukemia (CML). In some embodiments, the leukemia is chronic myeloid leukemia (CML), Philadelphia-positive acute lymphoblastic leukemia (Ph+ ALL), acute myelogenous leukemia (AML), or mixed phenotype acute leukemia. In some embodiments, the chronic myeloid leukemia (CML). Philadelphia-positive acute lymphoblastic leukemia (Ph+ ALL), acute myelogenous leukemia (AML), or mixed phenotype acute leukemia is refractory. In certain embodiments, the leukemia is chronic myeloid leukemia. In still further embodiments, the chronic myeloid leukemia is refractory chronic myeloid leukemia. In other embodiments, the chronic myeloid leukemia (CML), Philadelphia-positive acute lymphoblastic leukemia (Ph+ ALL), acute myelogenous leukemia (AML), or mixed phenotype acute leukemia is refractory due to an associated T315I mutation. In certain embodiments of the foregoing, the chronic myeloid leukemia is refractory chronic myeloid leukemia associated with a T315I mutation.

In one aspect, provided herein is a method of treating cancer in an individual in need thereof, wherein modulation of Bcr-Abl tyrosine kinase activity inhibits or ameliorates the pathology and/or symptomology of the cancer, comprising administering to the individual a therapeutically effective amount of a compound or composition provided herein. In one embodiment, provided herein is a method of treating cancer, wherein modulation of Bcr-Abl tyrosine kinase activity inhibits the pathology and/or symptomology of the cancer, in an individual, comprising administering to the individual a therapeutically effective amount of a compound or composition provided herein. In one embodiment, provided herein is a method of treating a cancer, wherein modulation of Bcr-Abl tyrosine kinase activity ameliorates the pathology and/or symptomology of the cancer, in an individual, comprising administering to the individual a therapeutically effective amount of a compound or composition provided herein.

In another aspect, provided herein is a method of preventing cancer, wherein modulation of Bcr-Abl tyrosine kinase activity prevents the pathology and/or symptomology of the cancer, in an individual, comprising administering to the individual a therapeutically effective amount of a compound or composition provided herein. In another aspect, provided herein is a method of delaying the onset and/or development of a cancer that is mediated by Bcr-Abl tyrosine kinase activity in an individual (such as a human) who is at risk for developing the cancer. It is appreciated that delayed development may encompass prevention in the event the individual does not develop the cancer.

In one aspect, provided herein is a method of delaying the onset and/or development of cancer in an individual in need thereof, comprising administering to the individual a therapeutically effective amount of a compound or composition provided herein. In some embodiments, the cancer is a leukemia. In certain embodiments, the cancer is chronic myeloid leukemia (CML). Philadelphia-positive acute lymphoblastic leukemia (Ph+ ALL), acute myelogenous leukemia (AML), or mixed phenotype acute leukemia. In some embodiments, the cancer is chronic myeloid leukemia. In some embodiments, the leukemia is chronic myeloid leukemia (CML), Philadelphia-positive acute lymphoblastic leukemia (Ph+ ALL), acute myelogenous leukemia (AML), or mixed phenotype acute leukemia. In some embodiments, the chronic myeloid leukemia (CML), Philadelphia-positive acute lymphoblastic leukemia (Ph+ ALL), acute myelogenous leukemia (AML), or mixed phenotype acute leukemia is refractory. In certain embodiments, the leukemia is chronic myeloid leukemia. In still further embodiments, the chronic myeloid leukemia is refractory chronic myeloid leukemia. In other embodiments, the chronic myeloid leukemia (CML), Philadelphia-positive acute lymphoblastic leukemia (Ph+ ALL), acute myelogenous leukemia (AML), or mixed phenotype acute leukemia is refractory due to an associated T315I mutation. In still yet other embodiments, the chronic myeloid leukemia is refractory chronic myeloid leukemia associated with a T315I mutation. In one aspect, provided herein is a method of delaying the onset and/or development of chronic myeloid leukemia in an individual in need thereof, comprising administering to the individual a therapeutically effective amount of a compound or composition provided herein. In one variation, provided herein is a method of delaying the onset and/or development of refractory chronic myeloid leukemia (CML), Philadelphia-positive acute lymphoblastic leukemia (Ph+ ALL), acute myelogenous leukemia (AML), or mixed phenotype acute leukemia in an individual in need thereof, comprising administering to the individual a therapeutically effective amount of a compound or composition provided herein. In one variation, provided herein is a method of delaying the onset and/or development of refractory chronic myeloid leukemia (CML), Philadelphia-positive acute lymphoblastic leukemia (Ph+ ALL), acute myelogenous leukemia (AML), or mixed phenotype acute leukemia associated with a T315I mutation in an individual in need thereof, comprising administering to the individual a therapeutically effective amount of a compound or composition provided herein.

In one aspect, provided herein is a compound of formula (I) or any variation thereof, or a pharmaceutically acceptable salt, solvate, hydrate, or co-crystal thereof, or a mixture of any of the foregoing, for use in therapy. In some embodiments, provided herein is a compound of formula (I) or any variation thereof, or a pharmaceutically acceptable salt, solvate, hydrate, or co-crystal thereof, or a mixture of any of the foregoing, or pharmaceutical composition comprising such compound, for use in the treatment of cancer. In some embodiments, provided is a compound of formula (I) or any variation thereof, or a pharmaceutically acceptable salt, solvate, hydrate, or co-crystal thereof, or a mixture of any of the foregoing, or a pharmaceutical composition comprising such compound, for use in the treatment of chronic myeloid leukemia (CML), Philadelphia-positive acute lymphoblastic leukemia (Ph+ ALL), acute myelogenous leukemia (AML), or mixed phenotype acute leukemia. In some embodiments, provided is a compound of formula (I) or any variation thereof, or a pharmaceutically acceptable salt, solvate, hydrate, or co-crystal thereof, or a mixture of any of the foregoing, or a pharmaceutical composition comprising such compound, for use in the treatment of chronic myeloid leukemia (CML). In some embodiments, provided is a compound of formula (I) or any variation thereof, or a pharmaceutically acceptable salt, solvate, hydrate, or co-crystal thereof, or a mixture of any of the foregoing, or a pharmaceutical composition comprising such compound, for use in the treatment of refractory chronic myeloid leukemia (CML), Philadelphia-positive acute lymphoblastic leukemia (Ph+ ALL), acute myelogenous leukemia (AML), or mixed phenotype acute leukemia. In some embodiments, provided is a compound of formula (I) or any variation thereof, or a pharmaceutically acceptable salt, solvate, hydrate, or co-crystal thereof, or a mixture of any of the foregoing, or a pharmaceutical composition comprising such compound, for use in the treatment of refractory chronic myeloid leukemia (CML), Philadelphia-positive acute lymphoblastic leukemia (Ph+ ALL), acute myelogenous leukemia (AML), or mixed phenotype acute leukemia associated with a T315I mutation.

In another embodiment, provided herein is a compound of formula (I) or any variation thereof, or a pharmaceutically acceptable salt, solvate, hydrate, or co-crystal thereof, or a mixture of any of the foregoing, for use in the manufacture of a medicament for the treatment of cancer. In another embodiment, provided herein is a compound of formula (I) or any variation thereof, or a pharmaceutically acceptable salt, solvate, hydrate, or co-crystal thereof, or a mixture of any of the foregoing, for use in the manufacture of a medicament for the treatment of chronic myeloid leukemia (CML), Philadelphia-positive acute lymphoblastic leukemia (Ph+ ALL), acute myelogenous leukemia (AML), or mixed phenotype acute leukemia. In some embodiments, the medicament is for the treatment of chronic myeloid leukemia. In some embodiments, the medicament is for the treatment of refractory chronic myeloid leukemia (CML), Philadelphia-positive acute lymphoblastic leukemia (Ph+ ALL), acute myelogenous leukemia (AML), or mixed phenotype acute leukemia. In certain embodiments, the medicament is for the treatment of refractory chronic myeloid leukemia. In other embodiments, the medicament is for the treatment of refractory chronic myeloid leukemia (CML), Philadelphia-positive acute lymphoblastic leukemia (Ph+ ALL), acute myelogenous leukemia (AML), or mixed phenotype acute leukemia associated with a T315I mutation. In some embodiments, the medicament is for the treatment of refractory chronic myeloid leukemia associated with a T315I mutation.

In some embodiments, the individual is a mammal. In some embodiments, the individual is a primate, dog, cat, rabbit, or rodent. In some embodiments, the individual is a primate. In some embodiments, the individual is a human. In some embodiments, the human is at least about or is about any of 18, 21, 30, 50, 60, 65, 70, 75, 80, or 85 years old. In some embodiments, the human is a child. In some embodiments, the human is less than about or about any of 21, 18, 15, 10, 5, 4, 3, 2, or 1 years old.

In some embodiments, the method further comprises administering one or more additional pharmaceutical agents. In some embodiments, the method further comprises administering radiation. In some embodiments, the method further comprises administering one or more additional pharmaceutical agents, including anti-microtubular therapies (e.g. paclitaxel, vincristine), topoisomerase inhibitors (e.g. adriamycin), alkylating agents (e.g. busulfan, cyclophosphamide), nucleotide synthesis inhibitors (hydroxyurea), DNA synthesis inhibitors (e.g. cytarabine), protein synthesis inhibitors (e.g. omacetaxine), developmental signaling pathway inhibitors (e.g. sonidegib, Hedgehog pathway), pro-apoptotic agents (e.g. venetoclax), Ab myristoyl-pocket binding inhibitors (e.g. asciminib), MEK1/2 inhibitors (e.g. trametinib, binimetinib), AKT inhibitors (e.g. ipatasertib), PI3K inhibitors (e.g. apelisib) and radiation.

VI. Dosing and Method of Administration

The dose of a compound described herein, or a pharmaceutically acceptable salt, solvate, hydrate, or co-crystal thereof, or a mixture of any of the foregoing, administered to an individual (such as a human) may vary with the particular compound or salt thereof, the method of administration, and the particular cancer, such as type and stage of cancer, being treated. In some embodiments, the amount of the compound, or a pharmaceutically acceptable salt, solvate, hydrate, or co-crystal thereof, or a mixture of any of the foregoing, is a therapeutically effective amount.

The compounds provided herein, or a pharmaceutically acceptable salt, solvate, hydrate, or co-crystal thereof, or a mixture of any of the foregoing, may be administered to an individual via various routes, including, e.g., intravenous, intramuscular, subcutaneous, oral, and transdermal.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein, or a pharmaceutically acceptable salt, solvate, hydrate, or co-crystal thereof, or a mixture of any of the foregoing, and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

VII. Articles of Manufacture and Kits

The present disclosure further provides articles of manufacture comprising a compound described herein, or a pharmaceutically acceptable salt, solvate, hydrate, or co-crystal thereof, or a mixture of any of the foregoing, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein, or a pharmaceutically acceptable salt, solvate, hydrate, or co-crystal thereof, or a mixture of any of the foregoing, thereof. The kits may be used for any one or more of the uses described herein, and, accordingly, may contain instructions for the treatment of any disease or described herein, for example for the treatment of cancer, including chronic myeloid leukemia (CML), Philadelphia-positive acute lymphoblastic leukemia (Ph+ ALL), acute myelogenous leukemia (AML), or mixed phenotype acute leukemia. In some embodiments, the cancer is chronic myeloid leukemia. In some embodiments, the cancer is refractory chronic myeloid leukemia. In certain embodiments of the foregoing, the cancer is refractory chronic myeloid leukemia associated with a T315I mutation.

The kits optionally further comprise a container comprising one or more additional pharmaceutical agents and which kits further comprise instructions on or in the package insert for treating the subject with an effective amount of the one or more additional pharmaceutical agents.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

Examples

It is understood that the present disclosure has been made only by way of example, and that numerous changes in the combination and arrangement of parts can be resorted to by those skilled in the art without departing from the spirit and scope of present disclosure.

Synthetic Examples

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure.

Abbreviations used in the Examples include the following: ACN: acetonitrile; Brettphos: 2-(dicyclohexylphosphino)3,6-dimethoxy-2',4',6'-triisopropyl-1,1'-biphenyl; dppf: 1,1'-ferrocenediyl-bis(diphenylphosphine); DCM: dichloromethane; DIAD: diisopropylazodicarboxylate; DIEA: N,N-diisopropylethylamine; DMAP: 4-dimethylaminopyridine; DMF: dimethylformamide; DMSO: dimethyl sulfoxide; EDA; ethylenediamine; EtOAc: ethyl acetate; EtOH: ethanol or ethyl alcohol; F-TEDA-BF$_4$: 1-Chloromethyl-4-fluoro-1,4-diazoniabicyclo[2.2.2]octane bis(tetrafluoroborate); $^1$H NMR: proton nuclear magnetic resonance; HATU: 1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium; LCMS: liquid chromatography-mass spectrometry; LDA: lithium diisopropylamide; LiHMDS: lithium hexamethyldisilazide; MeOH: methanol or methyl alcohol; NBS: N-bromosuccinimide; NIS: N-iodosuccinimide; NNMP: N-methyl-2-pyrrolidone; OAc: acetate; Py: pyridine; TBAB: tetra-n-butylammonium bromide; TBAF: tetra-n-butylammonium fluoride; TEA: triethylamine; TFA: trifluoroacetic acid; THF: tetrahydrofuran; and TLC: thin-layer chromatography.

Example S1: Synthesis of N-(2-(2-hydroxyphenyl)-1-methyl-1H-pyrrolo[2,3-c]pyridin-5-yl)cyclopropanecarboxamide (Compound 1)

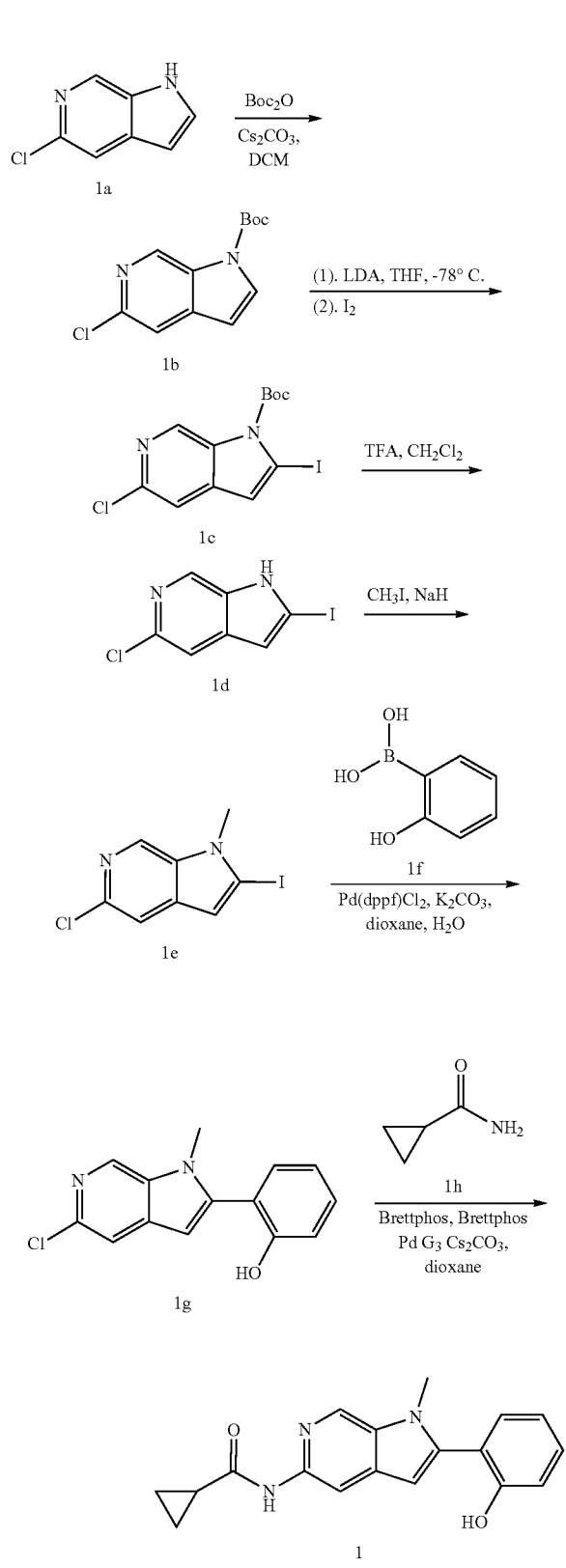

Step 1: Synthesis of tert-butyl 5-chloro-1H-pyrrolo[2,3-c]pyridine-1-carboxylate (Compound 1b)

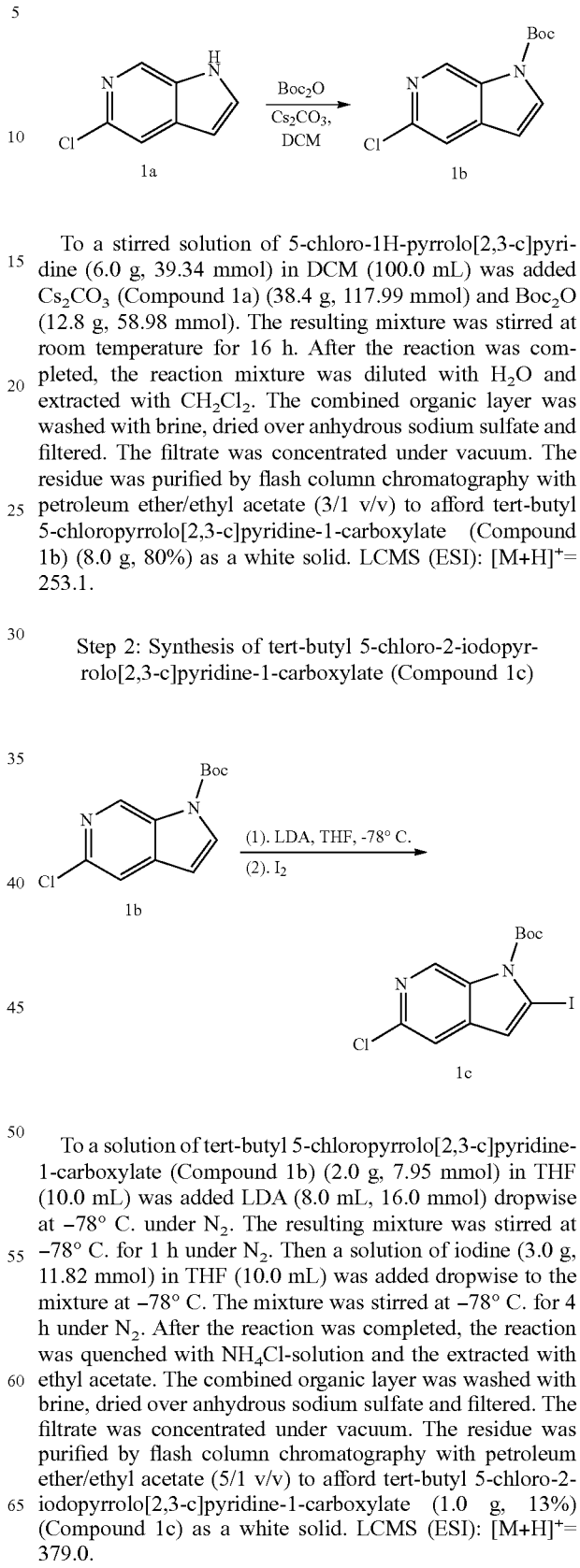

To a stirred solution of 5-chloro-1H-pyrrolo[2,3-c]pyridine (6.0 g, 39.34 mmol) in DCM (100.0 mL) was added $Cs_2CO_3$ (Compound 1a) (38.4 g, 117.99 mmol) and $Boc_2O$ (12.8 g, 58.98 mmol). The resulting mixture was stirred at room temperature for 16 h. After the reaction was completed, the reaction mixture was diluted with $H_2O$ and extracted with $CH_2Cl_2$. The combined organic layer was washed with brine, dried over anhydrous sodium sulfate and filtered. The filtrate was concentrated under vacuum. The residue was purified by flash column chromatography with petroleum ether/ethyl acetate (3/1 v/v) to afford tert-butyl 5-chloropyrrolo[2,3-c]pyridine-1-carboxylate (Compound 1b) (8.0 g, 80%) as a white solid. LCMS (ESI): $[M+H]^+$= 253.1.

Step 2: Synthesis of tert-butyl 5-chloro-2-iodopyrrolo[2,3-c]pyridine-1-carboxylate (Compound 1c)

To a solution of tert-butyl 5-chloropyrrolo[2,3-c]pyridine-1-carboxylate (Compound 1b) (2.0 g, 7.95 mmol) in THF (10.0 mL) was added LDA (8.0 mL, 16.0 mmol) dropwise at −78° C. under $N_2$. The resulting mixture was stirred at −78° C. for 1 h under $N_2$. Then a solution of iodine (3.0 g, 11.82 mmol) in THF (10.0 mL) was added dropwise to the mixture at −78° C. The mixture was stirred at −78° C. for 4 h under $N_2$. After the reaction was completed, the reaction was quenched with $NH_4Cl$-solution and the extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (5/1 v/v) to afford tert-butyl 5-chloro-2-iodopyrrolo[2,3-c]pyridine-1-carboxylate (1.0 g, 13%) (Compound 1c) as a white solid. LCMS (ESI): $[M+H]^+$= 379.0.

Step 3: Synthesis of 5-chloro-2-iodo-1H-pyrrolo[2,3-c]pyridine (Compound 1d)

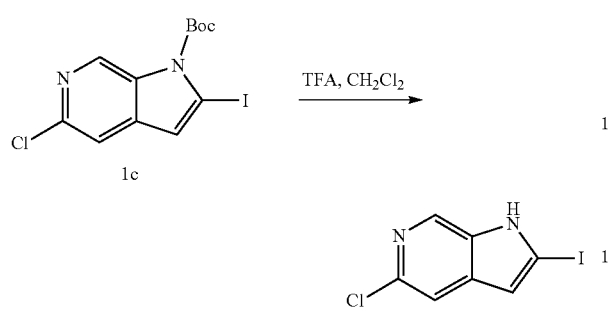

To a stirred solution of tert-butyl 5-chloro-2-iodopyrrolo[2,3-c]pyridine-1-carboxylate (Compound 1c) (1.0 g, 2.61 mmol) in CH$_2$Cl$_2$ (5.0 mL) was added TFA (3.0 mL). The resulting mixture was stirred at room temperature for 2 h. After the reaction was completed, the resulting solution was concentrated under vacuum. The residue was purified by flash column chromatography with petroleum ether/ethyl acetate (1/1, v/v) to afford 5-chloro-2-iodo-1H-pyrrolo[2,3-c]pyridine (Compound 1d) (700.0 mg, 95%) as a white solid. LCMS (ESI): [M+H]$^+$=278.9.

Step 4: Synthesis of 5-chloro-2-iodo-1-methylpyrrolo[2,3-c]pyridine (Compound 1e)

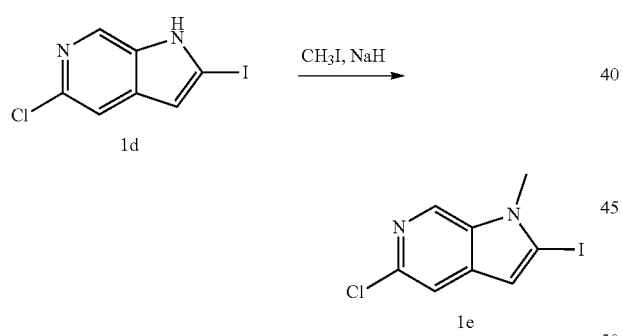

To a solution of 5-chloro-2-iodo-1H-pyrrolo[2,3-c]pyridine (Compound 1d) (970.0 mg, 3.48 mmol) in THF (5.0 mL) was added NaH (167.8 mg, 60%) at 0° C. The mixture was stirred at 0° C. for 2 h under N$_2$. Then a solution of CH$_3$I (70.8 mg, 0.44 mmol) in THF (5.0 mL) was added dropwise to the mixture. The mixture was stirred at 0° C. for 2 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/2, v/v) to afford 5-chloro-2-iodo-1-methylpyrrolo[2,3-c]pyridine (Compound 1e) (800.0 mg, 79%) as a white solid. LCMS (ESI): [M+H]$^+$=292.9.

Step 5: Synthesis of 2-[5-chloro-1-methylpyrrolo[2,3-c]pyridin-2-yl]phenol (Compound 1g)

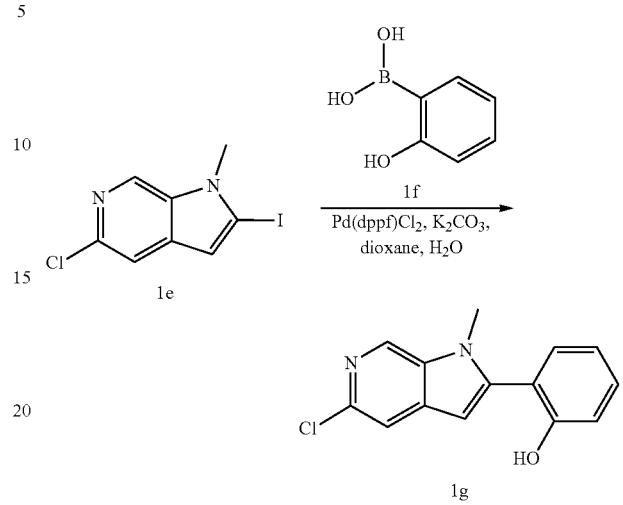

To a stirred solution of 5-chloro-2-iodo-1-methylpyrrolo[2,3-c]pyridine (200.0 mg, 0.68 mmol) in dioxane (Compound 1e) (10.0 mL) and H$_2$O (1.0 mL) was added 2-hydroxyphenylboronic acid (Compound 1f) (113.7 mg, 0.82 mmol), Pd(dppf)Cl$_2$ (100.6 mg, 0.13 mmol) and K$_2$CO$_3$ (283.5 mg, 2.05 mmol). The resulting mixture was stirred at 80° C. for 16 h under N$_2$. After the reaction was completed, the resulting mixture was concentrated under reduced pressure. The residue was purified by flash column chromatography with petroleum ether/ethyl acetate (1/2, v/v) to afford 2-[5-chloro-1-methylpyrrolo[2,3-c]pyridin-2-yl]phenol (Compound 1g) (130.0 mg, 73%) as a white solid. LCMS (ESI): [M+H]$^+$=259.1.

Step 6: Synthesis of N-[2-(2-hydroxyphenyl)-1-methylpyrrolo[2,3-c]pyridin-5-yl]cyclopropanecarboxamide (Compound 1)

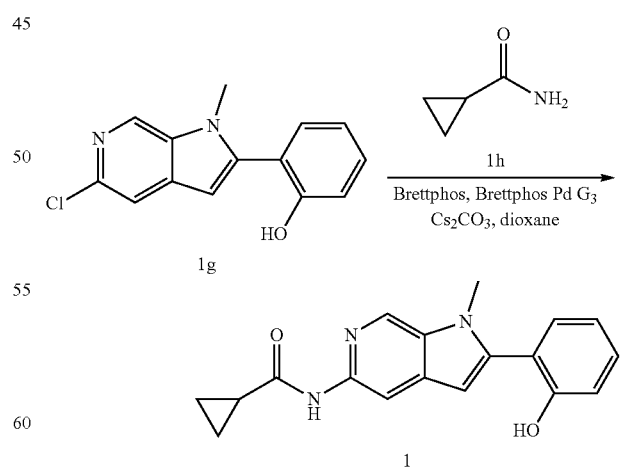

To a stirred solution of 2-[5-chloro-1-methylpyrrolo[2,3-c]pyridin-2-yl]phenol (Compound 1g) (120.0 mg, 0.46 mmol) in dioxane (5.0 mL) was added cyclopropanecarboxamide (Compound 1h) (118.4 mg, 1.39 mmol), BrettPhos Pd G3 (42.5 mg, 0.05 mmol), BrettPhos (49.9 mg, 0.09 mmol) and $Cs_2CO_3$ (453.8 mg, 1.39 mmol). The resulting mixture was stirred at 100° C. for 4 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by Prep-HPLC with the following conditions: Column: YMC-Actus Triart C18, 30×250 mm, 5 um; Mobile Phase A: Water (0.1% $NH_4HCO_3$), Mobile Phase B:ACN; Flow rate: 50 mL/min; Gradient: 43% B to 64% B in 7 min. Detector, UV 254 nm to afford N-[2-(2-hydroxyphenyl)-1-methylpyrrolo[2,3-c]pyridin-5-yl]cyclopropanecarboxamide (Compound 1) (26.8 mg, 19%) as a white solid. LCMS (ESI): $[M+H]^+$=308.0. $^1$H NMR (300 MHz, DMSO-$d_6$): δ 10.47 (s, 1H), 9.97 (s, 1H), 8.57 (s, 1H), 8.18 (s, 1H), 7.35-7.27 (m, 2H), 7.02-6.91 (m, 2H), 6.39 (s, 1H), 3.64 (s, 3H), 2.07-1.99 (m, 1H), 0.81-0.75 (m, 4H).

Example S2: Synthesis of N-(2-(2-methoxyphenyl)-1-methyl-1H-pyrrolo[2,3-c]pyridin-5-yl)cyclopropanecarboxamide (Compound 2)

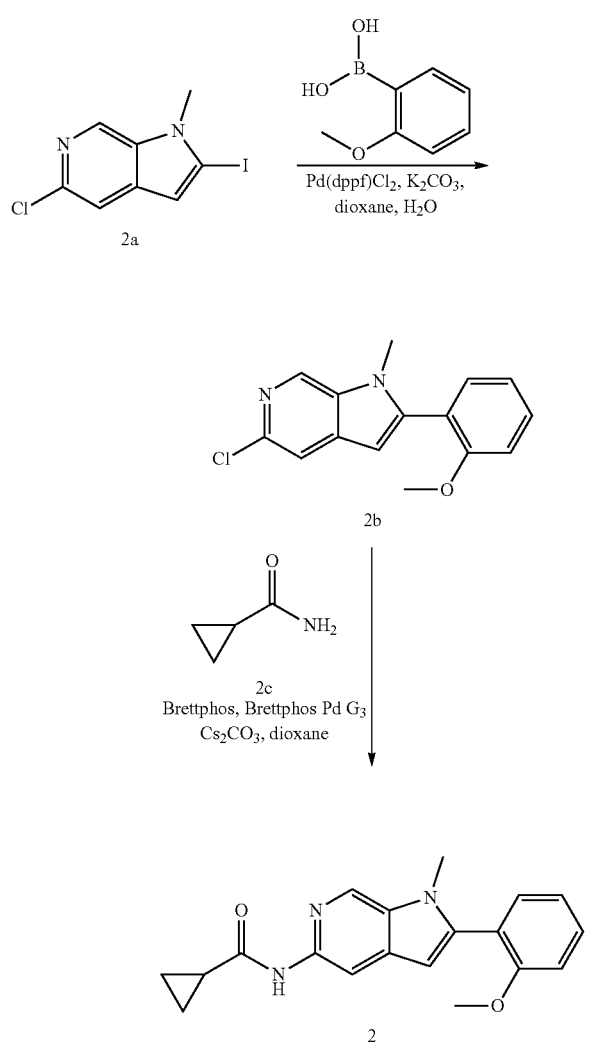

Step 1: Synthesis of 5-chloro-2-(2-methoxyphenyl)-1-methylpyrrolo[2,3-c]pyridine (Compound 2b)

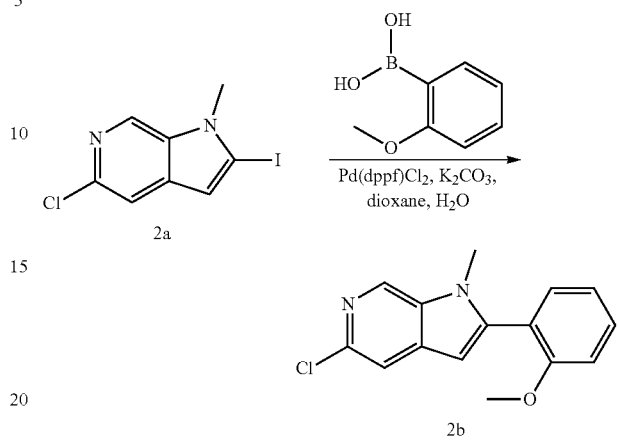

To a stirred solution of 5-chloro-2-iodo-1-methylpyrrolo[2,3-c]pyridine (Compound 2a) (200.0 mg, 0.68 mmol) in dioxane (10.0 mL) and $H_2O$ (1.0 mL) was added 2-methoxyphenylboronic acid (124.9 mg, 0.82 mol) and $K_2CO_3$ (283.5 mg, 2.05 mmol). The resulting mixture was stirred at 80° C. for 16 h under $N_2$. After the reaction was completed, the resulting mixture was concentrated under reduced pressure. The residue was purified by flash column chromatography with petroleum ether/ethyl acetate (1/2, v/v) to afford 5-chloro-2-(2-methoxyphenyl)-1-methylpyrrolo[2,3-c]pyridine (Compound 2b) (170.0 mg, 91%) as a yellow solid. LCMS (ESI): $[M+H]^+$=273.1.

Step 2: Synthesis of N-[2-(2-methoxyphenyl)-1-methylpyrrolo[2,3-c]pyridin-5-yl]cyclopropanecarboxamide (Compound 2)

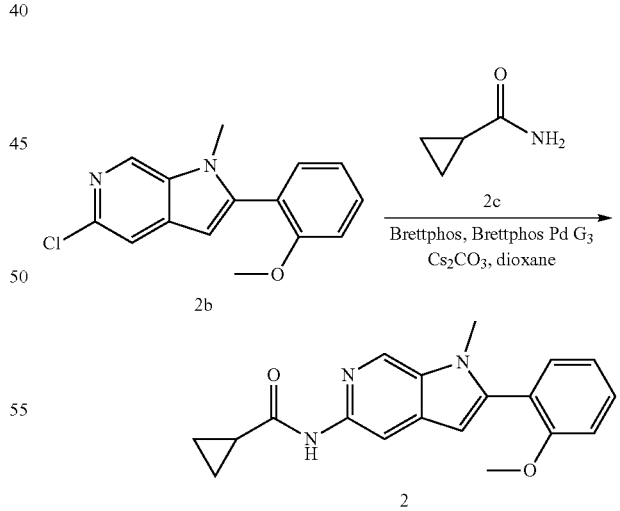

To a stirred solution of 5-chloro-2-(2-methoxyphenyl)-1-methylpyrrolo[2,3-c]pyridine (Compound 2b) (170.0 mg, 0.63 mmol) in dioxane (5.0 mL) was added cyclopropanecarboxamide (Compound 2c) (159.5 mg, 1.87 mmol), BrettPhos Pd $G_3$ (56.5 mg, 0.06 mmol), BrettPhos (66.9 mg, 0.15 mmol) and $Cs_2CO_3$ (609.8 mg, 1.87 mmol). The resulting mixture was stirred at 100° C. for 4 h. After the reaction was completed, the resulting mixture was diluted with H₂O and then extracted with ethyl acetate. The combined organic layer was washed with brine, dried over anhydrous sodium sulfate and filtered. The filtrate was concentrated under vacuum. The residue was purified by Prep-HPLC with the following conditions: Column: YMC-Actus Triart C18, 30×250 mm, 5 um; Mobile Phase A: Water (0.05% FA), Mobile Phase B:ACN; Flow rate: 60 mL/min; Gradient: 17% B to 40% B in 7 min. Detector, UV 254/220 nm to afford N-[2-(2-methoxyphenyl)-1-methylpyrrolo[2,3-c]pyridin-5-yl]cyclopropanecarboxamide (Compound 2) (63.2 mg, 32%) as a white solid. LCMS (ESI): [M+H]⁺= 322.1. ¹H NMR (300 MHz, DMSO-d₆): δ 10.52 (s, 1H), 8.60 (s, 1H), 8.17 (s, 1H), 7.55-7.49 (m, 1H), 7.39-7.35 (m, 1H), 7.21 (d, J=8.4 Hz, 1H), 7.12-7.07 (m, 1H), 6.43 (s, 1H), 3.81 (s, 3H), 3.60 (s, 3H), 2.03-1.98 (m, 1H), 0.81-0.76 (m, 4H).

Example S3: Synthesis of N-[2-(2-ethoxyphenyl)-1-methylpyrrolo[2,3-c]pyridin-5-yl]cyclopropanecarboxamide (Compound 3)

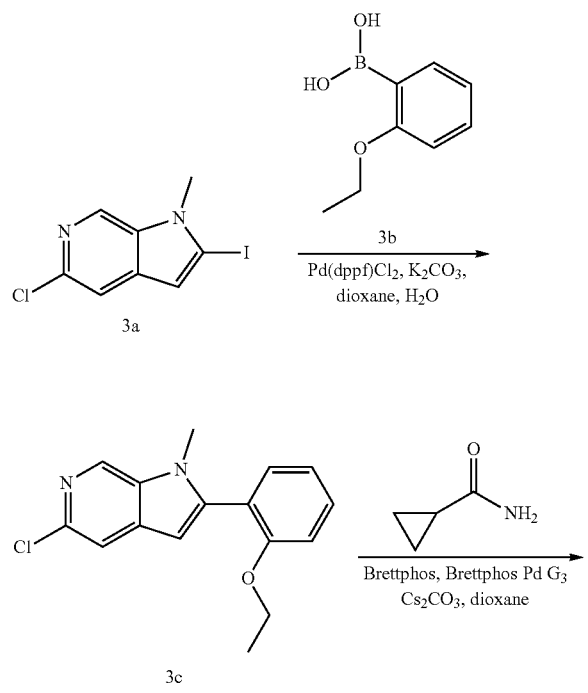

Step 1: Synthesis of 5-chloro-2-(2-ethoxyphenyl)-1-methylpyrrolo[2,3-c]pyridine (Compound 3c)

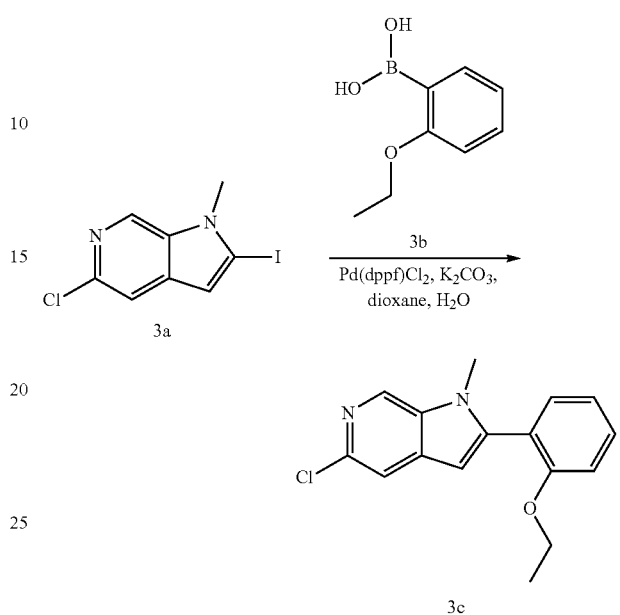

To a stirred mixture of 5-chloro-2-iodo-1-methylpyrrolo[2,3-c]pyridine (Compound 3a) (200.0 mg, 0.68 mmol) and 2-ethoxyphenylboronic acid (Compound 3b) (226.9 mg, 1.36 mmol) in 1,4-dioxane/H₂O (5.0/0.5 mL) was added Pd(dppf)Cl₂ (55.8 mg, 0.06 mmol) and K₂CO₃ (283.5 mg, 2.05 mmol). The resulting mixture was stirred at 80° C. for 12 h under N₂. After the reaction was completed, the reaction was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 5-chloro-2-(2-ethoxyphenyl)-1-methylpyrrolo[2,3-c]pyridine (Compound 3c) (170.0 mg, 87%) as a yellow oil. LCMS (ESI, m/z): [M+H]⁺= 287.1.

Step 2: Synthesis of N-[2-(2-ethoxyphenyl)-1-methylpyrrolo[2,3-c]pyridin-5-yl]cyclopropanecarboxamide (Compound 3)

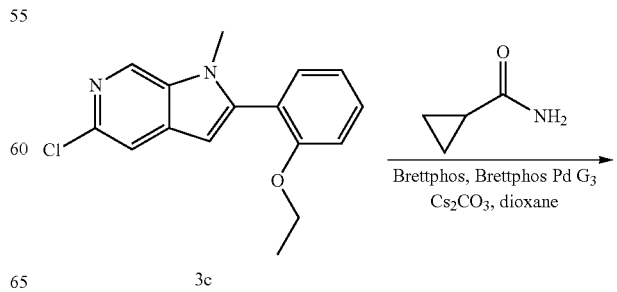

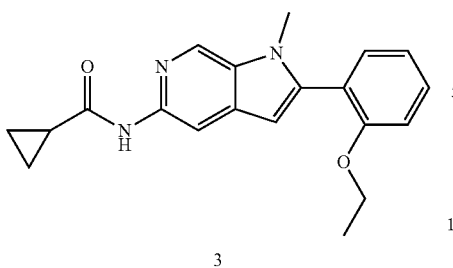

3

To a stirred mixture of 5-chloro-2-(2-ethoxyphenyl)-1-methylpyrrolo[2,3-c]pyridine (Compound 3c) (150.0 mg, 0.52 mmol) and cyclopropanecarboxamide (222.5 mg, 2.61 mmol) in dioxane (3.0 mL) were added BrettPhos Pd G$_3$ (47.4 mg, 0.05 mmol), Cs$_2$CO$_3$ (511.2 mg, 1.56 mmol) and BrettPhos (56.1 mg, 0.10 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A:Water (10 mmol/L NH$_4$HCO$_3$), Mobile Phase B: ACN; Flow rate: 60 mL/min; Gradient: 40% B to 62% B in 8 min; 254 nm; RT1:7.47 min) to afford N-[2-(2-ethoxyphenyl)-1-methylpyrrolo[2,3-c]pyridin-5-yl]cyclopropanecarboxamide (Compound 3) (59.9 mg, 34%) as a white solid. LCMS (ESI, m/z): [M+H]$^+$=336.2. $^1$H NMR (300 MHz, DMSO-d$_6$): δ 10.47 (s, 1H), 8.59 (s, 1H), 8.19 (s, 1H), 7.52-7.47 (m, 1H), 7.39-7.36 (m, 1H), 7.21-7.18 (m, 1H), 7.11-7.06 (m, 1H), 6.41 (d, J=0.6 Hz, 1H), 4.14-4.11 (m, 2H), 3.63 (s, 3H), 2.06-1.99 (m, 1H), 1.28-1.23 (m, 3H), 0.84-0.82 (m, 4H).

Example S4: Synthesis of N-[2-[2-(2-hydroxyethoxy)phenyl]-1-methylpyrrolo[2,3-c]pyridin-5-yl]cyclopropanecarboxamide (Compound 4)

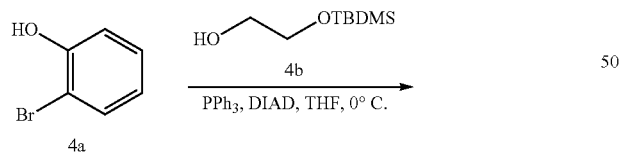

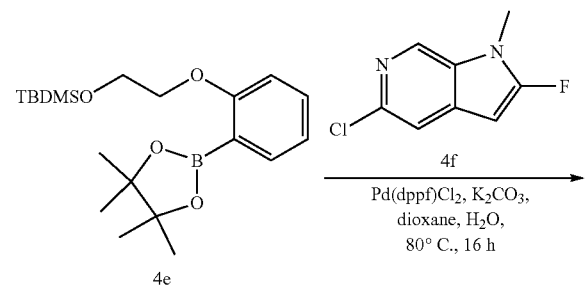

Step 1: Synthesis of [2-(2-bromophenoxy)ethoxy](tert-butyl)dimethylsilane (Compound 4c)

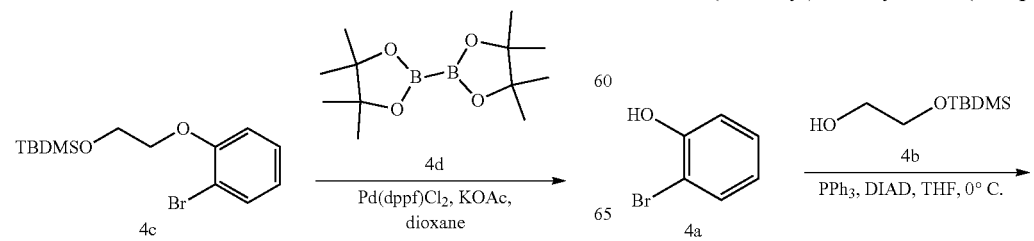

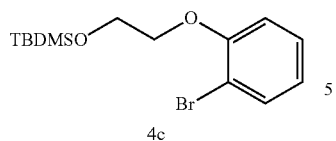

4c

To a mixture of 2-bromophenol (Compound 4a) (5.0 g, 28.90 mmol) and 2-[(tert-butyldimethylsilyl)oxy]ethanol (Compound 4b) (7.6 g, 43.32 mmol) in THF (100.0 mL) was added PPh$_3$ (11.3 g, 43.35 mmol) at room temperature under N$_2$. Then DIAD (8.7 g, 43.37 mmol) was added dropwise to the mixture at 0° C. under N$_2$. The resulting mixture was stirred at room temperature for 2 h. After the reaction was completed, the resulting mixture was concentrated under reduced pressure. The residue was purified by flash column chromatography with petroleum ether/ethyl acetate (10/1, v/v) to afford [2-(2-bromophenoxy)ethoxyl](tert-butyl)dimethylsilane (Compound 4c) (8.0 g, 83%) as a yellow solid.

Step 2: Synthesis of tert-butyldimethyl[2-[2-(4,4,5,5-tetramethyl-1,3,2-dioxaborolan-2-yl)phenoxy]ethoxy]silane (Compound 4e)

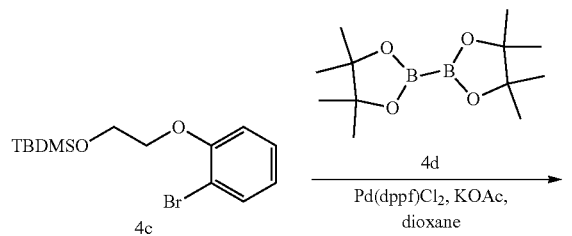

To a mixture of [2-(2-bromophenoxy)ethoxy](tert-butyl)dimethylsilane (Compound 4c) (1.0 g, 3.01 mmol) and 4,4,4',4',5,5,5',5'-octamethyl-2,2'-bi(1,3,2-dioxaborolane) (Compound 4d) (2.3 g, 9.05 mmol) in dioxane (10.0 mL) was added Pd(dppf)Cl$_2$ (0.2 g, 0.30 mmol) and KOAc (0.9 g, 9.05 mmol) at room temperature under N$_2$. The resulting mixture was stirred at 80° C. for 16 h. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (10/1, v/v) to afford tert-butyldimethyl[2-[2-(4,4,5,5-tetramethyl-1,3,2-dioxaborolan-2-yl)phenoxy]ethoxy]silane (Compound 4e) (700.0 mg, 61%) as a white solid.

Step 3: Synthesis of 2-(2-[2-[(tert-butyldimethylsilyl)oxy]ethoxy]phenyl)-5-chloro-1-methylpyrrolo[2,3-c]pyridine (Compound 4g)

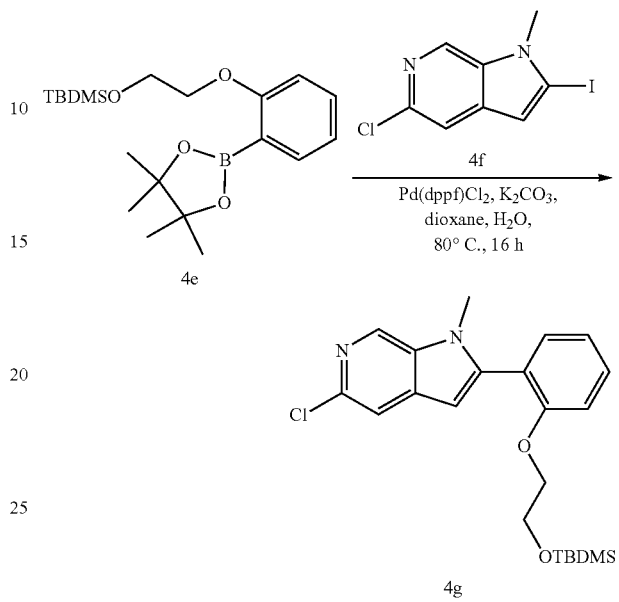

To a mixture of 5-chloro-2-iodo-1-methylpyrrolo[2,3-c]pyridine (Compound 4f) (300.0 mg, 1.02 mmol) and tert-butyldimethyl[2-[2-(4,4,5,5-tetramethyl-1,3,2-dioxaborolan-2-yl)phenoxy]ethoxy]silane (Compound 4e) (1.1 g, 3.07 mmol) in dioxane/H$_2$O (10.0/1.0 mL) was added Pd(dppf)Cl$_2$ (75.0 mg, 0.10 mmol) and K$_2$CO$_3$ (425.2 mg, 3.07 mmol) at room temperature under N$_2$. The resulting mixture was stirred at 80° C. for 16 h. After the reaction was completed, the reaction was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 2-(2-[2-[(tert-butyldimethylsilyl)oxy]ethoxy]phenyl)-5-chloro-1-methylpyrrolo[2,3-c]pyridine (Compound 4g) (100.0 mg, 23%) as a yellow solid. LCMS (ESI, m/z): [M+H]$^+$=417.2.

Step 4: Synthesis of N-[2-(2-[2-[(tert-butyldimethylsilyl)oxy]ethoxy]phenyl)-1-methylpyrrolo[2,3-c]pyridin-5-yl]cyclopropanecarboxamide (Compound 4i)

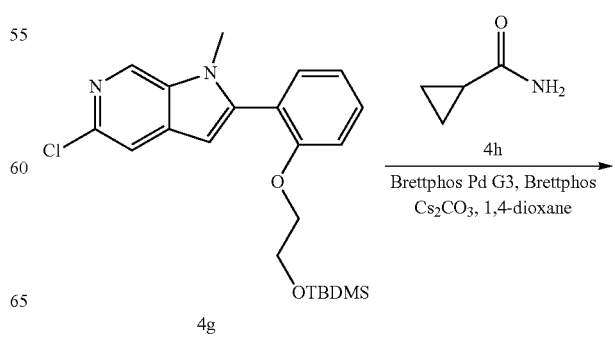

-continued

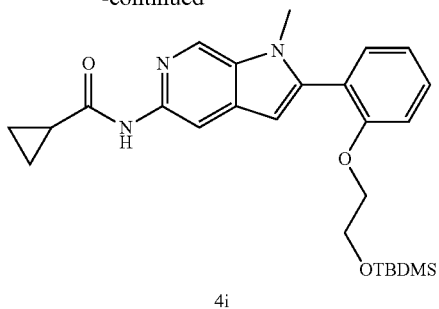

4i

To a mixture of 2-(2-[2-[(tert-butyldimethylsilyl)oxy] ethoxy]phenyl)-5-chloro-1-methylpyrrolo[2,3-c]pyridine (Compound 4g) (80.0 mg, 0.19 mmol) and cyclopropanecarboxamide (Compound 4h) (65.3 mg, 0.76 mmol) in dioxane (2.0 mL) was added Brettphos (20.5 mg, 0.03 mmol), BrettPhos Pd $G_3$ (17.3 mg, 0.02 mmol) and $Cs_2CO_3$ (187.5 mg, 0.57 mmol) at room temperature under $N_2$. The resulting mixture was stirred at 100° C. for 16 h. After the reaction was completed, the reaction was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford N-[2-(2-[2-[(tert-butyldimethylsilyl)oxy]ethoxy]phenyl)-1-methylpyrrolo[2,3-c]pyridin-5-yl]cyclopropanecarboxamide (Compound 41) (68.0 mg, 76%) as a white solid. LCMS (ESI, m/z): [M+H]⁺=466.2.

Step 5: Synthesis of N-[2-[2-(2-hydroxyethoxy) phenyl]-1-methylpyrrolo[2,3-c]pyridin-5-yl]cyclopropanecarboxamide (Compound 4)

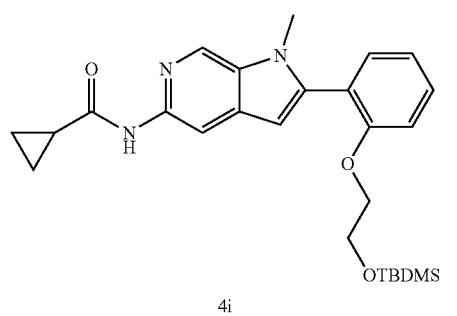

4i

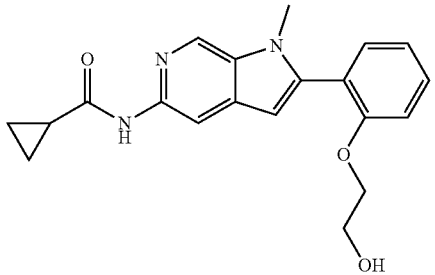

4

A solution of N-[2-(2-[2-[(tert-butyldimethylsilyl)oxy] ethoxy]phenyl)-1-methylpyrrolo[2,3-c]pyridin-5-yl]cyclopropanecarboxamide (Compound 41) (68.0 mg, 0.14 mmol) in HCl/1,4-dioxane (2.0 mL, 4 mol/L) was stirred at room temperature for 2 h. The resulting mixture was concentrated under vacuum. The residue was purified by Prep-HPLC with the following conditions (Column: Xselect CSH OBD Column 30×150 mm, 5 um; Mobile Phase A:Water (10 mmol/L $NH_4HCO_3$), Mobile Phase B: ACN; Flow rate: 60 mL/min; Gradient: 22% B to 48% B in 9 min; 220 nm; RT1:8.03) to afford N-[2-[2-(2-hydroxyethoxy) phenyl]-1-methylpyrrolo[2,3-c]pyridin-5-yl]cyclopropanecarboxamide (Compound 4) (15.1 mg, 29%) as a white solid. LCMS (ESI, m/z): [M+H]⁺=352.2. ¹H NMR (300 MHz, DMSO-$d_6$): δ 10.47 (s, 1H), 8.59 (s, 1H), 8.19 (s, 1H), 7.52-7.46 (m, 1H), 7.39-7.36 (m, 1H), 7.23-7.20 (m, 1H), 7.11-7.06 (m, 1H), 6.43 (d, J=0.6 Hz, 1H), 4.82-4.79 (m, 1H), 4.09-4.06 (m, 2H), 3.67-3.62 (m, 5H), 2.04-1.97 (m, 1H), 0.84-0.73 (m, 4H).

Example S5: Synthesis of N-(2-(2-(2-methoxyethoxy)phenyl)-1-methyl-1H-pyrrolo[2,3-c]pyridin-5-yl)cyclopropanecarboxamide (Compound 5)

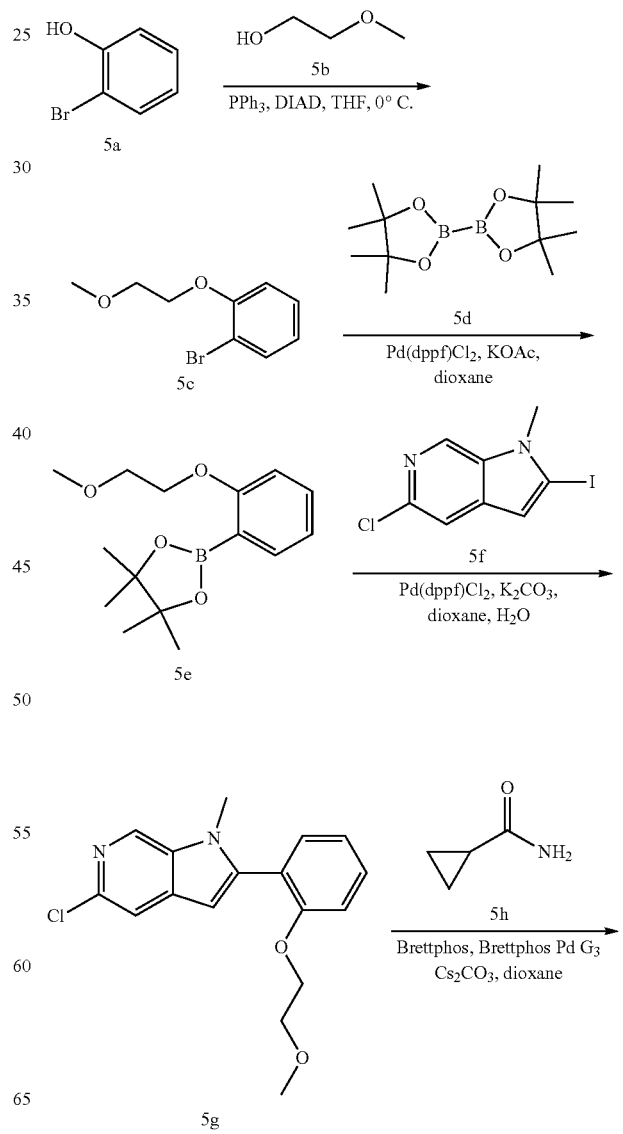

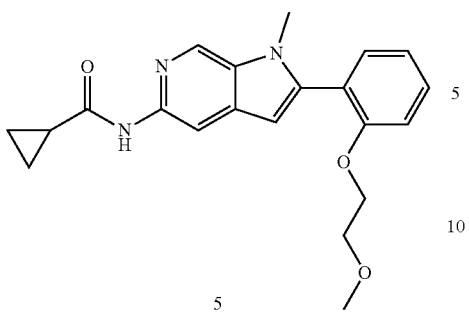

5

Step 1: Synthesis of 1-bromo-2-(2-methoxyethoxy)benzene (Compound 5c)

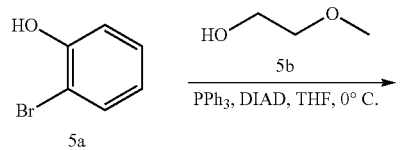

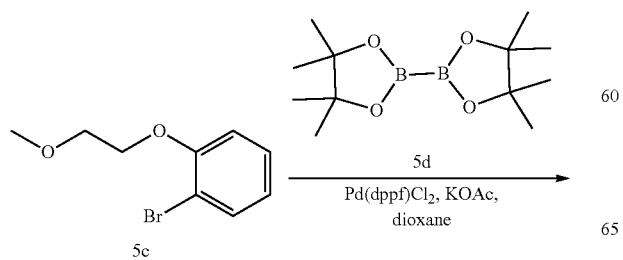

To a mixture of 2-bromophenol (Compound 5a) (2.0 g, 11.56 mmol) and PPh₃ (4.5 g, 17.34 mmol), 2-methoxyethanol (Compound 5b) (1.3 g, 17.34 mmol) in THF was added DIAD (3.5 g, 17.35 mmol) at 0° C. under N₂. The resulting mixture was stirred at room temperature for 2 h under N₂. After the reaction was completed, the resulting mixture was concentrated under vacuum. The residue was purified by flash column chromatography with petroleum ether/ethyl acetate (4/1, v/v) to afford 1-bromo-2-(2-methoxyethoxy)benzene (Compound 5c) (2.3 g, 86%) as a yellow oil.

Step 2: Synthesis of 2-[2-(2-methoxyethoxy)phenyl]-4,4,5,5-tetramethyl-1,3,2-dioxaborolane (Compound 5e)

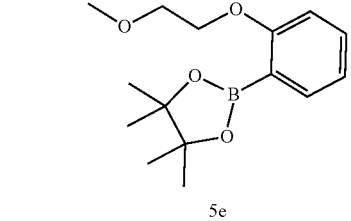

To a mixture of 1-bromo-2-(2-methoxyethoxy)benzene (Compound 5c) (1.1 g, 4.76 mmol) and 4,4,4',4',5,5,5',5'-octamethyl-2,2'-bi(1,3,2-dioxaborolane) (Compound 5d) (3.6 g, 14.29 mmol) in dioxane (20.0 mL) was added Pd(dppf)Cl₂ (348.2 mg, 0.47 mmol) and KOAc (1.4 g, 14.26 mmol) at room temperature under N₂. The resulting mixture was stirred at 80° C. for 16 h. After the reaction was completed, the reaction was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/1, v/v) to afford 2-[2-(2-methoxyethoxy)phenyl]-4,4,5,5-tetramethyl-1,3,2-dioxaborolane (Compound 5e) (700.0 mg, 52%) as a yellow oil. LCMS (ESI, m/z): [M+H]⁺=279.2.

Step 3: Synthesis of 5-chloro-2-[2-(2-methoxyethoxy)phenyl]-1-methylpyrrolo[2,3-c]pyridine (Compound 5g)

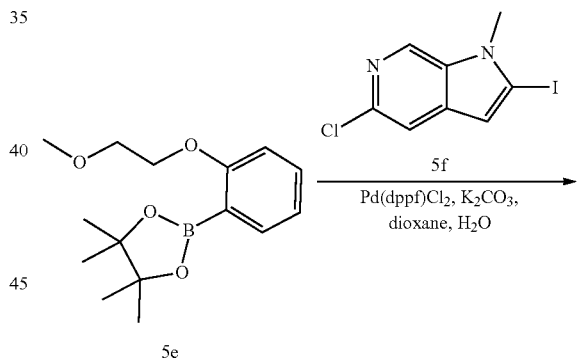

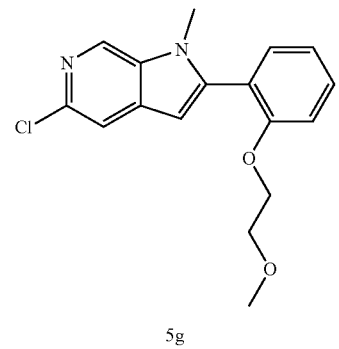

To a mixture of 5-chloro-2-iodo-1-methylpyrrolo[2,3-c]pyridine (Compound 5f) (200.0 mg, 0.68 mmol) and 2-[2-(2-methoxyethoxy)phenyl]-4,4,5,5-tetramethyl-1,3,2-dioxaborolane (Compound 5e) (380.3 mg, 1.36 mmol) in dioxane/H$_2$O (4/0.4 mL) was added Pd(dppf)Cl$_2$ (55.8 mg, 0.06 mmol) and K$_2$CO$_3$ (283.5 mg, 2.05 mmol) at room temperature under N$_2$. The resulting mixture was stirred at 80° C. for 16 h. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-chloro-2-[2-(2-methoxyethoxy)phenyl]-1-methylpyrrolo[2,3-c]pyridine (Compound 5g) (150.0 mg, 69%) as a yellow solid. LCMS (ESI, m/z): [M+H]$^+$=317.2.

Step 4: Synthesis of N-(2-(2-(2-methoxyethoxy)phenyl)-1-methyl-1H-pyrrolo[2,3-c]pyridin-5-yl)cyclopropanecarboxamide (Compound 5)

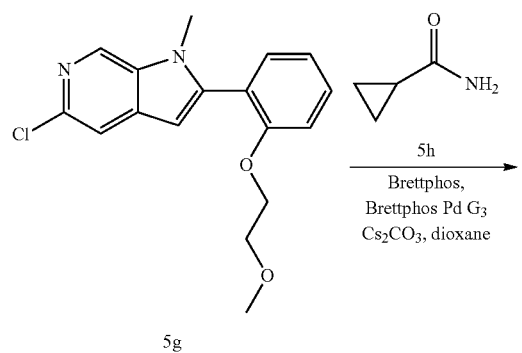

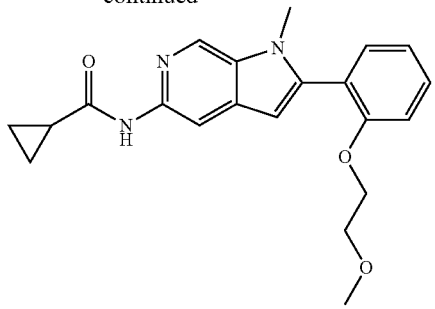

To a mixture of 5-chloro-2-[2-(2-methoxyethoxy)phenyl]-1-methylpyrrolo[2,3-c]pyridine (Compound 5g) (150.0 mg, 0.52 mmol) and cyclopropanecarboxamide (Compound 5h) (222.5 mg, 2.61 mmol) in dioxane (4.0 mL) was added BrettPhos Pd G$_3$ (47.4 mg, 0.05 mmol), Cs$_2$CO$_3$ (511.2 mg, 1.56 mmol) and BrettPhos (56.1 mg, 0.10 mmol) at room temperature. The resulting mixture was stirred at 100° C. for 16 h under N$_2$. After the reaction was completed, the reaction was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A:Water (10 mmol/L NH$_4$HCO$_3$), Mobile Phase B:ACN; Flow rate: 60 mL/min; Gradient: 35% B to 57% B in 8 min; 254 nm; RT1:7.3 min) to afford N-(2-(2-(2-methoxyethoxy)phenyl)-1-methyl-1H-pyrrolo[2,3-c]pyridin-5-yl)cyclopropanecarboxamide (Compound 5) (59.9 mg, 34%) as a white solid. LCMS (ESI, m/z): [M+H]$^+$=366.2. $^1$H NMR (400 MHz, DMSO-d$_6$): δ 10.47 (s, 1H), 8.59 (s, 1H), 8.19 (s, 1H), 7.52-7.47 (m, 1H), 7.39-7.37 (m, 1H), 7.21 (d, J=8.0 Hz, 1H), 7.12-7.08 (m, 1H), 6.43 (d, J=0.4 Hz, 1H), 4.18-4.16 (m, 2H), 3.64 (s, 3H), 3.60-3.58 (m, 2H), 3.18 (s, 3H), 2.08-2.00 (m, 1H), 0.87-0.84 (m, 4H).

Example S6: Synthesis of N-[2-(2-cyanophenyl)-1-methylpyrrolo[2,3-c]pyridin-5-yl]cyclopropanecarboxamide (Compound 6)

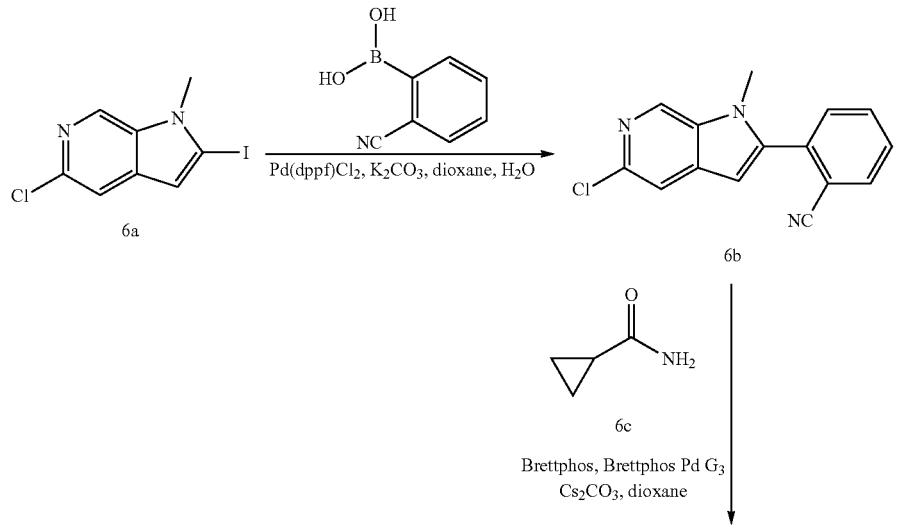

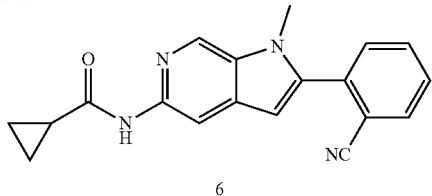

Step 1: Synthesis of 2-[5-chloro-1-methylpyrrolo[2,3-c]pyridin-2-yl]benzonitril (Compound 6b)

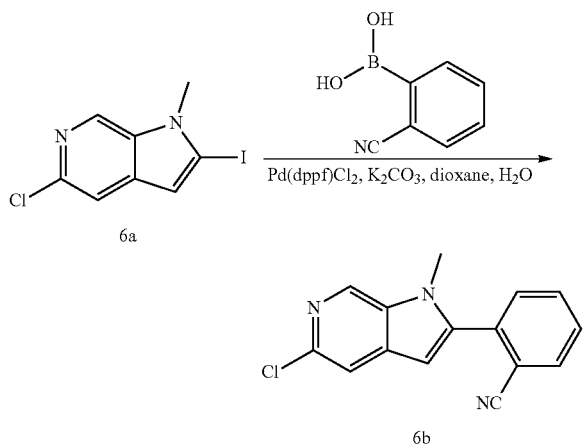

To a solution of 5-chloro-2-iodo-1-methylpyrrolo[2,3-c]pyridine (Compound 6a) (200.0 mg, 0.68 mmol) in dioxane/H$_2$O ((10.0/1.0 mL) was added 2-cyanophenylboronic acid (120.7 mg, 0.82 mmol), Pd(dppf)Cl$_2$ (100.6 mg, 0.17 mmol) and K$_2$CO$_3$ (283.5 mg, 2.05 mmol). The resulting mixture was stirred at 80° C. for 16 h under N$_2$. After the reaction was completed, the resulting mixture was concentrated under reduced pressure. The residue was purified by flash column chromatography with petroleum ether/ethyl acetate (1/2, v/v) to afford 2-[5-chloro-1-methylpyrrolo[2,3-c]pyridin-2-yl]benzonitrile (Compound 6b) (130.0 mg, 71%) as a yellow solid. LCMS (ESI): [M+H]$^+$=268.1.

Step 2: Synthesis of N-[2-(2-cyanophenyl)-1-methylpyrrolo[2,3-c]pyridin-5-yl]cyclopropanecarboxamide (Compound 6)

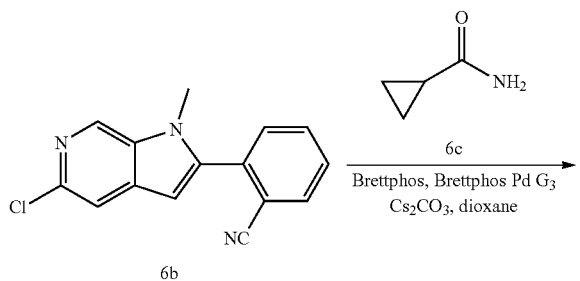

To a solution of 2-[5-chloro-1-methylpyrrolo[2,3-c]pyridin-2-yl]benzonitrile (Compound 6b) (110.0 mg, 0.41 mmol) in dioxane (5.0 mL) was added cyclopropanecarboxamide (Compound 6c) (105.0 mg, 1.24 mmol), BrettPhos Pd G$_3$ (37.0 mg, 0.04 mmol). BrettPhos (44.0 mg, 0.08 mmol) and Cs$_2$CO$_3$ (401.6 mg, 1.23 mmol). The resulting mixture was stirred at 100° C. for 4 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified Prep-HPLC with the following conditions: Column: YMC-Actus Triart C18, 30×250 mm, 5 um; Mobile Phase A: Water (10 mmol/L NH$_4$HCO$_3$), Mobile Phase B:ACN: Flow rate: 60 mL/min; Gradient: 35% B to 48% B in 7 min. Detector, UV 254/220 nm to afford N-[2-(2-cyanophenyl)-1-methylpyrrolo[2,3-c]pyridin-5-yl]cyclopropanecarboxamide (Compound 6) (28.6 mg, 22%) as a white solid. LCMS (ESI): [M+H]$^+$= 317.0. $^1$H NMR (300 MHz, DMSO-d$_6$): δ 10.57 (s, 1H), 8.72 (s, 1H), 8.26 (s, 1H), 8.07 (d, J=7.8 Hz, 1H), 7.89-7.86

(m, 1H), 7.78-7.70 (m, 2H), 6.73 (s, 1H), 3.73 (s, 3H), 2.06-1.94 (m, 1H), 0.82-0.76 (m, 4H).

Example S7: Synthesis of N-[2-(3-hydroxy-2-methylphenyl)-1-methylpyrrolo[2,3-c]pyridin-5-yl]cyclopropanecarboxamide (Compound 7)

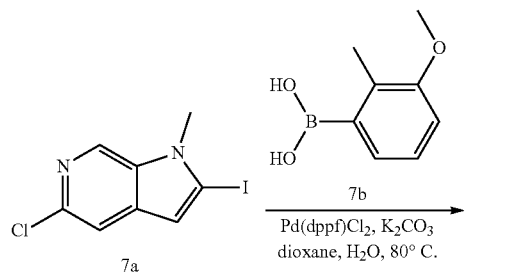

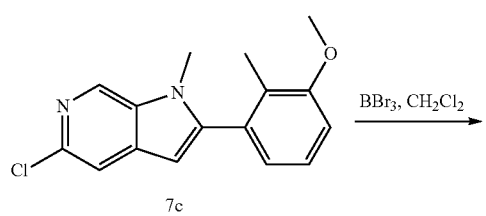

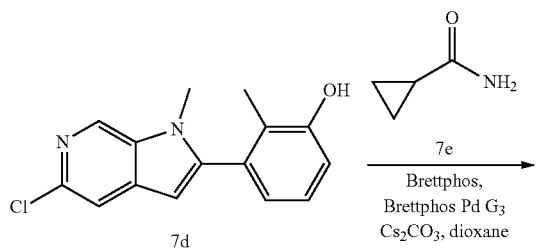

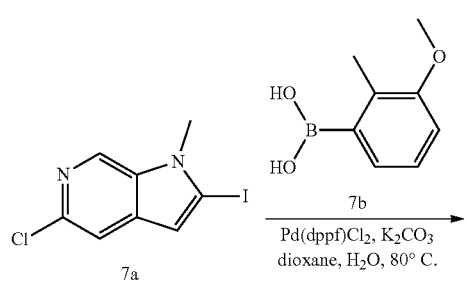

Step 1: Synthesis of 5-chloro-2-(3-methoxy-2-methylphenyl)-1-methylpyrrolo[2,3-c]pyridine (Compound 7c)

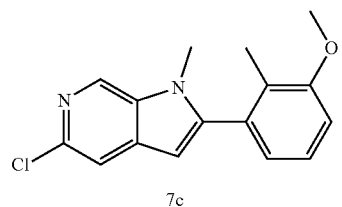

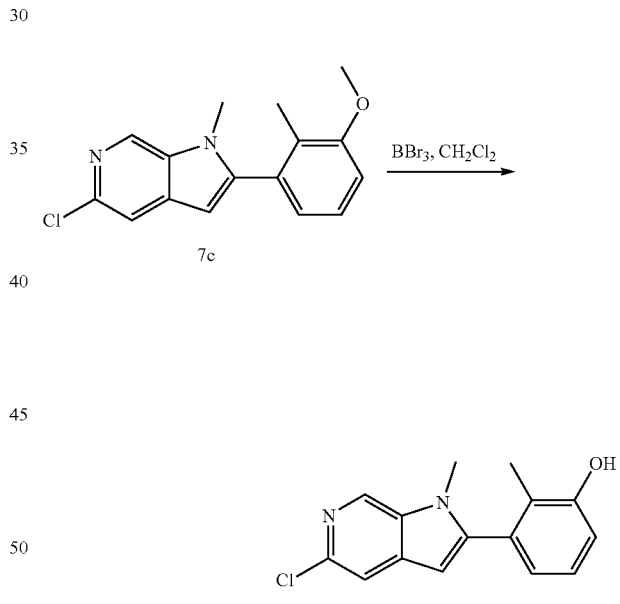

To a solution of 5-chloro-2-iodo-1-methylpyrrolo[2,3-c]pyridine (Compound 7a) 200.0 mg, 0.68 mmol) in dioxane (10.0 mL) and H₂O (1.0 mL) was added 3-methoxy-2-methylphenylboronic acid (Compound 7b) (136.2 mg, 0.82 mmol), Pd(dppf)Cl₂ (100.0 mg, 0.13 mmol) and K₂CO₃ (283.5 mg, 2.05 mmol) at room temperature under N₂. The resulting mixture was stirred at 80° C. for 16 h. After the reaction was completed, the mixture was concentrated under vacuum. The residue was purified by flash column chromatography with CH₂Cl₂/MeOH (97/3, v/v) to afford 5-chloro-2-(3-methoxy-2-methylphenyl)-1-methylpyrrolo[2,3-c]pyridine (Compound 7c) (150.0 mg, 76%) as a yellow solid. LCMS (ESI, m/z): [M+H]⁺=287.1.

Step 2: Synthesis of 3-[5-chloro-1-methylpyrrolo[2,3-c]pyridin-2-yl]-2-methylphenol (Compound 7d)

To a solution of 5-chloro-2-(3-methoxy-2-methylphenyl)-1-methylpyrrolo[2,3-c]pyridine (Compound 7c) (140.0 mg, 0.49 mmol) in DCM (2.0 mL) was added boron tribromide (1.5 mL, 1.50 mmol). The resulting mixture was stirred at room temperature for 2 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum to afford 3-[5-chloro-1-methylpyrrolo[2,3-c]pyridin-2-yl]-2-methylphenol (Compound 7d) (120.0 mg, crude) as a yellow solid. LCMS (ESI, m/z): [M+H]⁺=273.1.

Step 3: Synthesis of N-[2-(3-hydroxy-2-methylphenyl)-1-methylpyrrolo[2,3-c]pyridin-5-yl]cyclopropanecarboxamide (Compound 7)

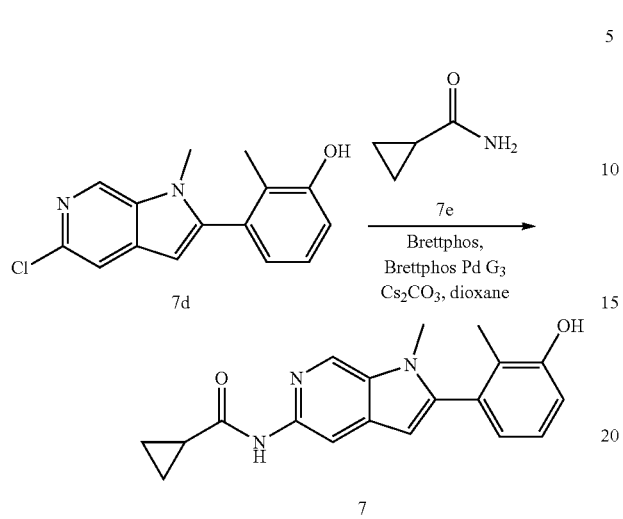

To a solution of 3-[5-chloro-1-methylpyrrolo[2,3-c]pyridin-2-yl]-2-methylphenol (Compound 7d) (130.0 mg, 0.47 mmol) in dioxane (2.0 mL) was added cyclopropanecarboxamide (Compound 7e) (60.8 mg, 0.71 mmol), Brettphos Pd $G_3$ (86.4 mg, 0.09 mmol), BrettPhos (102.3 mg, 0.19 mmol) and $Cs_2CO_3$ (465.9 mg, 1.43 mmol) at room temperature under $N_2$. The resulting mixture was stirred at 100° C. for 3 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified Prep-HPLC with the following conditions (Column: Xselect CSH OBD Column 30×150 mm, 5 um; Mobile Phase A:Water (0.1% FA), Mobile Phase B: ACN; Flow rate: 60 mL/min; Gradient: 5% B to 30% B in 8 min; 220 nm) to afford N-[2-(3-hydroxy-2-methylphenyl)-1-methylpyrrolo[2,3-c]pyridin-5-yl]cyclopropanecarboxamide (Compound 7) (10.4 mg, 6%) as a white solid. LCMS (ESI, m/z): $[M+H]^+$= 3221 $^1$H NMR (300 MHz, DMSO-$d_6$): δ 10.48 (s, 1H), 9.64 (s, 1H), 8.59 (s, 1H), 8.20 (s, 1H), 7.16-7.11 (m, 1H), 6.96-6.93 (m, 1H), 6.78-6.76 (m, 1H), 6.38 (d, J=0.6 Hz, 1H), 3.55 (s, 3H), 2.05-1.97 (m, 1H), 1.94 (s, 3H), 0.84-0.78 (m, 4H).

Example S8: Synthesis of N-[2-(4-hydroxy-2-methylphenyl)-1-methylpyrrolo[2,3-c]pyridin-5-yl]cyclopropanecarboxamide (Compound 8)

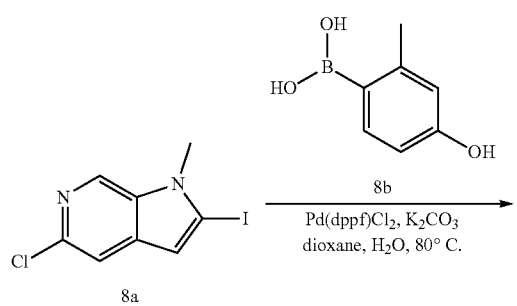

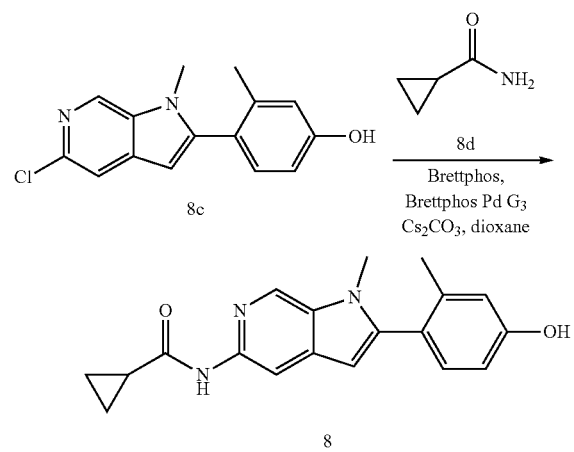

Step 1: Synthesis of 4-[5-chloro-1-methylpyrrolo[2,3-c]pyridin-2-yl]-3-methylphenol (Compound 8c)

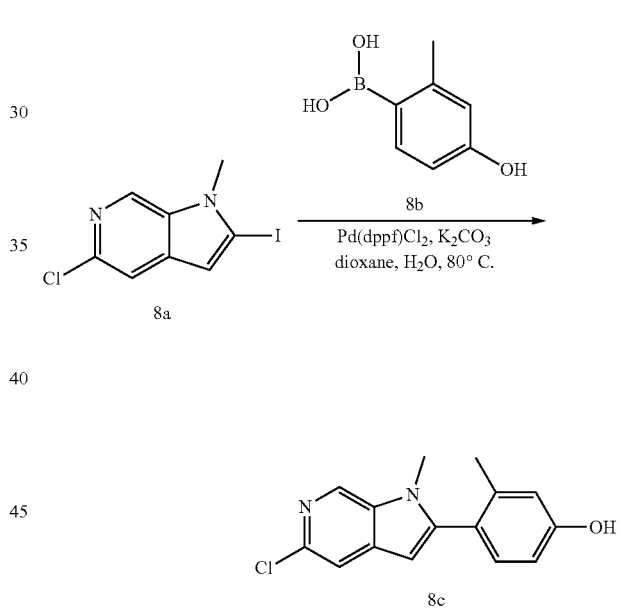

To a stirred mixture of 5-chloro-2-iodo-1-methylpyrrolo[2,3-c]pyridine (Compound 8a) (200.0 mg, 0.68 mmol) and 4-hydroxy-2-methylphenylboronic acid (Compound 8b) (124.6 mg, 0.82 mmol) in dioxane/$H_2O$ (2.0/0.2 mL) was added Pd(dppf)$Cl_2$ (100.0 mg, 0.13 mmol) and $K_2CO_3$ (283.5 mg, 2.05 mmol) at room temperature under $N_2$. The resulting mixture was stirred at 80° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (3/1, v/v) to afford 4-[5-chloro-1-methylpyrrolo[2,3-c]pyridin-2-yl]-3-methylphenol (Compound 8c) (85.0 mg, 45%) as a yellow solid. LCMS (ESI, m/z): $[M+H]^+$=273.2.

Step 2: Synthesis of N-[2-(4-hydroxy-2-methylphenyl)-1-methylpyrrolo[2,3-c]pyridin-5-yl]cyclopropanecarboxamide (Compound 8)

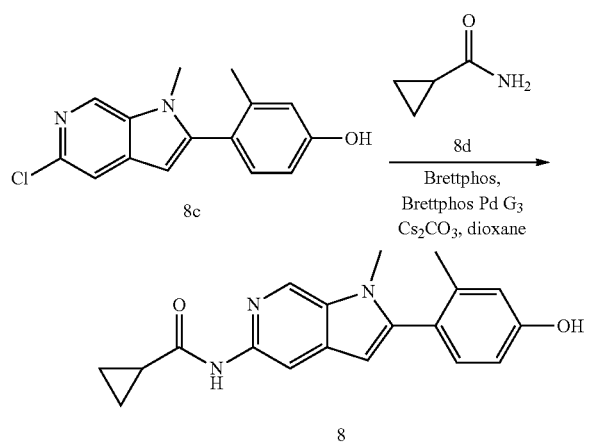

To a stirred mixture of 4-[5-chloro-1-methylpyrrolo[2,3-c]pyridin-2-yl]-3-methylphenol (Compound 8c) (85.0 mg, 0.31 mmol) and cyclopropanecarboxamide (Compound 8d) (79.5 mg, 0.93 mmol) in dioxane (2.0 mL) was added Cs$_2$CO$_3$ (304.6 mg, 0.93 mmol), Brettphos (33.4 mg, 0.06 mmol) and BrettPhos Pd G$_3$ (28.2 mg, 0.03 mmol) at room temperature N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by Prep-HPLC with the following conditions Column: YMC-Actus Triart C18, 20×250 mm, 5 um, 12 nm; Mobile Phase A:Water (10 mmol/L NH$_4$HCO$_3$), Mobile Phase B:ACN; Flow rate: 60 mL/min; Gradient: 28% B to 48% B in 8 min; 254/220 nm; to afford N-[2-(4-hydroxy-2-methylphenyl)-1-methylpyrrolo[2,3-c]pyridin-5-yl]cyclopropanecarboxamide (Compound 8) (38.0 mg, 37%) as a white solid. LCMS (ESI, m/z): [M+H]$^+$=322.1. $^1$H NMR (300 MHz, DMSO-d$_6$): δ 10.47 (s, 1H), 9.67 (s, 1H), 8.56 (s, 1H), 8.17 (s, 1H), 7.12 (d, J=8.1 Hz, 1H), 6.78-6.69 (m, 2H), 6.35 (s, 1H), 3.54 (s, 3H), 2.07 (s, 3H), 2.04-1.97 (m, 1H), 0.80-0.72 (m, 4H).

Example S9: Synthesis of N-[2-(3-methoxy-2-methylphenyl)-1-methylpyrrolo[2,3-C]pyridin-5-yl]cyclopropanecarboxamide (Compound 9)

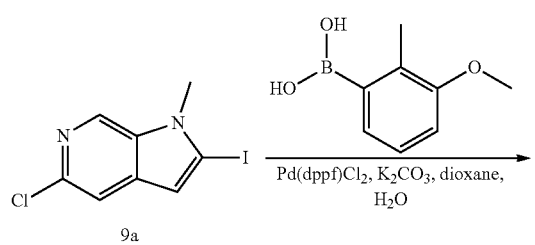

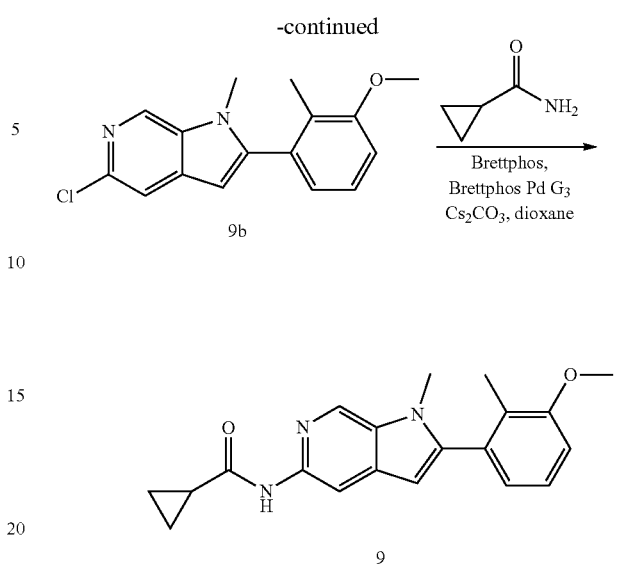

Step 1: Synthesis of 5-chloro-2-(3-methoxy-2-methylphenyl)-1-methylpyrrolo[2,3-c]pyridine (Compound 9b)

To a stirred solution of 5-chloro-2-iodo-1-methylpyrrolo[2,3-c]pyridine (Compound 9a) (200.0 mg, 0.68 mmol) in dioxane/H$_2$O (10.0/1.0 mL) was added 3-methoxy-2-methylphenylboronic acid (136.9 mg, 0.82 mmol), Pd(dppf)Cl$_2$ (50.3 mg, 0.68 mmol) and K$_2$CO$_3$ (283.5 mg, 2.05 mmol). The resulting mixture was stirred at 80° C. for 16 h. After the reaction was completed, the resulting mixture was concentrated under reduced pressure. The residue was purified by flash column chromatography with petroleum ether/ethyl acetate (1/2 v/v) to afford 5-chloro-2-(3-methoxy-2-methylphenyl)-1-methylpyrrolo[2,3-c]pyridine (Compound 9b) (150.0 mg, 77%) as a yellow solid. LCMS (ESI): [M+H]+= 287.1.

Step 2: Synthesis of N-[2-(3-methoxy-2-methylphenyl)-1-methylpyrrolo[2,3-c]pyridin-5-yl]cyclopropanecarboxamide (Compound 9)

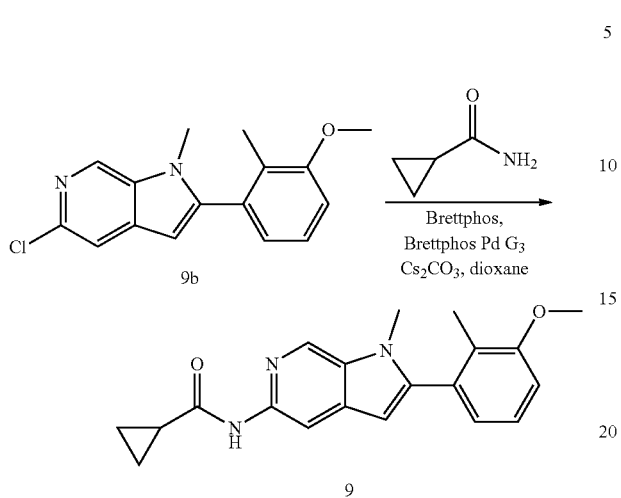

To a stirred solution of 5-chloro-2-(3-methoxy-2-methylphenyl)-1-methylpyrrolo[2,3-c]pyridine (Compound 9b) (150.0 mg, 0.53 mmol) in dioxane (5.0 mL) was added cyclopropanecarboxamide (133.5 mg, 1.59 mmol), BrettPhos Pd G$_3$ (47.2 mg, 0.02 mmol), BrettPhos (56.1 mg, 0.15 mmol) and Cs$_2$CO$_3$ (511.9 mg, 1.59 mmol). The resulting mixture was stirred at 100° C. for 4 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified Prep-HPLC with the following conditions: Column: YMC-Actus Triart C$_{18}$, 30×250 mm, 5 um; Mobile Phase A: Water (10 mmol/L NH$_4$HCO$_3$), Mobile Phase B:ACN; Flow rate: 60 mL/min; Gradient: 16% B to 25% B in 7 min. Detector, UV 254/220 nm to afford N-[2-(3-methoxy-2-methylphenyl)-1-methylpyrrolo[2,3-c]pyridin-5-yl]cyclopropanecarboxamide (Compound 9) (74.2 mg, 42%) as a white solid. LCMS (ESI): [M+H]$^+$=336.2. $^1$H NMR (400 MHz, DMSO-d$_6$): δ 10.51 (s, 1H), 8.61 (s, 1H), 8.21 (s, 1H), 7.34-7.30 (m, 1H), 7.12 (d, J=8.0 Hz, 1H), 6.93 (d, J=7.2 Hz, 1H), 6.41 (s, 1H), 3.86 (s, 3H), 3.55 (s, 3H), 2.03-1.98 (m, 4H), 0.84-0.79 (m, 4H).

Example S10: Synthesis of N-[2-(4-methoxy-2-methylphenyl)-1-methylpyrrolo[2,3-c]pyridin-5-yl]cyclopropanecarboxamide (Compound 10)

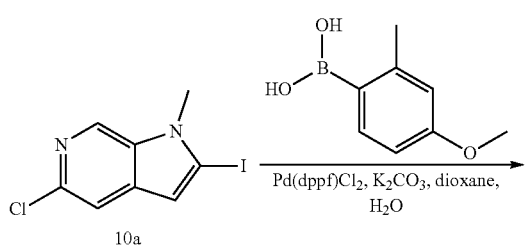

Step 1: Synthesis of 5-chloro-2-(4-methoxy-2-methylphenyl)-1-methylpyrrolo[2,3-c]pyridine (Compound 10b)

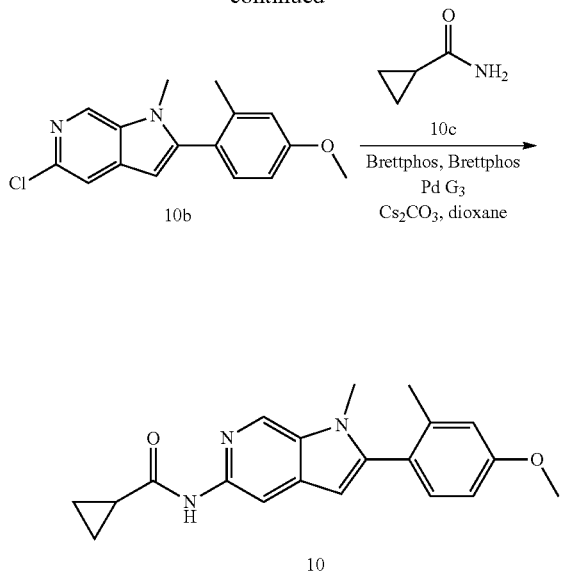

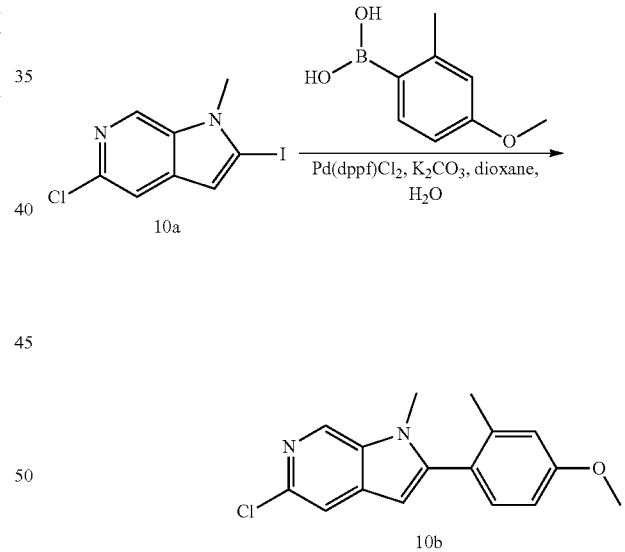

To a stirred solution of 5-chloro-2-iodo-1-methylpyrrolo[2,3-c]pyridine (Compound 10a) (200.0 mg, 0.68 mmol) in dioxane (10.0 mL) and H$_2$O (1.0 mL) was added 4-methoxy-2-methylphenylboronic acid (136.9 mg, 0.81 mmol) and K$_2$CO$_3$ (283.5 mg, 2.05 mmol). The resulting mixture was stirred at 80° C. for 16 h under N$_2$. After the reaction was completed, the resulting mixture was concentrated under reduced pressure. The residue was purified by flash column chromatography with petroleum ether/ethyl acetate (1/2, v/v) to afford 5-chloro-2-(4-methoxy-2-methylphenyl)-1-methylpyrrolo[2,3-c]pyridine (Compound 10b) (190.0 mg, 97%) as a white solid. LCMS (ESI): [M+H]$^+$=287.1.

Step 2: Synthesis of N-[2-(4-methoxy-2-methylphenyl)-1-methylpyrrolo[2,3-c]pyridin-5-yl]cyclopropanecarboxamide (Compound 10)

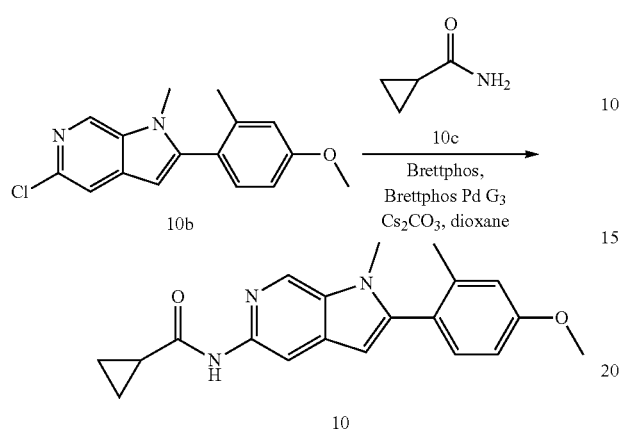

To a stirred solution of 5-chloro-2-(4-methoxy-2-methylphenyl)-1-methylpyrrolo[2,3-c]pyridine (Compound 10b) (190.0 mg, 0.63 mmol) in dioxane (10.0 mL) was added cyclopropanecarboxamide (Compound 10c) (169.7 mg, 1.98 mmol), BrettPhos Pd $G_3$ (60.6 mg, 0.06 mmol), BrettPhos (71.3 mg, 0.13 mmol) and $Cs_2CO_3$ (647.6 mg, 1.98 mmol). The resulting mixture was stirred at 100° C. for 4 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified Prep-HPLC with the following conditions: Column: YMC-Actus Triart C18, 30×250 mm, 5 um; Mobile Phase A: Water (10 mmol/L $NH_4HCO_3$), Mobile Phase B:ACN: Flow rate: 60 mL/min; Gradient: 29% B to 55% B in 10 min. Detector, UV 254 nm to afford N-[2-(4-methoxy-2-methylphenyl)-1-methylpyrrolo[2,3-c]pyridin-5-yl]cyclopropanecarboxamide (Compound 10) (115.9 mg, 52%) as a white solid. LCMS (ESI): $[M+H]^+$=336.2. $^1$H NMR (300 MHz, DMSO-$d_6$): δ 10.49 (s, 1H), 8.58 (s, 1H), 8.18 (s, 1H), 7.25 (d, J=8.4 Hz, 1H), 6.97 (d, J=2.1 Hz, 1H), 6.91-6.87 (m, 1H), 6.38 (s, 1H), 3.81 (s, 3H), 3.54 (s, 3H), 2.13 (s, 3H), 2.07-1.99 (m, 1H), 0.81-0.75 (m, 4H).

Example S11: Synthesis of N-[2-(2-methoxy-6-methylphenyl)-1-methylpyrrolo[2,3-c]pyridin-5-yl]cyclopropanecarboxamide (Compound 11)

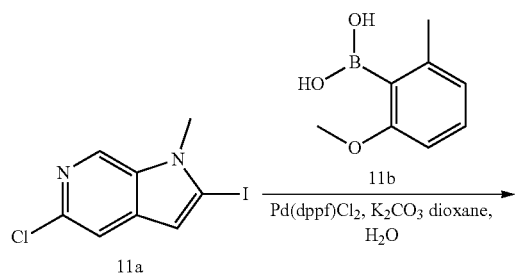

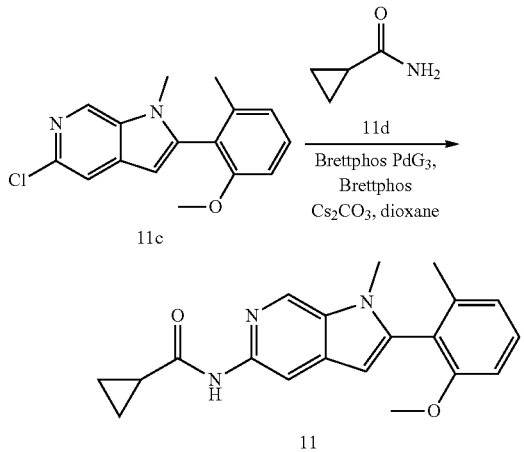

Step 1: Synthesis of 5-chloro-2-(2-methoxy-6-methylphenyl)-1-methylpyrrolo[2,3-c]pyridine (Compound 11c)

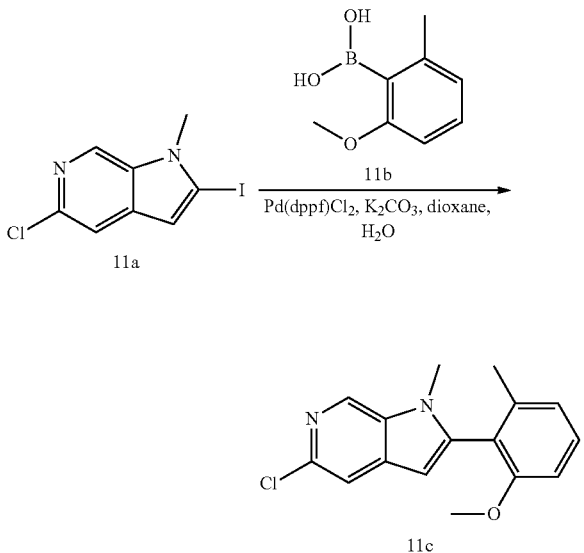

To a stirred mixture of 5-chloro-2-iodo-1-methylpyrrolo[2,3-c]pyridine (Compound 11a) (200.0 mg, 0.68 mmol) and 2-methoxy-6-methylphenylboronic acid (Compound 11b) (136.0 mg, 0.82 mmol) in dioxane/$H_2O$ (2.0/0.2 mL) was added $Pd(dppf)Cl_2$ (100.0 mg, 0.13 mmol) and $K_2CO_3$ (283.0 mg, 2.05 mmol) at room temperature under $N_2$. The resulting mixture was stirred at 80° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (3/1, v/v) to afford 5-chloro-2-(2-methoxy-6-methylphenyl)-1-methylpyrrolo[2,3-c]pyridine (Compound 11c) (60.0 mg, 30%) as a white solid. LCMS (ESI, m/z): $[M+H]^+$=287.1.

Step 2: Synthesis of N-[2-(2-methoxy-6-methylphenyl)-1-methylpyrrolo[2,3-c]pyridin-5-yl]cyclopropanecarboxamide (Compound 11)

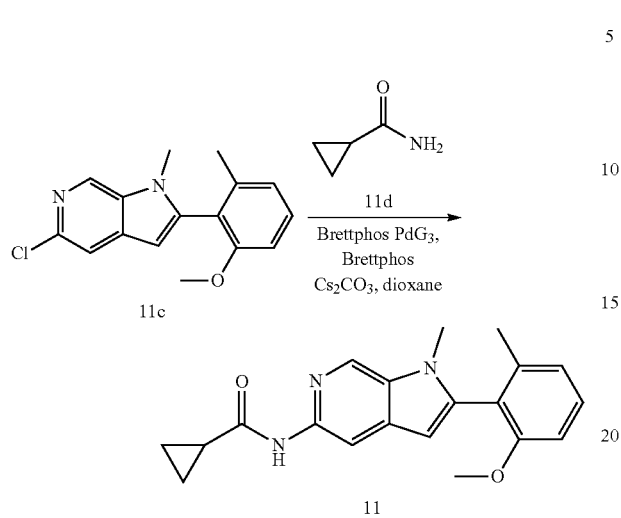

To a stirred mixture of 5-chloro-2-(2-methoxy-6-methylphenyl)-1-methylpyrrolo[2,3-c]pyridine (Compound 11c) (50.0 mg, 0.17 mmol) and cyclopropanecarboxamide (Compound 11d) (44.5 mg, 0.52 mmol) in dioxane (2.0 mL) was added $Cs_2CO_3$ (170.4 mg, 0.52 mmol). Brettphos (18.7 mg, 0.03 mmol) and BrettPhos Pd G3 (15.8 mg, 0.02 mmol). The resulting mixture was stirred at 100° C. for 16 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by Prep-HPLC with the following conditions Column: YMC-Actus Triart $C_{18}$, 30×250 mm, 5 um; Mobile Phase A:Water (10 mmol/L $NH_4HCO_3$), Mobile Phase B:ACN; Flow rate: 60 mL/min; Gradient: 46% B to 60% B in 8 min; 254 nm; to afford N-[2-(2-methoxy-6-methylphenyl)-1-methylpyrrolo[2,3-c]pyridin-5-yl]cyclopropanecarboxamide (Compound 11) (14.5 mg, 25%) as a white solid. LCMS (ESI, m/z): $[M+H]^+$=336.1. $^1$H NMR (300 MHz, DMSO-$d_6$): δ 10.47 (s, 1H), 8.58 (s, 1H), 8.17 (s, 1H), 7.42-7.36 (m, 1H), 7.01-6.97 (m, 2H), 6.34 (s, 1H), 3.70 (s, 3H), 3.47 (s, 3H), 2.06-1.96 (m, 4H), 0.81-0.75 (m, 4H).

Example S12: Synthesis of N-[2-(5-fluoro-2-methylphenyl)-1-methylpyrrolo[2,3-c]pyridin-5-yl]cyclopropanecarboxamide (Compound 12)

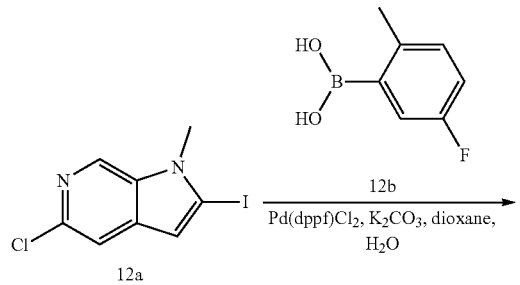

Step 1: Synthesis of 5-chloro-2-(5-fluoro-2-methylphenyl)-1-methylpyrrolo[2,3-c]pyridine (Compound 12c)

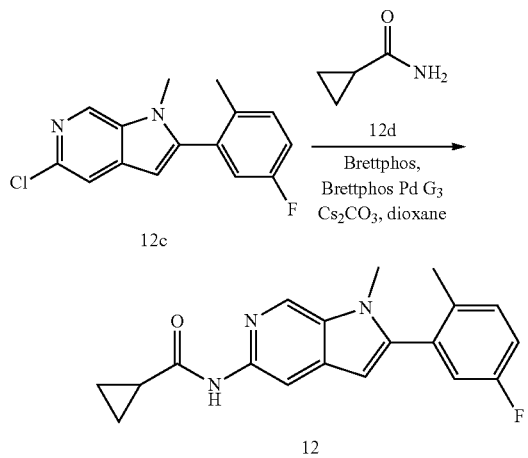

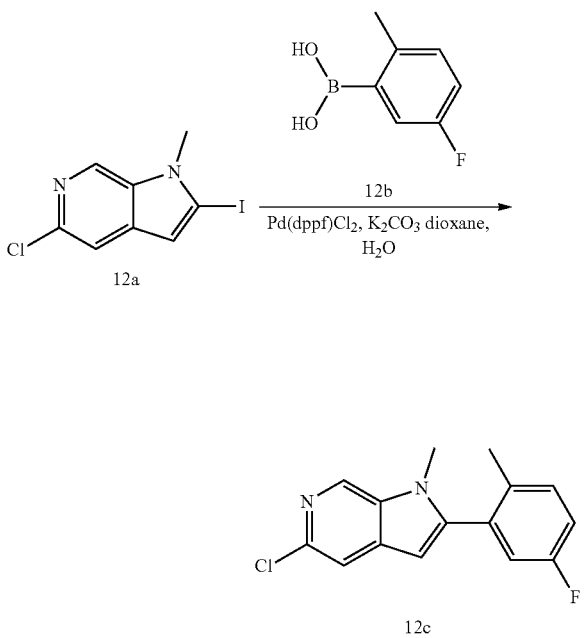

To a solution of 5-chloro-2-iodo-1-methylpyrrolo[2,3-c] pyridine (Compound 12a) (300.0 mg, 1.06 mmol) in dioxane/$H_2O$ (10.0/1.0 mL) was added 5-fluoro-2-methylphenylboronic acid (Compound 12b) (189.8 mg, 1.23 mmol), Pd(dppf)$Cl_2$ (75.5 mg, 0.13 mmol) and $K_2CO_3$ (425.5 mg, 3.77 mmol). The reaction mixture was stirred at 80° C. for 16 h. After the reaction was completed, the resulting mixture was concentrated under vacuum. The residue was purified by flash column chromatography with petroleum ether/ethyl acetate (1/2, v/v) to afford 5-chloro-2-(5-fluoro-2-methylphenyl)-1-methylpyrrolo[2,3-c]pyridine (Compound 12c) (200.0 mg, 71%) as a yellow oil. LCMS (ESI, m/z): $[M+H]^+$=275.1.

Step 2: Synthesis of N-[2-(5-fluoro-2-methylphenyl)-1-methylpyrrolo[2,3-c]pyridin-5-yl]cyclopropanecarboxamide (Compound 12)

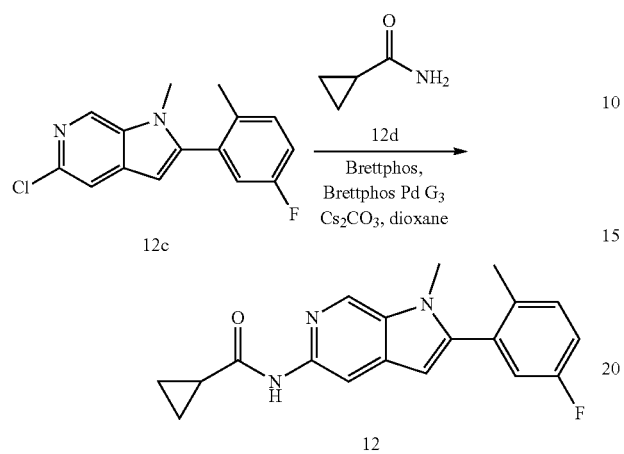

To a solution of 5-chloro-2-(5-fluoro-2-methylphenyl)-1-methylpyrrolo[2,3-c]pyridine (Compound 12c) (180.0 mg, 0.65 mmol) in dioxane (10.0 mL) was added cyclopropanecarboxamide (Compound 12d) (167.3 mg, 1.96 mmol), BrettPhos (35.7 mg, 0.06 mmol), BrettPhos Pd $G_3$ (118.9 mg, 0.13 mmol) and $Cs_2CO_3$ (640.4 mg, 1.96 mmol) under $N_2$. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with $CH_2Cl_2/CH_3OH$ (10/1, v/v) and then purified by Prep-HPLC with the following conditions (Column: YMC-Actus Triart C18, 30×250 mm, 5 um; Mobile Phase A: Water (10 mmol/L $NH_4HCO_3$), Mobile Phase B: ACN; Flow rate: 60 mL/min; Gradient: 49% B to 79% B in 7 min; 254 nm) to afford N-[2-(5-fluoro-2-methylphenyl)-1-methylpyrrolo[2,3-c]pyridin-5-yl]cyclopropanecarboxamide (Compound 12) (42.1 mg, 20%) as a white solid. LCMS (ESI, m/z): $[M+H]^+=324.2$. $^1H$ NMR (400 MHz, DMSO-$d_6$): δ 10.50 (s, 1H), 8.63 (s, 1H), 8.23 (s, 1H), 7.46-7.42 (m, 1H), 7.31-7.22 (m, 2H), 6.48 (s, 1H), 3.59 (s, 3H), 2.14 (s, 3H), 2.08-1.99 (m, 1H), 0.84-0.77 (m, 4H).

Example S13: Synthesis of N-[1-methyl-2-(4-methyl-2,3-dihydro-1H-indol-5-yl)pyrrolo[2,3-c]pyridin-5-yl]cyclopropanecarboxamide (Compound 13)

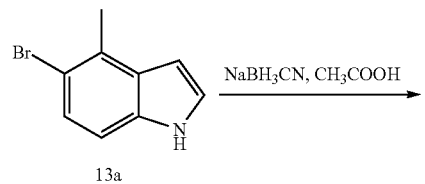

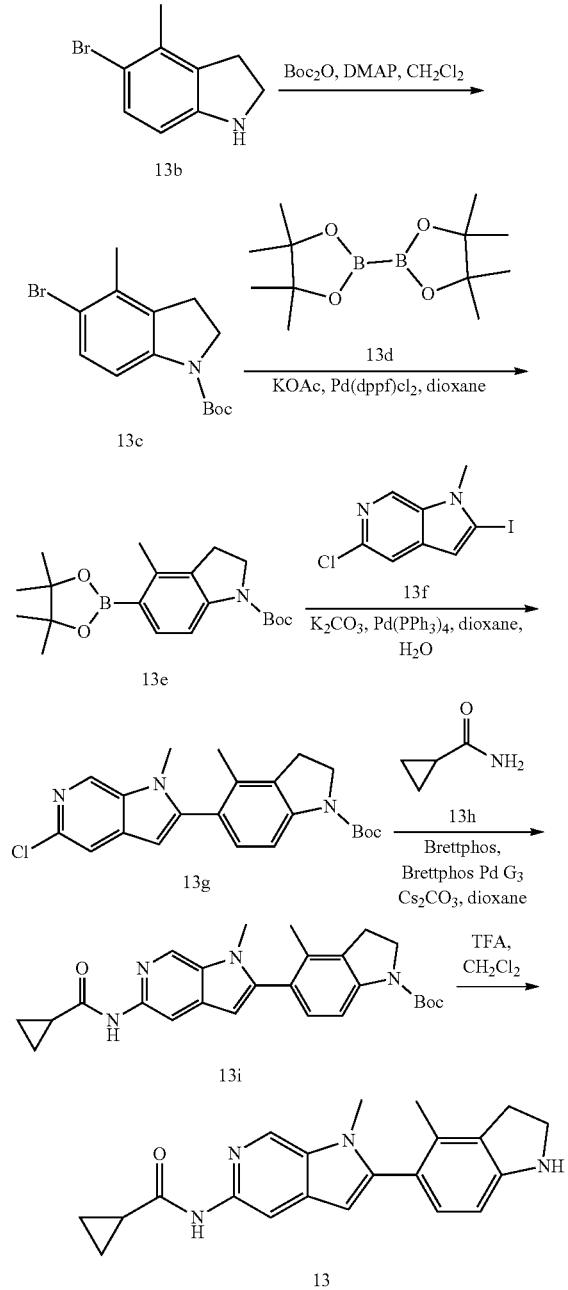

Step 1: Synthesis of 5-bromo-4-methyl-2,3-dihydro-1H-indole (Compound 13b)

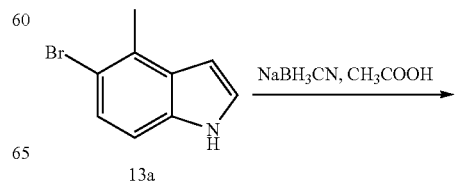

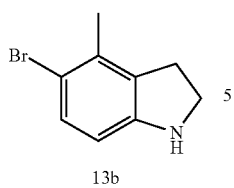

13b

To a solution of 5-bromo-4-methyl-1H-indole (Compound 13a) (880.0 mg, 4.18 mmol) in HOAc (15.0 mL) was added NaBH₃CN (1.0 g, 16.72 mmol) at 0° C. under N₂. The resulting mixture was stirred at room temperature for 2 h. After the reaction was completed, the pH value of the mixture was adjusted to 9 with NaOH (aq). The mixture was extracted with ethyl acetate. The combined organic layer was washed with brine, dried over anhydrous sodium sulfate and filtered. The filtrate was concentrated under reduced pressure. The residue was purified by reverse flash chromatography with petroleum ether/EtOAc (3/1, v/v) to afford 5-bromo-4-methyl-2,3-dihydro-1H-indole (Compound 13b) (800.0 mg, 90%) as a yellow solid LCMS (ESI, m/z): [M+H]⁺=212.0.

Step 2: Synthesis of tert-butyl 5-bromo-4-methyl-2,3-dihydroindole-1-carboxylate

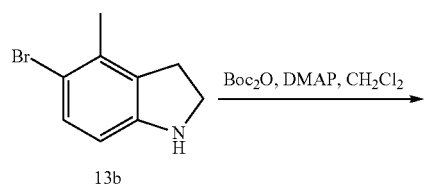

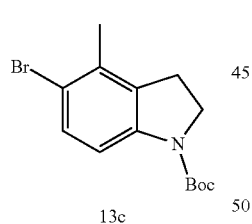

13c

To a mixture of 5-bromo-4-methyl-2,3-dihydro-1H-indole (800.0 mg, 3.77 mmol) and Boc₂O (2.5 g, 11.32 mmol) in DCM (20.0 mL) was added DMAP (460.8 mg, 3.72 mmol) at room temperature. The resulting mixture was stirred at room temperature for 16 h. After the reaction was completed, the reaction mixture was diluted with H₂O and extracted with CH₂C₂. The combined organic layer was washed with brine, dried over anhydrous sodium sulfate and filtered. The filtrate was concentrated under reduced pressure. The residue was purified by flash column chromatography with petroleum ether/EtOAc (8/1, v/v) to afford tert-butyl 5-bromo-4-methyl-2,3-dihydroindole-1-carboxylate (780.0 mg, 66%) as a white solid. LCMS (ESI, m/z): [M+H]⁺=312.1.

Step 3: Synthesis of tert-butyl 4-methyl-5-(4,4,5,5-tetramethyl-1,3,2-dioxaborolan-2-yl)-2,3-dihydroindole-1-carboxylate (Compound 13e)

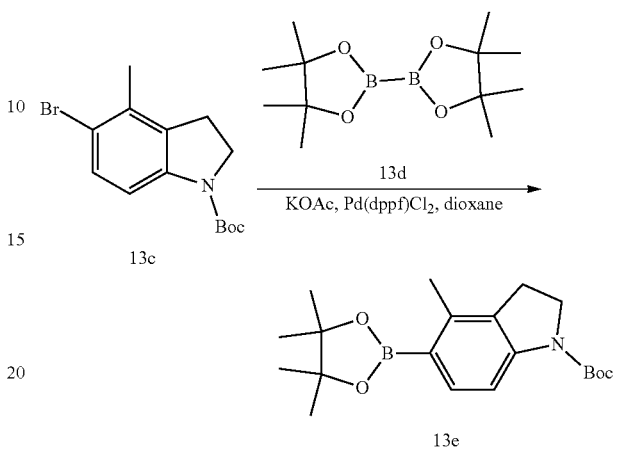

To a mixture of tert-butyl 5-bromo-4-methyl-2,3-dihydroindole-1-carboxylate (Compound 13c) (740.0 mg, 2.3 mmol) and bis(pinacolato) diboron (Compound 13d) (1.8 g, 7.12 mmol) in dioxane (20.0 mL) was added KOAc (697.8 mg, 7.12 mmol) and Pd(dppf)Ch₂ (173.4 mg, 0.23 mmol) at room temperature under N₂. The resulting mixture was stirred at 80° C. for 16 h. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (211, v/v) to afford tert-butyl 4-methyl-5-(4,4,5,5-tetramethyl-1,3,2-dioxaborolan-2-yl)-2,3-dihydroindole-1-carboxylate (Compound 13e) (750.0 mg, 88%) as a white solid. LCMS (ESI, m/z): [M+H]⁺= 360.2.

Step 4: Synthesis of tert-butyl 5-[5-chloro-1-methylpyrrolo[2,3-c]pyridin-2-yl]-4-methyl-2,3-dihydroindole-1-carboxylate (Compound 13g)

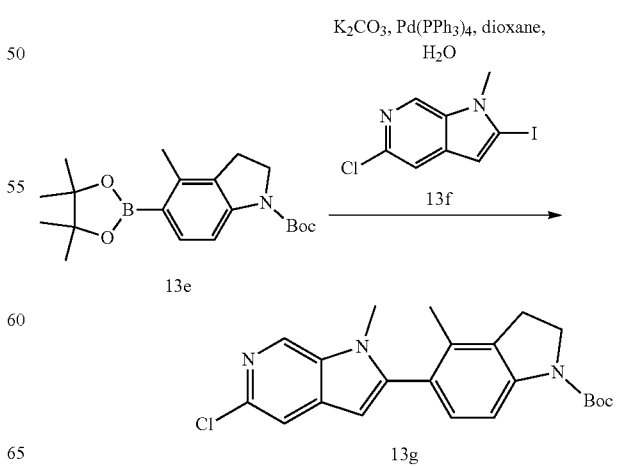

To a mixture of 5-chloro-2-iodo-1-methylpyrrolo[2,3-c]pyridine (300.0 mg, 1.02 mmol) and tert-butyl 4-methyl-5-(4,4,5,5-tetramethyl-1,3,2-dioxaborolan-2-yl)-2,3-dihydroindole-1-carboxylate (442.1 mg, 1.21 mmol) in dioxane/H₂O (5.0/0.5 mL) was added Pd(PPh₃)₄ (118.5 mg, 0.10 mmol) and K₂CO₃ (425.2 mg, 3.07 mmol) at room temperature under N₂. The resulting mixture was stirred at 100° C. for 16 h. After the reaction was completed, the mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford tert-butyl 5-[5-chloro-1-methylpyrrolo[2,3-c]pyridin-2-yl]-4-methyl-2,3-dihydroindole-1-carboxylate (170.0 mg, 41%) as a white solid. LCMS (ESI, m/z): [M+H]⁺=398.2.

Step 5: Synthesis of tert-butyl 5-[5-cyclopropaneamido-1-methylpyrrolo[2,3-c]pyridin-2-yl]-4-methyl-2,3-dihydroindole-1-carboxylate (Compound 13i)

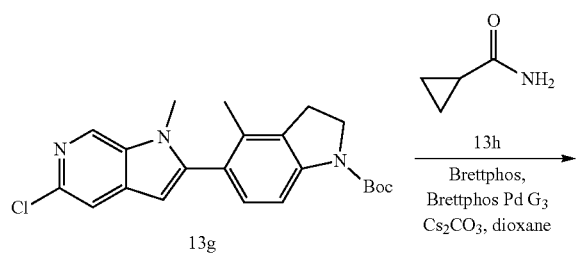

To a mixture of tert-butyl 5-[5-chloro-1-methylpyrrolo[2,3-c]pyridin-2-yl]-4-methyl-2,3-dihydroindole-1-carboxylate (Compound 13g) (150.0 mg, 0.37 mmol) and cyclopropanecarboxamide (Compound 13h) (128.3 mg, 1.50 mmol) in dioxane (3.0 mL) was added Brettphos Pd G3 (34.1 mg, 0.03 mmol), BrettPhos (40.0 mg, 0.07 mmol) and Cs₂CO₃ (368.4 mg, 1.13 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/7, v/v) to afford tert-butyl 5-[5-cyclopropaneamido-1-methylpyrrolo[2,3-c]pyridin-2-yl]-4-methyl-2,3-dihydroindole-1-carboxylate (Compound 13i) (150.0 mg, 89%) as a white solid. LCMS (ESI, m/z): [M+H]⁺=447.2.

Step 6: Synthesis of N-[1-methyl-2-(4-methyl-2,3-dihydro-1H-indol-5-yl)pyrrolo[2,3-c]pyridin-5-yl]cyclopropanecarboxamide (Compound 13)

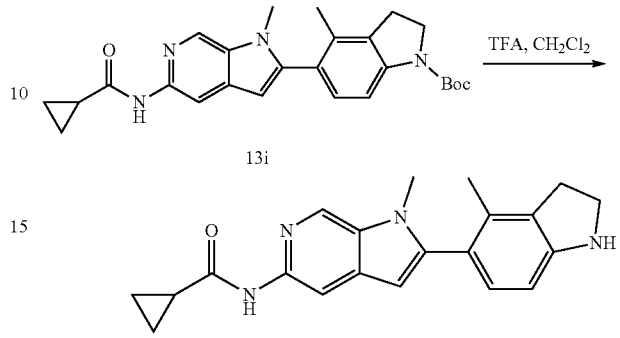

To a solution of tert-butyl 5-[5-cyclopropaneamido-1-methylpyrrolo[2,3-c]pyridin-2-yl]-4-methyl-2,3-dihydroindole-1-carboxylate (Compound 13i) (160.0 mg, 0.35 mmol) in DCM (2.0 mL) was added TFA (1.0 mL) at room temperature. The resulting mixture was stirred at room temperature for 3 h. After the reaction was completed, the resulting mixture was concentrated under vacuum. The residue was purified by Prep-HPLC with the following conditions (Column: XBridge Prep OBD C₁₈ Column, 30×150 mm, 5 um; Mobile Phase A:Water (10 mmol/L NH₄HCO₃), Mobile Phase B: ACN; Flow rate: 60 mL/min; Gradient: 32% B to 62% B in 10 min; 254 nm) to afford N-[1-methyl-2-(4-methyl-2,3-dihydro-1H-indol-5-yl)pyrrolo[2,3-c]pyridin-5-yl]cyclopropanecarboxamide (Compound 13) (29.2 mg, 23%) as a white solid. LCMS (ESI, m/z): [M+H]⁺=347.2. ¹H NMR (300 MHz, DMSO-d₆): δ 10.45 (s, 1H), 8.54 (s, 1H), 8.16 (s, 1H), 6.88 (d, J=7.8 Hz, 1H), 6.43 (d, J=7.8 Hz, 1H), 6.29 (s, 1H), 5.76 (s, 1H), 3.55-3.49 (m, 5H), 2.96-2.91 (m, 2H), 2.01-1.99 (m, 4H), 0.82-0.75 (m, 4H).

Example S14: Synthesis of N-(1-methyl-2-(6-methyl-1H-indol-5-yl)-1H-pyrrolo[2,3-c]pyridin-5-yl)cyclopropanecarboxamide (Compound 14)

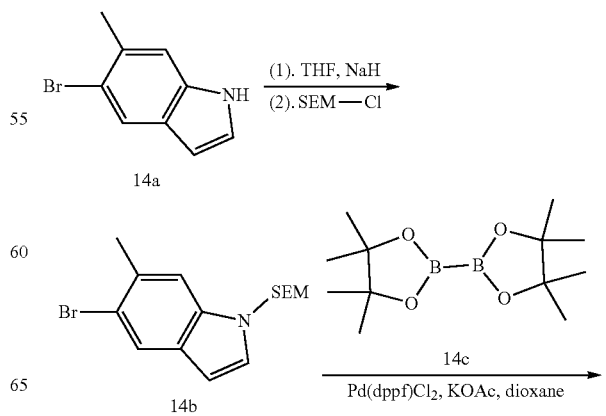

-continued

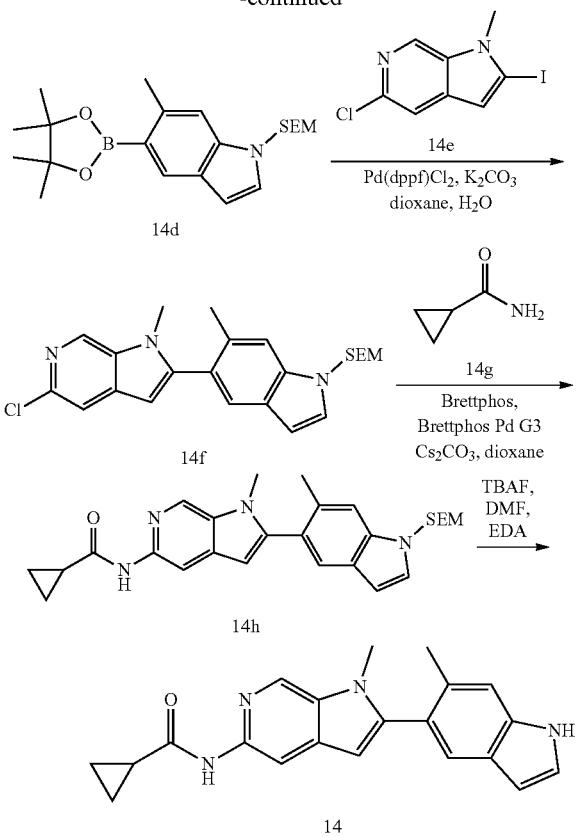

Step 1: Synthesis of 5-bromo-6-methyl-1-((2-(trimethylsilyl)ethoxy)methyl)-1H-indole (Compound 14b)

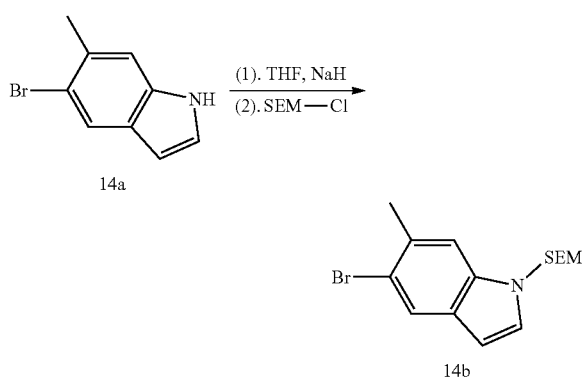

To a solution of 5-bromo-6-methyl-1H-indole (Compound 14a) (1.0 g, 4.76 mmol) in THF (20.0 mL) was added NaH (342.7 mg, 60%) at 0° C. under N₂. The resulting mixture was stirred at 0° C. for 1 h under N₂. Then SEM-Cl (1.2 g, 7.14 mmol) was added to the mixture at 0° C. The resulting mixture was stirred at 0° C. for 1 h under N₂. After the reaction was completed, the reaction was quenched with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (12/1, v/v) to afford 5-bromo-6-methyl-1-((2-(trimethylsilyl)ethoxy)methyl)-1H-indole (Compound 14b) (1.2 g, 74%) as a yellow oil. LCMS (ESI, m/z): [M+H]⁺=340.1.

Step 2: Synthesis of 6-methyl-5-(4,4,5,5-tetramethyl-1,3,2-dioxaborolan-2-yl)-1-((2-(trimethylsilyl)ethoxy)methyl)-1H-indole (Compound 14d)

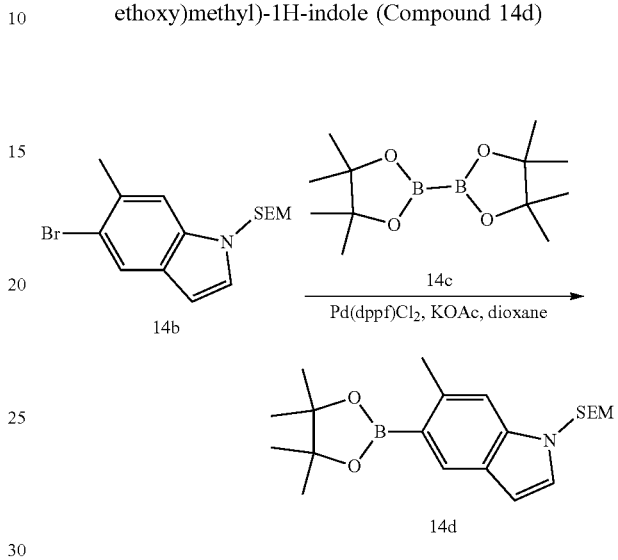

To a solution of 5-bromo-6-methyl-1-((2-(trimethylsilyl)ethoxy)methyl)-1H-indole (Compound 14b) (500.0 mg, 1.47 mmol) in dioxane (20.0 mL) was added 4,4,4',4',5,5,5',5'-octamethyl-2,2'-bi(1,3,2-dioxaborolane) (Compound 14c) (1.1 g, 4.41 mmol), KOAc (432.6 mg, 4.41 mmol) and Pd(dppf)Cl₂ (107.5 mg, 0.15 mmol) at room temperature under N₂. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (12/1, v/v) to afford 6-methyl-5-(4,4,5,5-tetramethyl-1,3,2-dioxaborolan-2-yl)-1-((2-(trimethylsilyl)ethoxy)methyl)-1H-indole (Compound 14d) (260.0 mg, 45%) as a brown oil. LCMS (ESI, m/z): [M+H]⁺=388.2.

Step 3: Synthesis of 5-chloro-1-methyl-2-(6-methyl-((2-(trimethylsilyl)ethoxy)methyl)-1H-indol-5-yl)-1H-pyrrolo[2,3-c]pyridine (Compound 14f)

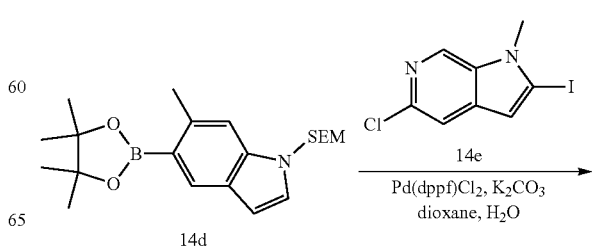

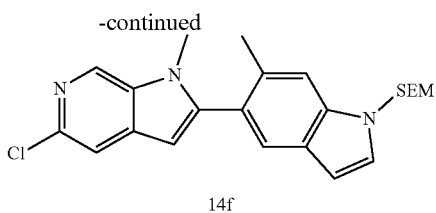

14f

To a solution of 6-methyl-5-(4,4,5,5-tetramethyl-1,3,2-dioxaborolan-2-yl)-1-((2-(trimethylsilyl)ethoxy)methyl)-1H-indole (Compound 14d) (260.0 mg, 0.67 mmol) in dioxane/H₂O (8.0/2.0 mL) was added 5-chloro-2-iodo-1-methyl-1H-pyrrolo[2,3-c]pyridine (Compound 14e) (196.3 mg, 0.67 mmol), K₂CO₃ (463.8 mg, 3.36 mmol) and Pd(dppf)Cl₂ (49.1 mg, 0.07 mmol) at room temperature under N₂. The resulting mixture was stirred at 80° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/1, v/v) to afford 5-chloro-1-methyl-2-(6-methyl-1-((2-(trimethylsilyl)ethoxy)methyl)-1H-indol-5-yl)-1H-pyrrolo[2,3-c]pyridine (Compound 14f) (150.0 mg, 52%) as a colorless oil. LCMS (ESI, m/z): [M+H]⁺=426.2.

Step 4: Synthesis of N-(1-methyl-2-(6-methyl-1-((2-(trimethylsilyl)ethoxy)methyl)-1H-indol-5-yl)-1H-pyrrolo[2,3-c]pyridin-5-yl)cyclopropanecarboramide (Compound 14h)

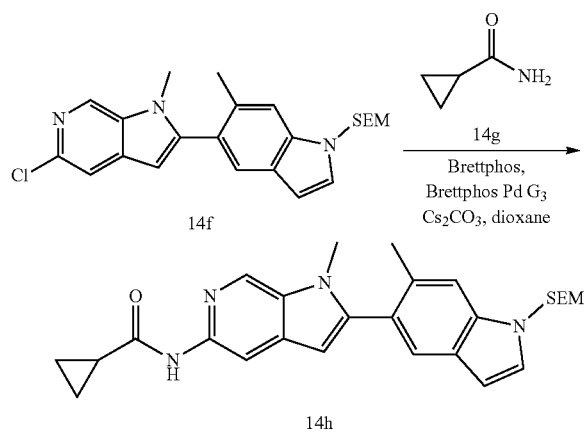

To a solution of 5-chloro-1-methyl-2-(6-methyl-1-((2-(trimethylsilyl)ethoxy)methyl)-1H-indol-5-yl)-1H-pyrrolo[2,3-c]pyridine (Compound 14f) (150.0 mg, 0.35 mmol) in dioxane (10.0 mL) was added cyclopropanecarboxamide (Compound 14g) (179.8 mg, 2.11 mmol), Cs₂CO₃ (344.2 mg, 1.06 mmol), Brettphos (37.8 mg, 0.07 mmol) and BrettPhos Pd G3 (31.9 mg, 0.04 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford N-(1-methyl-2-(6-methyl-1-((2-(trimethylsilyl)ethoxy)methyl)-1H-indol-5-yl)-1H-pyrrolo[2,3-c]pyridin-5-yl)cyclopropanecarboxamide (Compound 14h) (110.0 mg, 65%) as a white solid. LCMS (ESI, m/z): [M+H]⁺=475.2.

Step 5: Synthesis of N-(1-methyl-2-(6-methyl-1H-indol-5-yl)-1H-pyrrolo[2,3-c]pyridin-5-yl)cyclopropanecarboxamide (Compound 14)

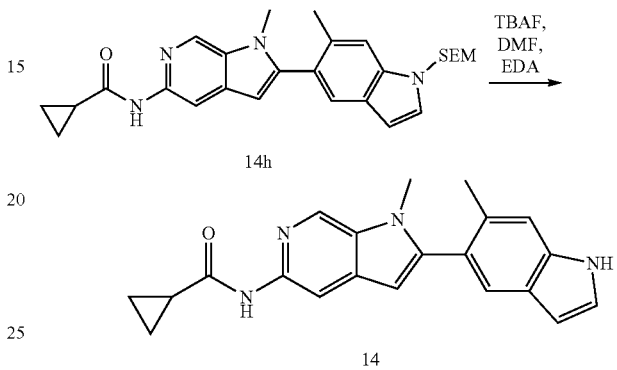

To a solution of N-(1-methyl-2-(6-methyl-1-((2-(trimethylsilyl)ethoxy)methyl)-1H-indol-5-yl)-1H-pyrrolo[2,3-c]pyridin-5-yl)cyclopropanecarboxamide (Compound 14h) (150.0 mg, 0.32 mmol) in DMF (5.0 mL) was added TBAF (1.0 mL, 0.95 mmol) and EDA (94.8 mg, 1.58 mmol) at room temperature. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by reverse phase flash column chromatography with 5-100% CH₃CN in H₂O and then purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 10% B to 35% B in 8 min; 254 nm) to afford N-(1-methyl-2-(6-methyl-1H-indol-5-yl)-1H-pyrrolo[2,3-c]pyridin-5-yl)cyclopropanecarboxamide (Compound 14) (5.6 mg, 5%) as a white solid. LCMS (ESI, m/z): [M+H]⁺=345.2. ¹H NMR (300 MHz, DMSO-d₆): δ 11.16 (s, 1H), 10.48 (s, 1H), 8.58 (s, 1H), 8.20 (s, 1H), 7.50 (s, 1H), 7.38-7.36 (m, 2H), 6.44 (s, 1H), 6.39 (s, 1H), 3.54 (s, 3H), 2.19 (s, 3H), 2.05-1.95 (m, 1H), 0.83-0.76 (m, 4H).

Example S15: Synthesis of N-[1-methyl-2-(4-methyl-1H-indol-5-yl)pyrrolo[2,3-c]pyridin-5-yl]cyclopropanecarboxamide (Compound 15)

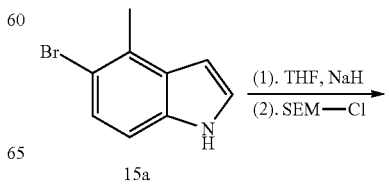

15a

-continued

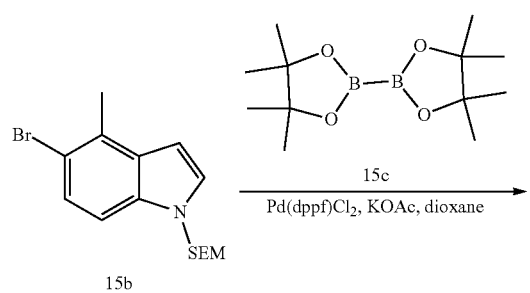

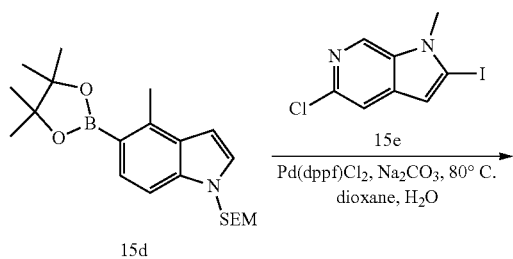

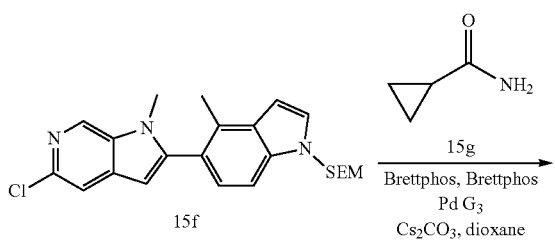

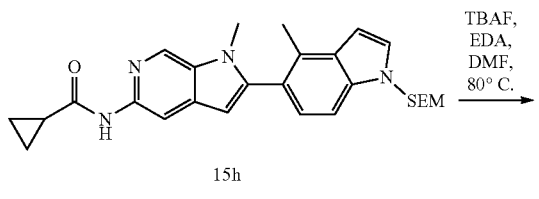

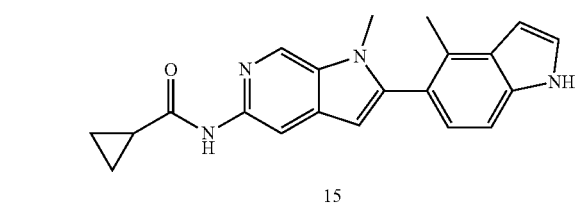

Step 1: Synthesis of 5-bromo-4-methyl-1-[[2-(trimethylsilyl)ethoxy]methyl]indole (Compound 15b)

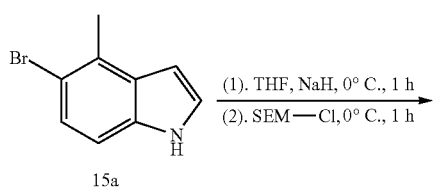

-continued

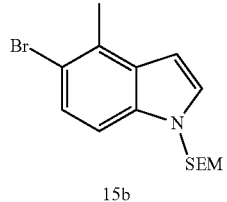

To a solution of 5-bromo-4-methyl-1H-indole (800.0 mg, 3.81 mmol) in THF (10.0 mL) was added NaH (182.8 mg, 60%) at room temperature. The resulting mixture was stirred at 0° for 1 h Then [2-(chloromethoxy) ethyl]trimethylsilane (695.1 mg, 4.17 mmol) was added dropwise to the mixture at 0° C. The resulting mixture was stirred at 0° C. for another 1 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (80/20, v/v) to afford 5-bromo-4-methyl-1-[[2-(trimethylsilyl)ethoxy]methyl]indole (1.2 g, 92%) as a colorless oil. LCMS (ESI, m/z): [M+H]⁺=340.1.

Step 2: Synthesis of 4-methyl-5-(4,4,5,5-tetramethyl-1,3,2-dioxaborolan-2-yl)-1-[[2-(trimethylsilyl)ethoxy]methyl]indole (Compound 15d)

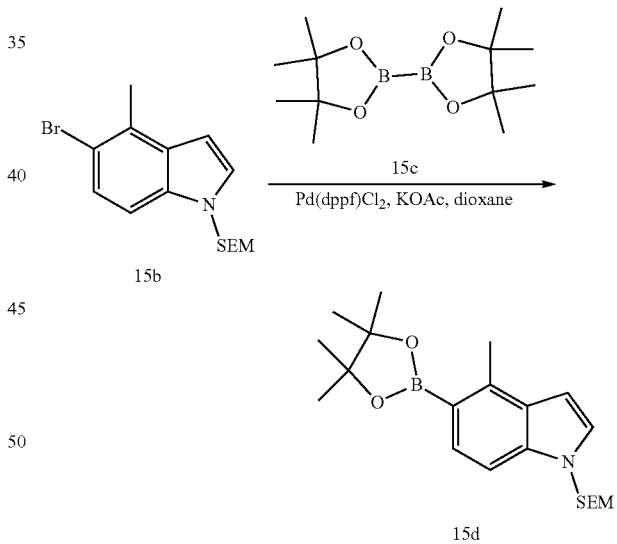

To a solution of 5-bromo-4-methyl-1-[[2-(trimethylsilyl)ethoxy]methyl]indole (600.0 mg, 1.76 mmol) in 1,4-dioxane (10.0 mL) was added 4,4,4',4',5,5,5',5'-octamethyl-2,2'-bi(1,3,2-dioxaborolane) (447.7 mg, 1.76 mmol), Pd(dppf)Cl₂ (258.0 mg, 0.35 mmol) and KOAc (519.1 mg, 5.29 mmol). The resulting mixture was stirred at 80° C. for 16 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under vacuum to afford 4-methyl-5-(4,4,5,5-tetramethyl-1,3,2-dioxaborolan-2-yl)-1-[[2-(trimethylsilyl)

ethoxy]methyl]indole (500.0 mg, crude) as a brown solid. LCMS (ESI, m/z): [M+H]+=388.2.

Step 3: Synthesis of 5-[5-chloro-1-methylpyrrolo[2,3-c]pyridin-2-yl-]4-methyl-1-[[2-(trimethylsilyl)ethoxy]methyl]indole (Compound 15f)

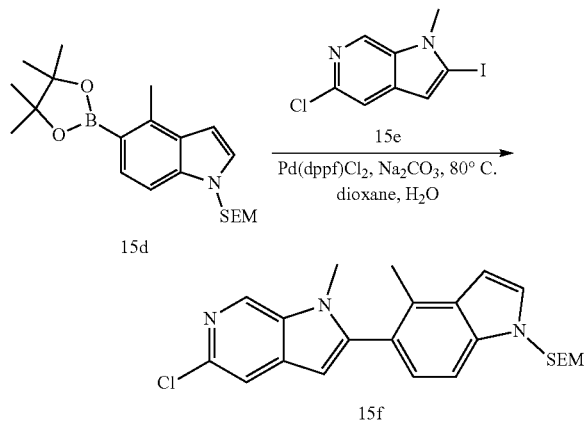

15d

To a solution of 4-methyl-5-(4,4,5,5-tetramethyl-1,3,2-dioxaborolan-2-yl)-1-[[2-(trimethylsilyl)ethoxy]methyl]indole (Compound 15d) (500.0 mg, 1.29 mmol) in 1,4-dioxane (10.0 mL) was added 5-chloro-2-iodo-1-methylpyrrolo[2,3-c]pyridine (Compound 15e) (377.5 mg, 1.29 mmol), Pd(dppf)Cl₂ (188.9 mg, 0.26 mmol), Na₂CO₃ (410.4 mg, 3.88 mmol) and H₂O (0.5 mL). The resulting mixture was stirred at 80° C. for 16 h under N₂. After the reaction was completed, the resulting mixture was concentrated under vacuum. The residue was purified by flash column chromatography with petroleum ether/ethyl acetate (50/50, v/v) to afford 5-[5-chloro-1-methylpyrrolo[2,3-c]pyridin-2-yl]-4-methyl-1-[[2-(trimethylsilyl)ethoxy]methyl]indole (150.0 mg, 23%) as a brown oil. LCMS (ESI, m/z): [M+H]+=426.2.

Step 4: Synthesis of N-[1-methyl-2-(4-methyl-1-[[2-(trimethylsilyl)ethoxy]methyl]indol-5-yl)pyrrolo[2,3-c]pyridin-5-yl]cyclopropanecarboxamide (Compound 15h)

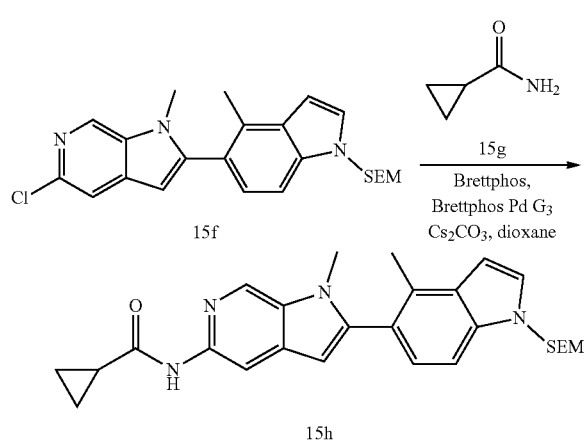

To a solution of 5-[5-chloro-1-methylpyrrolo[2,3-c]pyridin-2-yl]-4-methyl-1-[[2-(trimethylsilyl)ethoxy]methyl]indole (Compound 15f) (120.0 mg, 0.28 mmol) in 1,4-dioxane (5.0 mL) was added cyclopropanecarboxamide (Compound 15g) (119.8 mg, 1.41 mmol), Brettphos Pd G₃ (51.1 mg, 0.06 mmol), BrettPhos (60.5 mg, 0.12 mmol) and Cs₂CO₃ (275.3 mg, 0.85 mmol). The resulting mixture was stirred at 100° C. for 16 h under N₂. After the reaction was completed, the resulting mixture was diluted with H₂O and extracted with ethyl acetate. The combined organic layer was washed with brine, dried over anhydrous sodium sulfate and filtered. The combined organic layer was washed with brine, dried over anhydrous sodium sulfate and filtered. The filtrate was concentrated under vacuum. The residue was purified by flash column chromatography with CH₂Cl₂/CH₃OH (94/6, v/v) to afford N-[1-methyl-2-(4-methyl-1-[[2-(trimethylsilyl)ethoxy]methyl]indol-5-yl)pyrrolo[2,3-c]pyridin-5-yl]cyclopropanecarboxamide (Compound 15h) (130.0 mg, 97%) as a brown solid. LCMS (ESI, m/z): [M+H]+=475.2.

Step 5: Synthesis of N-[1-methyl-2-(4-methyl-1H-indol-5-yl)pyrrolo[2,3-c]pyridin-5-yl]cyclopropanecarboxamide (Compound 15)

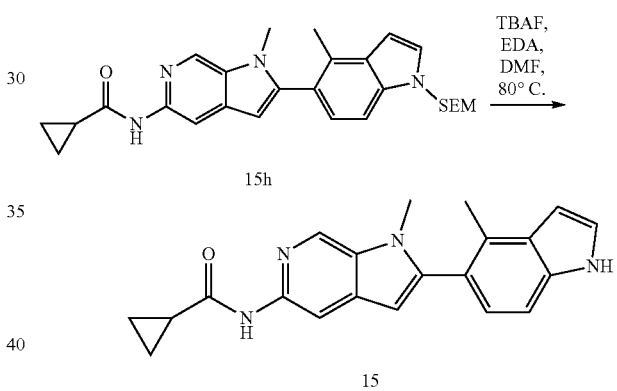

To a solution of N-[1-methyl-2-(4-methyl-1-[[2-(trimethylsilyl)ethoxy]methyl]indol-5-yl)pyrrolo[2,3-c]pyridin-5-yl]cyclopropanecarboxamide (Compound 15h) (100.0 mg, 0.21 mmol) in DMF (5.0 mL) was added ethylenediamine (63.3 mg, 1.05 mmol) and TBAF (330.5 mg, 1.26 mmol). The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by Prep-HPLC with the following conditions (Column: YMC-Actus Triart C18 Column, 30×250 mm, 5 um; Mobile Phase A:Water (10 mmol/L FA), Mobile Phase B: ACN; Flow rate: 60 mL/min; Gradient: 20% B to 60% B in 8 min; 254 nm) to afford N-[1-methyl-2-(4-methyl-1H-indol-5-yl)pyrrolo[2,3-c]pyridin-5-yl]cyclopropanecarboxamide (Compound 15) (7.1 mg, 9%) as a white solid. LCMS (ESI, m/z): [M+H]+=345.3. ¹H NMR (300 MHz, DMSO-d₆): δ 11.27 (s, 1H), 10.45 (s, 1H), 8.57 (s, 1H), 8.27-8.15 (m, 1H), 7.43-7.41 (m, 1H), 7.35 (d, J=8.1 Hz, 1H), 7.04 (d, J=8.4 Hz, 1H), 6.56 (d, J=8.1 Hz, 1H), 6.38 (s, 1H), 3.55 (s, 3H), 2.33 (s, 3H), 2.04-1.99 (m, 1H), 0.89-0.78 (m, 4H).

Example S16: Synthesis of N-(1-methyl-2-(6-methyl-1H-indazol-5-yl)-1H-pyrrolo[2,3-c]pyridin-5-yl)cyclopropanecarboxamide (Compound 16)

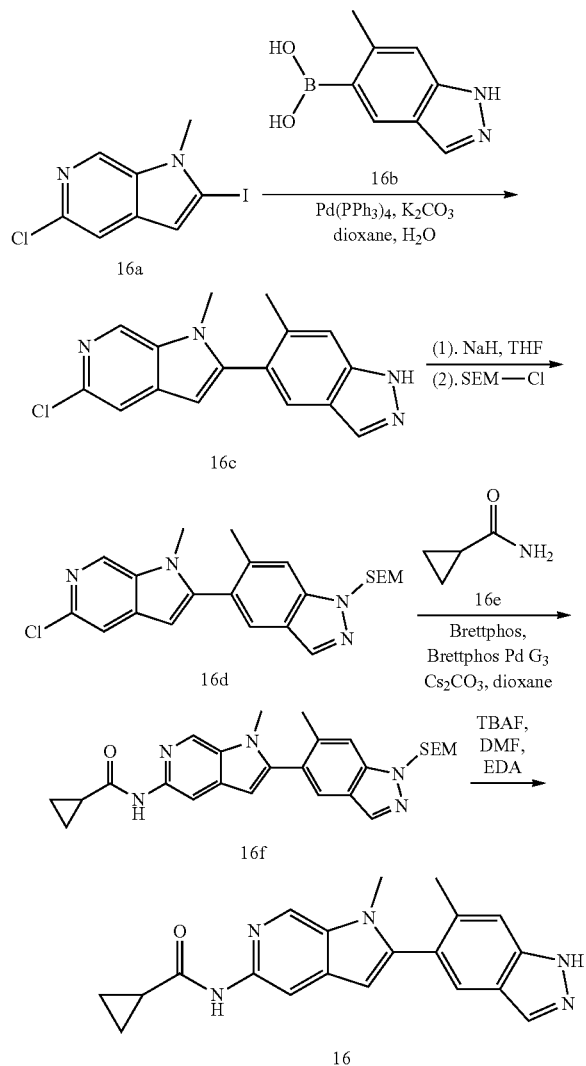

Step 1: Synthesis of 5-(5-chloro-1-methyl-1H-pyrrolo[2,3-c]pyridin-2-yl)-6-methyl-1H-indazole (Compound 16c)

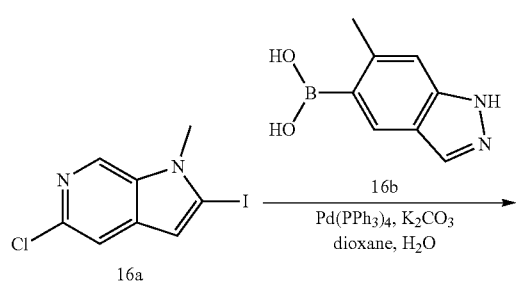

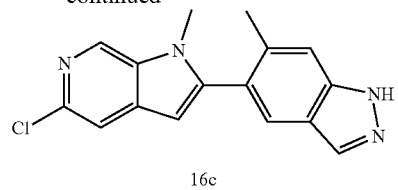

To a solution of 5-chloro-2-iodo-1-methyl-1H-pyrrolo[2,3-c]pyridine (Compound 16a) (500.0 mg, 1.71 mmol) in dioxane/H₂O (8.0/2.0 mL) was added (6-methyl-1H-indazol-5-yl)boronic acid (Compound 16b) (300.8 mg, 1.71 mmol), K₂CO₃ (708.8 mg, 5.13 mmol) and Pd(PPh₃)₄ (197.5 mg, 0.17 mmol) at room temperature under N₂. The resulting mixture was stirred at 80° C. for 2 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-(5-chloro-1-methyl-1H-pyrrolo[2,3-c]pyridin-2-yl)-6-methyl-1H-indazole (Compound 16c) (260.0 mg, 51%) as a white solid. LCMS (ESI, m/z): [M+H]⁺=297.1.

Step 2: Synthesis of 5-(5-chloro-1-methyl-1H-pyrrolo[2,3-c]pyridin-2-yl)-6-methyl-1-((2-(trimethylsilyl)ethoxy)methyl)-1H-indazole (Compound 16d)

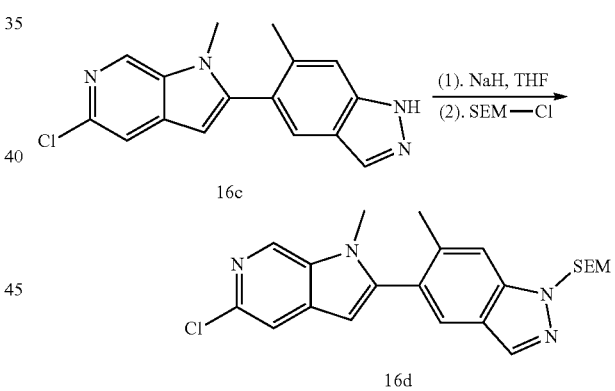

To a solution of 5-(5-chloro-1-methyl-1H-pyrrolo[2,3-c]pyridin-2-yl)-6-methyl-1H-indazole (Compound 16c) (260.0 mg, 0.88 mmol) in THF (5.0 mL) was added NaH (68.1 mg, 60%) at 0° C. under N₂. The resulting mixture was stirred at 0° C. for 1 h. Then SEM-Cl (219.1 mg, 1.31 mmol) was added the mixture at 0° C. under N₂. The resulting mixture was stirred at 0° C. for 1 h under N₂. After the reaction was completed, the reaction was quenched with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-(5-chloro-1-methyl-1H-pyrrolo[2,3-c]pyridin-2-yl)-6-methyl-1-((2-(trimethylsilyl)ethoxy)methyl)-1H-indazole (Compound 16d) (210.0 mg, 56%) as a yellow solid. LCMS (ESI, m/z): [M+H]⁺=427.2.

Step 3: Synthesis of N-(1-methyl-2-(6-methyl-1-((2-(trimethylsilyl)ethoxy)methyl)-1H-indazol-5-yl)-1H-pyrrolo[2,3-c]pyridin-5-yl)cyclopropanecarboxamide (Compound 16f)

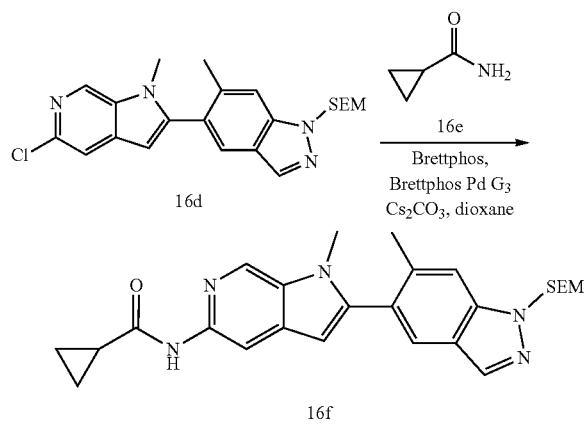

To a solution of 5-(5-chloro-1-methyl-1H-pyrrolo[2,3-c]pyridin-2-yl)-6-methyl-1-((2-(trimethylsilyl)ethoxy)methyl)-1H-indazole (Compound 16d) (210.0 mg, 0.49 mmol) in dioxane (10.0 mL) was added cyclopropanecarboxamide (Compound 16e) (251.1 mg, 2.95 mmol), $CS_2CO_3$ (480.7 mg, 1.48 mmol), Brettphos (52.8 mg, 0.10 mmol) and BrettPhos Pd 03 (44.6 mg, 0.05 mmol) at room temperature under $N_2$. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford N-(1-methyl-2-(6-methyl-1-((2-(trimethylsilyl)ethoxy)methyl)-1H-indazol-5-yl)-1H-pyrrolo[2,3-c]pyridin-5-yl)cyclopropanecarboxamide (Compound 16f) (200.0 mg, 85%) as a white solid. LCMS (ESI, m/z): $[M+H]^+=476.2$.

Step 4: Synthesis of N-(1-methyl-2-(6-methyl-1H-indazol-5-yl)-1H-pyrrolo[2,3-c]pyridin-5-yl)cyclopropanecarboramide (Compound 16)

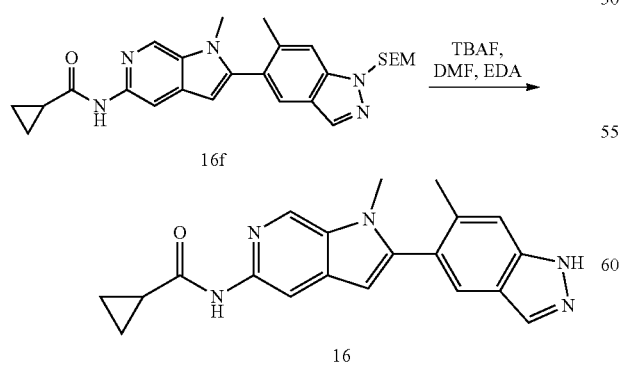

To a solution of N-(1-methyl-2-(6-methyl-1-((2-(trimethylsilyl)ethoxy)methyl)-1H-indazol-5-yl)-1H-pyrrolo[2,3-c]pyridin-5-yl)cyclopropanecarboxamide (Compound 16f) (250.0 mg, 0.53 mmol) in DMF (5.0 mL) was added TBAF (412.3 mg, 1.58 mmol) and EDA (157.7 mg, 2.63 mmol) at room temperature. The resulting mixture was stirred at 80° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with 5-100% $CH_3CN$ in $H_2O$ and then purified by Prep-HPLC with the following conditions (Column: YMC-Actus Triart $C_{18}$, 30×250 mm, 5 um; Mobile Phase A: Water (10 mmol/L $NH_4HCO_3$), Mobile Phase B: ACN; Flow rate: 60 mL/min; Gradient: 24% B to 54% B in 10 min; 254 nm) to afford N-(1-methyl-2-(6-methyl-1H-indazol-5-yl)-1H-pyrrolo[2,3-c]pyridin-5-yl)cyclopropanecarboxamide (Compound 16) (40.4 mg, 22%) as a white solid. LCMS (ESI, m/z): $[M+H]^+= 346.2$. $^1$H NMR (300 MHz, DMSO-$d_6$): δ 13.13 (s, 1H), 10.50 (s, 1H), 8.60 (s, 1H), 8.21 (s, 1H), 8.09 (s, 1H), 7.74 (s, 1H), 7.54 (s, 1H), 6.45 (s, 1H), 3.54 (s, 3H), 2.22 (s, 3H), 2.08-1.98 (m, 1H), 0.84-0.76 (m, 4H).

Example S17: Synthesis of N-[1-methyl-2-(6-methyl-1H-1,3-benzodiazol-5-yl)pyrrolo[2,3-c]pyridin-5-yl]cyclopropanecarboxamide (Compound 17)

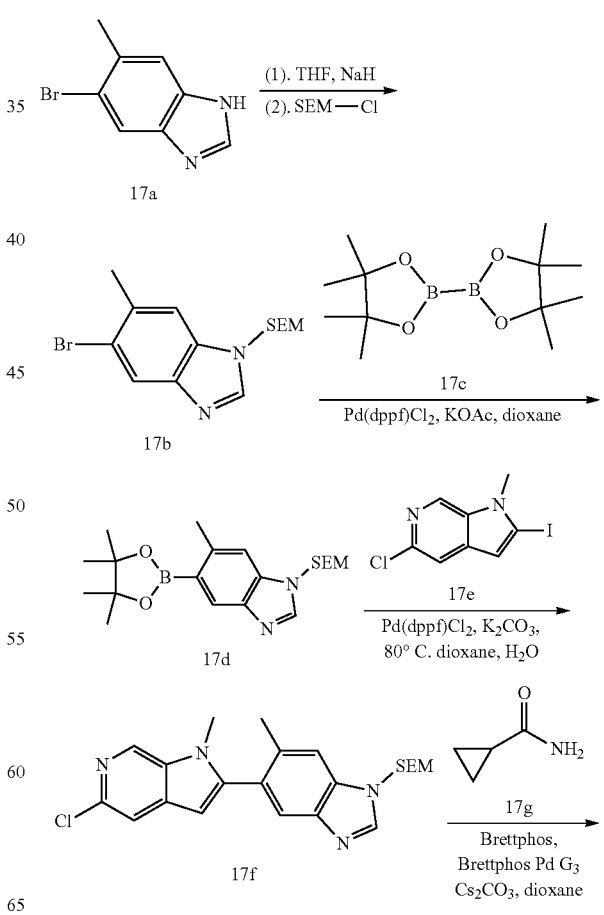

-continued

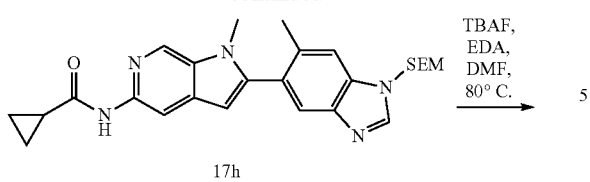

17h

TBAF, EDA, DMF, 80° C.

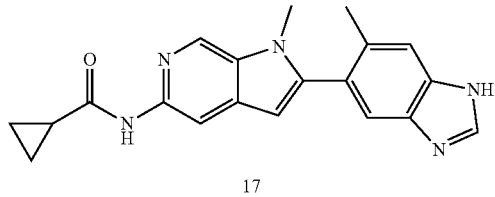

17

Step 1: Synthesis of 5-bromo-6-methyl-1-[[2-(trimethylsilyl)ethoxy]methyl]-1,3-benzodiazole (Compound 17b)

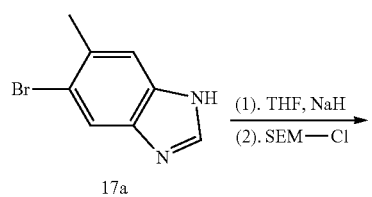

17a (1). THF, NaH
(2). SEM—Cl

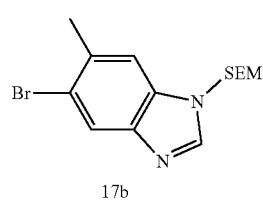

17b

To a solution of 5-bromo-6-methyl-1H-1,3-benzodiazole (Compound 17a) (800.0 mg, 3.79 mmol) in THF (10.0 mL) was added NaH (181.9 mg, 60%) at 0° C. under $N_2$. The resulting mixture was stirred at 0° C. for 1 h. Then [2-(chloromethoxy) ethyl]trimethylsilane (695.1 mg, 4.17 mmol) was added dropwise to the mixture at 0° C. The resulting mixture was stirred at 0° C. for another 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (80/20, v/v) to afford 5-bromo-6-methyl-1-[[2-(trimethylsilyl)ethoxy]methyl]-1,3-benzodiazole (Compound 17b) (900.0 mg, 69%) as a colorless oil. LCMS (ESI, m/z): $[M+H]^+=341.1$.

Step 2: Synthesis of 6-methyl-5-(4,4,5,5-tetramethyl-1,3,2-dioxaborolan-2-yl)-1-[[2-(trimethylsilyl)ethoxy]methyl]-1,3-benzodiazole (Compound 17d)

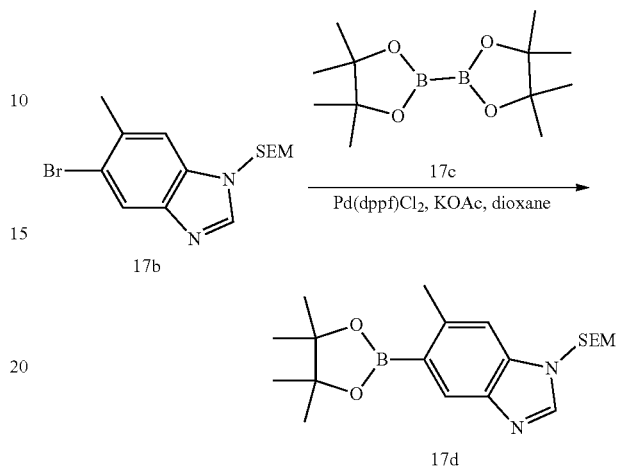

To a solution of 5-bromo-6-methyl-1-[[2-(trimethylsilyl)ethoxy]methyl]-1,3-benzodiazole (Compound 17b) (600.0 mg, 1.76 mmol) in 1,4-dioxane (10.0 mL) was added $Pd(dppf)Cl_2$ (257.2 mg, 0.35 mmol), KOAc (517.6 mg, 5.27 mmol) and 4,4,4',4',5,5,5',5'-octamethyl-2,2'-bi(1,3,2-dioxaborolane) (Compound 17c) (446.4 mg, 1.76 mmol). The resulting mixture was stirred at 80° C. for 16 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum to afford 6-methyl-5-(4,4,5,5-tetramethyl-1,3,2-dioxaborolan-2-yl)-1-[[2-(trimethylsilyl)ethoxy]methyl]-1,3-benzodiazole (Compound 17d) (800.0 mg, crude) as a black solid. LCMS (ESI, m/z): $[M+H]^+=389.2$.

Step 3: Synthesis of 5-[5-chloro-1-methylpyrrolo[2,3-c]pyridin-2-yl]-6-methyl-1-[[2-(trimethylsilyl)ethoxy]methyl]-1,3-benzodiazole (Compound 17f)

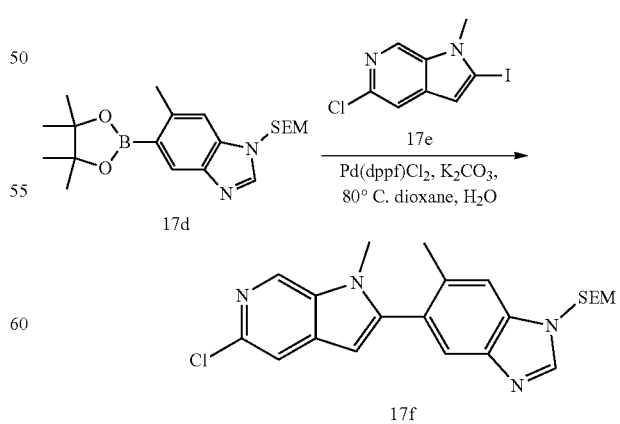

To a solution of 6-methyl-5-(4,4,5,5-tetramethyl-1,3,2-dioxaborolan-2-yl)-1-[[2-(trimethylsilyl)ethoxy]methyl]-1, 3-benzodiazole (Compound 17d) (800.0 mg, 2.06 mmol) in 1,4-dioxane (10.0 mL) was added 5-chloro-2-iodo-1-methylpyrrolo[2,3-c]pyridine (Compound 17e) (602.5 mg, 2.06 mmol), Pd(dppf)Cl$_2$ (301.4 mg, 0.41 mmol), K$_2$CO$_3$ (854.0 mg, 6.18 mmol) and H$_2$O (0.5 mL). The resulting mixture was stirred at 80° C. for 16 h under N$_2$. After the reaction was completed, the resulting mixture was concentrated under vacuum. The residue was purified by flash column chromatography with petroleum ether/ethyl acetate (65/35, v/v) to afford 5-[5-chloro-1-methylpyrrolo[2,3-c]pyridin-2-yl]-6-methyl-1-[[2-(trimethylsilyl)ethoxy]methyl]-1,3-benzodiazole (Compound 17f) (140.0 mg, 15%) as a brown oil. LCMS (ESI, m/z): [M+H]$^+$=427.2.

Step 4: Synthesis of N-[1-methyl-2-(6-methyl-1-[1,2-(trimethylsilyl)ethoxy]methyl-1,3-benzodiazol-5-yl)pyrrolo[2,3-c]pyridin-5-yl]cyclopropanecarboxamide (Compound 17h)

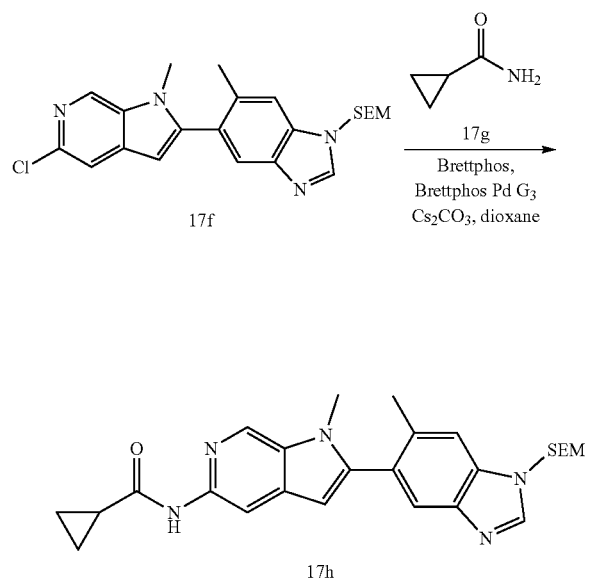

To a solution of 5-[5-chloro-1-methylpyrrolo[2,3-c]pyridin-2-yl]-6-methyl-1-[[2-(trimethylsilyl)ethoxy]methyl]-1,3-benzodiazole (Compound 17f) (110.0 mg, 0.26 mmol) in 1,4-dioxane (5.0 mL) was added cyclopropanecarboxamide (Compound 17g) (109.6 mg, 1.29 mmol), Brettphos Pd G$_3$ (46.7 mg, 0.05 mmol), BrettPhos (55.3 mg, 0.10 mmol) and Cs$_2$CO$_3$ (251.8 mg, 0.77 mmol). The resulting mixture was stirred at 100° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The combined organic layer was washed with brine, dried over anhydrous sodium sulfate and filtered. The filtrate was concentrated under vacuum. The residue was purified by flash column chromatography with CH$_2$Cl$_2$/CH$_3$OH (94/6, v/v) to afford N-[1-methyl-2-(6-methyl-1-[[2-(trimethylsilyl)ethoxy]methyl]-1,3-benzodiazol-5-yl)pyrrolo[2,3-c]pyridin-5-yl]cyclopropanecarboxamide (Compound 17h) (130.0 mg, 95%) as a yellow solid. LCMS (ESI, m/z): [M+H]$^+$=476.2.

Step 5: Synthesis of N-(1-methyl-2-(6-methyl-1H-benzo[d]imidazol-5-yl)-1H-pyrrolo[2,3-c]pyridin-5-yl) cyclopropanecarboxamide (Compound 17)

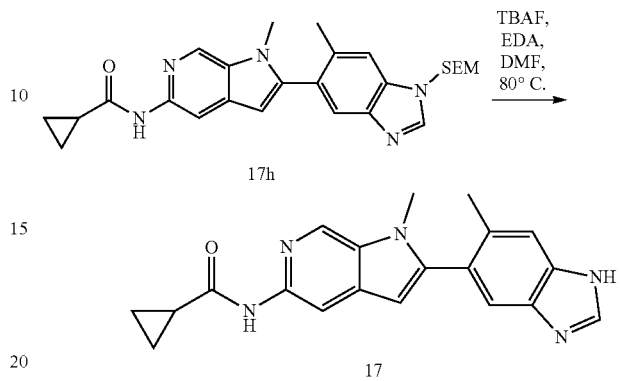

To a solution of N-[1-methyl-2-(6-methyl-1-[[2-(trimethylsilyl)ethoxy]methyl]-1,3-benzodiazol-5-yl)pyrrolo[2,3-c]pyridin-5-yl]cyclopropanecarboxamide (Compound 17h) (100.0 mg, 0.21 mmol) in DMF (5.0 mL) was added ethylenediamine (63.2 mg, 1.05 mmol) and TBAF (329.8 mg, 1.26 mmol). The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by Prep-HPLC with the following conditions (Column: YMC-Actus Triart C$_{18}$ Column, 30×250 mm, 5 um; Mobile Phase A:Water (10 mmol/L FA), Mobile Phase B: ACN; Flow rate: 60 mL/min; Gradient: 20% B to 60% B in 8 min; 254 nm) to afford N-[1-methyl-2-(6-methyl-1H-1,3-benzodiazol-5-yl)pyrrolo[2,3-c]pyridin-5-yl]cyclopropanecarboxamide (Compound 17) (7.9 mg, 10%) as a white solid. LCMS (ESI, m/z): [M+H]$^+$=346.3. $^1$H NMR (300 MHz, DMSO-d$_6$): δ 10.46 (s, 1H), 8.59 (s, 1H), 8.25-8.20 (m, 2H), 7.58-7.54 (m, 2H), 6.43 (s, 1H), 3.54 (s, 3H), 2.20 (s, 3H), 2.03-1.97 (m, 1H), 0.89-0.72 (m, 4H).

Example S18: Synthesis of N-[1-methyl-2-(4-methyl-1H-indazol-5-yl)pyrrolo[2,3-c]pyridin-5-yl] cyclopropanecarboxamide (Compound 18)

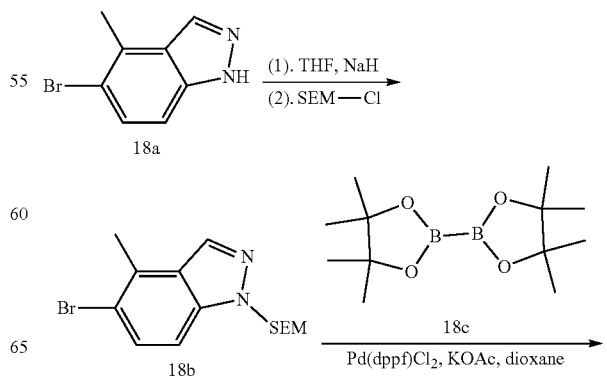

-continued

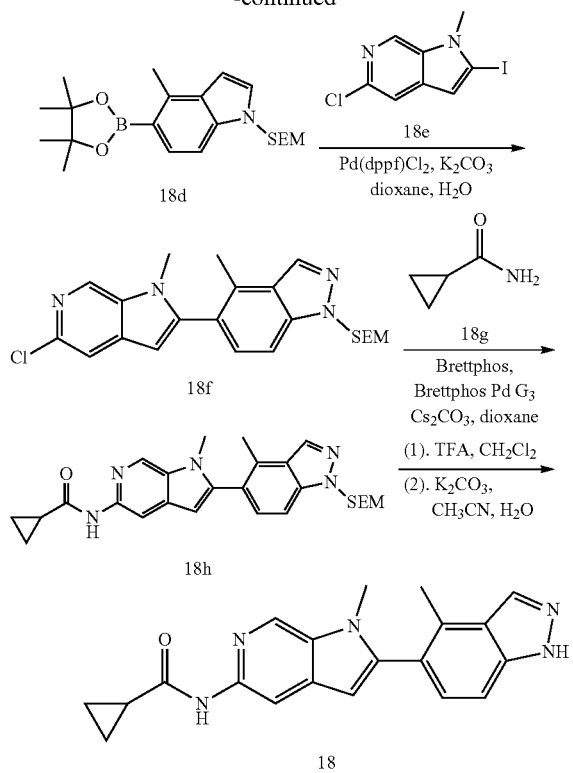

Step 1: Synthesis of 5-bromo-4-methyl-1-[[2-(trimethylsilyl)ethoxy]methyl]indazole (Compound 18b)

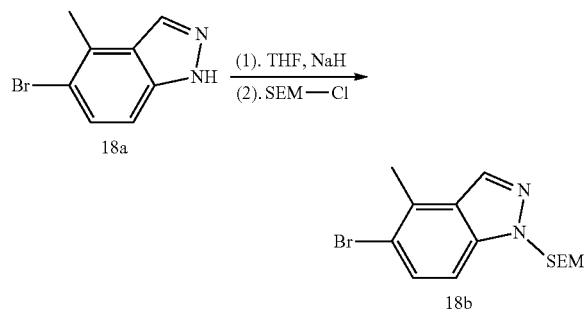

To a solution of 5-bromo-4-methyl-1H-indazole (Compound 18a) (500.0 mg, 2.39 mmol) in THF (10.0 mL) was added NaH (170.5 mg, 60%) at 0° C. under N₂. The mixture was stirred at 0° C. for 1 h. Then a solution of SEM-Cl (592.4 mg, 3.53 mmol) in THF (10.0 mL) was added dropwise to the mixture at 0° C. The mixture was stirred at 0° C. for another 2 h. After the reaction was completed, the reaction was quenched with water and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (5/1 v/v) to afford 5-bromo-4-methyl-1-[[2-(trimethylsilyl)ethoxy]methyl]indazole (Compound 18b) (800.0 mg, 90%) as a yellow oil. LCMS (ESI): [M+H]⁺=341.1.

Step 2: Synthesis of 4-methyl-5-(4,4,5,5-tetramethyl-1,3,2-dioxaborolan-2-yl)-1-[[2-(trimethylsilyl)ethoxy]methyl]indazole (Compound 18d)

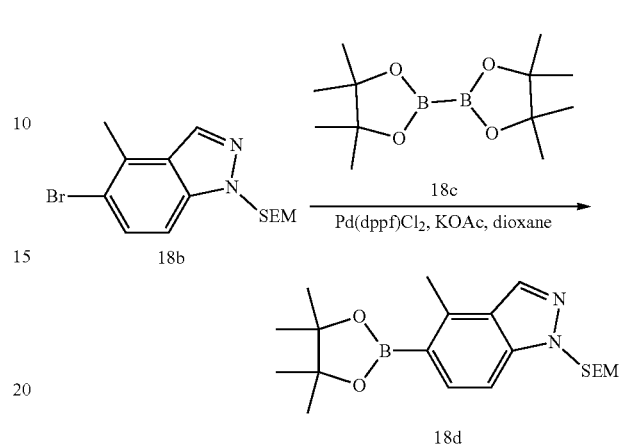

To a solution of 5-bromo-4-methyl-1-[[2-(trimethylsilyl)ethoxy]methyl]indazole (Compound 18b) (760.0 mg, 2.27 mmol) in dioxane (10.0 mL) was added bis(pinacolato)diboron (Compound 18c) (1.7 g, 6.80 mmol), Pd(dppf)Cl₂ (162.9 mg, 0.23 mmol) and KOAc (655.8 mg, 6.80 mmol). The resulting mixture was stirred at 80° C. for 16 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/2, v/v) to afford 4-methyl-5-(4,4,5,5-tetramethyl-1,3,2-dioxaborolan-2-yl)-1-[[2-(trimethylsilyl)ethoxy]methyl]indazole (Compound 18d) (700.0 mg, 81%) as a white solid. LCMS (ESI): [M+H]⁺=389.2.

Step 3: Synthesis of 5-[5-chloro-1-methylpyrrolo[2,3-c]pyridin-2-yl]-4-methyl-1-[[2-(trimethylsilyl)ethoxy]methyl]indazole (Compound 18f)

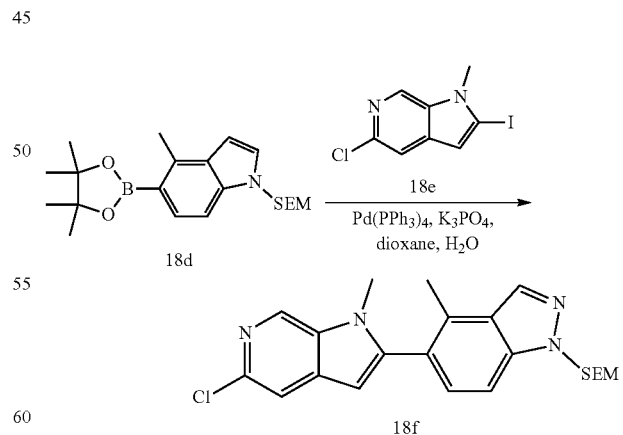

To a solution of 4-methyl-5-(4,4,5,5-tetramethyl-1,3,2-dioxaborolan-2-yl)-1-[[2-(trimethylsilyl)ethoxy]methyl]indazole (Compound 18d) (400.0 mg, 1.03 mmol) in dioxane/H₂O (20.0/2.0 mL) was added 5-chloro-2-iodo-1-methylpyrrolo[2,3-c]pyridine (Compound 18e) (301.4 mg, 1.03 mmol), Pd(PPh₃)₄ (119.1 mg, 0.13 mmol,) and K₃PO₄ (655.3 mg, 3.09 mmol). The resulting mixture was stirred at 100° C. for 12 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (2/1, v/v) to afford 5-[5-chloro-1-methylpyrrolo[2,3-c]pyridin-2-yl]-4-methyl-1-[[2-(trimethylsilyl)ethoxy]methyl]indazole (Compound 18f) (300.0 mg, 68%) as a white solid. LCMS (ESI): [M+H]⁺=427.2.

Step 4: Synthesis of N-[1-methyl-2-(4-methyl-1-[[2-(trimethylsilyl)ethoxy]methyl]indazol-5-yl)pyrrolo[2,3-c]pyridin-5-yl]cyclopropanecarboxamide (Compound 18h)

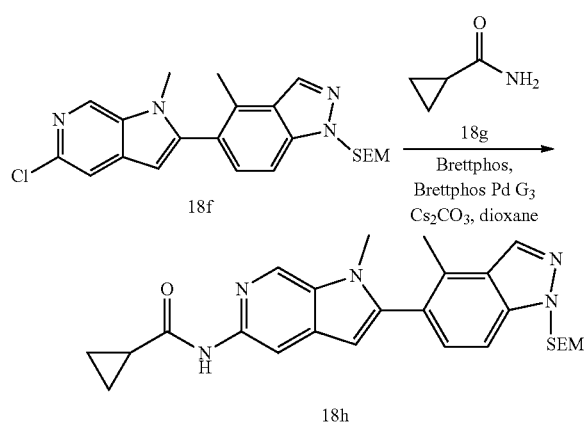

To a solution of 5-[5-chloro-1-methylpyrrolo[2,3-c]pyridin-2-yl]-4-methyl-1-[[2-(trimethylsilyl)ethoxy]methyl]indazole (Compound 18f) (300.0 mg, 0.73 mmol) in dioxane (10.0 mL) was added cyclopropanecarboxamide (Compound 18g) (179.7 mg, 2.18 mmol), BrettPhos (75.4 mg, 0.14 mmol), BrettPhos Pd G₃ (63.6 mg, 0.07 mmol) and Cs₂CO₃ (686.7 mg, 2.18 mmol). The resulting mixture was stirred at 100° C. for 4 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (2/1, v/v) to afford N-[1-methyl-2-(4-methyl-1-[[2-(trimethylsilyl)ethoxy]methyl]indazol-5-yl)pyrrolo[2,3-c]pyridin-5-yl]cyclopropanecarboxamide (Compound 18h) (140.0 mg, 42%) as a red solid. LCMS (ESI): [M+H]⁺=476.2.

Step 5: Synthesis of N-[1-methyl-2-(4-methyl-1H-indazol-5-yl)pyrrolo[2,3-c]pyridin-5-yl]cyclopropanecarboxamide (Compound 18)

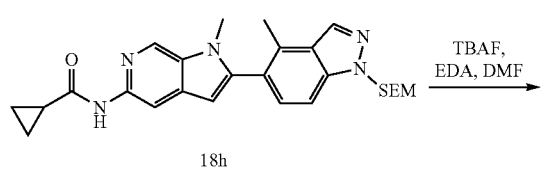

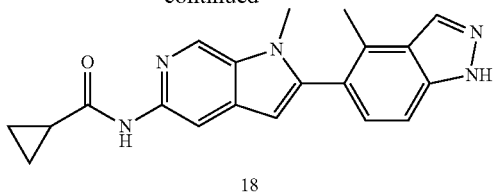

To a solution of N-[1-methyl-2-(4-methyl-1-[[2-(trimethylsilyl)ethoxy]methyl]indazol-5-yl)pyrrolo[2,3-c]pyridin-5-yl]cyclopropanecarboxamide (Compound 18h) (140.0 mg, 0.29 mmol) in DMF (7.0 mL) was added ethylenediamine (88.4 mg, 1.47 mmol) and TBAF (230.8 mg, 0.88 mmol). The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/1, v/v) and then purified by Prep-HPLC with the following conditions: Column: YMC-Actus Triart C18, 30×150 mm, 5 um; Mobile Phase A: Water (0.1% NH₄HCO₃), Mobile Phase B:ACN; Flow rate: 60 mL/min; Gradient: 23% B to 53% B in 10 min. Detector, UV 254 nm to afford N-[1-methyl-2-(4-methyl-1H-indazol-5-yl)pyrrolo[2,3-c]pyridin-5-yl]cyclopropanecarboxamide (Compound 18) (16.5 mg, 16%) as a white solid. LCMS (ESI): [M+H]⁺=346.1. ¹H NMR (300 MHz, DMSO-d₆): δ 13.22 (s, 1H), 10.48 (s, 1H), 8.61 (s, 1H), 8.26-8.21 (m, 2H), 7.49 (d, J=8.4 Hz, 1H), 7.30 (d, J=8.7 Hz, 1H), 6.45 (s, 1H), 3.57 (s, 3H), 2.43 (s, 3H), 2.08-1.97 (m, 1H), 0.82-0.76 (m, 4H).

Example S19: Synthesis of N-[1-methyl-2-(4-methyl-1H-1,3-benzodiazol-5-yl)pyrrolo[2,3-c]pyridin-5-yl]cyclopropanecarboxamide (Compound 19)

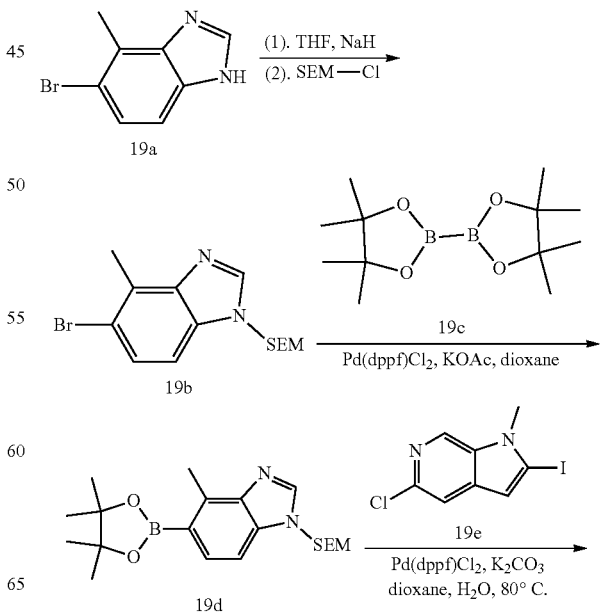

-continued

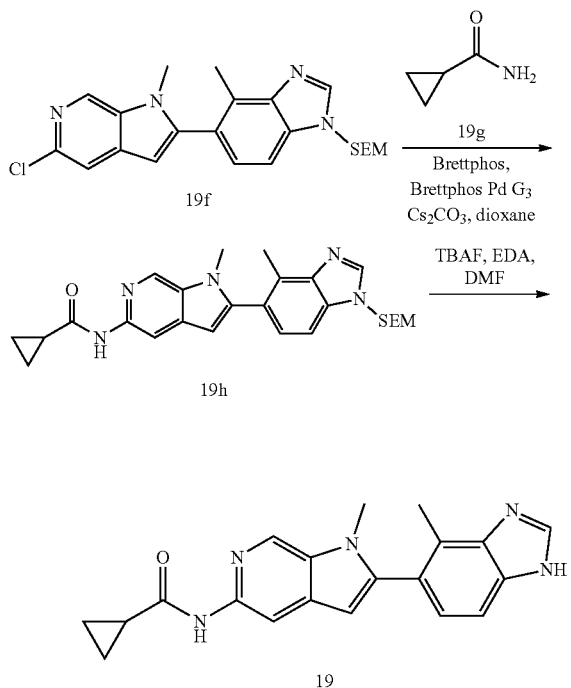

Step 1: Synthesis of 5-bromo-4-methyl-1-[[2-(trimethylsilyl)ethoxy]methyl]-1,3-benzodiazole (Compound 19b)

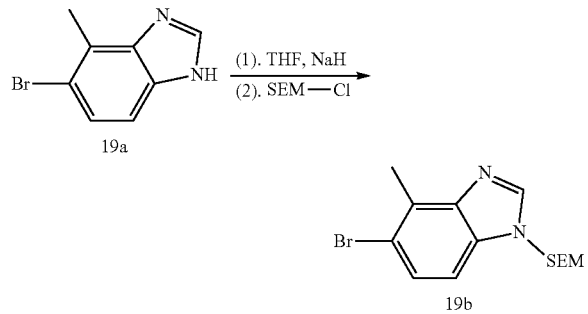

To a solution of 5-bromo-4-methyl-1H-1,3-benzodiazole (Compound 19a) (1.00 g, 4.73 mmol) in THF (10.0 mL) was added NaH (0.3 g, 60%) at 0° C. under N₂. The resulting mixture was stirred at 0° C. for 1 h. Then SEM-Cl (1.2 g, 7.07 mmol) was added dropwise to the mixture at 0° C. under N₂. The resulting mixture was stirred at room temperature for 1 h. After the reaction was completed, the reaction mixture was quenched with water and extracted with ethyl acetate. The combined organic layer was washed with brine, dried over anhydrous sodium sulfate and filtered. The resulting mixture was concentrated under reduced pressure. The residue was purified by flash column chromatography with petroleum ether/ethyl acetate (2/1, v/v) to afford 5-bromo-4-methyl-1-[[2-(trimethylsilyl)ethoxy]methyl]-1,3-benzodiazole (Compound 19b) (1.0 g, 61%) as a yellow oil. LCMS (ESI, m/z): [M+H]⁺=341.1.

Step 2: Synthesis of 4-methyl-5-(4,4,5,5-tetramethyl-1,3,2-dioxaborolan-2-yl)-1-[[2-(trimethylsilyl)ethoxy]methyl]-1,3-benzodiazole (Compound 19d)

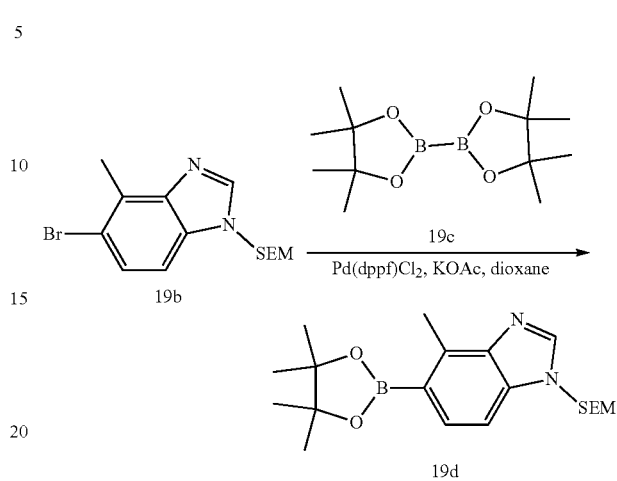

To a mixture of 5-bromo-4-methyl-1-[[2-(trimethylsilyl)ethoxy]methyl]-1,3-benzodiazole (Compound 19b) (950.0 mg, 2.78 mmol) and 4,4,4',4',5,5,5',5'-octamethyl-2,2'-bi(1,3,2-dioxaborolane) (Compound 19c) (2.1 g, 8.34 mmol) in dioxane (10.0 mL) was added Pd(dppf)Cl₂ (227.2 mg, 0.27 mmol) and KOAc (819.4 mg, 8.35 mmol) at room temperature under N₂. The resulting mixture was stirred at 100° C. for 16 h. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 4-methyl-5-(4,4,5,5-tetramethyl-1,3,2-dioxaborolan-2-yl)-1-[[2-(trimethylsilyl)ethoxy]methyl]-1,3-benzodiazole (Compound 19d) (2.0 g, crude) as a yellow oil. LCMS (ESI, m/z): [M+H]⁺=389.2.

Step 3: Synthesis of 5-[5-chloro-1-methylpyrrolo[2,3-c]pyridin-2-yl]-4-methyl-1-[[2-(trimethylsilyl)ethoxy]methyl]-1,3-benzodiazole (Compound 19f)

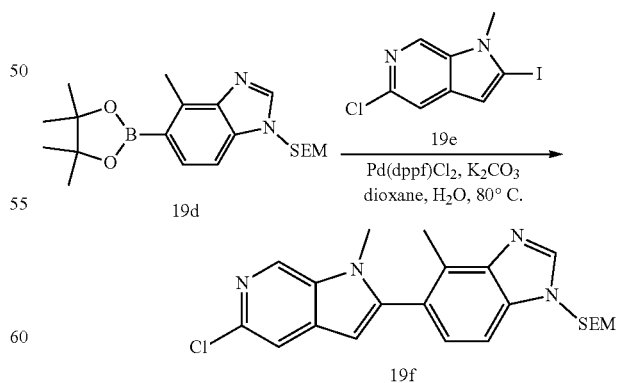

To a mixture of 4-methyl-5-(4,4,5,5-tetramethyl-1,3,2-dioxaborolan-2-yl)-1-[[2-(trimethylsilyl)ethoxy]methyl]-1,3-benzodiazole (Compound 19d) (1.0 g, 2.51 mmol) and 5-chloro-2-iodo-1-methyl-1H-pyrrolo[2,3-c]pyridine (Compound 19e) (250.0 mg, 0.86 mmol) in dioxane/H₂O (10.0/ 1.0 mL) was added Pd(dppf)Cl₂ (70.0 mg, 0.08 mmol) and K₂CO₃ (354.0 mg, 2.51 mmol) at room temperature under N₂. The resulting mixture was stirred at 80° C. for 16 h. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ ethyl acetate (1/1, v/v) to afford 5-[5-chloro-1-methylpyrrolo[2,3-c]pyridin-2-yl]-4-methyl-1-[[2-(trimethylsilyl) ethoxy]methyl]-1,3-benzodiazole (Compound 19f) (350.0 mg, 31%) as a white solid. LCMS (ESI, m/z): [M+H]⁺= 427.2.

Step 4: Synthesis of N-[1-methyl-2-(4-methyl-1-[[2-(trimethylsilyl)ethoxy]methyl]-1,3-benzodiazol-5-yl) pyrrolo[2,3-c]pyridin-5-yl]cyclopropanecarboxamide (Compound 19h)

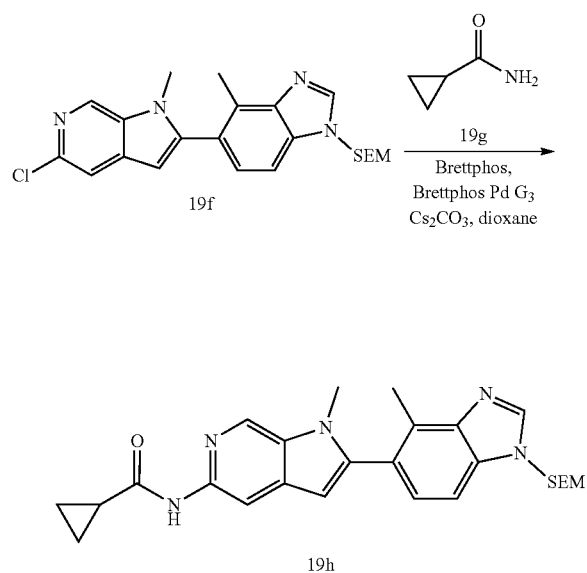

To a mixture of 5-[5-chloro-1-methylpyrrolo[2,3-c]pyridin-2-yl]-4-methyl-1-[[2-(trimethylsilyl)ethoxy]methyl]-1, 3-benzodiazole (Compound 19f) (300.0 mg, 0.70 mmol) and cyclopropanecarboxamide (Compound 19g) (239.1 mg, 2.81 mmol) in dioxane (5.0 mL) were added BrettPhos Pd G₃ (63.6 mg, 0.07 mmol), Cs₂CO₃ (686.7 mg, 2.10 mmol) and BrettPhos (75.4 mg, 0.14 mmol) at room temperature under N₂. The resulting mixture was stirred at 100° C. for 16 h. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with dichloromethane/ methyl alcohol (10/1, v/v) to afford N-[1-methyl-2-(4-methyl-1-[[2-(trimethylsilyl)ethoxy]methyl]-1,3-benzodiazol-5-yl)pyrrolo[2,3-c]pyridin-5-yl] cyclopropanecarboxamide (Compound 19h) (220.0 mg, 65%) as a yellow solid. LCMS (ESI, m/z): [M+H]⁺=476.2.

Step 5: Synthesis of N-[1-methyl-2-(4-methyl-1H-1, 3-benzodiazol-5-yl)pyrrolo[2,3-c]pyridin-5-yl]cyclopropanecarboxamide (Compound 19)

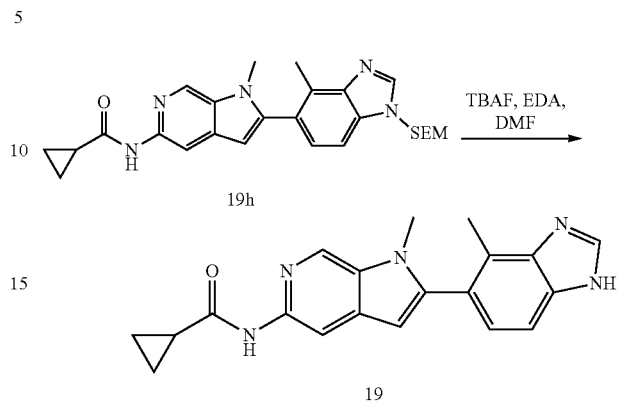

To a mixture of N-[1-methyl-2-(4-methyl-1-[[2-(trimethylsilyl)ethoxy]methyl]-1,3-benzodiazol-5-yl)pyrrolo[2,3-c] pyridin-5-yl]cyclopropanecarboxamide (Compound 19h) (170.0 mg, 0.36 mmol) and EDA (107.2 mg, 1.79 mmol) in DMF (2.0 mL) was added TBAF (280.3 mg, 1.07 mmol) at room temperature. The resulting mixture was stirred at 80° C. for 16 h. After the reaction was completed, the reaction was diluted with H₂O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: YMC-Actus Triart C18, 30×150 mm, 5 um; Mobile Phase A:Water (10 mmol/L NH₄HCO₃), Mobile Phase B:ACN; Flow rate: 60 mL/min; Gradient: 19% B to 41% B in 7 min; 254 nm) to afford N-[1-methyl-2-(4-methyl-1H-1,3-benzodiazol-5-yl)pyrrolo[2,3-c]pyridin-5-yl]cyclopropanecarboxamide (Compound 19) (31.4 mg, 25%) as a white solid. LCMS (ESI, m/z): [M+H]⁺=346.1. ¹H NMR (300 MHz, DMSO-d₆): δ 12.74-12.60 (m, 1H), 10.49 (s, 1H), 8.61 (s, 1H), 8.32 (s, 1H), 8.21 (s, 1H), 7.51 (br, s, 1H), 7.17 (d, J=8.1 Hz, 1H), 6.44 (s, 1H), 3.58 (s, 3H), 2.40 (s, 3H), 2.04-2.00 (m, 1H), 0.83-0.75 (m, 4H).

Example S20: Synthesis of N-[1-methyl-2-(3-methylpyridin-2-yl)pyrrolo[2,3-c]pyridin-5-yl]cyclopropanecarboxamide (Compound 20)

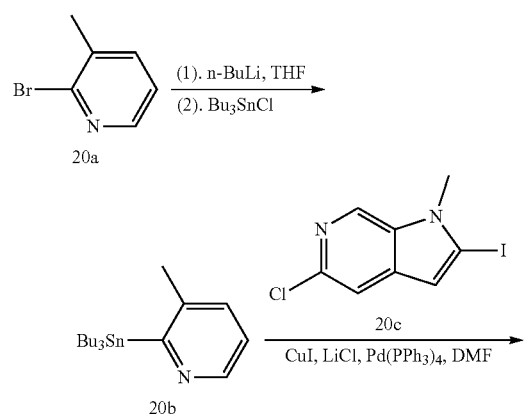

-continued

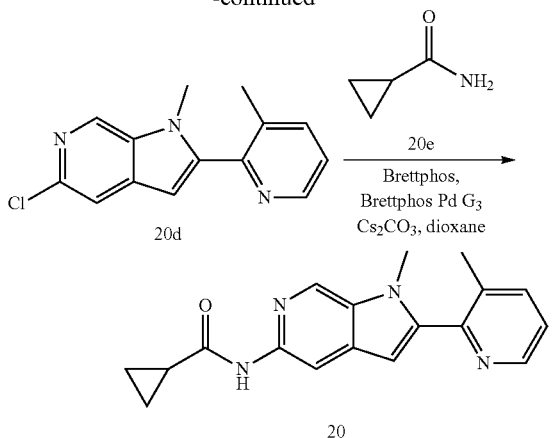

Step 1: Synthesis of 3-methyl-2-(tributylstannyl)pyridine (Compound 20b)

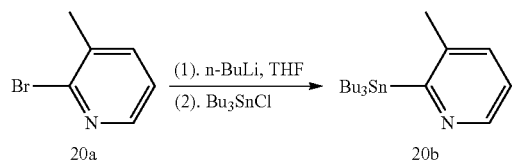

To a solution of 2-bromo-3-methylpyridine (Compound 20a) (5.0 g, 29.06 mmol) in THF (125.0 mL) was added n-BuLi (4.1 mL, 64.15 mmol) dropwise at −78° C. under N$_2$. The resulting mixture was stirred at −78° C. for 1 h. Then tributylchlorostannane (11.3 g, 34.8 mmol) was added dropwise to the mixture at −78° C. The resulting mixture was stirred at −78° C. for another 1 h. After the reaction was completed, the reaction mixture was quenched with saturated NH$_4$Cl and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (80/20, v/v) to afford 3-methyl-2-(tributylstannyl) pyridine (Compound 20b) (300.0 mg, 3%) as a colorless oil. LCMS (ESI): [M+H]$^+$=384.2.

Step 2: Synthesis of 2-[5-chloro-1-methylpyrrolo[2,3-c]pyridin-2-yl]-3-methylpyridine (Compound

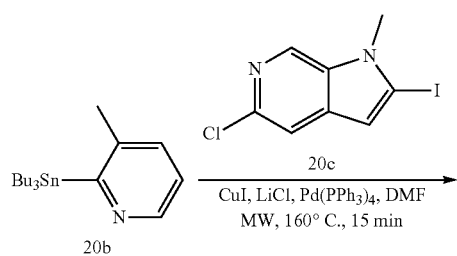

-continued

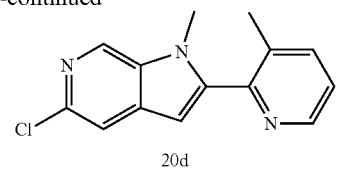

To a solution of 5-chloro-2-iodo-1-methylpyrrolo[2,3-c]pyridine (Compound 20c) (200.0 mg, 0.68 mmol) in DMF (2.0 mL) was added 3-methyl-2-(tributylstannyl) pyridine (Compound 20b) (522.6 mg, 1.36 mmol), CuI (13.0 mg, 0.07 mmol), LiCl (86.9 mg, 2.05 mmol) and Pd(PPh$_3$)$_4$ (79.0 mg, 0.07 mmol). The resulting mixture was irradiated with microwave (MW) at 160° C. for 15 min under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (90/10, v/v) to afford 2-[5-chloro-1-methylpyrrolo[2,3-c]pyridin-2-yl]-3-methylpyridine (Compound 20d) (170.0 mg, 96%) as a yellow oil. LCMS (ESI): [M+H]$^+$=258.1.

Step 3: Synthesis of N-[1-methyl-2-(3-methylpyridin-2-yl)pyrrolo[2,3-c]pyridin-5-yl]cyclopropanecarboxamide (Compound 20)

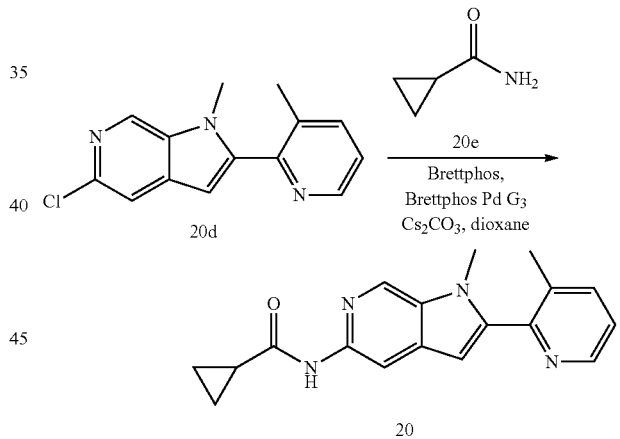

To a solution of 2-[5-chloro-1-methylpyrrolo[2,3-c]pyridin-2-yl]-3-methylpyridine (Compound 20d) (210.0 mg, 0.81 mmol) in 1,4-dioxane (10.0 mL) was added Brettphos Pd G$_3$ (147.7 mg, 0.16 mmol), BrettPhos (174.9 mg, 0.32 mmol), Cs$_2$CO$_3$ (796.4 mg, 2.44 mmol) and cyclopropanecarboxamide (Compound 20e) (104.0 mg, 1.22 mmol). The resulting mixture was stirred at 100° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with CH$_2$Cl$_2$/CH$_3$OH (94/6, v/v) and then purified by Prep-HPLC with the following conditions (Column: YMC-Actus Triart C$_{18}$ Column. 30×250 mm, 5 um; Mobile Phase A:Water (10 mmol/L NH$_4$HCO$_3$), Mobile Phase B: ACN; Flow rate: 60 mL/min; Gradient: 18% B to 42% B in 8 min; 254 nm) to afford N-[1-methyl-2-(3-methylpyridin-2-yl)pyrrolo[2,3-c]pyridin-5-yl]cyclopropanecarboxamide (Compound 20) (11.7 mg, 4%) as a white solid. LCMS (ESI, m/z): [M+H]$^+$=307.3. $^1$H NMR (300 MHz, DMSO-d$_6$): δ 10.52 (s, 1H), 8.67 (s, 1H), 8.60-8.58 (m, 1H), 8.24 (s, 1H), 7.87-7.84 (m, 1H), 7.44-7.40 (m, 1H), 6.67 (d, J=0.6 Hz, 1H), 3.73 (s, 3H), 2.35 (s, 3H), 2.08-2.00 (m, 1H), 0.85-0.78 (m, 4H).

Example S21: Synthesis of N-[1-methyl-2-(2-methylpyridin-3-yl)pyrrolo[2,3-c]pyridin-5-yl]cyclopropanecarboxamide (Compound 21)

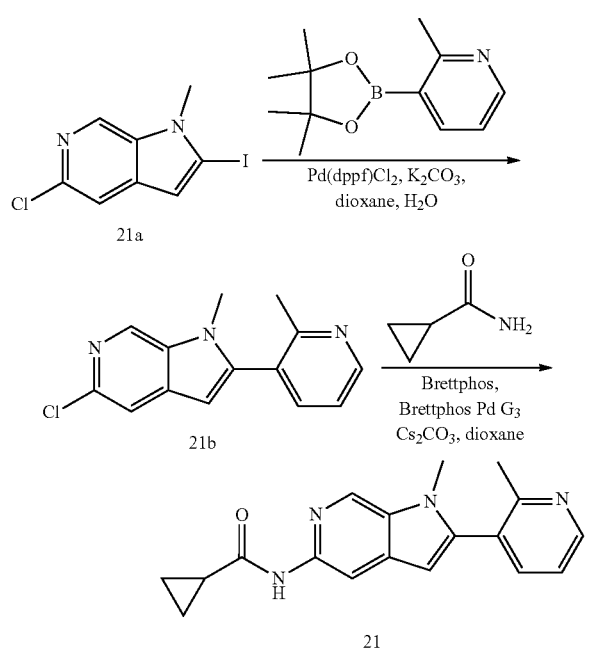

Step 1: Synthesis of 3-(5-chloro-1-methylpyrrolo[2,3-c]pyridin-2-yl-2-methylpyridine (Compound 21b)

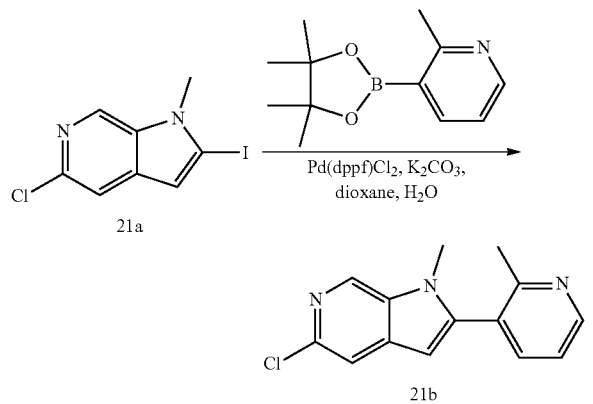

To a solution of 5-chloro-2-iodo-1-methylpyrrolo[2,3-c]pyridine (Compound 21a) (200.0 mg, 0.68 mmol) in dioxane/H$_2$O (10.0/1.0 mL) was added 2-methyl-3-(4,4,5,5-tetramethyl-1,3,2-dioxaborolan-2-yl)pyridine (179.8 mg, 0.08 mmol), Pd(dppf)Cl$_2$ (10.0 mg, 0.01 mmol) and K$_2$CO$_3$ (283.5 mg, 2.05 mmol). The resulting mixture was stirred at 80° C. for 16 h. After the reaction was completed, the resulting mixture was concentrated under reduced pressure. The residue was purified by flash column chromatography with petroleum ether/ethyl acetate (1/2, v/v) to afford 3-[5-chloro-1-methylpyrrolo[2,3-c]pyridin-2-yl]-2-methylpyridine (Compound 21b) (150.0 mg, 85%) as a yellow solid. LCMS (ESI): [M+H]$^+$=258.1.

Step 2: Synthesis of N-[1-methyl-2-(2-methylpyridin-3-yl)pyrrolo[2,3-c]pyridin-5-yl]cyclopropanecarboxamide (Compound 21)

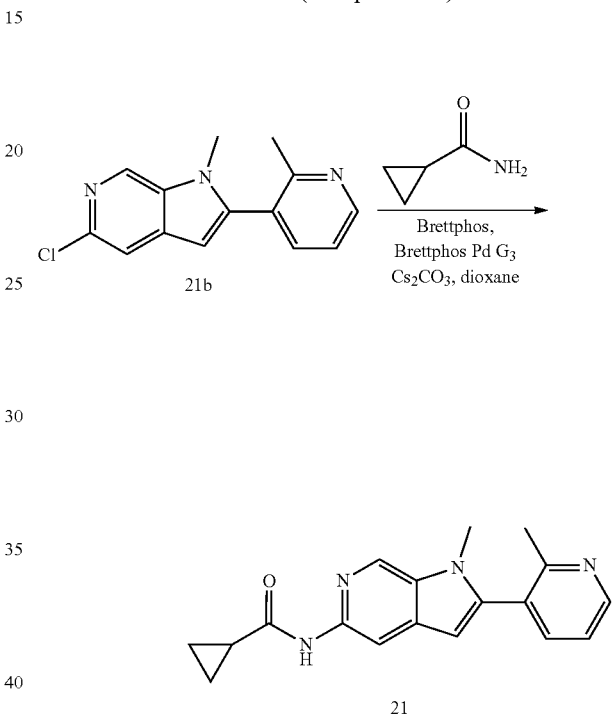

To a solution of 3-[5-chloro-1-methylpyrrolo[2,3-c]pyridin-2-yl]-2-methylpyridine (Compound 21b) (150.0 mg, 0.77 mmol) in dioxane (5.0 mL) was added cyclopropanecarboxamide (188.3 mg, 2.22 mmol), BrettPhos Pd G3 (66.8 mg, 0.07 mmol), BrettPhos (79.4 mg, 0.17 mmol) and Cs$_2$CO$_3$ (720.6 mg, 2.22 mmol). The resulting mixture was stirred at 100° C. for 4 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified Prep-HPLC with the following conditions: Column: YMC-Actus Triart C18, 30×250 mm, 5 um; Mobile Phase A: Water (10 mmol/L NH$_4$HCO$_3$), Mobile Phase B: ACN; Flow rate: 60 mL/min; Gradient: 27% B to 38% B in 8 min. Detector, UV 254/220 nm to afford N-[1-methyl-2-(2-methylpyridin-3-yl)pyrrolo[2,3-c]pyridin-5-yl]cyclopropanecarboxamide (Compound 21) (81.7 mg, 46%) as a white solid. LCMS (ESI): [M+H]$^+$=307.2. $^1$H NMR (300 MHz, DMSO-d$_6$): δ 10.52 (s, 1H), 8.64-8.59 (m, 2H), 8.22 (s, 1H), 7.80-7.76 (m, 1H), 7.41-7.37 (m, 1H), 6.53 (s, 1H), 3.59 (s, 3H), 2.37 (s, 3H), 2.05-1.95 (m, 1H), 0.82-0.76 (m, 4H).

Example S22: Synthesis of N-[2-(2-methoxypyridin-3-yl)-1-methylpyrrolo[2,3-c]pyridin-5-yl]cyclopropanecarboxamide (Compound 22)

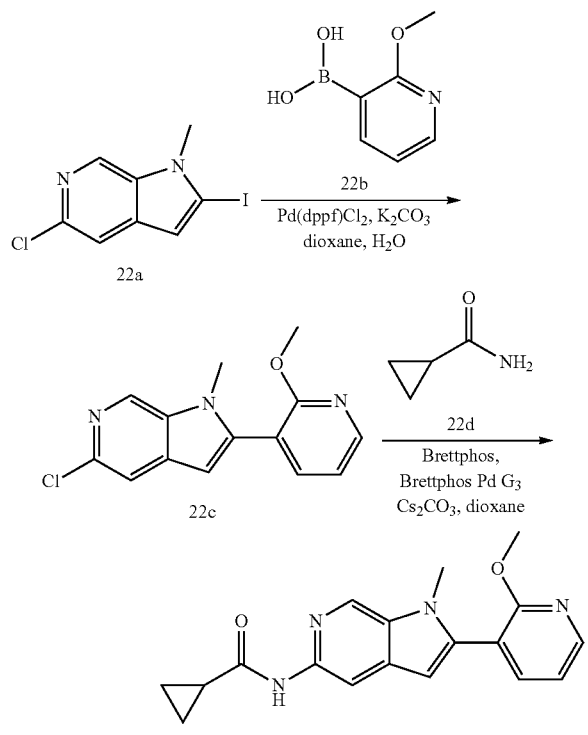

Step 1: Synthesis of 3-[5-chloro-1-methylpyrrolo[2,3-c]pyridin-2-yl]-2-methoxypyridine (Compound 22c)

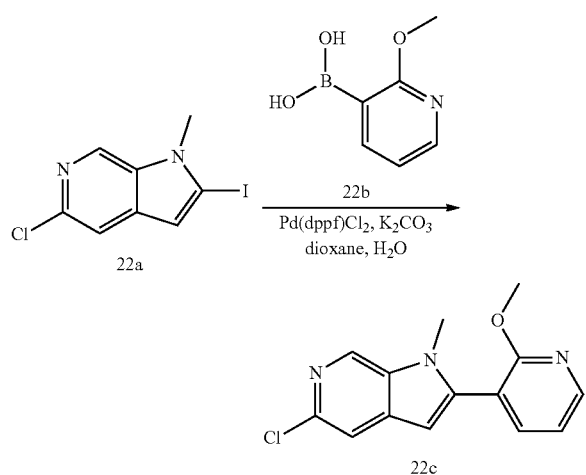

To a mixture of 5-chloro-2-iodo-1-methylpyrrolo[2,3-c]pyridine (Compound 22a) (300.0 mg, 1.02 mmol) and 2-methoxypyridin-3-ylboronic acid (Compound 22b) (313.7 mg, 2.05 mmol) in dioxane/H₂O (4.0/0.4 mL) was added Pd(dppf)Cl₂ (83.7 mg, 0.10 mmol) and K₂CO₃ (425.2 mg, 3.07 mmol) at room temperature under N₂. The resulting mixture was stirred at 80° C. for 12 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 3-[5-chloro-1-methylpyrrolo[2,3-c]pyridin-2-yl]-2-methoxypyridine (Compound 22c (230.0 mg, 82%) as a white solid. LCMS (ESI, m/z): [M+H]⁺=274.1.

Step 2: Synthesis of N-[2-(2-methoxypyridin-3-yl)-1-methylpyrrolo[2,3-c]pyridin-5-yl]cyclopropanecarboxamide (Compound 22)

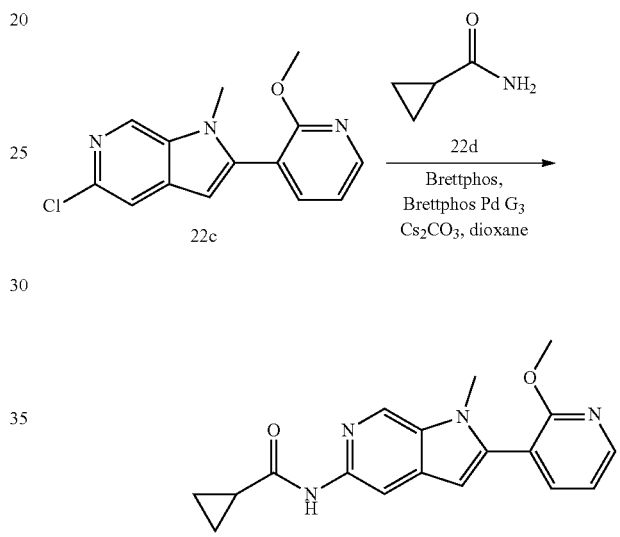

To a stirred mixture of 3-[5-chloro-1-methylpyrrolo[2,3-c]pyridin-2-yl]-2-methoxypyridine (Compound 22c) (100.0 mg, 0.37 mmol) and cyclopropanecarboxamide (Compound 22d) (155.4 mg, 1.82 mmol) in dioxane (3.0 mL) were added Cs₂CO₃ (357.1 mg, 1.10 mmol), BrettPhos (39.2 mg, 0.07 mmol) and BrettPhos Pd G3 (33.1 mg, 0.03 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: YMC-Actus Triart C18, 30×250 mm, 5 um; Mobile Phase A:Water (10 mmol/L NH₄HCO₃), Mobile Phase B:ACN; Flow rate: 60 mL/min; Gradient: 37% B to 67% B in 7 min; 254 nm) to afford N-[2-(2-methoxypyridin-3-yl)-1-methylpyrrolo[2,3-c]pyridin-5-yl]cyclopropanecarboxamide (Compound 22) (79.5 mg, 67%) as a white solid. LCMS (ESI, m/z): [M+H]⁺=323.2. ¹H NMR (300 MHz, DMSO-d₆): δ 10.49 (s, 1H), 8.63 (s, 1H), 8.36-8.34 (m, 1H), 8.21 (s, 1H), 7.86-7.83 (m, 1H), 7.20-7.16 (m, 1H), 6.52 (d, J=0.8 Hz, 1H), 3.92 (s, 3H), 3.64 (s, 3H), 2.03-1.98 (m, 1H), 0.84-0.78 (m, 4H).

Example S23: Synthesis of cis-2-(hydroxymethyl)-N-(2-(2-methoxyphenyl)-1-methyl-1H-pyrrolo[2,3-c]pyridin-5-yl)cyclopropane-1-carboxamide (Compound 23)

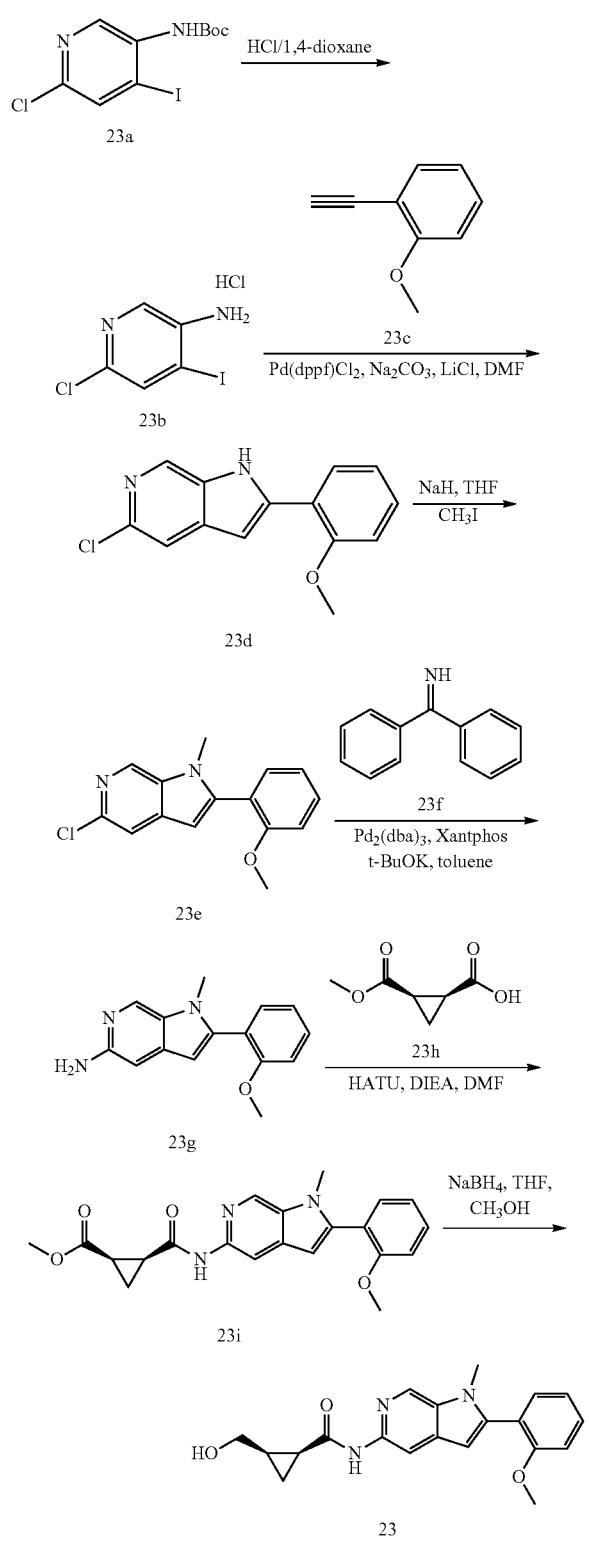

Step 1: Synthesis of 6-chloro-4-iodopyridin-3-amine hydrochloride (Compound 23b)

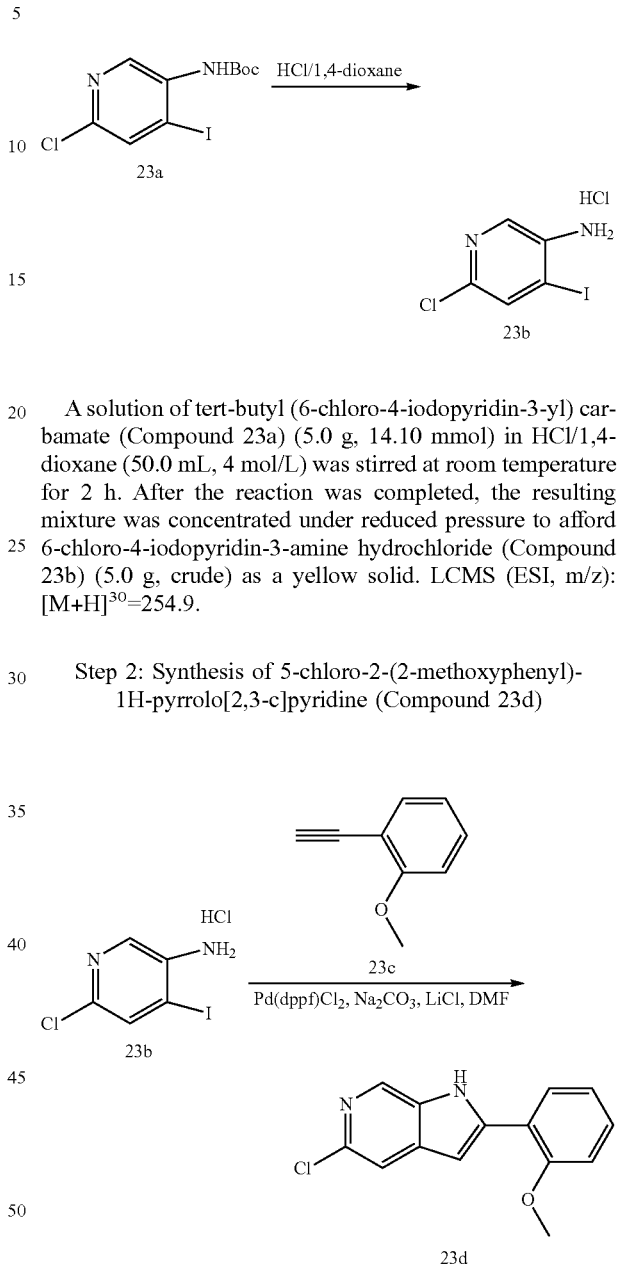

A solution of tert-butyl (6-chloro-4-iodopyridin-3-yl) carbamate (Compound 23a) (5.0 g, 14.10 mmol) in HCl/1,4-dioxane (50.0 mL, 4 mol/L) was stirred at room temperature for 2 h. After the reaction was completed, the resulting mixture was concentrated under reduced pressure to afford 6-chloro-4-iodopyridin-3-amine hydrochloride (Compound 23b) (5.0 g, crude) as a yellow solid. LCMS (ESI, m/z): $[M+H]^{3O}$=254.9.

Step 2: Synthesis of 5-chloro-2-(2-methoxyphenyl)-1H-pyrrolo[2,3-c]pyridine (Compound 23d)

To a solution of 6-chloro-4-iodopyridin-3-amine hydrochloride (Compound 23b) (2.0 g, crude) in DMF (20.0 mL) was added 1-ethynyl-2-methoxybenzene (Compound 23c) (1.3 g, 9.43 mmol), Na$_2$CO$_3$ (4.2 g, 39.3 mmol), LiCl (333.2 mg, 7.86 mmol) and Pd(dppf)Cl$_2$ (575.1 mg, 0.79 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford 5-chloro- 2-(2-methoxyphenyl)-1H-pyrrolo[2,3-c]pyridine (Compound 23d) (770.0 mg, 37%) as a brown solid. LCMS (ESI, m/z): [M+H]$^+$=259.1.

Step 3: Synthesis of 5-chloro-2-(2-methoxyphenyl)-1-methyl-1H-pyrrolo[2,3-c]pyridine (Compound 23e)

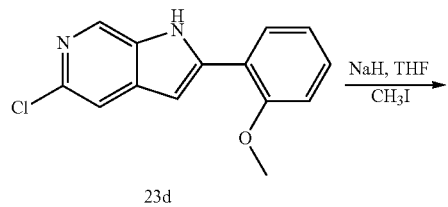

To a solution of 5-chloro-2-(2-methoxyphenyl)-1H-pyrrolo[2,3-c]pyridine (Compound 23d) (770 mg, 2.98 mmol) in THF (10.0 mL) was added NaH (371.1 mg, 60%) at 0° C. under N$_2$. The resulting mixture was stirred at 0° C. for 1 h under N$_2$. Then CH$_3$I (2.2 g, 15.5 mmol) was added dropwise to the mixture at 0° C. under N$_2$. The resulting mixture was stirred at 0° C. for another 1 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure to afford 5-chloro-2-(2-methoxyphenyl)-1-methyl-1H-pyrrolo[2,3-c]pyridine (Compound 23e) (800.0 mg, crude) as a brown solid. LCMS (ESI, m/z): [M+H]$^+$=273.2.

Step 4: Synthesis of 2-(2-methoxyphenyl)-1-methyl-1H-pyrrolo[2,3-c]pyridin-5-amine (Compound 23g)

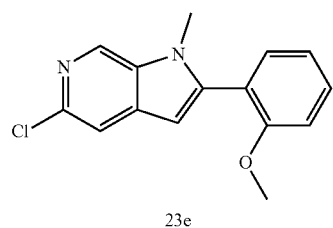

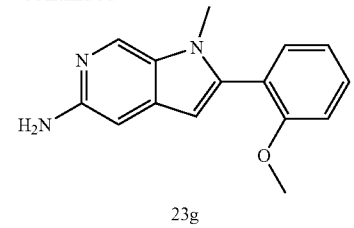

To a solution of 5-chloro-2-(2-methoxyphenyl)-1-methyl-1H-pyrrolo[2,3-c]pyridine (Compound 23e) (800.0 mg, crude) in toluene (10.0 mL) was added diphenylmethanimine (Compound 23f) (1.6 g, 8.80 mmol), t-BuOK (987.5 mg, 8.80 mmol), XantPhos (339.5 mg, 0.59 mmol) and Pd$_2$(dba)$_3$ (268.6 mg, 0.29 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/CH$_3$OH (87/13, v/v) to afford 2-(2-methoxyphenyl)-1-methyl-1H-pyrrolo[2,3-c]pyridin-5-amine (Compound 23g) (240.0 mg, 15%) as a brown solid. LCMS (ESI, m/z): [M+H]$^+$=254.1.

Step 5: Synthesis of methyl(cis)-2-((2-(2-methoxyphenyl)-1-methyl-1H-pyrrolo[2,3-c]pyridin-5-yl)carbamoyl)cyclopropane-1-carboxylate (Compound 23i)

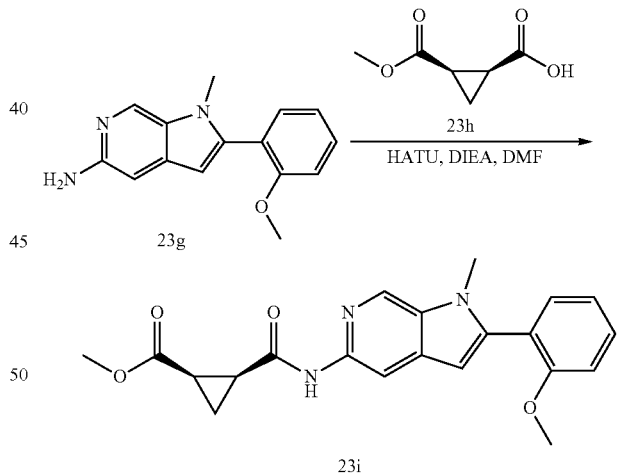

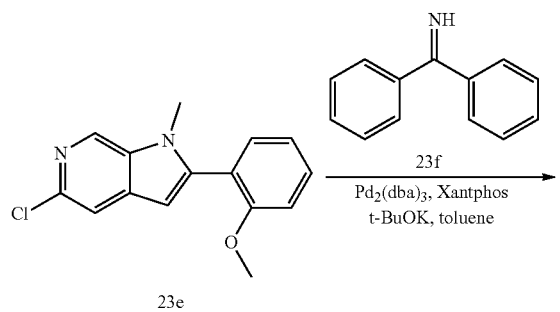

To a solution of 2-(2-methoxyphenyl)-1-methyl-1H-pyrrolo[2,3-c]pyridin-5-amine (Compound 23g) (240.0 mg, 0.95 mmol) in DMF (5.0 mL) was added cis-2-(methoxycarbonyl)cyclopropane-1-carboxylic acid (Compound 23h) (136.6 mg, 0.95 mmol), DIEA (612.3 mg, 4.74 mmol) and HATU (432.3 mg, 1.14 mmol) at 0° C. under N$_2$. The resulting mixture was stirred at room temperature for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/99, v/v) to afford methyl(cis)-2-((2-(2-methoxyphenyl)-1-methyl-1H-pyrrolo[2,3-c]pyridin-5-yl)carbamoyl)cyclopropane-1-carboxylate (Compound 23i) (190.0 mg, 53%) as a brown solid. LCMS (ESI, m/z): [M+H]⁺=380.2.

Step 6: Synthesis of cis-2-(hydroxymethyl)-N-(2-(2-methoxyphenyl)-1-methyl-1H-pyrrolo[2,3-c]pyridin-5-yl)cyclopropane-1-carboxamide (Compound 23)

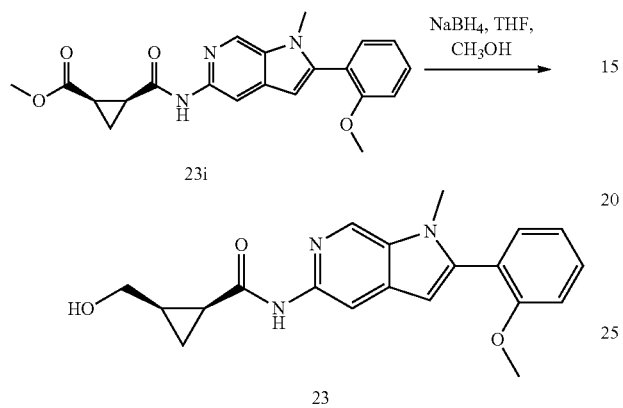

To a solution of methyl(cis)-2-((2-(2-methoxyphenyl)-1-methyl-1H-pyrrolo[2,3-c]pyridin-5-yl)carbamoyl)cyclopropane-1-carboxylate (Compound 23i) (170.0 mg, 0.45 mmol) in THF/CH₃OH (5.0/1.0 mL) was added NaBH₄ (169.5 mg, 4.48 mmol) at room temperature. The resulting mixture was stirred at room temperature for 16 h. After the reaction was completed, the resulting mixture was concentrated under reduced pressure. The residue was purified by Prep-HPLC with the following conditions (Column: XBridge Prep OBD C₁₈ Column, 19×250 mm, 5 um; Mobile Phase A: Water (10 mmol/L NH₄HCO₃), Mobile Phase B: MeOH—Preparative; Flow rate: 25 mL/min; Gradient: 54% B to 70% B in 7 min; 254 nm) to afford cis-2-(hydroxymethyl)-N-(2-(2-methoxyphenyl)-1-methyl-1H-pyrrolo[2,3-c]pyridin-5-yl)cyclopropane-1-carboxamide (Compound 23) (5.3 mg, 3%) as a white solid. LCMS (ESI, m/z): [M+H]⁺=352.2. ¹H NMR (300 MHz, DMSO-d₆): δ 10.40 (s, 1H), 8.59 (s, 1H), 8.21 (s, 1H), 7.56-7.50 (m, 1H), 7.39-7.36 (m, 1H), 7.21 (d, J=8.1 Hz, 1H), 7.13-7.08 (m, 1H), 6.42 (d, J=0.6 Hz, 1H), 4.48-4.45 (m, 1H), 3.82 (s, 3H), 3.69-3.55 (m, 5H), 2.10-2.07 (m, 1H), 1.50-1.34 (m, 1H), 0.98-0.90 (m, 2H).

Example S24: Synthesis of 5-chloro-2-(3-methoxy-2-methylphenyl)-1-methyl-1H-pyrrolo[2,3-c]pyridine (Compound 24)

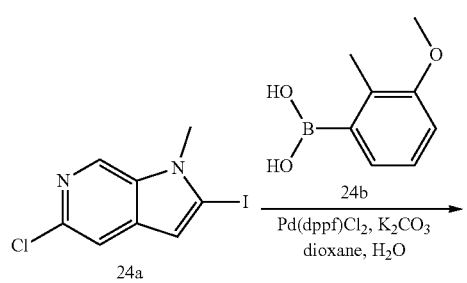

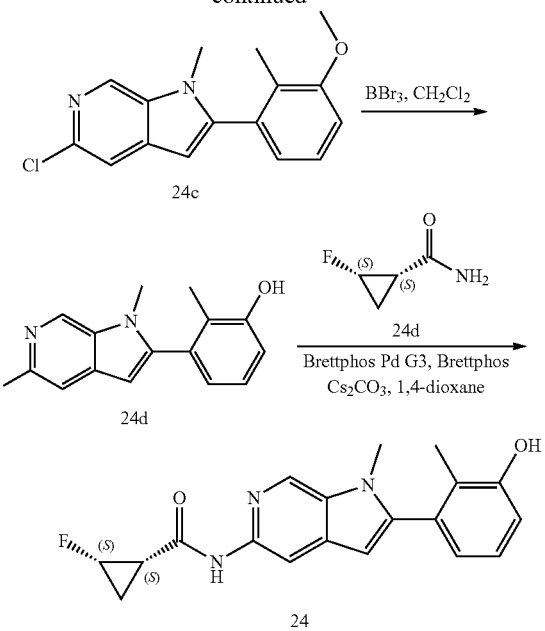

Step 1: Synthesis of 5-chloro-2-(3-methoxy-2-methylphenyl)-1-methyl-1H-pyrrolo[2,3-c]pyridine (Compound 24c)

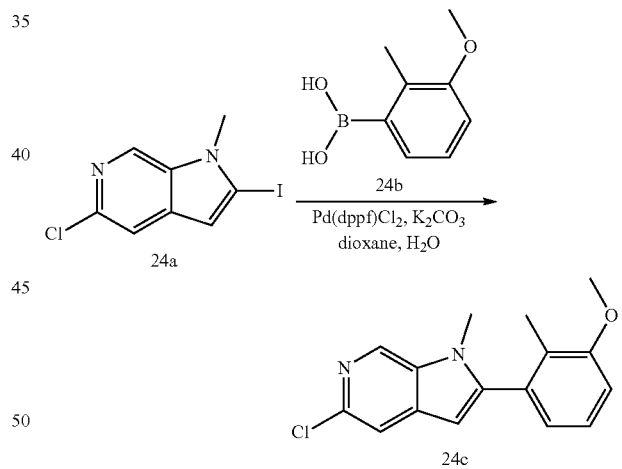

To a solution of 5-chloro-2-iodo-1-methylpyrrolo[2,3-c]pyridine (Compound 24a) (500.0 mg, 1.70 mmol) in 1,4-dioxane/H₂O (36.0/3.6 mL) was added K₂CO₃ (708.7 mg, 5.12 mmol), 3-methoxy-2-methylphenylboronic acid (Compound 24b) (425.5 mg, 2.56 mmol) and Pd(dppt)Cl₂ (250.1 mg, 0.34 mmol) under N₂. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with ether/ethyl acetate (87/13, v/v) to afford 5-chloro-2-(3-methoxy-2- methylphenyl)-1-methyl-1H-pyrrolo[2,3-c]pyridine (Compound 24c) (380.0 mg, 77%) as a yellow solid. LCMS (ESI, m/z): [M+H]+=287.1.

Step 2: Synthesis of 3-(5-chloro-1-methyl-1H-pyrrolo[2,3-c]pyridin-2-yl)-2-methylphenol (Compound 24d)

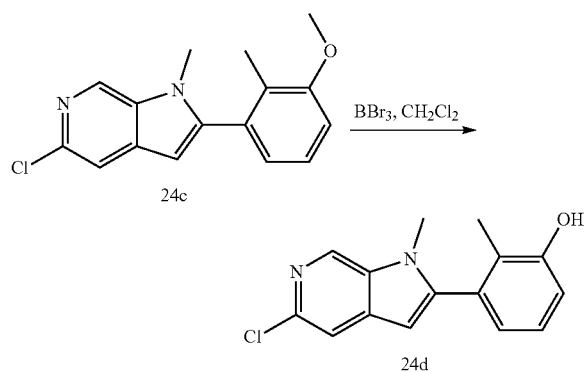

To a solution of 5-chloro-2-(3-methoxy-2-methylphenyl)-1-methyl-1H-pyrrolo[2,3-c]pyridine (Compound 24c) (380.0 mg, 1.32 mmol) in CH$_2$Cl$_2$ (5.0 mL) was added BBr$_3$ (1616.2 mg, 6.45 mmol) at 0° C. under N$_2$. The resulting mixture was stirred at 0° C. for 2.5 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with ether/ethyl acetate (85/15, v/v) to afford 3-(5-chloro-1-methyl-1H-pyrrolo[2,3-c]pyridin-2-yl)-2-methylphenol (Compound 24d) (380.0 mg, 99%) as a yellow solid. LCMS (ESI, m/z): [M+H]+=273.1.

Step 3: Synthesis of (1S,2S)-2-fluoro-N-(2-(3-hydroxy-2-methylphenyl)-1-methyl-1H-pyrrolo[2,3-c]pyridin-5-yl)cyclopropane-1-carboxamide (Compound 24)

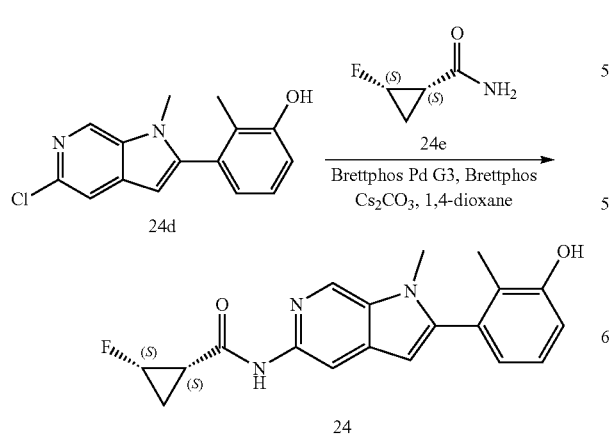

To a solution of 3-(5-chloro-1-methyl-1H-pyrrolo[2,3-c]pyridin-2-yl)-2-methylphenol (Compound 24d) (200.0 mg, 0.73 mmol) in dioxane (10.0 mL) was added Cs$_2$CO$_3$ (716.8 mg, 2.20 mmol), (1S,2S)-2-fluorocyclopropane-1-carboxamide (Compound 24e) (378.0 mg, 3.66 mmol), BrettPhos (157.4 mg, 0.29 mmol) and Brettphos Pd G3 (132.9 mg, 0.14 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (80/20, v/v) and then purified by Prep-HPLC with the following conditions (Column: Xselect CSH OBD Column 30×150 mm, 5 um; Mobile Phase A:Water (10 mmol/L NH$_4$HCO$_3$), Mobile Phase B: ACN; Flow rate: 60 mL/min; Gradient: 20% B to 38% B in 8 min; 220 nm) to afford (1S,2S)-2-fluoro-N-(2-(3-hydroxy-2-methylphenyl)-1-methyl-1H-pyrrolo[2,3-c]pyridin-5-yl) cyclopropane-1-carboxamide (Compound 24) (10.7 mg, 4%) as a white solid. LCMS (ESI, m/z): [M+H]+=340.1. $^1$H NMR (300 MHz, DMSO-d$_6$): δ 10.46 (s, 1H), 9.57 (s, 1H), 8.53 (s, 1H), 8.14 (s, 1H), 7.11-7.03 (m, 1H), 6.87 (d, J=8.1 Hz, 1H), 6.71 (d, J=7.5 Hz, 1H), 6.33 (s, 1H), 4.95-4.71 (m, 1H), 3.48 (s, 3H), 2.17-2.08 (m, 1H), 1.87 (s, 3H), 1.61-1.54 (m, 1H), 1.11-1.02 (m, 1H).

Example S25: Synthesis of (1S,2S)-2-fluoro-N-[2-(2-methoxy-6-methylphenyl)-1-methylpyrrolo[2,3-c]pyridin-5-yl]cyclopropane-1-carboxamide (Compound 25)

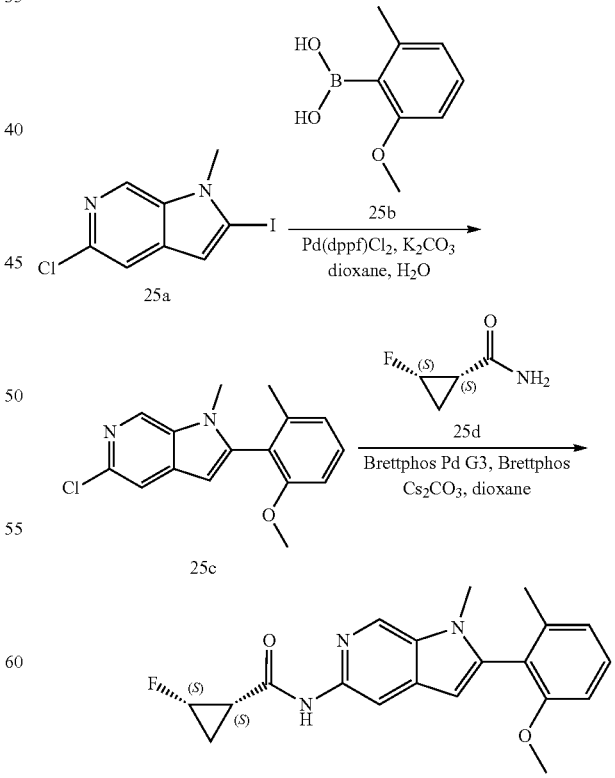

215

Step 1: Synthesis of 5-chloro-2-(2-methoxy-6-methylphenyl)-1-methylpyrrolo[2,3-c]pyridine (Compound 25c)

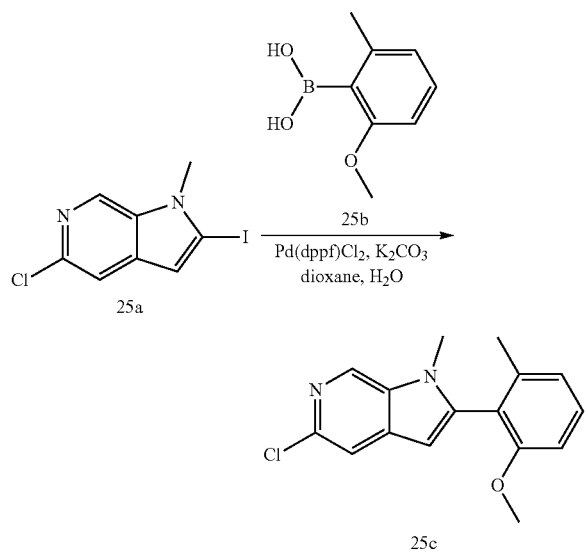

To a solution of 5-chloro-2-iodo-1-methylpyrrolo[2,3-c]pyridine (Compound 25a) (300.0 mg, 1.03 mmol) in 1,4-dioxane/H₂O (8.0 mL/2.0 mL) was added 2-methoxy-6-methylphenylboronic acid (Compound 25b) (204.3 mg, 1.23 mmol), K₂CO₃ (425.3 mg, 3.08 mmol) and Pd(dppf)Cl₂ (75.1 mg, 0.10 mmol) at room temperature under N₂. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash chromatography with petroleum ether/ethyl acetate (1/1, v/v) to afford 5-chloro-2-(2-methoxy-6-methylphenyl)-1-methylpyrrolo[2,3-c]pyridine (Compound 25c) (90.0 mg, 30%) as a brown oil. LCMS (ESI, m/z): [M+H]⁺=287.1.

Step 2: Synthesis of (1S,2S)-2-fluoro-N-[2-(2-methoxy-6-methylphenyl)-1-methylpyrrolo[2,3-c]pyridin-5-yl]cyclopropane-1-carboxamide (Compound 25)

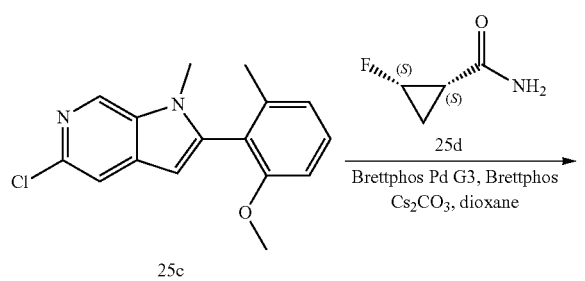

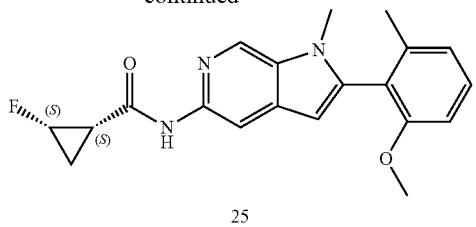

To a solution of 5-chloro-2-(2-methoxy-6-methylphenyl)-1-methylpyrrolo[2,3-c]pyridine (Compound 25c) (60.0 mg, 0.21 mmol) in 1,4-dioxane (6.0 mL) was added (1S,2S)-2-fluorocyclopropane-1-carboxamide (Compound 25d) (107.9 mg, 1.05 mmol), BrettPhos (22.5 mg, 0.04 mmol). Cs₂CO₃ (204.5 mg, 0.63 mmol) and BrettPhos Pd G3 (19.0 mg, 0.02 mmol) at room temperature under N₂. The reaction mixture was stirred with microwave at 120° C. for 1.5 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by Prep-HPLC with the following conditions (Column: XBridge Prep OBD C₁₈ Column, 30×150 mm, 5 um; Mobile Phase A:Water (10 mmol/L NH₄HCO₃), Mobile Phase B: ACN; Flow rate: 60 mL/min; Gradient: 40% B to 70% B in 7 min; 254 nm) to afford (1S,2S)-2-fluoro-N-[2-(2-methoxy-6-methylphenyl)-1-methylpyrrolo[2,3-c]pyridin-5-yl]cyclopropane-1-carboxamide (Compound 25) (10.3 mg, 13%) as a white solid. LCMS (ESI, m/z): [M+H]⁺=354.2. ¹H NMR (400 MHz, DMSO-d₆): δ 10.50 (s, 1H), 8.59 (s, 1H), 8.19 (s, 1H), 7.41-7.37 (m, 1H), 7.02-6.98 (m, 2H), 6.36 (s, 1H), 4.99-4.81 (m, 1H), 3.70 (s, 3H), 3.48 (s, 3H), 2.25-2.19 (m, 1H), 2.06 (s, 3H), 1.68-1.61 (m, 1H), 1.15-1.10 (m, 1H).

Example S26: Synthesis of (1S,2S)-2-fluoro-N-[2-(5-fluoro-2-methoxyphenyl)-1-methylpyrrolo[2,3-c]pyridin-5-yl]cyclopropane-1-carboxamide (Compound 26)

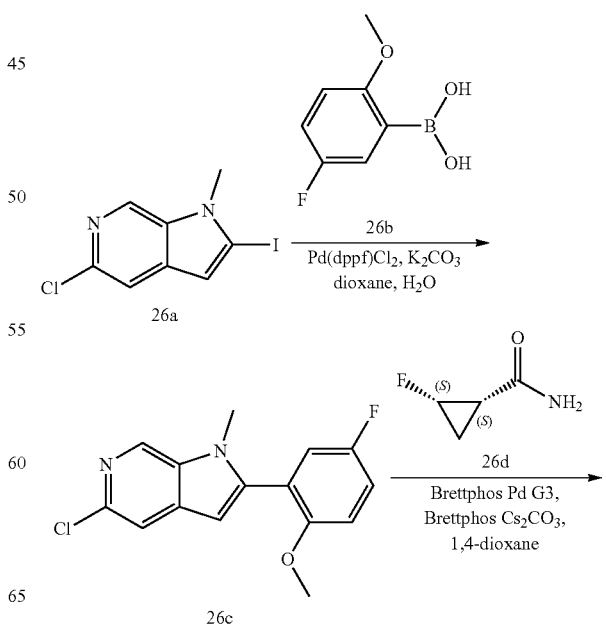

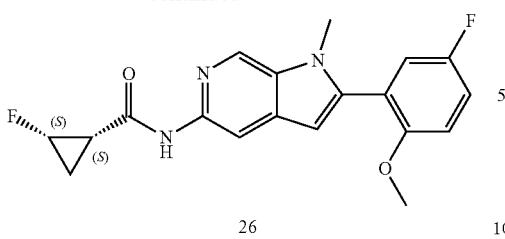

Step 1: Synthesis of 5-chloro-2-(5-fluoro-2-methoxyphenyl)-1-methylpyrrolo[2,3-c]pyridine (Compound 26c)

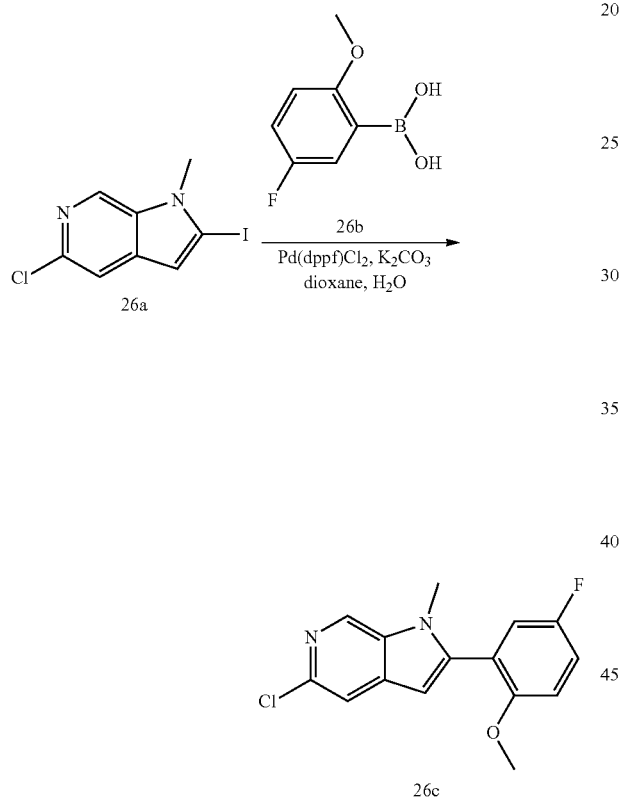

A mixture of 5-chloro-2-iodo-1-methylpyrrolo[2,3-c]pyridine (Compound 26a) (500.0 mg, 1.71 mmol), 5-fluoro-2-methoxyphenylboronic acid (Compound 26b) (348.6 mg, 2.05 mmol), $K_2CO_3$ (708.8 mg, 5.13 mmol) and Pd(dppf)Cl$_2$ (125.1 mg, 0.17 mmol) in dioxane (10.0 mL) and H$_2$O (2.0 mL) was stirred at 100° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with CH$_2$Cl$_2$/CH$_3$OH (94/6, v/v) to afford 5-chloro-2-(5-fluoro-2-methoxyphenyl)-1-methylpyrrolo[2,3-c]pyridine (Compound 26c) (483.5 mg, 97%) as a white solid. LCMS (ESI, m/z): [M+H]$^+$=291.1.

Step 2: Synthesis of (1S,2S)-2-fluoro-N-[2-(5-fluoro-2-methoxyphenyl)-1-methylpyrrolo[2,3-c]pyridin-5-yl]cyclopropane-1-carboxamide (Compound 26)

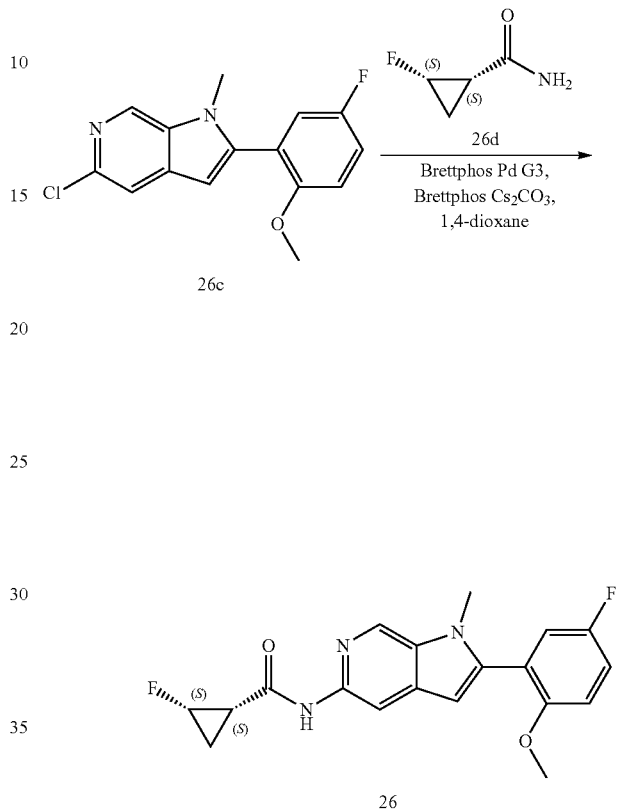

A mixture of 5-chloro-2-(5-fluoro-2-methoxyphenyl)-1-methylpyrrolo[2,3-c]pyridine (Compound 26c) (150.0 mg, 0.52 mmol), (0S,2S)-2-fluorocyclopropane-1-carboxamide (Compound 26d) (63.8 mg, 0.62 mmol), Cs$_2$CO$_3$ (213.9 mg, 1.55 mmol), BrettPhos (55.4 mg, 0.10 mmol) and BrettPhos Pd G3 (46.8 mg, 0.05 mmol) in dioxane (5.0 mL) was irradiated with microwave radiation at 100° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with CH$_2$Cl$_2$/CH$_3$OH (94/6, v/v) and then purified by Prep-HPLC with the following conditions (Column: YMC-Actus Triart C18, 30×250 mm, 5 um; Mobile Phase A: Water (10 mmol/L NH$_4$HCO$_3$), Mobile Phase B: ACN; Flow rate: 60 mL/min; Gradient: 25% B to 55% B in 10 min; 254 nm) to afford (1S,2S)-2-fluoro-N-[2-(5-fluoro-2-methoxyphenyl)-1-methylpyrrolo[2,3-c]pyridin-5-yl]cyclopropane-1-carboxamide (Compound 26) (10.4 mg, 5%) as a white solid. LCMS (ESI, m/z): [M+H]$^+$=358.1. $^1$H NMR (300 MHz, DMSO-d$_6$): δ 10.52 (s, 1H), 8.62 (s, 1H), 8.21 (s, 1H), 7.44-7.33 (m, 1H), 7.29-7.20 (m, 2H), 6.49 (s, 1H), 5.04-4.76 (m, 1H), 3.79 (s, 3H), 3.62 (s, 3H), 2.28-2.15 (m, 1H), 1.71-1.58 (m, 1H), 1.15-1.03 (m, 1H).

Example S27: Synthesis of (1S,2S)-2-fluoro-N-[2-(2-fluoro-6-methoxyphenyl)-1-methylpyrrolo[2,3-c]pyridin-5-yl]cyclopropane-1-carboxamide (Compound 27)

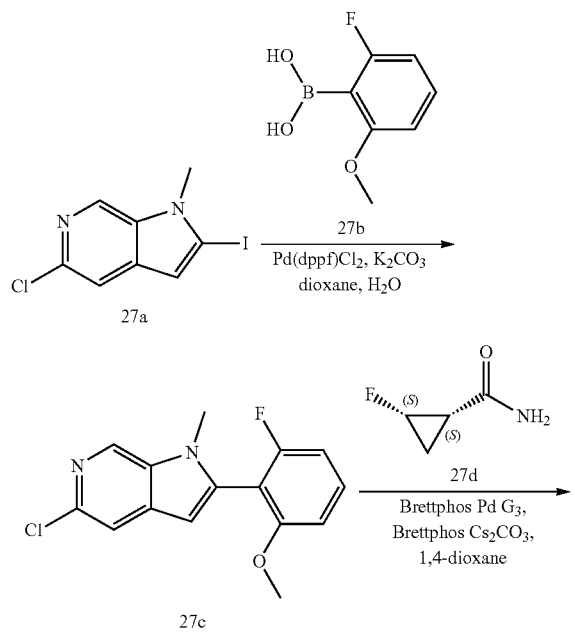

Step 1: Synthesis of 5-chloro-2-(2-fluoro-6-methoxyphenyl)-1-methylpyrrolo[2,3-c]pyridine (Compound 27c)

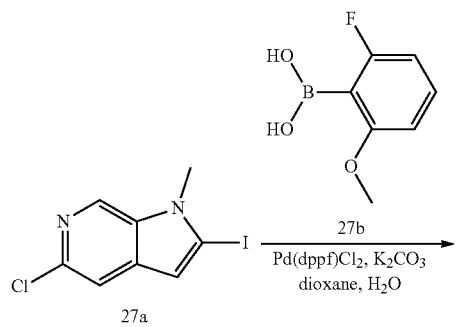

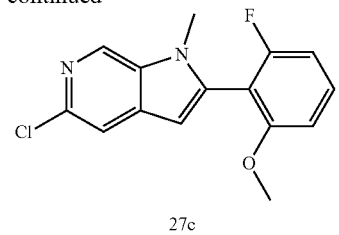

To a solution of 5-chloro-2-iodo-1-methylpyrrolo[2,3-c]pyridine (Compound 27a) (300.0 mg, 1.03 mmol) in 1,4-dioxane/H₂O (5.0/1.0 mL) was added 2-fluoro-6-methoxyphenylboronic acid (Compound 27b) (209.2 mg, 1.23 mmol), K₂CO₃ (425.3 mg, 3.08 mmol) and Pd(dppf)Cl₂ (75.05 mg, 0.10 mmol) at mom temperature under N₂. The resulting mixture was stirred at 80° C. for 3 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (52/48, v/v) to afford 5-chloro-2-(2-fluoro-6-methoxyphenyl)-1-methylpyrrolo[2,3-c]pyridine (Compound 27c) (100.0 mg, 33%) as a white solid. LCMS (ESI, m/z): [M+H]⁺=291.0.

Step 2: Synthesis of (1S,2S)-2-fluoro-N-[2-(2-fluoro-6-methoxyphenyl)-1-methylpyrrolo[2,3-c]pyridin-5-yl]cyclopropane-1-carboxamide (Compound 27)

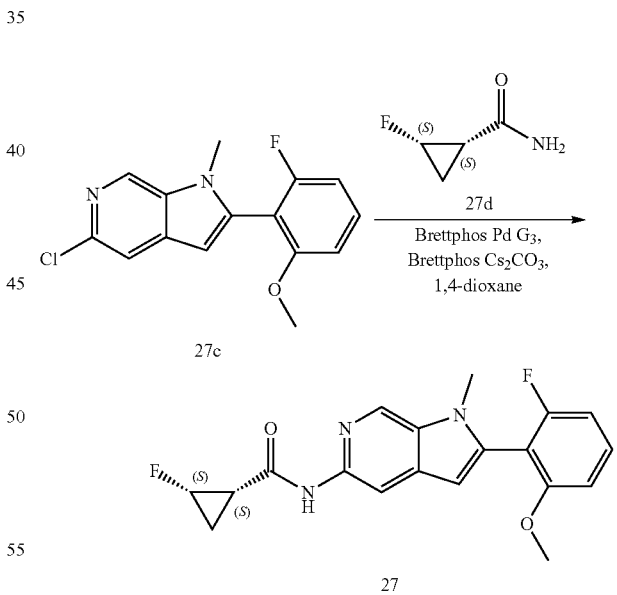

To a solution of 5-chloro-2-(2-fluoro-6-methoxyphenyl)-1-methylpyrrolo[2,3-c]pyridine (Compound 27c) (150.0 mg, 0.52 mmol) in 1,4-dioxane (5.0 mL) was added (1S,2S)-2-fluorocyclopropane-1-carboxamide (Compound 27d) (265.9 mg, 2.58 mmol), Cs₂CO₃ (504.3 mg, 1.55 mmol). BrettPhos (55.4 mg, 0.10 mmol) and Brettphos Pd G3 (46.77 mg, 0.05 mmol) at room temperature under N₂. The resulting mixture was stirred at 100° C. for 4 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (34/66, v/v) and then purified by Prep-HPLC with the following conditions (Column: YMC-Actus Triart C18, 30×250 mm, 5 um; Mobile Phase A:Water (10 mmol/L $NH_4HCO_3$), Mobile Phase B: ACN; Flow rate: 60 mL/min; Gradient: 45% B to 63% B in 7 min; 254 nm) to afford (1S,2S)-2-fluoro-N-[2-(2-fluoro-6-methoxyphenyl)-1-methylpyrrolo[2,3-c]pyridin-5-yl]cyclopropane-1-carboxamide (Compound 27) (22.5 mg, 12%) as a white solid. LCMS (ESI, m/z): $[M+H]^+$ =358.2. $^1$H NMR (400 MHz, DMSO-$d_6$): δ 10.54 (s, 1H), 8.64 (s, 1H), 8.22 (s, 1H), 7.58-7.51 (m, 1H), 7.32-7.00 (m, 2H), 6.51 (s, 1H), 5.01-4.81 (m, 1H), 3.81 (s, 3H), 3.59 (s, 3H), 2.25-2.18 (m, 1H), 1.71-1.63 (m, 1H), 1.11-1.05 (m, 1H).

Example S28: Synthesis of (1S,2S)-2-fluoro-N-(2-(6-methoxy-1H-benzo[d]imidazol-5-yl)-1-methyl-1H-pyrrolo[2,3-c]pyridin-5-yl)cyclopropanecarboxamide formate (Compound 28)

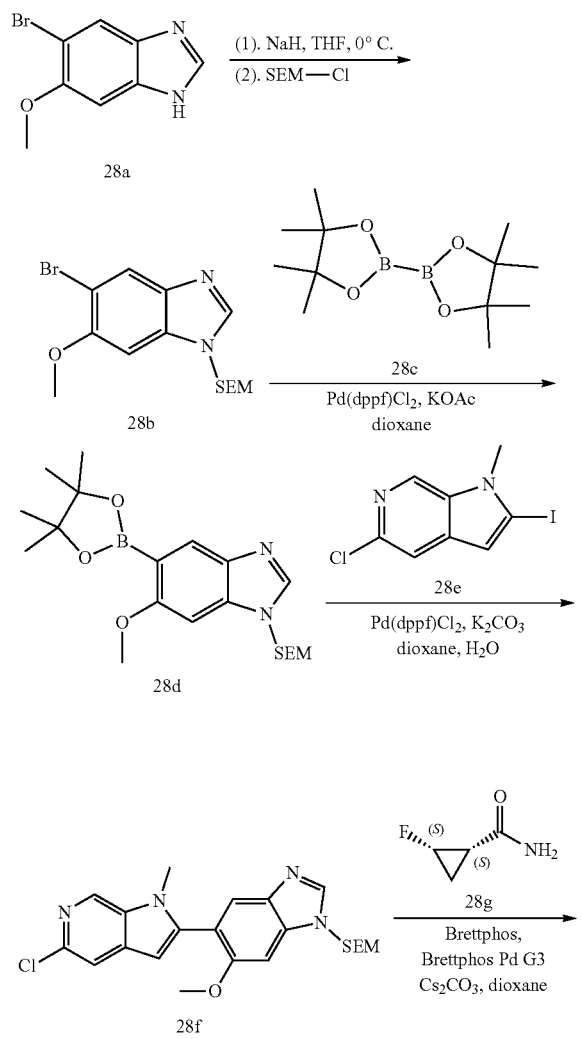

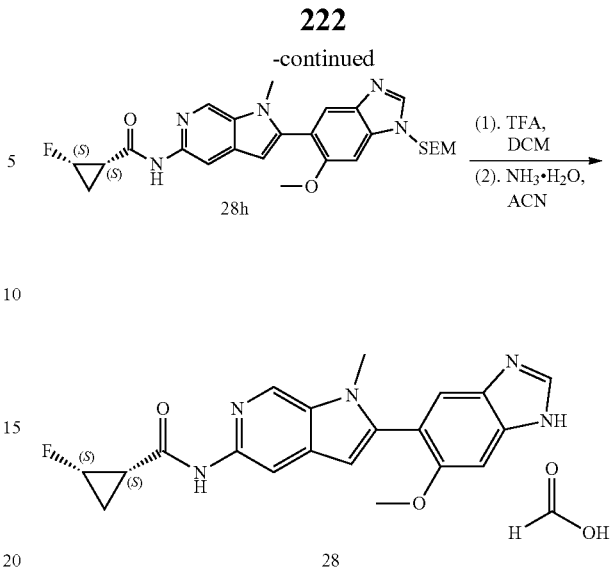

Step 1: Synthesis of 5-bromo-6-methoxy-1-((2-(trimethylsilyl)ethoxy)methyl)-1H-benzo[d]imidazole (Compound 28b)

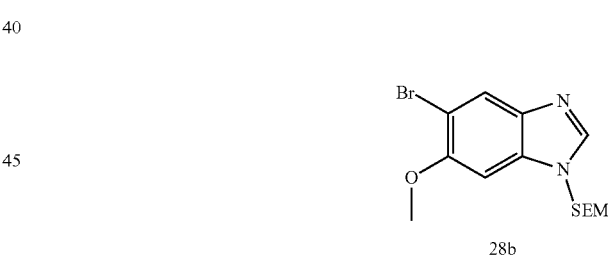

To a solution of 5-bromo-6-methoxy-1H-benzo[d]imidazole (750 mg, 3.30 mmol) in THF (30.0 mL) was added NaH (396.3 mg, 60%) at 0° C. under $N_2$. The resulting mixture was stirred at 0° C. for 1 h under $N_2$. Then SEM-Cl (826.0 mg, 4.96 mmol) was added dropwise to the mixture at 0° C. under $N_2$. The resulting mixture was stirred at 0° C. for another 1 h. After the reaction was completed, the reaction mixture was quenched with $H_2O$ at 0° C. and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (12/1, v/v) to afford 5-bromo-6-methoxy-1-((2-(trimethylsilyl)ethoxy)methyl)-1H-benzo[d]imidazole (1.0 g, 84%) as a brown oil. LCMS (ESI, m/z): $[M+H]^+$= 357.1.

Step 2: Synthesis of 6-methoxy-5-(4,4,5,5-tetramethyl-1,3,2-dioxaborolan-2-yl)-1-((2-(trimethylsilyl)ethoxy)methyl)-1H-benzo[d]imidazole (Compound 28d)

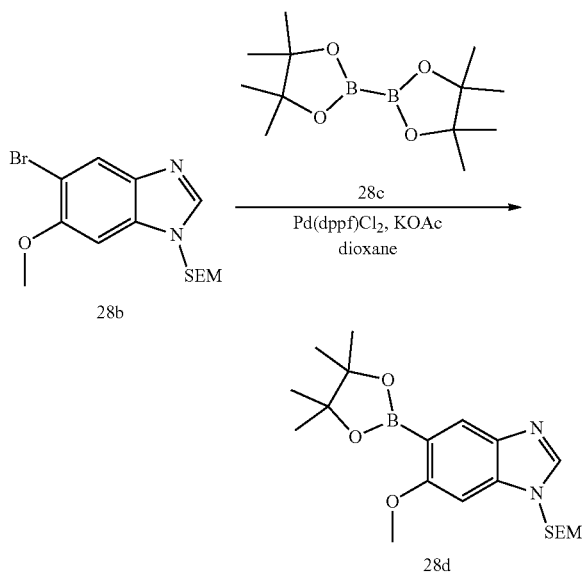

To a solution of 5-bromo-6-methoxy-1-((2-(trimethylsilyl)ethoxy)methyl)-1H-benzo[d]imidazole (Compound 28b) (300.0 mg, 0.84 mmol) in dioxane (10.0 mL) was added 4,4,4',4',5,5,5',5'-octamethyl-2,2'-bi(1,3,2-dioxaborolane) (Compound 28c) (639.6 mg, 2.52 mmol), KOAc (247.2 mg, 2.52 mmol) and Pd(dppf)Cl₂ (61.4 mg, 0.80 mmol) at room temperature under N₂. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/MeOH (10/1, v/v) to afford 6-methoxy-5-(4,4,5,5-tetramethyl-1,3,2-dioxaborolan-2-yl)-1-((2-(trimethylsilyl)ethoxy)methyl)-1H-benzo[d]imidazole (Compound 28d) (320.0 mg, 94%) as a brown oil. LCMS (ESI, m/z): [M+H]⁺= 405.2.

Step 3: Synthesis of 5-(5-chloro-1-methyl-1H-pyrrolo[2,3-c]pyridin-2-yl)-6-methoxy-1-((2-(trimethylsilyl)ethoxy)methyl)-1H-benzo[d]imidazole (Compound 28f)

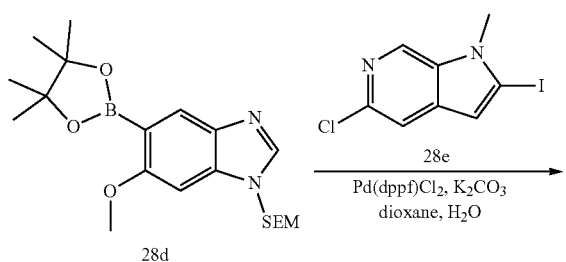

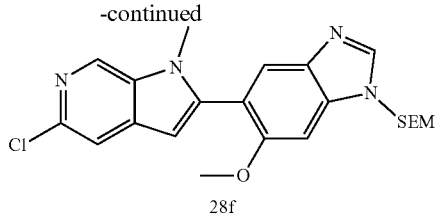

To a solution of 6-methoxy-5-(4,4,5,5-tetramethyl-1,3,2-dioxaborolan-2-yl)-1-((2-(trimethylsilyl)ethoxy)methyl)-1H-benzo[d]imidazole (Compound 28d) (260.0 mg, 0.64 mmol) in dioxane/H₂O (16.0/4.0 mL) was added 5-chloro-2-iodo-1-methyl-1H-pyrrolo[2,3-c]pyridine (Compound 28e) (188.1 mg, 0.64 mmol), K₂CO₃ (266.6 mg, 1.93 mmol) and Pd(dppf)Cl₂ (47.0 mg, 0.06 mmol) at room temperature under N₂. The resulting mixture was stirred at 80° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/MeOH (10/1, v/v) to afford 5-(5-chloro-1-methyl-1H-pyrrolo[2,3-c]pyridin-2-yl)-6-methoxy-1-((2-(trimethylsilyl)ethoxy)methyl)-1H-benzo[d]imidazole (Compound 28f) (250.0 mg, 87%) as a brown solid. LCMS (ESI, m/z): [M+H]⁺=443.2.

Step 4: Synthesis of (1S,2S)-2-fluoro-N-(2-(6-methoxy-1-((2-(trimethylsilyl)ethoxy)methyl)-1H-benzo[d]imidazol-5-yl)-1-methyl-1H-pyrrolo[2,3-c]pyridin-5-yl) cyclopropane-1-carboxamide (Compound 28h)

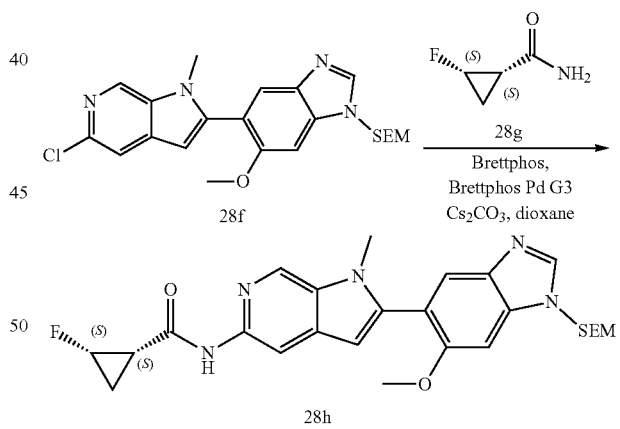

To a solution of 5-(5-chloro-1-methyl-1H-pyrrolo[2,3-c]pyridin-2-yl)-6-methoxy-1-((2-(trimethylsilyl)ethoxy)methyl)-1H-benzo[d]imidazole (Compound 28f) (400.0 mg, 0.90 mmol) in dioxane (20.0 mL) was added (1S,2S)-2-fluorocyclopropane-1-carboxamide (Compound 28g) (465.4 mg, 4.51 mmol), Cs₂CO₃ (882.5 mg, 2.71 mmol), Brettphos (96.9 mg, 0.18 mmol) and BrettPhos Pd G₃ (81.8 mg, 0.09 mmol) at room temperature under N₂. The final reaction mixture was irradiated with microwave radiation at 120° C. for 1.5 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/MeOH (10/1, v/v) to afford (1S,2S)-2-fluoro-N-(2-(6-methoxy-1-((2-(trimethylsilyl)ethoxy)methyl)-1H-benzo[d]imidazol-5-yl)-1-methyl-1H-pyrrolo[2,3-c]pyridin-5-yl)cyclopropane-1-carboxamide (Compound 28h) (60.0 mg, 13%) as a yellow solid. LCMS (ESI, m/z): [M+H]⁺=510.2.

Step 5: Synthesis of (1S,2S)-2-fluoro-N-(2-(6-methoxy-1H-benzo[d]imidazol-5-yl)-1-methyl-1H-pyrrolo[2,3-c]pyridin-5-yl)cyclopropanecarboxamide formate (Compound 28)

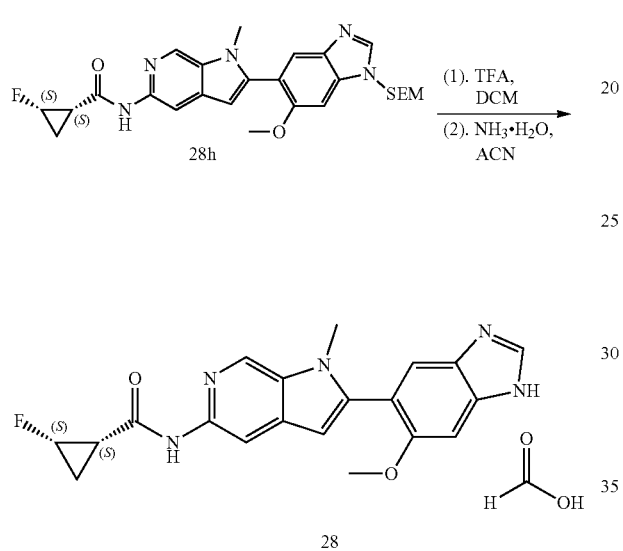

To a solution of (1S,2S)-2-fluoro-N-(2-(6-methoxy-1-((2-(trimethylsilyl)ethoxy)methyl)-1H-benzo[d]imidazol-5-yl)-1-methyl-1H-pyrrolo[2,3-c]pyridin-5-yl)cyclopropane-1-carboxamide (Compound 28h) (60.0 mg, 0.12 mmol) in DCM (3.0 mL) was added TFA (3.0 mL) at room temperature. The resulting mixture was stirred at room temperature for 3 h. The resulting mixture was concentrated under reduced pressure. The residue was re-dissolved in ACN (3.0 mL) and NH₃·H₂O (3.0 mL). The resulting mixture was stirred at room temperature for another 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 3% to 14% in 7 min; 254 nm) to afford (1S,2S)-2-fluoro-N-(2-(6-methoxy-1H-benzo[d]imidazol-5-yl)-1-methyl-1H-pyrrolo[2,3-c]pyridin-5-yl)cyclopropanecarboxamide formate (Compound 28) (2.9 mg, 5%) as a white solid. LCMS (ESI, m/z): [M+H]⁺=380.3. ¹H NMR (400 MHz, DMSO-d₆): δ 12.46 (s, 1H), 10.53 (s, 1H), 8.59 (s, 1H), 8.22-8.17 (m, 3H), 7.56 (s, 1H), 7.30 (s, 1H), 6.46 (s, 1H), 5.01-4.80 (m, 1H), 3.83 (s, 3H), 3.60 (s, 3H), 2.24-2.17 (m, 1H), 1.70-1.60 (m, 1H), 1.18-1.09 (m, 1H).

Example S29. Synthesis of (1S,2S)-2 fluoro-N-[2-(4-methoxy-1H-1,3-benzodiazol-5-yl)-1-methylpyrrolo[2,3-c]pyridin-5-yl]cyclopropane-1-carboxamide (Compound 29)

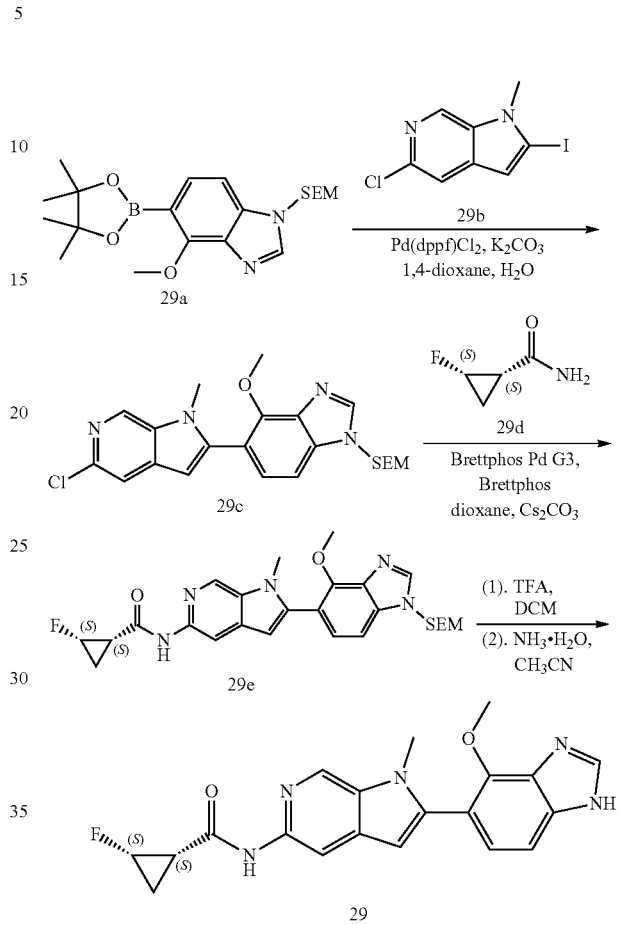

Step 1: Synthesis of 5-[5-chloro-1-methylpyrrolo[2,3-c]pyridin-2-yl]-4-methoxy-1-[[(2-(trimethylsilyl)ethoxy]methyl]-1,3-benzodiazole (Compound 29c)

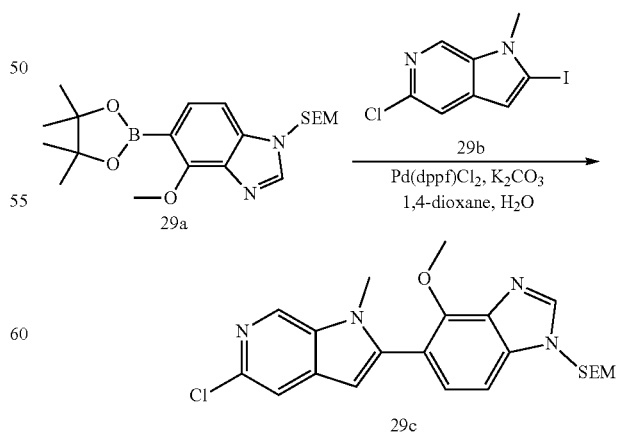

To a solution of 4-methoxy-5-(4,4,5,5-tetramethyl-1,3,2-dioxaborolan-2-yl)-1-[[2-(trimethylsilyl)ethoxy]methyl]-1, 3-benzodiazole (Compound 29a) (300.3 mg, 0.74 mmol) in 1,4-dioxane/H$_2$O (10.0 mL/2.0 mL) was added 5-chloro-2-iodo-1-methylpyrrolo[2,3-c]pyridine (Compound 29b) (181.0 mg, 0.62 mmol), K$_2$CO$_3$ (256.6 mg, 1.86 mmol) and Pd(dppf)Cl$_2$ (45.3 mg, 0.06 mmol) at room temperature under N$_2$. The resulting mixture was stirred at 80° C. for 16 bi. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/2, v/v) to afford 5-[5-chloro-1-methylpyrrolo[2,3-c]pyridin-2-yl]-4-methoxy-1-[[2-(trimethylsilyl)ethoxy]methyl]-1,3-benzodiazole (Compound 29c) (170.0 mg, 62%) as a yellow solid. LCMS (ESI, m/z): [M+H]$^+$=443.2.

Step 2: Synthesis of (1S,2S)-2-fluoro-N-[2-(4-methoxy-1-([2-(trimethylsilyl)ethoxymethyl]-1,3-benzodiazol-5-yl)-1-methylpyrrolo[2,3-c]pyridin-5-yl]cyclopropane-1-carboxamide (Compound 29e)

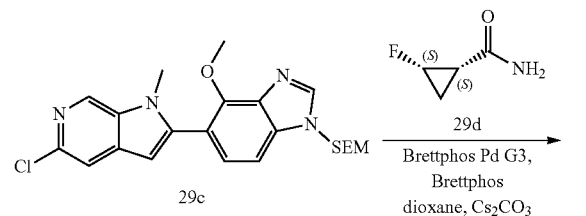

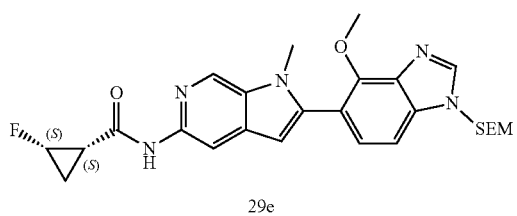

To a solution of 5-[5-chloro-1-methylpyrrolo[2,3-c]pyridin-2-yl]-4-methoxy-1-[[2-(trimethylsilyl)ethoxy]methyl]-1,3-benzodiazole (Compound 29c) (180.0 mg, 0.41 mmol) in 1,4-dioxane (15.0 mL) was added (0S,2S)-2-fluorocyclopropane-1-carboxamide (Compound 29d) (209.4 mg, 1.34 mmol), BrettPhos (43.6 mg, 0.08 mmol), Cs$_2$CO$_3$ (397.1 mg, 1.22 mmol) and BrettPhos Pd G3 (36.8 mg, 0.04 mmol) at room temperature under N$_2$. The resulting mixture was stirred at 100° C. for 4 h. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/MeOH (5/1, v/v) to afford (1S,2S)-2-fluoro-N-[2-(4-methoxy-1-[[2-(trimethylsilyl)ethoxy]methyl]-1,3-benzodiazol-5-yl)-1-methylpyrrolo[2,3-c]pyridin-5-yl]cyclopropane-1-carboxamide (Compound 29e) (60.0 mg, 16%) as a yellow oil. LCMS (ESI, m/z): [M+H]$^+$=510.2.

Step 3: Synthesis of (1S,2S)-2-fluoro-N-[2-(4-methoxy-1H-1,3-benzodiazol-5-yl)-1-methylpyrrolo[2,3-c]pyridin-5-yl]cyclopropane-1-carboxamide (Compound 29)

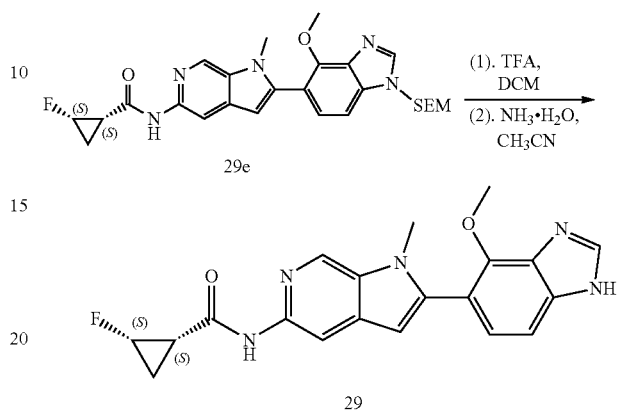

To a solution of (1S,2S)-2-fluoro-N-[2-(4-methoxy-1-[[2-(trimethylsilyl)ethoxy]methyl]-1,3-benzodiazol-5-yl)-1-methylpyrrolo[2,3-c]pyridin-5-yl]cyclopropane-1-carboxamide (Compound 29e) (181.0 mg, 0.36 mmol) in CH$_2$Cl$_2$ (8.0 mL) was added TFA (8.0 mL) at room temperature. The resulting mixture was stirred at room temperature for 4 h. After the reaction was completed, the resulting mixture was concentrated under reduced pressure. The residue was dissolved in CH$_3$CN (8.0 mL) and NH$_3$·H$_2$O (8.0 mL) at room temperature. The resulting mixture was stirred at room temperature for another 2 h. After the reaction was completed, the resulting mixture was concentrated under reduced pressure. The residue was purified by Prep-HPLC with the following conditions Column: (YMC-Actus Triart C18, 30×250 mm, 5 um; Mobile Phase A: Water (10 mmol/L NH$_4$HCO$_3$), Mobile Phase B: ACN; Flow rate: 60 mL/min; Gradient: 26% B to 35% B in 9 min; 254 nm) to afford (1S,2S)-2-fluoro-N-[2-(4-methoxy-1H-1,3-benzodiazol-5-yl)-1-methylpyrrolo[2,3-c]pyridin-5-yl]cyclopropane-1-carboxamide (Compound 29) (14.0 mg, 10%) as a white solid. LCMS (ESI, m/z): [M+H]$^+$=380.2. $^1$H NMR (400 MHz, DMSO-d$_6$): δ 12.69 (s, 1H), 10.50 (s, 1H), 8.59 (s, 1H), 8.27 (s, 1H), 8.20 (s, 1H), 7.29-7.16 (m, 2H), 6.41 (s, 1H), 4.98-4.82 (m, 1H), 4.32 (s, 3H), 3.72 (s, 3H), 2.33-2.19 (m, 1H), 1.71-1.59 (m, 1H), 1.16-1.10 (m, 1H).

Example S30: Synthesis of (1S,2S)-2-fluoro-N-(2-(7-methoxy-1H-indazol-6-yl)-1-methyl-1H-pyrrolo[2,3-c]pyridin-5-yl)cyclopropane-1-carboxamide (Compound 30)

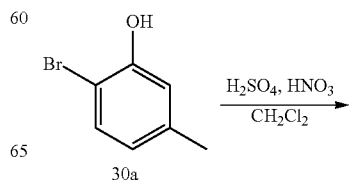

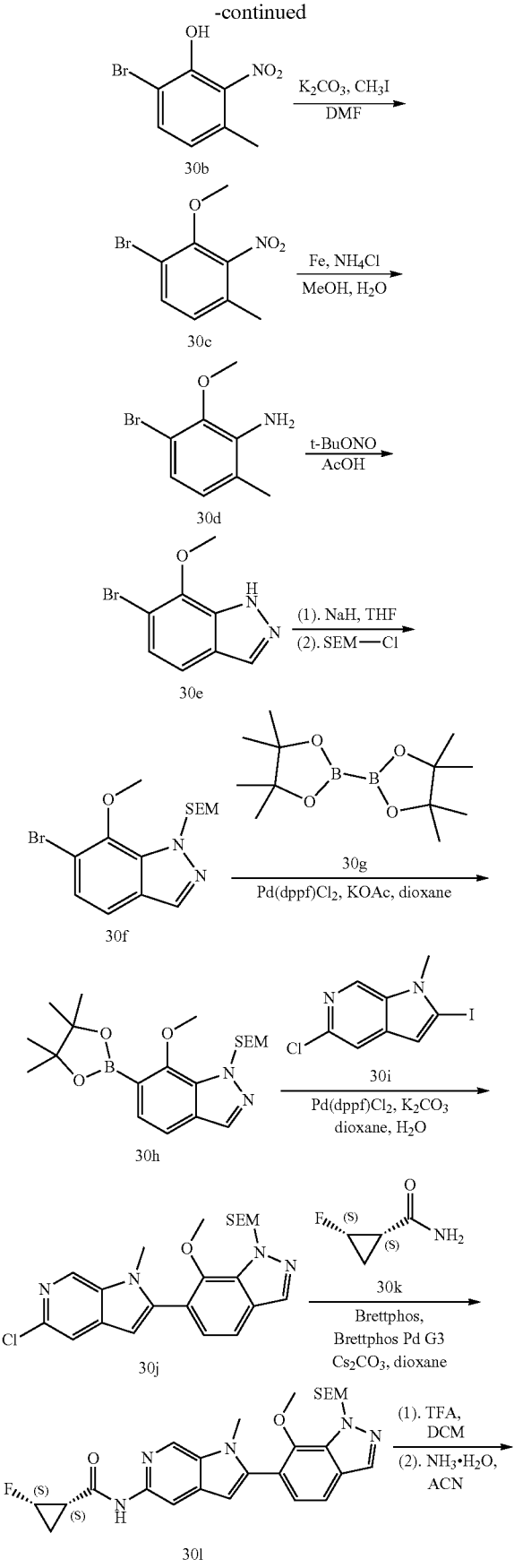

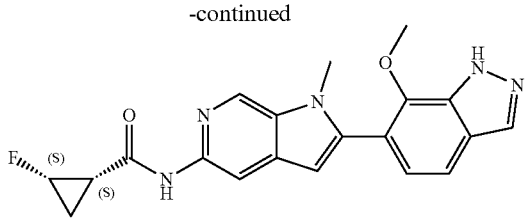

30

Step 1: Synthesis of
6-bromo-3-methyl-2-nitrophenol (Compound 30b)

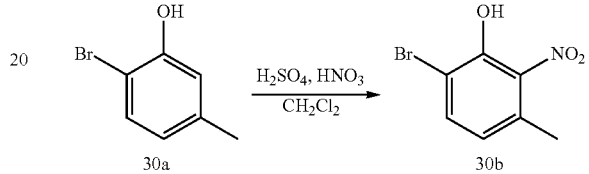

To a solution of 2-bromo-5-methylphenol (Compound 30a) (20.0 g, 106.9 mmol) in CH$_2$Cl$_2$ (80.0 mL) was added H$_2$SO$_4$ (7.4 mL, 75.55 mmol) at 0° C. under N$_2$. Then HNO$_3$ (8.0 mL, 126.85 mmol) was added dropwise to the mixture at 0° C. under N$_2$. The resulting mixture was stirred at room temperature for 2 h. After the reaction was completed, the resulting mixture was diluted with H$_2$O and extracted with CH$_2$Cl$_2$. The combined organic layer was washed with brine, dried over anhydrous sodium sulfate and filtered. The filtrate was concentrated under reduced pressure. The residue was purified by flash column chromatography with petroleum ether/ethyl acetate (10/1, v/v) to afford 6-bromo-3-methyl-2-nitrophenol (Compound 30b) (6.5 g, 26%) as a yellow solid. LCMS (ESI, m/z): [M+H]$^+$=232.0.

Step 2: Synthesis of
1-bromo-2-methoxy-4-methyl-3-nitrobenzene
(Compound 30c)

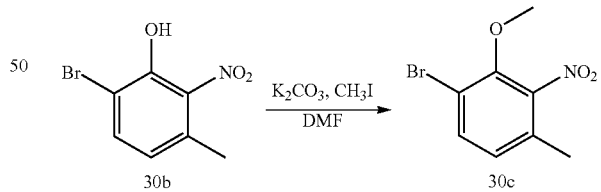

To a solution of 6-bromo-3-methyl-2-nitrophenol (Compound 30b) (6.5 g, 28.01 mmol) in DMF (20.0 mL) was added K$_2$CO$_3$ (11.6 g, 84.04 mmol) and CH$_3$I (6.0 g, 42.02 mmol) at room temperature. The resulting mixture was stirred at room temperature for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (10/1, v/v) to afford 1-bromo-2-methoxy-4-methyl-3-nitrobenzene (Compound 30c) (6.1 g, 88%) as a yellow oil. LCMS (ESI, m/z): [M+H]$^+$=246.0.

Step 3: Synthesis of 3-bromo-2-methoxy-6-methylaniline (Compound 30d)

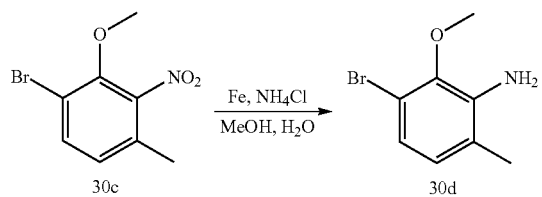

To a solution of 1-bromo-2-methoxy-4-methyl-3-nitrobenzene (Compound 30c) (1.5 g, 0.84 mmol) in MeOH/H$_2$O (16.0/4.0 mL) was added NH$_4$Cl (1.6 g, 30.48 mmol) at room temperature. Then Fe (1.7 g, 30.48 mmol) was added to the mixture at 80° C. The resulting mixture was stirred at 80° C. for 4 h. After the reaction was completed, the resulting mixture was filtered. The filtrate was concentrated under reduced pressure. The residue was purified by flash column chromatography with petroleum ether/ethyl acetate (5/1, v/v) to afford 3-bromo-2-methoxy-6-methylaniline (Compound 30d) (1.0 g, 75%) as a brown oil. LCMS (ESI, m/z): [M+H]$^+$=216.0.

Step 4: Synthesis of 6-bromo-7-methoxy-1H-indazole (Compound 30e)

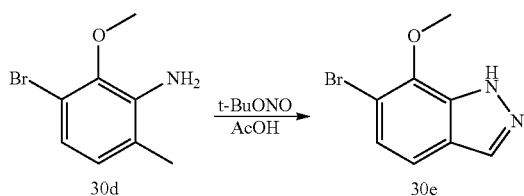

To a solution of 3-bromo-2-methoxy-6-methylaniline (Compound 30d) (1.4 g, 6.48 mmol) in AcOH (30.0 mL) was added tert-butyl nitrate (t-BuONO, 0.73 g, 7.09 mmol) at room temperature. The resulting mixture was stirred at 120° C. for 2 h. After the reaction was completed, the resulting mixture was concentrated under reduced pressure. The residue was purified by flash column chromatography with petroleum ether/ethyl acetate (5/1, v/v) to afford 6-bromo-7-methoxy-1H-indazole (Compound 30e) (1.0 g, 67%) as a yellow solid. LCMS (ESI, m/z): [M+H]$^+$=227.0.

Step 5: Synthesis of 6-bromo-7-methoxy-1-((2-(trimethylsilyl)ethoxy)methyl)-1H-indazole (Compound 30f)

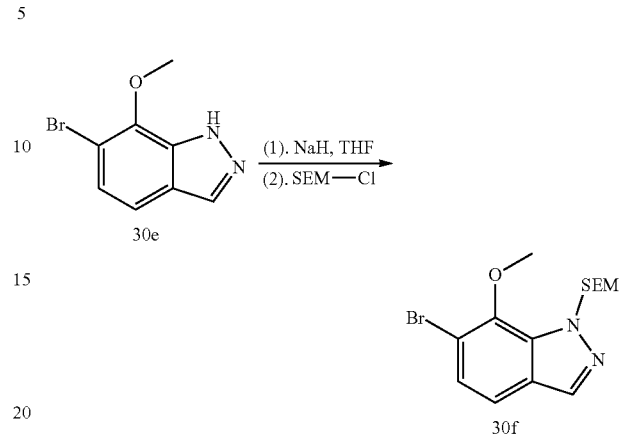

To a solution of 6-bromo-7-methoxy-1H-indazole (Compound 30e) (1.0 g, 4.40 mmol) in THF (30.0 mL) was added NaH (528.4 mg, 60%) at 0° C. under N$_2$. The resulting mixture was stirred at 0° C. for 1 h under N$_2$. Then SEM-Cl (1.1 g, 6.61 mmol) was added dropwise to the mixture at 0° C. under N$_2$. The resulting mixture was stirred at 0° C. for another 1 h under N$_2$. After the reaction was completed, the reaction mixture was quenched with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 6-bromo-7-methoxy-1-((2-(trimethylsilyl)ethoxy)methyl)-1H-indazole (Compound 30f) (1.4 g, 88%) as a yellow oil. LCMS (ESI, m/z): [M+H]$^+$=357.1.

Step 6: Synthesis of 7-methoxy-6-(4,4,5,5-tetramethyl-1,3,2-dioxaborolan-2-yl)-1-((2-(trimethylsilyl)ethoxy)methyl)-1H-indazole (Compound 30h)

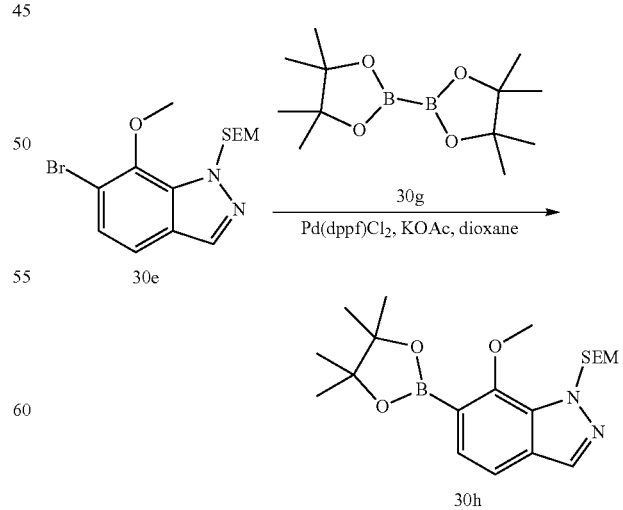

To a solution of 6-bromo-7-methoxy-1-((2-(trimethylsilyl)ethoxy)methyl)-1H-indazole (Compound 30f) (1.4 g, 3.92 mmol) in dioxane (20.0 mL) was added 4,4,4',4',5,5, 5',5'-octamethyl-2,2'-bi(1,3,2-dioxaborolane) (Compound 30g) (3.0 g, 11.75 mmol), KOAc (1.2 g, 11.75 mmol) and Pd(dppf)Cl$_2$ (0.3 g, 0.39 mmol) at room temperature under N$_2$. The resulting mixture was stirred at 80° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by reverse phase flash chromatography with CH$_3$OH/H$_2$O (85/15, v/v) to afford 7-methoxy-6-(4,4,5,5-tetramethyl-1,3,2-dioxaborolan-2-yl)-1-((2-(trimethylsilyl)ethoxy)methyl)-1H-indazole (Compound 30h) (350.0 mg, 22%) as a yellow oil. LCMS (ESI, m/z): [M+H]$^+$=405.2.

Step 7: Synthesis of 6-(5-chloro-1-methyl-1H-pyrrolo[2,3-c]pyridin-2-yl)-7-methoxy-1-((2-(trimethylsilyl)ethoxy)methyl)-1H-indazole (Compound 30j)

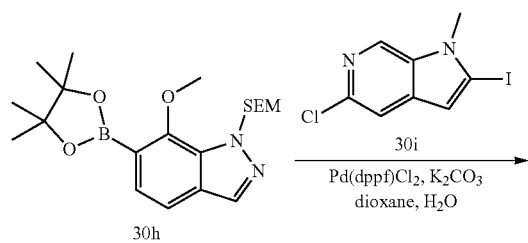

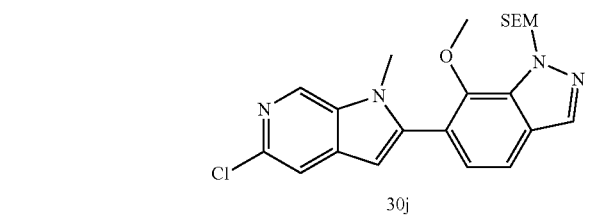

To a solution of 7-methoxy-6-(4,4,5,5-tetramethyl-1,3,2-dioxaborolan-2-yl)-1-((2-(trimethylsilyl)ethoxy)methyl)-1H-indazole (Compound 30h) (300.0 mg, 0.74 mmol) in dioxane/H$_2$O (10.0/2.0 mL) was added 5-chloro-2-iodo-1-methyl-1H-pyrrolo[2,3-c]pyridine (Compound 301) (217.0 mg, 0.74 mmol), K$_2$CO$_3$ (307.6 mg, 2.23 mmol) and Pd(dppf)Cl$_2$ (54.3 mg, 0.07 mmol) at room temperature under N$_2$. The resulting mixture was stirred at 80° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 6-(5-chloro-1-methyl-1H-pyrrolo[2,3-c]pyridin-2-yl)-7-methoxy-1-((2-(trimethylsilyl)ethoxy)methyl)-1H-indazole (Compound 30J) (200.0 mg, 60%) as a yellow oil. LCMS (ESI, m/z): [M+H]$^+$=443.2.

Step 8: Synthesis of (1S,2S)-2-fluoro-N-(2-(7-methoxy-1-((2-(trimethylsilyl)ethoxy)methyl)-1H-indazol-6-yl)-1-methyl-1H-pyrrolo[2,3-c]pyridin-5-yl)cyclopropane-1-carboxamide (Compound 301)

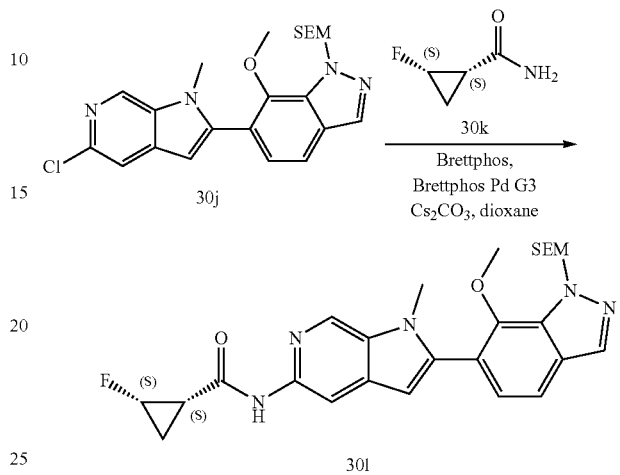

To a solution of 6-(5-chloro-1-methyl-1H-pyrrolo[2,3-c]pyridin-2-yl)-7-methoxy-1-((2-(trimethylsilyl)ethoxy)methyl)-1H-indazole (Compound 30j) (130.0 mg, 0.29 mmol) in dioxane (10.0 mL) was added (1S,2S)-2-fluorocyclopropane-1-carboxamide (Compound 30k) (151.3 mg, 1.47 mmol), Cs$_2$CO$_3$ (286.8 mg, 0.88 mmol), Brettphos (31.5 mg, 0.06 mmol) and BrettPhos Pd G3 (26.6 mg, 0.03 mmol) at room temperature under N$_2$. The resulting mixture was stirred at 100° C. for 4 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/MeOH (10/1, v/v) to afford (1S,2S)-2-fluoro-N-(2-(7-methoxy-1-((2-(trimethylsilyl)ethoxy)methyl)-1H-indazol-6-yl)-1-methyl-1H-pyrrolo[2,3-c]pyridin-5-yl)cyclopropane-1-carboxamide (Compound 301) (110.0 mg, 73%) as a yellow solid. LCMS (ESI, m/z): [M+H]$^+$=510.2.

Step 9: Synthesis of (1S,2S)-2-fluoro-N-(2-(7-methoxy-1H-indazol-6-yl)-1-methyl-1H-pyrrolo[2,3-c]pyridin-5-yl)cyclopropane-1-carboxamide (Compound 30)

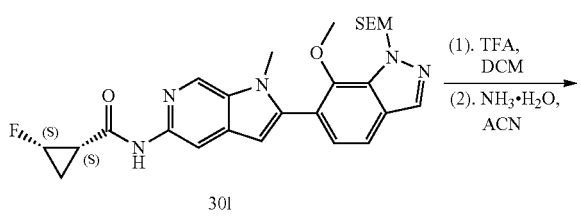

-continued

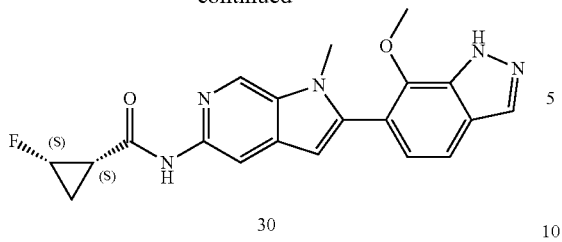

30

To a solution of (1S,2S)-2-fluoro-N-(2-(7-methoxy-1-((2-(trimethylsilyl)ethoxy)methyl)-1H-indazol-6-yl)-1-methyl-1H-pyrrolo[2,3-c]pyridin-5-yl)cyclopropane-1-carboxamide (Compound 301) (200.0 mg, 0.39 mmol) in DCM (3.0 mL) was added TFA (3.0 mL) at room temperature. The resulting mixture was stirred at mom temperature for 3 h. The resulting mixture was concentrated under reduced pressure. To the residue in ACN (3.0 mL) was added NH$_3$·H$_2$O (3.0 mL) at room temperature. The resulting mixture was stirred at room temperature for another 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 10% to 18% in 8 min; 254 nm) to afford (1S,2S)-2-fluoro-N-(2-(7-methoxy-1H-indazol-6-yl)-1-methyl-1H-pyrrolo[2,3-c]pyridin-5-yl)cyclopropane-1-carboxamide (Compound 30) (12.6 mg, 8%) as a light yellow solid. LCMS (ESI, m/z): [M+H]$^+$=380.2. $^1$H NMR (300 MHz, DMSO-d$_6$): δ 13.53 (s, 1H), 10.56 (s, 1H), 8.66 (s, 1H), 8.24-8.22 (m, 2H), 7.61 (d, J=8.4 Hz, 1H), 7.10 (d, J=8.4 Hz, 1H), 6.58 (s, 1H), 5.05-4.78 (m, 1H), 3.75 (s, 3H), 3.68 (s, 3H), 2.27-2.17 (m, 1H), 1.73-1.59 (m, 1H), 1.18-1.11 (m, 1H).

Example S31: Synthesis of (1S,2S)-N-[2-(2,3-dihydro-1H-indol-4-yl)-1-methylpyrrolo[2,3-c]pyridin-5-yl]-2-fluorocyclopropane-1-carboxamide (Compound 31)

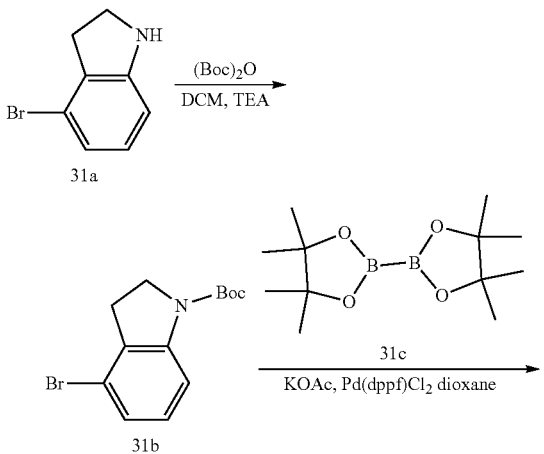

-continued

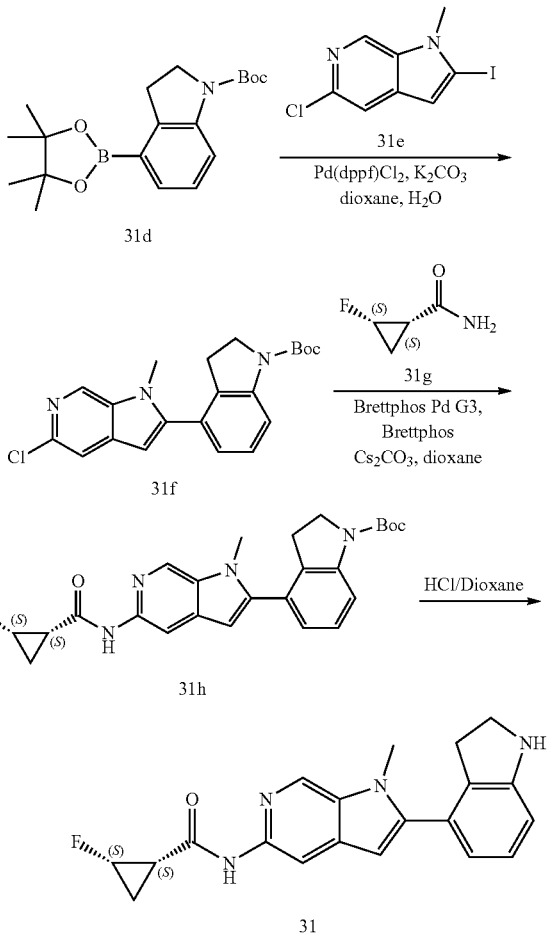

Step 1: Synthesis of tert-butyl 4-bromo-2,3-dihydroindole-1-carboxylate (Compound 31b)

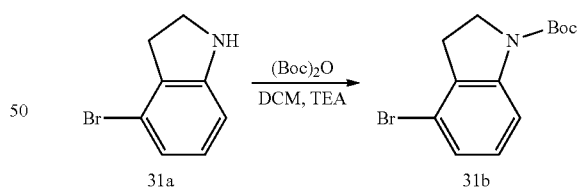

To a solution of 4-bromo-2,3-dihydro-1H-indole (Compound 31a) (2.0 g, 10.10 mmol) in CH$_2$Cl$_2$ (30.0 mL) was added TEA (3.1 g, 30.29 mmol) and di-tert-butyl dicarbonate (3.3 g, 15.15 mmol) at room temperature. The resulting mixture was stirred at room temperature for 16 h. After the reaction was completed, the mixture was concentrated under vacuum. The residue was purified by flash column chromatography with petroleum ether/ethyl acetate (30/70, v/v) to afford tert-butyl 4-bromo-2,3-dihydroindole-1-carboxylate (Compound 31b) (2.7 g, 90%) as a yellow solid. LCMS (ESI, m/z): [M+H]$^+$=298.0.

Step 2: Synthesis of tert-butyl 4-(4,4,5,5-tetramethyl-1,3,2-dioxaborolan-2-yl)-2,3-dihydroindole-1-carboxylate (Compound 31c)

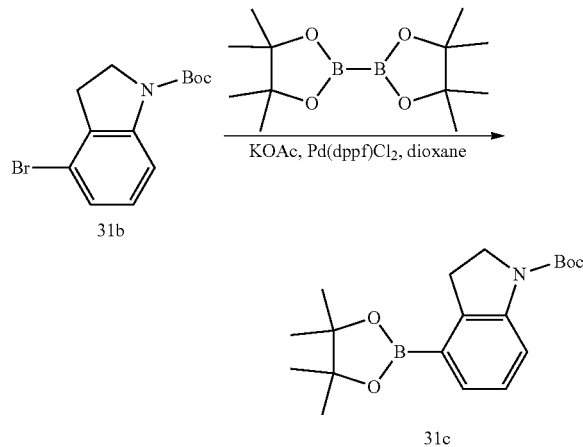

To a solution of tert-butyl 4-bromo-2,3-dihydroindole-1-carboxylate (Compound 31b) (2.7 g, 9.06 mmol) in 1,4-dioxane (30.0 mL) was added bis(pinacolato)diboron (6.9 g, 27.17 mmol), KOAc (2.7 g, 27.17 mmol) and Pd(dppf)Cl$_2$ (0.7 g, 0.91 mmol). The resulting mixture was stirred at 80° C. for 16 h under N$_2$. After the reaction was completed, the resulting mixture was concentrated under vacuum. The residue was purified by flash column chromatography with petroleum ether/ethyl acetate (5/95, v/v) to afford tert-butyl 4-(4,4,5,5-tetramethyl-1,3,2-dioxaborolan-2-yl)-2,3-dihydroindole-1-carboxylate (Compound 31c) (2.0 g, 63%) as a white solid. LCMS (ESI, m/z): [M+H]$^+$=346.2.

Step 3: Synthesis of tert-butyl 4-[5-chloro-1-methylpyrrolo[2,3-c]pyridin-2-yl]-2,3-dihydroindole-1-carboxylate (Compound 31e)

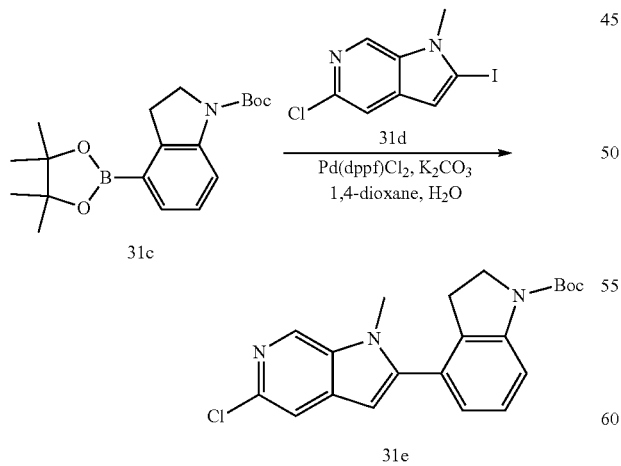

To a solution of tert-butyl 4-(4,4,5,5-tetramethyl-1,3,2-dioxaborolan-2-yl)-2,3-dihydroindole-1-carboxylate (Compound 31c) (400.0 mg, 1.16 mmol) in 1,4-dioxane/H$_2$O (15.0 mL/2.0 mL) was added 5-chloro-2-iodo-1-methylpyrrolo[2,3-c]pyridine (Compound 31d) (338.9 mg, 1.16 mmol), K$_2$CO$_3$ (480.4 mg, 3.48 mmol) and Pd(dppf)Cl$_2$ (84.8 mg, 0.12 mmol). The resulting mixture was stirred at 80° C. for 16 h. After the reaction was completed, the resulting mixture was concentrated under vacuum. The residue was purified by flash column chromatography with petroleum ether/ethyl acetate (70/30, v/v) to afford tert-butyl 4-[5-chloro-1-methylpyrrolo[2,3-c]pyridin-2-yl]-2,3-dihydroindole-1-carboxylate (Compound 31e) (360.0 mg, 81%) as a yellow solid. LCMS (ESI, m/z): [M+H]$^+$=384.1.

Step 4: Synthesis of tert-butyl 4-[5-[(1S,2S)-2-fluorocyclopropaneamido]-1-methylpyrrolo[2,3-c]pyridin-2-yl]-2,3-dihydroindole-1-carboxylate (Compound 31g)

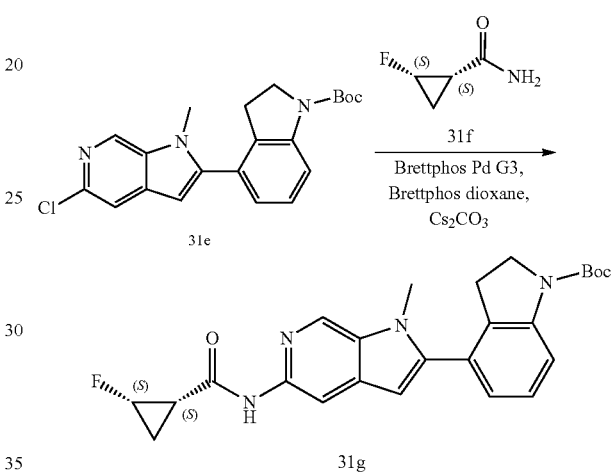

To a solution of tert-butyl 4-[5-chloro-1-methylpyrrolo[2,3-c]pyridin-2-yl]-2,3-dihydroindole-1-carboxylate (Compound 31e) (330.0 mg, 0.86 mmol) in 1,4-dioxane (10.0 mL) was added (1S,2S)-2-fluorocyclopropane-1-carboxamide (Compound 31f) (265.9 mg, 2.58 mmol), Cs$_2$CO$_3$ (840.3 mg, 2.58 mmol), BrettPhos (92.3 mg, 0.17 mmol) and BrettPhos Pd G3 (77.9 mg, 0.09 mmol). The resulting mixture was stirred at 100° C. for 16 h. After the reaction was completed, the resulting mixture was concentrated under vacuum. The residue was purified by flash column chromatography with petroleum ether/ethyl acetate (20/80, v/v) to afford tert-butyl 4-[5-[(1S,2S)-2-fluorocyclopropaneamido]-1-methylpyrrolo[2,3-c]pyridin-2-yl]-2,3-dihydroindole-1-carboxylate (Compound 31g) (250.0 mg, 64%) as a yellow solid. LCMS (ESI, m/z): [M+H]$^+$=451.2.

Step 5: Synthesis of (1S,2S)-N-[2-(2,3-dihydro-1H-indol-4-yl)-1-methylpyrrolo[2,3-c]pyridin-5-yl]-2-fluorocyclopropane-1-carboxamide (Compound 31)

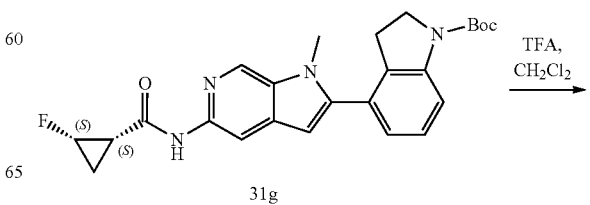

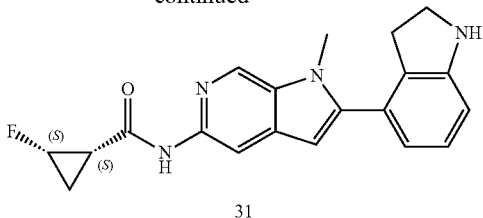

31

To a solution of tert-butyl 4-[5-[(1S,2S)-2-fluorocyclopropaneamido]-1-methylpyrrolo[2,3-c]pyridin-2-yl]-2,3-dihydroindole-1-carboxylate (Compound 31g) (200.0 mg, 0.44 mmol) in DCM (5.0 mL) was added TFA (1.0 mL). The resulting mixture was stirred at room temperature for 2 h. After the reaction was completed, the resulting mixture was concentrated under vacuum. The pH value of the mixture was adjusted to 7 with aq. NaHCO$_3$. The mixture was extracted with ethyl acetate. The combined organic layer was washed with brine, dried over anhydrous sodium sulfate and filtered. The filtrate was concentrated under vacuum. The residue was purified by Prep-HPLC with the following conditions (Column: YMC-Actus Triart C18 Column, 30×250 mm, 5 um; Mobile Phase A:Water (10 mmol/L NH$_4$HCO$_3$), Mobile Phase B: ACN; Flow rate: 60 mL/min; Gradient: 27% B to 57% B in 10 min; 254 nm) to afford (1S,2S)-N-[2-(2,3-dihydro-1H-indol-4-yl)-1-methylpyrrolo[2,3-c]pyridin-5-yl]-2-fluorocyclopropane-1-carboxamide (Compound 31) (14.0 mg, 9%) as a white solid. LCMS (ESI, m/z): [M+H]$^+$=351.2. $^1$H NMR (300 MHz, DMSO-d$_6$): δ 10.53 (s, 1H), 8.60 (s, 1H), 8.20 (s, 1H), 7.10-7.05 (m, 1H), 6.64-6.60 (m, 2H), 6.50 (s, 1H), 5.75 (s, 1H), 5.03-4.78 (m, 1H), 3.72 (s, 3H), 3.47-3.41 (m, 2H), 2.93-2.88 (m, 2H), 2.23-2.18 (m, 1H), 1.70-1.59 (m, 1H), 1.17-1.10 (m, 1H).

Example S32: Synthesis of (1S,2S)-2-fluoro-N-(2-(2-(methoxy-d$_3$)pyridin-3-yl)-1-methyl-1H-pyrrolo[2,3-c]pyridin-5-yl)cyclopropane-1-carboxamide (Compound 32)

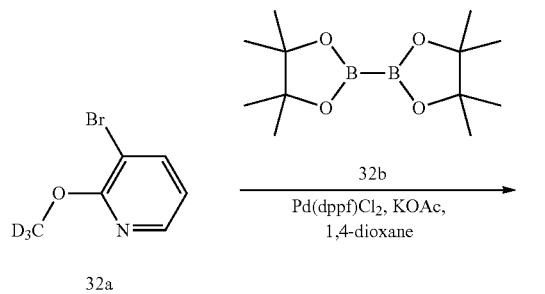

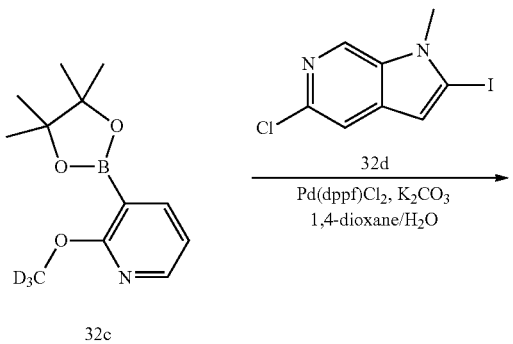

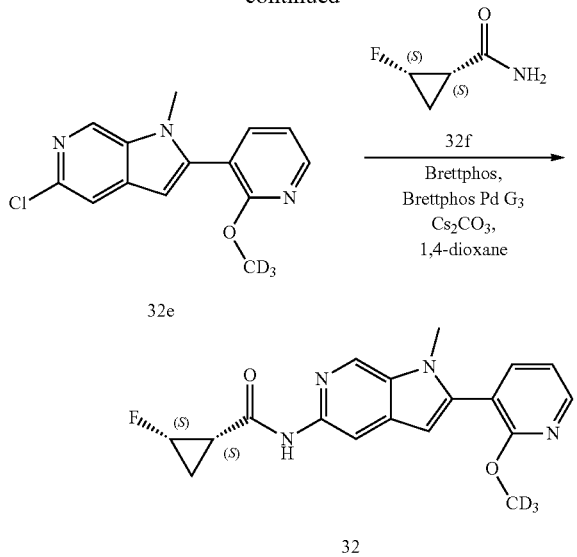

Step 1: Synthesis of 2-(methoxy-d$_3$)-3-(4,4,5,5-tetramethyl-1,3,2-dioxaborolan-2-yl)pyridine (Compound 32c)

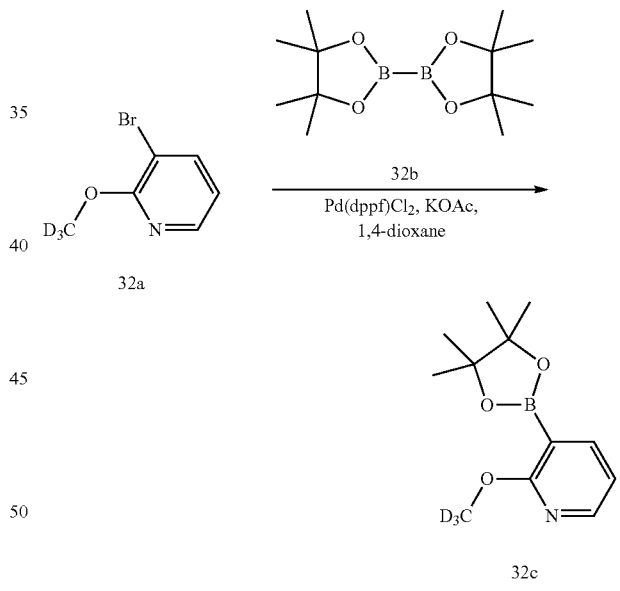

To a solution of 3-bromo-2-(methoxy-d$_3$)pyridine (Compound 32a) (1.0 g, 5.23 mmol) in 1,4-dioxane (20.0 mL) was added 4,4,4',4',5,5,5',5'-octamethyl-2,2'-bi(1,3,2-dioxaborolane) (Compound 32b) (2.7 g, 10.5 mmol), KOAc (1.5 g, 15.7 mmol) and Pd(dppf)Cl$_2$ (383.0 mg, 0.52 mmol) at room temperature under N$_2$. The resulting mixture was stirred at 80° C. for 16 h. After the reaction was completed, the resulting mixture was concentrated under reduced pressure. The residue was purified by flash column chromatography with petroleum ether/ethyl acetate (80/20, v/v) to afford 2-(methoxy-d$_3$)-3-(4,4,5,5-tetramethyl-1,3,2-dioxaborolan-2-yl)pyridine (Compound 32c) (1.2 g, 96%) as a brown oil. LCMS (ESI, m/z): [M+H]$^+$=239.2.

Step 2: Synthesis of 5-chloro-2-(2-(methoxy-d₃)pyridin-3-yl)-1-methyl-1H-pyrrolo[2,3-c]pyridine (Compound 32e)

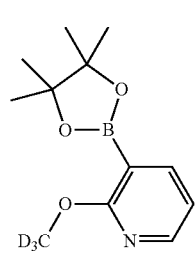 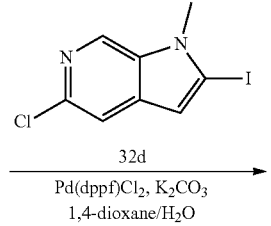

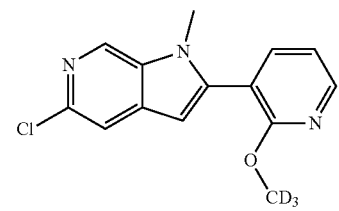

To a solution of 5-chloro-2-iodo-1-methyl-1H-pyrrolo[2,3-c]pyridine (Compound 32d) (600.0 mg, 2.05 mmol) in 1,4-dioxane/H₂O (10.0/2.0 mL) was added 2-(methoxy-d₃)-3-(4,4,5,5-tetramethyl-1,3,2-dioxaborolan-2-yl)pyridine (Compound 32c) (488.4 mg, 3.17 mmol), K₂CO₃ (850.5 mg, 6.15 mmol) and Pd(dppf)Cl₂ (150.1 mg, 0.21 mmol) at room temperature under N₂. The resulting mixture was stirred at 80° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (74/26, v/v) to afford 5-chloro-2-(2-(methoxy-d₃)pyridin-3-yl)-1-methyl-1H-pyrrolo[2,3-c]pyridine (Compound 32e) (490.0 mg, 86%) as a light yellow solid. LCMS (ESI, m/z): [M+H]⁺=277.1.

Step 3: Synthesis of (1S,2S)-2-fluoro-N-(2-(2-(methoxy-d₃)pyridin-3-yl)-1-methyl-1H-pyrrolo[2,3-c]pyridin-5-yl)cyclopropane-1-carboxamide (Compound 32)

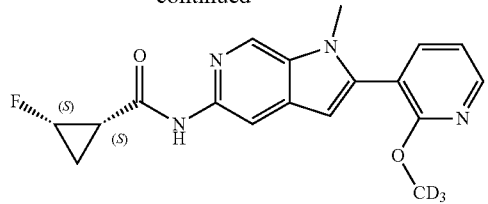

To a solution of 5-chloro-2-(2-(methoxy-d₃)pyridin-3-yl)-1-methyl-1H-pyrrolo[2,3-c]pyridine (Compound 32e) (190.0 mg, 0.69 mmol) in 1,4-dioxane (10.0 mL) was added (1S,2S)-2-fluorocyclopropane-1-carboxamide (Compound 32f) (353.9 mg, 3.43 mmol), Cs₂CO₃ (671.1 mg, 2.06 mmol), BrettPhos (73.1 mg, 0.14 mmol) and BrettPhos Pd G₃ (62.2 mg, 0.07 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/99, v/v) and then purified by Prep-HPLC with the following conditions (Column: XBridge Prep OBD C₁₈ Column, 30×150 mm, 5 um; Mobile Phase A: Water (10 mmol/L NH₄HCO₃), Mobile Phase B: ACN; Flow rate: 60 mL/min; Gradient: 35% B to 65% B in 7 min; 254 nm) to afford (1S,2S)-2-fluoro-N-(2-(2-(methoxy-d₃)pyridin-3-yl)-1-methyl-1H-pyrrolo[2,3-c]pyridin-5-yl)cyclopropane-1-carboxamide (Compound 32) (17.9 mg, 7%) as a white solid. LCMS (ESI, m/z): [M+H]⁺=344.2. ¹H NMR (400 MHz, DMSO-d₆): δ 10.54 (s, 1H), 8.64 (s, 1H), 8.35-8.33 (m, 1H), 8.22 (s, 1H), 7.86-7.83 (m, 1H), 7.19-7.16 (m, 1H), 6.53 (d, J=0.4 Hz, 1H), 5.00-4.80 (m, 1H), 3.64 (s, 3H), 2.22-2.19 (m, 1H), 1.69-1.63 (m, 1H), 1.20-1.05 (m, 1H).

Example S33: Synthesis of (1R,2R)-2-fluoro-N-(2-(2-(methoxy-d3)pyridin-3-yl)-1-methyl-1H-pyrrolo[2,3-c]pyridin-5-yl)cyclopropane-1-carboxamide (Compound 33)

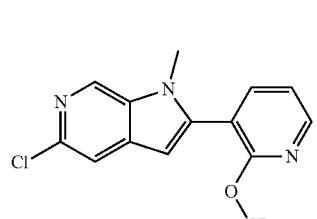 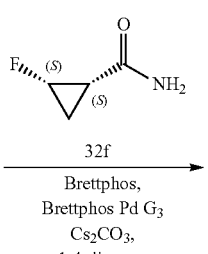 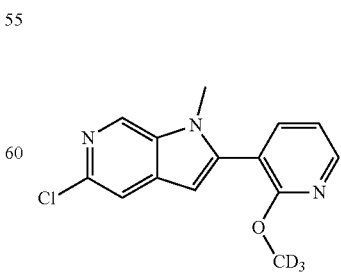 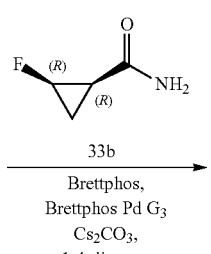

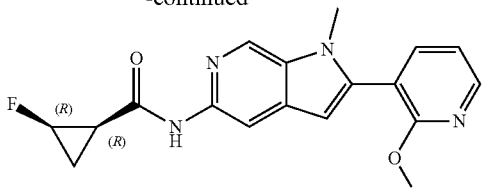

33

To a solution of 5-chloro-2-(2-(methoxy-d3)pyridin-3-yl)-1-methyl-1H-pyrrolo[2,3-c]pyridine (Compound 33a) (190.0 mg, 0.69 mmol) in 1,4-dioxane (6.0 mL) was added (1R,2R)-2-fluorocyclopropane-1-carboxamide (Compound 33b) (353.9 mg, 3.43 mmol), Cs$_2$CO$_3$ (671.1 mg, 2.06 mmol), BrettPhos (73.7 mg, 0.14 mmol) and BrettPhos Pd G$_3$ (62.2 mg, 0.07 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep OBD C$_{18}$ Column, 30×150 mm, 5 um; Mobile Phase A:Water (10 mmol/L NH$_4$HCO$_3$), Mobile Phase B: ACN; Flow rate: 60 mL/min; Gradient: 34% B to 64% B in 7 min; 254 nm) to afford (1R,2R)-2-fluoro-N-(2-(2-(methoxy-d3)pyridin-3-yl)-1-methyl-1H-pyrrolo[2,3-c]pyridin-5-yl)cyclopropane-1-carboxamide (Compound 33) (5.6 mg, 2%) as a white solid. LCMS (ESI, m/z): [M+H]$^+$=344.2. $^1$H NMR (300 MHz, DMSO-d$_6$): δ 10.69 (s, 1H), 8.65 (s, 1H), 8.35-8.33 (m, 1H), 8.07 (s, 1H), 7.85-7.83 (m, 1H), 7.19-7.16 (m, 1H), 6.52 (s, 1H), 4.97-4.79 (m, 1H), 3.64 (s, 3H), 2.58-2.49 (m, 1H), 1.52-1.43 (m, 1H), 1.27-1.21 (m, 1H).

Example S34: Synthesis of (1R,2R)-2-fluoro-N-[2-(2-methoxypyridin-3-yl)-1-methylpyrrolo[2,3-c]pyridin-5-yl]cyclopropane-1-carboxamide (Compound 34)

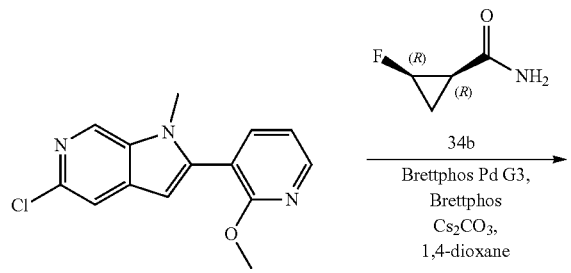

To a solution of 3-[5-chloro-1-methylpyrrolo[2,3-c]pyridin-2-yl]-2-methoxypyridine (Compound 34a) (160.0 mg, 0.59 mmol) in 1,4-dioxane (5.0 mL) was added (1R,2R)-2-fluorocyclopropane-1-carboxamide (Compound 34b) (72.3 mg, 0.70 mmol), Cs$_2$CO$_3$ (571.4 mg, 1.75 mmol), BrettPhos (62.8 mg, 0.12 mmol) and Brettphos Pd 03 (53.0 mg, 0.06 mmol) at room temperature under N$_2$. The resulting mixture was stirred at 100° C. for 2 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (44/56, v/v) and then purified by Prep-HPLC with the following conditions (Column: XBridge Prep OBD C$_{18}$ Column, 30×150 mm, 5 um; Mobile Phase A:Water (10 mmol/L NH$_4$HCO$_3$), Mobile Phase B: ACN; Flow rate: 60 mL/min; Gradient: 30% B to 60% B in 7 min; 254 nm) to afford (1R,2R)-2-fluoro-N-[2-(2-methoxypyridin-3-yl)-1-methylpyrrolo[2,3-c]pyridin-5-yl]cyclopropane-1-carboxamide (Compound 34) (36.0 mg, 18%) as a white solid. LCMS (ESI, m/z): [M+H]$^+$=341.2. $^1$H NMR (300 MHz, DMSO-d$_6$): δ 10.54 (s, 1H), 8.64 (s, 1H), 8.34 (d, J=3.3 Hz, 1H), 8.22 (s, 1H), 7.85 (d, J=7.5 Hz, 1H), 7.19-7.15 (m, 1H), 6.53 (s, 1H), 5.02-4.79 (m, 1H), 3.92 (s, 3H), 3.64 (s, 3H), 2.25-2.11 (m, 1H), 1.72-1.68 (m, 1H), 1.19-1.10 (m, 1H).

Example S35: Synthesis of (1S,2S)-2-fluoro-N-[2-(2-methoxypyridin-3-yl)-1-methylpyrrolo[2,3-c]pyridin-5-yl]cyclopropane-1-carboxamide (Compound 35)

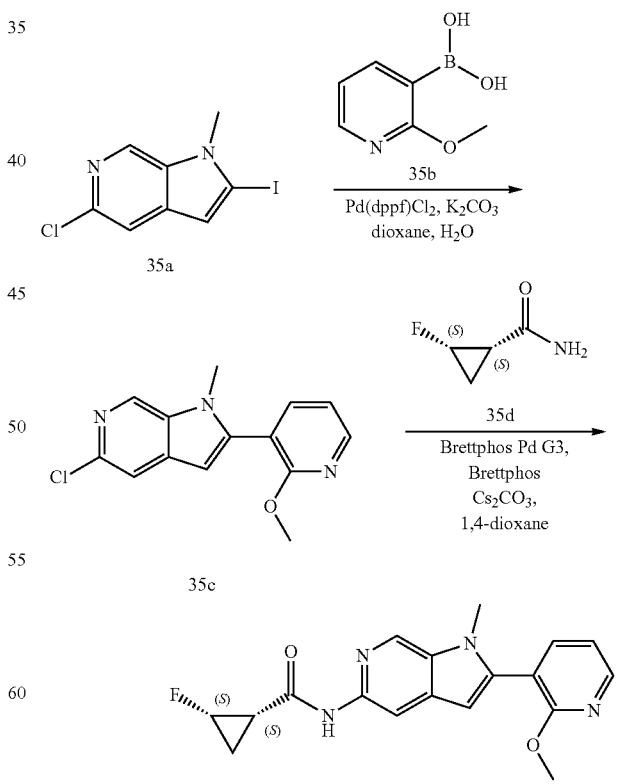

Step 1: Synthesis of 3-[5-chloro-1-methylpyrrolo[2,3-c]pyridin-2-yl]-2-methoxypyridine (Compound 35c)

To a solution of 5-chloro-2-iodo-1-methylpyrrolo[2,3-c]pyridine (Compound 35a) (0.6 g, 2.05 mmol) in dioxane (10.0 mL) and H₂O (2.0 mL) was added 2-methoxypyridin-3-ylboronic acid (Compound 35b) (0.4 g, 2.46 mmol), K₂CO₃ (0.9 g, 6.15 mmol) and Pd(dppt)Cl₂ (0.2 g, 0.21 mmol). The mixture was stirred at 80° C. for 16 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (60/40, v/v) to afford 3-[5-chloro-1-methylpyrrolo[2,3-c]pyridin-2-yl]-2-methoxypyridine (Compound 35c) (400.0 mg, 71%) as a yellow solid. LCMS (ESI, m/z): [M+H]⁺=274.1.

Step 2: Synthesis of (1S,2S)-2-fluoro-N-[2-(2-methoxypyridin-3-yl)-1-methylpyrrolo[2,3-c]pyridin-5-yl]cyclopropane-1-carboxamide (Compound 35)

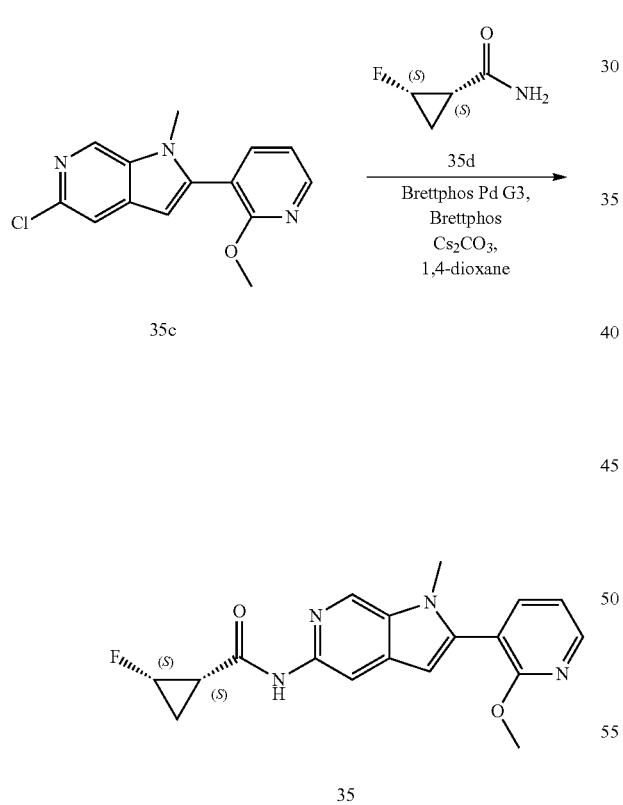

A mixture of 3-[5-chloro-1-methylpyrrolo[2,3-c]pyridin-2-yl]-2-methoxypyridine (Compound 35c) (200.0 mg, 0.73 mmol), (1S,2S)-2-fluorocyclopropane-1-carboxamide (Compound 35d) (90.4 mg, 0.88 mmol), Cs₂CO₃ (714.2 mg, 2.19 mmol), BrettPhos (78.4 mg, 0.15 mmol) and BrettPhos Pd G₃ (66.2 mg, 0.07 mmol) in dioxane (5.0 mL) was stirred at 100° C. for 2 h under N₂. After the reaction was completed, the mixture was evaporated in vacuo. The residue was purified by flash column chromatography with petroleum ether/ethyl acetate (0/100, v/v) and then purified by Prep-HPLC with the following conditions (Column: XBridge Prep OBD C₁₈ Column, 30×150 mm, 5 um; Mobile Phase A: Water (10 mmol/L NH₄HCO₃). Mobile Phase B: ACN; Flow rate: 60 mL/min; Gradient: 20% B to 50% B in 10 min; 254 nm; RT1:9.5 min) to afford (1S,2S)-2-fluoro-N-[2-(2-methoxypyridin-3-yl)-1-methylpyrrolo[2,3-c]pyridin-5-yl]cyclopropane-1-carboxamide (Compound 35) (23.3 mg, 9%) as a white solid. LCMS (ESI, m/z): [M+H]⁺= 341.1. ¹H NMR (300 MHz, DMSO-d₆): δ 10.52 (s, 1H), 8.64 (s, 1H), 8.35-8.33 (m, 1H), 8.21 (s, 1H), 7.86-7.83 (m, 1H), 7.19-7.15 (m, 1H), 6.53 (s, 1H), 5.04-4.77 (m, 1H), 3.92 (s, 3H), 3.64 (s, 3H), 2.23-2.18 (m, 1H), 1.70-1.59 (m, 1H), 1.17-1.09 (m, 1H).

Example S36: Synthesis of (1S,2S)-N-[2-(2-ethoxypyridin-3-yl)-1-methylpyrrolo[2,3-c]pyridin-5-yl]-2-fluorocyclopropane-1-carboxamide (Compound 36)

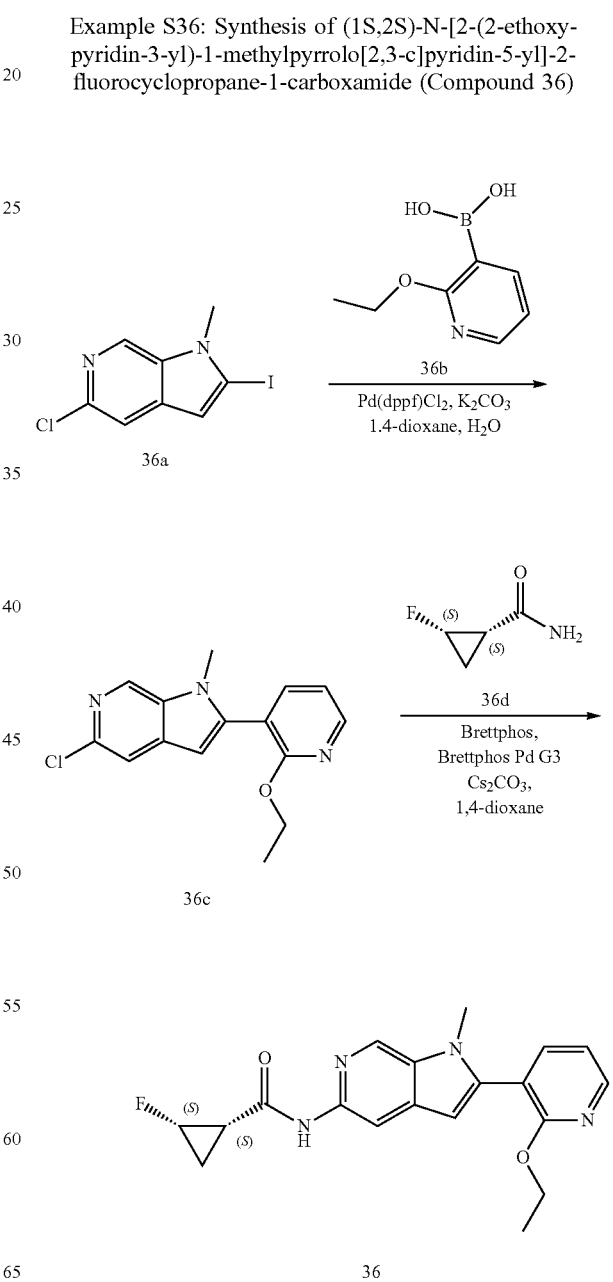

247

Step 1: Synthesis of 5-chloro-2-(2-ethoxypyridin-3-yl)-1-methyl-1H-pyrrolo[2,3-c]pyridine (Compound 36c)

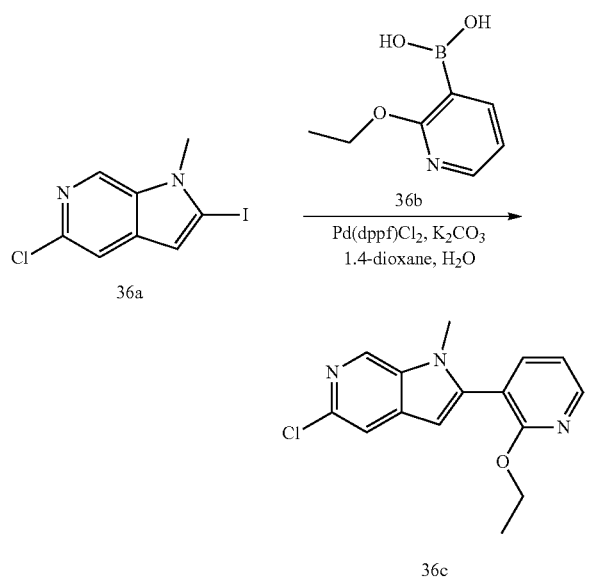

To a solution of 5-chloro-2-iodo-1-methyl-1H-pyrrolo[2,3-c]pyridine (Compound 36a) (600.0 mg, 2.05 mmol) in 1,4-dioxane/H$_2$O (20.0/4.0 mL) was added (2-ethoxypyridin-3-yl)boronic acid (Compound 36b) (342.5 mg, 2.05 mmol), K$_2$CO$_3$ (850.5 mg, 6.15 mmol) and Pd(dppf)Cl$_2$ (150.1 mg, 0.21 mmol) at room temperature under N$_2$. The resulting mixture was stirred at 80° C. for 2 h. After the reaction was completed, the resulting mixture was concentrated under reduced pressure. The residue was purified by flash column chromatography with petroleum ether/ethyl acetate (69/31, v/v) to afford 5-chloro-2-(2-ethoxypyridin-3-yl)-1-methyl-1H-pyrrolo[2,3-c]pyridine (Compound 36c) (410.0 mg, 69%) as a white solid. LCMS (ESI, m/z): [M+H]$^+$=288.1.

Step 2: Synthesis of (1S,2S)-N-[2-(2-ethoxypyridin-3-yl)-1-methylpyrrolo[2,3-c]pyridin-5-yl]-2-fluorocyclopropane-1-carboxamide (Compound 36)

248

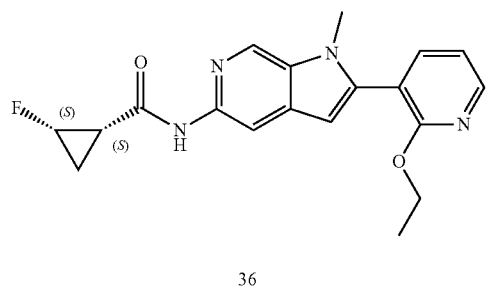

To a solution of 3-[5-chloro-1-methylpyrrolo[2,3-c]pyridin-2-yl]-2-ethoxypyridine (Compound 36c) (150.0 mg, 0.52 mmol) in 1,4-dioxane (10.0 mL) was added (1S,2S)-2-fluorocyclopropane-1-carboxamide (Compound 36d) (268.7 mg, 2.61 mmol), Cs$_2$CO$_3$ (509.54 mg, 1.56 mmol), BrettPhos (56.0 mg, 0.10 mmol) and BrettPhos Pd G3 (47.3 mg, 0.05 mmol) at room temperature under N$_2$. The resulting mixture was stirred at 100° C. for 16 h. After the reaction was completed, the resulting mixture was concentrated under reduced pressure. The residue was purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 12% B to 34% B in 7 min; 254 nm) to afford (1S,2S)-N-[2-(2-ethoxypyridin-3-yl)-1-methylpyrrolo[2,3-c]pyridin-5-yl]-2-fluorocyclopropane-1-carboxamide (Compound 36) (12.3 mg, 7%) as a white solid. LCMS (ESI, m/z): [M+H]$^+$=355.2. $^1$H NMR (400 MHz, DMSO-d$_6$): δ 10.54 (s, 1H), 8.64 (s, 1H), 8.33-8.31 (m, 1H), 8.22 (s, 1H), 7.85-7.82 (m, 1H), 7.17-7.14 (m, 1H), 6.53 (s, 1H), 5.05-4.78 (m, 1H), 4.44-4.38 (s, 2H), 3.66 (s, 3H), 2.26-2.16 (m, 1H), 1.72-1.59 (m, 1H), 1.30-1.26 (m, 3H), 1.18-1.11 (m, 1H).

Example S37: Synthesis of (1R,2R)-N-[2-(2-ethoxypyridin-3-yl)-1-methylpyrrolo[2,3-c]pyridin-5-yl]-2-fluorocyclopropane-1-carboxamide (Compound 37)

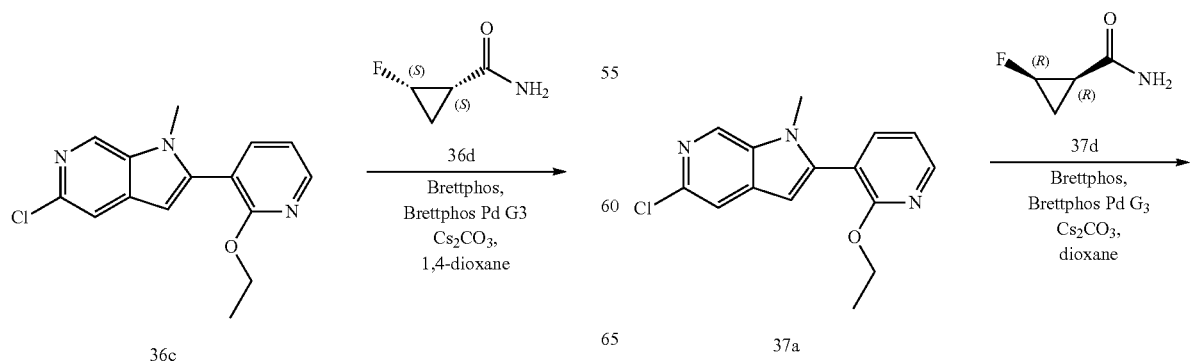

-continued

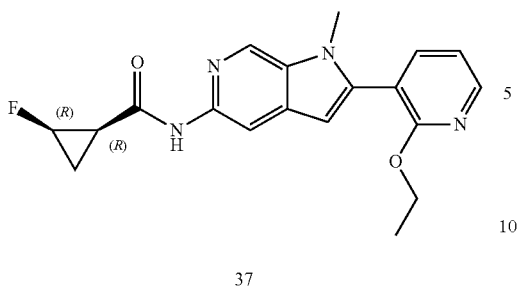

37

To a solution of 3-[5-chloro-1-methylpyrrolo[2,3-c]pyridin-2-yl]-2-ethoxypyridine (Compound 37a) (150.0 mg, 0.52 mmol) in 1,4-dioxane (12.0 mL) was added (1R,2R)-2-fluorocyclopropane-1-carboxamide (Compound 37b) (268.7 mg, 2.61 mmol), Cs$_2$CO$_3$ (509.54 mg, 1.56 mmol), BrettPhos (56.0 mg, 0.10 mmol) and BrettPhos Pd G3 (47.3 mg, 0.05 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A:Water (0.1% FA), Mobile Phase B: ACN; Flow rate: 60 mL/min; Gradient: 12% B to 34% B in 8 min; 254 nm) to afford (1R,2R)-N-[2-(2-ethoxypyridin-3-yl)-1-methylpyrrolo[2,3-c]pyridin-5-yl]-2-fluorocyclopropane-1-carboxamide (Compound 37) (12.9 mg, 6%) as a white solid. LCMS (ESI, m/z): [M+H]$^+$= 355.2. $^1$H NMR (300 MHz, DMSO-d$_6$): δ 10.62 (s, 1H), 8.66 (s, 1H), 8.34-8.32 (m, 1H), 8.21 (s, 1H), 7.86-7.83 (m, 1H), 7.18-7.14 (m, 1H), 6.55 (s, 1H), 5.05-4.78 (m, 1H), 4.44-4.37 (s, 2H), 3.67 (s, 3H), 2.26-2.16 (m, 1H), 1.72-1.59 (m, 1H), 1.31-1.26 (m, 3H), 1.18-1.11 (m, 1H).

Example S38: Synthesis of (1S,2S)-2-fluoro-N-[2-(5-fluoro-2,4-dimethoxypyridin-3-yl)-1-methylpyrrolo[2,3-c]pyridin-5-yl]cyclopropane-1-carboxamide (Compound 38)

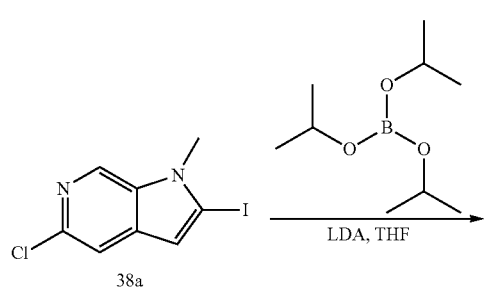

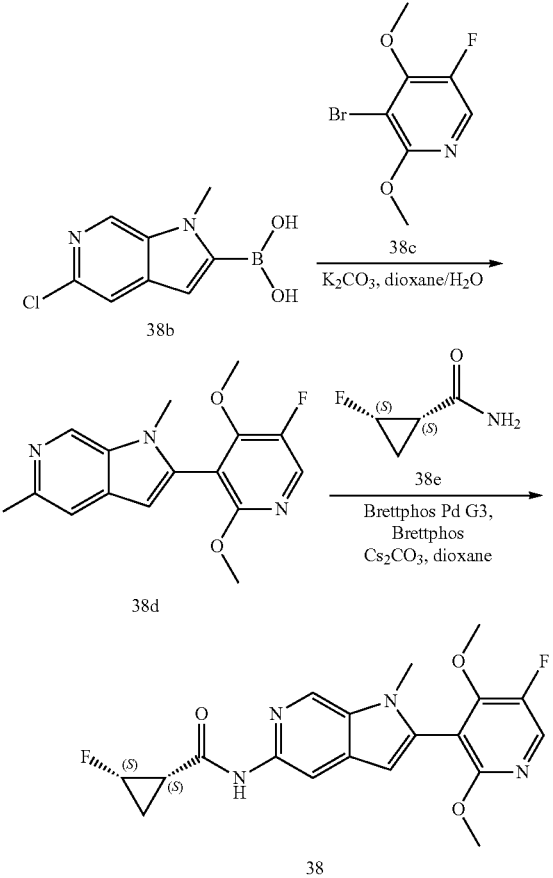

Step 1: Synthesis of 5-chloro-1-methylpyrrolo[2,3-c]pyridin-2-ylboronic acid (Compound 38b)

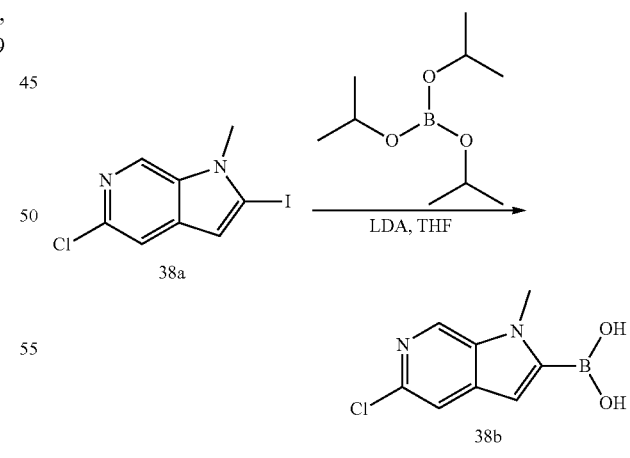

To a mixture of 5-chloro-2-iodo-1-methylpyrrolo[2,3-c]pyridine (Compound 38a) (3.0 g, 10.26 mmol) and triisopropyl borate (2.5 g, 13.33 mmol) in THF (60.0 mL) was added dropwise n-BuLi (4.9 mL, 2.5 mol/L) at −78° C. under N$_2$. The resulting mixture was stirred at −78° C. for 1 h under N$_2$. After the reaction was completed, The reaction was quenched with sat. NH$_4$Cl (aq.) at −78° C. The resulting Step 3: Synthesis of (1S,2S)-2-fluoro-N-[2-(5-fluoro-2,4-dimethoxypyridin-3-yl)-1-methylpyrrolo[2,3-c]pyridin-5-yl]cyclopropane-1-carboxamide (Compound 38)

Step 2: Synthesis of 3-[5-chloro-1-methylpyrrolo[2,3-c]pyridin-2-yl]-5-fluoro-2,4-dimethoxypyridine (Compound 38d)

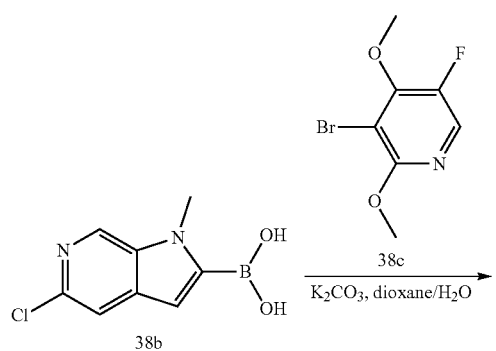

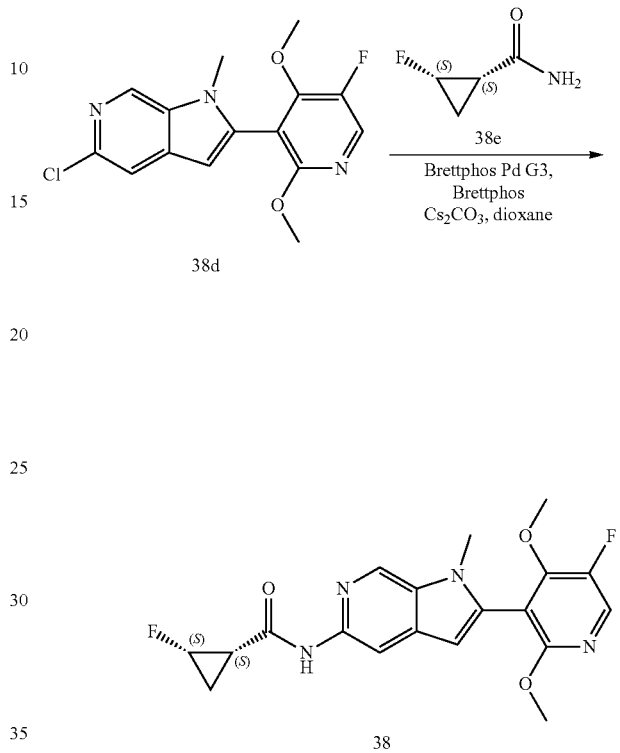

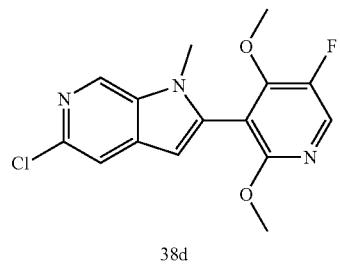

To a solution of 5-chloro-1-methylpyrrolo[2,3-c]pyridin-2-ylboronic acid (Compound 38b) (500.0 mg, crude) in dioxane/H₂O (15.0 mL/3.0 mL) was added 3-bromo-5-fluoro-2,4-dimethoxypyridine (Compound 38c) (560.9 mg, 2.37 mmol), K₂CO₃ (985.2 mg, 7.13 mmol) and Pd(PPh₃)₄ (274.6 mg, 0.24 mmol) at mom temperature under N₂. The resulting mixture was stirred at 100° C. for 16 h under N₂. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 3-[5-chloro-1-methylpyrrolo[2,3-c]pyridin-2-yl]-5-fluoro-2,4-dimethoxypyridine (Compound 38d) (380.0 mg, 50%) as a yellow oil. LCMS (ESI, m/z): [M+H]⁺=322.1.

To a solution of 3-[5-chloro-1-methylpyrrolo[2,3-c]pyridin-2-yl]-5-fluoro-2,4-dimethoxypyridine (Compound 38d) (350.0 mg, 1.09 mmol) in 1,4-dioxane (15.0 mL) was added (1S,2S)-2-fluorocyclopropane-1-carboxamide (Compound 38e) (506.7 mg, 5.44 mmol), BrettPhos (116.8 mg, 0.22 mmol), Cs₂CO₃ (1063.3 mg, 3.26 mmol) and BrettPhos Pd G3 (98.6 mg, 0.11 mmol) at room temperature under N₂. The resulting mixture was stirred with microwave radiation at 120° C. for 1.5 h. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/2, v/v) and then purified by Prep-HPLC with the following conditions Column: (Prep OBD C₁₈ Column, 30×150 mm, 5 um; Mobile Phase A:Water (10 mmol/L NH₄HCO₃), Mobile Phase B: ACN; Flow rate: 60 mL/min; Gradient: 25% B to 55% B in 9 min; 254 nm) to afford (1S,2S)-2-fluoro-N-[2-(5-fluoro-2,4-dimethoxypyridin-3-yl)-1-methylpyrrolo[2,3-c]pyridin-5-yl]cyclopropane-1-carboxamide (Compound 38) (13.0 mg, 3%) as a white solid. LCMS (ESI, m/z): [M+H]⁺=389.1. ¹H NMR (400 MHz, DMSO-d₆): δ 10.55 (s, 1H), 8.64 (s, 1H), 8.32 (d, J=3.6 Hz, 1H), 8.20 (s, 1H), 6.50 (s, 1H), 5.01-4.80 (m, 1H), 3.88 (s, 3H), 3.80 (s, 3H), 3.59 (s, 3H), 2.22-2.18 (m, 1H), 1.70-1.60 (m, 1H), 1.17-1.10 (m, 1H).

Example S39: Synthesis of (1S,2S)-N-[2-(4,6-dimethoxypyrimidin-5-yl)-1-methylpyrrolo[2,3-c]pyridin-5-yl]-2-fluorocyclopropane-1-carboxamide (Compound 39)

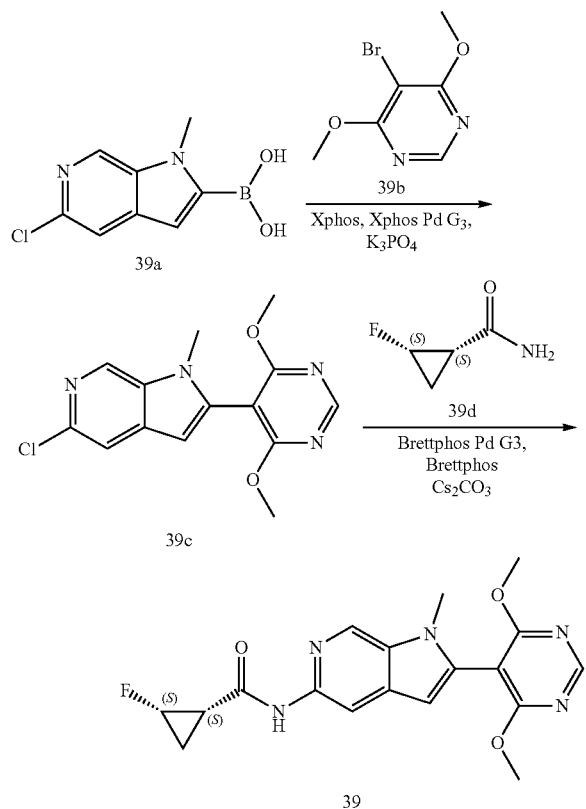

Step 1: Synthesis of 5-[5-chloro-1-methylpyrrolo[2,3-c]pyridin-2-yl]-4,6-dimethoxypyrimidine (Compound 39c)

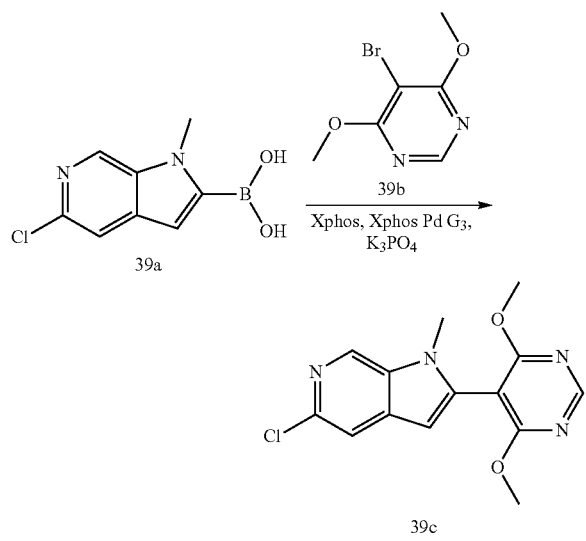

To a solution of 5-chloro-1-methylpyrrolo[2,3-c]pyridin-2-ylboronic acid (Compound 39a) (200.0 mg, 0.95 mmol) in dioxane/H$_2$O (5.0/0.8 mL) was added 5-bromo-4,6-dimethoxypyrimidine (Compound 39b) (249.8 mg, 1.14 mmol). K$_3$PO$_4$ (403.5 mg, 1.90 mmol), XPhos (90.6 mg, 0.19 mmol) and XPhos Pd G$_3$ (109.8 mg, 0.01 mmol) at room temperature under N$_2$. The resulting mixture was stirred at 60° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (65/35, v/v) to afford 5-[5-chloro-1-methylpyrrolo[2,3-c]pyridin-2-yl]-4,6-dimethoxypyrimidine (Compound 39c) (180.0 mg, 62%) as a white solid. LCMS (ESI, m/z): [M+H]$^+$=305.1.

Step 2: Synthesis of (1S,2S)-N-[2-(4,6-dimethoxypyrimidin-5-yl)-1-methylpyrrolo[2,3-c]pyridin-5-yl]-2-fluorocyclopropane-1-carboxamide (Compound 39)

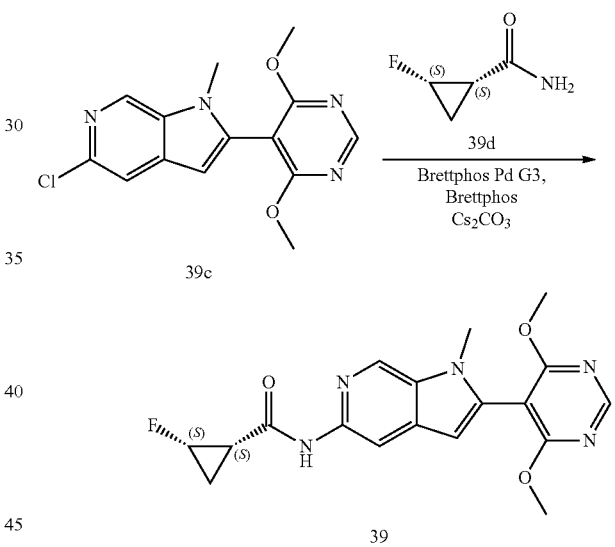

To a solution of 5-[5-chloro-1-methylpyrrolo[2,3-c]pyridin-2-yl]-4,6-dimethoxypyrimidine (Compound 39c) (60.0 mg, 0.19 mmol) in 1,4-dioxane (4.0 mL) was added (1S,2S)-2-fluorocyclopropane-1-carboxamide (Compound 39d) (101.5 mg, 0.98 mmol), Cs$_2$CO$_3$ (192.4 mg, 0.59 mmol), BrettPhos (21.1 mg, 0.04 mmol) and BrettPhos Pd G3 (17.8 mg, 0.02 mmol) at room temperature under N$_2$. The resulting mixture was stirred at 100° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A:Water (10 mmol/L NH$_4$HCO$_3$), Mobile Phase B: ACN: Flow rate: 60 mL/min; Gradient: 33% B to 43% B in 9 min; 254 nm;) to afford (1S,2S)-N-[2-(4,6-dimethoxypyrimidin-5-yl)-1-methylpyrrolo[2,3-c]pyridin-5-yl]-2-fluorocyclopropane-1-carboxamide (7.1 mg, 9%) as a white solid. LCMS (ESI, m/z):

[M+H]⁺=372.2. ¹H NMR (400 MHz, DMSO-d₆): δ 10.54 (s, 1H), 8.66 (s, 1H), 8.62 (s, 1H), 8.19 (s, 1H), 6.49 (s, 1H), 5.01-4.80 (m, 1H), 3.92 (s, 6H), 3.58 (s, 3H), 2.25-2.15 (m, 1H), 1.68-1.61 (m, 1H), 1.16-1.12 (m, 1H).

Example S40: Synthesis of cis-N-(2-(2-methoxyphenyl)-1-methyl-1H-pyrrolo[2,3-c]pyridin-5-yl)-2-((4-methylpiperazin-1-yl)methyl)cyclopropane-1-carboxamide (Compound 40)

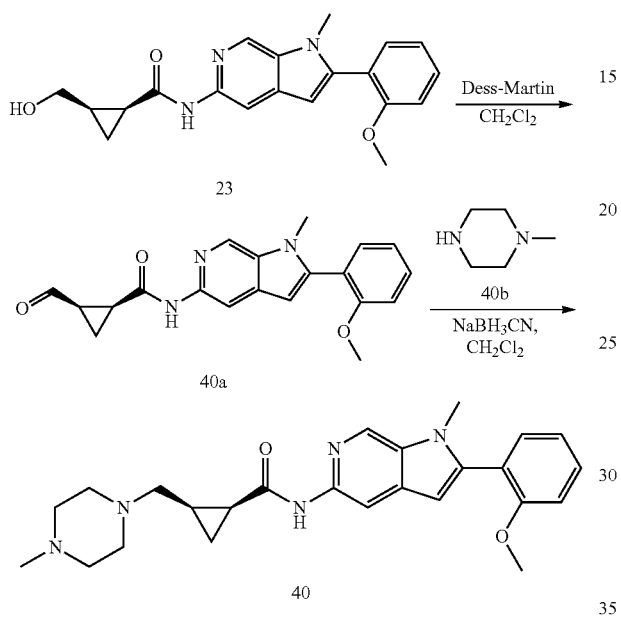

Step 1: Synthesis of cis-2-formyl-N-(2-(2-methoxyphenyl)-1-methyl-1H-pyrrolo[2,3-c]pyridin-5-yl)cyclopropane-1-carboxamide (Compound 40a)

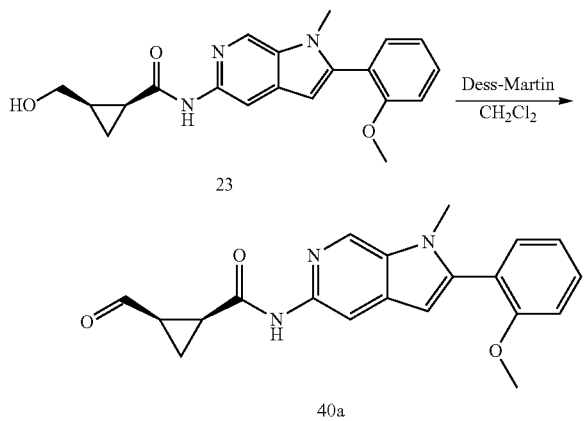

To a solution of cis-2-(hydroxymethyl)-N-(2-(2-methoxyphenyl)-1-methyl-1H-pyrrolo[2,3-c]pyridin-5-yl)cyclopropane-1-carboxamide (Compound 23) (200.0 mg, 0.57 mmol) in CH₂Cl₂ (10.0 mL) was added Dess-Martin (362.1 mg, 0.85 mmol) at room temperature. The resulting mixture was stirred at room temperature for 1.5 h. After the reaction was completed, the resulting mixture was diluted with H₂O and extracted with CH₂Cl₂. The combined organic layer was washed with brine, dried over anhydrous sodium sulfate and filtered. The filtrate was concentrated under reduced pressure to afford cis-2-formyl-N-(2-(2-methoxyphenyl)-1-methyl-1H-pyrrolo[2,3-c]pyridin-5-yl)cyclopropane-1-carboxamide (Compound 40a) (340.0 mg, crude) as a yellow solid. LCMS (ESI, m/z): [M+H]⁺=350.1.

Step 2: Synthesis of cis-N-(2-(2-methoxyphenyl)-1-methyl-1H-pyrrolo[2,3-c]pyridin-5-yl)-2-((4-methylpiperazin-1-yl)methyl)cyclopropane-1-carboxamide (Compound 40)

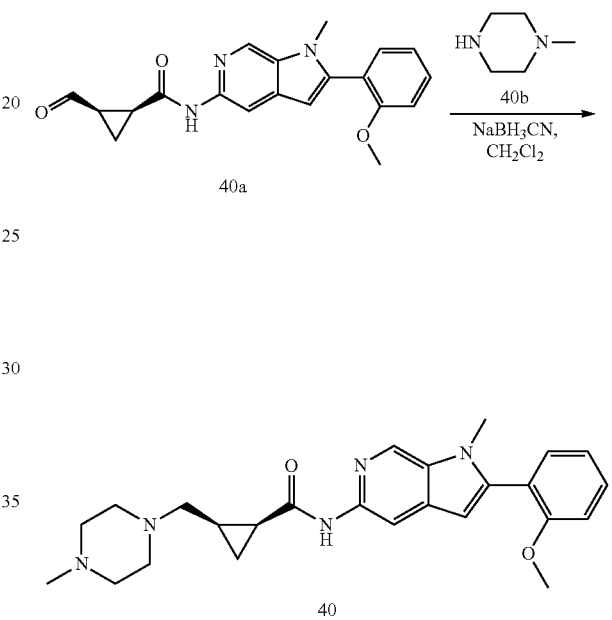

To a solution of cis-2-formyl-N-(2-(2-methoxyphenyl)-1-methyl-1H-pyrrolo[2,3-c]pyridin-5-yl)cyclopropane-1-carboxamide (Compound 40a) (200.0 mg, 0.57 mmol) in CH₂Cl₂ (10.0 mL) was added 1-methylpiperazine (Compound 40b) (114.7 mg, 1.15 mmol) and NaBH₃CN (71.9 mg, 1.15 mmol) at room temperature under N₂. The resulting mixture was stirred at room temperature for 2 h. After the reaction was completed, the resulting mixture was quenched with CH₃OH. The resulting mixture was concentrated under reduced pressure. The residue was purified by flash column chromatography with CH₂Cl₂/CH₃OH (85/15, v/v) and then purified by Prep-HPLC with the following conditions (Column: XBridge Prep OBD C₁₈ Column, 30×150 mm, 5 um; Mobile Phase A: Water (10 mmol/L NH₄HCO₃). Mobile Phase B: ACN: Flow rate: 60 mL/min; Gradient: 28% B to 58% B in 7 min; 254 nm) to afford cis-N-(2-(2-methoxyphenyl)-1-methyl-1H-pyrrolo[2,3-c]pyridin-5-yl)-2-((4-methylpiperazin-1-yl)methyl)cyclopropane-1-carboxamide (Compound 40) (6.6 mg, 3%) as a light yellow solid. LCMS (ESI, m/z): [M+H]⁺=434.4. ¹H NMR (300 MHz, DMSO-d₆): δ 10.42 (s, 1H), 8.58 (s, 1H), 8.19 (s, 1H), 7.56-7.50 (m, 1H), 7.39-7.36 (m, 1H), 7.21 (d, J=8.1 Hz, 1H), 7.13-7.08 (m, 1H), 6.43 (s, 1H), 3.81 (s, 3H), 3.60 (s, 3H), 2.62-2.56 (m, 2H), 2.46-2.19 (m, 8H), 2.12-2.05 (m, 4H), 1.32-1.27 (m, 1H), 1.01-0.94 (m, 1H), 0.89-0.83 (m, 1H).

Example S41: Synthesis of cis-N-(2-(2-methoxyphenyl)-1-methyl-1H-pyrrolo[2,3-c]pyridin-5-yl)-2-(morpholinomethyl)cyclopropane-1-carboxamide (Compound 41)

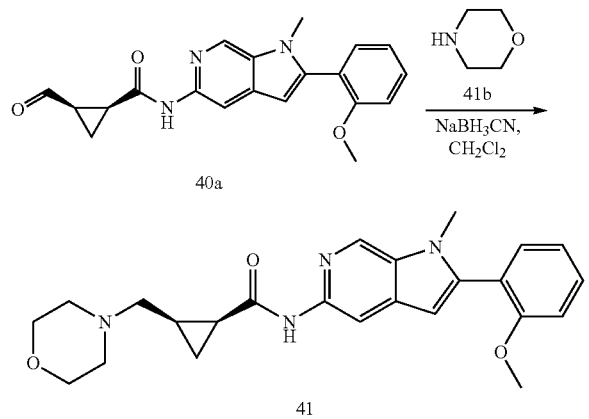 [SMILES: COc1ccccc1-c1cc2cc(NC(=O)[C@H]3C[C@H]3C=O)ncc2n1C ; C1COCCN1 ; COc1ccccc1-c1cc2cc(NC(=O)[C@H]3C[C@H]3CN3CCOCC3)ncc2n1C]

To a solution of cis-2-formyl-N-(2-(2-methoxyphenyl)-1-methyl-1H-pyrrolo[2,3-c]pyridin-5-yl)cyclopropane-1-carboxamide (Compound 40a) (340.0 mg, 0.97 mmol) in $CH_2Cl_2$ (10.0 mL) was added morpholine (Compound 41b) (169.6 mg, 1.95 mmol) and $NaBH_3CN$ (122.3 mg, 1.95 mmol) in portions at room temperature under N. The resulting mixture was stirred at room temperature for 2 h. After the reaction was completed, the resulting mixture was quenched with $CH_3OH$. The resulting mixture was concentrated under reduced pressure. The residue was purified by flash column chromatography with $CH_2Cl_2/CH_3OH$ (85/15, v/v) and then purified by Prep-HPLC with the following conditions (Column: Xselect CSH OBD Column 30×150 mm, 5 um; Mobile Phase A: Water (10 mmol/L $NH_4HCO_3$), Mobile Phase B: ACN; Flow rate: 60 mL/min; Gradient: 32% B to 43% B in 7 min; 254 nm) to afford cis-N-(2-(2-methoxyphenyl)-1-methyl-1H-pyrrolo[2,3-c]pyridin-5-yl)-2-(morpholinomethyl)cyclopropane-1-carboxamide (Compound 41) (14.3 mg, 3%) as a light yellow solid. LCMS (ESI, m/z): $[M+H]^+$= 421.1. $^1H$ NMR (300 MHz, DMSO-$d_6$): δ 10.42 (s, 1H), 8.58 (s, 1H), 8.20 (s, 1H), 7.56-7.50 (m, 1H), 7.39-7.36 (m, 1H), 7.21 (d, J=8.1 Hz, 1H), 7.13-7.08 (m, 1H), 6.43 (d, J=0.3 Hz, 1H), 3.81 (s, 3H), 3.60 (s, 3H), 3.53-3.50 (m, 4H), 2.62-2.56 (m, 2H), 2.39-2.37 (m, 4H), 2.12-2.06 (m, 1H), 1.35-1.23 (m, 1H), 1.02-0.96 (m, 1H), 0.91-0.85 (m, 1H).

Example S42: Synthesis of N-(2-(2-fluorophenyl)-1,3-dimethyl-1H-pyrrolo[2,3-c]pyridin-5-yl)cyclopropanecarboxamide (Compound 42)

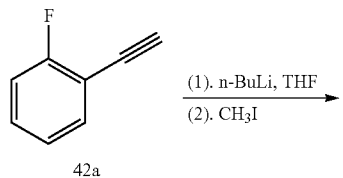

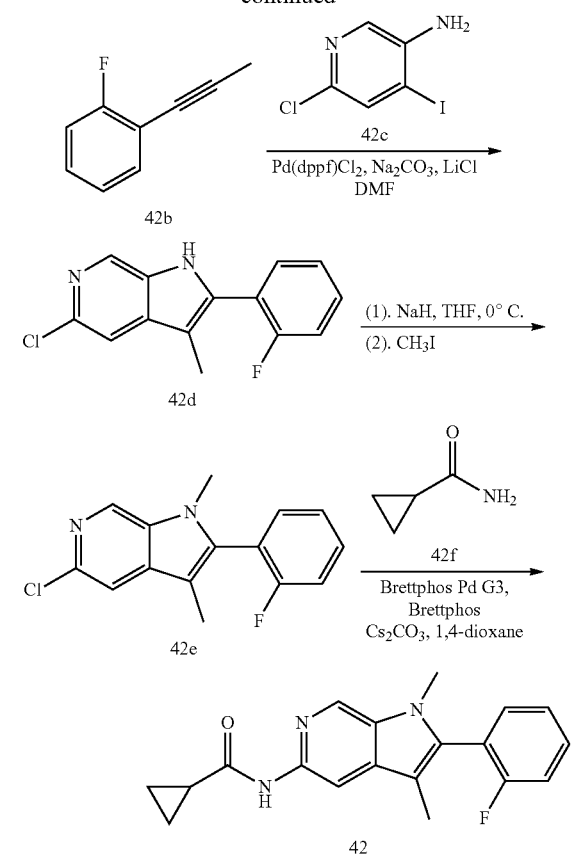

Step 1: Synthesis of 1-fluoro-2-(prop-1-yn-1-yl)benzene (Compound 42b)

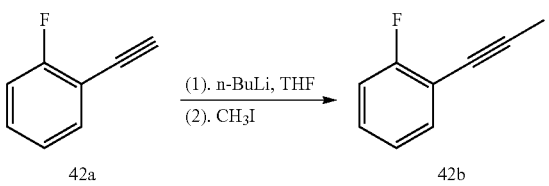

To a solution of 1-ethynyl-2-fluorobenzene (Compound 42a) (5.0 g, 41.62 mmol) in THF (100.0 mL) was added n-BuLi (34.0 mL, 2.5 mol/L) dropwise at −78° C. under $N_2$. The resulting mixture was stirred at −78° C. for 1 h. Then $CH_3I$ (29.5 g, 208.12 mmol) was added dropwise to the mixture at −78° C. The resulting mixture was stirred at room temperature for 2 h. After the reaction was completed, the reaction was quenched with $NH_4Cl$ solution at 0° C. and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (99/1, v/v) to afford 1-fluoro-2-(prop-1-yn-1-yl)benzene (Compound 42b) (4.6 g, 80%) as a colorless oil.

Step 2: Synthesis of 5-chloro-2-(2-fluorophenyl)-3-methyl-1H-pyrrolo[2,3-c]pyridine (Compound 42d)

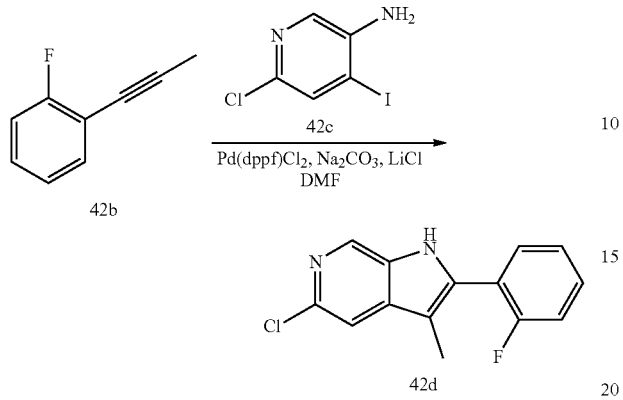

To a solution of 1-fluoro-2-(prop-1-yn-1-yl)benzene (Compound 42b) (276.8 mg, 2.06 mmol) in DMF (10.0 mL) was added 6-chloro-4-iodopyridin-3-amine (Compound 42c) (350.0 mg, 1.37 mmol), Na$_2$CO$_3$ (728.9 mg, 6.87 mmol), LiCl (58.3 mg, 1.37 mmol) and Pd(dppf)Cl$_2$ (100.6 mg, 0.14 mmol) at room temperature under N$_2$. The resulting mixture was stirred at 100° C. for 16 h. After the reaction was completed, the reaction was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (36/64, v/v) to afford 5-chloro-2-(2-fluorophenyl)-3-methyl-1H-pyrrolo[2,3-c]pyridine (Compound 42d) (160.0 mg, 44%) as a white solid. LCMS (ESI, m/z): [M+H]$^+$=261.1.

Step 3: Synthesis of 5-chloro-2-(2-fluorophenyl)-1,3-dimethyl-1H-pyrrolo[2,3-c]pyridine (Compound 42e)

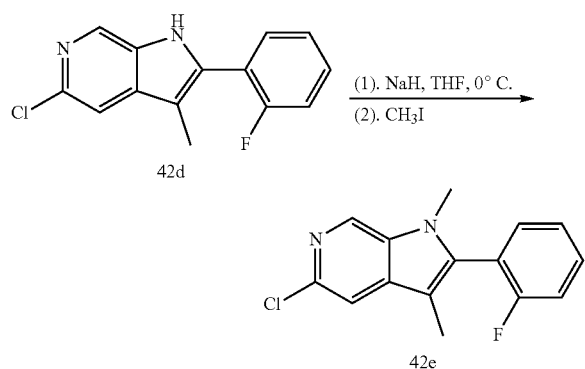 [SMILES: Cc1c(-c2ccccc2F)[nH]c2cnc(Cl)cc12 ; Cc1c(-c2ccccc2F)n(C)c2cnc(Cl)cc12]

To a solution of 5-chloro-2-(2-fluorophenyl)-3-methyl-1H-pyrrolo[2,3-c]pyridine (Compound 42d) (160.0 mg, 0.61 mmol) in THF (5.0 mL) was added NaH (73.64 mg, 60%) at 0° C. under N$_2$. The resulting mixture was stirred at 0° C. for 1 h. Then CH$_3$I (435.5 mg, 3.07 mmol) was added to the mixture at 0° C. The resulting mixture was stirred at 0° C. for 1 h. After the reaction was completed, the reaction was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (73/27, v/v) to afford 5-chloro-2-(2-fluorophenyl)-1,3-dimethyl-1H-pyrrolo[2,3-c]pyridine (Compound 42e) (130.0 mg, 77%) as a yellow solid. LCMS (ESI, m/z): [M+H]$^+$=275.1.

Step 4: Synthesis of N-(2-(2-fluorophenyl)-1,3-dimethyl-1H-pyrrolo[2,3-c]pyridin-5-yl)cyclopropanecarboxamide (Compound 42)

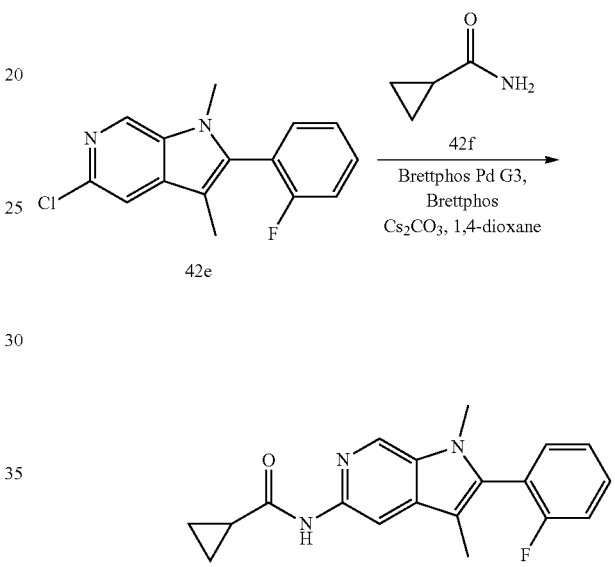

To a solution of 5-chloro-2-(2-fluorophenyl)-1,3-dimethyl-1H-pyrrolo[2,3-c]pyridine (Compound 42e) (100.0 mg, 0.36 mmol) in 1,4-dioxane (10.0 mL) was added cyclopropanecarboxamide (Compound 42f) (154.9 mg, 1.82 mmol). Cs$_2$CO$_3$ (154.9 mg, 1.82 mmol), BrettPhos (39.1 mg, 0.07 mmol) and BrettPhos Pd G3 (33.0 mg, 0.04 mmol) at room temperature under N$_2$. The resulting mixture was stirred at 100° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (26/74, v/v) and then purified by Prep-HPLC with the following conditions (Column: XBridge Prep OBD C$_{18}$ Column, 30×150 mm, 5 um; Mobile Phase A:Water (10 mmol/L NH$_4$HCO$_3$), Mobile Phase B: ACN; Flow rate: 60 mL/min; Gradient: 48% B to 78% B in 7 min; 254 nm) to afford N-(2-(2-fluorophenyl)-1,3-dimethyl-1H-pyrrolo[2,3-c]pyridin-5-yl)cyclopropanecarboxamide (Compound 42) (43.9 mg, 37%) as a white solid. LCMS (ESI, m/z): [M+H]$^+$=324.2. H NMR (300 MHz, DMSO-d$_6$): δ 10.53 (s, 1H), 8.62 (d, J=0.9 Hz, 1H), 8.22 (s, 1H), 7.66-7.40 (m, 4H), 3.62 (s, 3H), 2.09-1.98 (m, 4H), 0.86-0.78 (m, 4H).

Example S43: Synthesis of (1S,2S)-2-fluoro-N-(2-(2-methoxyphenyl)-1,3-dimethyl-1H-pyrrolo[2,3-c]pyridin-5-yl)cyclopropane-1-carboxamide (Compound 43)

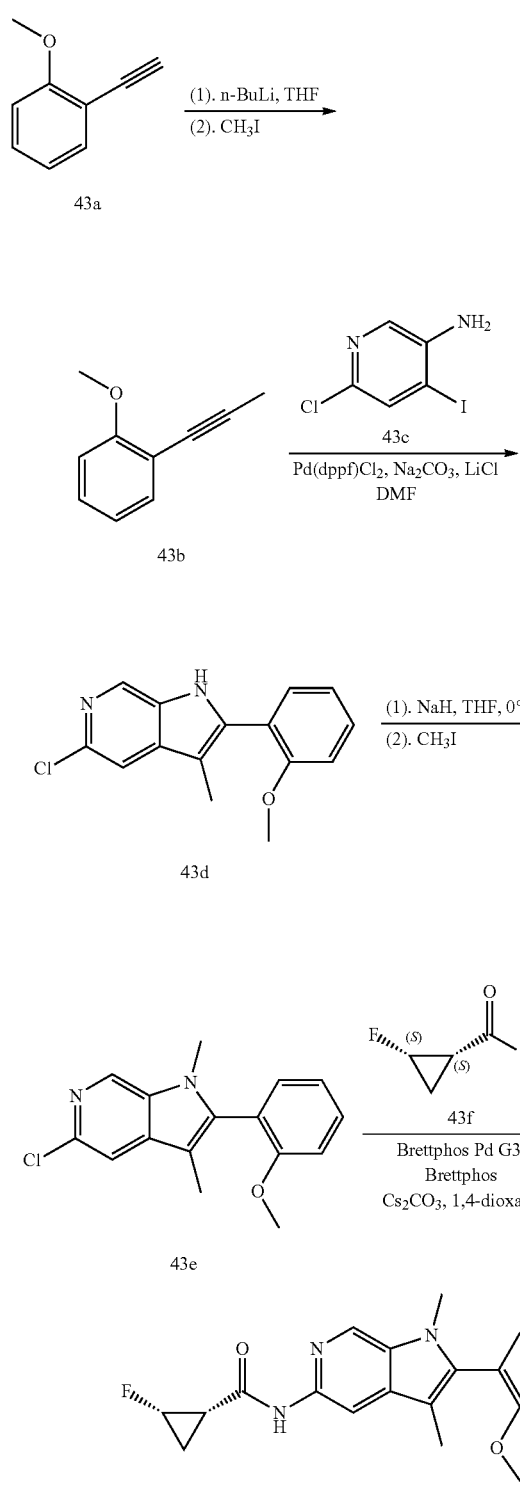

Step 1: Synthesis of 1-methoxy-2-(prop-1-yn-1-yl)benzene (Compound 43b)

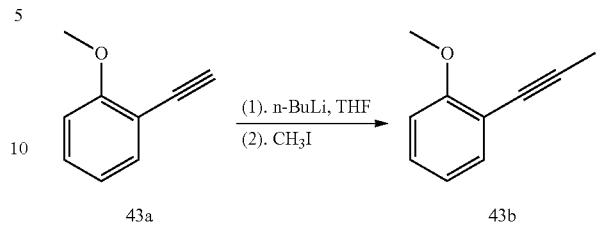

To a solution of 1-ethynyl-2-methoxybenzene (Compound 43a) (2.0 g, 15.13 mmol) in THF (30.0 mL) was added n-BuLi (9.0 mL, 2.5 mol/L) dropwise at −78° C. under $N_2$. The resulting mixture was stirred at −78° C. for 1 h. After the reaction was completed, $CH_3I$ (10.7 g, 75.67 mmol) was added dropwise to the mixture at −78° C. The resulting mixture was stirred at room temperature for 2 h. After the reaction was completed, the reaction was quenched with $NH_4Cl$ solution and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (93/7, v/v) to afford 1-methoxy-2-(prop-1-yn-1-yl)benzene (Compound 43b) (2.1 g, 94%) as a colorless oil. LCMS (ESI, m/z): $[M+H]^+=147.1$.

Step 2: Synthesis of 5-chloro-2-(2-methoxyphenyl)-3-methyl-1H-pyrrolo[2,3-c]pyridine (Compound 43d)

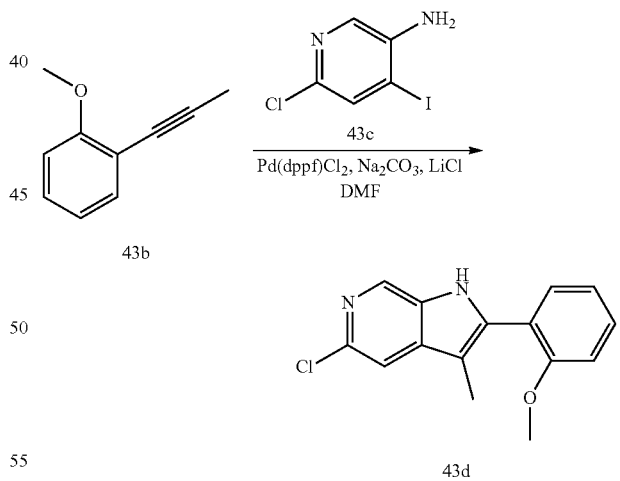

To a solution of 6-chloro-4-iodopyridin-3-amine) (Compound 43c) (1.0 g, 3.93 mmol) in DMF (15.0 mL) was added 1-methoxy-2-(prop-1-yn-1-yl)benzene (Compound 43b) (689.4 mg, 4.72 mmol), $Na_2CO_3$ (2.1 g, 19.65 mmol), LiCl (166.6 mg, 3.93 mmol) and Pd(dppf)$Cl_2$ (287.6 mg, 0.39 mmol) at room temperature under $N_2$. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (58/42, v/v) to afford 5-chloro-2-(2-methoxyphenyl)-3-methyl-1H-pyrrolo[2,3-c]pyridine (Compound 43d) (350.0 mg, 34%) as a brown oil. LCMS (ESI, m/z): [M+H]⁺=273.1.

Step 3: Synthesis of 5-chloro-2-(2-methoxyphenyl)-1,3-dimethyl-1H-pyrrolo[2,3-c]pyridine (Compound 43e)

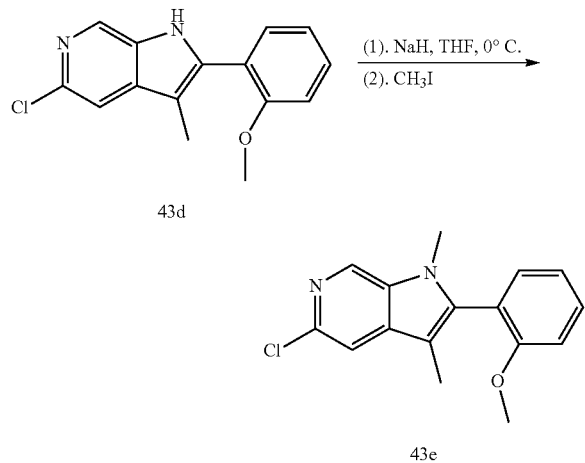

To a solution of 5-chloro-2-(2-methoxyphenyl)-3-methyl-1H-pyrrolo[2,3-c]pyridine (Compound 43d) (350.0 mg, 1.28 mmol) in THF (10.0 mL) was added NaH (154.0 mg, 60%) at 0° C. under N₂. The resulting mixture was stirred at 0° C. for 1 h. Then CH₃I (910.8 mg, 6.42 mmol) was added to the mixture at 0° C. The resulting mixture was stirred at 0° C. for another 1 h. After the reaction was completed, the reaction was quenched with NH₄Cl solution and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (70/30, v/v) to afford 5-chloro-2-(2-methoxyphenyl)-1,3-dimethyl-1H-pyrrolo[2,3-c]pyridine (Compound 43e) (190.0 mg, 51%) as a white solid. LCMS (ESI, m/z): [M+H]⁺=287.1.

Step 4: Synthesis of (1S,2S)-2-fluoro-N-(2-(2-methoxyphenyl)-1,3-dimethyl-1H-pyrrolo[2,3-c]pyridin-5-yl)cyclopropane-1-carboxamide (Compound 43)

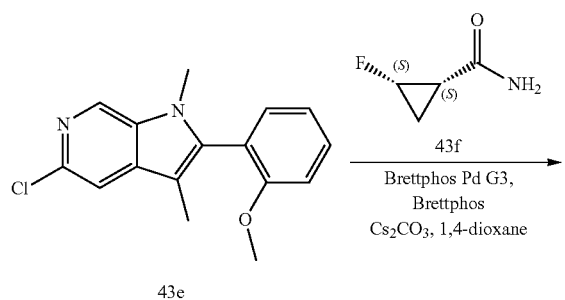

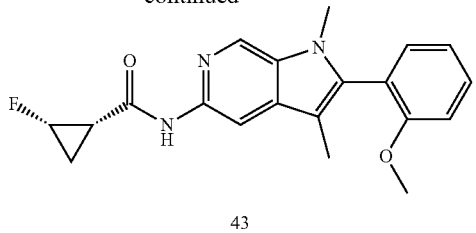

To a solution of 5-chloro-2-(2-methoxyphenyl)-1,3-dimethyl-1H-pyrrolo[2,3-c]pyridine (Compound 43e) (190.0 mg, 0.66 mmol) in 1,4-dioxane (5.0 mL) was added (1S,2S)-2-fluorocyclopropane-1-carboxamide (Compound 43f) (341.5 mg, 3.31 mmol), Cs₂CO₃ (647.6 mg, 1.99 mmol), BrettPhos (71.1 mg, 0.13 mmol) and BrettPhos Pd G3 (60.1 mg, 0.06 mmol) at room temperature under N₂. The resulting mixture was irradiated with microwave radiation at 120° C. for 1.5 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (16/84, v/v) and then purified by Prep-HPLC with the following conditions (Column: YMC-Actus Triart C18, 30×250 mm, 5 um; Mobile Phase A:Water (10 mmol/L NH₄HCO₃), Mobile Phase B:ACN; Flow rate: 60 mL/min; Gradient: 45% B to 75% B in 7 min; 254 nm) to afford (1S,2S)-2-fluoro-N-(2-(2-methoxyphenyl)-1,3-dimethyl-1H-pyrrolo[2,3-c]pyridin-5-yl)cyclopropane-1-carboxamide (Compound 43) (34.1 mg, 14%) as a white solid. LCMS (ESI, m/z): [M+H]⁺=354.1. ¹H NMR (300 MHz, DMSO-d₆): δ 10.55 (s, 1H), 8.56 (d, J=1.2 Hz, 1H), 8.19 (s, 1H), 7.56-7.51 (m, 1H), 7.33-7.30 (m, 1H), 7.23 (d, J=8.1 Hz, 1H), 7.15-7.10 (m, 1H), 5.04-4.79 (m, 1H), 3.79 (s, 3H), 3.54 (s, 3H), 2.24-2.19 (m, 1H), 2.05 (s, 3H), 1.71-1.60 (m, 1H), 1.18-1.11 (m, 1H).

Example S44: Synthesis of (1R,2R)-2-fluoro-N-[2-(2-methoxyphenyl)-1,3-dimethylpyrrolo[2,3-c]pyridin-5-yl]cyclopropane-1-carboxamide (Compound 44)

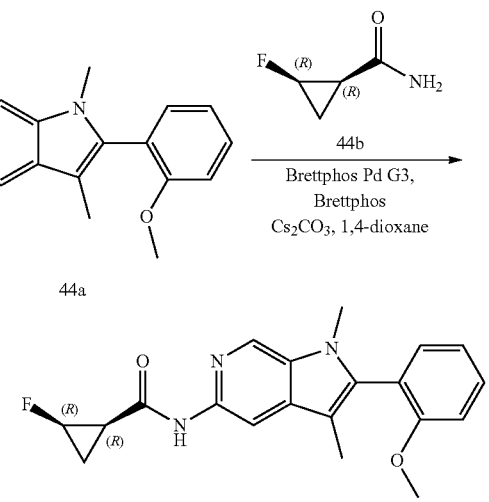

To a solution of 5-chloro-2-(2-methoxyphenyl)-1,3-dimethylpyrrolo[2,3-c]pyridine (Compound 44a) (190.0 mg, 0.66 mmol) in 1,4-dioxane (5.0 mL) was added (1R,2R)-2-fluorocyclopropane-1-carboxamide (Compound 44b) (341.5 mg, 3.31 mmol), Cs$_2$CO$_3$ (647.6 mg, 1.99 mmol), BrettPhos (71.1 mg, 0.13 mmol) and BrettPhos Pd G3 (60.1 mg, 0.07 mmol) at room temperature under N$_2$. The resulting mixture was irradiated with microwave radiation at 120° C. for 1.5 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: YMC-Actus Triart C18, 30×250 mm, 5 um; Mobile Phase A:Water (10 mmol/L NH$_4$HCO$_3$), Mobile Phase B: ACN; Flow rate: 60 mL/min; Gradient: 35% B to 65% B in 10 min; 254 nm) to afford (1R,2R)-2-fluoro-N-[2-(2-methoxyphenyl)-1,3-dimethylpyrrolo[2,3-c]pyridin-5-yl]cyclopropane-1-carboxamide (Compound 44) (17.0 mg, 7%) as a white solid. LCMS (ESI, m/z): [M+H]$^+$=354.2, $^1$H NMR (400 MHz, DMSO-d$_6$): δ 10.53 (s, 1H), 8.56 (s, 1H), 8.19 (s, 1H), 7.56-7.51 (m, 1H), 7.31 (d, J=7.6 Hz, 1H), 7.23 (d, J=8.4 Hz, 1H), 7.15-7.11 (m, 1H), 5.02-4.81 (m, 1H), 3.79 (s, 3H), 3.54 (s, 3H), 2.25-2.18 (m, 1H), 2.05 (s, 3H), 1.71-1.63 (m, 1H), 1.20-1.10 (m, 1H).

Example S45: Synthesis of (1R,2R)-2-fluoro-N-[2-(2-fluoro-6-methoxyphenyl)-1,3-dimethylpyrrolo[2,3-c]pyridin-5-yl]cyclopropane-1-carboxamide (Compound 45)

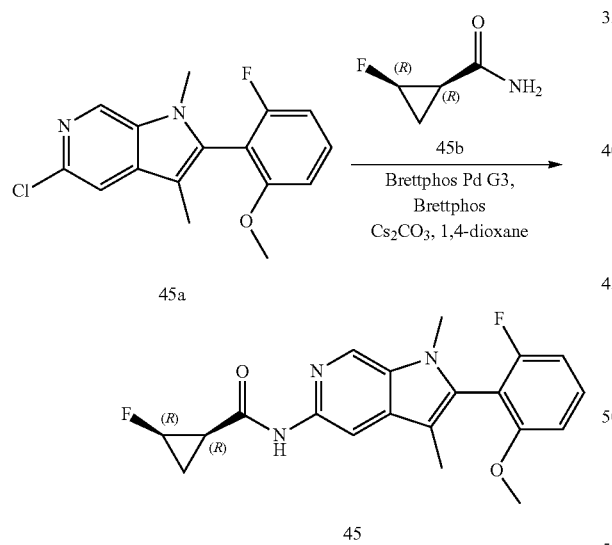

To a solution of 5-chloro-2-(2-fluoro-6-methoxyphenyl)-1,3-dimethylpyrrolo[2,3-c]pyridine (Compound 45a) (150.0 mg, 0.49 mmol) in 1,4-dioxane (6.0 mL) was added (1R,2R)-2-fluorocyclopropane-1-carboxamide (Compound 45b) (253.7 mg, 2.46 mmol), Cs$_2$CO$_3$ (481.1 mg, 1.48 mmol), BrettPhos (52.8 mg, 0.10 mmol) and BrettPhos Pd G3 (44.6 mg, 0.05 mmol) at room temperature under N$_2$. The resulting mixture was irradiated with microwave radiation at 120° C. for 1.5 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep OBD C$_{18}$ Column, 30×150 mm, 5 um; Mobile Phase A:Water (10 mmol/L NH$_4$HCO$_3$), Mobile Phase B: ACN; Flow rate: 60 mL/min; Gradient: 34% B to 64% B in 10 min; 254 nm) to afford (1R,2R)-2-fluoro-N-[2-(2-fluoro-6-methoxyphenyl)-1,3-dimethylpyrrolo[2,3-c]pyridin-5-yl]cyclopropane-1-carboxamide (Compound 45) (2.2 mg, 1%) as a white solid. LCMS (ESI, m/z): [M+H]$^+$=372.2. H NMR (300 MHz, DMSO-d$_6$): δ 10.49 (s, 1H), 8.52 (s, 1H), 8.13 (s, 1H), 7.56-7.48 (m, 1H), 7.04-6.93 (m, 2H), 4.96-4.72 (m, 1H), 3.73 (s, 3H), 3.47 (s, 3H), 2.21-2.10 (m, 1H), 1.94 (s, 3H), 1.65-1.54 (m, 1H), 1.17-1.02 (m, 1H).

Example S46: Synthesis of N-(3-fluoro-1-methyl-2-o-tolyl-1H-pyrrolo[2,3-c]pyridin-5-yl)cyclopropanecarboxamide (Compound 46)

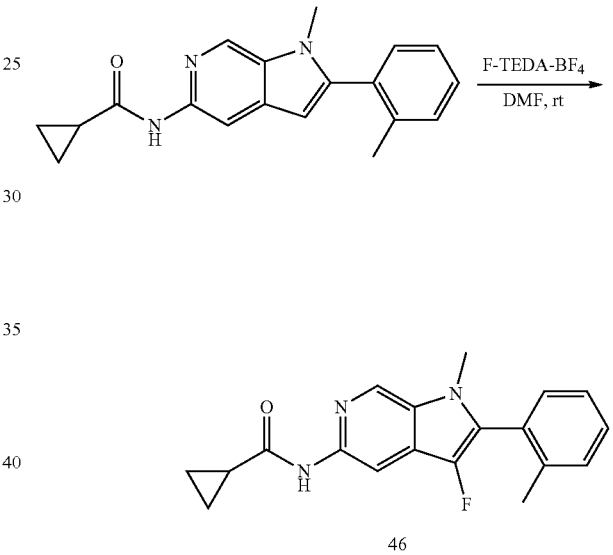

To a solution of N-[1-methyl-2-(2-methylphenyl)pyrrolo[2,3-c]pyridin-5-yl]cyclopropanecarboxamide (230.0 mg, 0.73 mmol) in DMF (10.0 mL) was added F-TEDA-BF$_4$ (213.5 mg, 0.63 mmol) at room temperature under N$_2$. The resulting mixture was stirred at room temperature for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by Prep-HPLC with the following conditions (Column: XBridge Prep OBD C$_{18}$ Column, 30×150 mm, 5 um; Mobile Phase A:Water (10 mmol/L NH$_4$HCO$_3$), Mobile Phase B: ACN: Flow rate: 60 mL/min; Gradient: 41% B to 71% B in 7 min; 254 nm) to afford N-(3-fluoro-1-methyl-2-o-tolyl-1H-pyrrolo[2,3-c]pyridin-5-yl)cyclopropanecarboxamide (Compound 46) (15.2 mg, 6%) as a white solid. LCMS (ESI, m/z): [M+H]$^+$=324.2. $^1$H NMR (400 MHz, DMSO-d$_6$): δ 10.65 (s, 1H), 8.72 (s, 1H), 8.23 (s, 1H), 7.47-7.39 (m, 4H), 3.57 (s, 3H), 2.13 (s, 3H), 2.05-1.95 (m, 1H), 0.83-0.78 (m, 4H).

Example S47: Synthesis of N-[3-cyano-2-(2-methoxyphenyl)-1-methylpyrrolo[2,3-c]pyridin-5-yl]cyclopropanecarboxamide (Compound 47)

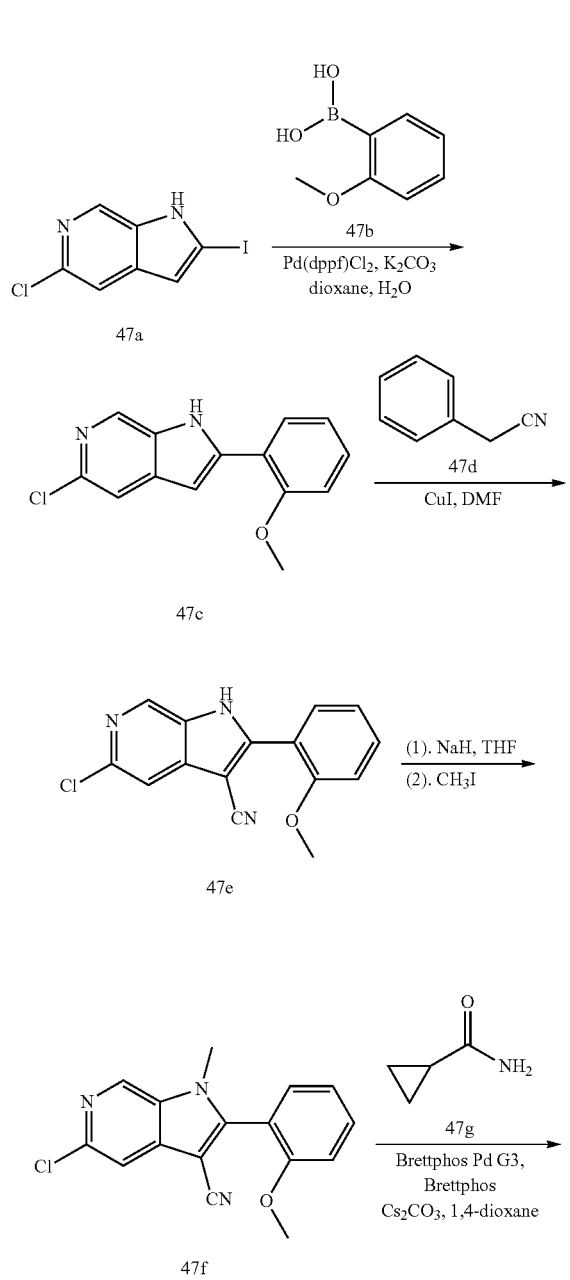

Step 1: Synthesis of 5-chloro-2-(2-methoxyphenyl)-1H-pyrrolo[2,3-]pyridine (Compound 47C)

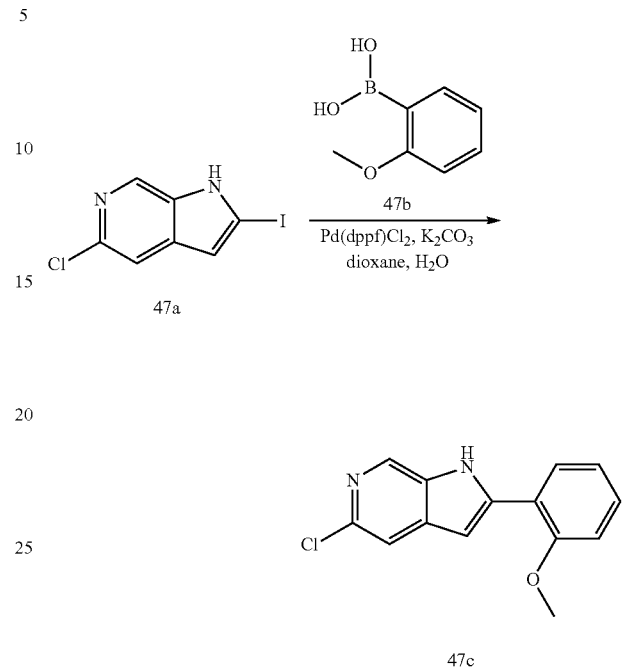

To a solution of 5-chloro-2-iodo-1H-pyrrolo[2,3-c]pyridine (Compound 47a) (500.0 mg, 1.80 mmol) in 1,4-dioxane/H₂O (10.0/2.0 mL) was added 2-methoxyphenylboronic acid (Compound 47b) (545.7 mg, 3.59 mmol), K₂CO₃ (744.4 mg, 5.39 mmol) and Pd(dppf)Cl₂ (131.4 mg, 0.18 mmol) at room temperature under N₂. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-chloro-2-(2-methoxyphenyl)-1H-pyrrolo[2,3-c]pyridine (Compound 47c) (350.0 mg, 75%) as a white solid. LCMS (ESI, m/z): [M+H]⁺=259.1.

Step 2: Synthesis of 5-chloro-2-(2-methoxyphenyl)-1H-pyrrolo[2,3-c]pyridine-3-carbonitrile (Compound 47e)

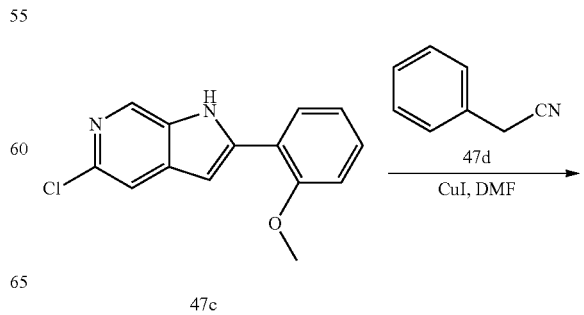

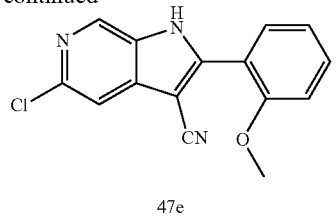

47e

To a solution of 5-chloro-2-(2-methoxyphenyl)-1H-pyrrolo[2,3-c]pyridine (Compound 47c) (350.0 mg, 1.35 mmol) in DMF (4.0 mL) was added phenylacetonitrile (Compound 47d) (792.5 mg, 6.76 mmol) and CuI (309.2 mg, 1.62 mmol) at room temperature under $N_2$. The resulting mixture was stirred at 120° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford 5-chloro-2-(2-methoxyphenyl)-1H-pyrrolo[2,3-c]pyridine-3-carbonitrile (Compound 47e) (200.0 mg, 52%) as a white solid. LCMS (ESI, m/z): [M+H]$^+$=284.1.

Step 3: Synthesis of 5-chloro-2-(2-methoxyphenyl)-1-methylpyrrolo[2,3-c]pyridine-3-carbonitrile (Compound 47n)

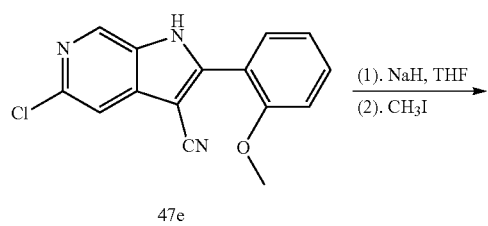

To a solution of 5-chloro-2-(2-methoxyphenyl)-1H-pyrrolo[2,3-c]pyridine-3-carbonitrile (Compound 47e) (150.0 mg, 0.53 mmol) in THF (5.0 mL) was added NaH (84.6 mg, 60%) at 0° C. under $N_2$. The resulting mixture was stirred at 0° C. for 1 h. Then CH$_3$I (225.1 mg, 1.59 mmol) was added to the mixture at 0° C. under $N_2$. The resulting mixture was stirred at 0° C. for another 1 h. After the reaction was completed, the reaction mixture was quenched with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-chloro-2-(2-methoxyphenyl)-1-methylpyrrolo[2,3-c]pyridine-3-carbonitrile (Compound 47f) (100.0 mg, 63%) as a white solid. LCMS (ESI, m/z): [M+H]$^+$=298.1.

Step 4: Synthesis of N-[3-cyano-2-(2-methyoxyphenyl)-1-methylpyrrolo[2,3-c]pyridin-5-yl]cyclopropanecarboxamide (Compound 47)

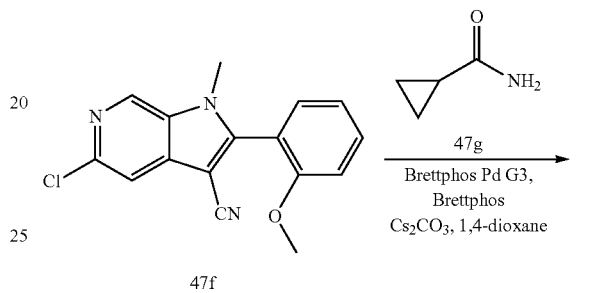

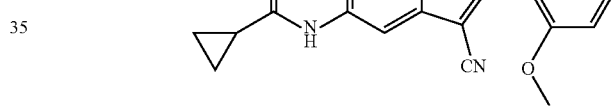

47

To a solution of 5-chloro-2-(2-methoxyphenyl)-1-methylpyrrolo[2,3-c]pyridine-3-carbonitrile (Compound 47l) (100.0 mg, 0.35 mmol) in 1,4-dioxane (6.0 mL) was added cyclopropanecarboxamide (Compound 47g) (150.0 mg, 1.76 mmol), BrettPhos (37.8 mg, 0.07 mmol), $Cs_2CO_3$ (344.5 mg, 1.06 mmol) and BrettPhos Pd G3 (32.0 mg, 0.04 mmol) at room temperature under $N_2$. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: YMC-Actus Triart C18, 20×250 mm, 5 um, 12 nm; Mobile Phase A:Water (10 mmol/L $NH_4HCO_3$), Mobile Phase B: ACN; Flow rate: 60 mL/min; Gradient: 52% B to 82% B in 7 min; 254 nm) to afford N-[3-cyano-2-(2-methoxyphenyl)-1-methylpyrrolo[2,3-c]pyridin-5-yl]cyclopropanecarboxamide (Compound 47) (18.1 mg, 14%) as a white solid. LCMS (ESI, m/z): [M+H]$^+$=347.1. $^1$H NMR (300 MHz, DMSO-d$_6$): δ 10.84 (s, 1H), 8.83 (d, J=0.6 Hz, 1H), 8.35 (s, 1H), 7.68-7.62 (m, 1H), 7.52-7.49 (m, 1H), 7.32 (d, J=8.4 Hz, 1H), 7.23-7.18 (m, 1H), 3.86 (s, 3H), 3.69 (s, 3H), 2.06-2.02 (m, 1H), 0.85-0.81 (m, 4H).

Example S48: Synthesis of (1S,2S)-2-fluoro-N-[2-(2-methoxyphenyl)-3-methyl-1H-pyrrolo[3,2-c]pyridin-6-yl]cyclopropane-1-carboxamide (Compound 48)

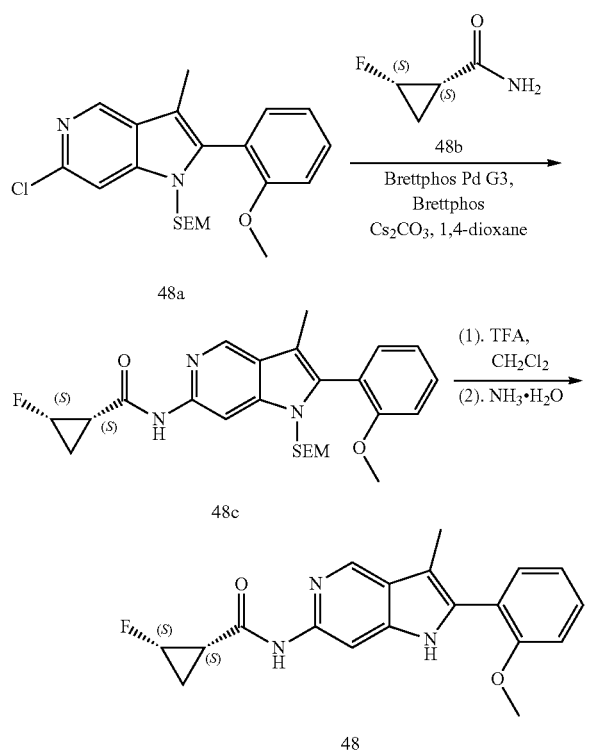

Step 1: Synthesis of (1S,2S)-2-fluoro-N-[2-(2-methoxyphenyl)-3-methyl-1-[[2-(trimethylsilyl)ethoxy]methyl]pyrrolo[3,2-c]pyridin-6-yl]cyclopropane-1-carboxamide (Compound 48c)

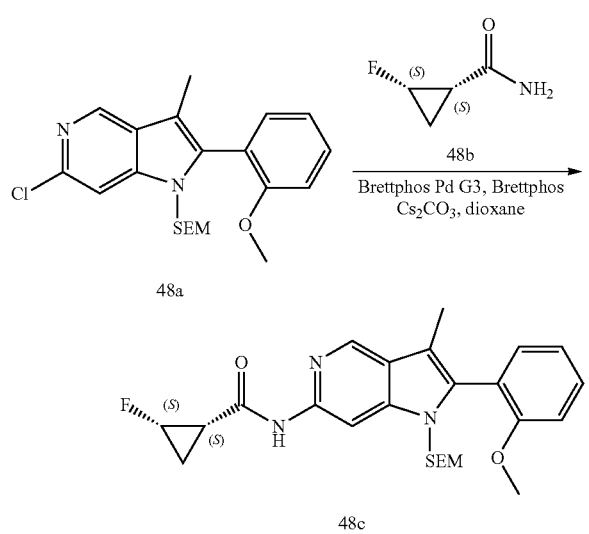

To a solution of 6-chloro-2-(2-methoxyphenyl)-3-methyl-1-[[2-(trimethylsilyl)ethoxy]methyl]pyrrolo[3,2-c]pyridine (Compound 48a) (260.0 mg, 0.64 mmol) in dioxane (10.0 mL) was added (1S,2S)-2-fluorocyclopropane-1-carboxamide (Compound 48b) (199.5 mg, 1.93 mmol), Brettphos Pd G3 (58.4 mg, 0.06 mmol), BrettPhos (69.2 mg, 0.12 mmol) and Cs₂CO₃ (630.6 mg, 1.96 mmol) at room temperature. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford (1S,2S)-2-fluoro-N-[2-(2-methoxyphenyl)-3-methyl-1-[[2-(trimethylsilyl)ethoxy]methyl]pyrrolo[3,2-c]pyridin-6-yl]cyclopropane-1-carboxamide (Compound 48c) (120.0 mg, 40%) as a colorless oil. LCMS (ESI): [M+H]⁺=470.2.

Step 2: Synthesis of (1S,2S)-2-fluoro-N-[2-(2-methoxyphenyl)-3-methyl-1H-pyrrolo[3,2-c]pyridin-6-yl]cyclopropane-1-carboxamide (Compound 48)

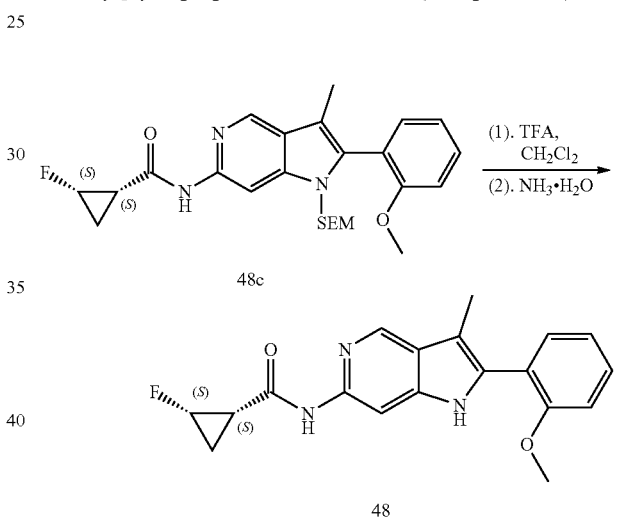

To a solution of (1S,2S)-2-fluoro-N-[2-(2-methoxyphenyl)-3-methyl-1-[[2-(trimethylsilyl)ethoxy]methyl]pyrrolo[3,2-c]pyridin-6-yl]cyclopropane-1-carboxamide (Compound 48c) (80.0 mg, 0.17 mmol) in CH₂Cl₂ (2.0 mL) was added TFA (2.0 mL) at mom temperature. The resulting mixture was stirred at room temperature for 2 h. The resulting mixture was concentrated under reduced pressure. The residue was dissolved in CH₃CN (2.0 mL) and NH₃·H₂O (2.0 mL). The resulting mixture was stirred at room temperature for another 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue purified by Prep-HPLC with the following conditions (Column: XBridge Prep OBD C₁₈ Column, 30×150 mm, 5 um; Mobile Phase A:Water (0.1% FA), Mobile Phase B: ACN; Flow rate: 60 mL/min; Gradient: 19% B to 23% B in 8 min; 220 nm) to afford (1S,2S)-2-fluoro-N-[2-(2-methoxyphenyl)-3-methyl-1H-pyrrolo[3,2-c]pyridin-6-yl]cyclopropane-1-carboxamide (Compound 48) (12.4 mg, 22%) as a white solid. LCMS (ESI, m/z):

[M+H]⁺=340.1. ¹H NMR (300 MHz, DMSO-d₆): δ 11.40 and 11.18 (s, total 1H), 10.58 and 10.56 (s, total 1H), 8.53 (s, 1H), 8.18 (d, J=3.9 Hz, 1H), 7.45-7.31 (m, 2H), 7.18-7.04 (m, 2H), 5.02-4.79 (m, 1H), 3.76 (s, 3H), 2.28-2.17 (m, 4H), 1.71-1.60 (m, 1H), 1.17-1.10 (m, 1H).

Example S49: Synthesis of N-[2-(4-hydroxy-2-methylphenyl)-1-methylpyrrolo[3,2-c]pyridin-6-yl]cyclopropanecarboxamide (Compound 49)

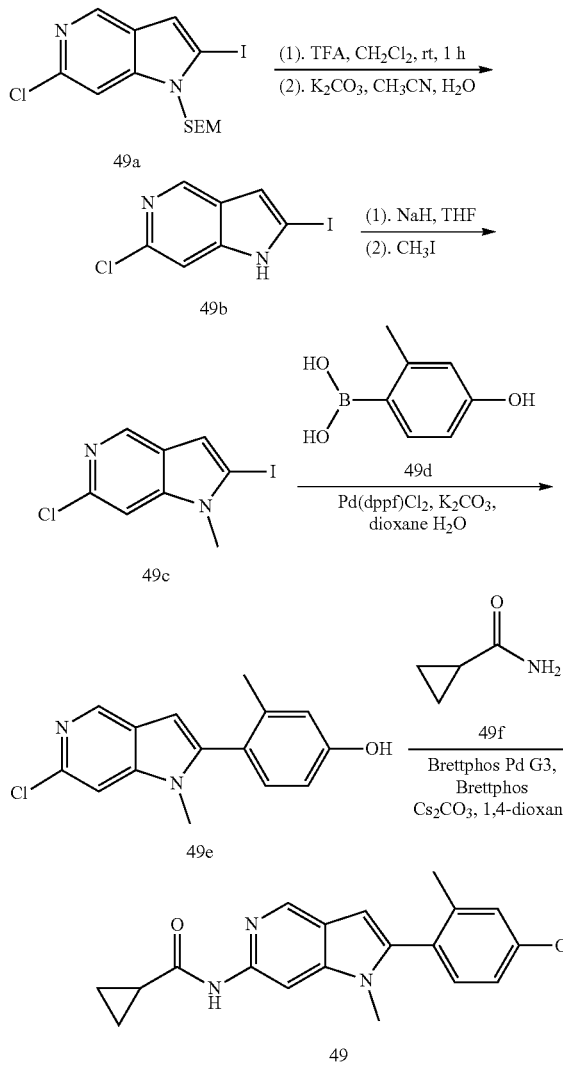

Step 1: Synthesis of 6-chloro-2-iodo-1H-pyrrolo[3,2-c]pyridine (Compound 49b)

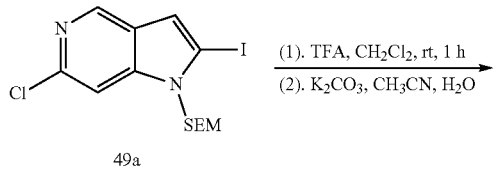

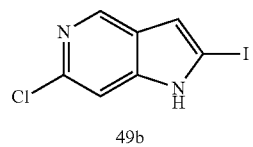

To a solution of 6-chloro-2-iodo-1-[[2-(trimethylsilyl)ethoxy]methyl]pyrrolo[3,2-c]pyridine (Compound 49a) (5.0 g, 12.23 mmol) in CH₂Cl₂ (10.0 mL) was added TFA (10.0 mL) at room temperature. The resulting mixture was stirred at room temperature for 1 h. The reaction mixture was evaporated in vacuo. The residue was re-dissolved in ACN/H₂O (20.0/4.0 mL). Then K₂CO₃ (16.9 g, 122.33 mmol) was added to the mixture. The reaction mixture was stirred at room temperature for another 16 h. After the reaction was completed, the resulting mixture was diluted with H₂O and extracted with EtOAc. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 6-chloro-2-iodo-1H-pyrrolo[3,2-c]pyridine (Compound 49b) (2.5 g, 71%) as a white solid. LCMS (ESI, m/z): [M+H]⁺=278.9.

Step 2: Synthesis of 6-chloro-2-iodo-1-methylpyrrolo[3,2-c]pyridine (Compound 49)

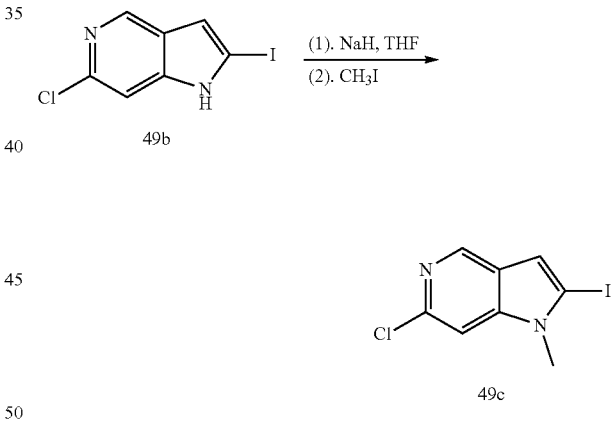

To a solution of 6-chloro-2-iodo-1H-pyrrolo[3,2-c]pyridine (Compound 49b) (630.0 mg, 2.26 mmol) in THF (20.0 mL) was added NaH (271.5 mg, 60%) at 0° C. under N₂. The resulting mixture was stirred at 0° C. for 1 h. Then CH₃I (481.7 mg, 3.40 mmol) was added to the mixture at 0° C. under N₂. The resulting mixture was stirred at 0° C. for another 1 h. After the reaction was completed, the reaction mixture was quenched with NH₄Cl and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 6-chloro-2-iodo-1-methylpyrrolo[3,2-c]pyridine (Compound 49c) (530.0 mg, 80%) as a white solid. LCMS (ESI, m/z): [M+H]⁺=292.9.

Step 3: Synthesis of 4-[6-chloro-1-methylpyrrolo[3,2-c]pyridin-2-yl]-3-methylphenol (Compound 49e)

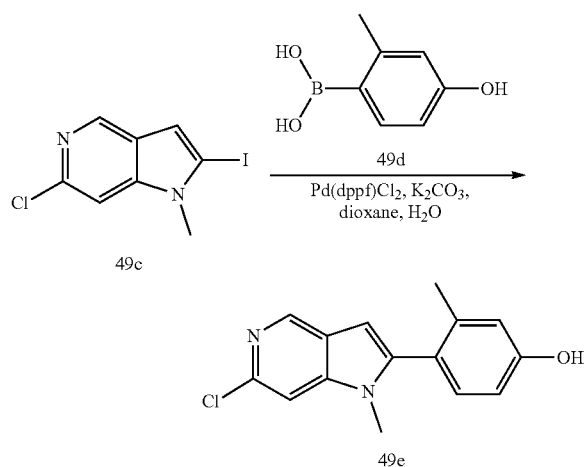

To a solution of 6-chloro-2-iodo-1-methylpyrrolo[3,2-c]pyridine (Compound 49c) (480.0 mg, 1.64 mmol) in 1,4-dioxane/H$_2$O (10.0/2.0 mL) was added 4-hydroxy-2-methylphenylboronic acid (Compound 49d) (299.2 mg, 1.97 mmol), K$_2$CO$_3$ (680.4 mg, 4.92 mmol) and Pd(dppt)Cl$_2$ (134.0 mg, 0.16 mmol) at room temperature under N$_2$. The resulting mixture was stirred at 80° C. for 16 h. After the reaction was completed, the reaction was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (4/1, v/v) to afford 4-[6-chloro-1-methylpyrrolo[3,2-c]pyridin-2-yl]-3-methylphenol (Compound 49e) (125.0 mg, 27%) as a pink solid. LCMS (ESI, m/z): [M+H]$^+$=273.1.

Step 4: Synthesis of N-[2-(4-hydroxy-2-methylphenyl)-1-methylpyrrolo[3,2-c]pyridin-6-yl]cyclopropanecarboxamide (Compound 49)

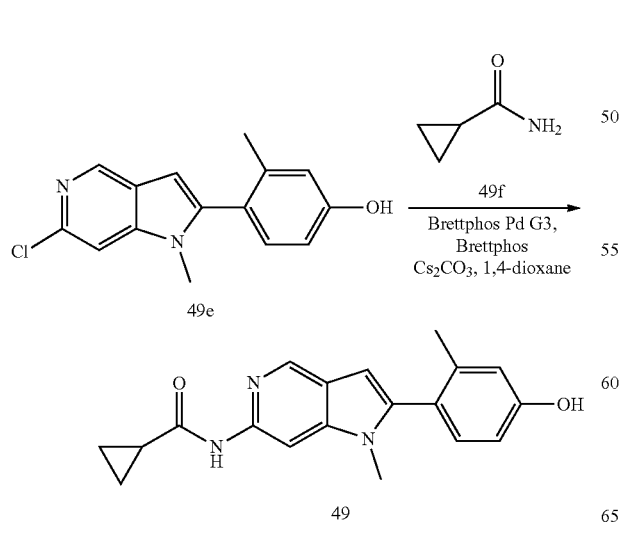

To a solution of 4-[6-chloro-1-methylpyrrolo[3,2-c]pyridin-2-yl]-3-methylphenol (Compound 49e) (95.0 mg, 0.35 mmol) in 1,4-dioxane (5.0 mL) was added cyclopropanecarboxamide (Compound 49f) (592.9 mg, 6.97 mmol), Cs$_2$CO$_3$ (340.5 mg, 1.05 mmol), BrettPhos (37.4 mg, 0.07 mmol) and BrettPhos Pd G3 (31.6 mg, 0.04 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep OBD C$_{18}$ Column, 30×150 mm, 5 um; Mobile Phase A:Water (10 mmol NH$_4$HCO$_3$), Mobile Phase B: ACN; Flow rate: 60 mL/min; Gradient: 31% B to 61% B in 7 min; 254 nm) to afford N-[2-(4-hydroxy-2-methylphenyl)-1-methylpyrrolo[3,2-c]pyridin-6-yl]cyclopropanecarboxamide (Compound 49) (27.9 mg, 24%) as a white solid. LCMS (ESI, m/z): [M+H]$^+$=322.2. $^1$H NMR (300 MHz, DMSO-d$_6$): δ 10.61 (s, 1H), 9.69 (s, 1H), 8.53 (s, 1H), 8.13 (s, 1H), 7.12 (d, J=8.4 Hz, 1H), 6.78-6.69 (m, 2H), 6.41 (s, 1H), 3.58 (s, 3H), 2.07-2.00 (m, 4H), 0.86-0.78 (m, 4H).

Example S50: Synthesis of N-[2-(2-methoxypyridin-3-yl)-1-methylpyrrolo[3,2-c]pyridin-6-yl]cyclopropanecarboxamide (Compound 50)

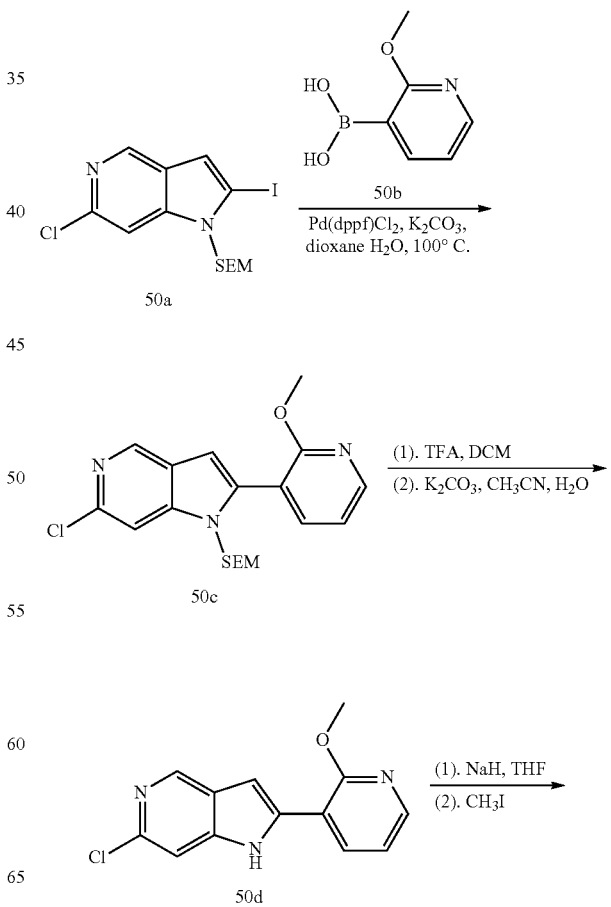

277

-continued

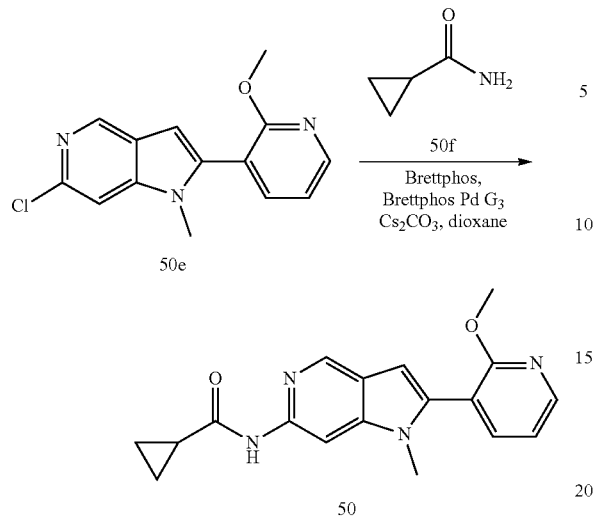

278

Step 2: Synthesis of 3-[6-chloro-1H-pyrrolo[3,2-c]pyridin-2-yl]-2-methoxypyridine (Compound 50d)

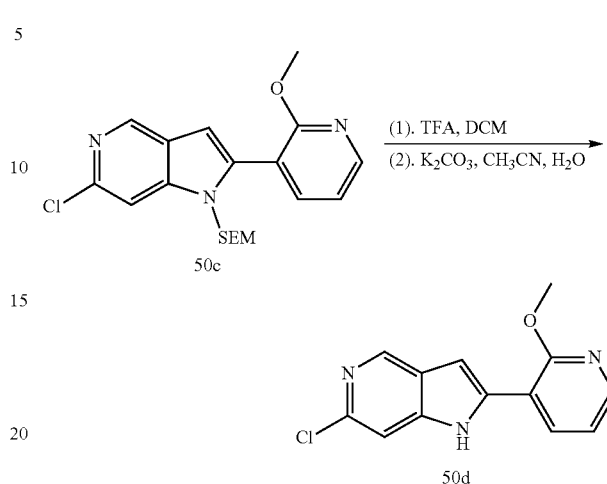

Step 1: Synthesis of 3-(6-chloro-1-[[2-(trimethylsilyl)ethoxy]methyl]pyrrolo[3,2-c]pyridin-2-yl)-2-methoxypyridine (Compound 50c)

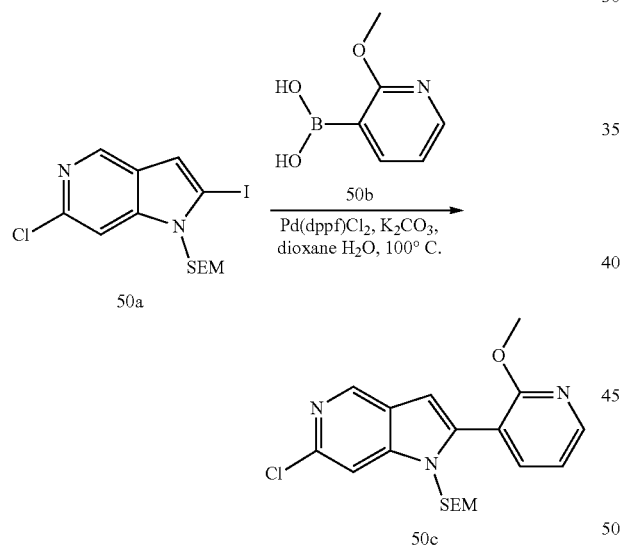

To a solution of 6-chloro-2-iodo-1-[[2-(trimethylsilyl)ethoxy]methyl]pyrrolo[3,2-c]pyridine (Compound 50a) (500.0 mg, 1.23 mmol) in dioxane/$H_2O$ (10.0/1.0 mL) was added 2-methoxypyridin-3-ylboronic acid (Compound 50b) (224.5 mg, 1.48 mmol), $K_2CO_I$ (507.9 mg, 3.70 mmol) and Pd(dppf)$Cl_2$ (179.1 mg, 0.25 mmol). The mixture was stirred at 100° C. for 4 h under $N_2$. After the reaction was completed, the resulting mixture was concentrated under reduced pressure. The residue was purified by flash column chromatography with petroleum ether/ethyl acetate (2/1, v/v) to afford 3-(6-chloro-1-[[2-(trimethylsilyl)ethoxy]methyl]pyrrolo[3,2-c]pyridin-2-yl)-2-methoxypyridine (Compound 50c) (430.0 mg, 90%) as a yellow oil. LCMS (ESI, m/z): [M+H]$^+$=390.1.

To a solution of 3-(6-chloro-1-[[2-(trimethylsilyl)ethoxy]methyl]pyrrolo[3,2-c]pyridin-2-yl)-2-methoxypyridine (Compound 50c) (430.0 mg, 1.13 mmol) in DCM (5.0 mL) was added TFA (5.0 mL). The mixture was stirred at room temperature for 2 h. The mixture was evaporated under reduced pressure. The residue was re-dissolved in ACN/$H_2O$ (5.0/1.0 mL). Then $K_2CO_3$ (914.4 mg, 6.62 mmol) was added to the mixture. The mixture was stirred at room temperature for another 16 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/1, v/v) to afford 3-[6-chloro-1H-pyrrolo[3,2-c]pyridin-2-yl]-2-methoxypyridine (Compound 50d) (170.0 mg, 59%) as a yellow solid. LCMS (ESI, m/z): [M+H]$^+$=260.1.

Step 3: Synthesis of 3-[6-chloro-1-methylpyrrolo[3,2-c]pyridin-2-yl]-2-methoxypyridine (Compound 50e)

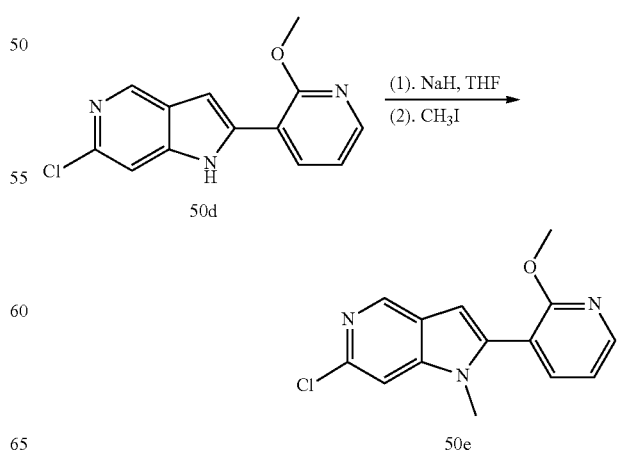

To a solution of 3-[6-chloro-1H-pyrrolo[3,2-c]pyridin-2-yl]-2-methoxypyridine (Compound 50d) (170.0 mg, 0.65 mmol) in THF (5.0 mL) was added NaH (47.1 mg, 60%) at 0° C. under N₂. The mixture was stirred at 0° C. for 2 h under N₂. Then a solution of CH₃I (139.6 mg, 0.94 mmol) in THF (5.0 mL) was added dropwise to the mixture at 0° C. The mixture was stirred at 0° C. for another 2 h. After the reaction was completed, the resulting mixture was quenched with water and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/2, v/v) to afford 3-[6-chloro-1-methylpyrrolo[3,2-c]pyridin-2-yl]-2-methoxypyridine (Compound 50e) (140.0 mg, 78%) as a yellow solid. LCMS (ESI, m/z): [M+H]⁺=274.1.

Step 4: Synthesis of N-[2-(2-methoxypyridin-3-yl)-1-methylpyrrolo[3,2-c]pyridin-6-yl]cyclopropanecarboxamide (Compound 50)

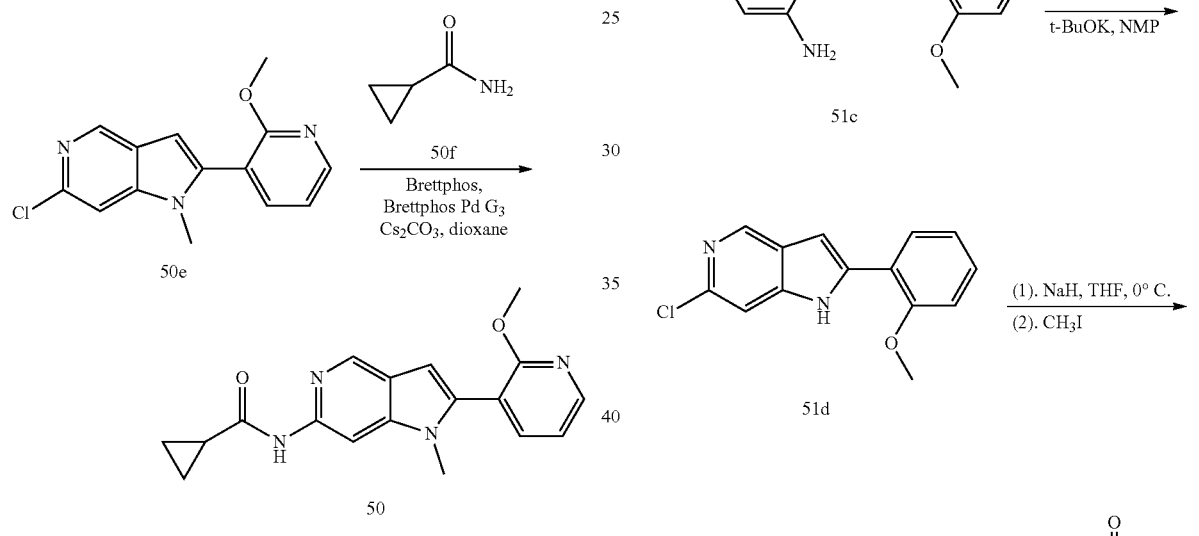

To a solution of 3-[6-chloro-1-methylpyrrolo[3,2-c]pyridin-2-yl]-2-methoxypyridine (Compound 50e) (120.0 mg, 0.38 mmol) in dioxane (10.0 mL) was added cyclopropanecarboxamide (Compound 50f) (111.9 mg, 1.35 mmol), Brettphos Pd G3 (39.7 mg, 0.04 mmol), BrettPhos (47.6 mg, 0.08 mmol) and Cs₂CO₃ (428.5 mg, 1.35 mmol) at room temperature under N₂. The reaction mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by Prep-HPLC with the following conditions (Column: XBridge Prep OBD C₁₈ Column, 30×150 mm, 5 um; Mobile Phase A:Water (10 mmol/L NH₄HCO₃), Mobile Phase B: ACN; Flow rate: 60 mL/min; Gradient: 33% B to 63% B in 7 min; 254 nm) to afford N-[2-(2-methoxypyridin-3-yl)-1-methylpyrrolo[3,2-c]pyridin-6-yl]cyclopropanecarboxamide (Compound 50) (32.4 mg, 23%) as a white solid. LCMS (ESI, m/z): [M+H]⁺=323.2. ¹H NMR (300 MHz, DMSO-d₆): δ 10.64 (s, 1H), 8.57 (s, 1H), 8.33-8.30 (m, 1H), 8.15 (s, 1H), 7.83-7.80 (m, 1H), 7.18-7.14 (m, 1H), 6.59 (s, 1H), 3.91 (s, 3H), 3.49 (s, 3H), 2.06-1.98 (m, 1H), 0.83-0.78 (m, 4H).

Example S51: Synthesis of (1S,2S)-2-fluoro-N-[2-(2-methoxyphenyl)-1-methylpyrrolo[3,2-c]pyridin-6-yl]cyclopropane-1-carboxamide (Compound 51)

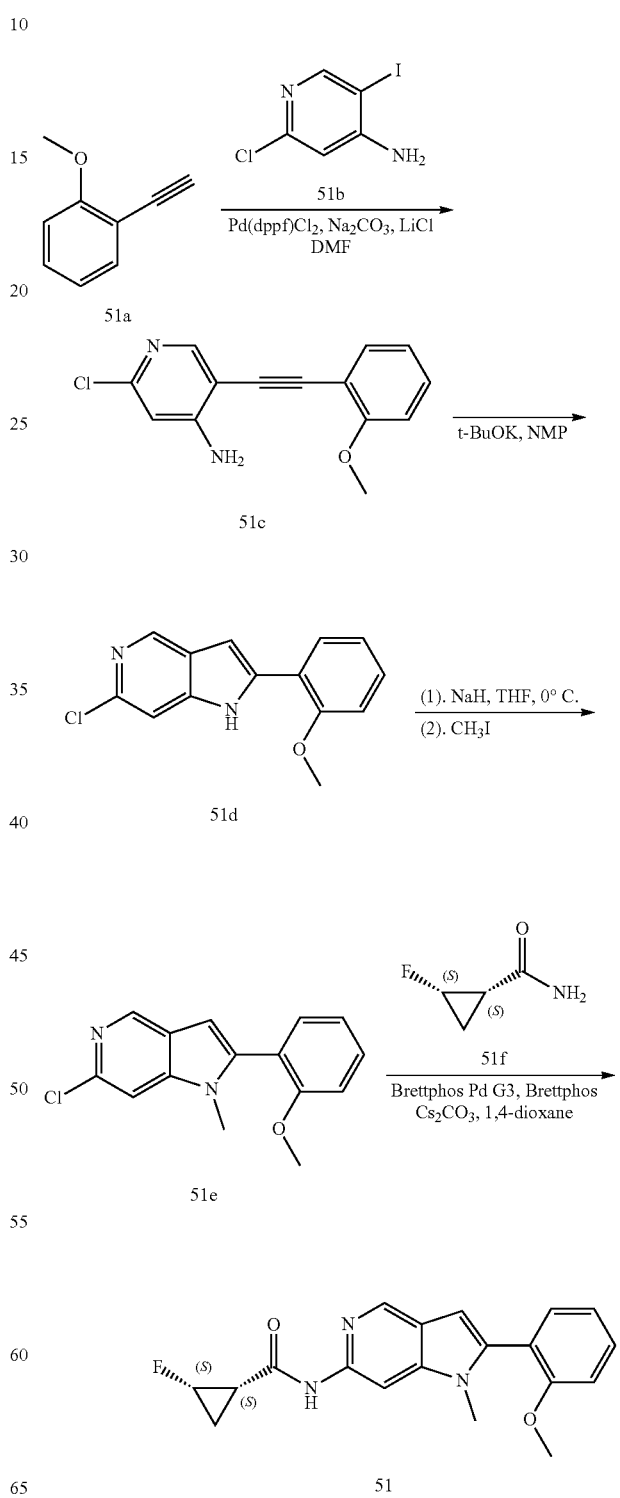

Step 1: Synthesis of 2-chloro-5-((2-methoxyphenyl)ethynyl)pyridin-4-amine (Compound 51c)

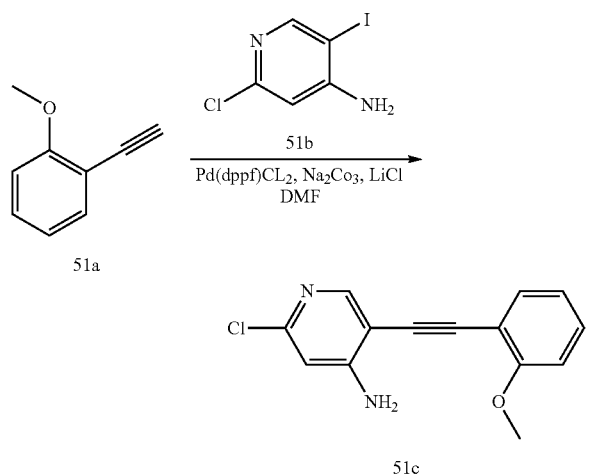

To a solution of 1-ethynyl-2-methoxybenzene (Compound 51a) (1.0 g, 7.56 mmol) in DMF (10.0 mL) was added 2-chloro-5-iodopyridin-4-amine (Compound 51b) (2.3 g, 9.08 mmol), Na$_2$CO$_3$ (4.0 g, 37.83 mmol), LiCl (320.7 mg, 7.56 mmol) and Pd(dppf)Cl$_2$ (553.6 mg, 0.75 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (94/6, v/v) to afford 2-chloro-5-((2-methoxyphenyl)ethynyl)pyridin-4-amine (Compound 51c) (600.0 mg, 30%) as a brown solid. LCMS (ESI, m/z): [M+H]$^+$=259.1.

Step 2: Synthesis of 6-chloro-2-(2-methoxyphenyl)-1H-pyrrolo[3,2-c]pyridine (Compound 51d)

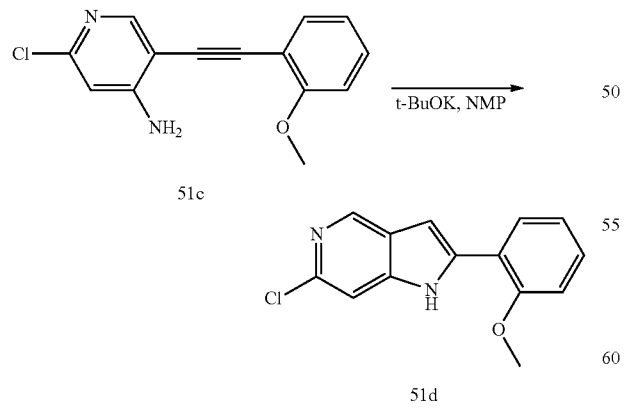

To a solution of 2-chloro-5-[2-(2-methoxyphenyl)ethynyl]pyridin-4-amine (Compound 51c) (400.0 mg, 1.54 mmol) in NMP (7.0 mL) was added t-BuOK (867.5 mg, 7.73 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure to afford 6-chloro-2-(2-methoxyphenyl)-1H-pyrrolo[3,2-c]pyridine (Compound 51d) (240.0 mg, crude) as a yellow solid. LCMS (ESI, m/z): [M+H]$^+$=259.1.

Step 3: Synthesis of 6-chloro-2-(2-methoxyphenyl)-1-methylpyrrolo[3,2-c]pyridine (Compound 51e)

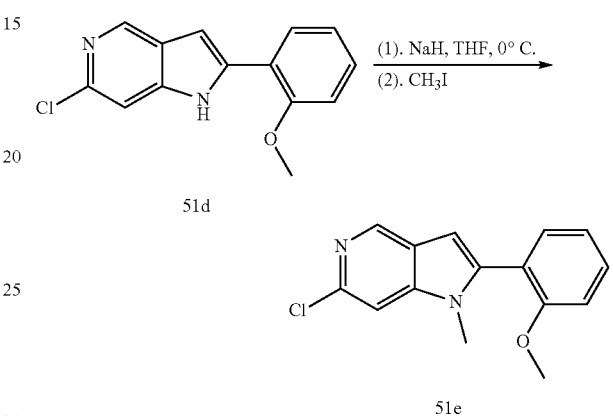

To a solution of 6-chloro-2-(2-methoxyphenyl)-1H-pyrrolo[3,2-c]pyridine (Compound 51d) (240.0 mg, 0.93 mmol) in THF (5.0 mL) was added NaH (26.7 mg, 60%) at 0° C. under N$_2$. The resulting mixture was stirred at 0° C. for 1 h under N$_2$. Then CH$_3$I (158.1 mg, 1.11 mmol) was added dropwise to the mixture at 0° C. under N$_2$. The resulting mixture was stirred at 0° C. for another 1 h. After the reaction was completed, the mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (4/1, v/v) to afford 6-chloro-2-(2-methoxyphenyl)-1-methylpyrrolo[3,2-c]pyridine (Compound 51e) (230.0 mg, 91%) as a black solid. LCMS (ESI, m/z): [M+H]$^+$=273.1.

Step 4: Synthesis of (1S,2S)-2-fluoro-N-[2-(2-methoxyphenyl)-1-methylpyrrolo[3,2-c]pyridin-6-yl]cyclopropane-1-carboxamide (Compound 51)

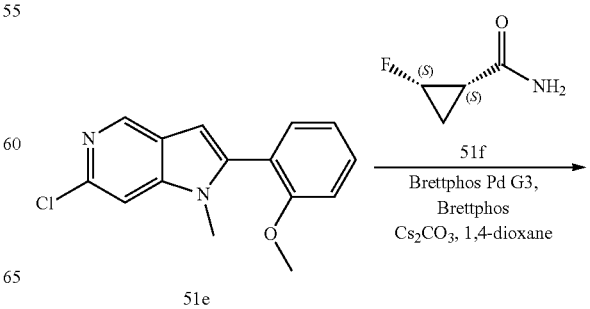

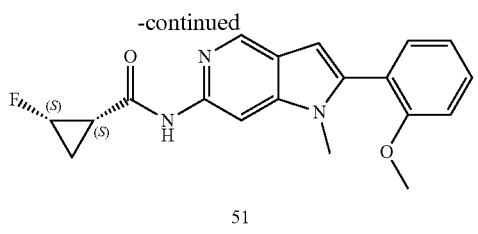

51

To a solution of 6-chloro-2-(2-methoxyphenyl)-1-methylpyrrolo[3,2-c]pyridine (Compound 51e) (200.0 mg, 0.73 mmol) in dioxane (3.0 ml) was added (1S,2S)-2-fluorocyclopropane-1-carboxamide (Compound 51f) (226.8 mg, 2.20 mmol), BrettPhos (39.4 mg, 0.07 mmol), Cs$_2$CO$_3$ (716.8 mg, 2.20 mmol) and BrettPhos Pd G3 (132.9 mg, 0.07 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) and then purified by Prep-HPLC with the following conditions (Column: Xselect CSH OBD Column 30×150 mm, 5 um; Mobile Phase A:Water (0.1% FA), Mobile Phase B: ACN; Flow rate: 60 mL/min; Gradient: 5% B to 35% B in 7 min; 254 nm;) to afford (1S,2S)-2-fluoro-N-[2-(2-methoxyphenyl)-1-methylpyrrolo[3,2-c]pyridin-6-yl]cyclopropane-1-carboxamide (Compound 51) (42.3 mg, 17%) as a white solid. LCMS (ESI, m/z): [M+H]$^+$=340.2. $^1$H NMR (400 MHz, DMSO-d$_6$): δ 10.64 (s, 1H), 8.54 (s, 1H), 8.12 (s, 1H), 7.50-7.46 (m, 1H), 7.35-7.33 (m, 1H), 7.17 (d, J=8.0 Hz, 1H), 7.08-7.05 (m, 1H), 6.48 (s, 1H), 5.00-4.80 (m, 1H), 3.78 (s, 3H), 3.45 (s, 3H), 2.23-2.20 (m, 1H), 1.69-1.60 (m, 1H), 1.17-1.11 (m, 1H).

Example S52: Synthesis of (1S,2S)-2-fluoro-N-(2-(2-methoxyphenyl)-1,3-dimethyl-1H-pyrrolo[3,2-c]pyridin-6-yl)cyclopropane-1-carboxamide (Compound 52)

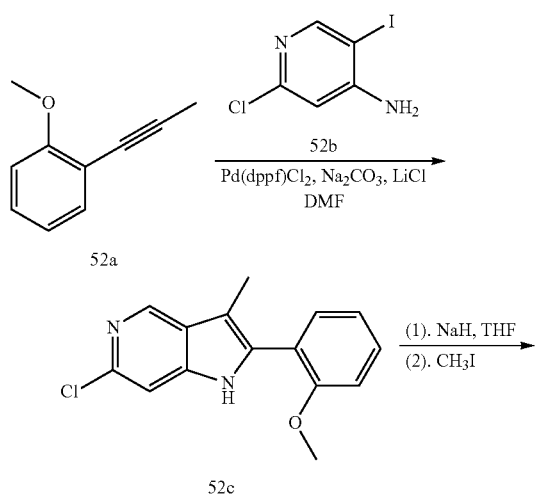

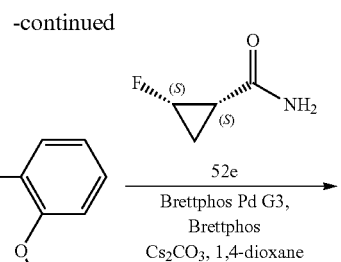

52d

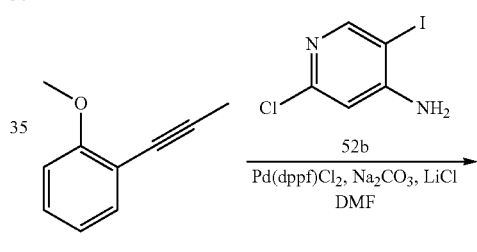

52

Step 1: Synthesis of 6-chloro-2-(2-methoxyphenyl)-3-methyl-1H-pyrrolo[3,2-c]pyridine (Compound 52c)

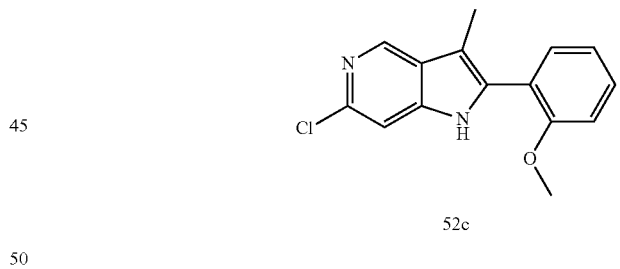

To a solution of 2-chloro-5-iodopyridin-4-amine (Compound 52b) (2.5 g, 9.63 mmol) in DMF (40.0 mL) was added 1-methoxy-2-(prop-1-yn-1-yl)benzene (Compound 52a) (1.7 g, 11.55 mmol), Na$_2$CO$_3$ (5.1 g, 48.1 mmol), LiCl (408.2 mg, 9.63 mmol) and Pd(dppf)Cl$_2$ (704.5 mg, 0.96 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (74/26, v/v) to afford 6-chloro-2-(2-methoxyphenyl)-3-methyl-1H-pyrrolo[3,2-c]pyridine (Compound 52c) (1.5 g, 57%) as a yellow solid. LCMS (ESI, m/z): [M+H]$^+$=273.1.

Step 2: Synthesis of 6-chloro-2-(2-methoxyphenyl)-1,3-dimethyl-1H-pyrrolo[3,2-c]pyridine (Compound 52d)

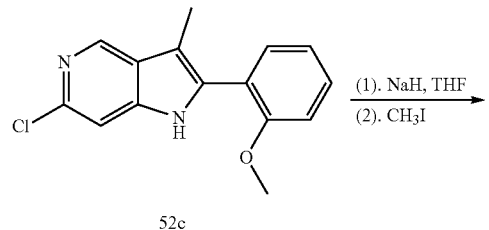

52c

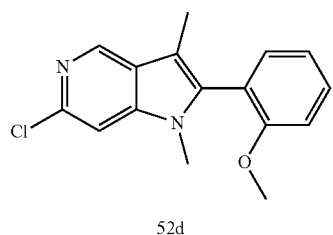

52d

To a solution of 6-chloro-2-(2-methoxyphenyl)-3-methyl-1H-pyrrolo[3,2-c]pyridine (Compound 52c) (1.5 g, 5.86 mmol) in THF (30.0 mL) was added NaH (703.9 mg, 60%) at 0° C. under N₂. The resulting mixture was stirred at 0° C. for 1 h. Then CH₃I (4.2 g, 29.31 mmol) was added dropwise to the mixture at 0° C. under N₂. The resulting mixture was stirred at 0° C. for another 1 h. After the reaction was completed, the reaction mixture was quenched with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (79/21, v/v) to afford 5-chloro-2-(2-methoxyphenyl)-1,3-dimethyl-1H-pyrrolo[2,3-c]pyridine (Compound 52d) (960.0 mg, 57%) as a light yellow solid. LCMS (ESI, m/z): [M+H]⁺=287.1.

Step 3: Synthesis of (1S,2S)-2-fluoro-N-(2-(2-methoxyphenyl)-1,3-dimethyl-1H-pyrrolo[3,2-c]pyridin-6-cyclopropane-1-carboxamide (Compound 52)

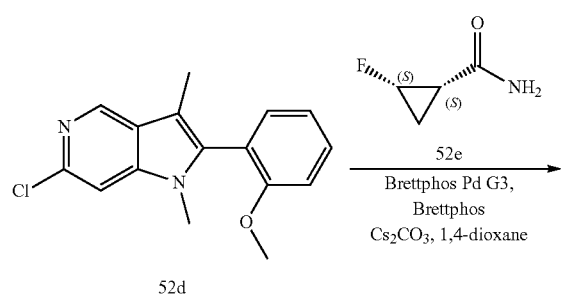

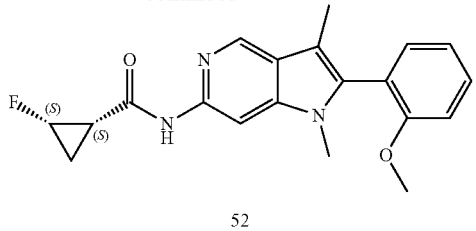

52

To a solution of 6-chloro-2-(2-methoxyphenyl)-1,3-dimethyl-1H-pyrrolo[3,2-c]pyridine (Compound 52d) (200.0 mg, 0.70 mmol) in 1,4-dioxane (10.0 mL) was added (1S,2S)-2-fluorocyclopropane-1-carboxamide (Compound 52e) (359.5 mg, 3.49 mmol), Cs₂CO₃ (681.7 mg, 2.09 mmol), BrettPhos (74.9 mg, 0.14 mmol) and BrettPhos Pd G3 (63.2 mg, 0.07 mmol) at room temperature under N₂. The resulting mixture was irradiated with microwave radiation at 120° C. for 1.5 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (30/70, v/v) and then purified by Prep-HPLC with the following conditions (Column: XBridge Prep OBD C₁₈ Column, 30×150 mm, 5 um; Mobile Phase A:Water (10 mmol/L NH₄HCO₃), Mobile Phase B:ACN; Flow rate: 60 mL/min; Gradient: 47% B to 77% B in 7 min; 254 nm) to afford (1S,2S)-2-fluoro-N-(2-(2-methoxyphenyl)-1,3-dimethyl-1H-pyrrolo[3,2-c]pyridin-6-yl)cyclopropane-1-carboxamide (Compound 52) (46.4 mg, 18%) as a white solid. LCMS (ESI, m/z): [M+H]⁺= 354.2, ¹H NMR (300 MHz, DMSO-d₆): δ 10.65 (s, 1H), 8.55 (d, J=0.9 Hz, 1H), 8.10 (s, 1H), 7.54-7.48 (m, 1H), 7.31-7.28 (m, 1H), 7.21 (d, J=8.4 Hz, 1H), 7.14-7.09 (m, 1H), 5.05-4.80 (m, 1H), 3.78 (s, 3H), 3.40 (s, 3H), 2.26-2.21 (m, 1H), 2.13 (s, 3H), 1.71-1.62 (m, 1H), 1.20-1.12 (m, 1H).

Example S53: Synthesis of (1R,2R)-2-fluoro-N-[2-(2-methoxyphenyl)-1,3-dimethylpyrrolo[3,2-c]pyridin-6-yl]cyclopropane-1-carboxamide (Compound 53)

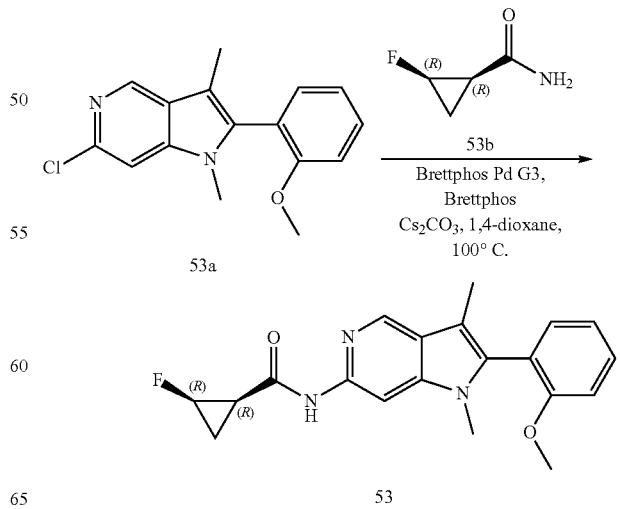

To a solution of 6-chloro-2-(2-methoxyphenyl)-1,3-dimethylpyrrolo[3,2-c]pyridine (Compound 53a) (200.0 mg, 0.69 mmol) in 1,4-dioxane (10.0 mL) was added (1R,2R)-2-fluorocyclopropane-1-carboxamide (Compound 53b) (359.5 mg, 3.49 mmol), Cs$_2$CO$_3$ (681.7 mg, 2.09 mmol), BrettPhos (74.9 mg, 0.14 mmol) and BrettPhos Pd G3 (63.2 mg, 0.07 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep OBD C$_{18}$ Column, 30×150 mm, 5 um; Mobile Phase A:Water (10 mmol/L NH$_4$HCO$_3$), Mobile Phase B: ACN; Flow rate: 60 mL/min; Gradient: 37% B to 67% B in 7 min; 254 nm) to afford (1R,2R)-2-fluoro-N-[2-(2-methoxyphenyl)-1,3-dimethylpyrrolo[3,2-c]pyridin-6-yl]cyclopropane-1-carboxamide (Compound 53) (11.2 mg, 4%) as a white solid. LCMS (ESI, m/z): [M+H]$^+$=354.2. $^1$H NMR (400 MHz, DMSO-d$_6$): δ 10.66 (s, 1H), 8.54 (s, 1H), 8.10 (s, 1H), 7.53-7.49 (m, 1H), 7.29 (d, J=7.6 Hz, 1H), 7.21 (d, J=8.0 Hz, 1H), 7.13-7.09 (m, 1H), 5.02-4.82 (m, 1H), 3.78 (s, 3H), 3.40 (s, 3H), 2.33-2.23 (m, 1H), 2.13 (s, 3H), 1.69-1.63 (m, 1H), 1.20-1.15 (m, 1H).

Example S54: Synthesis of (1S,2S)-2-fluoro-N-(2-(2-fluoro-6-methoxyphenyl)-1,3-dimethyl-1H-pyrrolo[3,2-c]pyridin-6-yl)cyclopropane-1-carboxamide (Compound 54)

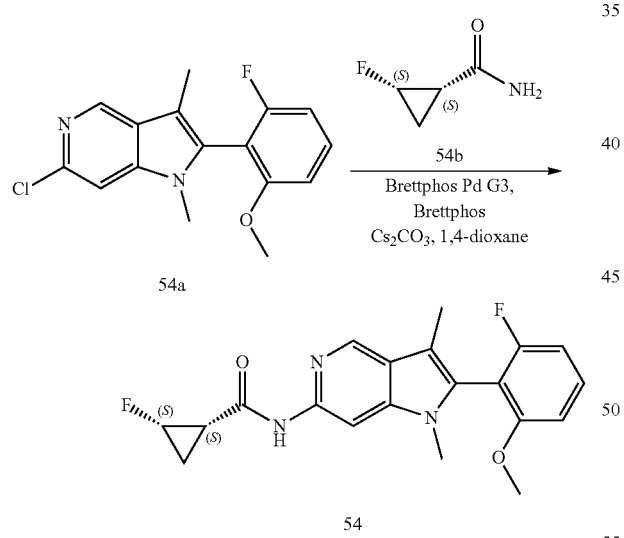

To a solution of 6-chloro-2-(2-fluoro-6-methoxyphenyl)-1,3-dimethyl-1H-pyrrolo[3,2-c]pyridine (Compound 54a) (80.0 mg, 0.26 mmol) in 1,4-dioxane (2.0 mL) was added (1S,2S)-2-fluorocyclopropane-1-carboxamide (Compound 54b) (135.3 mg, 1.31 mmol), Cs$_2$CO$_3$ (256.6 mg, 0.79 mmol), BrettPhos (28.2 mg, 0.05 mmol) and BrettPhos Pd G3 (23.8 mg, 0.03 mmol) at room temperature under N$_2$. The resulting mixture was stirred at 100° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (17/83, v/v) and then purified by Prep-HPLC with the following conditions (Column: XBridge Prep OBD C$_{18}$ Column, 30×150 mm, 5 um; Mobile Phase A:Water (10 mmol/L NH$_4$HCO$_3$), Mobile Phase B:ACN; Flow rate: 60 mL/min; Gradient: 36% B to 66% B in 10 min; 254 nm) to afford (1S,2S)-2-fluoro-N-(2-(2-fluoro-6-methoxyphenyl)-1,3-dimethyl-1H-pyrrolo[3,2-c]pyridin-6-yl)cyclopropane-1-carboxamide (Compound 54) (12.2 mg, 12%) as a white solid. LCMS (ESI, m/z): [M+H]$^+$=372.2. $^1$H NMR (300 MHz, DMSO-d$_6$): δ 10.70 (s, 1H), 8.57 (d, J=0.9 Hz, 1H), 8.12 (s, 1H), 7.61-7.53 (m, 1H), 7.09-6.99 (m, 2H), 5.05-4.79 (m, 1H), 3.80 (s, 3H), 3.40 (s, 3H), 2.29-2.22 (m, 1H), 2.10 (s, 3H), 1.72-1.61 (m, 1H), 1.20-1.13 (m, 1H).

Example S55: Synthesis of (1R,2R)-2-fluoro-N-[2-(2-fluoro-6-methoxyphenyl)-1,3-dimethylpyrrolo[3,2-c]pyridin-6-yl]cyclopropane-1-carboxamide (Compound 55)

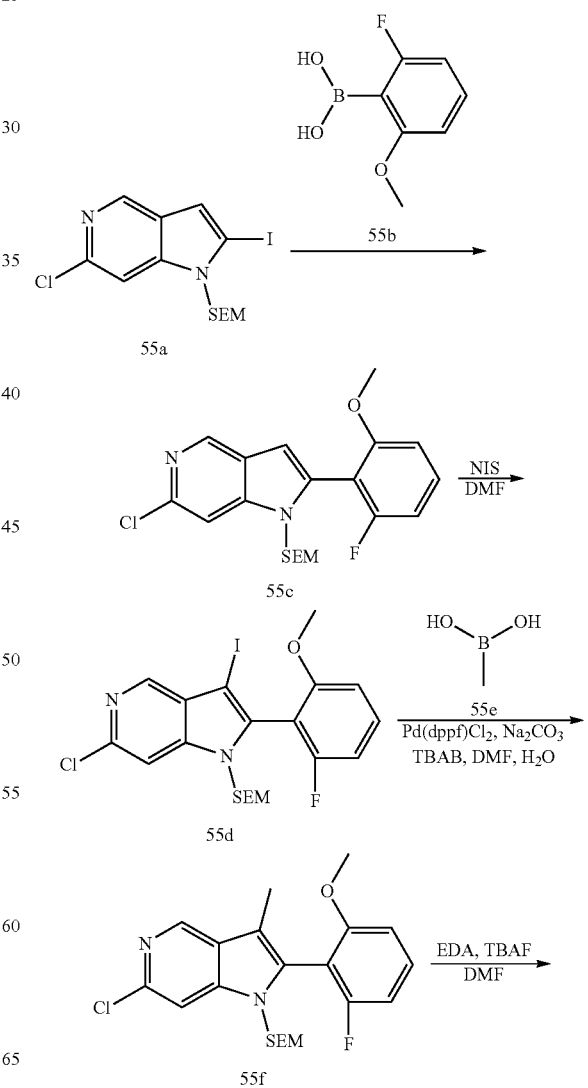

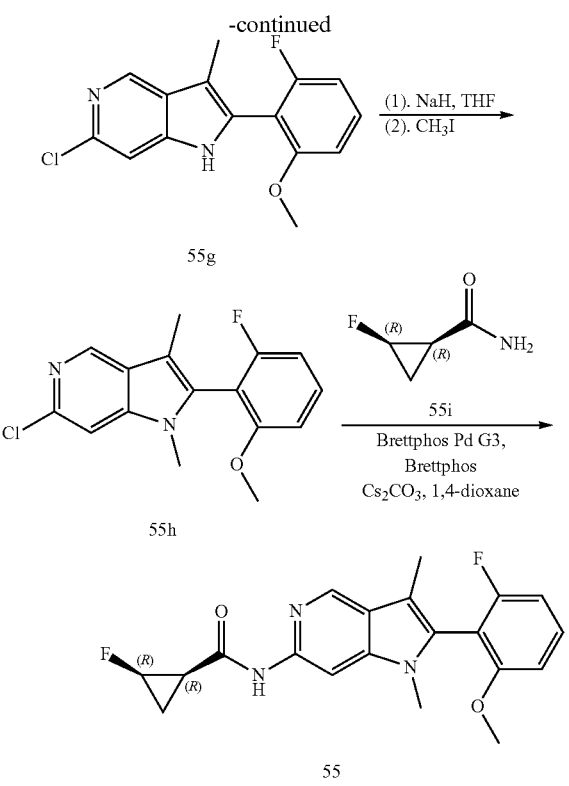

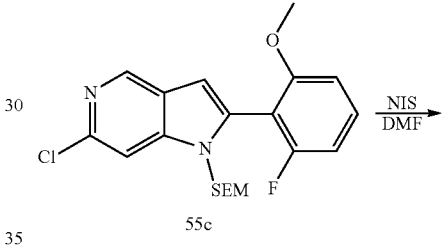

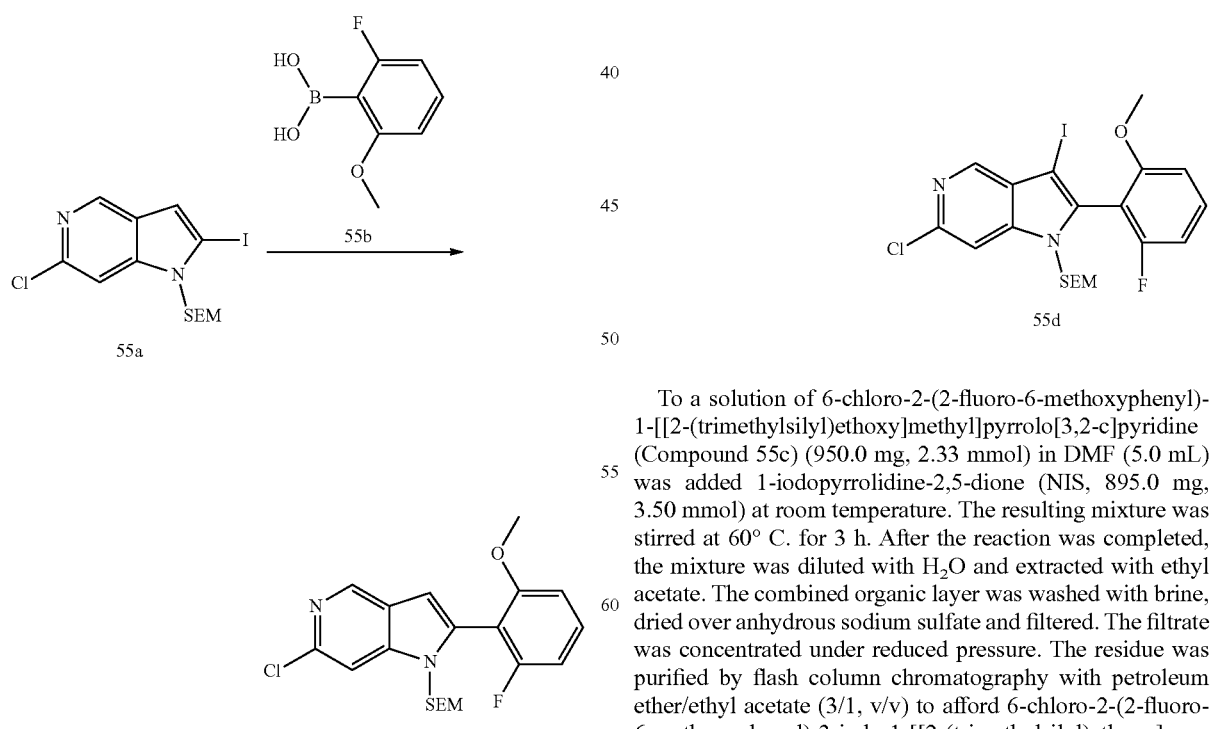

To a solution of 6-chloro-2-iodo-1-[[2-(trimethylsilyl)ethoxy]methyl]pyrrolo[3,2-c]pyridine (Compound 55a) (3.0 g, 7.34 mmol) in 1,4-dioxane/H$_2$O (25.0/5.0 mL) was added 3-fluoro-2-methoxyphenylboronic acid (Compound 55b) (1.5 g, 8.81 mmol), K$_2$CO$_3$ (2.0 g, 14.68 mmol) and Pd(PPh$_3$)$_4$ (0.6 g, 0.73 mmol) at room temperature under N$_2$. The resulting mixture was stirred at 100° C. for 16 h under N$_2$. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (4/1, v/v) to afford 6-chloro-2-(2-fluoro-6-methoxyphenyl)-1-[[2-(trimethylsilyl)ethoxy]methyl]pyrrolo[3,2-c]pyridine (Compound 55c) (1.0 g, 48%) as a yellow green oil. LCMS (ESI, m/z): [M+H]$^+$=407.1.

Step 2: Synthesis of 6-chloro-2-(2-fluoro-6-methoxyphenyl)-3-iodo-1-[[2-(trimethylsilyl)ethoxy]methyl]pyrrolo[3,2-c]pyridine (Compound 55d)

To a solution of 6-chloro-2-(2-fluoro-6-methoxyphenyl)-1-[[2-(trimethylsilyl)ethoxy]methyl]pyrrolo[3,2-c]pyridine (Compound 55c) (950.0 mg, 2.33 mmol) in DMF (5.0 mL) was added 1-iodopyrrolidine-2,5-dione (NIS, 895.0 mg, 3.50 mmol) at room temperature. The resulting mixture was stirred at 60° C. for 3 h. After the reaction was completed, the mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/1, v/v) to afford 6-chloro-2-(2-fluoro-6-methoxyphenyl)-3-iodo-1-[[2-(trimethylsilyl)ethoxy]methyl]pyrrolo[3,2-c]pyridine (Compound 55d) (870.0 mg, 69%) as a brown oil. LCMS (ESI, m/z): [M+H]$^+$=533.0.

Step 3: Synthesis of 6-chloro-2-(2-fluoro-6-methoxyphenyl)-3-methyl-1-[[2-(trimethylsilyl)ethoxy]methyl]pyrrolo[3,2-c]pyridine (Compound 55f)

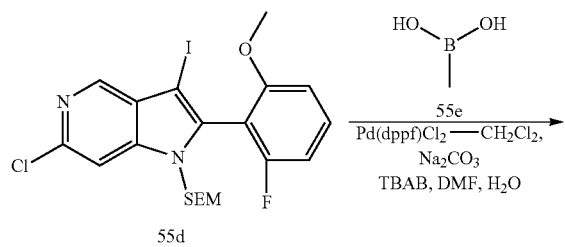

To a solution of 6-chloro-2-(2-fluoro-6-methoxyphenyl)-3-iodo-1-[[2-(trimethylsilyl)ethoxy]methyl]pyrrolo[3,2-c]pyridine (Compound 55d) (820.0 mg, 1.54 mmol) in DMF/H₂O (16.0/4.0 mL) was added methylboronic acid (Compound 55e) (460.6 mg, 7.69 mmol), Na₂CO₃ (489.3 mg, 4.62 mmol), TBAB (99.2 mg, 0.31 mmol) and Pd(dppf)Cl₂·CH₂Cl₂ (125.7 mg, 0.15 mmol) at room temperature under N₂. The resulting mixture was stirred at 80° C. for 16 h. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/1, v/v) to afford 6-chloro-2-(2-fluoro-6-methoxyphenyl)-3-methyl-1-[[2-(trimethylsilyl)ethoxy]methyl]pyrrolo[3,2-c]pyridine (Compound 55f) (435.0 mg, 67%) as a brown oil. LCMS (ESI, m/z): [M+H]⁺=421.1.

Step 4: Synthesis of 6-chloro-2-(2-fluoro-6-methoxyphenyl)-3-methyl-1H-pyrrolo[3,2-c]pyridine (Compound 55g)

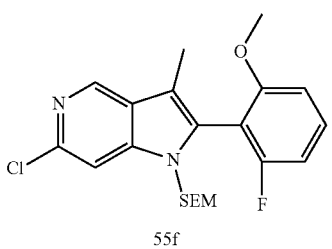

To a solution of 6-chloro-2-(2-fluoro-6-methoxyphenyl)-3-methyl-1-[[2-(trimethylsilyl)ethoxy]methyl]pyrrolo[3,2-c]pyridine (Compound 55f) (385.0 mg, 0.92 mmol) in DMF (5.0 mL) was added ethane-1,2-diamine (274.8 mg, 4.57 mmol) and TBAF (717.4 mg, 2.74 mmol). The resulting mixture was stirred at 80° C. for 16 h. After the reaction was completed, the reaction was diluted with H₂O and extracted with ethyl acetate. The combined organic layer was washed with brine, dried over anhydrous sodium sulfate and filtered. The filtrate was concentrated under reduced pressure. The residue was purified by reverse phase flash column chromatography with H₂O/ACN (1/3, v/v) to afford 6-chloro-2-(2-fluoro-6-methoxyphenyl)-3-methyl-1H-pyrrolo[3,2-c]pyridine (Compound 55g) (200.0 mg, 75%) as a brown oil. LCMS (ESI, m/z): [M+H]⁺=291.1.

Step 5: Synthesis of 6-chloro-2-(2-fluoro-6-methoxyphenyl)-1,3-dimethylpyrrolo[3,2-c]pyridine (Compound 55h)

To a solution of 6-chloro-2-(2-fluoro-6-methoxyphenyl)-3-methyl-1H-pyrrolo[3,2-c]pyridine (Compound 55g) (150.0 mg, 0.52 mmol) in THF (15.0 mL) was added NaH (61.9 mg, 60%) at 0° C. under N₂. The resulting mixture was stirred at 0° C. for 1 h Then CH₃I (219.7 mg, 1.55 mmol) was added to the mixture at 0° C. The resulting mixture was stirred at 0° C. for another 1 h. After the reaction was completed, the reaction mixture was quenched with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 6-chloro-2-(2-fluoro-6-methoxyphenyl)-1,3-dimethylpyrrolo[3,2-c]pyridine (Compound 55h) (150.0 mg, 95%) as a colorless oil. LCMS (ESI, m/z): [M+H]+=305.1.

Step 6: Synthesis of (1R,2R)-2-fluoro-N-[2-(2-fluoro-6-methoxyphenyl)-1,3-dimethylpyrrolo[3,2-c]pyridin-6-yl]cyclopropane-1-carboxamide (Compound 55)

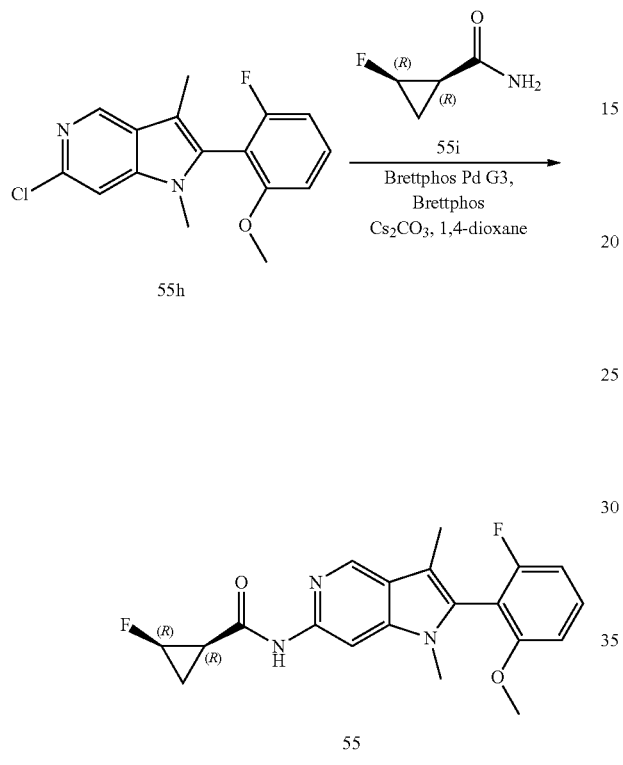

To a solution of 6-chloro-2-(2-fluoro-6-methoxyphenyl)-1,3-dimethylpyrrolo[3,2-c]pyridine (Compound 55h) (150.0 mg, 0.49 mmol) in 1,4-dioxane (6.0 mL) was added (1R,2R)-2-fluorocyclopropane-1-carboxamide (Compound 55I) (253.7 mg, 2.46 mmol), Cs$_2$CO$_3$ (481.1 mg, 1.48 mmol), BrettPhos (52.8 mg, 0.10 mmol) and BrettPhos Pd G3 (44.6 mg, 0.05 mmol) at room temperature under N$_2$. The resulting mixture was irradiated with microwave radiation at 120° C. for 1.5 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep OBD C$_{18}$ Column. 30×150 mm, 5 um; Mobile Phase A:Water (10 mmol/L NH$_4$HCO$_3$), Mobile Phase B: ACN; Flow rate: 60 mL/min; Gradient: 36% B to 66% B in 10 min; 254 nm) to afford (1R,2R)-2-fluoro-N-[2-(2-fluoro-6-methoxyphenyl)-1,3-dimethylpyrrolo[3,2-c]pyridin-6-yl]cyclopropane-1-carboxamide (Compound 55) (13.5 mg, 7%) as a white solid. LCMS (ESI, m/z): [M+H]+ =372.2. H NMR (300 MHz, DMSO-d$_6$): δ 10.68 (s, 1H), 8.57 (s, 1H), 8.11 (s, 1H), 7.60-7.52 (m, 1H), 7.08-6.98 (m, 2H), 5.04-4.79 (m, 1H), 3.80 (s, 3H), 3.31 (s, 3H), 2.73-2.21 (m, 1H), 2.09 (s, 3H), 1.72-1.61 (m, 1H), 1.21-1.12 (m, 1H).

Example S56: Synthesis of (1S,2S)-2-fluoro-N-[2-(2-methoxypyridin-3-yl)-1,3-dimethylpyrrolo[3,2-c]pyridin-6-yl]cyclopropane-1-carboxamide (Compound 56)

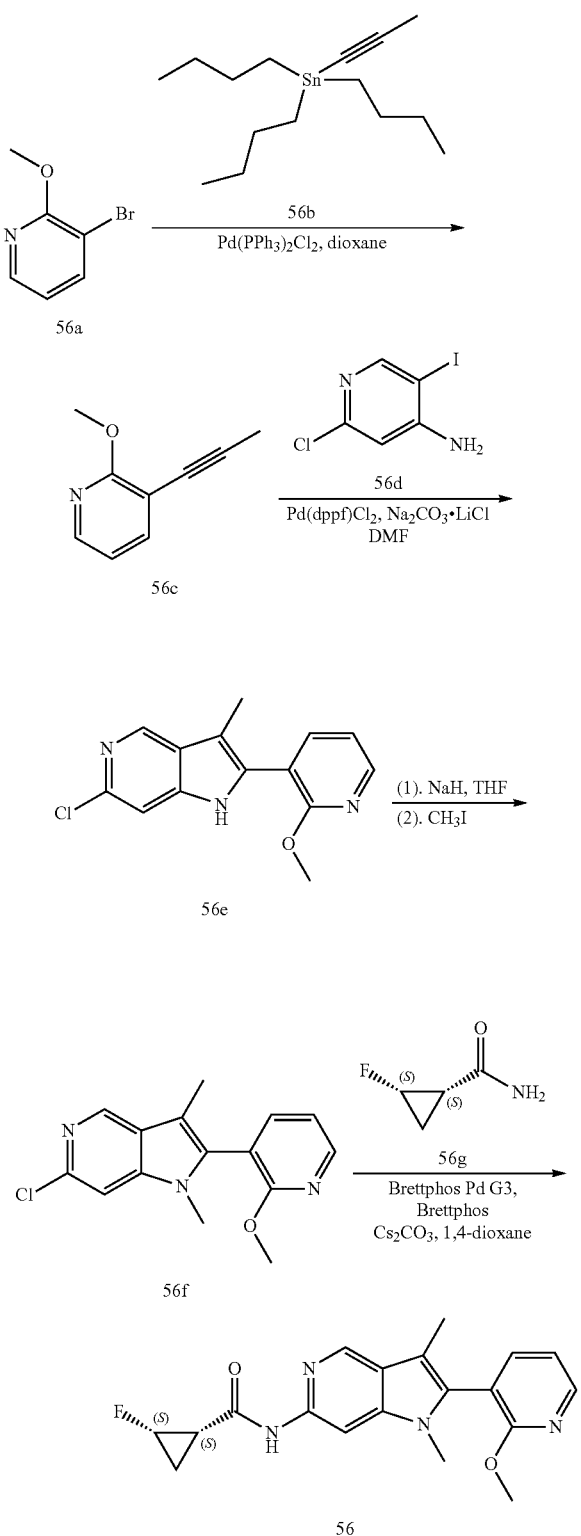

Step 1: Synthesis of 2-methoxy-3-(prop-1-yn-1-yl)pyridine (Compound 56c)

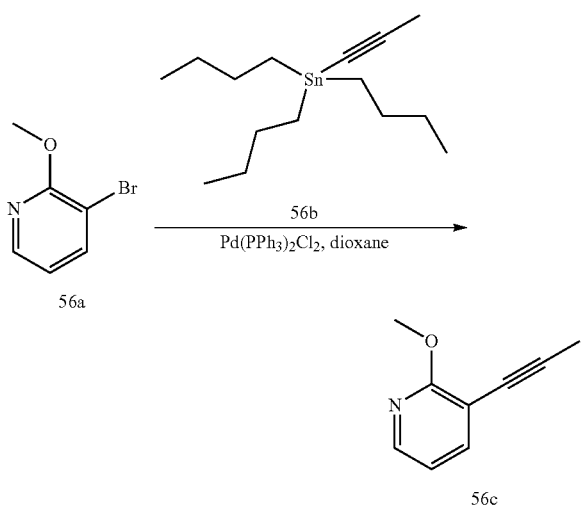

To a solution of 3-bromo-2-methoxypyridine (Compound 56a) (2.0 g, 10.64 mmol) in dioxane (25.0 mL) was added tributyl(prop-1-yn-1-yl)stannane (Compound 56b) (3.9 g, 11.70 mmol) and Pd(PPh₃)₂Cl₂ (0.8 g, 1.07 mmol) at room temperature under N₂. The resulting mixture was stirred at 100° C. for 16 h under N₂. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (10/1, v/v) to afford 2-methoxy-3-(prop-1-yn-1-yl)pyridine (Compound 56c) (569.0 mg, 36%) as a yellow oil. LCMS (ESI, m/z): [M+H]⁺= 148.2.

Step 2: Synthesis of 3-[6-chloro-3-methyl-1H-pyrrolo[3,2-c]pyridin-2-yl]-2-methoxypyridine (Compound 56e)

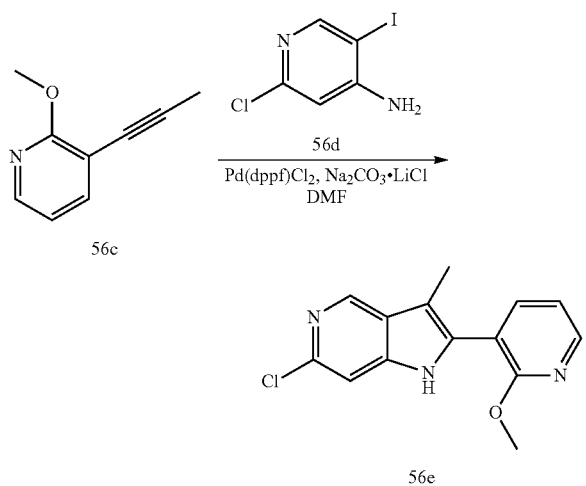

To a solution of 2-methoxy-3-(prop-1-yn-1-yl)pyridine (Compound 56c) (439.0 mg, 2.98 mmol) in DMF (20.0 mL) was added 2-chloro-5-iodopyridin-4-amine (Compound 56d) (632.5 mg, 2.49 mmol), Na₂CO₃ (1.3 g, 12.43 mol), LiCl (105.4 mg, 2.49 mmol) and Pd(dppf)Cl₂ (201.0 mg, 0.25 mmol) at room temperature under N₂. The resulting mixture was stirred at 100° C. for 16 h. After the reaction was completed, the mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 3-[6-chloro-3-methyl-1H-pyrrolo[3,2-c]pyridin-2-yl]-2-methoxypyridine (Compound 56e) (100.0 mg, 15%) as a yellow solid. LCMS (ESI, m/z): [M+H]⁺=274.1.

Step 3: Synthesis of 3-[6-chloro-1,3-dimethylpyrrolo[3,2-c]pyridin-2-yl]-2-methoxypyridine (Compound 56f)

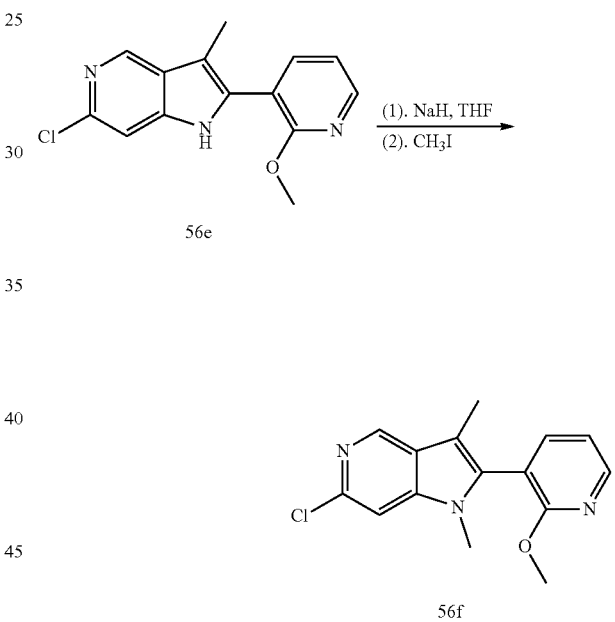

To a solution of 3-[6-chloro-3-methyl-1H-pyrrolo[3,2-c]pyridin-2-yl]-2-methoxypyridine (Compound 56e) (100.0 mg, 0.37 mmol) in THF (20.0 mL) was added NaH (43.8 mg, 60%) at 0° C. under N₂. The resulting mixture was stirred at 0° C. for 1 h. Then methyl iodide (259.3 mg, 1.83 mmol) was added dropwise to the mixture at 0° C. under N₂. The resulting mixture was stirred at 0° C. for another 1 h. After the reaction was completed, the reaction mixture was quenched with water and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 3-[6-chloro-1,3-dimethylpyrrolo[3,2-c]pyridin-2-yl]-2-methoxypyridine (Compound 56) (90.0 mg, 85%) as a white solid. LCMS (ESI, m/z): [M+H]⁺=288.1.

Step 4: Synthesis of (1S,2S)-2-fluoro-N-[2-(2-methoxypyridin-3-yl)-1,3-dimethylpyrrolo[3,2-c]pyridin-6-yl]cyclopropane-1-carboxamide (Compound 56)

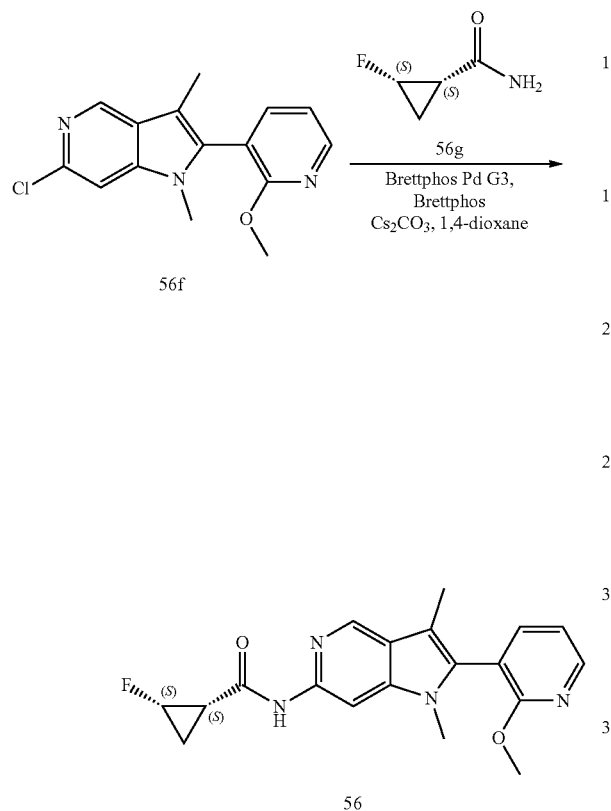

To a solution of 3-[6-chloro-1,3-dimethylpyrrolo[3,2-c]pyridine-2-yl]-2-methoxypyridine (Compound 56) (80.0 mg, 0.28 mmol) in 1,4-dioxane (4.0 mL) was added (1S,2S)-2-fluorocyclopropane-1-carboxamide (Compound 56g) (143.3 mg, 1.39 mmol), BrettPhos (29.9 mg, 0.06 mmol), $Cs_2CO_3$ (271.8 mg, 0.83 mmol) and BrettPhos Pd G3 (25.2 mg, 0.03 mmol) at room temperature under $N_2$. The resulting mixture was stirred with microwave at 120° C. for 1.5 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by Prep-HPLC with the following conditions Column: (XBridge Prep OBD $C_{18}$ Column, 30×150 mm, 5 um; Mobile Phase A:Water (10 mmol/L $NH_4HCO_3$), Mobile Phase B: ACN; Flow rate: 60 mL/min; Gradient: 25% B to 55% B in 10 min; 254 nm) to afford (1S,2S)-2-fluoro-N-[2-(2-methoxypyridin-3-yl)-1,3-dimethylpyrrolo[3,2-c]pyridin-6-yl]cyclopropane-1-carboxamide (Compound 56) (5.1 mg, 5%) as a white solid. LCMS (ESI, m/z): $[M+H]^+$=355.1. $^1H$ NMR (300 MHz, DMSO-$d_6$): δ 10.68 (s, 1H), 8.57 (s, 1H), 8.34-8.32 (m, 1H), 8.11 (s, 1H), 7.77 (d, J=7.2 Hz, 1H), 7.20-7.16 (m, 1H), 5.05-4.78 (m, 1H), 3.88 (s, 3H), 3.42 (s, 3H), 2.28-2.19 (m, 1H), 2.14 (s, 3H), 1.73-1.59 (m, 1H), 1.22-1.12 (m, 1H).

Example S57: Synthesis of (1S,2S)-2-fluoro-N-(2-(5-fluoro-2-methoxypyridin-3-yl)-1,3-dimethyl-1H-pyrrolo[3,2-c]pyridin-6-yl)cyclopropane-1-carboxamide (Compound 57)

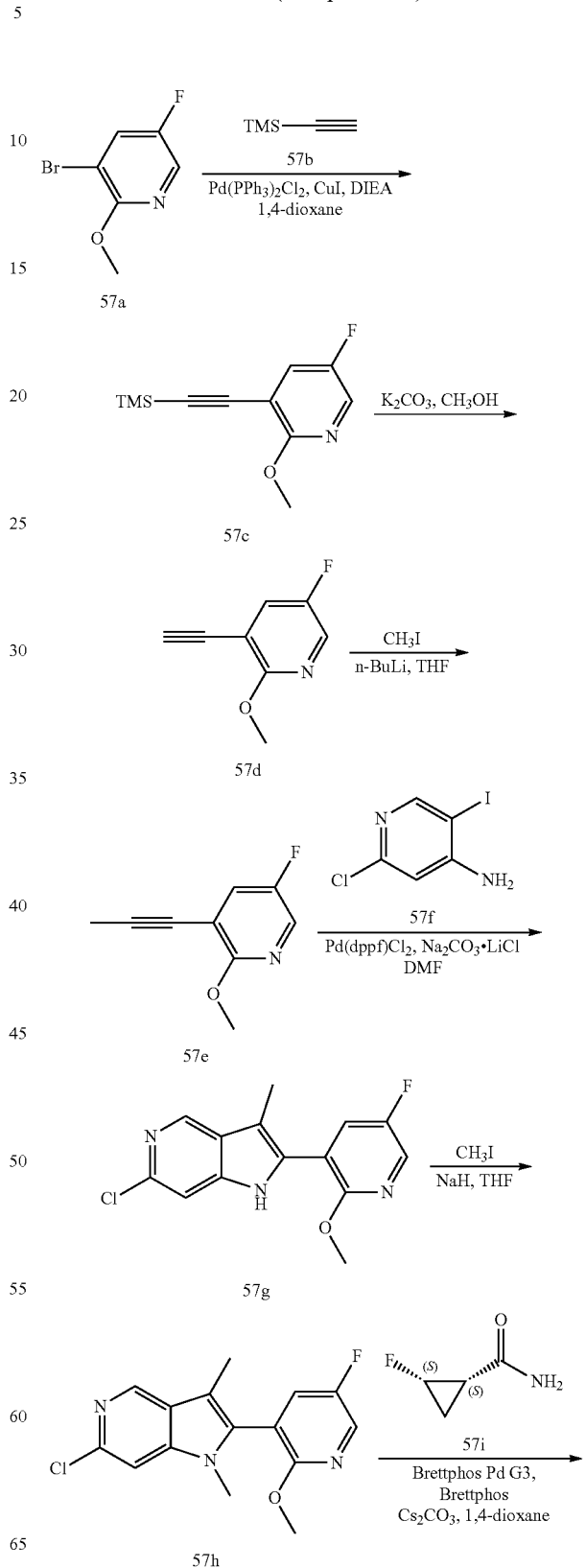

299

-continued

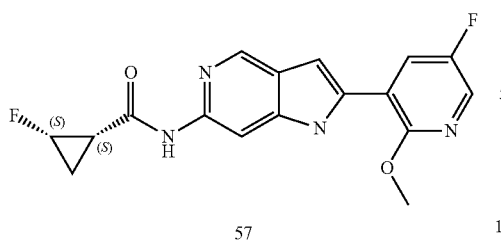

57

Step 1: Synthesis of 5-fluoro-2-methoxy-3-((trimethylsilyl)ethynyl)pyridine (Compound 57c)

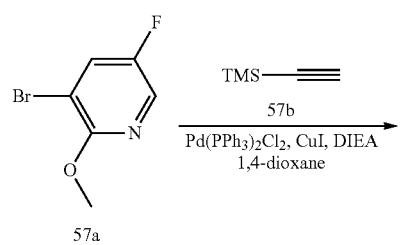

To a solution of 3-bromo-5-fluoro-2-methoxypyridine (Compound 57a) (5.0 g, 24.27 mmol) in 1,4-dioxane (50.0 mL) was added ethynyltrimethylsilane (Compound 57b) (2.6 g, 26.68 mmol), DIEA (12.6 g, 97.08 mmol), CuI (460.0 mg, 2.42 mmol) and Pd(PPh₃)₂Cl₂ (1.7 g, 2.43 mmol) at room temperature under N₂. The resulting mixture was stirred at 70° C. for 1 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (94/6, v/v) to afford 5-fluoro-2-methoxy-3-((trimethylsilyl)ethynyl)pyridine (Compound 57c) (3.8 g, 62%) as a yellow oil. LCMS (ESI, m/z): [M+H]⁺=224.1.

300

Step 2: Synthesis of 3-ethynyl-5-fluoro-2-methoxypyridine (Compound 57d)

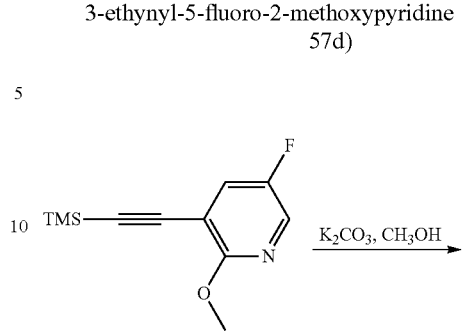

To a solution of 5-fluoro-2-methoxy-3-((trimethylsilyl)ethynyl)pyridine (Compound 57c) (3.3 g, 15.09 mmol) in CH₃OH (30.0 mL) was added K₂CO₃ (6.3 g, 45.27 mmol) at room temperature. The resulting mixture was stirred at room temperature for 2 h. After the reaction was completed, the resulting mixture was filtered. The filtrate was concentrated under reduced pressure. The residue was purified by flash column chromatography with petroleum ether/ethyl acetate (97/3, v/v) to afford 3-ethynyl-5-fluoro-2-methoxypyridine (Compound 57d) (1.8 g, 78%) as a white solid. LCMS (ESI, m/z): [M+H]⁺=152.0.

Step 3: Synthesis of 5-fluoro-2-methoxy-3-(prop-1-yn-1-yl)pyridine (Compound 57e)

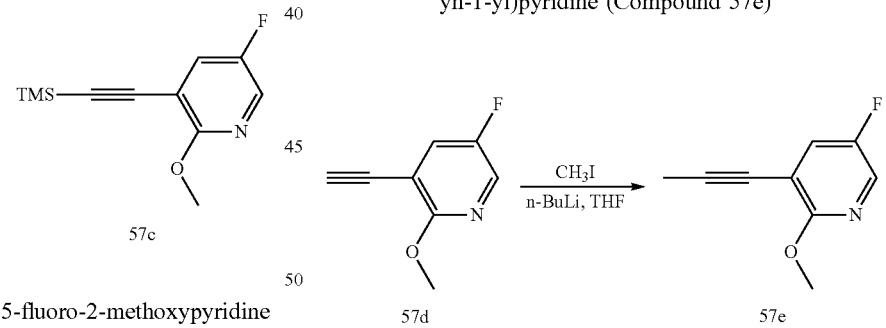

To a solution of 3-ethynyl-5-fluoro-2-methoxypyridine (Compound 57d) (1.0 g, 6.62 mmol) in THF (10.0 mL) was added n-BuLi (2.9 mL, 7.28 mmol) dropwise at −78° C. under N₂. The resulting mixture was stirred for 1 h at −78 C under N₂. Then CH₃I (1.1 g, 7.94 mmol) was added dropwise to the mixture at −78 C. The resulting mixture was stirred at room temperature for another 3 h. After the reaction was completed, the resulting mixture was quenched with aq. NH₄Cl and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (96/4, v/v) to afford 5-fluoro-2-methoxy-3-

(prop-1-yn-1-yl)pyridine (Compound 57e) (622.0 mg, 57%) as a white solid. LCMS (ESI, m/z): [M+H]⁺=166.1.

Step 4: Synthesis of 6-chloro-2-(5-fluoro-2-methoxypyridin-3-yl)-3-methyl-1H-pyrrolo[3,2-c]pyridine (Compound 57g)

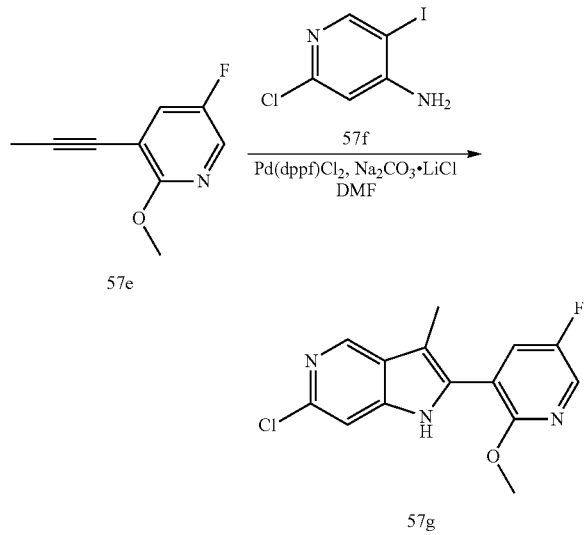

To a solution of 5-fluoro-2-methoxy-3-(prop-1-yn-1-yl)pyridine (schemCompound 57e) (1.3 g, 8.11 mmol) in DMF (10.0 mL) was added 2-chloro-5-iodopyridin-4-amine (Compound 57f) (2.1 g, 8.11 mmol), Na₂CO₃ (4.3 g, 40.56 mmol), LiCl (336.8 mg, 8.02 mmol) and Pd(dppf)Cl₂ (593.0 mg, 0.81 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum petroleum ether/ethyl acetate (80/20, v/v) to afford 6-chloro-2-(5-fluoro-2-methoxypyridin-3-yl)-3-methyl-1H-pyrrolo[3,2-c]pyridine (Compound 57g) (460.0 mg, 13%) as a yellow solid. LCMS (ESI, m/z): [M+H]⁺=292.1.

Step 5: Synthesis of 6-chloro-2-(5-fluoro-2-methoxypyridin-3-yl)-1,3-dimethyl-1H-pyrrolo[3,2-c]pyridine (Compound 57h)

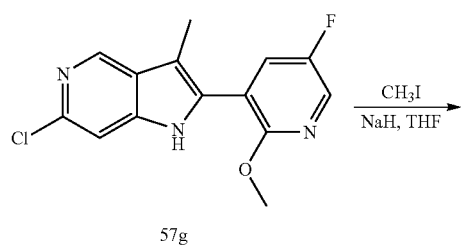

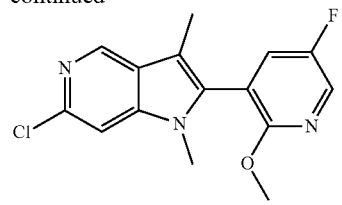

To a solution of 6-chloro-2-(5-fluoro-2-methoxypyridin-3-yl)-3-methyl-1H-pyrrolo[3,2-c]pyridine (Compound 57g) (200.0 mg, 0.69 mmol) in THF (5.0 mL) was added NaH (49.4 mg, 60%) at 0° C. under N₂. The resulting mixture was stirred at 0° C. for 1 h. Then CH₃I (486.6 mg, 3.43 mmol) was added dropwise to the mixture at 0 C under N₂. The resulting mixture was stirred at 0 C for another 1 h. After the reaction was completed, the resulting mixture was quenched with H₂O and extracted with ethyl acetate. The combined organic layer was washed with brine, dried over anhydrous sodium sulfate and filtered. The filtrate was concentrated under reduced pressure to afford 6-chloro-2-(5-fluoro-2-methoxypyridin-3-yl)-1,3-dimethyl-1H-pyrrolo[3,2-c]pyridine (Compound 57h) (220.0 mg, crude) as a yellow solid. LCMS (ESI, m/z): [M+H]⁺=306.1.

Step 6: Synthesis of (1S,2S)-2-fluoro-N-(2-(5-fluoro-2-methoxypyridin-3-yl)-1,3-dimethyl-1H-pyrrolo[3,2-c]pyridin-6-yl)cyclopropane-1-carboxamide (Compound 57)

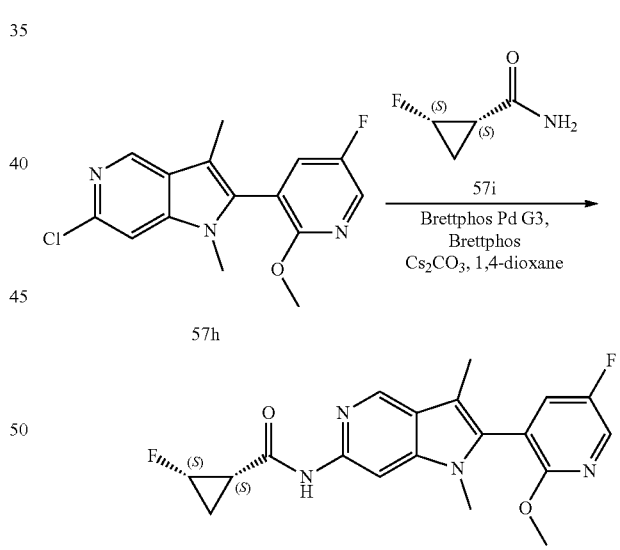

To a solution of 6-chloro-2-(5-fluoro-2-methoxypyridin-3-yl)-1,3-dimethyl-1H-pyrrolo[3,2-c]pyridine (Compound 57h) (220.0 mg, 0.72 mmol) in 1,4-dioxane (5.0 mL) was added (1S,2S)-2-fluorocyclopropane-1-carboxamide (Compound 57I) (370.9 mg, 3.59 mmol), Cs₂CO₃ (703.3 mg, 2.15 mmol), BrettPhos (77.2 mg, 0.14 mmol) and BrettPhos Pd G3 (65.2 mg, 0.07 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous Na$_2$SO$_4$ and filtered. The filtrate was concentrated under reduced pressure. The residue was purified by flash column chromatography with petroleum ether/ethyl acetate (64/36, v/v) and then purified by Prep-HPLC with the following conditions (Column: Xselect CSH OBD Column 30×150 mm, 5 um; Mobile Phase A: Water (10 mmol/L NH$_4$HCO$_3$), Mobile Phase B: ACN; Flow rate: 60 mL/min; Gradient: 40% B to 50% B in 7 min; 254 nm) to afford (1S,2S)-2-fluoro-N-(2-(5-fluoro-2-methoxypyridin-3-yl)-1,3-dimethyl-1H-pyrrolo[3,2-c]pyridin-6-yl)cyclopropane-1-carboxamide (Compound 57) (10.5 mg, 3%) as a white solid. LCMS (ESI, m/z): [M+H]$^+$=373.2. $^1$H NMR (300 MHz, DMSO-d$_6$): δ 10.73 (s, 1H), 8.60 (s, 1H), 8.34 (d, J=3.0 Hz, 1H), 8.13 (s, 1H), 7.88 (d, J=8.4 Hz, 1H), 5.07-4.79 (m, 1H), 3.88 (s, 3H), 3.46 (s, 3H), 2.27-2.22 (m, 1H), 2.17 (s, 3H), 1.71-1.60 (m, 1H), 1.22-1.17 (m, 1H).

Example S58: Synthesis of N-[3-fluoro-1-methyl-2-(2-methylphenyl)pyrrolo[3,2-c]pyridin-6-yl]cyclopropanecarboxamide (Compound 58)

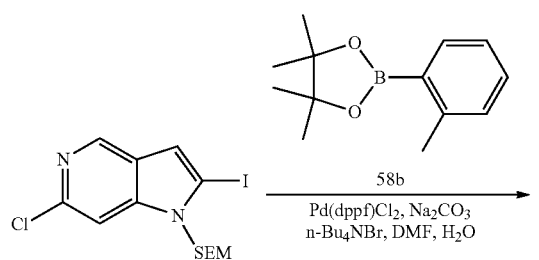

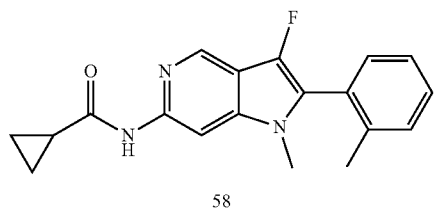

Step 1: Synthesis of 6-chloro-2-(2-methylphenyl)-1-[[2-(trimethylsilyl)ethoxy]methyl]pyrrolo[3,2-c]pyridine (Compound 58c)

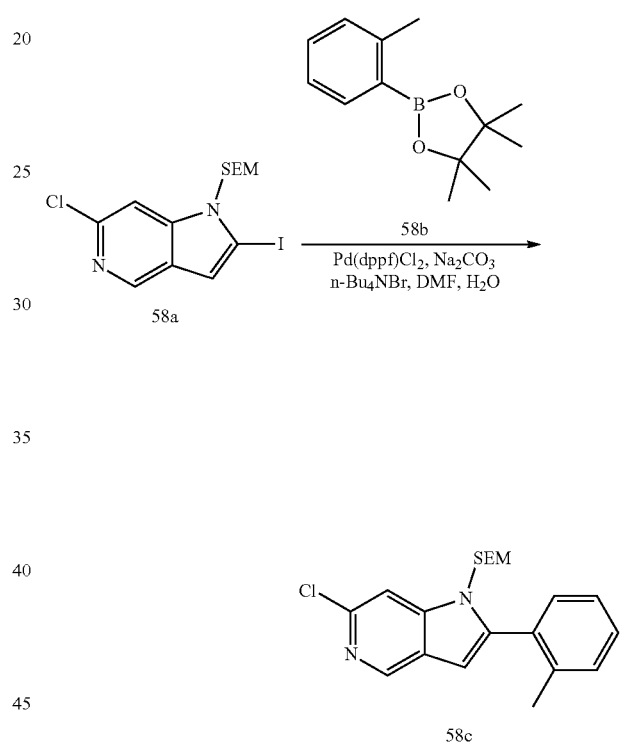

To a solution of 6-chloro-2-iodo-1-[[2-(trimethylsilyl)ethoxy]methyl]pyrrolo[3,2-c]pyridine (Compound 58a) (1.5 g, 3.67 mmol) in DMF (30.0 mL) and H$_2$O (5.0 ml) was added 4,4,5,5-tetramethyl-2-(2-methylphenyl)-1,3,2-dioxaborolane (Compound 58b) (1.2 g, 5.51 mmol), Na$_2$CO$_3$ (1.2 g, 11.01 mmol). TBAB (0.3 g, 0.73 mmol) and Pd(dppf)Cl$_2$ (0.3 mg, 0.37 mmol) at room temperature under N$_2$. The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (80/20, v/v) to afford 6-chloro-2-(2-methylphenyl)-1-[[2-(trimethylsilyl)ethoxy]methyl]pyrrolo[3,2-c]pyridine (Compound 58) (1.0 g, 73%) as a white solid. LCMS (ESI, m/z): [M+H]$^+$= 373.1.

Step 2: Synthesis of 6-chloro-3-fluoro-2-(2-methylphenyl)-1-[[2-(trimethylsilyl)ethoxy]methyl]pyrrolo[3,2-c]pyridine (Compound 58d)

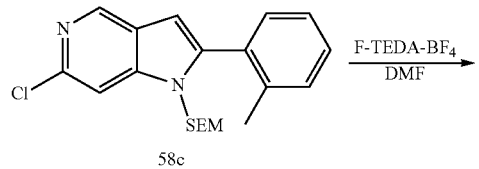

58c

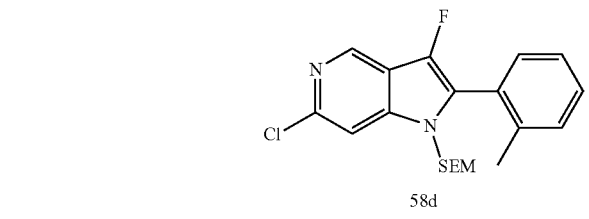

58d

To a solution of 6-chloro-2-(2-methylphenyl)-1-[[2-(trimethylsilyl)ethoxy]methyl]pyrrolo[3,2-c]pyridine (Compound 58c) (600.0 mg, 1.61 mmol) in DMF (10.0 mL) was added F-TEDA-BF$_4$ (455.9 mg, 1.29 mmol) at room temperature under N$_2$. The resulting mixture was stirred at temperature for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (95/5, v/v) to afford 6-chloro-3-fluoro-2-(2-methylphenyl)-1-[[2-(trimethylsilyl)ethoxy]methyl]pyrrolo[3,2-c]pyridine (Compound 58d) (400.0 mg, 54%) as a white oil. LCMS (ESI, m/z): [M+H]$^+$=391.1.

Step 3: Synthesis of 6-chloro-3-fluoro-2-(2-methylphenyl)-1H-pyrrolo[3,2-c]pyridine (Compound 58e)

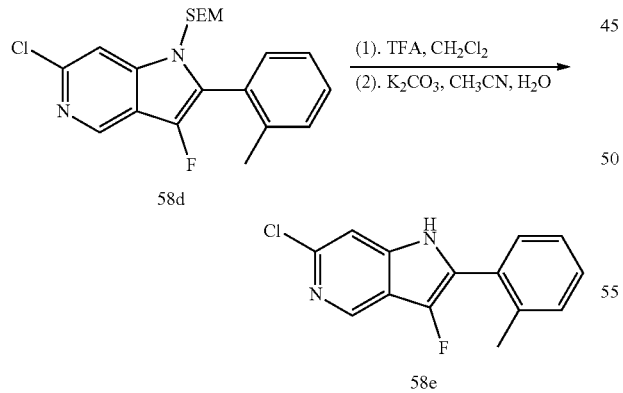

To a stirred mixture of 6-chloro-3-fluoro-2-(2-methylphenyl)-1-[[2-(trimethylsilyl)ethoxy]methyl]pyrrolo[3,2-c]pyridine (Compound 58d) (400.0 mg, 1.02 mmol) in DCM (4.0 mL) was added TFA (4.0 mL). The resulting mixture was stirred at room temperature for 3 h. The resulting mixture was concentrated under reduced pressure. The residue was re-dissolved in ACN (5.0 mL) and H$_2$O (1.0 mL). Then K$_2$CO$_3$ (1.4 g, 10.23 mmol) was added to the mixture. The resulting mixture was stirred at room temperature for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (94/6, v/v) to afford 6-chloro-3-fluoro-2-(2-methylphenyl)-1H-pyrrolo[3,2-c]pyridine (Compound 58e) (159.0 mg, 60%) as a white solid. LCMS (ESI, m/z): [M+H]$^+$=261.1.

Step 4: Synthesis of 6-chloro-3-fluoro-1-methyl-2-(2-methylphenyl)pyrrolo[3,2-c]pyridine (Compound 58f)

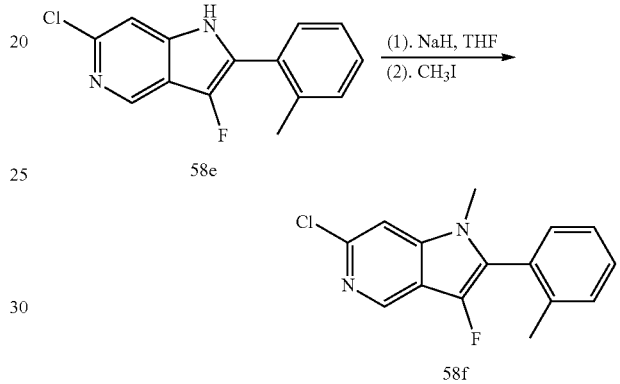

To a solution of 6-chloro-3-fluoro-2-(2-methylphenyl)-1H-pyrrolo[3,2-c]pyridine (Compound 58e) (159.0 mg, 0.61 mmol) in THF (5.0 mL) was added NaH (14.6 mg, 60%) at 0° C. under N$_2$. The resulting mixture was stirred at 0° C. for 1 h under N$_2$. After the reaction was completed, CH$_3$I (173.1 mg, 1.22 mmol) was added to the mixture at 0° C. under N$_2$. The resulting mixture was stirred at 0° C. for 1 h$_2$. After the reaction was completed, the reaction was quenched with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (90/10, v/v) to afford 6-chloro-3-fluoro-1-methyl-2-(2-methylphenyl)pyrrolo[3,2-c]pyridine (Compound 58f) (135.0 mg, 80%) as a white solid. LCMS (ESI, m/z): [M+H]$^+$=275.1.

Step 5: Synthesis of N-[3-fluoro-1-methyl-2-(2-methylphenyl)pyrrolo[3,2-c]pyridin-6-yl]cyclopropanecarboxamide (Compound 58)

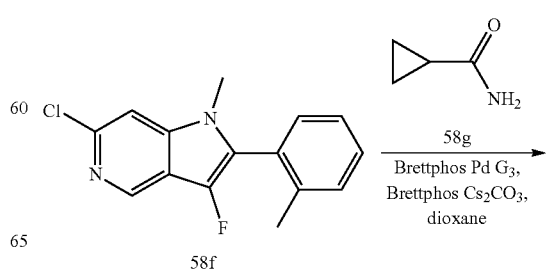

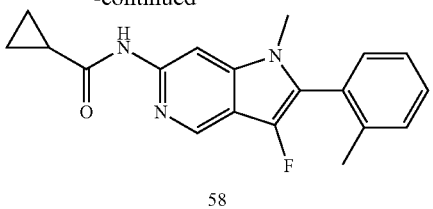

58

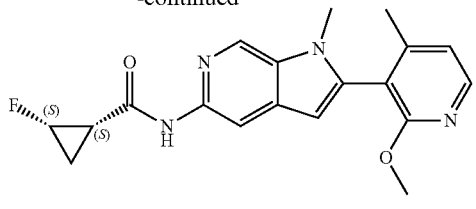

59

To a solution of 6-chloro-3-fluoro-1-methyl-2-(2-methylphenyl)pyrrolo[3,2-c]pyridine (Compound 58f) (100.0 mg, 0.36 mmol) in 1,4-dioxane (5.0 mL) was added cyclopropanecarboxamide (Compound 58g) (92.9 mg, 1.09 mmol). BrettPhos Pd G3 (66.0 mg, 0.07 mmol), Cs$_2$CO$_3$ (355.8 mg, 1.09 mmol) and BrettPhos (78.1 mg, 0.15 mmol) at room temperature under N$_2$. The resulting mixture was stirred at 100° C. for 3 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (80/20, v/v) and then purified by Prep-HPLC with the following conditions (Column: YMC-Actus Triart C18, 30×250 mm, 5 um; Mobile Phase A: Water (10 mmol/L NH$_4$HCO$_3$), Mobile Phase B:ACN; Flow rate: 60 mL/min; Gradient: 53% B to 83% B in 7 min; 254 nm) to afford N-[3-fluoro-1-methyl-2-(2-methylphenyl)pyrrolo[3,2-c]pyridin-6-yl]cyclopropanecarboxamide (Compound 58) (46.7 mg, 39%) as a white solid. LCMS (ESI, m/z): [M+H]$^+$=324.1. $^1$H NMR (400 MHz, DMSO-d$_6$): δ 10.74 (s, 1H), 8.64 (s, 1H), 8.18 (s, 1H), 7.44-7.38 (m, 4H), 3.40 (s, 3H), 2.20 (s, 3H), 2.07-2.00 (m, 1H), 0.84-0.80 (m, 4H).

Example S59: Synthesis of (1S,2S)-2-fluoro-N-[2-(2-methoxy-4-methylpyridin-3-yl)-1-methylpyrrolo[2,3-c]pyridin-5-yl]cyclopropane-1-carboxamide (Compound 59)

Step 1: Synthesis of 3-[5-chloro-1-methylpyrrolo[2,3-c]pyridin-2-yl]-2-methoxy-4-methylpyridine (Compound 59c)

To a mixture of 5-chloro-2-iodo-1-methylpyrrolo[2,3-c]pyridine (Compound 59a) (300.0 mg, 1.03 mmol) in 1,4-dioxane/H$_2$O (8.0 mL/2.0 mL) was added 2-methoxy-4-methyl-3-(4,4,5,5-tetramethyl-1,3,2-dioxaborolan-2-yl)pyridine (Compound 59b) (306.6 mg, 1.23 mmol), K$_2$CO$_3$ (425.3 mg, 3.08 mmol) and Pd(dppf)Cl$_2$ (75.1 mg, 0.10 mmol) at room temperature under N$_2$. The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash chromatography with petroleum ether/ethyl acetate (1/1, v/v) to afford 3-[5-chloro-1-methylpyrrolo[2,3-c]pyridin-2-yl]-2-methoxy-4-methylpyridine (Compound 59c) (160.0 mg, 54%) as a white solid. LCMS (ESI, m/z): [M+H]$^+$=288.1.

Step 2: Synthesis of (1S,2S)-2-fluoro-N-[2-(2-methoxy-4-methylpyridin-3-yl)-1-methylpyrrolo[2,3-c]pyridin-5-yl]cyclopropane-1-carboxamide (Compound 59)

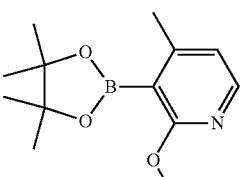

59a

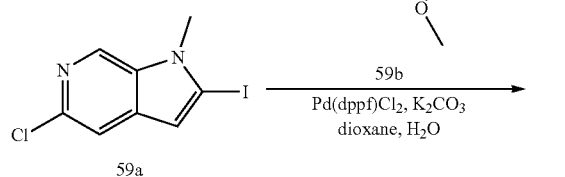

59c

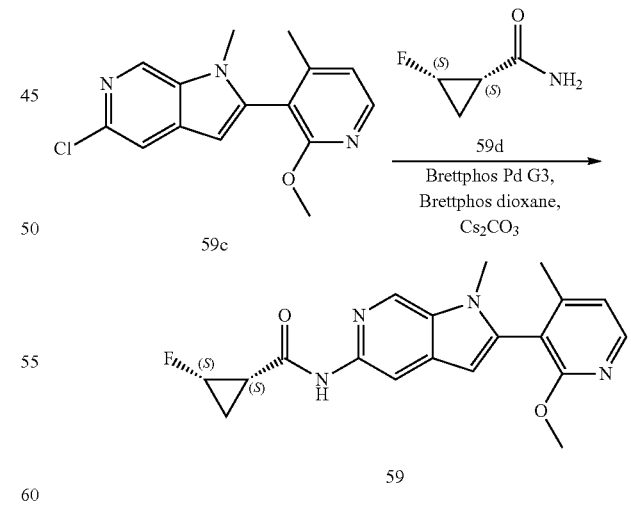

To a solution of 3-[5-chloro-1-methylpyrrolo[2,3-c]pyridin-2-yl]-2-methoxy-4-methylpyridine (Compound 59c) (160.0 mg, 0.56 mmol) in 1,4-dioxane (10.0 mL) was added (1S,2S)-2-fluorocyclopropane-1-carboxamide (Compound 59d) (286.6 mg, 2.78 mmol), BrettPhos (59.7 mg, 0.11 mmol), Cs$_2$CO$_3$ (543.5 mg, 1.67 mmol) and BrettPhos Pd 03

(50.4 mg, 0.06 mmol mmol) at room temperature under N$_2$. The final reaction mixture was stirred with microwave at 120° C. for 1.5 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by Prep-HPLC with the following conditions (Column: Xselect CSH OBD Column 30×150 mm, 5 um; Mobile Phase A:Water (10 mmol/L NH$_4$HCO$_3$), Mobile Phase B: ACN; Flow rate: 60 mL/min; Gradient: 36% B to 45% B in 8 min; 254 nm) to afford (1S,2S)-2-fluoro-N-[2-(2-methoxy-4-methylpyridin-3-yl)-1-methylpyrrolo[2,3-c]pyridin-5-yl]cyclopropane-1-carboxamide (Compound 59) (5.1 mg, 2%) as a white solid. LCMS (ESI, m/z): [M+H]$^+$=355.1. $^1$H NMR (400 MHz, DMSO-d$_6$): δ 10.53 (s, 1H), 8.63 (s, 1H), 8.21-8.18 (m, 2H), 7.07 (d, J=5.2 Hz, 1H), 6.45 (s, 1H), 5.00-4.80 (m, 1H), 3.81 (s, 3H), 3.52 (s, 3H), 2.24-2.17 (m, 1H), 2.13 (s, 3H), 1.70-1.62 (m, 1H), 1.19-1.09 (m, 1H).

Example S60: Synthesis of (1S,2S)-2-fluoro-N-[2-(5-fluoro-2-methoxypyridin-3 yl)-1,3-dimethylpyrrolo[2,3-c]pyridin-5-yl]cyclopropane-1-carboxamide (Compound 60)

Step 1: Synthesis of 3-[5-chloro-1-methylpyrrolo[2,3-c]pyridin-2-yl]-5-fluoro-2-methoxypyridine (Compound 60a)

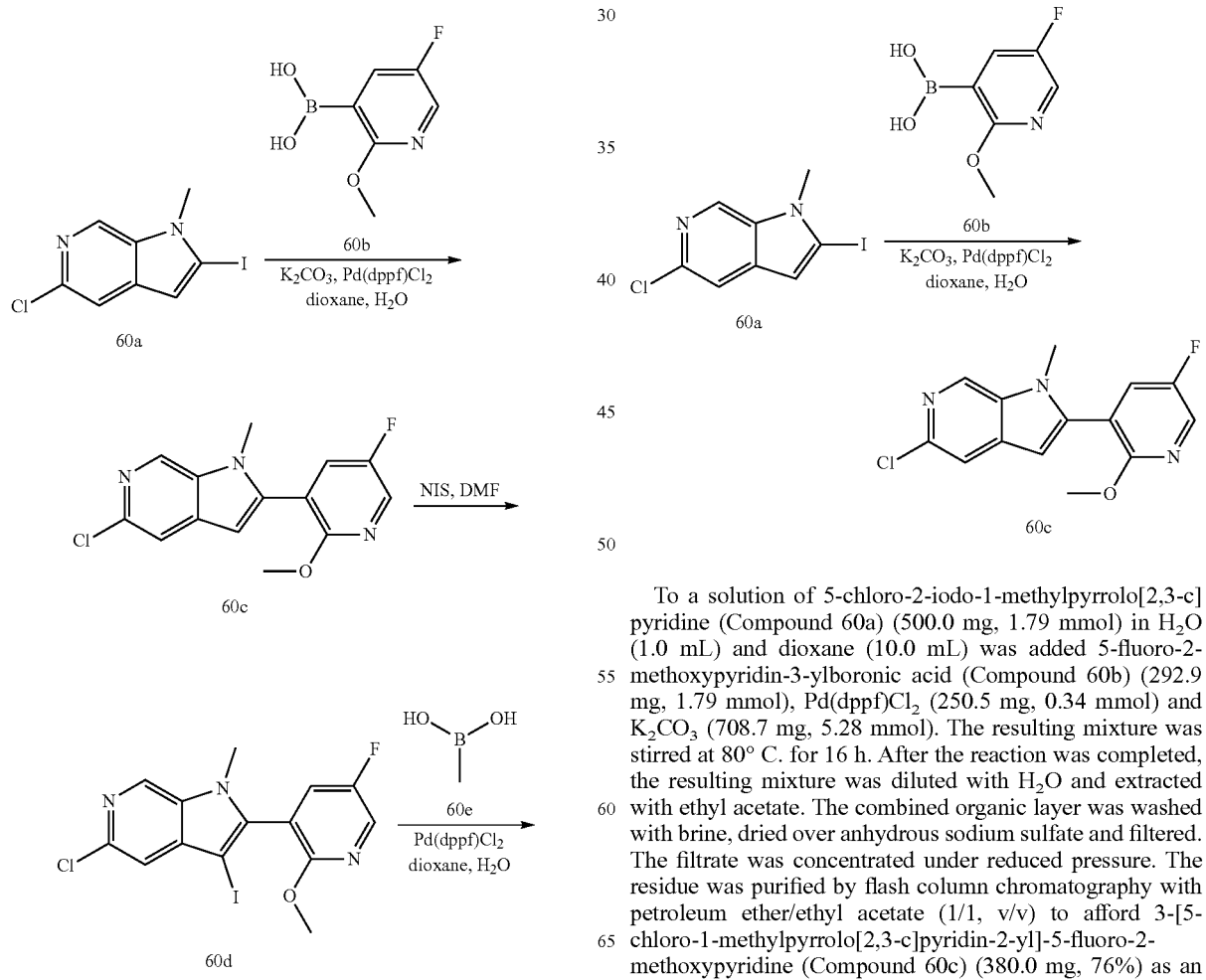

To a solution of 5-chloro-2-iodo-1-methylpyrrolo[2,3-c]pyridine (Compound 60a) (500.0 mg, 1.79 mmol) in H$_2$O (1.0 mL) and dioxane (10.0 mL) was added 5-fluoro-2-methoxypyridin-3-ylboronic acid (Compound 60b) (292.9 mg, 1.79 mmol), Pd(dppf)Cl$_2$ (250.5 mg, 0.34 mmol) and K$_2$CO$_3$ (708.7 mg, 5.28 mmol). The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 3-[5-chloro-1-methylpyrrolo[2,3-c]pyridin-2-yl]-5-fluoro-2-methoxypyridine (Compound 60c) (380.0 mg, 76%) as an off-white solid. LCMS (ESI, m/z): [M+H]$^+$=292.1.

Step 2: Synthesis of 3-[5-chloro-3-iodo-1-methylpyrrolo[2,3-c]pyridin-2-yl]-5-fluoro-2-methoxypyridine (Compound 60d)

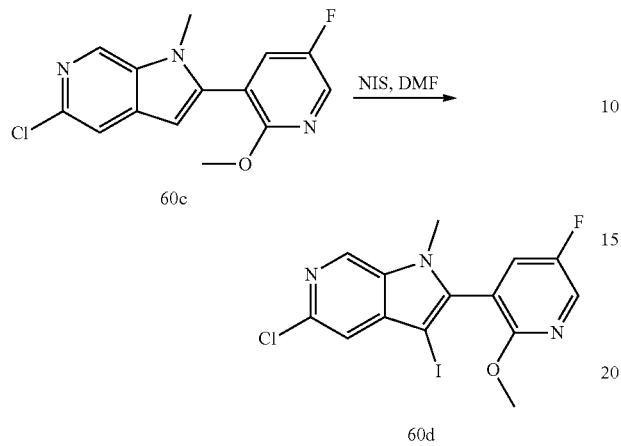

To a solution of 3-[5-chloro-1-methylpyrrolo[2,3-c]pyridin-2-yl]-5-fluoro-2-methoxypyridine (Compound 60c) (360.0 mg, 1.23 mmol) in DMF (5.0 mL) was added NIS (515.3 mg, 2.92 mmol). The resulting mixture was stirred at 60° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 3-[5-chloro-3-iodo-1-methylpyrrolo[2,3-c]pyridin-2-yl]-5-fluoro-2-methoxypyridine (Compound 60d) (250.0 mg, 49%) as a white solid. LCMS (ESI, m/z): [M+H]⁺=418.0.

Step 3: Synthesis of 3-[5-chloro-1,3-dimethylpyrrolo[2,3-c]pyridin-2-yl]-5-fluoro-2-methoxypyridine (Compound 60f)

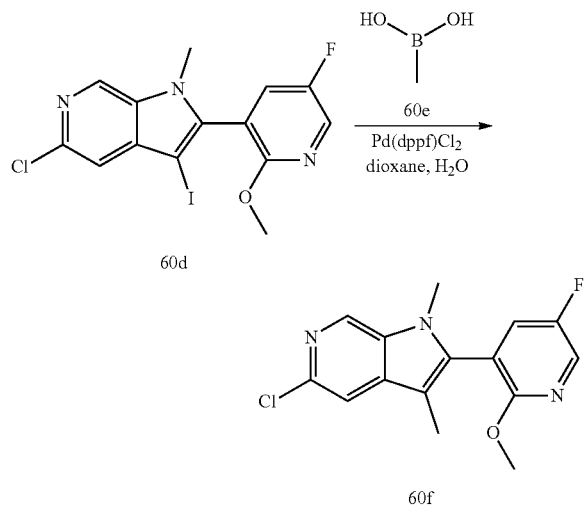

To a solution of 3-[5-chloro-3-iodo-1-methylpyrrolo[2,3-c]pyridin-2-yl]-5-fluoro-2-methoxypyridine (Compound 60d) (480.0 mg, 1.19 mmol) in dioxane (10.0 mL) and H₂O (1.0 mL) was added methylboronic acid (Compound 60e) (344.1 mg, 5.77 mmol), Pd(dppf)Cl₂ (84.1 mg, 0.15 mmol) and K₂CO₃ (476.6 mg, 3.48 mmol). The resulting mixture was stirred at 100° C. for 2 h under N₂. The resulting mixture was concentrated under reduced pressure. The residue was purified by flash column chromatography with petroleum ether/ethyl acetate (1/1, v/v) to afford 3-[5-chloro-1,3-dimethylpyrrolo[2,3-c]pyridin-2-yl]-5-fluoro-2-methoxypyridine (Compound 60f) (200.0 mg, 57%) as a yellow oil. LCMS (ESI, m/z): [M+H]⁺=306.1.

Step 4: Synthesis of (1S,2S)-2-fluoro-N-[2-(5-fluoro-2-methoxypyridin-3-yl)-1,3-dimethylpyrrolo[2,3-c]pyridin-5-yl]cyclopropane-1-carboxamide (Compound 60)

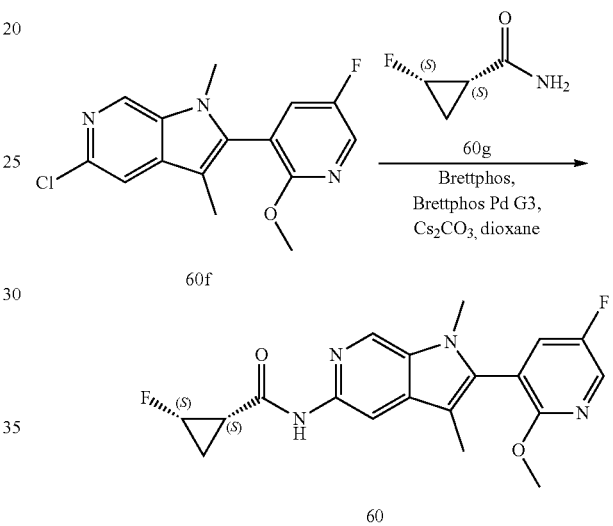

To a solution of 3-[5-chloro-1,3-dimethylpyrrolo[2,3-c]pyridin-2-yl]-5-fluoro-2-methoxypyridine (Compound 60f) (160.0 mg, 0.53 mmol) in dioxane (5.0 mL) was added (1S,2S)-2-fluorocyclopropane-1-carboxamide (Compound 60g) (64.4 mg, 0.68 mmol), BrettPhos (56.8 mg, 0.15 mmol), BrettPhos Pd G₃ (47.4 mg, 0.05 mmol) and Cs₂CO₃ (511.5 mg, 1.57 mmol) at room temperature under N₂. The resulting mixture was stirred at 100° C. for 3 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with dichloromethane/CH₃OH (10/1, v/v) and then purified by Prep-HPLC with the following conditions (Column: XBridge Prep OBD C18 Column. 30×150 mm, 5 um; Mobile Phase A:Water (10 mmol/L NH₄HCO₃), Mobile Phase B: ACN; Flow rate: 60 mL/min; Gradient: 41% B to 50% B in 8 min; 254 nm) to afford (1S,2S)-2-fluoro-N-[2-(5-fluoro-2-methoxypyridin-3-yl)-1,3-dimethylpyrrolo[2,3-c]pyridin-5-yl]cyclopropane-1-carboxamide (Compound 60) (9.5 mg, 5%) as a white solid. LCMS (ESI, m/z): [M+H]⁺=373.2. ¹H NMR (300 MHz, DMSO-d₆): δ 10.56 (s, 1H), 8.61 (s. 1H), 8.36 (d, J=3.0 Hz, 1H), 8.20 (s, 1H), 7.93-7.88 (m, 1H), 5.04-4.77 (m, 1H), 3.88 (s, 3H), 3.59 (s, 3H), 2.31-2.12 (m, 1H), 2.08 (s, 3H), 1.70-1.60 (m, 1H), 1.17-1.12 (m, 1H).

Example S61: Synthesis of (1S,2S)-2-fluoro-N-(2-(2-methoxypyridin-3-yl)-1,3-dimethyl-1H-pyrrolo[2,3-c]pyridin-5-yl)cyclopropanecarboxamide (Compound 61)

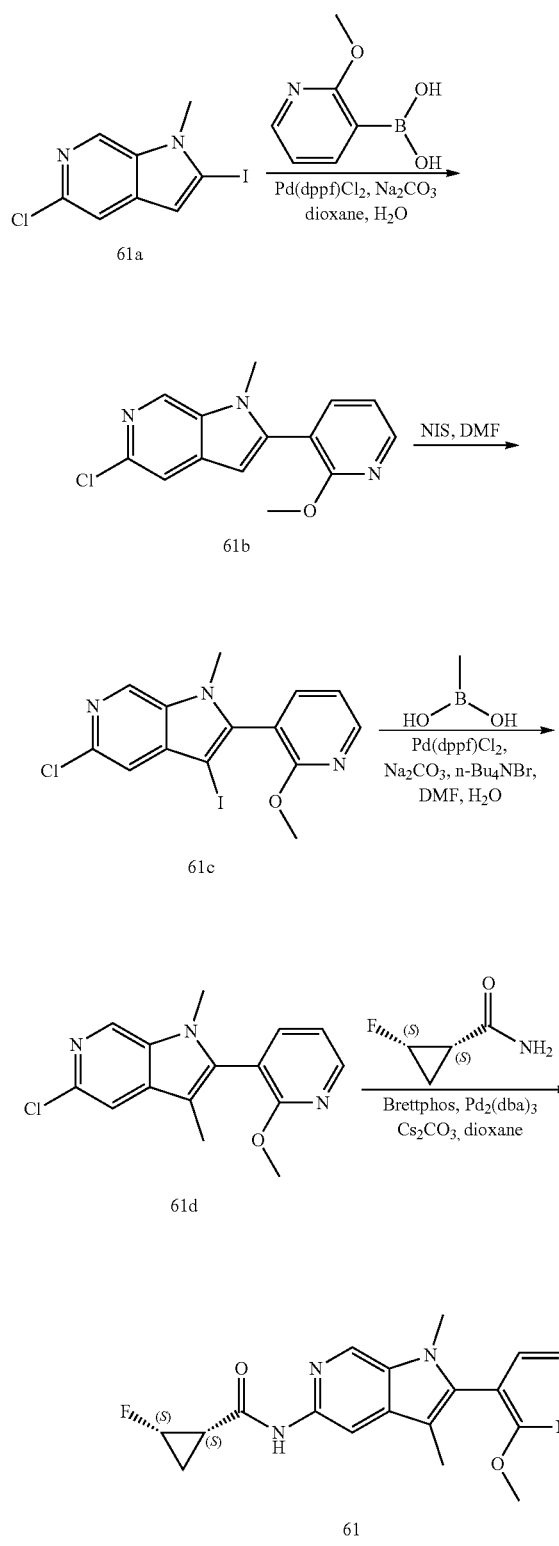

Step 1: Synthesis of 3-[5-chloro-1-methylpyrrolo[2,3-c]pyridin-2-yl]-2-methoxypyridine (Compound 61b)

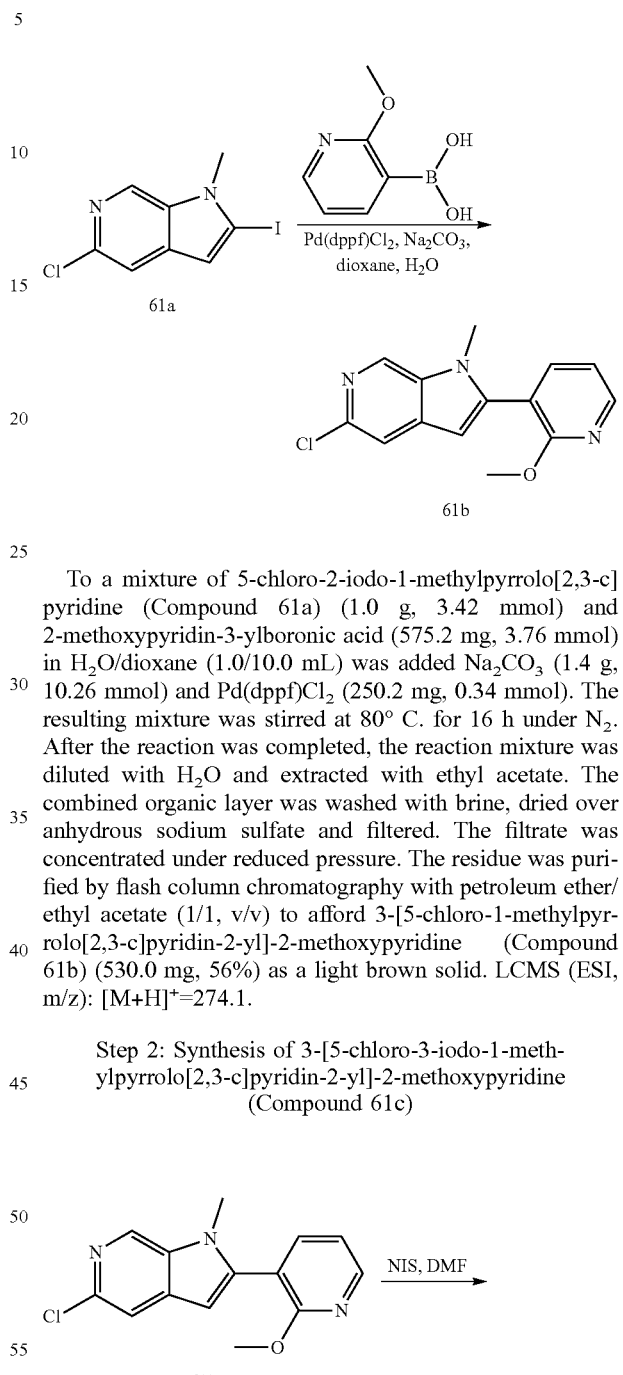

To a mixture of 5-chloro-2-iodo-1-methylpyrrolo[2,3-c]pyridine (Compound 61a) (1.0 g, 3.42 mmol) and 2-methoxypyridin-3-ylboronic acid (575.2 mg, 3.76 mmol) in H₂O/dioxane (1.0/10.0 mL) was added Na₂CO₃ (1.4 g, 10.26 mmol) and Pd(dppf)Cl₂ (250.2 mg, 0.34 mmol). The resulting mixture was stirred at 80° C. for 16 h under N₂. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 3-[5-chloro-1-methylpyrrolo[2,3-c]pyridin-2-yl]-2-methoxypyridine (Compound 61b) (530.0 mg, 56%) as a light brown solid. LCMS (ESI, m/z): [M+H]⁺=274.1.

Step 2: Synthesis of 3-[5-chloro-3-iodo-1-methylpyrrolo[2,3-c]pyridin-2-yl]-2-methoxypyridine (Compound 61c)

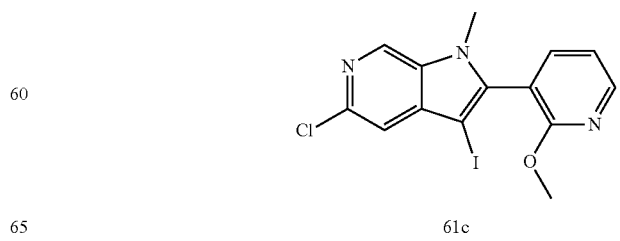

A mixture of 3-[5-chloro-1-methylpyrrolo[2,3-c]pyridin-2-yl]-2-methoxypyridine (Compound 61b) (500.0 mg, 1.83 mmol) and NIS (986.3 mg, 4.39 mmol) in DMF (10.0 mL) was stirred at 60° C. for 3 h. After the reaction was completed, the reaction mixture was quenched with NaHSO$_3$ solution. The resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 3-[5-chloro-3-iodo-1-methylpyrrolo[2,3-c]pyridin-2-yl]-2-methoxypyridine (Compound 61c) (580.0 mg, 79%) as a light yellow solid. LCMS (ESI, m/z): [M+H]$^+$=400.0.

Step 3: Synthesis of 3-[5-chloro-1,3-dimethylpyrrolo[2,3-c]pyridin-2-yl]-2-methoxypyridine (Compound 61d)

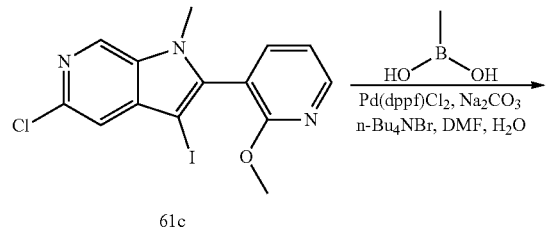

61c

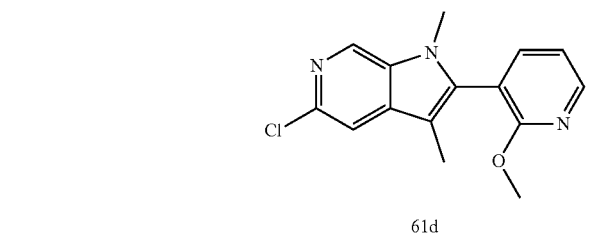

61d

To a mixture of 3-[5-chloro-3-iodo-1-methylpyrrolo[2,3-c]pyridin-2-yl]-2-methoxypyridine (Compound 61c) (540.0 mg, 1.35 mmol) and methylboronic acid (808.9 mg, 13.51 mmol) in H$_2$O/DMF (1.0/5.0 mL) was added Na$_2$CO$_3$ (429.7 mg, 4.05 mmol), tetrabutylazanium bromide (348.5 mg, 1.08 mmol) and Pd(dppf)Cl$_2$ (197.8 mg, 0.27 mmol). The resulting mixture was stirred at 80° C. for 3 h under N$_2$. After the reaction was completed, the resulting mixture was diluted with water and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/CH$_3$OH (9/1, v/v) to afford 3-[5-chloro-1,3-dimethylpyrrolo[2,3-c]pyridin-2-yl]-2-methoxypyridine (Compound 61d) (260.0 mg, 66%) as a dark yellow oil. LCMS (ESI, m/z): [M+H]$^+$=288.1.

Step 4: Synthesis of (1S,2S)-2-fluoro-N-(2-(2-methoxypyridin-3-yl)-1,3-dimethyl-1H-pyrrolo[2,3-c]pyridin-5-yl)cyclopropanecarboxamide (Compound 61)

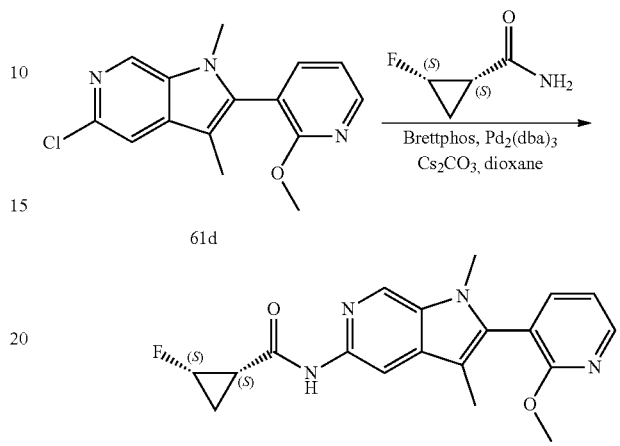

To a mixture of 3-[5-chloro-1,3-dimethylpyrrolo[2,3-c]pyridin-2-yl]-2-methoxypyridine (Compound 61d) (220.0 mg, 0.77 mmol) and (1S,2S)-2-fluorocyclopropane-1-carboxamide (394.1 mg, 3.83 mmol) in dioxane (5.0 mL) was added Cs$_2$CO$_3$ (747.3 mg, 2.30 mmol), BrettPhos (164.2 mg, 0.31 mmol) and Pd$_2$(dba)$_3$ (138.6 mg, 0.15 mmol). The resulting mixture was stirred at 80° C. for 3 h under N$_2$. After the reaction was completed, the resulting mixture was diluted with water and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A:water (10 mmol/L NH$_4$HCO$_3$), Mobile Phase B: ACN; Flow rate: 60 mL/min; Gradient: 34% B to 44% B in 9 min; 254/220 nm) to afford (0S,2S)-2-fluoro-N-(2-(2-methoxypyridin-3-yl)-1,3-dimethyl-1H-pyrrolo[2,3-c]pyridin-5-yl)cyclopropanecarboxamide (Compound 61) (11.3 mg, 4%) as a white solid. LCMS (ESI, m/z): [M+H]$^+$=355.1. $^1$H NMR (300 MHz, DMSO-d$_6$): δ 10.55 (s, 1H), 8.59 (d, J=0.9 Hz, 1H), 8.37-8.34 (m, 1H), 8.20 (s, 1H), 7.81 (d, J=7.2 Hz, 1H), 7.22-7.18 (m, 1H), 5.03-4.79 (m, 1H), 3.89 (s, 3H), 3.56 (s, 3H), 2.27-2.18 (m, 1H), 2.05 (s, 3H), 1.69-1.60 (m, 1H), 1.19-1.08 (m, 1H).

Example S62: Synthesis of (1S,2S)-N-(1-ethyl-2-(5-fluoro-2-methoxypyridin-3-yl)-1H-pyrrolo[2,3-c]pyridin-5-yl)-2-fluorocyclopropane-1-carboxamide (Compound 62)

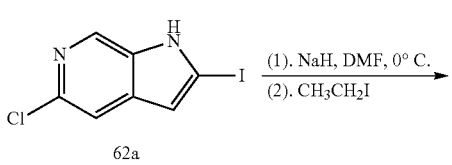

62a

317
-continued

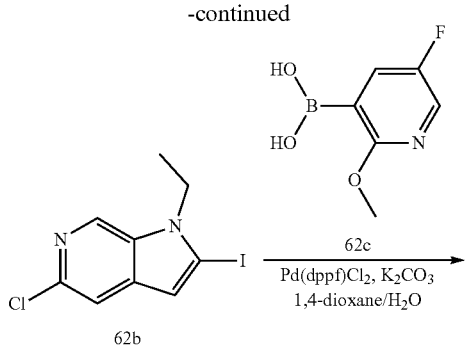

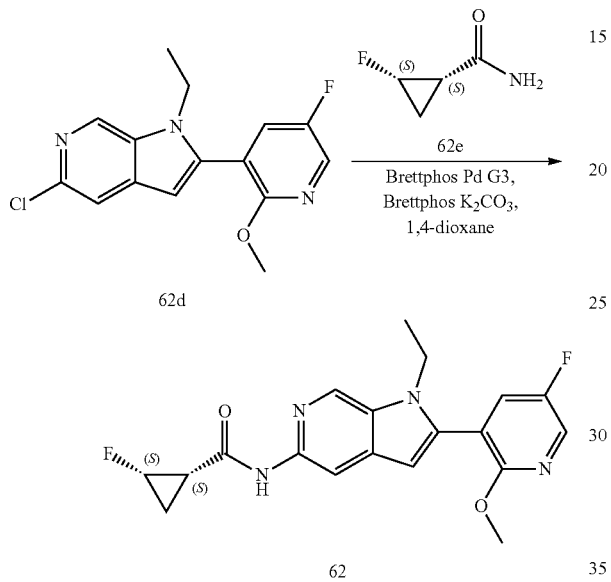

Step 1: Synthesis of 5-chloro-1-ethyl-2-iodo-1H-pyrrolo[2,3-c]pyridine (Compound 62b)

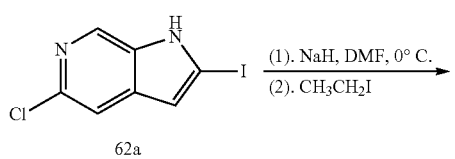

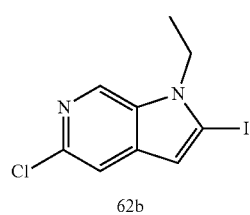

To a solution of 5-chloro-2-iodo-1H-pyrrolo[2,3-c]pyridine (Compound 62a) (1.0 g, 3.59 mmol) in DMF (10.0 mL)

318 was added NaH (430.9 mg, 60%) at 0° C. under $N_2$. The resulting mixture was stirred at 0° C. for 1 h under $N_2$. Then iodoethane (2.8 g, 17.96 mmol) was added dropwise to the mixture at 0° C. under $N_2$. The resulting mixture was stirred at 0° C. for another 1 h. After the reaction was completed, the reaction mixture was quenched with $H_2O$ and filtered. The solid was collected and dried to afford 5-chloro-1-ethyl-2-iodopyrrolo[2,3-c]pyridine (Compound 62b) (830.0 mg, crude) as a yellow solid. LCMS (ESI, m/z): $[M+H]^+$=306.9.

Step 2: Synthesis of 5-chloro-1-ethyl-2-(5-fluoro-2-methoxypyridin-3-yl)-1H-pyrrolo[2,3-c]pyridine (Compound 62d)

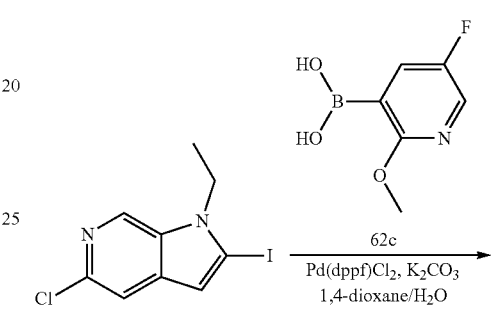

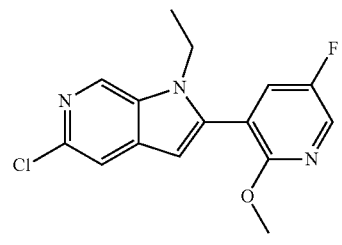

To a solution of 5-chloro-1-ethyl-2-iodopyrrolo[2,3-c]pyridine (Compound 62b) (300.0 mg, 0.98 mmol) in 1,4-dioxane/$H_2O$ (10.0/2.0 mL) was added 5-fluoro-2-methoxypyridin-3-ylboronic acid (Compound 62c) (167.3 mg, 0.98 mmol), $K_2CO_3$ (405.8 mg, 2.94 mmol) and Pd(dppf)$Cl_2$ (71.6 mg, 0.10 mmol) at room temperature under $N_2$. The resulting mixture was stirred at 80° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (60/40, v/v) to afford 5-chloro-1-ethyl-2-(5-fluoro-2-methoxypyridin-3-yl)-1H-pyrrolo[2,3-c]pyridine (Compound 62d) (210.0 mg, 70%) as a white solid. LCMS (ESI, m/z): $[M+H]^+$=306.1.

Step 3: Synthesis of (1S,2S)-N-(1-ethyl-2-(5-fluoro-2-methoxypyridin-3-yl)-1H-pyrrolo[2,3-c]pyridin-5-yl)-2-fluorocyclopropane-1-carboxamide (Compound 62)

Example S63: Synthesis of (1S,2S)-N-(1-ethyl-2-(2-methoxypyridin-3-yl)-1H-pyrrolo[2,3-c]pyridin-5-yl)-2-fluorocyclopropane-1-carboxamide (Compound 63)

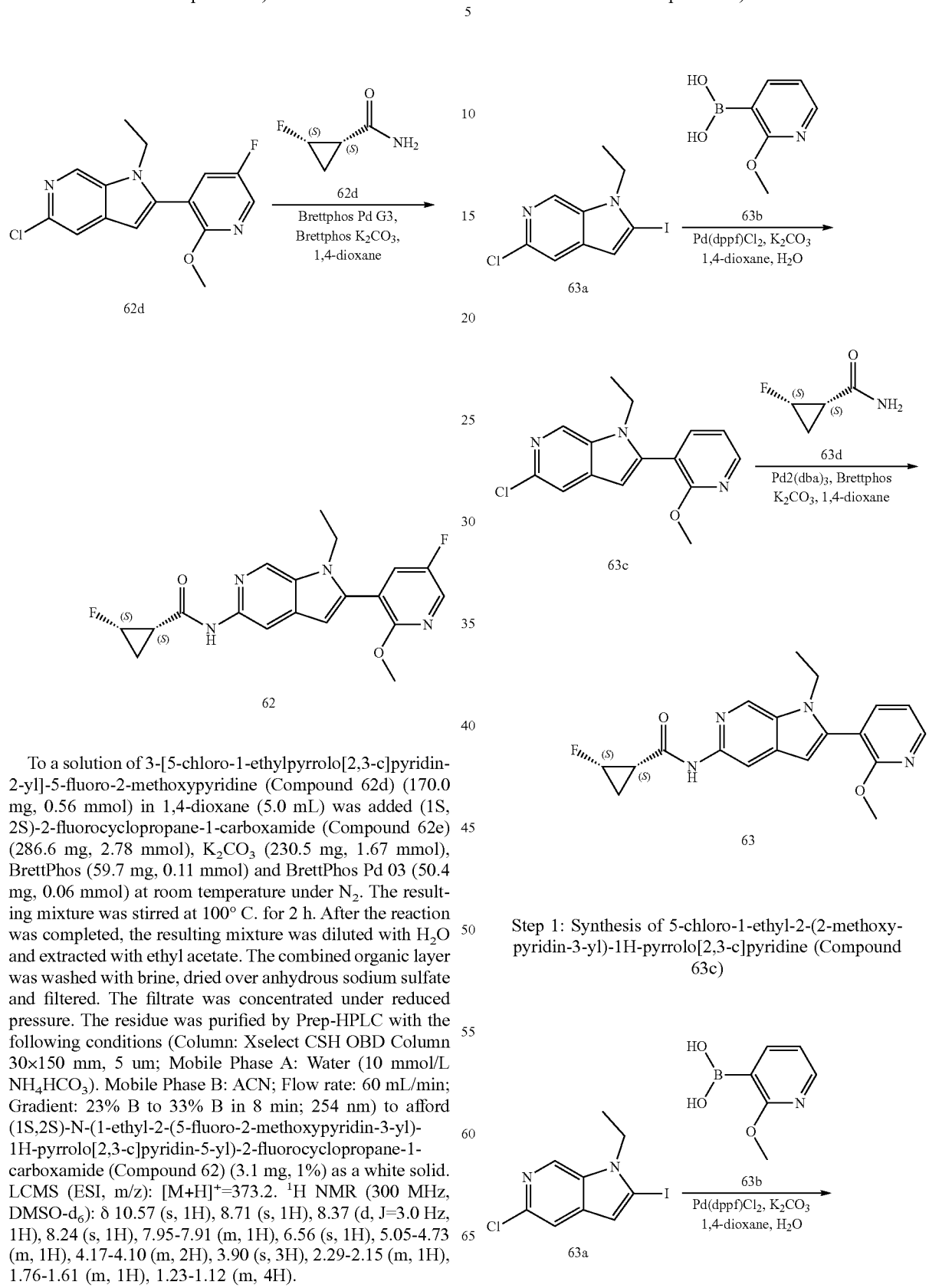

To a solution of 3-[5-chloro-1-ethylpyrrolo[2,3-c]pyridin-2-yl]-5-fluoro-2-methoxypyridine (Compound 62d) (170.0 mg, 0.56 mmol) in 1,4-dioxane (5.0 mL) was added (1S,2S)-2-fluorocyclopropane-1-carboxamide (Compound 62e) (286.6 mg, 2.78 mmol), $K_2CO_3$ (230.5 mg, 1.67 mmol), BrettPhos (59.7 mg, 0.11 mmol) and BrettPhos Pd O3 (50.4 mg, 0.06 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A: Water (10 mmol/L $NH_4HCO_3$). Mobile Phase B: ACN; Flow rate: 60 mL/min; Gradient: 23% B to 33% B in 8 min; 254 nm) to afford (1S,2S)-N-(1-ethyl-2-(5-fluoro-2-methoxypyridin-3-yl)-1H-pyrrolo[2,3-c]pyridin-5-yl)-2-fluorocyclopropane-1-carboxamide (Compound 62) (3.1 mg, 1%) as a white solid. LCMS (ESI, m/z): [M+H]$^+$=373.2. $^1$H NMR (300 MHz, DMSO-$d_6$): δ 10.57 (s, 1H), 8.71 (s, 1H), 8.37 (d, J=3.0 Hz, 1H), 8.24 (s, 1H), 7.95-7.91 (m, 1H), 6.56 (s, 1H), 5.05-4.73 (m, 1H), 4.17-4.10 (m, 2H), 3.90 (s, 3H), 2.29-2.15 (m, 1H), 1.76-1.61 (m, 1H), 1.23-1.12 (m, 4H).

Step 1: Synthesis of 5-chloro-1-ethyl-2-(2-methoxypyridin-3-yl)-1H-pyrrolo[2,3-c]pyridine (Compound 63c)

-continued

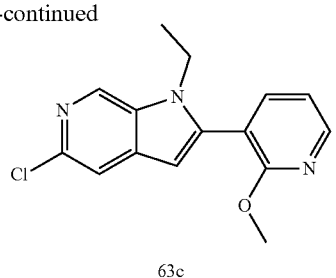

63c

To a solution of 5-chloro-1-ethyl-2-iodopyrrolo[2,3-c]pyridine (Compound 63a) (380.0 mg, 1.24 mmol) in 1,4-dioxane/H₂O (10.0/2.0 mL) was added 2-methoxypyridin-3-ylboronic acid (Compound 63b) (189.6 mg, 1.24 mmol), K₂CO₃ (514.0 mg, 3.72 mmol) and Pd(dppf)Cl₂ (90.7 mg, 0.12 mmol) at room temperature under N₂. The resulting mixture was stirred at 80° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford 5-chloro-1-ethyl-2-(2-methoxypyridin-3-yl)-1H-pyrrolo[2,3-c]pyridine (Compound 63c) (350.0 mg, 98%) as a yellow solid. LCMS (ESI, m/z): [M+H]⁺=288.1.

Step 2: Synthesis of (1S,2S)-N-(1-ethyl-2-(2-methoxypyridin-3-yl)-1H-pyrrolo[2,3-c]pyridin-5-yl)-2-fluorocyclopropane-1-carboxamide (Compound 63)

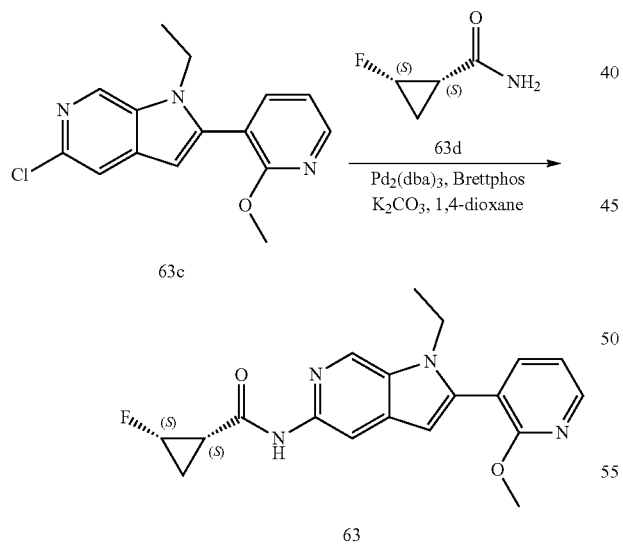

To a mixture of 3-[5-chloro-1-ethylpyrrolo[2,3-c]pyridin-2-yl]-2-methoxypyridine (Compound 63c) (190.0 mg, 0.66 mmol) and (1S,2S)-2-fluorocyclopropane-1-carboxamide (Compound 63d) (340.4 mg, 3.30 mmol) in 1,4-dioxane (10.0 mL) was added K₂CO₃ (273.8 mg, 1.98 mmol), BrettPhos (70.9 mg, 0.13 mmol) and Pd₂(dba)₃ (60.5 mg, 0.07 mmol) at room temperature under N₂. The reaction mixture was stirred with microwave at 120° C. for 1.5 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A: Water (10 mmol/L NH₄HCO₃). Mobile Phase B: ACN: Flow rate: 60 mL/min; Gradient: 38% B to 48% B in 8 min; 254 nm) to afford (1S,2S)-N-[1-ethyl-2-(2-methoxypyridin-3-yl)pyrrolo[2,3-c]pyridin-5-yl]-2-fluorocyclopropane-1-carboxamide (Compound 63) (15.5 mg, 6%) as a white solid. LCMS (ESI, m/z): [M+H]⁺=355.1. ¹H NMR (300 MHz, DMSO-d₆): δ 10.56 (s, 1H), 8.68 (s, 1H), 8.37-8.34 (m, 1H), 8.22 (s, 1H), 7.85-7.82 (m, 1H), 7.20-7.16 (m, 1H), 6.49 (s, 1H), 5.03-4.79 (m, 1H), 4.12-4.04 (m, 2H), 3.90 (s, 3H), 2.24-2.19 (m, 1H), 1.70-1.61 (m, 1H), 1.20-1.10 (m, 4H).

Example S64: Synthesis of (1S,2S)-2-fluoro-N-(2-(2-methoxypyridin-3-yl)-1-(methyl-d3)-1H-pyrrolo[2,3-c]pyridin-5-yl)cyclopropane-1-carboxamide (Compound 64)

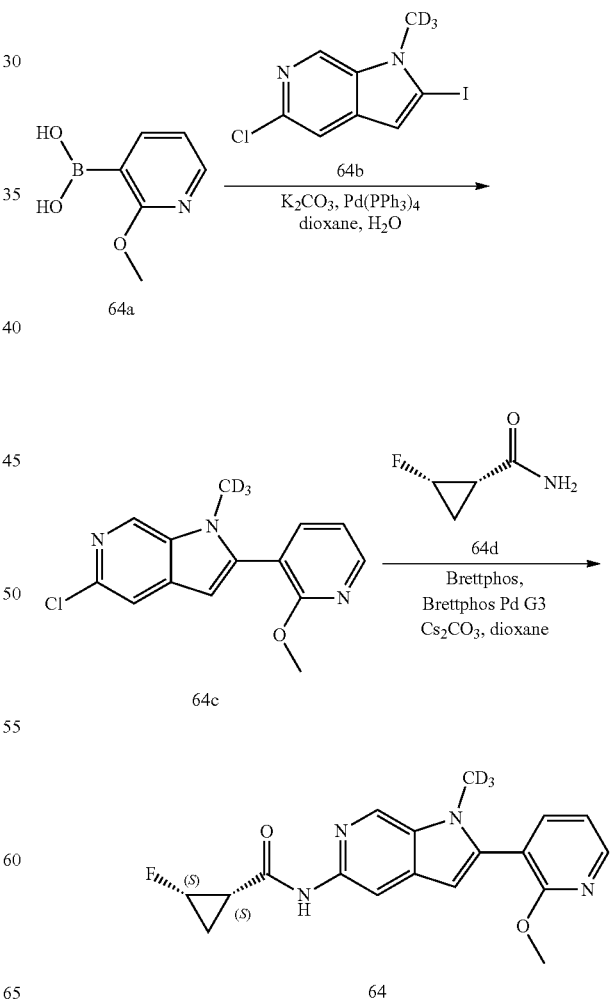

Step 1: Synthesis of 5-chloro-2-(2-methoxypyridin-3-yl)-1-(methyl-d3)-1H-pyrrolo[2,3-c]pyridine (Compound 64c)

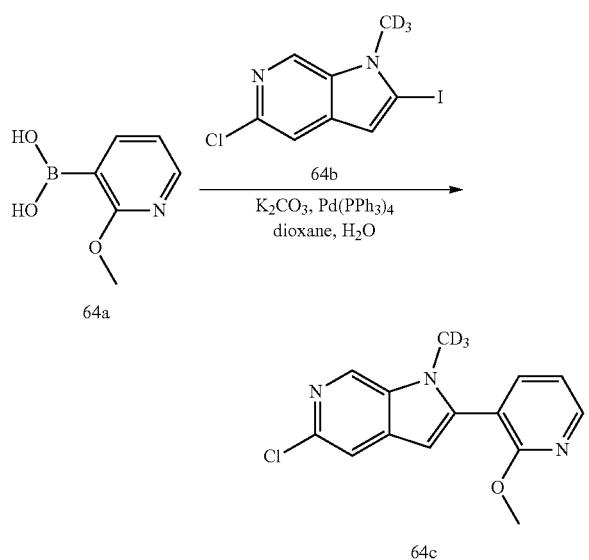

To a solution of (2-methoxypyridin-3-yl)boronic acid (Compound 64a) (200.0 mg, 1.31 mmol) in dioxane/H₂O (5.0/1.0 mL) was added 5-chloro-2-iodo-1-(methyl-d3)-1H-pyrrolo[2,3-c]pyridine (Compound 64b) (386.5 mg, 1.31 mmol), K₂CO₃ (542.2 mg, 3.92 mmol) and Pd(PPh₃)₄ (151.1 mg, 0.13 mmol) at room temperature under N₂. The resulting mixture was stirred at 80° C. for 2 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 5-chloro-2-(2-methoxypyridin-3-yl)-1-(methyl-d3)-1H-pyrrolo[2,3-c]pyridine (Compound 64c) (130.0 mg, 35%) as a yellow oil. LCMS (ESI, m/z): [M+H]⁺= 277.1.

Step 2: Synthesis of (1S,2S)-2-fluoro-N-(2-(2-methoxypyridin-3-yl)-1-(methyl-d3)-1H-pyrrolo[2,3-c]pyridin-5-yl)cyclopropane-1-carboxamide (Compound 64)

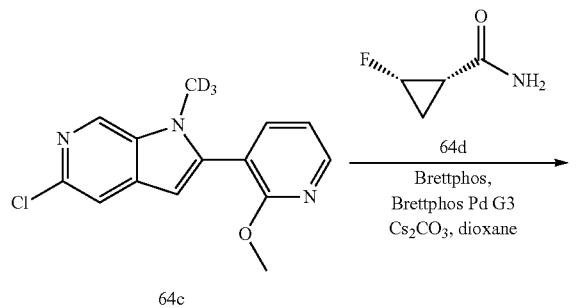

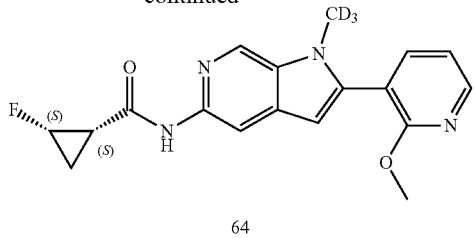

To a solution of 5-chloro-2-(2-methoxypyridin-3-yl)-1-(methyl-d3)-1H-pyrrolo[2,3-c]pyridine (Compound 64c) (110.0 mg, 0.40 mmol) in dioxane (5.0 mL) was added (1S,2S)-2-fluorocyclopropane-1-carboxamide (Compound 64d) (204.9 mg, 1.99 mmol), Cs₂CO₃ (338.5 mg, 1.19 mmol), Brettphos (42.7 mg, 0.08 mmol) and Brettphos Pd G3 (36.0 mg, 0.04 mmol) at room temperature under N₂. The resulting mixture was stirred at 100° C. for 4 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/CH₃OH (10/1, v/v) and then purified by Prep-HPLC with the following conditions (Column: XBridge Prep OBD C18 Column, 30×150 mm, 5 um; Mobile Phase A: Water (10 mmol/L NH₄HCO₃), Mobile Phase B: ACN; Flow rate: 60 mL/min; Gradient: 21% to 51% in 9 min; 254 nm) to afford (1S,2S)-2-fluoro-N-(2-(2-methoxypyridin-3-yl)-1-(methyl-d3)-1H-pyrrolo[2,3-c]pyridin-5-yl)cyclopropane-1-carboxamide (Compound 64) (6.5 mg, 4%) as a white solid. LCMS (ESI, m/z): [M+H]⁺=344.1. ¹H NMR (300 MHz, DMSO-d₆): δ 10.55 (s, 1H), 8.64 (s, 1H), 8.35 (s, 1H), 8.22 (s, 1H), 7.86-7.84 (m, 1H), 7.23-7.17 (m, 1H), 6.54 (s, 1H), 5.09-4.72 (m, 1H), 3.92 (s, 3H), 2.25-2.16 (m, 1H), 1.79-1.53 (m, 1H), 1.22-1.05 (m, 1H).

Example S65: Synthesis of (1S,2S)-2-fluoro-N-(2-(5-fluoro-2-methoxypyridin-3-yl)-1-(methyl-d3)-1H-pyrrolo[2,3-c]pyridin-5-yl)cyclopropane-1-carboxamide (Compound 65)

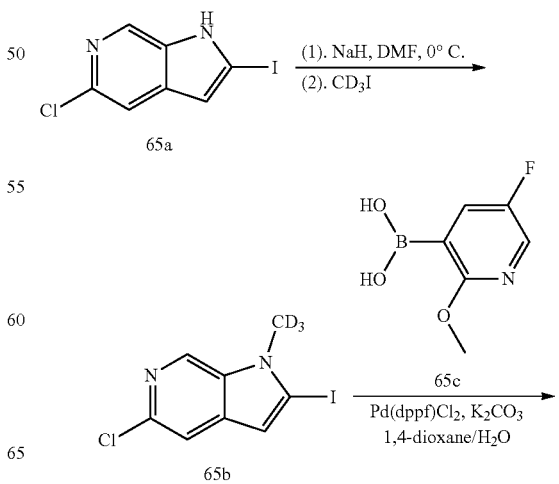

325

-continued

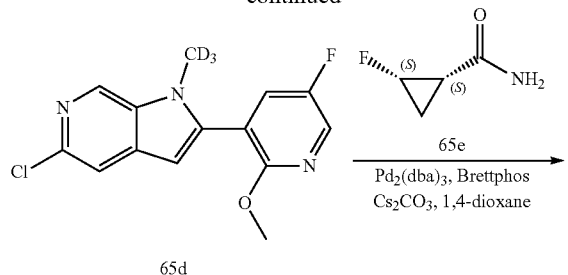

326

Step 2: Synthesis of 5-chloro-2-(5-fluoro-2-methoxypyridin-3-yl)-1-(methyl-d3)-1H-pyrrolo[2,3-c]pyridine (Compound 65d)

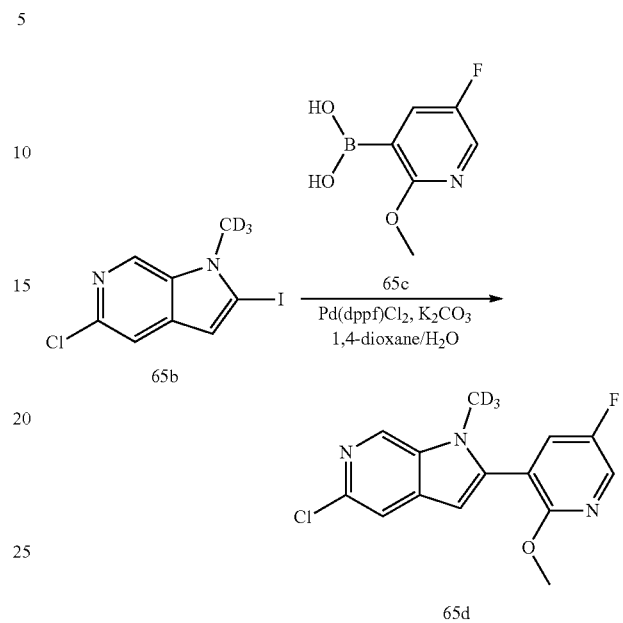

Step 1: Synthesis of 5-chloro-2-iodo-1-(methyl-d3)-1H-pyrrolo[2,3-c]pyridine (Compound 65b)

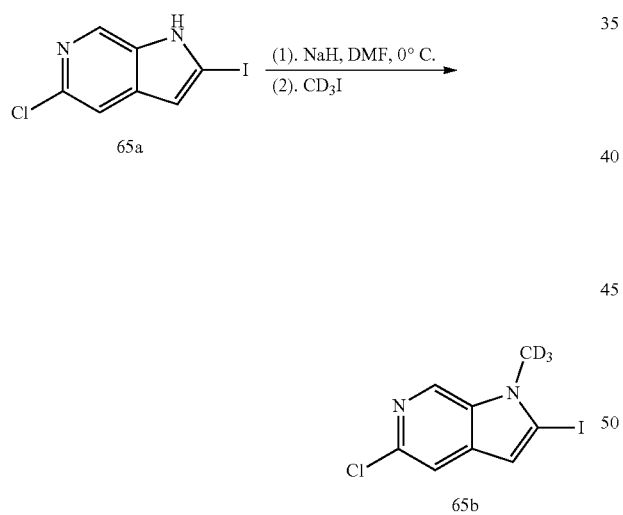

To a solution of 5-chloro-2-iodo-1H-pyrrolo[2,3-c]pyridine (Compound 65a) (700.0 mg, 2.51 mmol) in DMF (10.0 mL) was added NaH (301.6 mg, 60%) at 0° C. under $N_2$. The resulting mixture was stirred at 0° C. for 1 h. Then iodomethane-d3 (1.8 g, 12.56 mmol) was added dropwise to the mixture at 0° C. under $N_2$. The resulting mixture was stirred at 0° C. for another 1 h. After the reaction was completed, the reaction was quenched with $H_2O$ at 0° C. and then filtered. The solid was collected and dried to afford 5-chloro-2-iodo-1-(methyl-d3)-1H-pyrrolo[2,3-c]pyridine (Compound 65b) (740.0 mg, crude) as a yellow solid. LCMS (ESI, m/z): [M+H]$^+$=295.9.

To a solution of 5-chloro-2-iodo-1-(methyl-d3)-1H-pyrrolo[2,3-c]pyridine (Compound 65b) (200.0 mg, 0.67 mmol) in 1,4-dioxane/$H_2O$ (5.0/1.0 mL) was added (5-fluoro-2-methoxypyridin-3-yl)boronic acid (Compound 65c) (115.7 mg, 0.67 mmol). $K_2CO_3$ (280.6 mg, 2.03 mmol) and Pd(dppf)Cl$_2$ (49.5 mg, 0.07 mmol) at room temperature under $N_2$. The resulting mixture was stirred at 80° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (63/37, v/v) to afford 5-chloro-2-(5-fluoro-2-methoxypyridin-3-yl)-1-(methyl-d3)-1H-pyrrolo[2,3-c]pyridine (Compound 65d) (160.0 mg, 80%) as a white solid. LCMS (ESI, m/z): [M+H]$^+$=295.1.

Step 3: Synthesis of (1S,2S)-2-fluoro-N-(2-(5-fluoro-2-methoxypyridin-3-yl)-1-(methyl-d3)-1H-pyrrolo[2,3-c]pyridin-5-yl)cyclopropane-1-carboxamide (Compound 65)

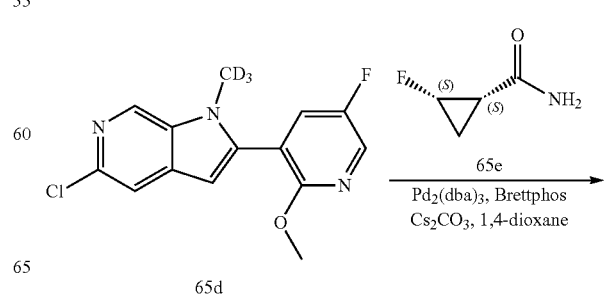

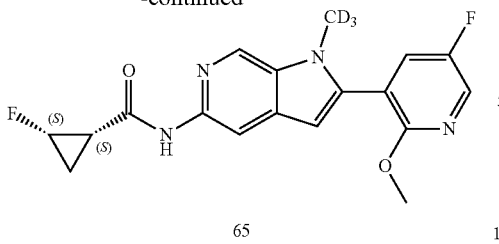

65

To a solution of 5-chloro-2-(5-fluoro-2-methoxypyridin-3-yl)-1-(methyl-d3)-1H-pyrrolo[2,3-c]pyridine (Compound 65d) (120.0 mg, 0.41 mmol) in 1,4-dioxane (6.0 mL) was added (1S,2S)-2-fluorocyclopropane-1-carboxamide (Compound 65e) (209.9 mg, 2.04 mmol), $Cs_2CO_3$ (397.9 mg, 1.22 mmol), BrettPhos (43.7 mg, 0.08 mmol) and $Pd_2(dba)_3$ (37.3 mg, 0.04 mmol) at room temperature under $N_2$. The resulting mixture was stirred at 100° C. for 4 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (20/80, v/v) and then purified by Prep-HPLC with the following conditions (Column: Xselect CSH OBD Column 30×150 mm, 5 um; Mobile Phase A: Water (10 mmol/L $NH_4HCO_3$), Mobile Phase B: ACN; Flow rate: 8 mL/min; Gradient: 40% B to 50% B in 8 min; 254 nm) to afford (1S,2S)-2-fluoro-N-(2-(5-fluoro-2-methoxypyridin-3-yl)-1-(methyl-d3)-1H-pyrrolo[2,3-c]pyridin-5-yl)cyclopropane-1-carboxamide (Compound 65) (5.4 mg, 3%) as a white solid. LCMS (ESI, m/z): $[M+H]^+$=362.1, $^1H$ NMR (300 MHz, DMSO-$d_6$): δ 10.57 (s, 1H), 8.67 (s, 1H), 8.35 (d, J=3.0 Hz, 1H), 8.23 (s, 1H), 7.94-7.90 (m, 1H), 6.61 (d, J=0.6 Hz, 1H), 5.05-4.77 (m, 1H), 3.91 (s, 3H), 2.23-2.19 (m, 1H), 1.71-1.60 (m, 1H), 1.18-1.14 (m, 1H).

Example S66: Synthesis of (1S,2S)-N-[2-(5-chloro-2-methoxypyridin-3-yl)-1-methylpyrrolo[2,3-c]pyridin-5-yl]-2-fluorocyclopropane-1-carboxamide (Compound 66)

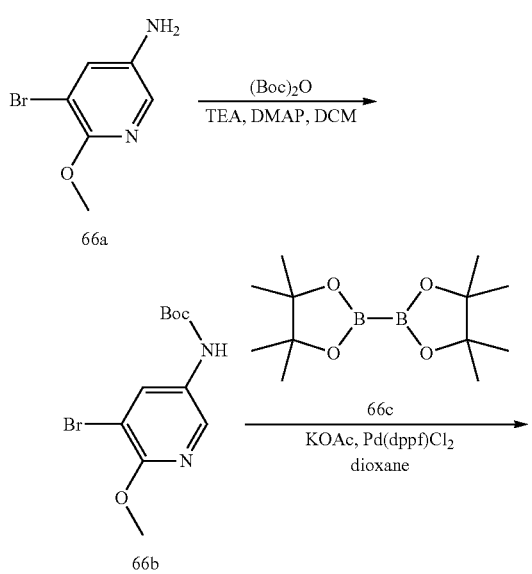

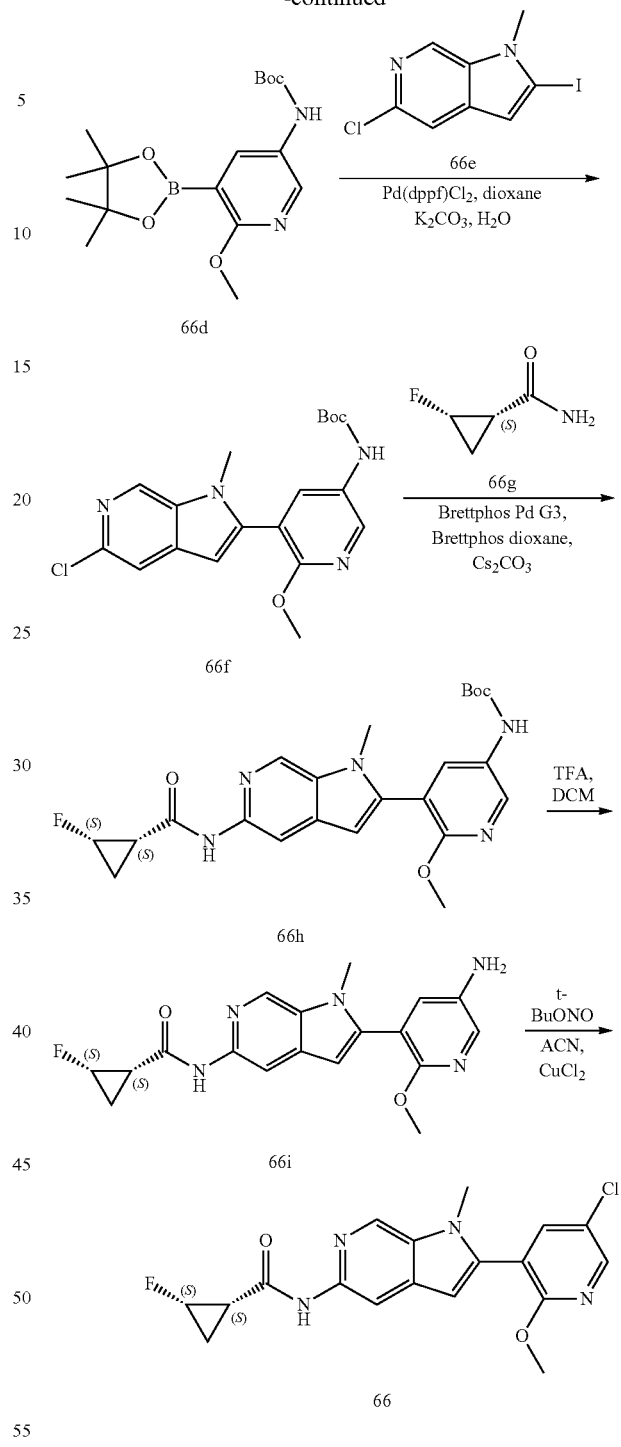

Step 1: Synthesis of tert-butyl N-(5-bromo-6-methoxypyridin-3-yl)carbamate (Compound 66b)

To a solution of 5-bromo-6-methoxypyridin-3-amine (Compound 66a) (4.0 g, 19.70 mmol) in DCM (50.0 mL) were added TEA (4.0 g, 39.60 mmol), DMAP (0.5 g, 3.94 mmol) and di-tert-butyl dicarbonate (5.2 g, 23.64 mmol) at room temperature. The resulting mixture was stirred at room temperature for 16 h. After the reaction was completed, the resulting mixture was concentrated under reduced pressure. The residue was purified by flash column chromatography with petroleum ether/ethyl acetate (2/1, v/v) to afford tert-butyl N-(5-bromo-6-methoxypyridin-3-yl)carbamate (Compound 66b) (4.5 g, 52%) as a colorless oil. LCMS (ESI, m/z): [M+H]$^+$=303.0.

Step 2: Synthesis of tert-butyl N-[6-methoxy-5-(4,4,5,5-tetramethyl-1,3,2-dioxaborolan-2-yl)pyridin-3-yl]carbamate (Compound 66d)

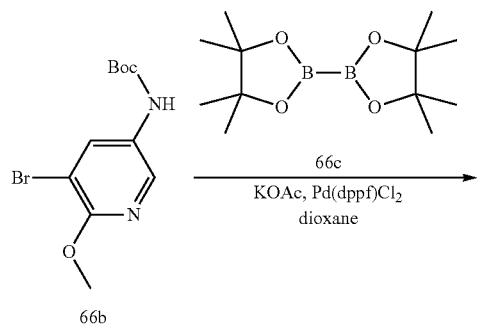

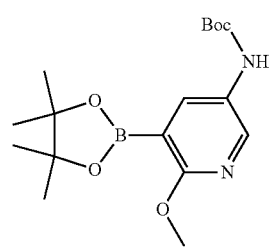

To a solution of tert-butyl N-(5-bromo-6-methoxypyridin-3-yl)carbamate (Compound 66b) (3.2 g, 5.28 mmol) in dioxane (64.0 mL) was added bis(pinacolato)diboron (Compound 66c) (2.0 g, 7.92 mmol), KOAc (1.6 g, 15.83 mmol) and Pd(dppf)Cl$_2$ (0.4 g, 0.53 mmol) at room temperature under N$_2$. The resulting mixture was stirred at 80° C. for 16 h under N$_2$. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by reverse phase flash chromatography with H$_2$O/ACN (1/1, v/v) to afford tert-butyl N-[6-methoxy-5-(4,4,5-tetramethyl-1,3,2-dioxaborolan-2-yl)pyridin-3-yl]carbamate (Compound 66d) (780.0 mg, 42%) as a yellow oil. LCMS (ESI, m/z): [M+H]$^+$=351.2.

Step 3: Synthesis of tert-butyl N-(5-[5-chloro-1-methylpyrrolo[2,3-c]pyridin-2-yl]-6-methoxypyridin-3-yl)carbamate (Compound 66f)

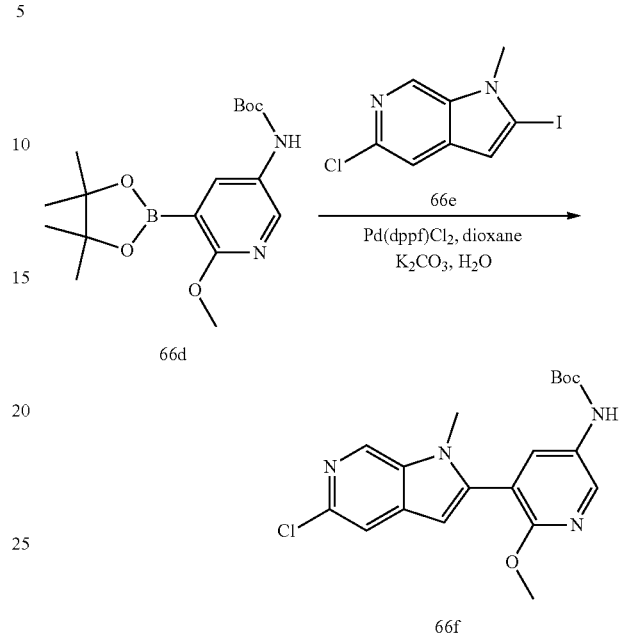

To a solution of tert-butyl N-[6-methoxy-5-(4,4,5,5-tetramethyl-1,3,2-dioxaborolan-2-yl)pyridin-3-yl]carbamate (Compound 66d) (1.3 g, 3.71 mmol) in dioxane/H$_2$O (50.0 mL/10.0 mL) was added 5-chloro-2-iodo-1-methylpyrrolo[2,3-c]pyridine (Compound 66e) (1.1 g, 3.71 mmol), K$_2$CO$_3$ (1.5 g, 11.14 mmol) and Pd(dppf)Cl$_2$ (0.3 g, 0.37 mmol) at room temperature under N$_2$. The resulting mixture was stirred at 80° C. for 16 h under N$_2$. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford tert-butyl N-(5-[5-chloro-1-methylpyrrolo[2,3-c]pyridin-2-yl]-6-methoxypyridin-3-yl)carbamate (Compound 66f) (1.2 g, 83%) as a white solid. LCMS (ESI, m/z): [M+H]$^+$=389.1.

Step 4: Synthesis of N-(5-[5-[(1S,2S)-2-fluorocyclopropaneamido]-1-methylpyrrolo[2,3-c]pyridin-2-yl]-6-methoxypyridin-3-yl)carbamate (Compound 66h)

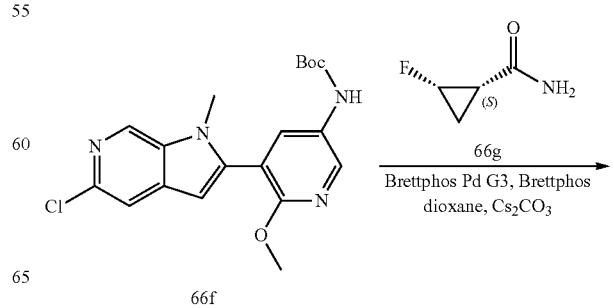

-continued

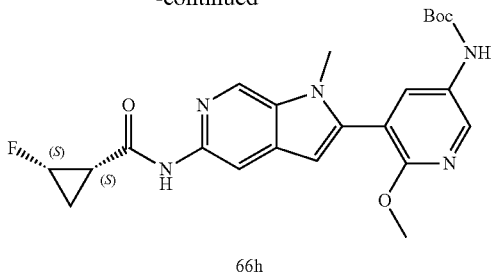

66h

To a solution of tert-butyl N-(5-[5-chloro-1-methylpyrrolo[2,3-c]pyridin-2-yl]-6-methoxypyridin-3-yl)carbamate (Compound 66f) (600.0 mg, 1.54 mmol) in 1,4-dioxane (10.0 mL) was added (1S,2S)-2-fluorocyclopropane-1-carboxamide (Compound 66g) (795.4 mg, 7.72 mmol), BrettPhos (165.7 mg, 0.31 mmol), $Cs_2CO_3$ (1508.2 mg, 4.63 mmol) and BrettPhos Pd G3 (139.9 mg, 0.15 mmol) at room temperature under $N_2$. The reaction mixture was stirred with microwave at 120° C. for 1.5 h. After the reaction was completed, the reaction mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/10, v/v) to afford tert-butyl N-(5-[5-[(1S,2S)-2-fluorocyclopropaneamido]-1-methylpyrrolo[2,3-c]pyridin-2-yl]-6-methoxypyridin-3-yl)carbamate (Compound 66h) (370.0 mg, 53%) as a yellow oil. LCMS (ESI, m/z): $[M+H]^+=456.2$.

Step 5: Synthesis of (1S,2S)-N-[2-(5-amino-2-methoxypyridin-3-yl)-1-methylpyrrolo[2,3-c]pyridin-5-yl]-2-fluorocyclopropane-1-carboxamide (Compound 66i)

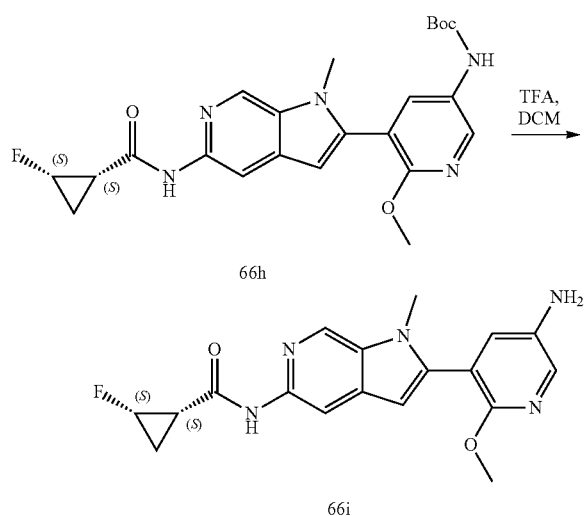

To a solution of tert-butyl N-(5-[5-[(1S,2S)-2-fluorocyclopropaneamido]-1-methylpyrrolo[2,3-c]pyridin-2-yl]-6-methoxypyridin-3-yl)carbamate (Compound 66h) (100.0 mg, 0.22 mmol) in DCM (10.0 mL) was added TFA (1.0 mL) at room temperature. The resulting mixture was stirred at room temperature for 30 min. After the reaction was completed, the reaction mixture was diluted with $H_2O$. The pH value of the mixture was adjusted to 7 with aq·$NaHCO_3$ and then extracted with ethyl acetate. The combined organic layer was washed with brine, dried over anhydrous sodium sulfate and filtered. The filtrate was concentrated under reduced pressure to afford (1S,2S)-N-[2-(5-amino-2-methoxypyridin-3-yl)-1-methylpyrrolo[2,3-c]pyridin-5-yl]-2-fluorocyclopropane-1-carboxamide (Compound 66i) (80.0 mg, 32%) as a yellow solid. LCMS (ESI, m/z): $[M+H]^+=356.1$.

Step 6: Synthesis of (1S,2S)-N-[2-(5-chloro-2-methoxypyridin-3-yl)-1-methylpyrrolo[2,3-c]pyridin-5-yl]-2-fluorocyclopropane-1-carboxamide (Compound 66)

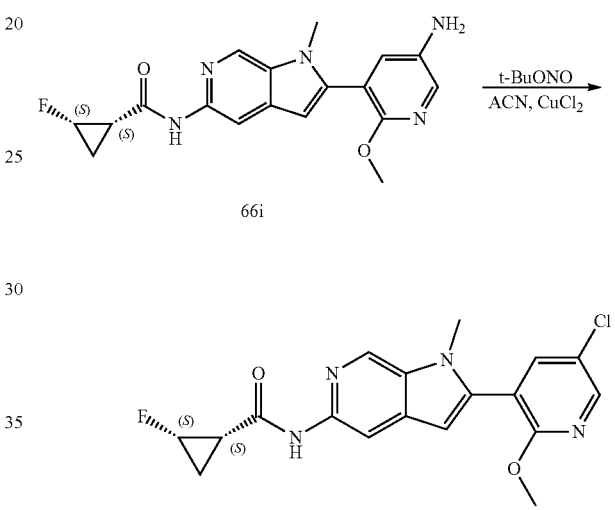

To a solution of (1S,2S)-N-[2-(5-amino-2-methoxypyridin-3-yl)-1-methylpyrrolo[2,3-c]pyridin-5-yl]-2-fluorocyclopropane-1-carboxamide (Compound 66i) (70.0 mg, 0.20 mmol) in ACN (4.0 mL) was added 2-methyl-2-propylnitrite (30.5 mg, 0.30 mmol) and $CuCl_2$ (13.2 mg, 0.10 mmol) at room temperature. The resulting mixture was stirred at 80° C. for 2 h. After the reaction was completed, the reaction mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash chromatography with ACN/$H_2O$ (1/1, v/v) and then purified by Prep-HPLC with the following conditions Column: (Xselect CSH OBD Column 30×150 mm, 5 um; Mobile Phase A:Water (10 mmol/L $NH_4HCO_3$), Mobile Phase B: ACN; Flow rate: 60 mL/min; Gradient: 46% B to 55% B in 8 min; 254 nm) to afford (1S,2S)-N-[2-(5-chloro-2-methoxypyridin-3-yl)-1-methylpyrrolo[2,3-c]pyridin-5-yl]-2-fluorocyclopropane-1-carboxamide (Compound 66) (2.3 mg, 3%) as a yellow solid. LCMS (ESI, m/z): $[M+H]^+=375.1$. $^1H$ NMR (300 MHz, $CD_3OD$): δ 8.56 (s, 1H), 8.30 (d, J=2.4 Hz, 1H), 8.18 (s, 1H), 7.86 (d, J=2.4 Hz, 1H), 6.58 (s, 1H), 5.02-4.77 (m, 1H), 3.99 (s, 3H), 3.74 (s, 3H), 2.16-2.06 (m, 1H), 1.87-1.74 (m, 1H), 1.25-1.15 (m, 1H).

Example S67: Synthesis of (1S,2S)-N-[2-(5-cyano-2-methoxypyridin-3-yl)-1-methylpyrrolo[2,3-c]pyridin-5-yl]-2-fluorocyclopropane-1-carboxamide (Compound 67)

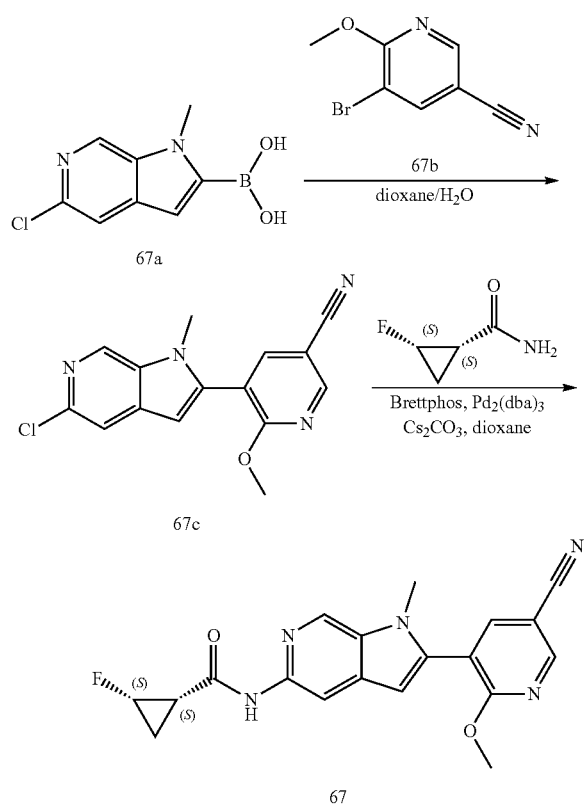

Step 1: Synthesis of 5-(5-chloro-1-methyl-1H-pyrrolo[2,3-c]pyridin-2-yl)-6-methoxynicotinonitrile (Compound 67c)

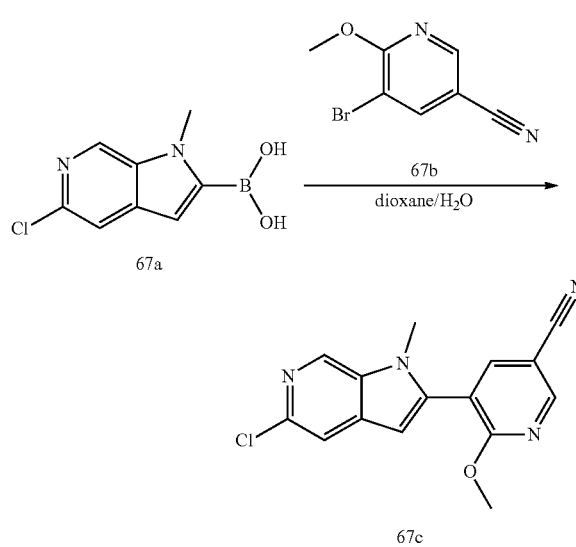

Step 1: To a mixture of 5-chloro-1-methylpyrrolo[2,3-c]pyridin-2-ylboronic acid (Compound 67a) (300.0 mg, 1.43 mmol) and 5-bromo-6-methoxypyridine-3-carbonitrile (Compound 67b) (364.5 mg, 1.71 mmol) in H₂O/dioxane (1.0/10.0 mL) was added K₃PO₄ (591.1 mg, 4.28 mmol), XPhos Pd G3 (120.7 mg, 0.14 mmol) and XPhos (135.9 mg, 0.9 mmol). The resulting mixture was stirred at 80° C. for 4 h under N₂. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-(5-chloro-1-methyl-1H-pyrrolo[2,3-c]pyridin-2-yl)-6-methoxynicotinonitrile (Compound 67c) (94.0 mg, 21%) as a white solid. LCMS (ESI, m/z): [M+H]⁺=299.1.

Step 2: Synthesis of (1S,2S)-N-[2-(5-cyano-2-methoxypyridin-3-yl)-1-methylpyrrolo[2,3-c]pyridin-5-yl]-2-fluorocyclopropane-1-carboxamide (Compound 67)

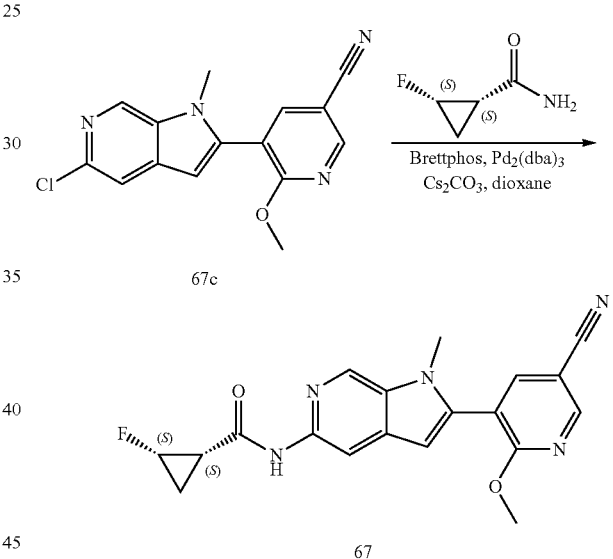

To a mixture of 5-[5-chloro-1-methylpyrrolo[2,3-c]pyridin-2-yl]-6-methoxypyridine-3-carbonitrile (Compound 67c) (76.0 mg, 0.25 mmol) and (1S,2S)-2-fluorocyclopropane-1-carboxamide (131.1 mg, 1.27 mmol) in dioxane (5.0 mL) was added Cs₂CO₃ (248.7 mg, 0.76 mmol), BrettPhos (54.6 mg, 0.10 mmol) and Pd₂(dba)₃ (46.6 mg, 0.05 mmol). The resulting mixture was stirred at 80° C. for 6 h under N₂. After the reaction was completed, the resulting mixture was diluted with water and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A:water (0.1% FA), Mobile Phase B: ACN; Flow rate: 60 mL/min; Gradient: 12% B to 22% B in 10 min; 254/220 nm to afford (1S,2S)-N-[2-(5-cyano-2-methoxypyridin-3-yl)-1-methylpyrrolo[2,3-c]pyridin-5-yl]-2-fluorocyclopropane-1-carboxamide (Compound 67) (20.8 mg, 22%) as a white solid. LCMS (ESI, m/z): [M+H]⁺=366.3. ¹H NMR (300 MHz, DMSO-d$_6$): δ 10.58 (s, 1H), 8.86 (d, J=2.1 Hz, 1H), 8.67 (s, 1H), 8.35 (d, J=2.1 Hz, 1H), 8.23 (s, 1H), 6.63 (s, 1H), 5.04-4.79 (m, 1H), 4.00 (s, 3H), 3.66 (s, 3H), 2.26-2.16 (m, 1H), 1.70-1.58 (m, 1H), 1.19-1.15 (m, 1H).

Example S68: Synthesis of (1S,2S)-2-fluoro-N-(2-(4-methoxypyrimidin-5-yl)-1-methyl-1H-pyrrolo[2,3-c]pyridin-5-yl)cyclopropane-1-carboxamide (Compound 68)

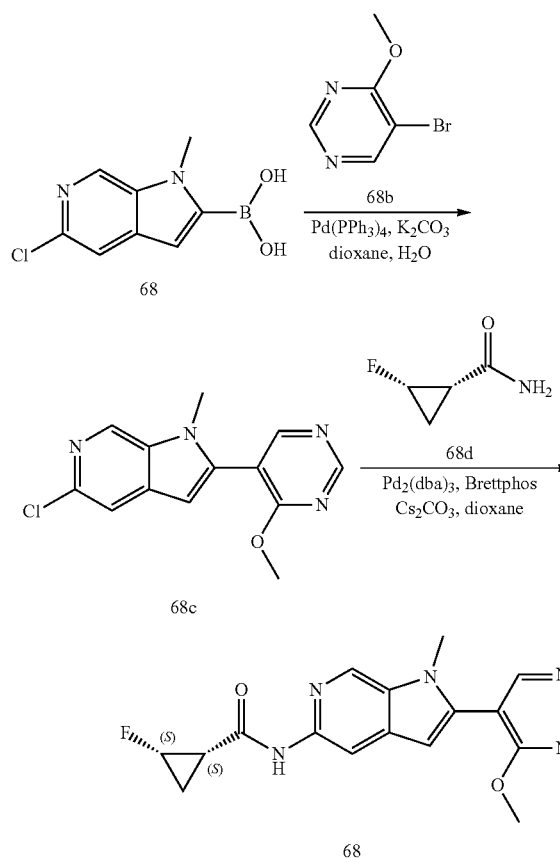

Step 1: Synthesis of 5-chloro-2-(4-methoxypyrimidin-5-yl)-1-methyl-1H-pyrrolo[2,3-c]pyridine (Compound 68c)

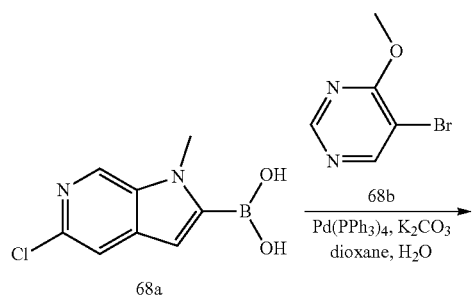

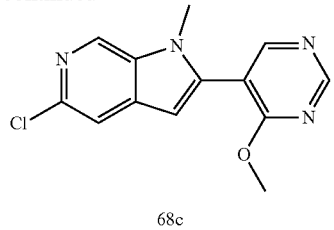

To a solution of (5-chloro-1-methyl-1H-pyrrolo[2,3-c]pyridin-2-yl)boronic acid (Compound 68a) (222.7 mg, 1.06 mmol) in dioxane/H$_2$O (5.0/1.0 mL) was added 5-bromo-4-methoxypyrimidine (Compound 68b) (200.0 mg, 1.06 mmol), K$_2$CO$_3$ (438.7 mg, 3.17 mmol) and Pd(PPh$_3$)$_4$ (122.3 mg, 0.11 mmol) at room temperature under N$_2$. The resulting mixture was stirred at 80° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/2, v/v) to afford 5-chloro-2-(4-methoxypyrimidin-5-yl)-1-methyl-1H-pyrrolo[2,3-c]pyridine (Compound 68c) (80.0 mg, 27%) as a yellow solid. LCMS (ESI, m/z): [M+H]$^+$=275.1.

Step 2: Synthesis of (1S,2S)-2-fluoro-N-(2-(4-methoxypyrimidin-5-yl)-1-methyl-1H-pyrrolo[2,3-c]pyridin-5-yl)cyclopropane-1-carboxamide (Compound 68)

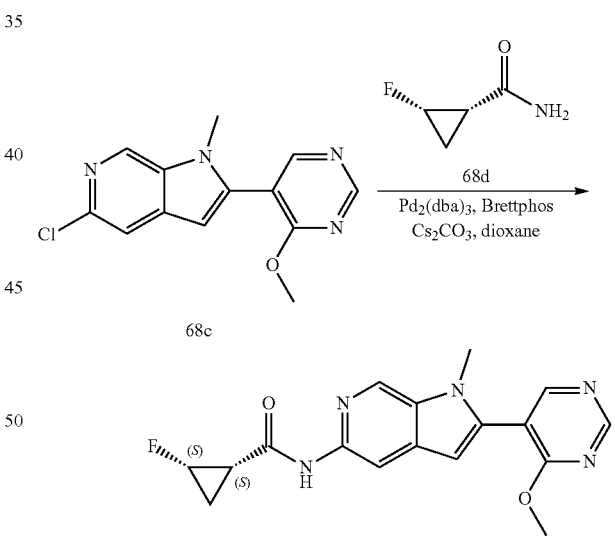

To a solution of 5-chloro-2-(4-methoxypyrimidin-5-yl)-1-methyl-1H-pyrrolo[2,3-c]pyridine (Compound 68c) (70.0 mg, 0.26 mmol) in dioxane (2.0 mL) was added (1S,2S)-2-fluorocyclopropane-1-carboxamide (Compound 68d) (131.4 mg, 1.27 mmol), Cs$_2$CO$_3$ (249.1 mg, 0.76 mmol), Brettphos (27.4 mg, 0.05 mmol) and Pd$_2$(dba)$_3$ (23.1 mg, 0.03 mmol) at room temperature under N$_2$. The resulting mixture was stirred at 100° C. for 4 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by reverse flash chromatography with CH$_3$CN/H$_2$O (40/60, v/v) and then purified by Prep-HPLC with the following conditions (Column: XBridge Prep OBD C18 Column, 30×150 mm, 5 um; Mobile Phase A: Water (10 mmol/L NH$_4$HCO$_3$), Mobile Phase B: ACN; Flow rate: 60 mL/min; Gradient: 14% to 44% in 9 min; 254 nm) to afford (1S,2S)-2-fluoro-N-(2-(4-methoxypyrimidin-5-yl)-1-methyl-1H-pyrrolo[2,3-c]pyridin-5-yl)cyclopropane-1-carboxamide (Compound 68) (2.0 mg, 2%) as a white solid. LCMS (ESI, m/z): [M+H]$^+$=342.1. $^1$H NMR (300 MHz, DMSO-d$_6$): δ 10.58 (s, 1H), 8.95 (s, 1H), 8.68 (s, 2H), 8.24 (s, 1H), 6.65 (s, 1H), 5.03-4.79 (m, 1H), 4.02 (s, 3H), 3.68 (s, 3H), 2.24-2.10 (m, 1H), 1.70-1.61 (m, 1H), 1.18-1.11 (m, 1H).

Example S69: Synthesis of (1S,2S)-2-fluoro-N-[2-(5-methoxy-1,3-benzothiazol-6-yl)-1-methylpyrrolo[2,3-c]pyridin-5-yl]cyclopropane-1-carboxamide (Compound 69)

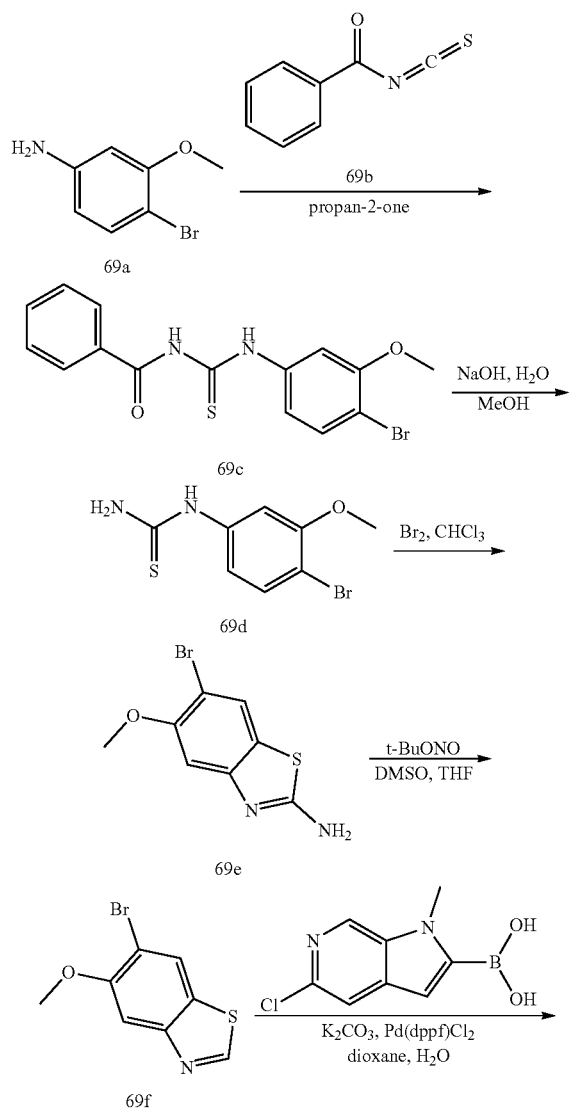

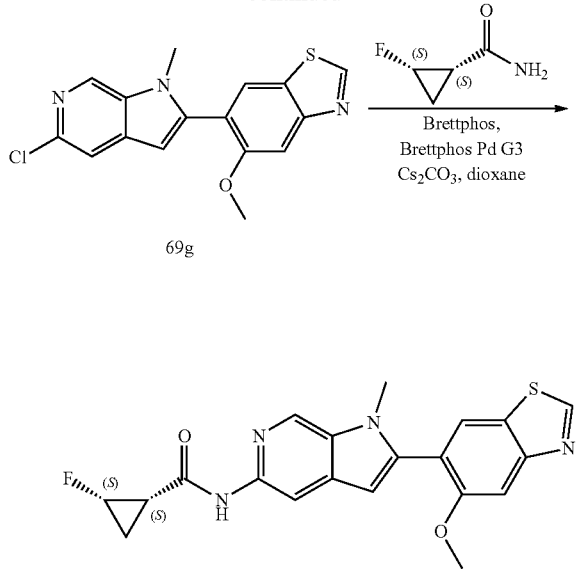

Step 1: Synthesis of 1-benzoyl-3-(4-bromo-3-methyloxyphenyl)thiourea (Compound 69c)

To a solution of 4-bromo-3-methoxyaniline (Compound 69a) (10.0 g, 49.49 mmol) in propan-2-one (100.0 mL) was added benzoyl isothiocyanate (Compound 69b) (8.8 g, 49.53 mmol) at room temperature. The resulting mixture was stirred at 60° C. for 2 h. After the reaction was completed, the reaction mixture was filtered. The solid was washed with CH$_3$OH and dried to afford 1-benzoyl-3-(4-bromo-3-methoxyphenyl)thiourea (Compound 69c) (13.0 g, 72%) as a white solid. LCMS (ESI, m/z): [M+H]$^+$=365.0.

Step 2: Synthesis of 4-bromo-3-methoxyphenylthiourea (Compound 69d)

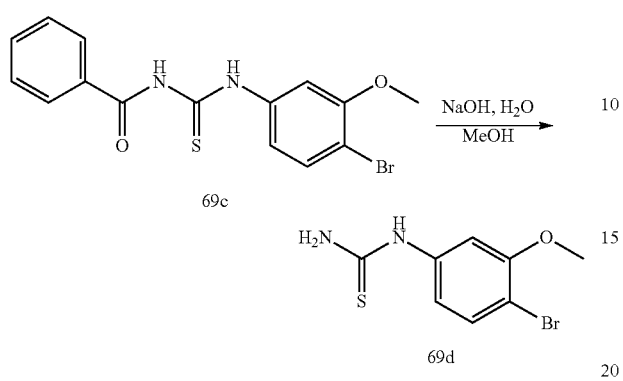

To a solution of 1-benzoyl-3-(4-bromo-3-methoxyphenyl)thiourea (Compound 69c) (7.0 g, 19.15 mmol) in H$_2$O (35.0 mL) and MeOH (70.0 mL) was added NaOH (0.8 g, 21.01 mmol) at room temperature. The resulting mixture was stirred at 80° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure to afford 4-bromo-3-methoxyphenylthiourea (Compound 69d) (4.5 g, crude) as a white solid. LCMS (ESI, m/z): [M+H]$^+$=261.0.

Step 3: Synthesis of 6-bromo-5-methoxy-1,3-benzothiazol-2-amine (Compound 69e)

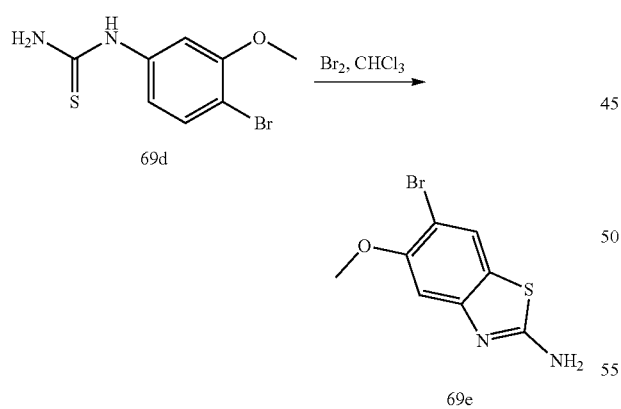

To a solution of 4-bromo-3-methoxyphenylthiourea (Compound 69d) (4.5 g, 17.22 mmol) in CHCl$_3$ (70.0 mL) was added dropwise Br$_2$ (3.3 g, 20.65 mmol) at 0° C. The resulting mixture was stirred at room temperature for 16 h. After the reaction was completed, the reaction mixture was filtered. The solid was collected and dried to afford 6-bromo-5-methoxy-1,3-benzothiazol-2-amine (Compound 69e) (3.0 g, 67%) as an off-white solid. LCMS (ESI, m/z): [M+H]$^+$=258.9.

Step 4: Synthesis of 6-bromo-5-methoxy-1,3-benzothiazole (Compound 69f)

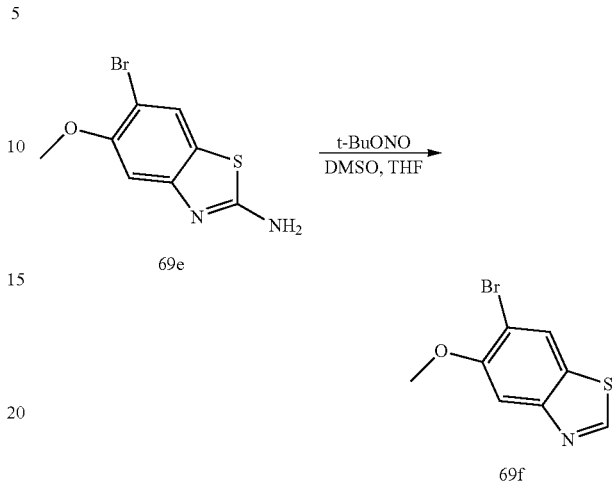

To a solution of 6-bromo-5-methoxy-1,3-benzothiazol-2-amine (Compound 69e) (3.0 g, 11.58 mmol) in THF (30.0 mL) was added t-BuONO (1.8 g, 17.36 mmol) and DMSO (0.07 g, 0.93 mmol). The resulting mixture was stirred at room temperature for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 6-bromo-5-methoxy-1,3-benzothiazole (Compound 69f) (680.0 mg, 24%) as a brown solid. LCMS (ESI, m/z): [M+H]$^+$=243.9.

Step 5: Synthesis of 6-[5-chloro-1-methylpyrrolo[2,3-c]pyridin-2-yl]-5-methoxy-1,3-benzothiazole (Compound 69g)

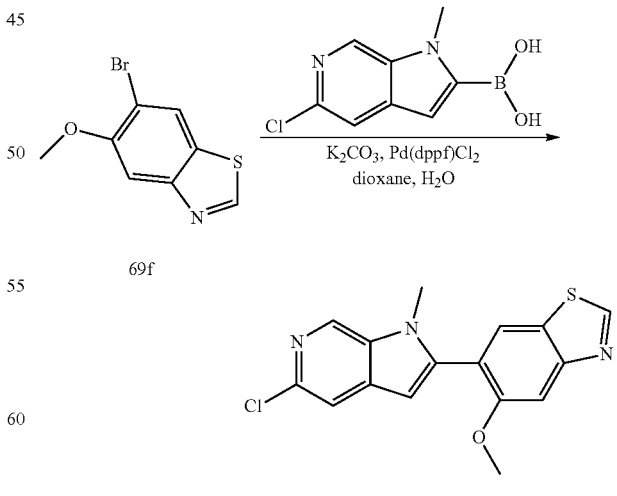

To a solution of 6-bromo-5-methoxy-1,3-benzothiazole (Compound 69f) (300.0 mg, 1.29 mmol) in dioxane/H$_2$O (5.0 mL/0.5 mL) was added $K_2CO_3$ (509.4 mg, 3.67 mmol), 5-chloro-1-methylpyrrolo[2,3-c]pyridin-2-ylboronic acid (258.6 mg, 1.29 mmol) and $Pd(dppf)Cl_2$ (89.9 mg, 0.13 mmol) at room temperature under $N_2$. The resulting mixture was stirred at 80° C. for 2 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 6-[5-chloro-1-methylpyrrolo[2,3-c]pyridin-2-yl]-5-methoxy-1,3-benzothiazole (Compound 69g) (160.0 mg, 59%) as an off-white oil. LCMS (ESI, m/z): $[M+H]^+$=330.0.

Step 6: Synthesis of (1S,2S)-2-fluoro-N-[2-(5-methoxy-1,3-benzothiazol-6-yl)-1-methylpyrrolo[2,3-c]pyridin-5-yl]cyclopropane-1-carboxamide (Compound 69)

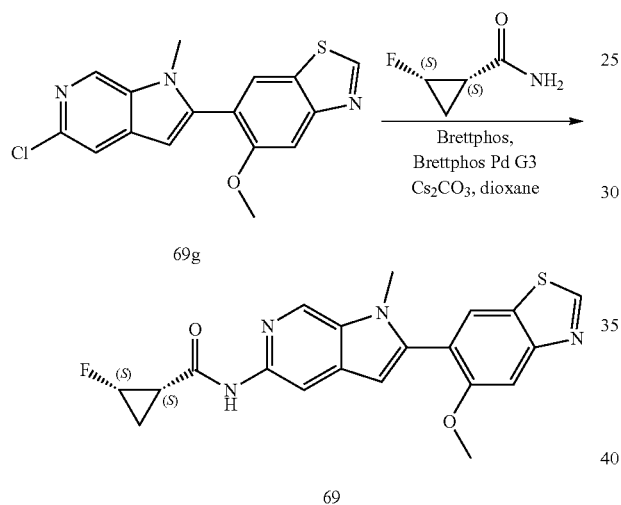

To a solution of 6-[5-chloro-1-methylpyrrolo[2,3-c]pyridin-2-yl]-5-methoxy-1,3-benzothiazole (Compound 69g) (160.0 mg, 0.48 mmol) in dioxane (5.0 mL) was added (1S,2S)-2-fluorocyclopropane-1-carboxamide (250.0 mg, 2.46 mmol), Brettphos (52.8 mg, 0.09 mmol), BrettPhos Pd G3 (43.9 mg, 0.09 mmol) and $Cs_2CO_3$ (474.2 mg, 1.45 mmol) at room temperature under $N_2$. The resulting mixture was stirred at 100° C. for 2 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (35/66, v/v) and then purified by Prep-HPLC with the following conditions (Column: XBridge Prep OBD C18 Column, 30×150 mm, 5 um; Mobile Phase A:Water (0.1% FA), Mobile Phase B: ACN; Flow rate: 60 mL/min; Gradient: 12% B to 22% B in 9 min; 254 nm) to afford (1S,2S)-2-fluoro-N-[2-(5-methoxy-1,3-benzothiazol-6-yl)-1-methylpyrrolo[2,3-c]pyridin-5-yl]cyclopropane-1-carboxamide (Compound 69) (1.1 mg, 1%) as a white solid. LCMS (ESI, m/z): $[M+H]^+$=397.1. $^1$H NMR (300 MHz, DMSO-$d_6$): δ 10.57 (s, 1H), 9.47 (s, 1H), 8.64 (s, 1H), 8.23 (s, 1H), 8.20 (s, 1H), 7.86 (s, 1H), 6.53 (s, 1H), 5.05-4.77 (m, 1H), 3.91 (s, 3H), 3.63 (s, 3H), 2.31-2.21 (m, 1H), 1.72-1.58 (m, 1H), 1.23-1.13 (m, 1H).

Example S70: Synthesis of (1S,2S)-2-fluoro-N-[2-(6-methoxy-1,3-benzothiazol-5-yl)-1-methylpyrrolo[2,3-c]pyridin-5-yl]cyclopropane-1-carboxamide (Compound 70)

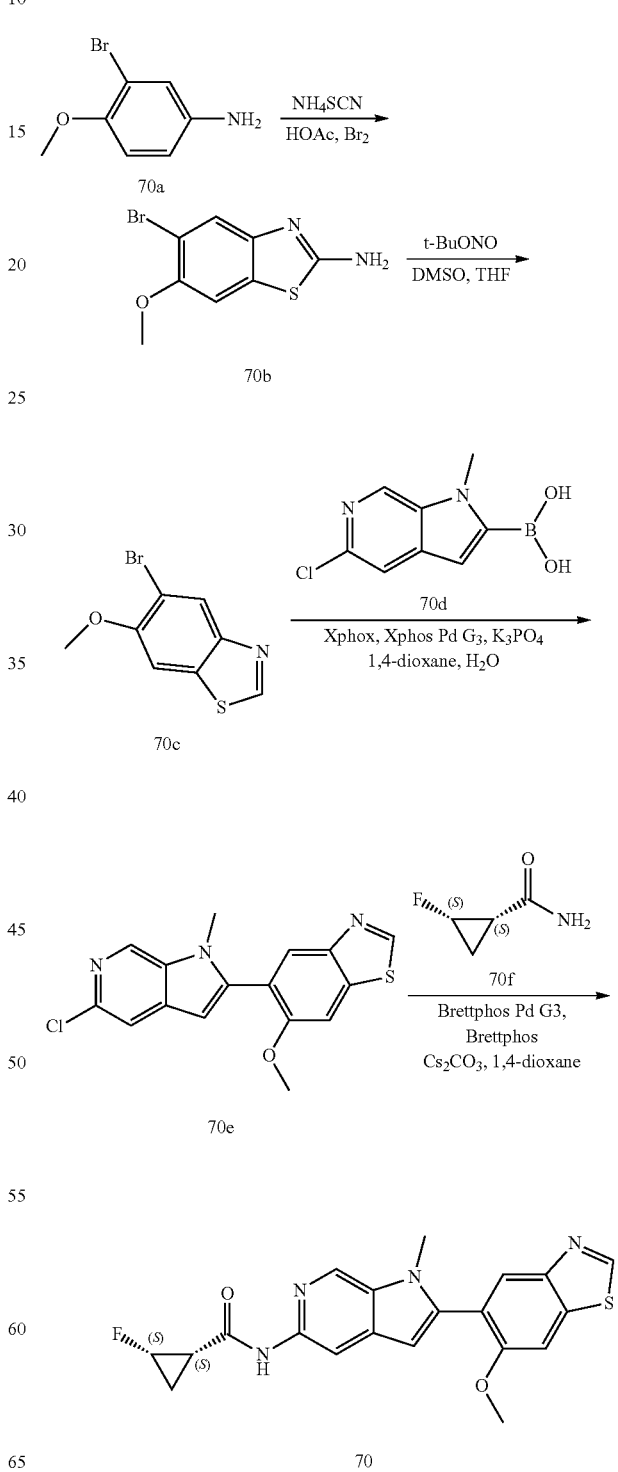

Step 1: Synthesis of 5-bromo-6-methoxy-1,3-benzothiazol-2-amine (Compound 70b)

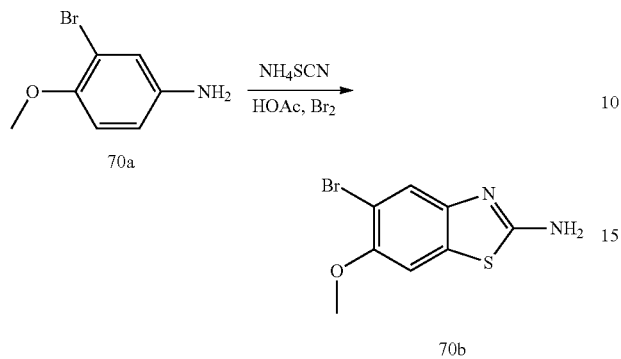

To a solution of 3-bromo-4-methoxyaniline (Compound 70a) (2.0 g, 9.90 mmol) in HOAc (10.0 mL) was added ammonium thiocyanate (3.8 g, 49.88 mmol) at room temperature under $N_2$. The resulting mixture was stirred at room temperature for 1 h. Then $Br_2$ (0.6 mL) was added dropwise to the mixture at 0° C. The resulting mixture was stirred at 0° C. for another 2 h. After the reaction was completed, the reaction mixture was quenched with saturated $NH_4Cl$ solution at 0° C. and then concentrated under reduced pressure. the pH of the residue was adjusted to 12 with $NH_3 \cdot H_2O$. The resulting mixture was extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (20/80, v/v) to afford 5-bromo-6-methoxy-1,3-benzothiazol-2-amine (Compound 70b) (3.0 g, 93%) as an off-white solid. LCMS (ESI, m/z): $[M+H]^+$=258.9.

Step 2: Synthesis of 5-bromo-6-methoxy-1,3-benzothiazole (Compound 70c)

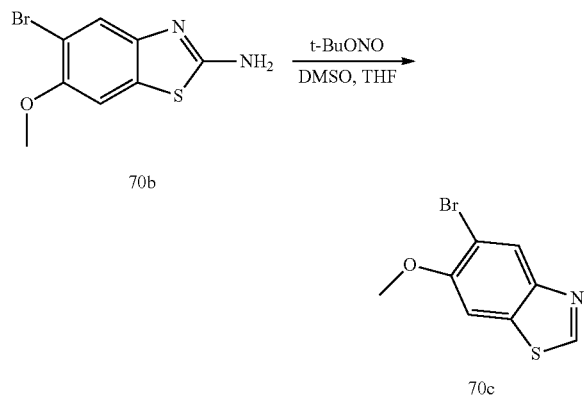

To a solution of 5-bromo-6-methoxy-1,3-benzothiazol-2-amine (Compound 70b) (2.7 g, 10.42 mmol) in THF (10.0 mL) was added DMSO (90.0 mg, 1.15 mmol) and t-BuONO (1.8 g, 17.45 mmol) at room temperature under $N_2$. The resulting mixture was stirred at 30° C. for 1 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (88/12, v/v) to afford 5-bromo-6-methoxy-1,3-benzothiazole (Compound 70c) (1.4 g, 44%) as a white solid. LCMS (ESI, m/z): $[M+H]^+$=243.9.

Step 3: Synthesis of 5-[5-chloro-1-methylpyrrolo[2,3-c]pyridin-2-yl]-6-methoxy-1,3-benzothiazole (Compound 70e)

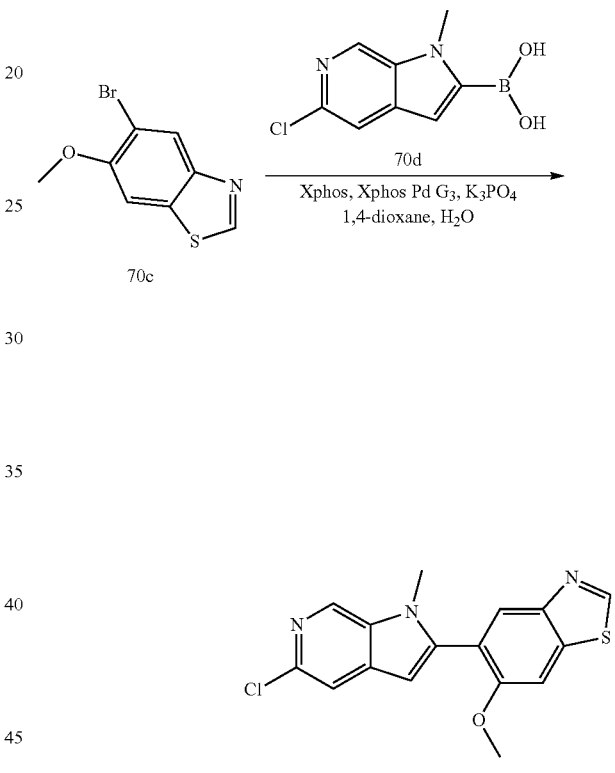

To a solution of 5-bromo-6-methoxy-1,3-benzothiazole (Compound 70c) (200.0 mg, 0.82 mmol) in 1,4-dioxane/$H_2O$ (5.0/1.0 mL) was added 5-chloro-1-methylpyrrolo[2,3-c]pyridin-2-ylboronic acid (Compound 70d) (170.6 mg, 0.81 mmol), $K_3PO_4$ (521.7 mg, 2.46 mmol), Xphos (78.1 mg, 0.16 mmol) and Xphos Pd G3 (69.3 mg, 0.08 mmol) at room temperature under $N_2$. The resulting mixture was stirred at 60° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (56/44, v/v) to afford 5-[5-chloro-1-methylpyrrolo[2,3-c]pyridin-2-yl]-6-methoxy-1,3-benzothiazole (Compound 70e) (140.0 mg, 52%) as a white solid. LCMS (ESI, m/z): $[M+H]^+$=330.0.

Step 4: Synthesis of (1S,2S)-2-fluoro-N-[2-(6-methoxy-1,3-benzothiazol-5-yl)-1-methylpyrrolo[2,3-c]pyridin-5-yl]cyclopropane-1-carboxamide (Compound 70)

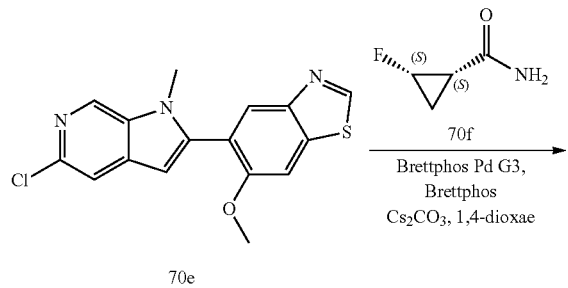

To a solution of 5-[5-chloro-1-methylpyrrolo[2,3-c]pyridin-2-yl]-6-methoxy-1,3-benzothiazole (Compound 70e) (120.0 mg, 0.36 mmol) in 1,4-dioxane (5.0 mL) was added (1S,2S)-2-fluorocyclopropane-1-carboxamide (Compound 70f) (187.5 mg, 1.82 mmol), $Cs_2CO_3$ (355.6 mg, 1.09 mmol), BrettPhos (39.0 mg, 0.07 mmol) and BrettPhos Pd G3 (33.0 mg, 0.04 mmol) at room temperature under $N_2$. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (0/100, v/v) and then purified by Prep-HPLC with the following conditions (Column: Xselect CSH OBD Column 30×150 mm, 5 um; Mobile Phase A: Water (10 mmol/L $NH_4HCO_3$), Mobile Phase B: ACN; Flow rate: 60 mL/min; Gradient: 36% B to 46% B in 8 min; 254 nm) to afford (1S,2S)-2-fluoro-N-[2-(6-methoxy-1,3-benzothiazol-5-yl)-1-methylpyrrolo[2,3-c]pyridin-5-yl]cyclopropane-1-carboxamide (Compound 70) (9.4 mg, 7%) as a white solid. LCMS (ESI, m/z): $[M+H]^+$=397.2. $^1H$ NMR (400 MHz, DMSO-$d_6$): δ 10.55 (s, 1H), 9.30 (s, 1H), 8.63 (s, 1H), 8.23 (s, 1H), 8.05 (s, 1H), 8.00 (s, 1H), 6.55 (s, 1H), 4.99-4.81 (m, 1H), 3.89 (s, 3H), 3.63 (s, 3H), 2.23-2.19 (m, 1H), 1.70-1.61 (m, 1H), 1.16-1.08 (m, 1H).

Example S71: Synthesis of (1S,2S)-2-fluoro-N-(2-(7-methoxyimidazo[1,2-a]pyridin-6-yl)-1-methyl-1H-pyrrolo[2,3-c]pyridin-5-yl)cyclopropane-1-carboxamide (Compound 71)

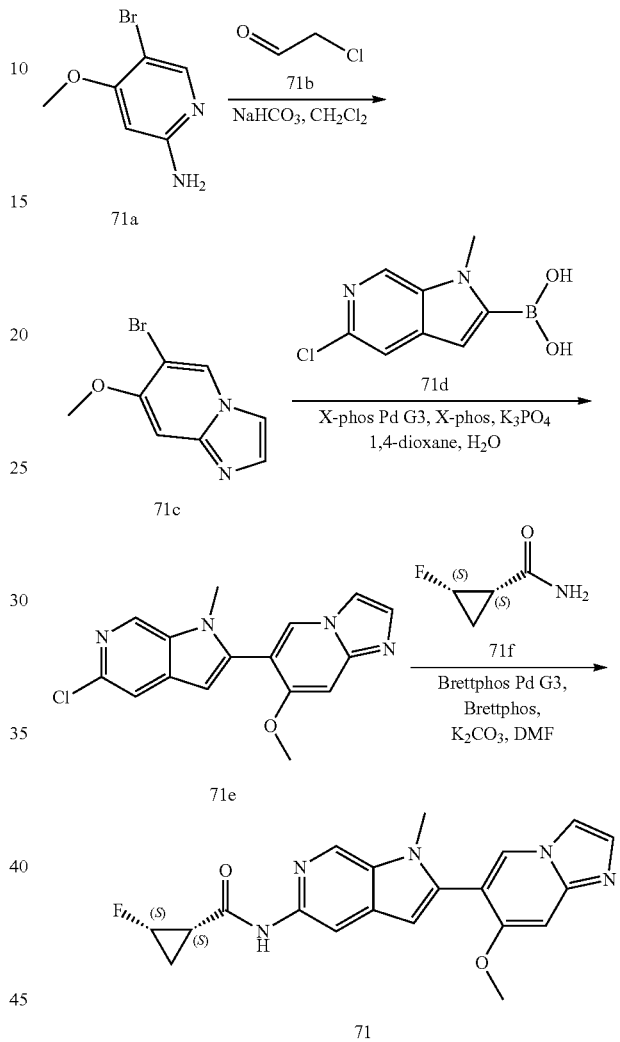

Step 1: Synthesis of 6-bromo-7-methoxyimidazo[1,2-a]pyridine (Compound 71c)

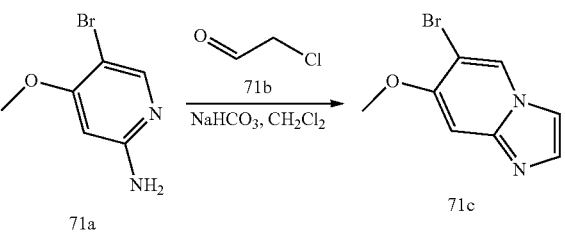

To a solution of 5-bromo-4-methoxypyridin-2-amine (Compound 71a) (500.0 mg, 2.46 mmol) in $CH_2Cl_2$ (10.0 mL) and saturated NaHCO$_3$ solution (10.0 mL) was added 2-chloroacetaldehyde (Compound 71b) (1063.0 mg, 5.42 mmol) at room temperature. The resulting mixture was stirred at room temperature for 16 h. After the reaction was completed, the resulting mixture was diluted with H$_2$O and extracted with CH$_2$Cl$_2$. The combined organic layer was washed with brine, dried over anhydrous sodium sulfate and filtered. The filtrate was concentrated under reduced pressure. The residue was purified by flash column chromatography with CH$_2$Cl$_2$/MeOH (10/1, v/v) to afford 6-bromo-7-methoxyimidazo[1,2-a]pyridine (Compound 71c) (230.0 mg, 66%) as a brown solid. LCMS (ESI, m/z): [M+H]$^+$= 227.0.

Step 2: Synthesis of 6-(5-chloro-1-methyl-1H-pyrrolo[2,3-c]pyridin-2-yl)-7-methoxyimidazo[1,2-a]pyridine (Compound 71e)

Step 3: Synthesis of (1S,2S)-2-fluoro-N-(2-(7-methoxyimidazo[1,2-a]pyridin-6-yl)-1-methyl-1H-pyrrolo[2,3-c]pyridin-5-yl)cyclopropane-1-carboxamide (Compound 71)

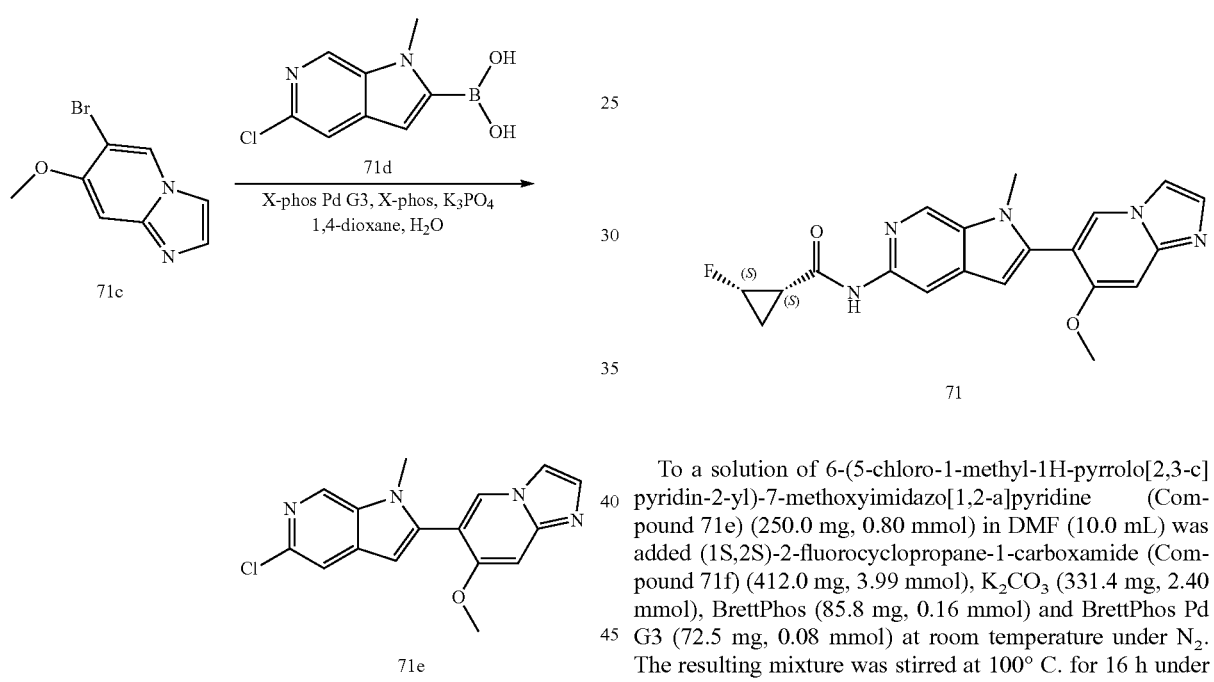

To a solution of 6-bromo-7-methoxyimidazo[1,2-a]pyridine (Compound 71c) (320.0 mg, 1.41 mmol) in 1,4-dioxane/H$_2$O (10.0 mL/2.0 mL) was added (5-chloro-1-methyl-1H-pyrrolo[2,3-c]pyridin-2-yl)boronic acid (Compound 71d) (444.8 mg, 2.11 mmol), K$_3$PO$_4$ (598.3 mg, 2.82 mmol), X-phos (134.4 mg, 0.28 mmol) and X-phos Pd G3 (119.3 mg, 0.14 mmol) at room temperature under N$_2$. The resulting mixture was stirred at 60° C. for 2 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/MeOH (91/9, v/v) to afford 6-(5-chloro-1-methyl-1H-pyrrolo[2,3-c]pyridin-2-yl)-7-methoxyimidazo[1,2-a]pyridine (Compound 71e) (270.0 mg, 61%) as a brown solid. LCMS (ESI, m/z): [M+H]$^+$=313.1.

To a solution of 6-(5-chloro-1-methyl-1H-pyrrolo[2,3-c]pyridin-2-yl)-7-methoxyimidazo[1,2-a]pyridine (Compound 71e) (250.0 mg, 0.80 mmol) in DMF (10.0 mL) was added (1S,2S)-2-fluorocyclopropane-1-carboxamide (Compound 71f) (412.0 mg, 3.99 mmol), K$_2$CO$_3$ (331.4 mg, 2.40 mmol), BrettPhos (85.8 mg, 0.16 mmol) and BrettPhos Pd G3 (72.5 mg, 0.08 mmol) at room temperature under N$_2$. The resulting mixture was stirred at 100° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/MeOH (91/9, v/v) and then purified by Prep-HPLC with the following conditions (Column: Xselect CSH OBD Column 30×150 mm 5 um Mobile Phase A: Water (10 mmol/L NH$_4$HCO$_3$), Mobile Phase B: ACN; Flow rate: 60 mL/min; Gradient: 24% B to 34% B in 8 min; 254 nm) to afford (1S,2S)-2-fluoro-N-(2-(7-methoxyimidazo[1,2-a]pyridin-6-yl)-1-methyl-1H-pyrrolo[2,3-c]pyridin-5-yl)cyclopropane-1-carboxamide (Compound 71) (10.0 mg, 3%) as a white solid. LCMS (ESI, m/z): [M+H]$^+$=380.2. $^1$H NMR (300 MHz, DMSO-d$_6$: δ 10.55 (s, 1H), 8.64 (d, J=1.5 Hz, 2H), 8.23 (s, 1H), 7.81 (s, 1H), 7.49 (d, J=1.2 Hz, 1H), 7.13 (s, 1H), 6.57 (s, 1H), 5.04-4.77 (nm, 1H), 3.86 (s, 3H), 3.65 (s, 3H), 2.26-2.16 (m, 1H), 1.76-1.62 (m, 1H), 1.25-1.05 (m, 1H).

Example S72: Synthesis of (1S,2S)-N-[2-(4,6-dimethoxy-2-methylpyrimidin-5-yl)-1-methylpyrrolo[2,3-c]pyridin-5-yl]-2-fluorocyclopropane-1-carboxamide (Compound 72)

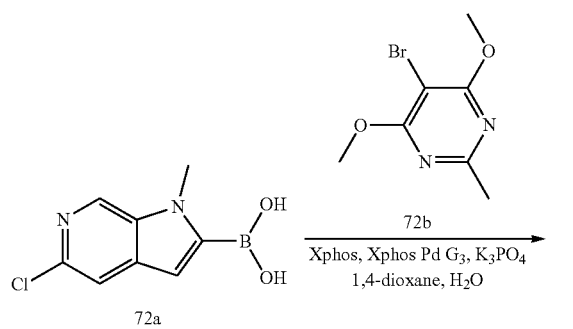

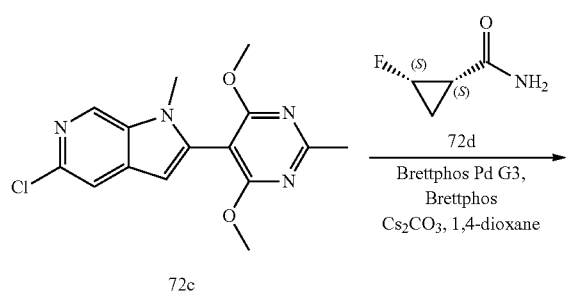

Step 1: Synthesis of 5-[5-chloro-1-methylpyrrolo[2,3-c]pyridin-2-yl]-4,6-dimethoxy-2-methylpyrimidine (Compound 72c)

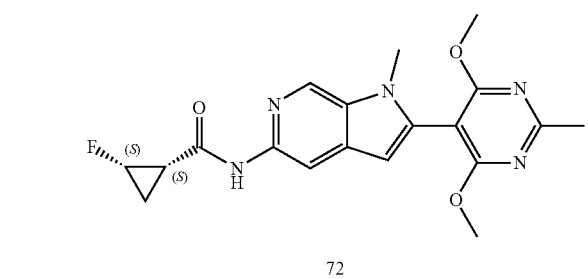

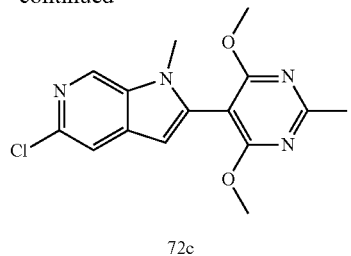

To a solution of 5-chloro-1-methylpyrrolo[2,3-c]pyridin-2-ylboronic acid (Compound 72a) (200.0 mg, 0.95 mmol) in 1,4-dioxane/H$_2$O (5.0/1.0 mL) was added 5-bromo-4,6-dimethoxy-2-methylpyrimidine (Compound 72b) (265.8 mg, 1.14 mmol). K$_3$PO$_4$ (403.5 mg, 1.90 mmol), XPhos (90.6 mg, 0.19 mmol) and XPhos Pd G3 (109.8 mg, 0.10 mmol) at room temperature under N$_2$. The resulting mixture was stirred at 60° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (65/35, v/v) to afford 5-[5-chloro-1-methylpyrrolo[2,3-c]pyridin-2-yl]-4,6-dimethoxy-2-methylpyrimidine (Compound 72c) (130.0 mg, 43%) as a white solid. LCMS (ESI, m/z): [M+H]$^+$=319.1.

Step 2: Synthesis of (1S,2S)-N-[2-(4,6-dimethoxy-2-methylpyrimidin-5-yl)-1-methylpyrrolo[2,3-c]pyridin-5-yl]-2-fluorocyclopropane-1-carboxamide (Compound 72)

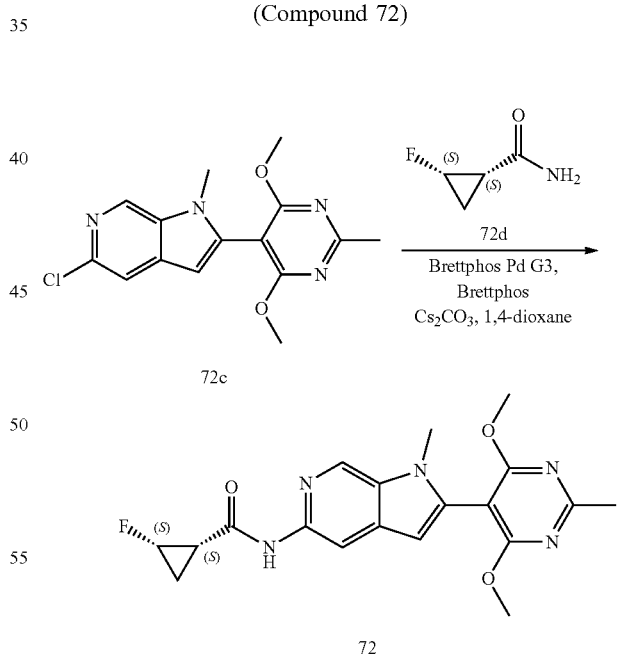

To a solution of 5-[5-chloro-1-methylpyrrolo[2,3-c]pyridin-2-yl]-4,6-dimethoxy-2-methylpyrimidine (Compound 72c) (110.0 mg, 0.34 mmol) in 1,4-dioxane (4.0 mL) was added (1S,2S)-2-fluorocyclopropane-1-carboxamide (Compound 72d) (103.5 mg, 1.72 mmol), Cs$_2$CO$_3$ (337.3 mg, 1.05 mmol), BrettPhos (37.1 mg, 0.07 mmol) and BrettPhos Pd G3 (31.8 mg, 0.04 mmol) at room temperature under N$_2$.

The resulting mixture was stirred at 100° C. for 2 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 17% B to 27% B in 8 min, 254 nm) to afford (1S,2S)-N-[2-(4,6-dimethoxy-2-methylpyrimidin-5-yl)-1-methylpyrrolo[2,3-c]pyridin-5-yl]-2-fluorocyclopropane-1-carboxamide (Compound 72) (8.1 mg, 6%) as a white solid. LCMS (ESI, m/z): [M+H]⁺=386.2. ¹H NMR (400 MHz, DMSO-d₆): δ 10.51 (s, 1H), 8.60 (s, 1H), 8.18 (s, 1H), 6.45 (s, 1H), 4.99-4.81 (m, 1H), 3.89 (s, 6H), 3.56 (s, 3H), 2.57 (s, 3H), 2.21-2.18 (m, 1H), 1.70-1.60 (m, 1H), 1.21-1.08 (m, 1H).

Example S73: Synthesis of (1S,2S)-N-[2-(1H-1,3-benzodiazol-4-yl)-1-methylpyrrolo[2,3-c]pyridin-5-yl]-2-fluorocyclopropane-1-carboxamide (Compound 73)

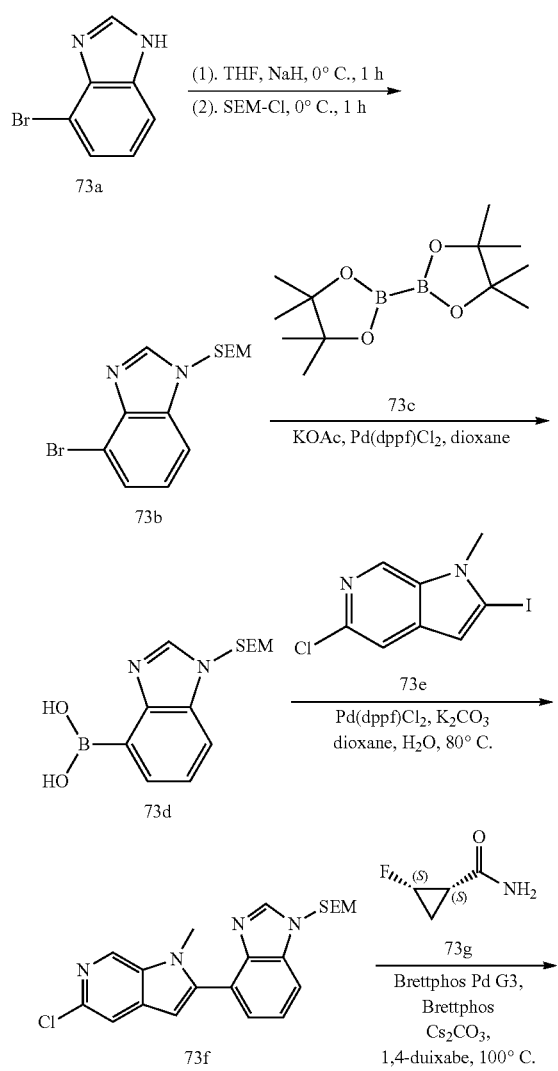

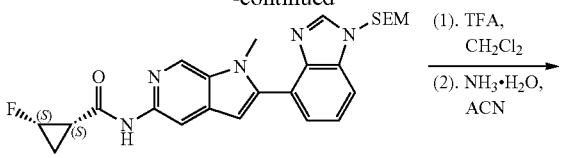

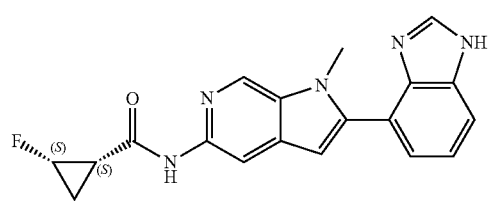

Step 1: Synthesis of 4-bromo-1-[[2-(trimethylsilyl)ethoxy]methyl]-1,3-benzodiazole (Compound 73b)

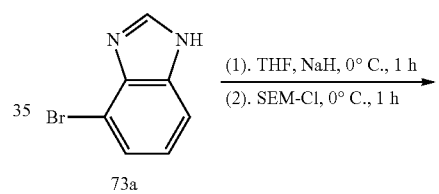

To a solution of 4-bromo-1H-1,3-benzodiazole (Compound 73a) (1.0 g, 5.07 mmol) in THF (10.0 mL) was added NaH (182.6 mg, 60%) at 0° C. under N₂. The resulting mixture was stirred at 0° C. for 1 h. Then SEM-Cl (1.2 g, 7.61 mmol) was added to the mixture at 0° C. The resulting mixture was stirred at room temperature for another 2 h under N₂. After the reaction was completed, the reaction mixture was quenched with saturated NH₄Cl solution and then concentrated under reduced pressure. The residue was purified by flash column chromatography with petroleum ether/EtOAc (2/1, v/v) to afford 4-bromo-1-[[2-(trimethylsilyl)ethoxy]methyl]-1,3-benzodiazole (Compound 73b) (1.5 g, 90%) as a yellow oil. LCMS (ESI, m/z): [M+H]⁺=327.0.

Step 2: Synthesis of 1-[[2-(trimethylsilyl)ethoxy]methyl]-1,3-benzodiazol-4-ylboronic acid (Compound 73d)

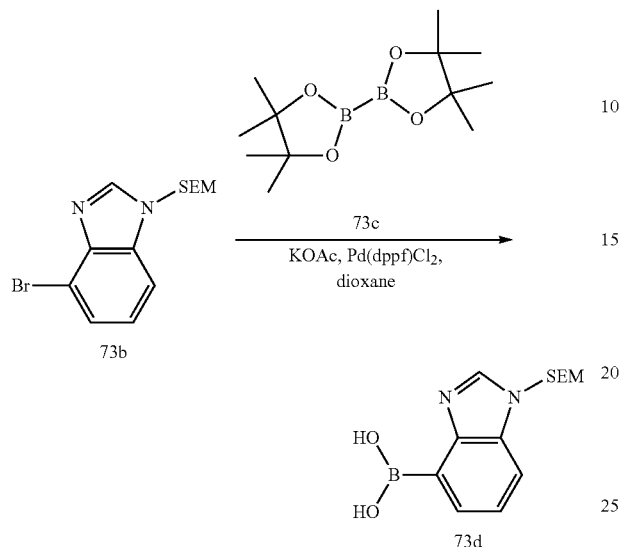

To a mixture of 4-bromo-1-[[2-(trimethylsilyl)ethoxy]methyl]-1,3-benzodiazole (Compound 73b) (1.7 g, 5.19 mmol) and bis(pinacolato)diboron (Compound 73c) (3.9 g, 15.5 mmol) in dioxane (20.0 mL) was added KOAc (1.5 g, 15.5 mmol) and Pd(dppf)Cl$_2$ (0.3 g, 0.51 mmol) at room temperature under N$_2$. The resulting mixture was stirred at 80° C. for 16 h under N$_2$. After the reaction was completed, the resulting mixture was filtered. The filtrate was concentrated under reduced pressure. The residue was purified by reverse phase flash chromatography ACN/H$_2$O (2/1, v/v) to afford 1-[[2-(trimethylsilyl)ethoxy]methyl]-1,3-benzodiazol-4-ylboronic acid (Compound 73d) (1.1 g, 79%) as a dark yellow oil. LCMS (ESI, m/z): [M+H]$^+$=293.1.

Step 3: Synthesis of 4-[5-chloro-1-methylpyrrolo[2,3-c]pyridin-2-yl]-1-[[2-(trimethylsilyl)ethoxy]methyl]-1,3-benzodiazole (Compound 73f)

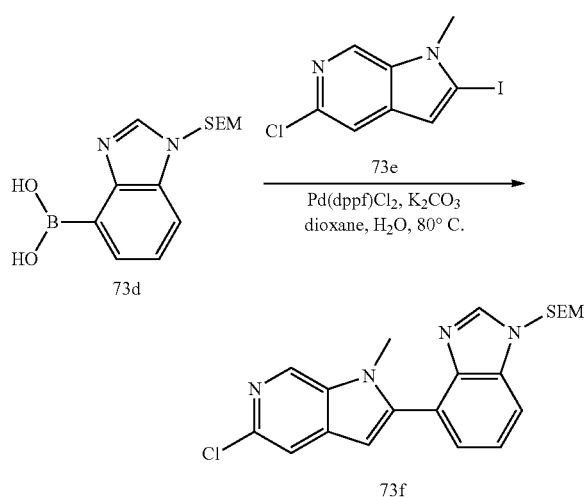

To a mixture of 1-[[2-(trimethylsilyl)ethoxy]methyl]-1,3-benzodiazol-4-ylboronic acid (Compound 73d) (1.1 g, 3.76 mmol) and 5-chloro-2-iodo-1-methylpyrrolo[2,3-c]pyridine (Compound 73e) (880.8 mg, 3.01 mmol) in dioxane/H$_2$O (15.0/1.5 mL) was added K$_2$CO$_3$ (1.5 g, 11.29 mmol) and Pd(dppf)Cl$_2$ (275.4 mg, 0.37 mmol) at room temperature under N$_2$. The resulting mixture was stirred at 80° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/EtOAc (3/7, v/v) to afford 4-[5-chloro-1-methylpyrrolo[2,3-c]pyridin-2-yl]-1-[[2-(trimethylsilyl)ethoxy]methyl]-1,3-benzodiazole (Compound 73f) (900.0 mg, 57%) as a white solid. LCMS (ESI, m/z): [M+H]$^+$=413.1.

Step 4: Synthesis of (1S,2S)-2-fluoro-N-[1-methyl-2-(1-[[2-(trimethylsilyl)ethoxy]methyl]-1,3-benzodiazol-4-yl)pyrrolo[2,3-c]pyridin-5-yl]cyclopropane-1-carboxamide (Compound 73h)

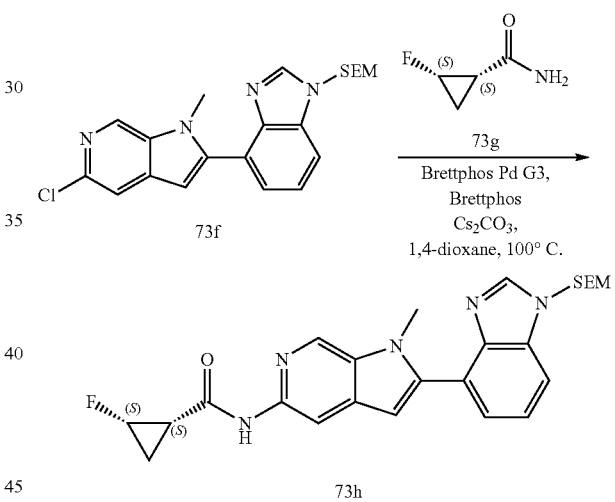

To a mixture of 4-[5-chloro-1-methylpyrrolo[2,3-c]pyridin-2-yl]-1-[[2-(trimethylsilyl)ethoxy]methyl]-1,3-benzodiazole (Compound 73f) (300.0 mg, 0.72 mmol) and (0S,2S)-2-fluorocyclopropane-1-carboxamide (Compound 73g) (299.5 mg, 2.90 mmol) in dioxane (5.0 mL) was added Brettphos Pd G3 (65.8 mg, 0.07 mmol), Cs$_2$CO$_3$ (710.0 mg, 2.17 mmol) and BrettPhos (13.0 mg, 0.02 mmol) at room temperature under N$_2$. The resulting mixture was stirred at 100° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with DCM/MeOH (10/1, v/v) to afford (1S,2S)-2-fluoro-N-[1-methyl-2-(0.1-[[2-(trimethylsilyl)ethoxy]methyl]-1,3-benzodiazol-4-yl)pyrrolo[2,3-c]pyridin-5-yl]cyclopropane-1-carboxamide (Compound 73h) (110.0 mg, 31%) as a white solid. LCMS (ESI, m/z): [M+H]$^+$=480.2.

Step 5: Synthesis of (1S,2S)-N-[2-(1H-1,3-benzodi-azol-4-yl)-1-methylpyrrolo[2,3-c]pyridin-5-yl]-2-fluorocyclopropane-1-carboxamide (Compound 73)

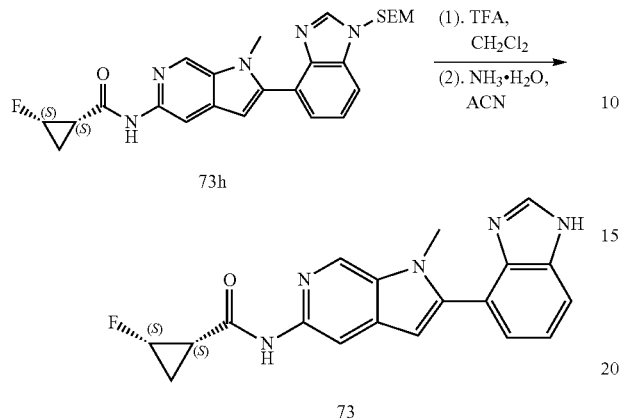

To a solution of (1S,2S)-2-fluoro-N-[1-methyl-2-(1-[[2-(trimethylsilyl)ethoxy]methyl]-1,3-benzodiazol-4-yl)pyrrolo[2,3-c]pyridin-5-yl]cyclopropane-1-carboxamide (Compound 73h) (100.0 mg, 0.20 mmol) in DCM (1.0 mL) was added TFA (1.0 mL) at room temperature. The resulting mixture was stirred at room temperature for 2 h. The resulting mixture was concentrated under vacuum. To the above residue was added ACN (1.0 mL) and NH₃·H₂O (2.0 mL) at room temperature. The resulting mixture was stirred at room temperature for another 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep OBD C18 Column, 30×150 mm, 5 um; Mobile Phase A:Water (10 mmol/L NH₄HCO₃), Mobile Phase B: ACN; Flow rate: 60 mL/min; Gradient: 13% B to 43% B in 10 min; 254 nm) to afford (1S,2S)-N-[2-(1H-1,3-benzodiazol-4-yl)-1-methylpyrrolo[2,3-c]pyridin-5-yl]-2-fluorocyclopropane-1-carboxamide (Compound 73) (5.1 mg, 7.0%) as a yellow solid. LCMS (ESI, m/z): [M+H]⁺=350.2. ¹H NMR (300 MHz, CD₃OD): δ 8.62 (s, 1H), 8.25 (s, 1H), 8.20 (s, 1H), 7.79-7.77 (m, 1H), 7.48-7.41 (m, 2H), 6.69 (s, 1H), 5.00-4.77 (m, 1H), 3.77 (s, 3H), 2.15-2.08 (m, 1H), 1.88-1.75 (m, 1H), 1.25-1.18 (m, 1H).

Example S74: Synthesis of (1S,2S)-2-fluoro-N-[2-(6-methoxy-1H-indazol-5-yl)-1-methylpyrrolo[2,3-c]pyridin-5-yl]cyclopropane-1-carboxamide (Compound 74)

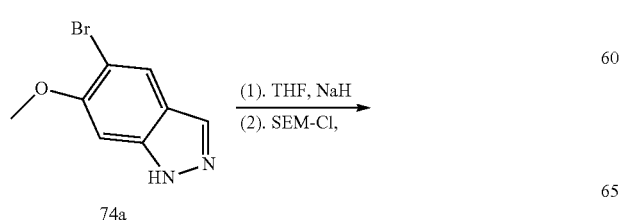

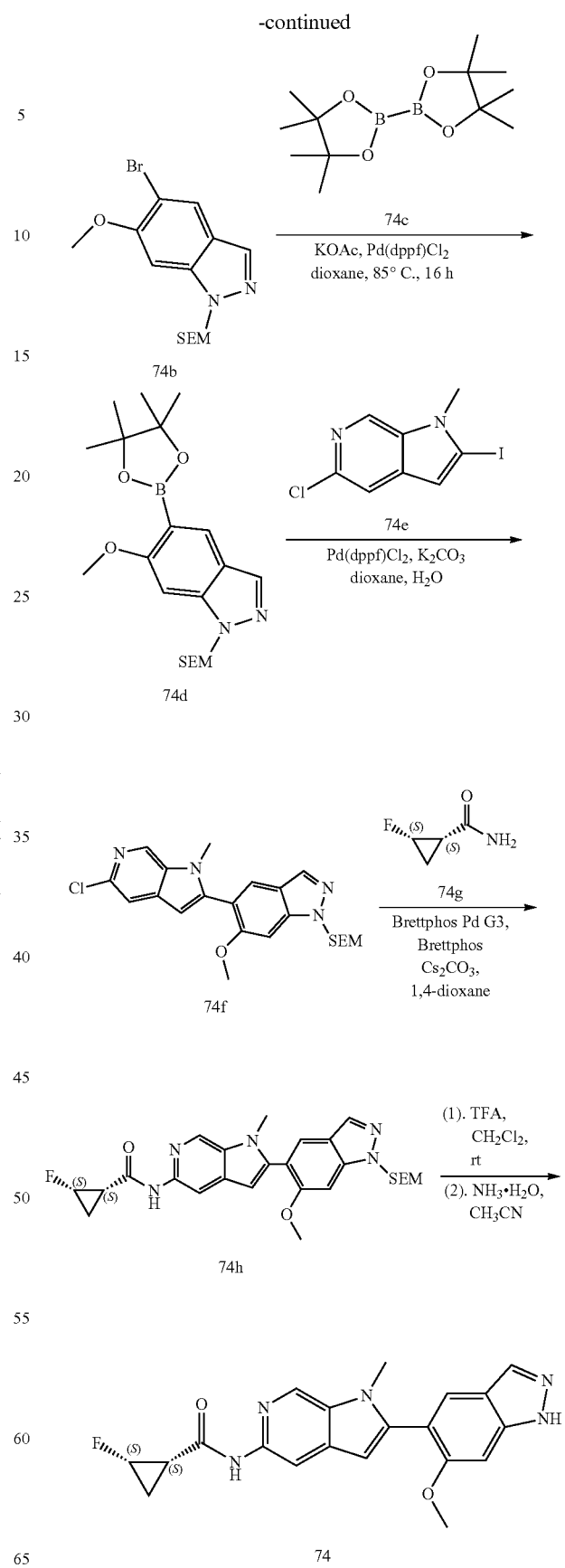

Step 1: Synthesis of 4-bromo-1-[[2-(trimethylsilyl)ethoxy]methyl]-1,3-benzodiazole (Compound 74b)

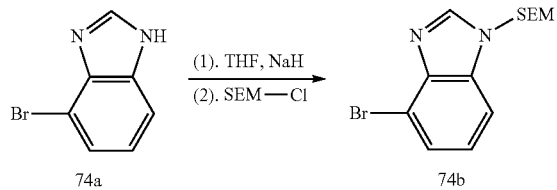 [SMILES: Brc1cccc2[nH]cnc12 ; C[Si](C)(C)CCOCCl ; C[Si](C)(C)CCOCn1cnc2c(Br)cccc21]

To a solution of 4-bromo-1H-1,3-benzodiazole (Compound 74a) (1.0 g, 5.07 mmol) in THF (10.0 mL) was added NaH (182.6 mg, 60%) at 0° C. under $N_2$. The resulting mixture was stirred at 0° C. for 1 h. Then SEM-Cl (1.2 g, 7.61 mmol) was added to the mixture at 0° C. The resulting mixture was stirred at room temperature for additional 2 h under $N_2$. After the reaction was completed, the reaction mixture was quenched with saturated $NH_4Cl$ solution and then concentrated under reduced pressure. The residue was purified by flash column chromatography with petroleum ether/ethyl acetate (2/1, v/v) to afford 4-bromo-1-[[2-(trimethylsilyl)ethoxy]methyl]-1,3-benzodiazole (Compound 74b) (1.5 g, 90%) as a yellow oil. LCMS (ESI, m/z): $[M+H]^+$=327.0.

Step 2: Synthesis of 6-methoxy-5-(4,4,5,5-tetramethyl-1,3,2-dioxaborolan-2-yl)-1-[[2-(trimethylsilyl)ethoxy]methyl]indazole (Compound 74d)

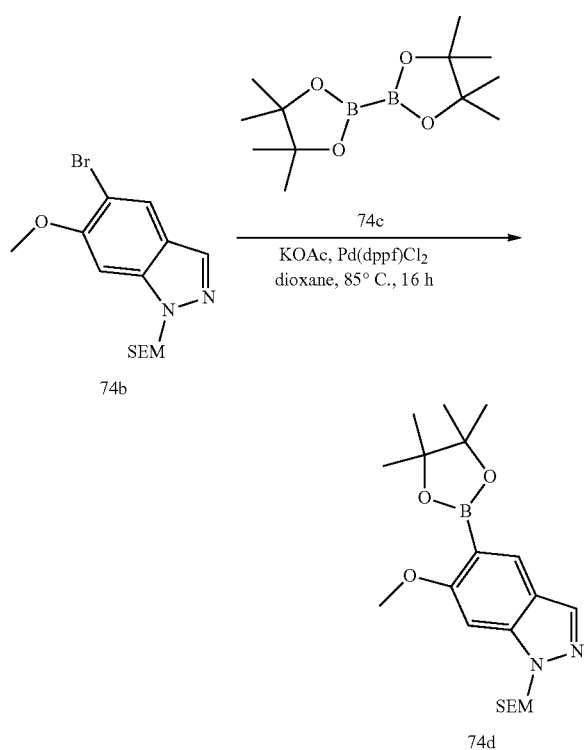

To a solution of 5-bromo-6-methoxy-1-[[2-(trimethylsilyl)ethoxy]methyl]indazole (Compound 74b) (1.40 g, 3.91 mmol) in dioxane (20.0 mL) was added Pd(dppf)Cl₂ (286.6 mg, 0.39 mmol), KOAc (1.1 g, 11.75 mmol) and bis(pinacolato)diboron (Compound 74c) (2.9 g, 11.75 mmol) at room temperature under $N_2$. The resulting mixture was stirred at 85° C. for 16 h under $N_2$. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with petroleum ether/EtOAc (2/1, v/v) to afford 6-methoxy-5-(4,4,5,5-tetramethyl-1,3,2-dioxaborolan-2-yl)-1-[[2-(trimethylsilyl)ethoxy]methyl]indazole (Compound 74d) (1.4 g, 88%) as a yellow oil. LCMS (ESI, m/z): $[M+H]^+$=405.2.

Step 3: Synthesis of 5-[5-chloro-1-methylpyrrolo[2,3-c]pyridin-2-yl]-6-methoxy-1-[[2(trimethylsilyl)ethoxy]methyl]indazole (Compound 74f)

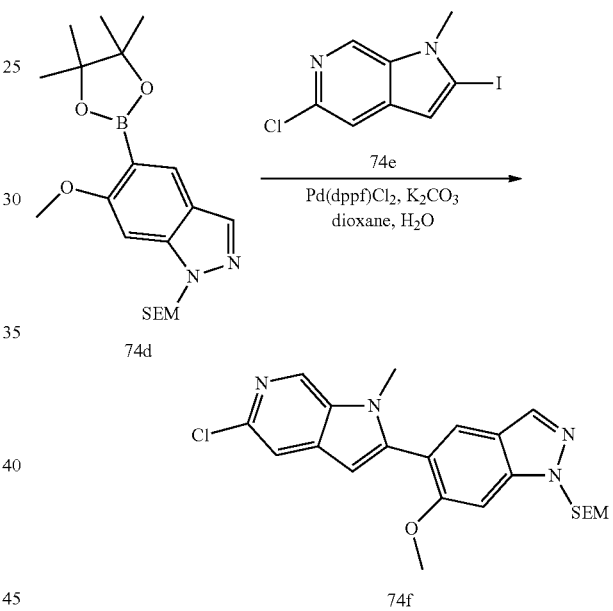

To a mixture of 6-methoxy-5-(4,4,5,5-tetramethyl-1,3,2-dioxaborolan-2-yl)-1-[[2-(trimethylsilyl)ethoxy]methyl]indazole (Compound 74d) (400.0 mg, 0.98 mmol) and 5-chloro-2-iodo-1-methylpyrrolo[2,3-c]pyridine (Compound 74e) (231.4 mg, 0.79 mmol) in dioxane/$H_2O$ (5.0/0.5 mL) was added $K_2CO_3$ (410.1 mg, 2.96 mmol) and Pd(dppf)Cl₂ (72.3 mg, 0.09 mmol) at room temperature under $N_2$. The resulting mixture was stirred at 80° C. for 16 h. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with petroleum ether/EtOAc (1/6, v/v) to afford 5-[5-chloro-1-methylpyrrolo[2,3-c]pyridin-2-yl]-6-methoxy-1-[[2-(trimethylsilyl)ethoxy]methyl]indazole (Compound 74f) (150.0 mg, 34%) as a yellow solid. LCMS (ESI, m/z): $[M+H]^+$=443.2.

Step 4: Synthesis of (1S,2S)-2-fluoro-N-[2-(6-methoxy-1-[[2-(trimethylsilyl)ethoxy]methyl]indazol-5-yl)-1-methylpyrrolo[2,3-]pyridin-5-yl]cyclopropane-1-carboxamide (Compound 74h)

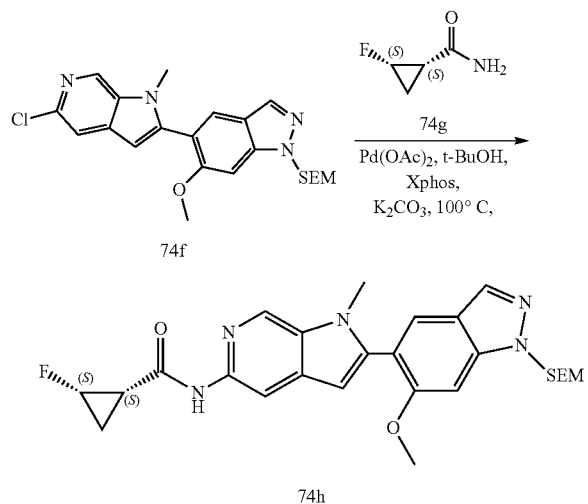

To a mixture of 5-[5-chloro-1-methylpyrrolo[2,3-c]pyridin-2-yl]-6-methoxy-1-[[2-(trimethylsilyl)ethoxy]methyl] indazole (Compound 74f) (130.0 mg, 0.29 mmol) and (1S,2S)-2-fluorocyclopropane-1-carboxamide (Compound 74g) (181.5 mg, 1.76 mmol) in t-BuOH (4.0 mL) were added Pd(OAc)$_2$ (6.5 mg, 0.02 mmol), K$_2$CO$_3$ (121.6 mg, 0.88 mmol) and X-Phos (32.1 mg, 0.06 mmol) at room temperature under N$_2$. The resulting mixture was stirred at 100° C. for 16 h. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography petroleum ether/EtOAc (1/8, v/v) to afford (1S,2S)-2-fluoro-N-[2-(6-methoxy-1-[[2-(trimethylsilyl)ethoxy]methyl]indazol-5-yl)-1-methylpyrrolo[2,3-c]pyridin-5-yl]cyclopropane-1-carboxamide (Compound 74h) (130.0 mg, 86%) as a yellow solid. LCMS (ESI, m/z): [M+H]$^+$=510.2.

Step 5: Synthesis of (1S,2S)-2-fluoro-N-[2-(6-methoxy-1H-indazol-5-yl)-1-methylpyrrolo[2,3-c]pyridin-5-yl]cyclopropane-1-carboxamide (Compound 74)

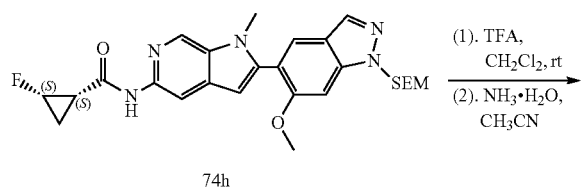

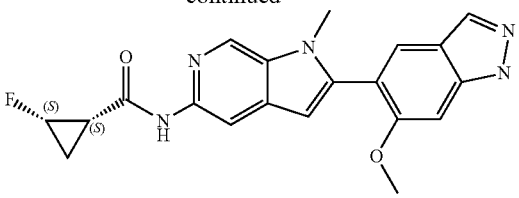

To a solution of (1S,2S)-2-fluoro-N-[2-(6-methoxy-1-[[2-(trimethylsilyl)ethoxy]methyl]indazol-5-yl)-1-methylpyrrolo[2,3-c]pyridin-5-yl]cyclopropane-1-carboxamide (Compound 74h) (150.0 mg, 0.29 mmol) in DCM (2.0 mL) was added TFA (1.0 mL) at room temperature. The resulting mixture was stirred at room temperature for 1 h. The resulting mixture was concentrated under vacuum. To the above residue was added NH$_3$·H$_2$O (3.0 mL) and ACN (1.0 mL) at room temperature. The resulting mixture was stirred at room temperature for 16 h. After the reaction was completed, the reaction was diluted with water and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep OBD C18 Column, 19×150 mm, 5 um; Mobile Phase A:Water (10 mmol/L NH$_4$HCO$_3$), Mobile Phase B: MeOH-Preparative; Flow rate: 25 mL/min; Gradient: 41% B to 59% B in 7 min; 254 nm) to afford (1S,2S)-2-fluoro-N-[2-(6-methoxy-1H-indazol-5-yl)-1-methylpyrrolo[2,3-c]pyridin-5-yl]cyclopropane-1-carboxamide (Compound 74) (5.6 mg, 5%) as a white solid. LCMS (ESI, m/z): [M+H]$^+$=380.2. $^1$H NMR (300 MHz, DMSO-d$_6$): δ 13.04 (s, 1H), 10.52 (s, 1H), 8.59 (s, 1H), 8.21 (s, 1H), 8.04 (s, 1H), 7.75 (s, 1H), 7.12 (s, 1H), 6.45 (s, 1H), 5.04-4.77 (m, 1H), 3.86 (s, 3H), 3.59 (s, 3H), 2.37-2.16 (m, 1H), 1.72-1.61 (m, 1H), 1.21-1.09 (m, 1H).

Example S75: Synthesis of (1S,2S)-N-[2-(2,4-dimethoxypyridin-3-yl)-1-methylpyrrolo[2,3-c]pyridin-5-yl]-2-fluorocyclopropane-1-carboxamide (Compound 75)

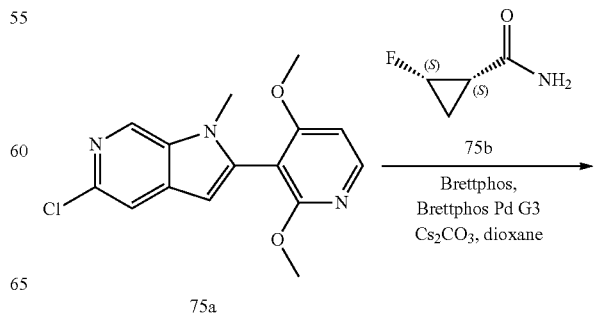

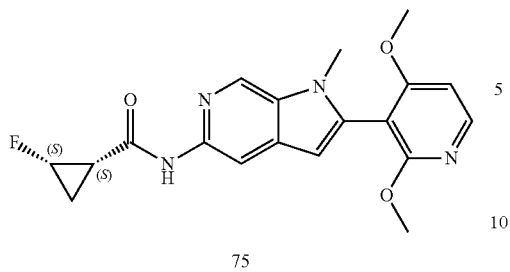

75

To a solution of 3-[5-chloro-1-methylpyrrolo[2,3-c]pyridin-2-yl]-2,4-dimethoxypyridine (Compound 75a) (180.0 mg, 0.59 mmol) in 1,4-dioxane (5.0 mL) was added (1S, 2S)-2-fluorocyclopropane-1-carboxamide (Compound 75b) (610.9 mg, 5.93 mmol), $Cs_2CO_3$ (579.2 mg, 1.78 mmol), BrettPhos (63.6 mg, 0.12 mmol) and BrettPhos Pd 03 (53.7 mg, 0.06 mmol). The mixture was stirred with microwave at 120° C. for 1.5 h. After the reaction was completed, the resulting mixture was concentrated under vacuum. The residue was purified by flash column chromatography with petroleum ether/ethyl acetate (60/40, v/v) and then purified by Prep-HPLC with the following conditions (Column: Xselect CSH OBD Column, 30×150 mm, 5 um; Mobile Phase A:Water (10 mmol/L $NH_4HCO_3$), Mobile Phase B: ACN; Flow rate: 60 mL/min; Gradient: 29% B to 39% B in 8 min; 254 nm) to afford (1S,2S)-N-[2-(2,4-dimethoxypyridin-3-yl)-1-methylpyrrolo[2,3-c]pyridin-5-yl]-2-fluorocyclopropane-1-carboxamide (Compound 75) (44.0 mg, 20%) as a white solid. LCMS (ESI, m/z): $[M+H]^+$=371.2. $^1H$ NMR (300 MHz, DMSO-$d_6$): δ 10.51 (s, 1H), 8.60 (s, 1H), 8.26 (d, J=6.0 Hz, 1H), 8.18 (s, 1H), 6.98 (d, J=6.0 Hz, 1H), 6.41 (s, 1H), 5.03-4.78 (m, 1H), 3.82 (s, 6H), 3.54 (s, 3H), 2.23-2.18 (m, 1H), 1.71-1.60 (m, 1H), 1.17-1.09 (m, 1H).

Example S76: Synthesis of (1S,2S)-2-fluoro-N-[2-(5-fluoro-2-methoxypyridin-3-yl)-1-methylpyrrolo[2,3-c]pyridin-5-yl]cyclopropane-1-carboxamide (Compound 76)

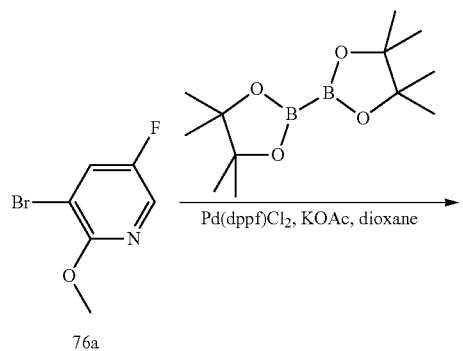

Step 1: Synthesis of 5-fluoro-2-methoxy-3-(4,4,5,5-tetramethyl-1,3,2-dioxaborolan-2-yl)pyridine (Compound 76b)

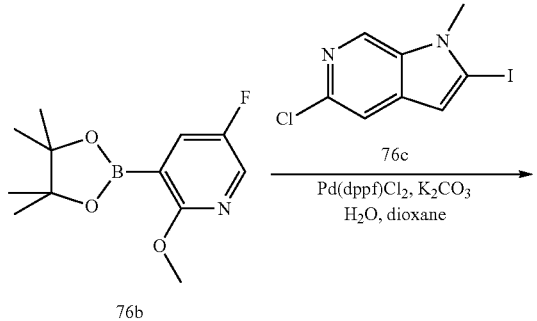

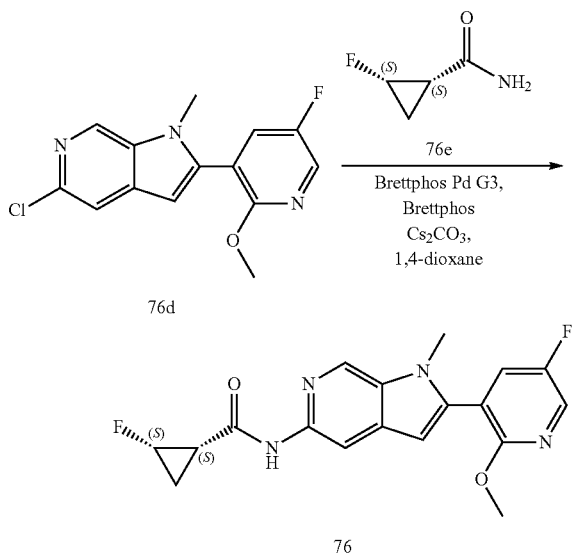

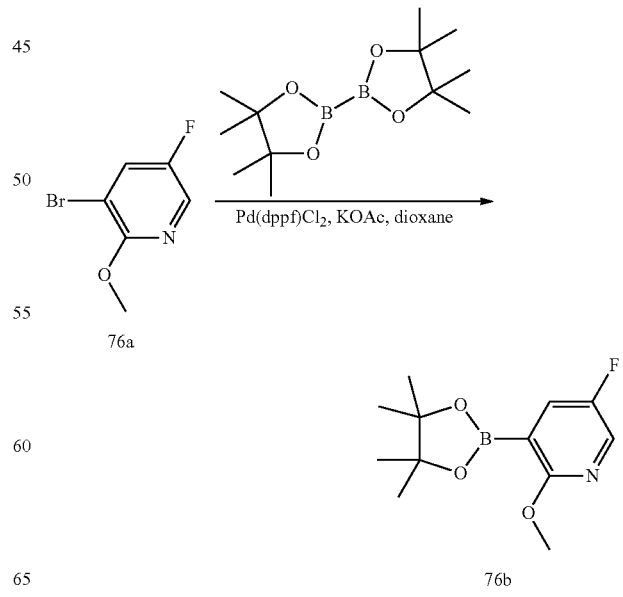

To a solution of 3-bromo-5-fluoro-2-methoxypyridine (Compound 76a) (1.0 g, 4.85 mmol) in dioxane (10.0 mL) was added 4,4,4',4',5,5,5',5'-octamethyl-2,2'-bi(1,3,2-dioxaborolane) (1.4 g, 5.82 mmol), KOAc (1.4 g, 14.56 mmol) and Pd(dppf)Cl₂ (710.3 mg, 0.97 mmol) at room temperature under N₂. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (90/10, v/v) to afford 5-fluoro-2-methoxy-3-(4,4,5,5-tetramethyl-1,3,2-dioxaborolan-2-yl)pyridine (Compound 76b) (450.0 mg, 36%) as a white solid. LCMS (ESI, m/z): [M+H]⁺=254.1.

Step 2: Synthesis of 3-[5-chloro-1-methylpyrrolo[2,3-c]pyridin-2-yl]-5-fluoro-2-methoxypyridine (Compound 76d)

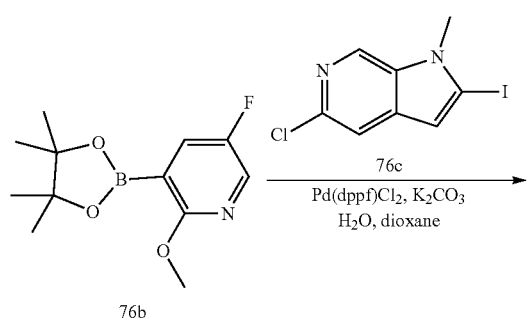

76b

76c
Pd(dppf)Cl₂, K₂CO₃
H₂O, dioxane

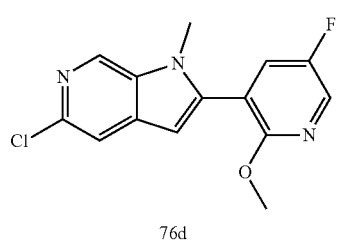

76d

To a solution of 5-fluoro-2-methoxy-3-(4,4,5,5-tetramethyl-1,3,2-dioxaborolan-2-yl)pyridine (Compound 76b) (400.0 mg, 1.58 mmol) in dioxane/H₂O (5.0/0.5 mL) was added 5-chloro-2-iodo-1-methylpyrrolo[2,3-c]pyridine (Compound 76c) (554.7 mg, 1.89 mmol), Pd(dppf)Cl₂ (231.2 mg, 0.31 mmol) and K₂CO₃ (655.3 mg, 4.74 mmol) at room temperature under N₂. The resulting mixture was stirred at 80° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford 3-[5-chloro-1-methylpyrrolo[2,3-c]pyridin-2-yl]-5-fluoro-2-methoxypyridine (Compound 76d) (400.0 mg, 86%) as a yellow solid. LCMS (ESI, m/z): [M+H]⁺=292.1.

Step 3: Synthesis of (1S,2S)-2-fluoro-N-[2-(5-fluoro-2-methoxypyridin-3-yl)-1-methylpyrrolo[2,3-c]pyridin-5-yl]cyclopropane-1-carboxamide (Compound 76)

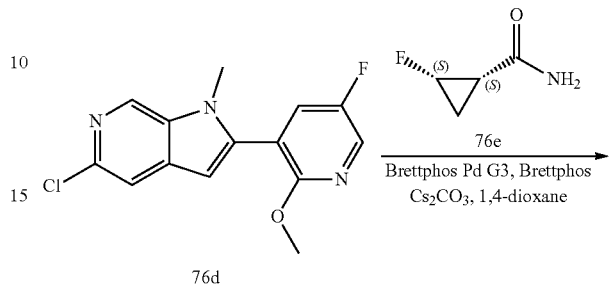

76d

76e
Brettphos Pd G3, Brettphos
Cs₂CO₃, 1,4-dioxane

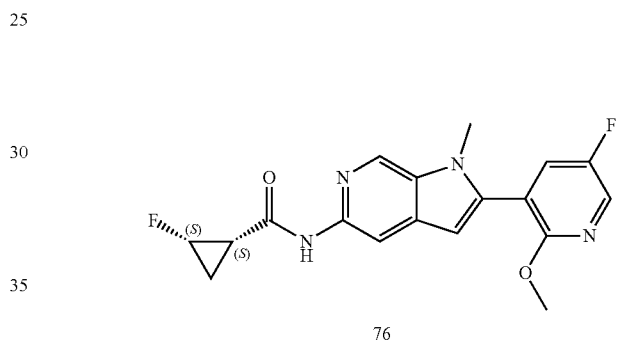

76

To a solution of 3-[5-chloro-1-methylpyrrolo[2,3-c]pyridin-2-yl]-5-fluoro-2-methoxypyridine (Compound 76d) (320.0 mg, 1.09 mmol) in dioxane (5.0 mL) was added (1S,2S)-2-fluorocyclopropanecarboxamide (Compound 76e) (565.4 mg, 5.48 mmol), BrettPhos (235.5 mg, 0.43 mmol), BrettPhos Pd G3 (198.8 mg, 0.21 mmol) and Cs₂CO₃ (1.0 g, 3.29 mmol) at room temperature under N₂. The resulting mixture was stirred at 100° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (60/40, v/v) and then purified by Prep-HPLC with the following conditions (Column: YMC-Actus Triart C18, 30×250 mm, 5 um; Mobile Phase A:Water (10 mmol/L NH₄HCO₃), Mobile Phase B: ACN; Flow rate: 60 mL/min; Gradient: 45% B to 75% B in 7 min; 254 nm) to afford (1S,2S)-2-fluoro-N-[2-(5-fluoro-2-methoxypyridin-3-yl)-1-methylpyrrolo[2,3-c]pyridin-5-yl]cyclopropane-1-carboxamide (Compound 76) (31.3 mg, 7%) as a white solid. LCMS (ESI, m/z): [M+H]⁺=359.3. ¹H NMR (300 MHz, DMSO-d₆): δ 10.59 (s, 1H), 8.67 (s, 1H), 8.35 (d, J=3.0 Hz, 1H), 8.23 (s, 1H), 7.94-7.90 (m, 1H), 6.60 (d, J=0.6 Hz, 1H), 5.05-4.77 (m, 1H), 3.90 (s, 3H), 3.67 (s, 3H), 2.25-2.16 (m, 1H), 1.72-1.62 (m, 1H), 1.22-1.12 (m, 1H).

Example S77: Synthesis of 3-ethyl-1-[2-(2-methoxyphenyl)-1-methylpyrrolo[2,3-c]pyridin-5-yl]urea (Compound 77)

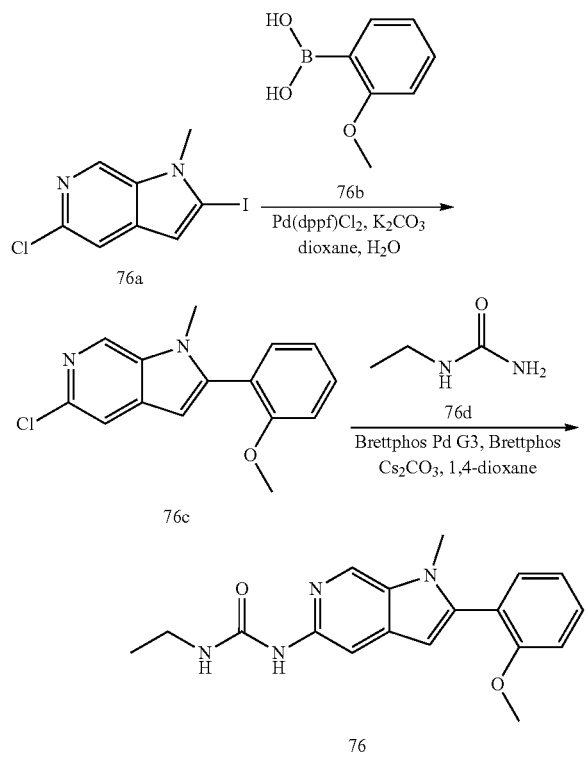

Step 1: Synthesis of 5-chloro-2-(2-methoxyphenyl)-1-methylpyrrolo[2,3-c]pyridine (Compound 76c)

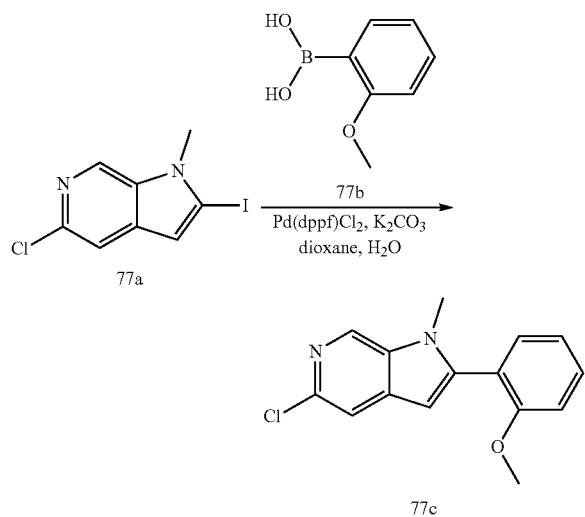 [SMILES: Cn1c(I)cc2cc(Cl)ncc21 ; COc1ccccc1B(O)O ; COc1ccccc1-c1cc2cc(Cl)ncc2n1C]

To a solution of 5-chloro-2-iodo-1-methylpyrrolo[2,3-c]pyridine (Compound 77a) (200.0 mg, 0.68 mmol) in dioxane/H$_2$O (5.0/1.0 mL) was added 2-methoxyphenylboronic acid (Compound 77b) (124.7 mg, 0.82 mmol), K$_2$CO$_3$ (283.5 mg, 2.05 mmol) and Pd(dppf)Cl$_2$ (50.0 mg, 0.07 mmol) at room temperature under N$_2$. The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (70/30, v/v) to afford 5-chloro-2-(2-methoxyphenyl)-1-methylpyrrolo[2,3-c]pyridine (Compound 77c (140.0 mg, 75%) as a yellow solid. LCMS (ESI, m/z): [M+H]$^+$=273.1.

Step 2: Synthesis of 3-ethyl-1-[2-(2-methoxyphenyl)-1-methylpyrrolo[2,3-c]pyridin-5-yl]urea (Compound 77)

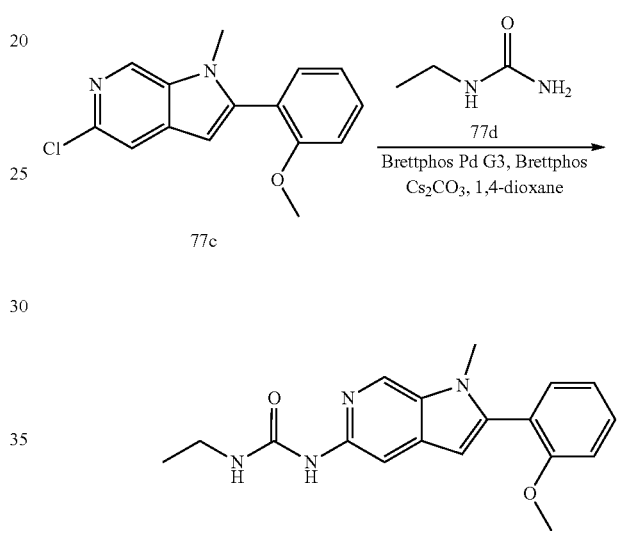

To a solution of 5-chloro-2-(2-methoxyphenyl)-1-methylpyrrolo[2,3-c]pyridine (Compound 77c) (120.0 mg, 0.44 mmol) in 1,4-dioxane (4.0 mL) was added ethylurea (Compound 77d) (116.3 mg, 1.32 mmol), Cs$_2$CO$_3$ (430.1 mg, 1.32 mmol), BrettPhos (47.2 mg, 0.08 mmol) and BrettPhos Pd G3 (39.9 mg, 0.04 mmol) at room temperature under N$_2$. The resulting mixture was stirred at 100° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (80/20, v/v) and then purified by Prep-HPLC with the following conditions (Column: YMC-Actus Triart C18, 30×250 mm, 5 um; Mobile Phase A: Water (10 mmol/L NH$_4$HCO$_3$), Mobile Phase B: ACN; Flow rate: 60 mL/min; Gradient: 44% B to 53% B in 8 min; 254 nm) to afford 3-ethyl-1-[2-(2-methoxyphenyl)-1-methylpyrrolo[2,3-c]pyridin-5-yl]urea (Compound 77) (34.7 mg, 24%) as a white solid. LCMS (ESI, m/z): [M+H]$^+$=325.2. $^1$H NMR (400 MHz, DMSO-d$_6$): δ 8.74 (s. 1H), 8.48 (s, 1H), 7.88 (s, 1H), 7.54-7.49 (m, 2H), 7.37-7.35 (m, 1H), 7.20 (d, J=8.0 Hz, 1H), 7.11-7.07 (m, 1H), 6.35 (s, 1H), 3.80 (s, 3H), 3.55 (s, 3H), 3.23-3.16. (m, 2H), 1.12-1.08 (m, 3H).

Example S78: Synthesis of 3-ethyl-1-[2-(2-methoxypyridin-3-yl)-1-methylpyrrolo[2,3-c]pyridin-5-yl]urea (Compound 78)

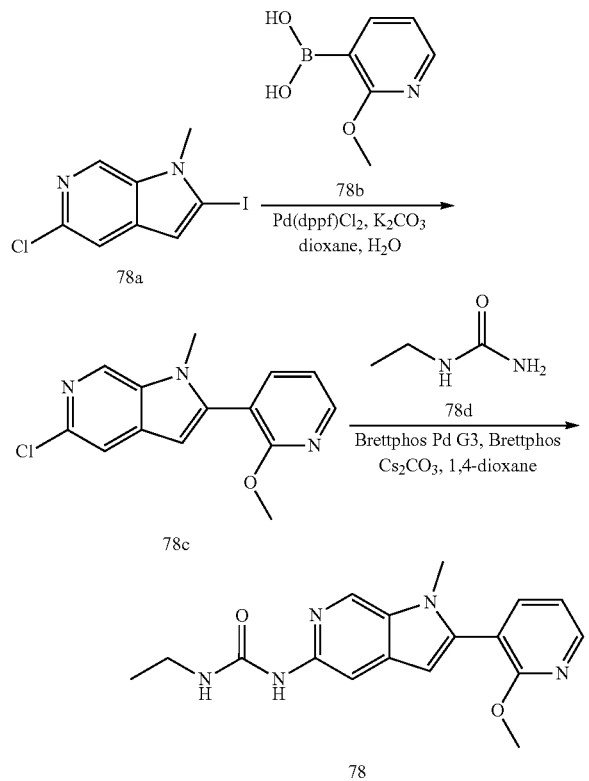

Step 1: Synthesis of 0.3-[5-chloro-1-methylpyrrolo[2,3-c]pyridin-2-yl]-2-methoxypyridine (Compound 78c)

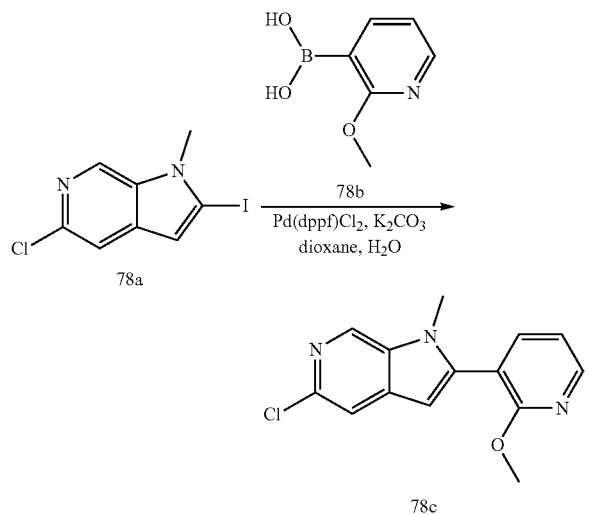

To a solution of 5-chloro-2-iodo-1-methylpyrrolo[2,3-c]pyridine (Compound 78a) (220.0 mg, 0.75 mmol) in dioxane/H$_2$O (5.0/1.0 mL) was added 2-methoxypyridin-3-ylboronic acid (Compound 78b) (138.0 mg, 0.90 mmol), K$_2$CO$_3$ (311.8 mg, 2.25 mmol) and Pd(dppf)Cl$_2$ (50.0 mg, 0.07 mmol) at room temperature under N$_2$. The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (64/36, v/v) to afford 3-[5-chloro-1-methylpyrrolo[2,3-c]pyridin-2-yl]-2-methoxypyridine (Compound 78c) (160.0 mg, 78%) as a yellow solid. LCMS (ESI, m/z): [M+H]$^+$=274.1.

Step 2: Preparation of 3-ethyl-1-[2-(2-methoxypyridin-3-yl)-1-methylpyrrolo[2,3-c]pyridin-5-yl]urea (Compound 78)

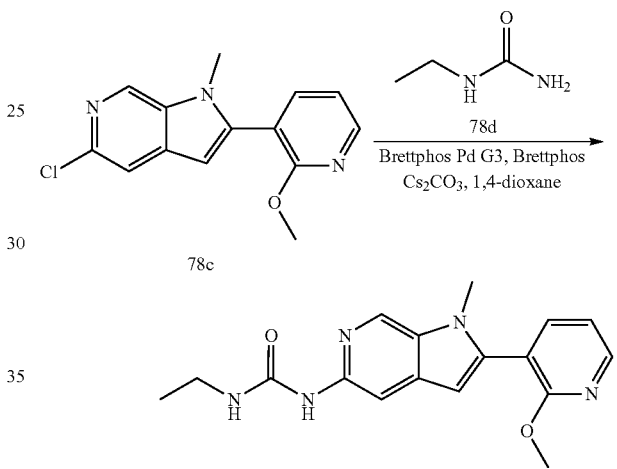

To a solution of 3-[5-chloro-1-methylpyrrolo[2,3-c]pyridin-2-yl]-2-methoxypyridine (Compound 78c) (140.0 mg, 0.51 mmol) in 1,4-dioxane (4.0 mL) was added ethylurea (Compound 78d) (125.3 mg, 2.55 mmol), Cs$_2$CO$_3$ (499.9 mg, 1.53 mmol), BrettPhos (54.9 mg, 0.10 mmol) and BrettPhos Pd G$_3$ (46.3 mg, 0.05 mmol) at room temperature under N$_2$. The resulting mixture was stirred at 100° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (84/16, v/v) and then purified by Prep-HPLC with the following conditions (Column: YMC-Actus Triart C18, 30×250 mm, 5 um; Mobile Phase A: Water (10 mmol/L NH$_4$HCO$_3$), Mobile Phase B: ACN; Flow rate: 60 mL/min; Gradient: 37% B to 46% B in 8 min; 254 nm) to afford 3-ethyl-1-[2-(2-methoxypyridin-3-yl)-1-methylpyrrolo[2,3-c]pyridin-5-yl]urea (Compound 78) (36.2 mg, 24%) as a white solid. LCMS (ESI, m/z): [M+H]$^+$=326.2. $^1$H NMR (400 MHz, DMSO-d$_6$): δ 8.75 (s, 1H), 8.52 (s, 1H), 8.35-8.33 (m, 1H), 7.84-7.80 (m, 2H), 7.54 (s, 1H), 7.18-7.15 (m, 1H), 6.44 (s, 1H), 3.91 (s, 3H), 3.59 (s, 3H), 3.22-3.16 (m, 2H), 1.12-1.08 (m, 3H).

Example S79: Synthesis of 3-[2-(2-methoxyphenyl)-1-methylpyrrolo[2,3-c]pyridin-5-yl]-1-[2-(4-methylpiperazin-1-yl)ethyl]urea (Compound 79)

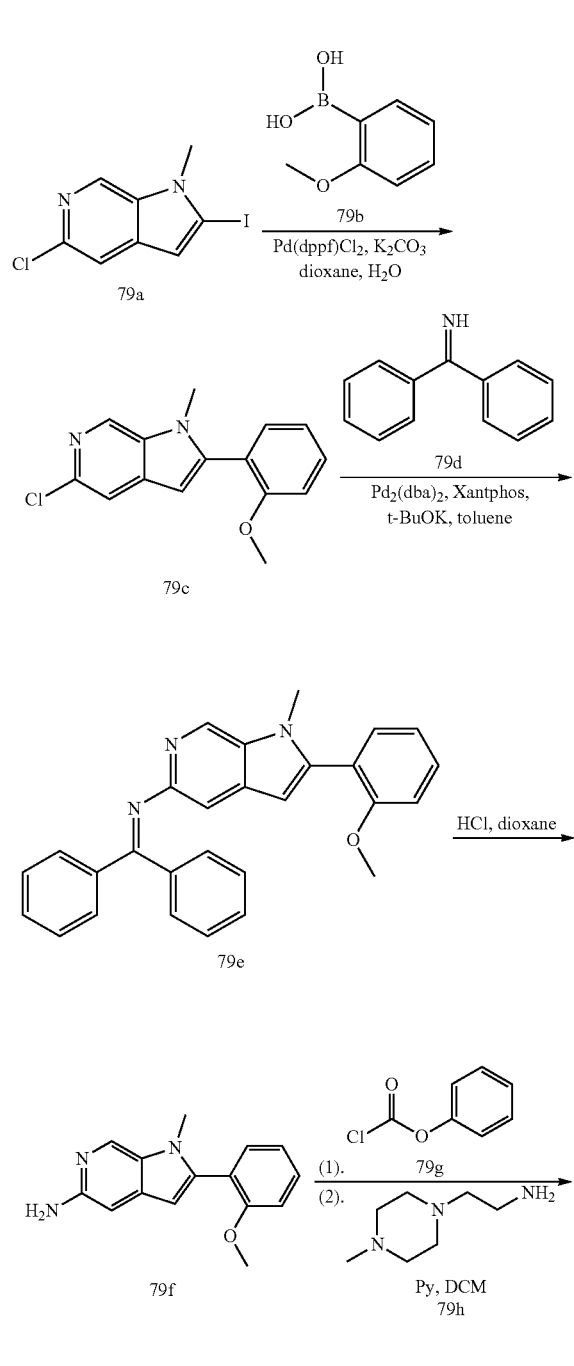

Step 1: Synthesis of 5-chloro-2-(2-methoxyphenyl)-1-methylpyrrolo[2,3-c]pyridine (Compound 79c)

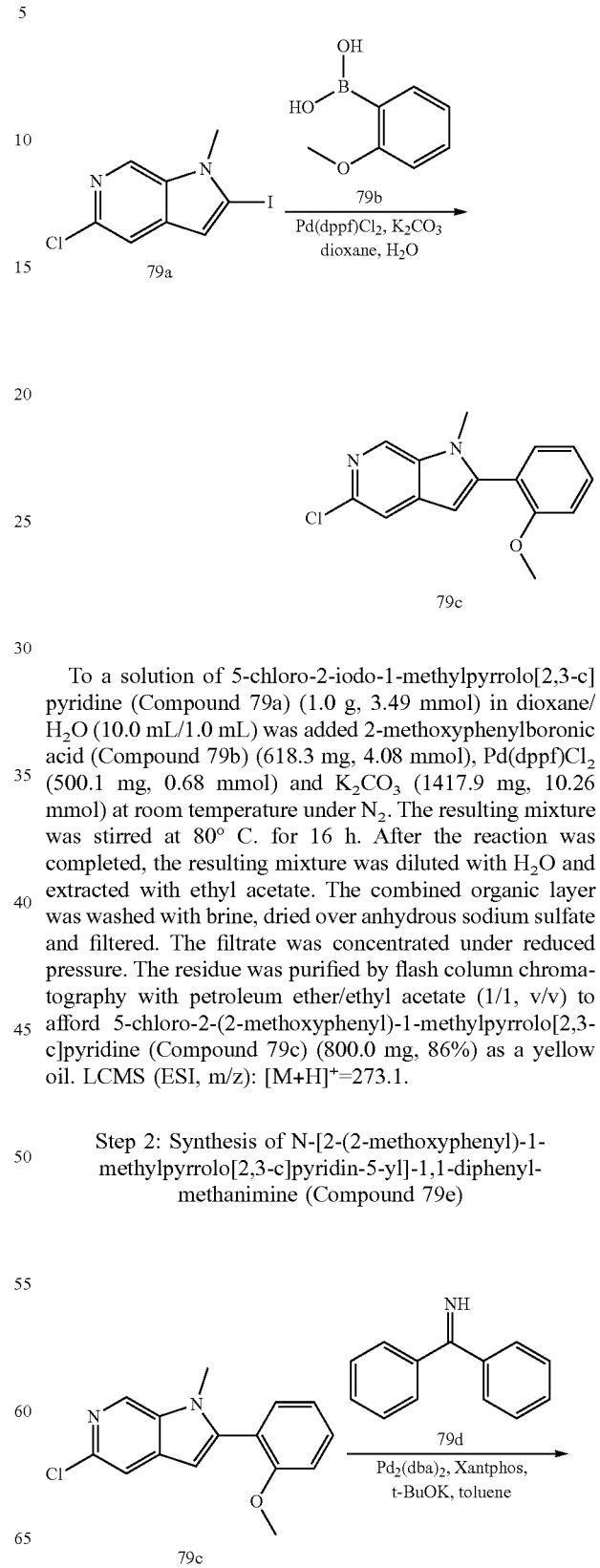

To a solution of 5-chloro-2-iodo-1-methylpyrrolo[2,3-c]pyridine (Compound 79a) (1.0 g, 3.49 mmol) in dioxane/$H_2O$ (10.0 mL/1.0 mL) was added 2-methoxyphenylboronic acid (Compound 79b) (618.3 mg, 4.08 mmol), Pd(dppf)$Cl_2$ (500.1 mg, 0.68 mmol) and $K_2CO_3$ (1417.9 mg, 10.26 mmol) at room temperature under $N_2$. The resulting mixture was stirred at 80° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-chloro-2-(2-methoxyphenyl)-1-methylpyrrolo[2,3-c]pyridine (Compound 79c) (800.0 mg, 86%) as a yellow oil. LCMS (ESI, m/z): $[M+H]^+$=273.1.

Step 2: Synthesis of N-[2-(2-methoxyphenyl)-1-methylpyrrolo[2,3-c]pyridin-5-yl]-1,1-diphenyl-methanimine (Compound 79e)

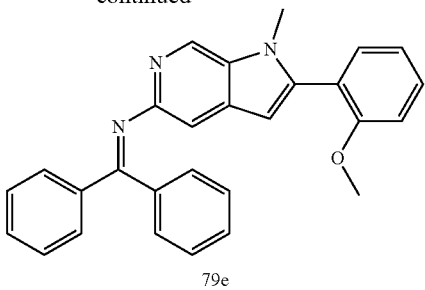

79e

To a solution of 5-chloro-2-(2-methoxyphenyl)-1-methylpyrrolo[2,3-c]pyridine (Compound 79c) (750.0 mg, 2.75 mmol) in toluene (10.0 mL) was added diphenylmethanimine (Compound 79d) (1495.2 mg, 8.25 mmol), Xantphos (318.2 mg, 0.55 mmol), t-BuOK (925.7 mg, 8.25 mmol) and Pd$_2$(dba)$_3$ (503.6 mg, 0.55 mmol) at room temperature under N$_2$. The resulting mixture was stirred at 80° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/2, v/v) to afford N-[2-(2-methoxyphenyl)-1-methylpyrrolo[2,3-c]pyridin-5-yl]-1,1-diphenylmethanimine (Compound 79e) (220.0 mg, 31%) as a yellow oil. LCMS (ESI, m/z): [M+H]$^+$=418.2.

Step 3: Synthesis of 2-(2-methoxyphenyl)-1-methylpyrrolo[2,3-c]pyridin-5-amine (Compound 79f)

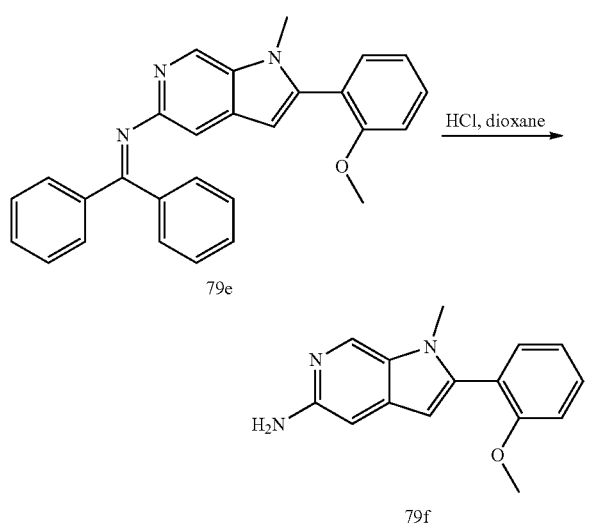 [SMILES: COc1ccccc1-c1cc2cc(N=C(c3ccccc3)c3ccccc3)ncc2n1C ; COc1ccccc1-c1cc2cc(N)ncc2n1C]

The solution of N-[2-(2-methoxyphenyl)-1-methylpyrrolo[2,3-c]pyridin-5-yl]-1,1-diphenylmethanimine (Compound 79e) (200.0 mg, 0.47 mmol) in HCl/1,4-dioxane (10.0 mL, 4 mol/L) was stirred at room temperature for 2 h. After the reaction was completed, the resulting mixture was diluted with H$_2$O. The pH value of the mixture was adjusted to 7 with aq·NaHCO$_3$ and then extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (85/15, v/v) to afford 2-(2-methoxyphenyl)-1-methylpyrrolo[2,3-c]pyridin-5-amine (Compound 79f) (100.0 mg, 82%) as a yellow oil. LCMS (ESI, m/z): [M+H]$^+$= 254.1.

Step 4: Synthesis of 3-[2-(2-methoxyphenyl)-1-methylpyrrolo[2,3-c]pyridin-5-yl]-1-[2-(4-methylpiperazin-1-yl)ethyl]urea (Compound 79)

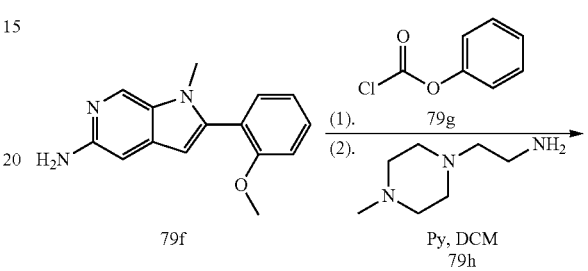

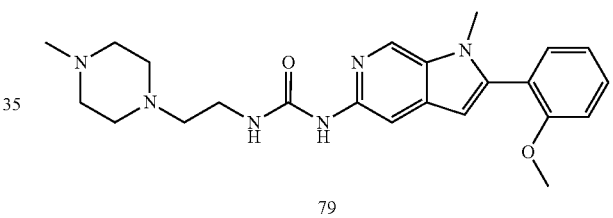

79

To a solution of 2-(2-methoxyphenyl)-1-methylpyrrolo[2,3-c]pyridin-5-amine (Compound 79f) (120.0 mg, 0.47 mmol) in pyridine/DCM (1.0 mL/8.0 ml) was added phenyl chloroformate (Compound 79g) (74.2 mg, 0.47 mmol). The resulting mixture was stirred at room temperature for 12 h. The resulting mixture was concentrated under vacuum. A solution of 2-(4-methylpiperazin-1-yl)ethanamine (Compound 79h) (203.7 mg, 1.42 mmol) in pyridine (10.0 mL) was added to the residue. The resulting mixture was stirred at 60° C. for another 2 h under N$_2$. After the reaction was completed, the resulting mixture was concentrated under vacuum. The residue was purified by reverse phase flash column chromatography with CH$_3$CN/H$_2$O (9/1, v/v) and then purified by Prep-HPLC with the following conditions (Column: YMC-Actus Triart C18 Column, 30×150 mm, 5 um; Mobile Phase A:Water (10 mmol/L NH$_4$HCO$_3$), Mobile Phase B: ACN; Flow rate: 60 mL/min; Gradient: 37% B to 67% B in 8 min; 254 nm) to afford 3-[2-(2-methoxyphenyl)-1-methylpyrrolo[2,3-c]pyridin-5-yl]-1-[2-(4-methylpiperazin-1-yl)ethyl]urea (Compound 79) (14.1 mg, 7%) as a red solid. LCMS (ESI, m/z): [M+H]$^+$=423.4. $^1$H NMR (300 MHz, DMSO-d$_6$): δ 8.85 (s, 1H), 8.47 (s, 1H), 8.02 (s, 1H), 7.55-7.49 (m, 2H), 7.37 (d, J=9.3 Hz, 1H), 7.21 (d, J=8.1 Hz, 1H), 7.13-7.07 (m, 1H), 6.35 (s, 1H), 3.81 (s, 3H), 3.56 (s, 3H), 3.32-3.27 (m, 2H), 2.52-2.40 (m, 10H), 2.17 (s, 3H).

Example S80: Synthesis of 1-(2-(2-methoxyphenyl)-1-methyl-1H-pyrrolo[2,3-c]pyridin-5-yl)-3-(2-morpholinoethyl)urea (Compound 80)

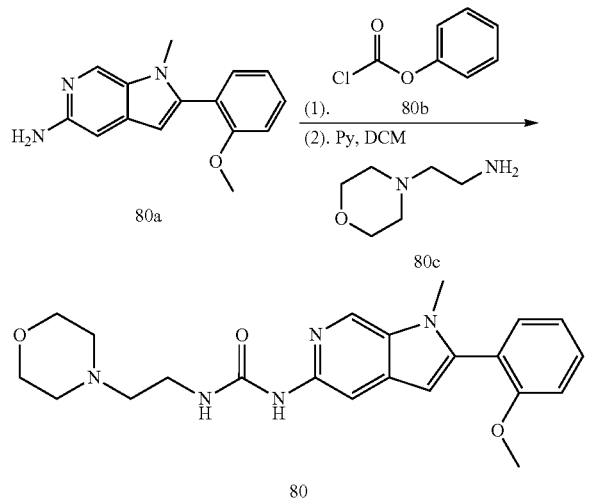 [SMILES: COc1ccccc1-c1cc2cc(N)ncc2n1C ; NCCN1CCOCC1 ; O=C(Cl)Oc1ccccc1 ; COc1ccccc1-c1cc2cc(NC(=O)NCCN3CCOCC3)ncc2n1C]

To a solution of 2-(2-methoxyphenyl)-1-methylpyrrolo[2,3-c]pyridin-5-amine (Compound 80a) (170.0 mg, 0.67 mmol) in pyridine/DCM (5.0 mL/40.0 mL) was added phenyl chloroformate (Compound 80b) (105.8 mg, 0.67 mmol) at 0° C. The mixture was stirred at room temperature for 12 h under $N_2$. The resulting mixture was concentrated under vacuum. A solution of N-aminoethylmorpholine (Compound 80c) (262.2 mg, 2.03 mmol) in pyridine (10.0 mL) was added to the residue. The resulting mixture was stirred at 60° C. for another 2 h. After the reaction was completed, the mixture was evaporated in vacuo. The residue was purified by reverse flash column chromatography with $CH_3CN/H_2O$ (9/1, v/v) and then purified by Prep-HPLC with the following conditions (Column: YMC-Actus Triart C18 Column, 30×150 mm, 5 um; Mobile Phase A:Water (10 mmol/L $NH_4HCO_3$), Mobile Phase B: ACN; Flow rate: 60 mL/min; Gradient: 29% B to 59% B in 8 min; 254 nm) to afford 1-(2-(2-methoxyphenyl)-1-methyl-1H-pyrrolo[2,3-c]pyridin-5-yl)-3-(2-morpholinoethyl)urea (Compound 80) (6.0 mg, 2%) as a red solid. LCMS (ESI, m/z): [M+H]$^+$=410.3. $^1$H NMR (300 MHz, DMSO-d$_6$): δ 8.87 (s, 1H), 8.48 (s, 1H), 8.05 (s, 1H), 7.55-7.49 (m, 2H), 7.38-7.35 (m, 1H), 7.21 (d, J=8.1 Hz, 1H), 7.13-7.07 (m, 1H), 6.35 (s, 1H), 3.81 (s, 3H), 3.64-3.61 (m, 4H), 3.57 (s, 3H), 3.32-3.27 (m, 2H), 2.52-2.41 (m, 6H).

Example S81: Synthesis of 3-[2-(2,6-dimethoxyphenyl)-1-methylpyrrolo[2,3-c]pyridin-5-yl]-1-[2-(piperazin-1-yl)ethyl]urea (Compound 81)

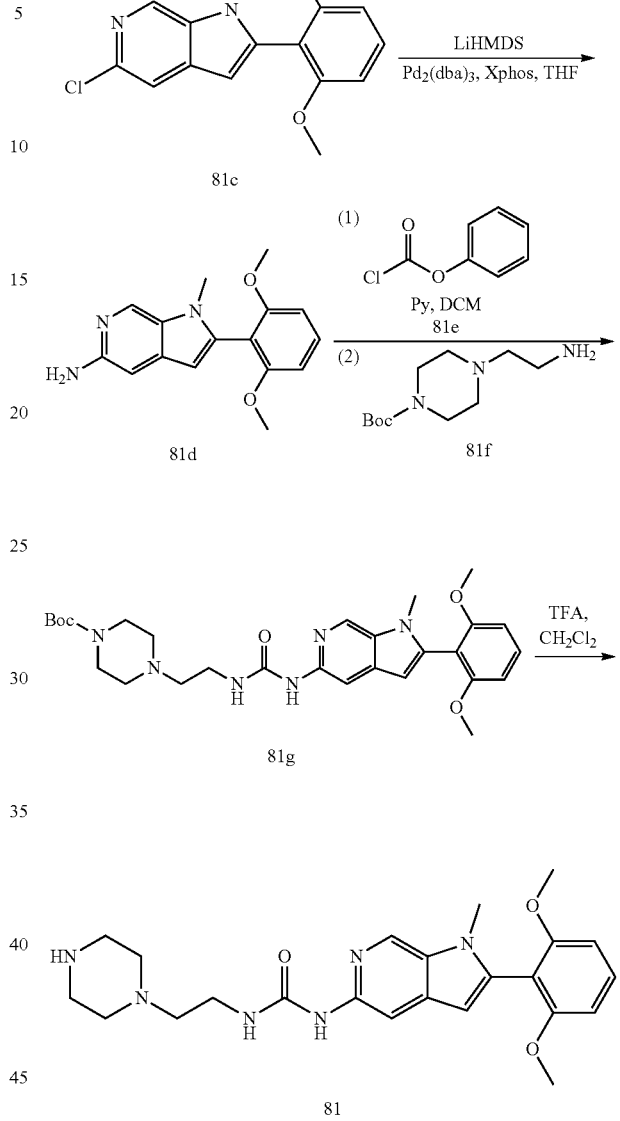

Step 1: Synthesis of 5-chloro-2-(2,6-dimethoxyphenyl)-1-methylpyrrolo[2,3-c]pyridine (Compound 81c)

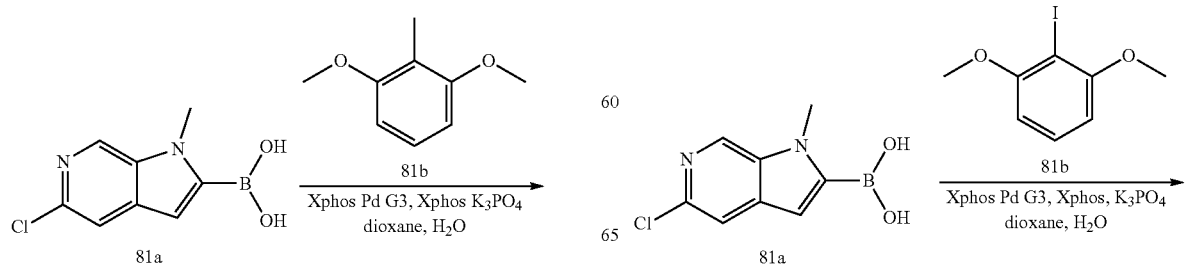

-continued

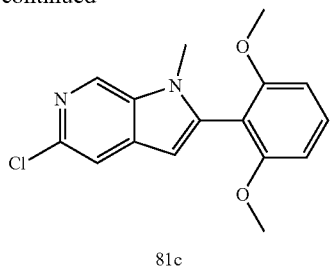

81c

To a solution of 5-chloro-1-methylpyrrolo[2,3-c]pyridin-2-ylboronic acid (Compound 81a) (500.0 mg, 2.38 mmol) in dioxane/H₂O (20.0 mL/4.0 mL) was added 2-iodo-1,3-dimethoxybenzene (Compound 81b) (627.5 mg, 2.38 mmol), XPhos (226.6 mg, 0.48 mmol), K₃PO₄ (827.8 mg, 4.75 mmol) and XPhos Pd G3 (201.1 mg, 0.24 mmol) at room temperature under N₂. The resulting mixture was stirred at 60° C. for 2 h under N₂. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 5-chloro-2-(2,6-dimethoxyphenyl)-1-methylpyrrolo[2,3-c]pyridine (Compound 81c) (230.0 mg, 34%) as a yellow oil. LCMS (ESI, m/z): [M+H]⁺=303.1.

Step 2: Synthesis of 2-(2,6-dimethoxyphenyl)-1-methylpyrrolo[2,3-c]pyridin-5-amine (Compound 81d)

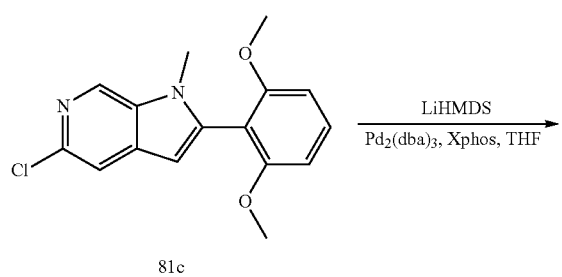

To a solution of 5-chloro-2-(2,6-dimethoxyphenyl)-1-methylpyrrolo[2,3-c]pyridine (Compound 81c) (190.0 mg, 0.63 mmol) in THF (10.0 mL) was added LiHMDS (0.3 mL, 1.3 mol/L), XPhos (59.8 mg, 0.13 mmol) and Pd₂(dba)₃ (57.5 mg, 0.06 mmol) at room temperature under N₂. The resulting mixture was stirred at 60° C. for 30 min. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by reverse phase flash chromatography with ACN/H₂O (1/1, v/v) to afford 2-(2,6-dimethoxyphenyl)-1-methylpyrrolo[2,3-c]pyridin-5-amine (Compound 81d) (110.0 mg, 62%) as a yellow solid. LCMS (ESI, m/z): [M+H]⁺=284.2.

Step 3: Synthesis of tert-butyl 4-[2-([[2-(2,6-dimethoxyphenyl)-1-methylpyrrolo[2,3-c]pyridin-5-yl]carbamoyl]amino)ethyl]piperazine-1-carboxylate (Compound 81g)

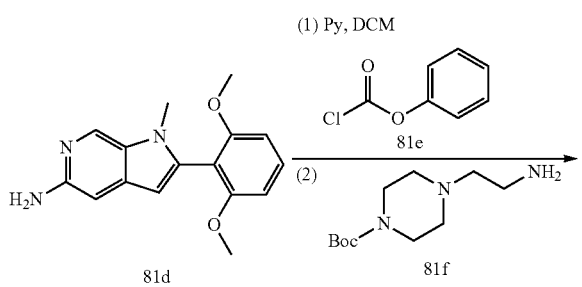

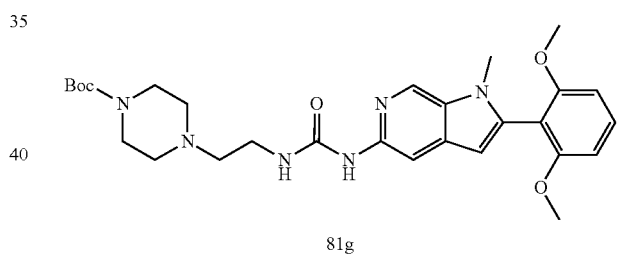

To a solution of 2-(2,6-dimethoxyphenyl)-1-methylpyrrolo[2,3-c]pyridin-5-amine (Compound 81d) (90.0 mg, 0.32 mmol) in DCM (9.0 mL) was added pyridine (101.8 mg, 1.27 mmol) and phenyl chloroformate (Compound 81e) (59.7 mg, 0.38 mmol) at room temperature. The resulting mixture was stirred at room temperature for 16 h under N₂. The resulting mixture was concentrated under reduced pressure. To the residue in pyridine (9.0 mL) was added tert-butyl 4-(2-aminoethyl)piperazine-1-carboxylate (Compound 81f) (364.2 mg, 1.59 mmol) at room temperature. The resulting mixture was stirred at 60° C. for another 4 h. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/MeOH (10/1, v/v) to afford tert-butyl 4-[2-([[2-(2,6-dimethoxyphenyl)-1-methylpyrrolo[2,3-c]pyridin-5-yl]carbamoyl]amino)ethyl]piperazine-1-carboxylate (Compound 81g) (110.0 mg, 64%) as a light brown oil. LCMS (ESI, m/z): [M+H]⁺=539.3.

Step 4: Synthesis of 3-[2-(2,6-dimethoxyphenyl)-1-methylpyrrolo[2,3-c]pyridin-5-yl]-1-[2-(piperazin-1-yl)ethyl]urea (Compound 81)

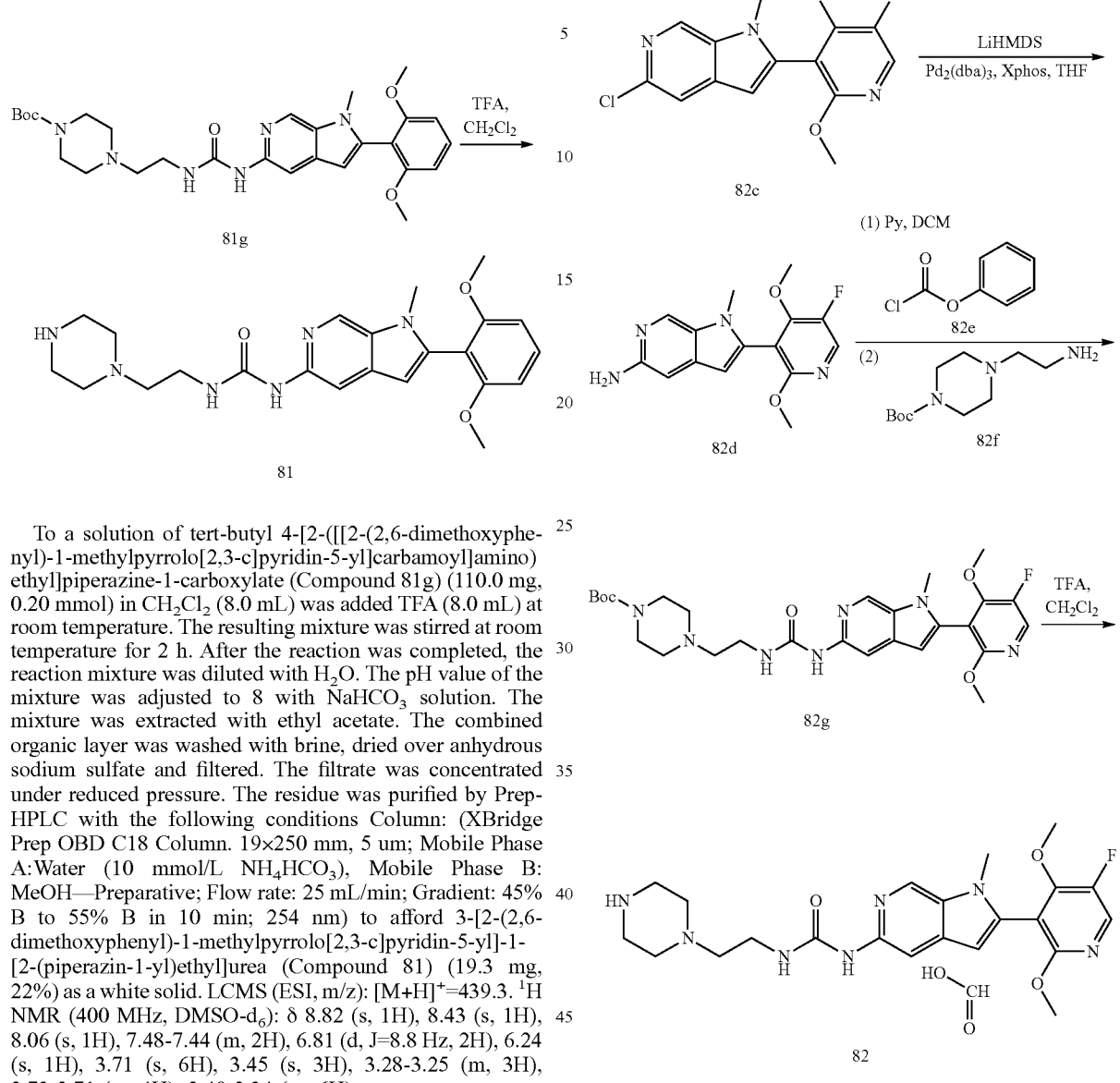

To a solution of tert-butyl 4-[2-([[2-(2,6-dimethoxyphenyl)-1-methylpyrrolo[2,3-c]pyridin-5-yl]carbamoyl]amino)ethyl]piperazine-1-carboxylate (Compound 81g) (110.0 mg, 0.20 mmol) in $CH_2Cl_2$ (8.0 mL) was added TFA (8.0 mL) at room temperature. The resulting mixture was stirred at room temperature for 2 h. After the reaction was completed, the reaction mixture was diluted with $H_2O$. The pH value of the mixture was adjusted to 8 with $NaHCO_3$ solution. The mixture was extracted with ethyl acetate. The combined organic layer was washed with brine, dried over anhydrous sodium sulfate and filtered. The filtrate was concentrated under reduced pressure. The residue was purified by Prep-HPLC with the following conditions Column: (XBridge Prep OBD C18 Column. 19×250 mm, 5 um; Mobile Phase A:Water (10 mmol/L $NH_4HCO_3$), Mobile Phase B: MeOH—Preparative; Flow rate: 25 mL/min; Gradient: 45% B to 55% B in 10 min; 254 nm) to afford 3-[2-(2,6-dimethoxyphenyl)-1-methylpyrrolo[2,3-c]pyridin-5-yl]-1-[2-(piperazin-1-yl)ethyl]urea (Compound 81) (19.3 mg, 22%) as a white solid. LCMS (ESI, m/z): $[M+H]^+=439.3$. $^1H$ NMR (400 MHz, DMSO-$d_6$): δ 8.82 (s, 1H), 8.43 (s, 1H), 8.06 (s, 1H), 7.48-7.44 (m, 2H), 6.81 (d, J=8.8 Hz, 2H), 6.24 (s, 1H), 3.71 (s, 6H), 3.45 (s, 3H), 3.28-3.25 (m, 3H), 2.73-2.71 (m, 4H), 2.40-2.34 (m, 6H).

Example S82: Synthesis of 3-[2-(5-fluoro-2,4-dimethoxypyridin-3 yl)-1-methylpyrrolo[2,3-c]pyridin-5-yl]-1-[2-(piperazin-1-yl)ethyl]urea formic acid (Compound 82)

Step 1: Synthesis of 3-[5-chloro-1-methylpyrrolo[2,3-c]pyridin-2-yl]-5-fluoro-2,4-dimethoxypyridine (Compound 82c)

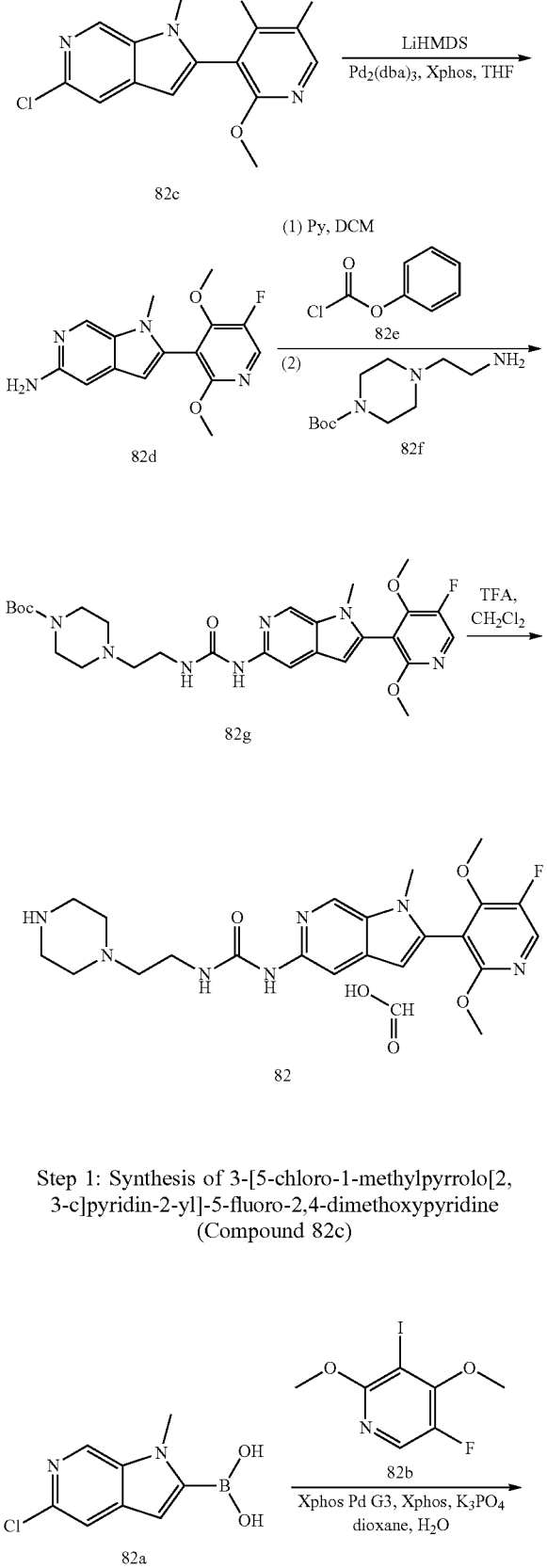

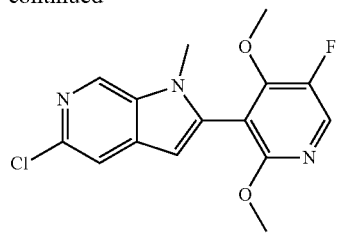

82c

To a solution of 5-chloro-1-methylpyrrolo[2,3-c]pyridin-2-ylboronic acid (Compound 82a) (500.0 mg, 2.38 mmol) in 1,4-dioxane/H$_2$O (20.0 mL/4.0 mL) was added 5-fluoro-3-iodo-2,4-dimethoxypyridine (Compound 82b) (672.6 mg, 2.38 mmol), XPhos (226.6 mg, 0.48 mmol), K$_3$PO$_4$ (1.0 g, 4.76 mmol) and Xphos Pd G3 (201.1 mg, 0.24 mmol) at room temperature under N$_2$. The resulting mixture was stirred at 70° C. for 3 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/2, v/v) to afford 3-[5-chloro-1-methylpyrrolo[2,3-c]pyridin-2-yl]-5-fluoro-2,4-dimethoxypyridine (Compound 82c) (358.0 mg, 46%) as a yellow oil. LCMS (ESI, m/z): [M+H]$^+$=322.1.

Step 2: Synthesis of 2-(5-fluoro-2,4-dimethoxypyridin-3-yl)-1-methylpyrrolo[2,3-c]pyridin-5-amine (Compound 82d)

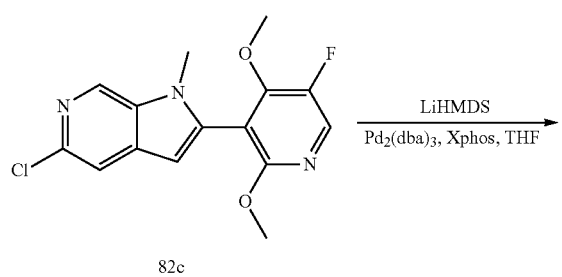

To a solution of 3-[5-chloro-1-methylpyrrolo[2,3-c]pyridin-2-yl]-5-fluoro-2,4-dimethoxypyridine (Compound 82c) (338.0 mg, 1.05 mmol) in THF (30.0 mL) was added XPhos (100.2 mg, 0.21 mmol), Pd$_2$(dba)$_3$ (96.2 mg, 0.11 mmol) and LiHMDS (1.57 mL, 1 mol/L) at room temperature under N$_2$. The resulting mixture was stirred at 65° C. for 2.5 h under N$_2$. After the reaction was completed, the resulting mixture was concentrated under reduced pressure. The residue was purified by flash column chromatography with CH$_2$Cl$_2$/methanol (9/1, v/v) to afford 2-(5-fluoro-2,4-dimethoxypyridin-3-yl)-1-methylpyrrolo[2,3-c]pyridin-5-amine (Compound 82d) (279.0 mg, 87%) as a brown solid. LCMS (ESI, m/z): [M+H]$^+$=303.1.

Step 3: Synthesis of tert-butyl 4-[2-([[2-(5-fluoro-2,4-dimethoxypyridin-3-yl)-1-methylpyrrolo[2,3-c]pyridin-5-yl]carbamoyl]amino)ethyl]piperazine-1-carboxylate (Compound 82)

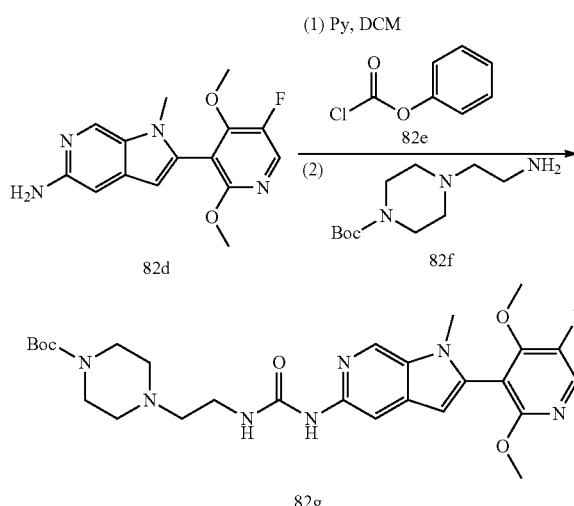

To a solution of 2-(5-fluoro-2,4-dimethoxypyridin-3-yl)-1-methylpyrrolo[2,3-c]pyridin-5-amine (Compound 82d) (160.0 mg, 0.53 mmol) in DCM (10.0 mL) was added pyridine (167.5 mg, 2.12 mmol) and phenyl chloroformate (Compound 82c) (149.2 mg, 0.95 mmol) at room temperature. The resulting mixture was stirred at room temperature for 3 h. The resulting mixture was concentrated under reduced pressure. To the above residue was added tert-butyl 4-(2-aminoethyl)piperazine-1-carboxylate (Compound 82f) (364.1 mg, 1.59 mmol) and pyridine (10.0 mL) at room temperature. The resulting mixture was stirred at 60° C. for another 2 h. After the reaction was completed, the resulting mixture was concentrated under reduced pressure. The residue was purified by flash column chromatography with CH$_2$Cl$_2$/CH$_3$OH (4/1, v/v) to afford tert-butyl 4-[2-([[2-(5-fluoro-2,4-dimethoxypyridin-3-yl)-1-methylpyrrolo[2,3-c]pyridin-5-yl]carbamoyl]amino)ethyl]piperazine-1-carboxylate (Compound 82g) (190.0 mg, 64%) as a brown oil. LCMS (ESI, m/z): [M+H]$^+$=558.3.

Step 4: Synthesis of 3-[2-(5-fluoro-2,4-dimethoxypyridin-3-yl)-1-methylpyrrolo[2,3-c]pyridin-5-yl]-1-[2-(piperazin-1-yl)ethyl]urea formic acid (Compound 82)

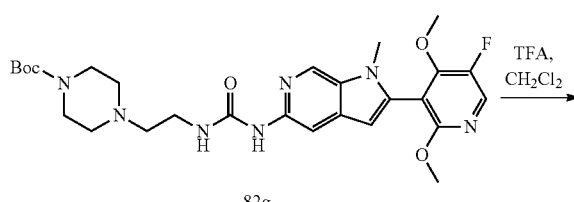

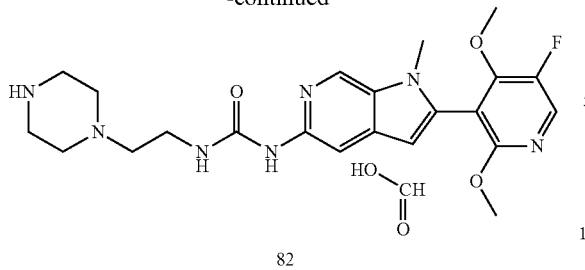

82

To a solution of tert-butyl 4-[2-([[2-(5-fluoro-2,4-dimethoxypyridin-3-yl)-1-methylpyrrolo[2,3-c]pyridin-5-yl]carbamoyl]amino)ethyl]piperazine-1-carboxylate (Compound 82g) (190 mg, 0.34 mmol) in $CH_2Cl_2$ (6.0 mL) was added TFA (6.0 mL) at room temperature. The resulting mixture was stirred at room temperature for 3 h. After the reaction was completed, the resulting mixture was concentrated under reduced pressure. The residue was diluted with $H_2O$. The pH value of the mixture was adjusted to 8 with $NaHCO_3$ solution. The mixture was extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 4% B to 16% B in 8 min; 254/220 nm) to afford 3-[2-(5-fluoro-2,4-dimethoxypyridin-3-yl)-1-methylpyrrolo[2,3-c]pyridin-5-yl]-1-[2-(piperazin-1-yl)ethyl]urea (Compound 82); formic acid (21.6 mg, 12%) as an off-white semi-solid. LCMS (ESI, m/z): $[M+H]^+$= 458.2. $^1H$ NMR (400 MHz, DMSO-$d_6$): δ 8.89 (s, 1H), 8.53 (s, 1H), 8.35 (s, 1H), 8.32 (d, J=3.6 Hz, 1H), 8.01-7.95 (m, 1H), 7.52 (s, 1H), 6.41 (s, 1H), 3.87 (s, 3H), 3.73 (s, 3H), 3.56 (s, 3H), 3.31-3.26 (m, 2H), 2.99-2.91 (m, 4H), 2.67-2.49 (m, 4H).

Example S83: Synthesis of 3-[2-(2,4-dimethoxypyridin-3-yl)-1-methylpyrrolo[2,3-c]pyridin-5-yl]-1-[2-(4-ethylpiperazin-1-yl)ethyl]urea formic acid (Compound 83)

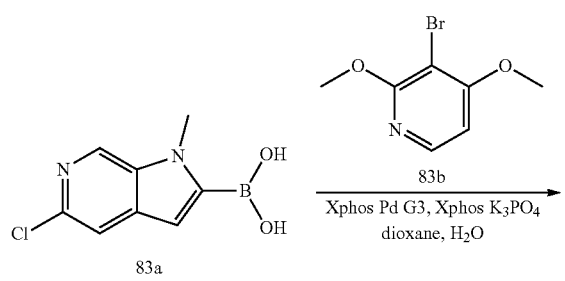

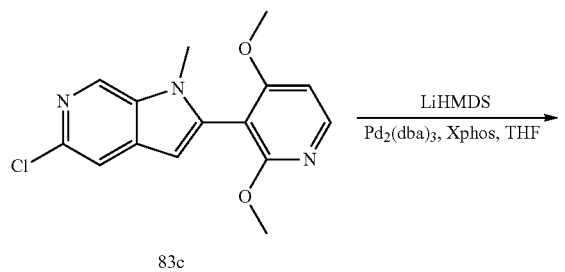

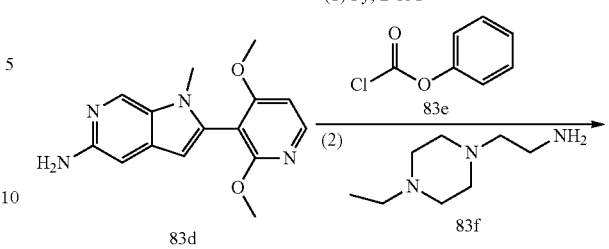

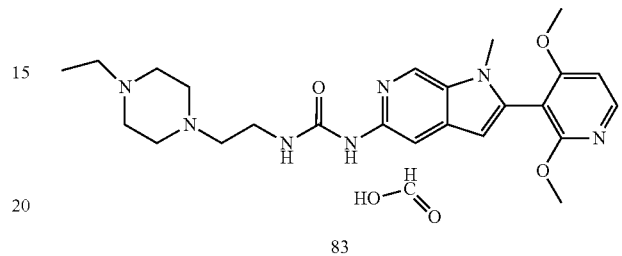

83

Step 1: Synthesis of 3-[5-chloro-1-methylpyrrolo[2,3-c]pyridin-2-yl]-2,4-dimethoxypyridine (Compound 83c)

To a solution of 5-chloro-1-methylpyrrolo[2,3-c]pyridin-2-ylboronic acid (Compound 83a) (500.0 mg, 2.38 mmol) in 1,4-dioxane/$H_2O$ (20.0 mL/4.0 mL) was added 3-bromo-2,4-dimethoxypyridine (Compound 83b) (518.1 mg, 2.38 mmol), XPhos (226.6 mg, 0.48 mmol), $K_3PO_4$ (1.0 g, 4.75 mmol) and XPhos Pd G3 (201.1 mg, 0.24 mmol) at room temperature under $N_2$. The resulting mixture was stirred at 80° C. for 4 h under $N_2$. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/2, v/v) to afford 3-[5-chloro-1-methylpyrrolo[2,3-c]pyridin-2-yl]-2,4-dimethoxypyridine (Compound 83c) (325.0 mg, 45%) as a yellow oil. LCMS (ESI, m/z): $[M+H]^+$=304.1.

Step 2: Synthesis of 3-[5-chloro-1-methylpyrrolo[2,3-c]pyridin-2-yl]-2,4-dimethoxypyridine (Compound 83d)

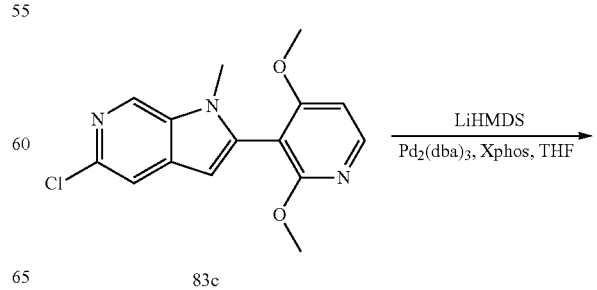

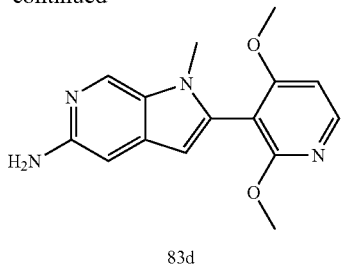

83d

To a solution of 3-[5-chloro-1-methylpyrrolo[2,3-c]pyridin-2-yl]-2,4-dimethoxypyridine (Compound 83c) (300.0 mg, 0.99 mmol) in THF (20.0 mL) was added XPhos (94.2 mg, 0.20 mmol), Pd$_2$(dba)$_3$ (90.4 mg, 0.10 mmol) and LiHMDS (1.5 mL, 1.0 mol/L) at room temperature under N$_2$. The resulting mixture was stirred at 65° C. for 4 h under N$_2$. After the reaction was completed. the resulting mixture was concentrated under reduced pressure. The residue was purified by flash column chromatography with CH$_2$Cl$_2$/CH$_3$OH (13/1, v/v) to afford 2-(2,4-dimethoxypyridin-3-yl)-1-methylpyrrolo[2,3-c]pyridin-5-amine (Compound 83d) (226.0 mg, 80%) as a light brown solid. LCMS (ESI, m/z): [M+H]$^+$=285.1.

Step 3: Synthesis of 3-[2-(2,4-dimethoxypyridin-3-yl)-1-methylpyrrolo[2,3-c]pyridin-5-yl]-1-[2-(4-ethylpiperazin-1-yl)ethyl]urea formic acid (Compound 83)

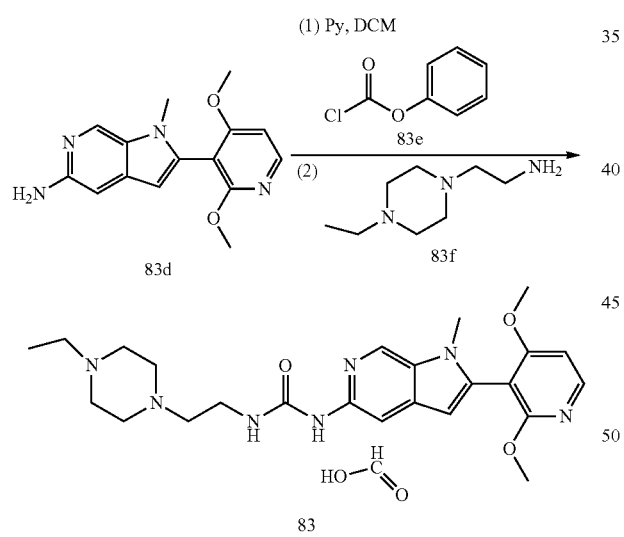

To a solution of 2-(2,4-dimethoxypyridin-3-yl)-1-methylpyrrolo[2,3-c]pyridin-5-amine (Compound 83d) (100.0 mg, 0.35 mmol) in DCM (6.0 mL) was added pyridine (111.3 mg, 1.41 mmol) and phenyl chloroformate (Compound 83e) (110.1 mg, 0.70 mmol) at room temperature. The resulting mixture was stirred at room temperature for 3 h. The resulting mixture was concentrated under reduced pressure. To the above residue were added 2-(4-ethylpiperazin-1-yl)ethanamine (Compound 83) (276.6 mg, 1.76 mmol) and pyridine (6.0 mL) at room temperature. The resulting mixture was stirred at 60° C. for 16 h. After the reaction was completed, the resulting mixture was concentrated under reduced pressure. The residue was purified by flash column chromatography with CH$_2$Cl$_2$/CH$_3$OH (4/1, v/v) and then purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 3% B to 20% B in 8 min; 254/220 nm) to afford 3-[2-(2,4-dimethoxypyridin-3-yl)-1-methylpyrrolo[2,3-c]pyridin-5-yl]-1-[2-(4-ethylpiperazin-1-yl)ethyl]urea (Compound 83); formic acid (10.0 mg, 5%) as a light yellow solid. LCMS (ESI, m/z): [M+H]$^+$=468.4. $^1$H NMR (400 MHz, DMSO-d$_6$): δ 8.85 (s, 1H), 8.46 (s, 1H), 8.26-8.24 (m, 1H), 8.19 (s, 1H), 7.95-7.93 (m, 1H), 7.48 (s, 1H), 6.97-6.96 (m, 1H), 6.32 (d, J=2.4 Hz, 1H), 3.81 (s, 3H), 3.80 (s, 3H), 3.48 (s, 4H), 3.29-3.25 (m, 4H), 2.50-2.31 (m, 9H), 1.01-0.98 (m, 3H).

Example S84: Synthesis of 1-[2-(4-ethylpiperazin-1-yl)ethyl]-3-[2-(5-fluoro-2,4-dimethoxypyridin-3-yl)-1-methylpyrrolo[2,3-c]pyridin-5-yl]urea (Compound 84)

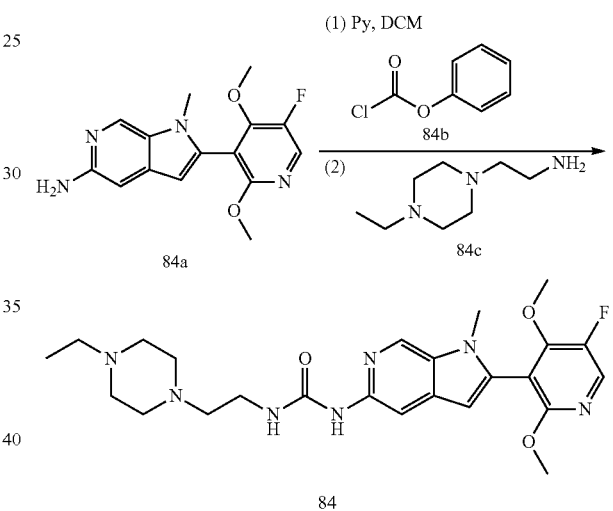

To a solution of 2-(5-fluoro-2,4-dimethoxypyridin-3-yl)-1-methylpyrrolo[2,3-c]pyridin-5-amine (Compound 84a) (72.0 mg, 0.24 mmol) in DCM (6.0 mL) was added pyridine (75.4 mg, 0.95 mmol) and phenyl chloroformate (Compound 84b) (89.5 mg, 0.57 mmol) at room temperature. The resulting mixture was stirred at room temperature for 16 h. The resulting mixture was concentrated under reduced pressure. To the above residue were added 2-(4-ethylpiperazin-1-yl)ethanamine (Compound 84c) (187.3 mg, 1.19 mmol) and pyridine (6.0 mL) at room temperature. The resulting mixture was stirred at 60° C. for another 2 h. After the reaction was completed, the resulting mixture was concentrated under reduced pressure. The residue was purified by flash column chromatography with CH$_2$Cl$_2$/CH$_3$OH (4/1, v/v) and then purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 3% B to 18% B in 8 min; 254/220 nm;) to afford 1-[2-(4-ethylpiperazin-1-yl)ethyl]-3-[2-(5-fluoro-2,4-dimethoxypyridin-3-yl)-1-methylpyrrolo[2,3-c]pyridin-5-yl]urea (Compound 84) (10.0 mg, 8%) as a white solid. LCMS (ESI, m/z): [M+H]$^+$= 486.2. $^1$H NMR (400 MHz, DMSO-d$_6$): δ 8.88 (s, 1H), 8.50 (d, J=4.4 Hz, 1H), 8.33-8.31 (m, 1H), 7.86 (s, 1H), 7.53 (s, 1H), 6.41 (d, J=4.8 Hz, 1H), 3.88 (s, 3H), 3.80 (s, 3H), 3.55-3.43 (m, 4H), 3.28-3.18 (m, 4H), 2.50-2.32 (m, 9H), 1.02-0.99 (m, 3H).

Example S85: Synthesis of (1S,2S)-N-[2-(4-cyclopropoxy-6-methoxypyrimidin-5-yl)-1-methylpyrrolo[2,3-c]pyridin-5-yl]-2-fluorocyclopropane-1-carboxamide (Compound 85)

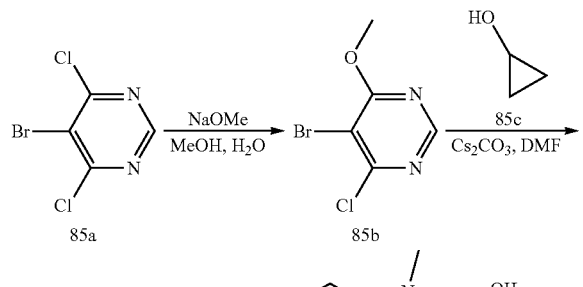

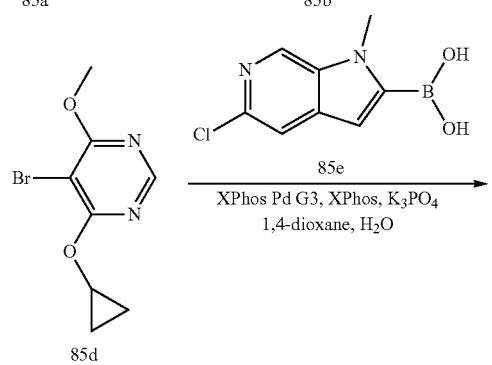

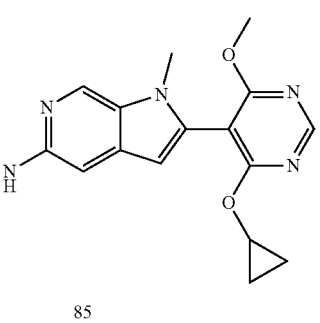

Step 1: Synthesis of 5-bromo-4-chloro-6-methoxypyrimidine (Compound 85b)

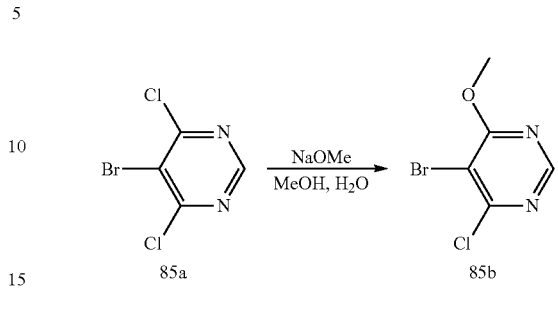

To a solution of 5-bromo-4,6-dichloropyrimidine (Compound 85a) (10.0 g, 43.89 mmol) in MeOH/H$_2$O (100.0 mL/100.0 mL) was added NaOMe (2.1 g, 39.50 mmol) at 0° C. under N$_2$. The resulting mixture was stirred at 0° C. for 1 h and then stirred at room temperature for 3 h. After the reaction was completed, the reaction mixture was diluted with H$_2$O and extracted with ethyl acetate. The combined organic layer was washed with brine, dried over anhydrous sodium sulfate and filtered. The filtrate was evaporated in vacuo to afford 5-bromo-4-chloro-6-methoxypyrimidine (Compound 85b) (9.0 g, crude) as a white solid. LCMS (ESI, m/z): [M+H]$^+$=222.9.

Step 2: Synthesis of 5-bromo-4-cyclopropoxy-6-methoxypyrimidine (Compound 85d)

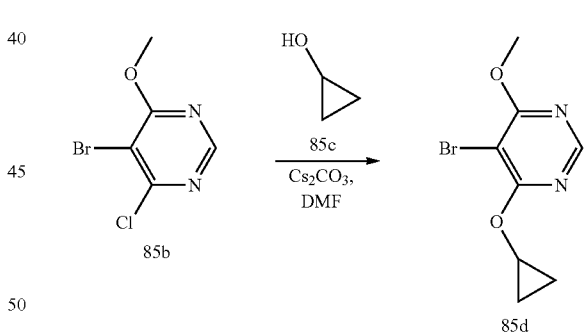

To a solution of 5-bromo-4-chloro-6-methoxypyrimidine (Compound 85b) (9.4 g, crude) in DMF (120.0 mL) was added cyclopropanol (Compound 85c) (3.2 g, 54.69 mmol) and Cs$_2$CO$_3$ (20.6 g, 63.10 mmol) at room temperature. The resulting mixture was stirred at 80° C. for 16 h. After the reaction was completed, the reaction mixture was diluted with water and extracted with ethyl acetate. The combined organic layer was washed with brine, dried over anhydrous sodium sulfate and filtered. The filtrate was evaporated in vacuo. The residue was purified by flash column chromatography with petroleum ether/ethyl acetate (10/1, v/v) to afford 5-bromo-4-cyclopropoxy-6-methoxypyrimidine (Compound 85d) (4.0 g, 39%) as a white solid. LCMS (ESI, m/z): [M+H]$^+$=245.0.

Step 3: Synthesis of 5-[5-chloro-1-methylpyrrolo[2,3-c]pyridin-2-yl]-4-cyclopropoxy-6-methoxypyrimidine (Compound 85f)

Step 4: Synthesis of (1S,2S)-N-[2-(4-cyclopropoxy-6-methoxypyrimidin-5-yl)-1-methylpyrrolo[2,3-c]pyridin-5-yl]-2-fluorocyclopropane-1-carboxamide (Compound 85)

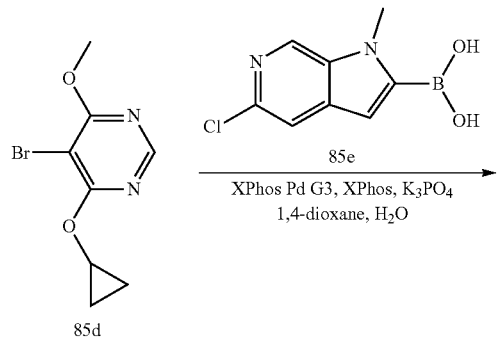

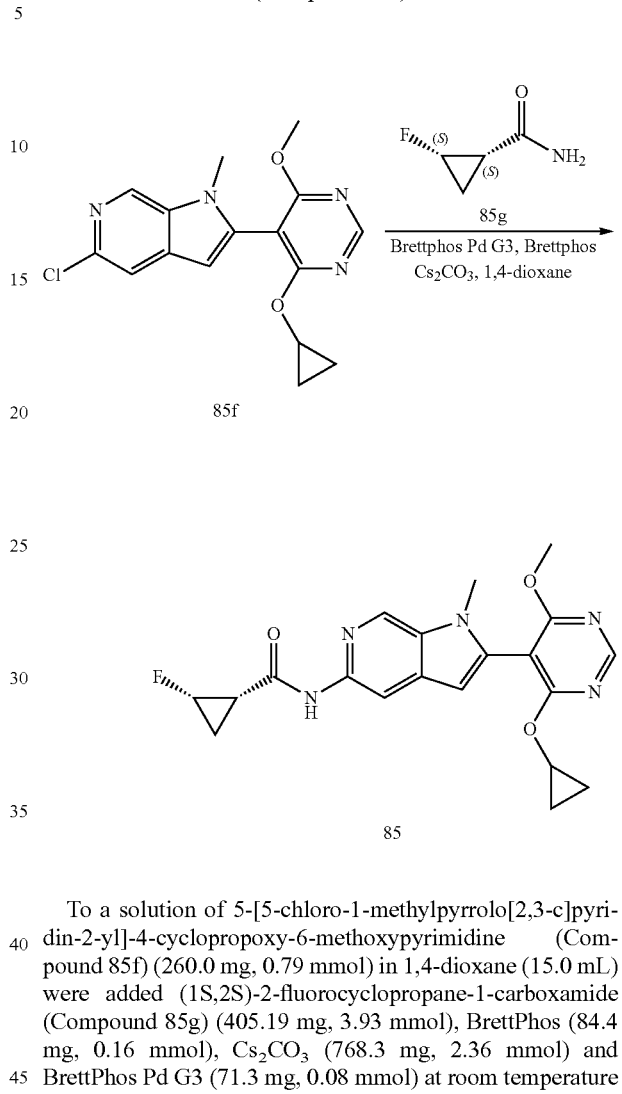

To a solution of 5-bromo-4-cyclopropoxy-6-methoxypyrimidine (Compound 85d) (500.0 mg, 2.04 mmol) in dioxane/H$_2$O (20.0 mL/4.0 mL) were added 5-chloro-1-methylpyrrolo[2,3-c]pyridin-2-ylboronic acid (Compound 85e) (429.3 mg, 2.04 mmol), X-Phos (194.5 mg, 0.41 mmol), K$_3$PO$_4$ (1299.2 mg, 6.12 mmol) XPhos Pd G3 (172.7 mg, 0.20 mmol) at room temperature under N$_2$. The resulting mixture was stirred at 60° C. for 2 h under N$_2$. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-[5-chloro-1-methylpyrrolo[2,3-c]pyridin-2-yl]-4-cyclopropoxy-6-methoxypyrimidine (Compound 85f) (300.0 mg, 44%) as a yellow solid. LCMS (ESI, m/z): [M+H]$^+$=331.1.

To a solution of 5-[5-chloro-1-methylpyrrolo[2,3-c]pyridin-2-yl]-4-cyclopropoxy-6-methoxypyrimidine (Compound 85f) (260.0 mg, 0.79 mmol) in 1,4-dioxane (15.0 mL) were added (1S,2S)-2-fluorocyclopropane-1-carboxamide (Compound 85g) (405.19 mg, 3.93 mmol), BrettPhos (84.4 mg, 0.16 mmol), Cs$_2$CO$_3$ (768.3 mg, 2.36 mmol) and BrettPhos Pd G3 (71.3 mg, 0.08 mmol) at room temperature under N$_2$. The resulting mixture was stirred at 100° C. for 16 h under N$_2$. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) and then purified by Prep-HPLC with the following conditions Column: (CSH OBD Column 30×150 mm, 5 um; Mobile Phase A:Water (10 mmol/L NH$_4$HCO$_3$), Mobile Phase B: ACN; Flow rate: 60 mL/min; Gradient: 34% B to 44% B in 8 min; 254 nm) to afford (1S,2S)-N-[2-(4-cyclopropoxy-6-methoxypyrimidin-5-yl)-1-methylpyrrolo[2,3-c]pyridin-5-yl]-2-fluorocyclopropane-1-carboxamide (Compound 85) (14.9 mg, 5%) as a white solid. LCMS (ESI, m/z): [M+H]$^+$=398.1. $^1$H NMR (400 MHz, DMSO-d$_6$): δ 10.54 (s, 1H), 8.68 (s, 1H), 8.61 (s, 1H), 8.18 (s, 1H), 6.46 (s, 1H), 5.00-4.80 (m, 1H), 4.40-4.36 (m, 1H), 3.92 (s, 3H), 3.55 (s, 3H), 2.21-2.18 (m, 1H), 1.69-1.63 (m, 1H), 1.19-1.03 (m, 1H), 0.85-0.72 (m, 2H), 0.61-0.52 (m, 2H).

Example S86: Synthesis of (1S,2S)-2-fluoro-N-(2-(4-methoxy-2-methylpyridin-3-yl)-1-methyl-1H-pyrrolo[2,3-c]pyridin-5-yl)cyclopropane-1-carboxamide (Compound 86)

Step 1: Synthesis of 4-methoxy-2-methyl-3-nitropyridine

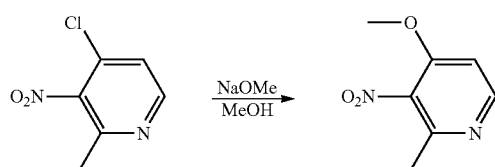

To a solution of 4-chloro-2-methyl-3-nitropyridine (500.0 mg, 2.89 mmol) in MeOH (10.0 mL) was added NaOMe (469.6 mg, 8.69 mmol) at room temperature. The resulting mixture was stirred at 70° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure to afford 4-methoxy-2-methyl-3-nitropyridine (450.0 mg, crude) as a yellow solid. LCMS (ESI, m/z): [M+H]⁺=169.1.

Step 2: Synthesis of 4-methoxy-2-methylpyridin-3-amine

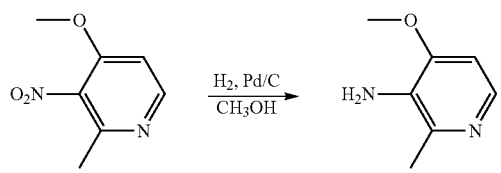

To a solution of 4-methoxy-2-methyl-3-nitropyridine (400.0 mg, crude) in CH₃OH (20.0 mL) was added Pd/C (101.3 mg, dry) at room temperature under N₂. The resulting mixture was stirred at room temperature for 16 h under H₂. After the reaction was completed, the resulting mixture was filtered. The filtrate was concentrated under reduced pressure to afford 4-methoxy-2-methylpyridin-3-amine (300.0 mg, crude) as a yellow solid. LCMS (ESI, m/z): [M+H]⁺=139.1

Step 3: Synthesis of 3-iodo-4-methoxy-2-methylpyridine

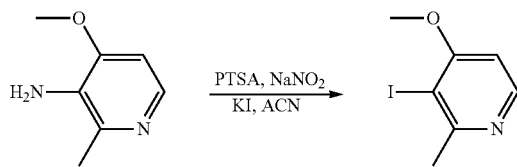

To a solution of 4-methoxy-2-methylpyridin-3-amine (300.0 mg, crude) in ACN (10.0 mL) was added KI (1081.3 mg, 6.51 mmol), NaNO₂ (449.4 mg, 6.51 mmol) and PTSA (1495.6 mg, 8.69 mmol) at room temperature. The resulting mixture was stirred at room temperature for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/MeOH (97/3, v/v) to afford 3-iodo-4-methoxy-2-methylpyridine (270.0 mg, 49%) as a brown solid. LCMS (ESI, m/z): [M+H]⁺=250.0.

Step 4: Synthesis of 5-chloro-2-(4-methoxy-2-methylpyridin-3-yl)-1-methyl-1H-pyrrolo[2,3-c]pyridine

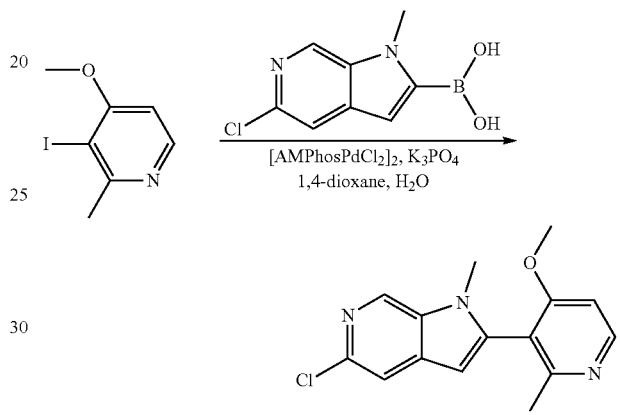

To a solution of 3-iodo-4-methoxy-2-methylpyridine (230.0 mg, 0.92 mmol) in 1,4-dioxane/H₂O (10.0 mL/2.0 mL) was added 5-chloro-1-methylpyrrolo[2,3-c]pyridin-2-ylboronic acid (233.2 mg, 1.11 mmol), K₃PO₄ (392.1 mg, 1.85 mmol) and [AMPhosPdCl₂]₂ (65.4 mg, 0.09 mmol) at room temperature under N₂. The resulting mixture was stirred at 100° C. for 3 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl/MeOH (92/8, v/v) to afford 5-chloro-2-(4-methoxy-2-methylpyridin-3-yl)-1-methyl-1H-pyrrolo[2,3-c]pyridine (130.0 mg, 49%) as a yellow solid. LCMS (ESI, m/z): [M+H]⁺=288.1.

Step 5: Synthesis of (1S,2S)-2-fluoro-N-(2-(4-methoxy-2-methylpyridin-3-yl)-1-methyl-1H-pyrrolo[2,3-c]pyridin-5-yl)cyclopropane-1-carboxamide (Compound 86)

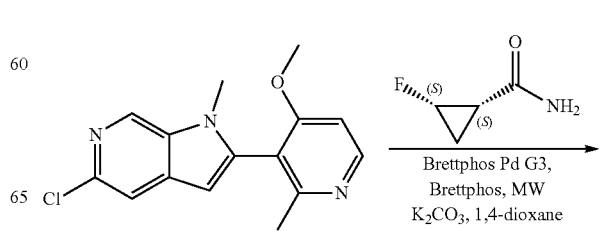

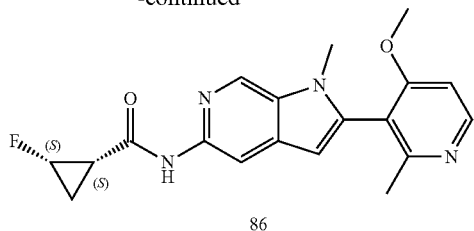

86

To a solution of 5-chloro-2-(4-methoxy-2-methylpyridin-3-yl)-1-methyl-1H-pyrrolo[2,3-c]pyridine (130.0 mg, 0.45 mmol) in 1,4-dioxane (10.0 mL) was added (1S,2S)-2-fluorocyclopropane-1-carboxamide (232.9 mg, 2.26 mmol), K$_2$CO$_3$ (187.3 mg, 1.36 mmol), BrettPhos (48.5 mg, 0.09 mmol) and BrettPhos Pd G3 (40.9 mg, 0.05 mmol) at room temperature under N$_2$. The resulting mixture was stirred at 100° C. for 2 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/MeOH (91/9, v/v) and then purified by Prep-HPLC with the following conditions (Column: XBridge Prep OBD C18 Column, 30×150 mm, 5 um; Mobile Phase A: Water (10 mmol/L NH$_4$HCO$_3$), Mobile Phase B: ACN; Flow rate: 60 mL/min; Gradient: 11% B to 41% B in 9 min, 254 nm) to afford (1S,2S)-2-fluoro-N-(2-(4-methoxy-2-methylpyridin-3-yl)-1-methyl-1H-pyrrolo[2,3-c]pyridin-5-yl)cyclopropane-1-carboxamide (Compound 86) (3.2 mg, 2%) as a white solid. LCMS (ESI, m/z): [M+H]$^+$=355.2. $^1$H NMR (300 MHz, DMSO-d$_6$): δ 10.56 (s, 1H), 8.63 (s, 1H), 8.49 (d, J=5.4 Hz, 1H), 8.22 (s, 1H), 7.10 (d, J=5.7 Hz, 1H), 6.46 (s, 1H), 5.03-4.81 (m, 1H), 3.80 (s, 3H), 3.52 (s, 3H), 2.25-2.14 (m, 4H), 1.70-1.62 (m, 1H), 1.24-1.14 (m, 1H).

Example S87: Synthesis of 1-(2-(2,6-dimethoxyphenyl)-1-methyl-1H-pyrrolo[2,3-c]pyridin-5-yl)-3-(2-(4-ethylpiperazin-1-yl)ethyl)urea (Compound 87)

Step 1: Synthesis of 5-chloro-2-(2,6-dimethoxyphenyl)-1-methyl-1H-pyrrolo[2,3-c]pyridine

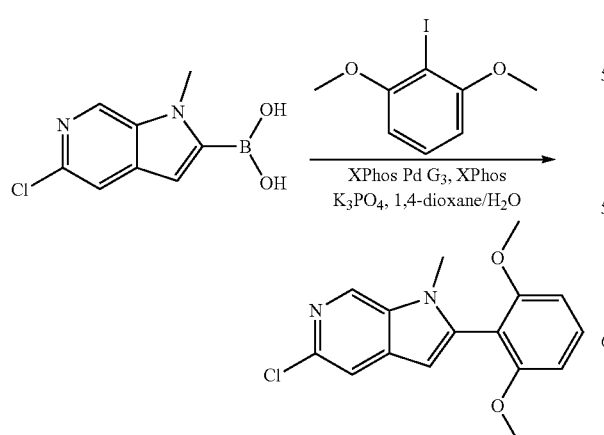

To a solution of (5-chloro-1-methyl-1H-pyrrolo[2,3-c]pyridin-2-yl)boronic acid (239.1 mg, 1.14 mmol) in 1,4-dioxane/H$_2$O (10.0 mL/2.0 mL) was added 2-iodo-1,3-dimethoxybenzene (250.0 mg, 0.95 mmol), K$_3$PO$_4$ (261.7 mg, 0.78 mmol), XPhos (90.3 mg, 0.19 mmol) and XPhos Pd G3 (80.1 mg, 0.10 mmol) at room temperature under N$_2$. The resulting mixture was stirred at 80° C. for 2 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with ether/ethyl acetate (92/8, v/v) to afford 5-chloro-2-(2,6-dimethoxyphenyl)-1-methyl-1H-pyrrolo[2,3-c]pyridine (180.0 mg, 62%) as a yellow solid. LCMS (ESI, m/z): [M+H]$^+$=303.1.

Step 2: Synthesis of 2-(2,6-dimethoxyphenyl)-1-methyl-1H-pyrrolo[2,3-c]pyridin-5-amine

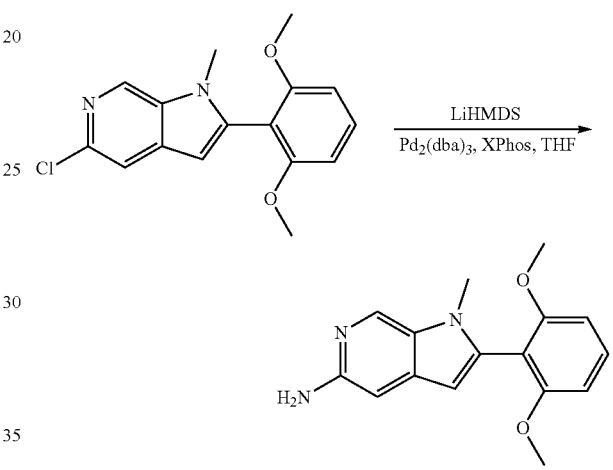

To a solution of 5-chloro-2-(2,6-dimethoxyphenyl)-1-methyl-1H-pyrrolo[2,3-c]pyridine (160.0 mg, 0.53 mmol) in THF (5.0 mL) was added XPhos (50.4 mg, 0.11 mmol), Pd$_2$(dba)$_3$ (48.4 mg, 0.05 mmol) and LiHMDS (1.1 mL, 1.0 mol/L) at room temperature under N$_2$. The resulting mixture was stirred at 60° C. for 1 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum CH$_2$Cl$_2$/MeOH (92/8, v/v) to afford 2-(2,6-dimethoxyphenyl)-1-methyl-1H-pyrrolo[2,3-c]pyridin-5-amine (120.0 mg, 80%) as a yellow solid. LCMS (ESI, m/z): [M+H]$^+$=284.1.

Step 3: Synthesis of 1-(2-(2,6-dimethoxyphenyl)-1-methyl-1H-pyrrolo[2,3-c]pyridin-5-yl)-3-(2-(4-ethylpiperazin-1-yl)ethyl)urea

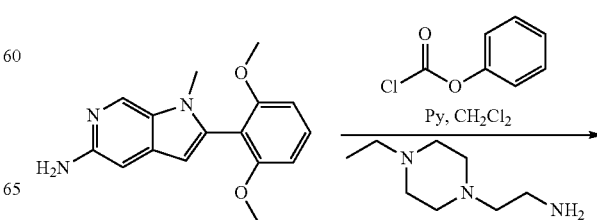

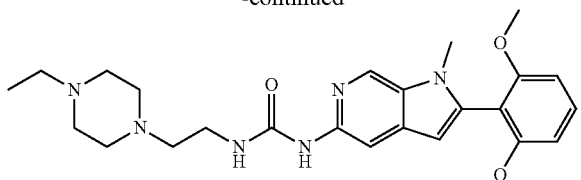

87

To a solution of 2-(2,6-dimethoxyphenyl)-1-methyl-1H-pyrrolo[2,3-c]pyridin-5-amine (80.0 mg, 0.28 mmol) in CH$_2$Cl$_2$ (4.0 mL) was added phenyl chloroformate (53.1 mg, 0.34 mmol) and pyridine (90.5 mg, 1.13 mmol) at room temperature. The resulting mixture was stirred at room temperature for 16 h. The resulting mixture was concentrated under reduced pressure. To the residue was added pyridine (4.0 mL) and 2-(4-ethylpiperazin-1-yl)ethanamine (133.2 mg, 0.85 mmol) at room temperature. The resulting mixture was stirred at 60° C. for 3 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (79/21, v/v) and then purified by prep-HPLC with the following conditions (Column: Xselect CSH OBD Column 30×150 mm, 5 um; Mobile Phase A: Water (10 mmol/L NH$_4$HCO$_3$), Mobile Phase B: ACN; Flow rate: 60 mL/min; Gradient: 34% B to 44% B in 8 min; 254 nm) to afford 1-(2-(2,6-dimethoxyphenyl)-1-methyl-1H-pyrrolo[2,3-c]pyridin-5-yl)-3-(2-(4-ethylpiperazin-1-yl)ethyl)urea (8.2 mg, 6%) as a white solid. LCMS (ESI, m/z): [M+H]$^+$=467.3. $^1$H NMR (400 MHz, DMSO-d$_6$): δ 8.82 (s, 1H), 8.43 (s, 1H), 8.03 (s, 1H), 7.46-7.44 (m, 2H), 6.81 (d, J=8.4 Hz, 2H), 6.24 (d, J=0.8 Hz, 1H), 3.71 (s, 6H), 3.45 (s, 3H), 3.33-3.25 (m, 2H), 2.51-2.49 (m, 8H), 2.42-2.31 (m, 4H), 1.01-0.99 (m, 3H).

Example S88: Synthesis of (1S,2S)-2-fluoro-N-(2-(5-fluoro-2-(methoxy-d$_3$)pyridin-3-yl)-1-(methyl-d$_3$)-1H-pyrrolo[2,3-c]pyridin-5-yl)cyclopropane-1-carboxamide (Compound 88)

Step 1: Synthesis of 3-bromo-5-fluoro-2-(methoxy-d$_3$)pyridine

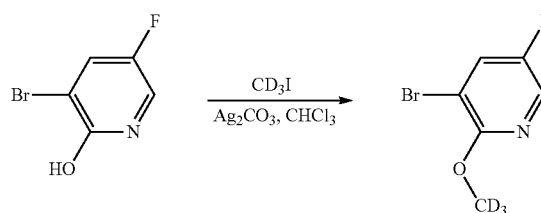

To a solution of 3-bromo-5-fluoropyridin-2-ol (4.0 g, 20.84 mmol) in CHCl$_3$ (40.0 mL) was added Ag$_2$CO$_3$ (23.0 g, 82.67 mmol) and CD$_3$I (24.2 g, 126.44 mmol) at room temperature. The resulting mixture was stirred at room temperature for 4 h. After the reaction was completed, the resulting mixture was filtered. The filtrate was concentrated under reduced pressure. The residue was purified by flash column chromatography with petroleum ether/ethyl acetate (99/1, v/v) to afford 3-bromo-5-fluoro-2-(methoxy-d$_3$)pyridine (700.0 mg, 16%) as a colorless oil. LCMS (ESI, m/z): [M+H]$^+$=209.0.

Step 2: Synthesis of 5-fluoro-2-(methoxy-d$_3$)-3-(4,4,5,5-tetramethyl-1,3,2-dioxaborolan-2-yl)pyridine

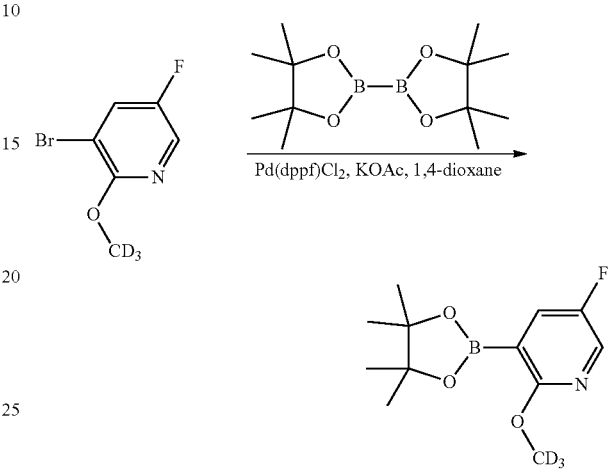

To a solution of 3-bromo-5-fluoro-2-(methoxy-d$_3$)pyridine (500.0 mg, 0.59 mmol) in 1,4-dioxane (20.0 mL) was added 4,4,4',4',5,5,5',5'-octamethyl-2,2'-bi(1,3,2-dioxaborolane) (1.8 g, 7.18 mmol), KOAc (704.3 mg, 7.18 mmol) and Pd(dppf)Cl$_2$ (350.0 mg, 0.48 mmol) at room temperature under N$_2$. The resulting mixture was stirred at 100° C. for 4 h under N$_2$. After the reaction was completed, the resulting mixture was concentrated under reduced pressure to afford 5-fluoro-2-(methoxy-d$_3$)-3-(4,4,5,5-tetramethyl-1,3,2-dioxaborolan-2-yl)pyridine (800.0 mg, crude) as a brown solid. LCMS (ESI, m/z): [M+H]$^+$=257.1.

Step 3: Synthesis of 5-chloro-2-(5-fluoro-2-(methoxy-d$_3$)pyridin-3-yl)-1-(methyl-d$_3$)-1H-pyrrolo[2,3-c]pyridine

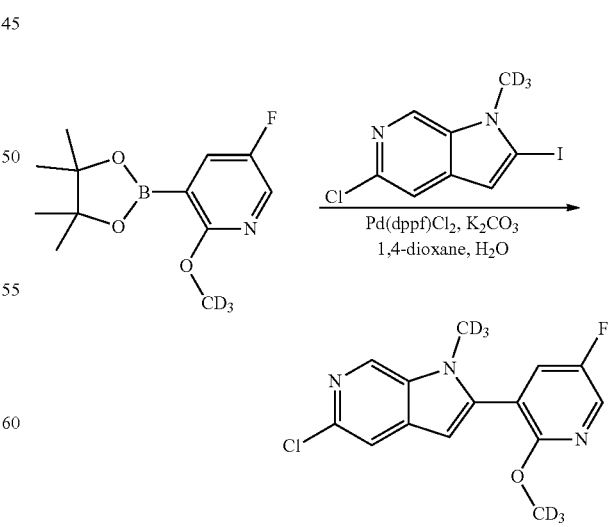

To a solution of 5-fluoro-2-(methoxy-d$_3$)-3-(4,4,5,5-tetramethyl-1,3,2-dioxaborolan-2-yl)pyridine (800.0 mg, crude) in 1,4-dioxane/H₂O (20.0/4.0 mL) was added 5-chloro-2-iodo-1-(methyl-d3)-1H-pyrrolo[2,3-c]pyridine (679.6 mg, 2.30 mmol), K₂CO₃ (953.2 mg, 6.90 mmol) and Pd(dppf)Cl₂ (374.6 mg, 0.46 mmol) at room temperature under N₂. The resulting mixture was stirred at 80° C. for 2 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford 5-chloro-2-(5-fluoro-2-(methoxy-d₃)pyridin-3-yl)-1-(methyl-d₃)-1H-pyrrolo[2,3-c]pyridine (400.0 mg, 58%) as a yellow solid. LCMS (ESI, m/z): [M+H]⁺=298.1.

Step 4: Synthesis of (1S,2S)-2-fluoro-N-(2-(5-fluoro-2-(methoxy-d₃)pyridin-3-yl)-1-(methyl-d₃)-1H-pyrrolo[2,3-c]pyridin-5-yl)cyclopropane-1-carboxamide (Compound 88)

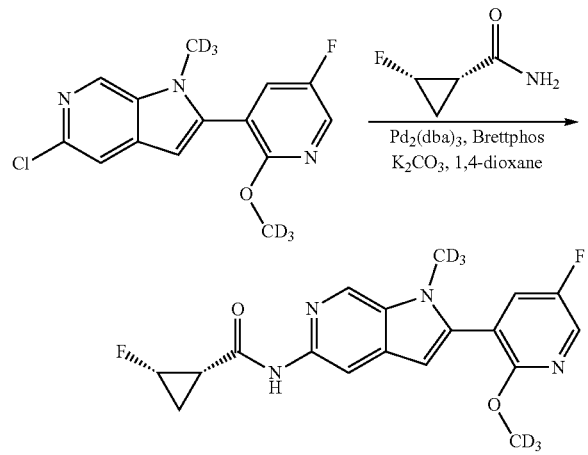

88

To a solution of 5-chloro-2-(5-fluoro-2-(methoxy-d3)pyridin-3-yl)-1-(methyl-d3)-1H-pyrrolo[2,3-c]pyridine (200.0 mg, 0.67 mmol) in 1,4-dioxane (10.0 mL) was added (1S,2S)-2-fluorocyclopropane-1-carboxamide (346.3 mg, 3.36 mmol). K₂CO₃ (278.5 mg, 2.02 mmol), BrettPhos (72.1 mg, 0.13 mmol) and Pd₂(dba)₃ (61.5 mg, 0.07 mmol) at room temperature under N₂. The resulting mixture was stirred at 100° C. for 16 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/CH₃OH (98/2, v/v) and then purified by Prep-HPLC with the following conditions (Column: XBridge Prep OBD C18 Column, 30×150 mm, 5 um; Mobile Phase A: Water (10 mmol/L NH₄HCO₃), Mobile Phase B: ACN; Flow rate: 60 mL/min; Gradient: 26% B to 56% B in 9 min; 254 nm) to afford (1S,2S)-2-fluoro-N-(2-(5-fluoro-2-(methoxy-d₃)pyridin-3-yl)-1-(methyl-d₃)-1H-pyrrolo[2,3-c]pyridin-5-yl)cyclopropane-1-carboxamide (Compound 88) (2.3 mg, 1%) as a white solid. LCMS (ESI, m/z): [M+H]⁺=365.2. ¹H NMR (300 MHz, DMSO-d₆): δ 10.59 (s, 1H), 8.67 (s, 1H), 8.36 (d, J=3.0 Hz, 1H), 8.24 (s, 1H), 7.94-7.91 (m, 1H), 6.61 (d, J=0.6 Hz, 1H), 5.02-4.81 (m, 1H), 2.23-2.19 (m, 1H), 1.73-1.62 (m, 1H), 1.18-1.11 (m, 1H).

Example S89: Synthesis of (1S,2S)-2-fluoro-N-[2-(4-fluoro-2-methoxypyridin-3-yl)-1-methylpyrrolo[2,3-c]pyridin-5-yl]cyclopropane-1-carboxamide (Compound 89)

Step 1: Synthesis of 3-bromo-4-fluoro-2-methoxypyridine

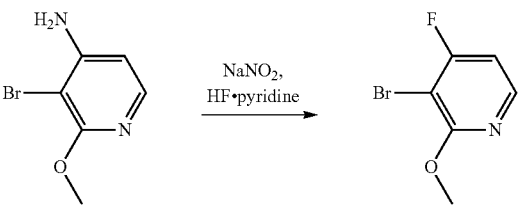

To a solution of 3-bromo-2-methoxypyridin-4-amine (500.0 mg, 2.46 mmol) in HF-pyridine (3.6 mL) was added NaNO₂ (254.9 mg, 3.70 mmol) at −10° C. The resulting mixture was stirred at 60° C. for 1 h. After the reaction was completed, The pH value of the mixture was adjusted to 7 with aq·NaHCO₃. The reaction mixture was extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (80/20, v/v) to afford 3-bromo-4-fluoro-2-methoxypyridine (340.0 mg, 67%) as a yellow solid. LCMS (ESI, m/z): [M+H]⁺=206.0.

Step 2: Synthesis of 3-[5-chloro-1-methylpyrrolo[2,3-c]pyridin-2-yl]-4-fluoro-2-methoxypyridine

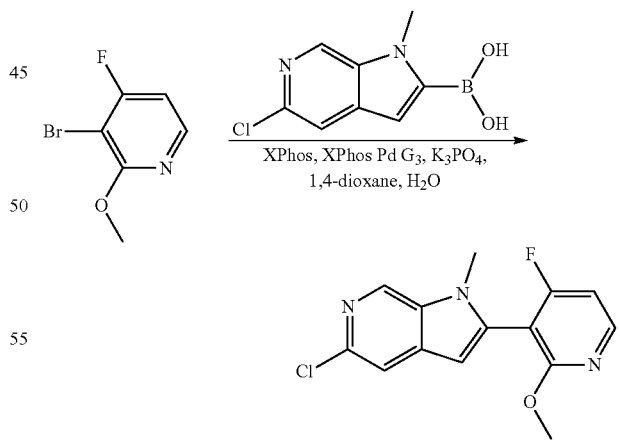

To a solution of 3-bromo-4-fluoro-2-methoxypyridine (300.0 mg, 1.46 mmol) in 1,4-dioxane/H₂O (10.0 mL/2.0 mL) was added 5-chloro-1-methylpyrrolo[2,3-c]pyridin-2-ylboronic acid (306.4 mg, 1.46 mmol), K₃PO₄ (927.3 mg, 4.37 mmol), X-Phos (138.8 mg, 0.29 mmol) and XPhos Pd G3 (123.3 mg, 0.15 mmol) at room temperature. The resulting mixture was stirred at 80° C. for 2 h under N₂. After the Step 3: Synthesis of (1S,2S)-2-fluoro-N-[2-(4-fluoro-2-methoxypyridin-3-yl)-1-methylpyrrolo[2,3-c]pyridin-5-yl]cyclopropane-1-carboxamide (Compound 89)

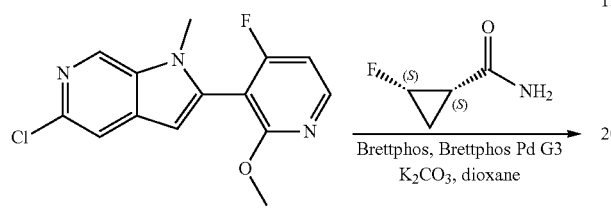

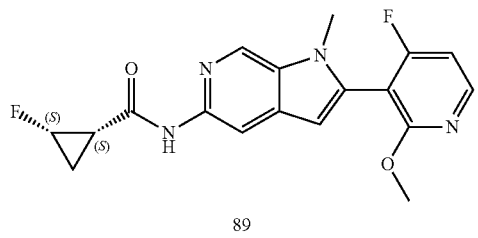

To a solution of 3-[5-chloro-1-methylpyrrolo[2,3-c]pyridin-2-yl]-4-fluoro-2-methoxypyridine (130.0 mg, 0.45 mmol) in 1,4-dioxane (5.0 mL) was added (1S,2S)-2-fluorocyclopropane-1-carboxamide (275.7 mg, 2.68 mmol). $K_2CO_3$ (184.77 mg, 1.338 mmol), BrettPhos (47.8 mg, 0.09 mmol) and BrettPhos Pd G3 (40.4 mg, 0.05 mmol) at room temperature. The resulting mixture was irradiated with microwave radiation at 120° C. for 3 h. After the reaction was completed, the resulting mixture was concentrated under vacuum. The residue was purified by flash column chromatography with petroleum ether/ethyl acetate (5/95, v/v) and then purified by Prep-HPLC with the following conditions (Column: Xselect CSH OBD Column, 30×150 mm, 5 um; Mobile Phase A:Water (10 mmol/L $NH_4HCO_3$), Mobile Phase B: ACN; Flow rate: 60 mL/min; Gradient: 30% B to 40% B in 10 min; 254 nm) to afford (1S,2S)-2-fluoro-N-[2-(4-fluoro-2-methoxypyridin-3-yl)-1-methylpyrrolo[2,3-c]pyridin-5-yl]cyclopropane-1-carboxamide (Compound 89) (9.0 mg, 5%) as a white solid. LCMS (ESI, m/z): $[M+H]^+$=359.2. $^1H$ NMR (300 MHz, DMSO-$d_6$): δ 10.56 (s, 1H), 8.65 (s, 1H), 8.40-8.35 (m, 1H), 8.21 (s, 1H), 7.21-7.16 (m, 1H), 6.58 (s, 1H), 5.01-4.77 (m, 1H), 3.90 (s, 3H), 3.60 (s, 3H), 2.21-2.17 (m, 1H), 1.68-1.59 (m, 1H), 1.15-1.08 (m, 1H).

Example S90: Synthesis of (1S,2S)-N-[2-(4-cyclopropoxy-2-methoxypyridin-3-yl)-1-methylpyrrolo[2,3-c]pyridin-5-yl]-2-fluorocyclopropane-1-carboxamide (Compound 90)

Step 1: Synthesis of 4-cyclopropoxy-2-methoxy-3-nitropyridine

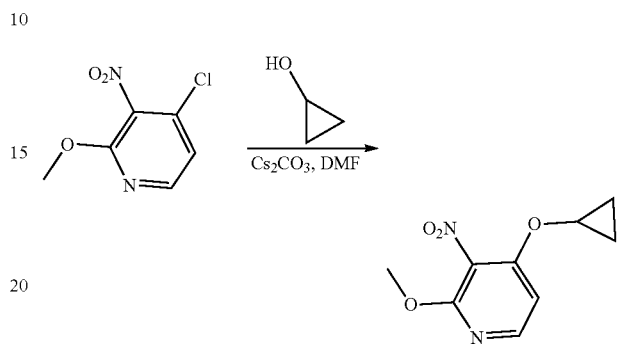

To a solution of 4-chloro-2-methoxy-3-nitropyridine (3.0 g, 15.91 mmol) in DMF (125.0 mL) was added $Cs_2CO_3$ (7.8 g, 23.86 mmol) and cyclopropanol (0.9 g, 15.91 mmol) at room temperature. The resulting mixture was stirred at 80° C. for 16 h. After the reaction was completed, the reaction mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (10/1, v/v) to afford 4-cyclopropoxy-2-methoxy-3-nitropyridine (1.7 g, 51%) as a white solid. LCMS (ESI, m/z): $[M+H]^+$=211.1.

Step 2: Synthesis of 4-cyclopropoxy-2-methoxypyridin-3-amine

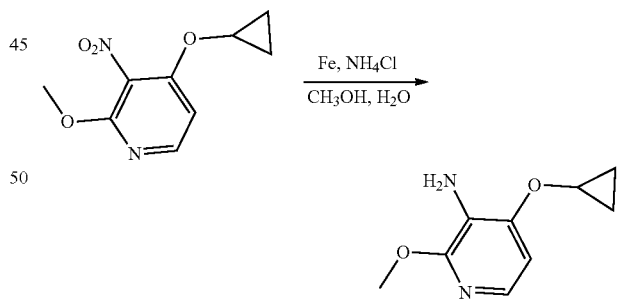

To a solution of 4-cyclopropoxy-2-methoxy-3-nitropyridine (1.7 g, 8.09 mmol) in $CH_3OH$ (60.0 mL)/$H_2O$ (12.0 mL) was added $NH_4Cl$ (1.7 g, 32.35 mmol) and Fe (1.4 g, 24.26 mmol) at room temperature. The resulting mixture was stirred at 80° C. for 3 h. After the reaction was completed, the resulting mixture was filtered. The filtrate was concentrated under reduced pressure. The residue was purified by flash column chromatography with petroleum ether/ethyl acetate (2/1, v/v) to afford 4-cyclopropoxy-2-methoxypyridin-3-amine (1.3 g, 89%) as a yellow oil. LCMS (ESI, m/z): $[M+H]^+$=181.1.

Step 3: Synthesis of 4-cyclopropoxy-3-iodo-2-methoxypyridine

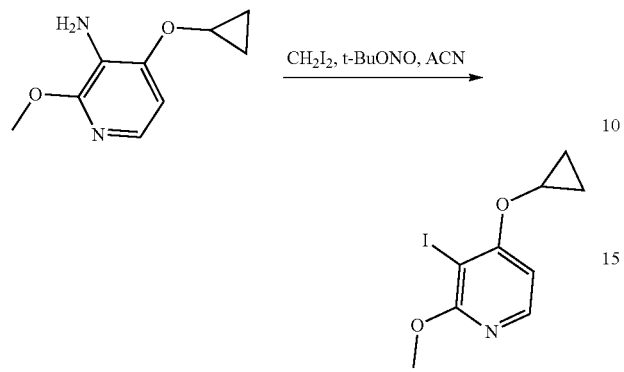

To a solution of 4-cyclopropoxy-2-methoxypyridin-3-amine (1.3 g, 7.21 mmol) in ACN (40.0 mL) was added CH$_2$I$_2$ (1.9 g, 7.21 mmol) and t-BuNO$_2$ (3.4 g, 32.46 mmol) at room temperature. The resulting mixture was stirred at 80° C. for 3 h. After the reaction was completed, the reaction was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 4-cyclopropoxy-3-iodo-2-methoxypyridine (1.2 g, 57%) as a white solid. LCMS (ESI, m/z): [M+H]$^+$=292.0.

Step 4: Synthesis of 3-[5-chloro-1-methylpyrrolo[2,3-c]pyridin-2-yl]-4-cyclopropoxy-2-methoxypyridine

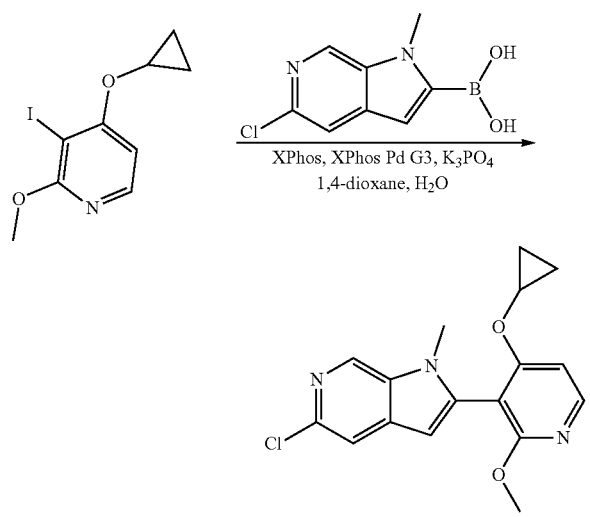

To a solution of 4-cyclopropoxy-3-iodo-2-methoxypyridine (600.0 mg, 2.06 mmol) in dioxane/H$_2$O (30.0 mL/6.0 mL) was added 5-chloro-1-methylpyrrolo[2,3-c]pyridin-2-ylboronic acid (433.7 mg, 2.06 mmol), K$_3$PO$_4$ (1312.6 mg, 6.18 mmol), XPhos Pd G3 (174.5 mg, 0.21 mmol) and X-Phos (196.5 mg, 0.41 mmol) at room temperature under N$_2$. The resulting mixture was stirred at 60° C. for 16 h under N$_2$. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 3-{5-chloro-1-methylpyrrolo[2,3-c]pyridin-2-yl}-4-cyclopropoxy-2-methoxypyridine (300.0 mg, 44%) as a colorless oil. LCMS (ESI, m/z): [M+H]$^+$=330.1.

Step 5: Synthesis of (1S,2S)-N-[2-(4-cyclopropoxy-2-methoxypyridin-3-yl)-1-methylpyrrolo[2,3-c]pyridin-5-yl]-2-fluorocyclopropane-1-carboxamide (Compound 90)

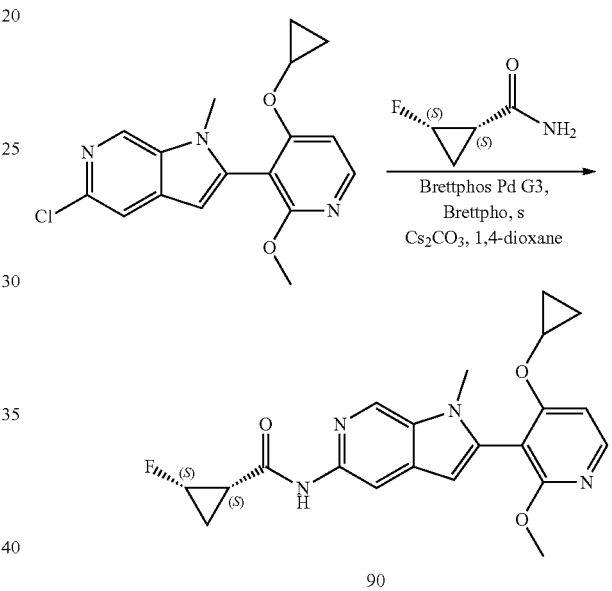

To a solution of 3-{5-chloro-1-methylpyrrolo[2,3-c]pyridin-2-yl}-4-cyclopropoxy-2-methoxypyridine (240.0 mg, 0.73 mmol) in 1,4-dioxane (15.0 mL) was added (1S,2S)-2-fluorocyclopropane-1-carboxamide (375.1 mg, 3.64 mmol), BrettPhos ((78.1 mg, 0.15 mmol), Cs$_2$CO$_3$ (711.4 mg, 2.18 mmol) and BrettPhos Pd G3 (66.0 mg, 0.07 mmol) at room temperature under N$_2$. The resulting mixture was stirred at 100° C. for 16 h under N$_2$. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/MeOH (10/1, v/v) and then purified by Prep-HPLC with the following conditions (Column: XBridge Prep OBD C18 Column, 30×150 mm, 5 um; Mobile Phase A:Water (10 mmol/L NH$_4$HCO$_3$), Mobile Phase B: ACN; Flow rate: 60 mL/min; Gradient: 27% B to 57% B in 7 min; 254 nm) to afford (1S,2S)-N-[2-(4-cyclopropoxy-2-methoxypyridin-3-yl)-1-methylpyrrolo[2,3-c]pyridin-5-yl]-2-fluorocyclopropane-1-carboxamide (Compound 90) (6.1 mg, 2%) as a white solid. LCMS (ESI, m/z): [M+H]$^+$=397.2. $^1$H NMR (400 MHz, DMSO-d$_6$): δ 11.00 (s, 1H), 8.69 (s, 1H), 8.29 (d, J=6.0 Hz, 1H), 8.03 (s, 1H), 7.22 (d, J=5.6 Hz, 1H), 6.54 (s, 1H), 5.07-4.86 (m, 1H), 4.03-3.99 (m, 1H), 3.82 (s, 3H), 3.55 (s, 3H), 2.24-2.17 (m, 1H), 1.73-1.63 (m, 1H), 1.24-1.17 (m, 1H), 0.80-0.76 (m, 2H), 0.65-0.63 (m, 2H).

Example S91: Synthesis of (1S,2S)-N-(2-(4,6-dimethoxypyrimidin-5-yl)-3-methyl-1H-pyrrolo[3,2-c]pyridin-6-yl)-2-fluorocyclopropane-1-carboxamide (Compound 91)

Step 1: Synthesis of 4,6-dimethoxy-5-((trimethylsilyl)ethynyl)pyrimidine

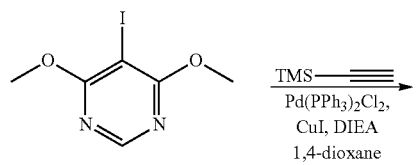

To a solution of 5-iodo-4,6-dimethoxypyrimidine (3.0 g, 11.28 mmol) in DMF (60.0 mL) was added ethynyltrimethylsilane (3.3 g, 33.84 mmol), TEA (3.3 g, 33.84 mmol), CuI (214.8 mg, 1.13 mmol) and Pd(PPh$_3$)$_2$Cl$_2$ (825.3 mg, 1.17 mmol) at room temperature under N$_2$. The resulting mixture was stirred at 80° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (89/11, v/v) to afford 4,6-dimethoxy-5-((trimethylsilyl)ethynyl)pyrimidine (2.6 g, 97%) as a light yellow oil. LCMS (ESI, m/z): [M+H]$^+$=237.1.

Step 2: Synthesis of 5-ethynyl-4,6-dimethoxypyrimidine

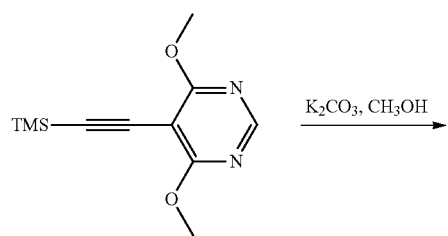

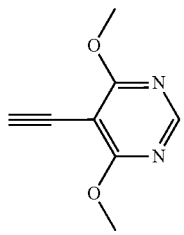

To a solution of 4,6-dimethoxy-5-((trimethylsilyl)ethynyl)pyrimidine (2.6 g, 11.00 mmol) in CH$_3$OH (50.0 mL) was added K$_2$CO$_3$ (4.6 g, 33.00 mmol) at room temperature. The resulting mixture was stirred at room temperature for 16 h. After the reaction was completed, the resulting mixture was filtered. The filtrate was concentrated under reduced pressure. The residue was purified by flash column chromatography with petroleum ether/ethyl acetate (98/2, v/v) to afford 5-ethynyl-4,6-dimethoxypyrimidine (1.6 g, 89%) as a brown solid. LCMS (ESI, m/z): [M+H]$^+$=165.1.

Step 3: Synthesis of 4,6-dimethoxy-5-(prop-1-yn-1-yl)pyrimidine

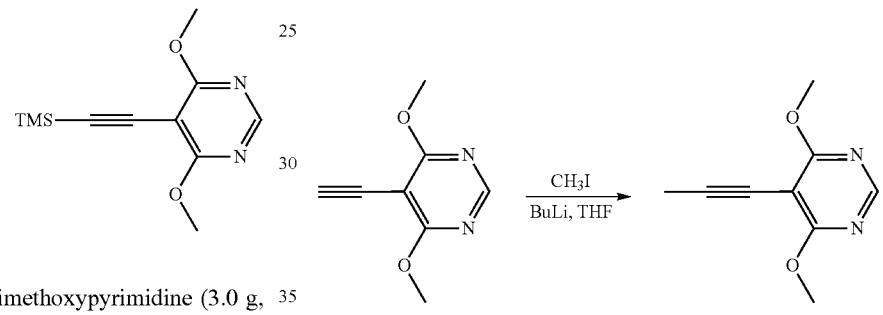

To a solution of 5-ethynyl-4,6-dimethoxypyrimidine (800.0 mg, 4.87 mmol) in THF (40.0 mL) was added dropwise n-BuLi (0.6 mL, 2.5 mol/L) at −78° C. under N$_2$. The resulting mixture was stirred at −78° C. for 1 h under N$_2$. Then CH$_3$I (3.5 g, 34.37 mmol) was added dropwise to the mixture at −78° C. under N$_2$. The resulting mixture was stirred at room temperature for 2 h. After the reaction was completed, the resulting mixture was quenched with aq. NH$_4$Cl and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (94/6, v/v) to afford 4,6-dimethoxy-5-(prop-1-yn-1-yl)pyrimidine (400 mg, 46%) as a white solid. LCMS (ESI, m/z): [M+H]$^+$=179.1.

Step 4: Synthesis of 6-chloro-2-(4,6-dimethoxypyrimidin-5-yl)-3-methyl-1H-pyrrolo[3,2-c]pyridine

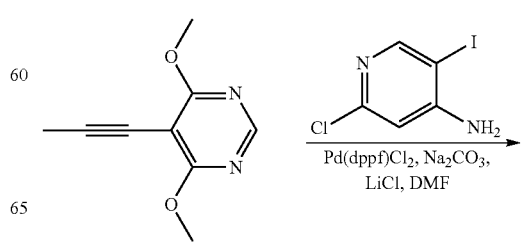

-continued

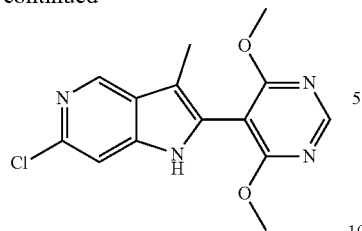

To a solution of 4,6-dimethoxy-5-(prop-1-yn-1-yl)pyrimidine (400.0 mg, 2.25 mmol) in DMF (6.0 mL) was added 2-chloro-5-iodopyridin-4-amine (571.2 mg, 2.24 mmol), LiCl (95.2 mg, 2.24), Na$_2$CO$_3$ (1.2 g, 11.2 mmol) and Pd(dppf)Cl$_2$ (164.3 mg, 0.23 mmol) at room temperature under N$_2$. The resulting mixture was stirred at 100° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford 6-chloro-2-(4,6-dimethoxypyrimidin-5-yl)-3-methyl-1H-pyrrolo[3,2-c]pyridine (80.0 mg, 9%) as a brown solid. LCMS (ESI, m/z): [M+H]$^+$=305.1.

Step 5: Synthesis of 6-chloro-2-(4,6-dimethoxypyrimidin-5-yl)-3-methyl-1-((2-(trimethylsilyl)ethoxy)methyl)-1H-pyrrolo[3,2-c]pyridine

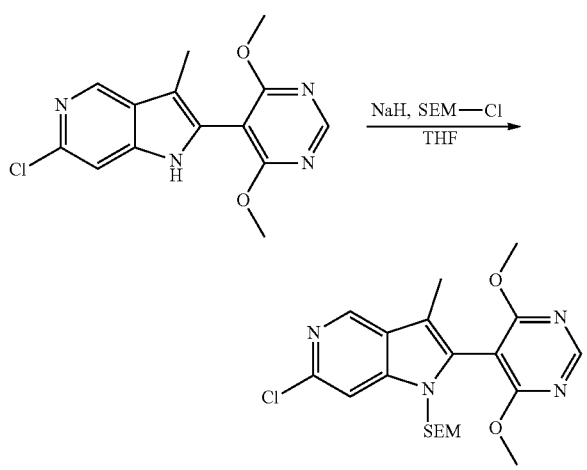

To a solution of 6-chloro-2-(4,6-dimethoxypyrimidin-5-yl)-3-methyl-1H-pyrrolo[3,2-c]pyridine (80.0 mg, 0.26 mmol) in THF (5.0 mL) was added NaH (31.5 mg, 60%) at 0° C. under N$_2$. The resulting mixture was stirred at 0° C. for 1 h. Then SEM-Cl (65.6 mg, 0.39 mmol) was added dropwise to the mixture at 0° C. under N$_2$. The resulting mixture was stirred at 0° C. for another 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (98/2, v/v) to afford 6-chloro-2-(4,6-dimethoxypyrimidin-5-yl)-3-methyl-1-((2-(trimethylsilyl)ethoxy)methyl)-1H-pyrrolo[3,2-c]pyridine (80.0 mg, 70%) as a light yellow oil. LCMS (ESI, m/z): [M+H]$^+$=435.2.

Step 6: Synthesis of (1S,2S)-N-(2-(4,6-dimethoxypyrimidin-5-yl)-3-methyl-1-((2-(trimethylsilyl)ethoxy)methyl)-1H-pyrrolo[3,2-c]pyridin-6-yl)-2-fluorocyclopropane-1-carboxamide

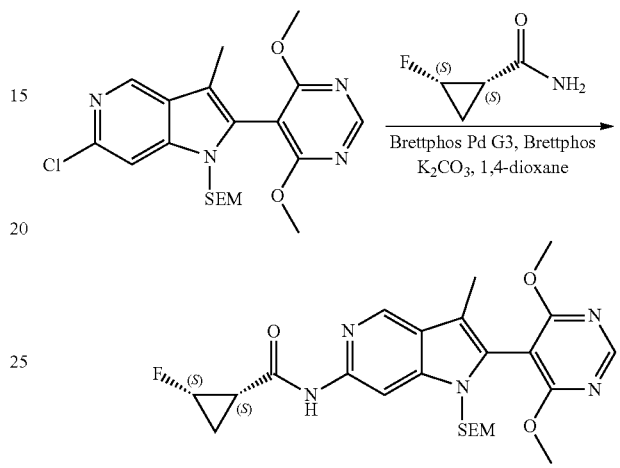

To a solution of 6-chloro-2-(4,6-dimethoxypyrimidin-5-yl)-3-methyl-1-((2-(trimethylsilyl)ethoxy)methyl)-1H-pyrrolo[3,2-c]pyridine (80.0 mg, 0.18 mmol) in 1,4-dioxane (2.0 mL) was added (1S,2S)-2-fluorocyclopropane-1-carboxamide (189.6 mg, 1.84 mmol), K$_2$CO$_3$ (76.5 mg, 0.55 mmol), BrettPhos (19.7 mg, 0.04 mmol) and BrettPhos Pd G3 (16.7 mg, 0.02 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (58/42, v/v) to afford (1S,2S)-N-(2-(4,6-dimethoxypyrimidin-5-yl)-3-methyl-1-((2-(trimethylsilyl)ethoxy)methyl)-1H-pyrrolo[3,2-c]pyridin-6-yl)-2-fluorocyclopropane-1-carboxamide (12.0 mg, 13%) as a yellow solid. LCMS (ESI, m/z): [M+H]$^+$=502.2.

Step 7: Synthesis of (1S,2S)-N-(2-(4,6-dimethoxypyrimidin-5-yl)-3-methyl-1H-pyrrolo[3,2-c]pyridin-6-yl)-2-fluorocyclopropane-1-carboxamide (Compound 91)

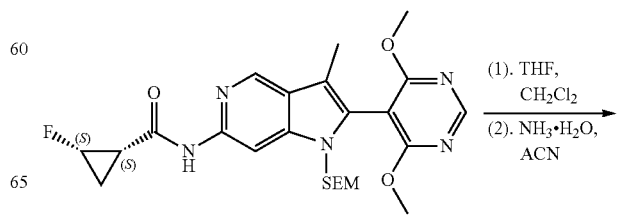

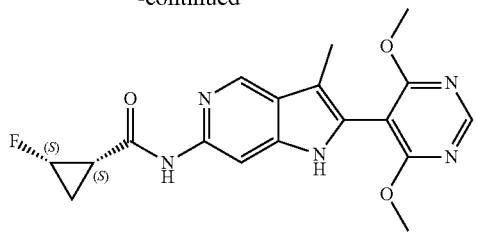

91

To a solution of (1S,2S)-N-(2-(4,6-dimethoxypyrimidin-5-yl)-3-methyl-1-((2-(trimethylsilyl)ethoxy)methyl)-1H-pyrrolo[3,2-c]pyridin-6-yl)-2-fluorocyclopropane-1-carboxamide (10.0 mg, 0.16 mmol) in CH$_2$Cl$_2$ (1.0 mL) was added TFA (1.0 mL) at room temperature. The resulting mixture was stirred at room temperature for 2 h. The resulting mixture was concentrated under reduced pressure. To the residue in ACN (1.0 mL) was added NH$_3$·H$_2$O (1.0 mL) at room temperature. The resulting mixture was stirred at room temperature for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by reverse phase flash column chromatography with CH$_3$CN/H$_2$O (66/34, v/v) to afford (1S,2S)-N-(2-(4,6-dimethoxypyrimidin-5-yl)-3-methyl-1H-pyrrolo[3,2-c]pyridin-6-yl)-2-fluorocyclopropane-1-carboxamide (Compound 91) (1.2 mg, 16%) as a white solid. LCMS (ESI, m/z): [M+H]$^+$=372.2. $^1$H NMR (400 MHz, DMSO-d$_6$): δ 11.17 (s, 1H), 10.59 (s, 1H), 8.60 (s, 1H), 8.53 (s, 1H), 8.04 (s, 1H), 5.01-4.80 (m, 1H), 3.94 (s, 6H), 2.23-2.18 (m, 1H), 2.09 (s, 3H), 1.69-1.61 (m, 1H), 1.20-1.08 (m, 1H).

Example S92: Synthesis of (1S,2S)-N-[2-(4-ethyl-6-methoxypyrimidin-5-yl)-1-methylpyrrolo[2,3-c]pyridin-5-yl]-2-fluorocyclopropane-1-carboxamide (Compound 92)

Step 1: Synthesis of 4-ethenyl-6-methoxypyrimidine

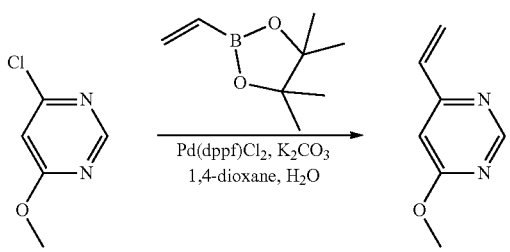

To a solution of 4-chloro-6-methoxypyrimidine (5.0 g, 34.59 mmol) in 1,4-dioxane/H$_2$O (120.0 mL/24.0 mL) was added 2-ethenyl-4,4,5,5-tetramethyl-1,3,2-dioxaborolane (5.3 g, 34.59 mmol), K$_2$CO$_3$ (14.3 g, 103.76 mmol) and Pd(dppf)Cl$_2$ (2.5 g, 3.46 mmol) at room temperature under N$_2$. The resulting mixture was stirred at 80° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 4-ethenyl-6-methoxypyrimidine (2.7 g, 57%) as a yellow oil. LCMS (ESI, m/z): [M+H]$^+$=137.1.

Step 2: Synthesis of 4-ethyl-6-methoxypyrimidine

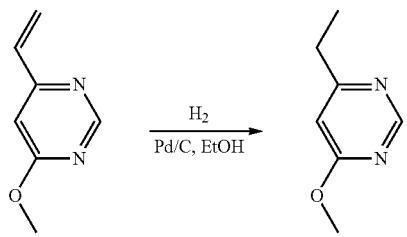

To a solution of 4-ethenyl-6-methoxypyrimidine (2.8 g, 20.35 mmol) in EtOH (90.0 mL) was added Pd/C (649.5 mg, dry) at room temperature. The resulting mixture was stirred at room temperature for 16 h under H$_2$. After the reaction was completed, the resulting mixture was filtered. The filtrate was concentrated under reduced pressure to afford 4-ethyl-6-methoxypyrimidine (2.5 g, crude) as a yellow oil. LCMS (ESI, m/z): [M+H]$^+$=139.1.

Step 3: Synthesis of 4-ethyl-5-iodo-6-methoxypyrimidine

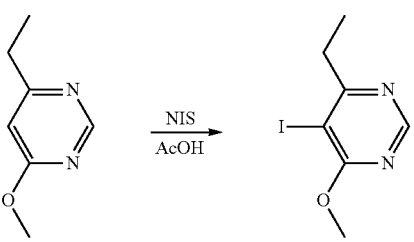

To a solution of 4-ethyl-6-methoxypyrimidine (2.5 g, 17.73 mmol) in AcOH (80.0 mL) was added NIS (4.0 g, 17.73 mmol) at room temperature. The resulting mixture was stirred at 65° C. for 4 h. After the reaction was completed, the resulting mixture was diluted with H$_2$O and extracted with ethyl acetate. The combined organic layers were washed with brine, dried over anhydrous sodium sulfate and filtered. The filtrate was concentrated under reduced pressure. The residue was purified by reverse phase flash chromatography with H$_2$O/ACN (2/1, v/v) to afford 4-ethyl-5-iodo-6-methoxypyrimidine (101.2 mg, 2%) as a yellow oil. LCMS (ESI, m/z): [M+H]$^+$=265.0.

Step 4: Synthesis of 5-(5-chloro-1-methylpyrrolo[2,3-c]pyridin-2-yl)-4-ethyl-6-methoxypyrimidine

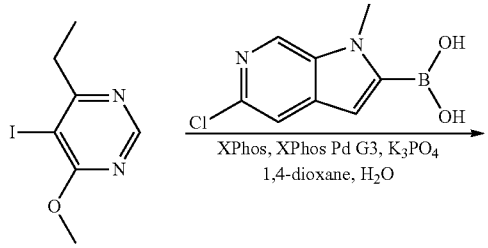

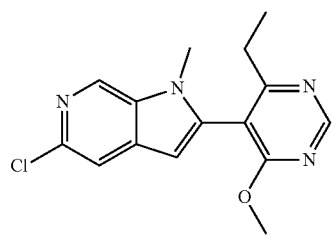

To a solution of 4-ethyl-5-iodo-6-methoxypyrimidine (112.0 mg, 0.45 mmol) in 1,4-dioxane/H₂O (3.0 mL/0.6 mL) was added 5-chloro-1-methylpyrrolo[2,3-c]pyridin-2-ylboronic acid (94.3 mg, 0.45 mmol), XPhos (42.7 mg, 0.09 mmol), K₃PO₄ (190.2 mg, 0.90 mmol) and XPhos Pd G3 (37.9 mg, 0.05 mmol) at room temperature under N₂. The resulting mixture was stirred at 60° C. for 2 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/CH₃OH (10/1, v/v) to afford 5-[5-chloro-1-methylpyrrolo[2,3-c]pyridin-2-yl]-4-ethyl-6-methoxypyrimidine (76.0 mg, 56%) as a brown solid. LCMS (ESI, m/z): [M+H]⁺=303.1.

Step 5: Synthesis of (1S,2S)-N-[2-(4-ethyl-6-methoxypyrimidin-5-yl)-1-methylpyrrolo[2,3-c]pyridin-5-yl]-2-fluorocyclopropane-1-carboxamide (Compound 92)

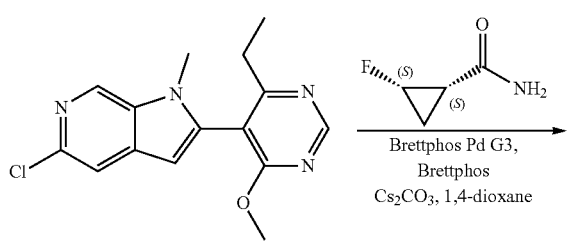

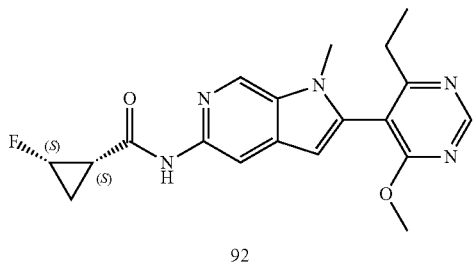

To a solution of 5-{5-chloro-1-methylpyrrolo[2,3-c]pyridin-2-yl}-4-ethyl-6-methoxypyrimidine (105.0 mg, 0.35 mmol) in 1,4-dioxane (4.0 mL) was added (1S,2S)-2-fluorocyclopropane-1-carboxamide (178.8 mg, 1.74 mmol), Brettphos (37.2 mg, 0.07 mmol), Cs₂CO₃ (339.0 mg, 1.04 mmol) and Brettphos Pd G3 (31.4 mg, 0.04 mmol) at room temperature under N₂. The resulting mixture was stirred at 100° C. for 16 h under N₂. After the reaction was completed, The resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/CH₃OH (4/1, v/v) and then purified by Prep-HPLC with the following conditions (Column: YMC-Actus Triart C18 ExRS, 30 mm×150 mm, 5 um; Mobile Phase A: Water (10 mmol/L NH₄HCO₃), Mobile Phase B: ACN; Flow rate: 60 mL/min; Gradient: 25% B to 48% B in 8 min, 254 nm) to afford (1S,2S)-N-[2-(4-ethyl-6-methoxypyrimidin-5-yl)-1-methylpyrrolo[2,3-c]pyridin-5-yl]-2-fluorocyclopropane-1-carboxamide (Compound 92) (2.7 mg, 2%) as a white solid. LCMS (ESI, m/z): [M+H]⁺=370.2. ¹H NMR (400 MHz, DMSO-d₆): δ 10.56 (s, 1H), 8.87 (s, 1H), 8.66 (s, 1H), 8.23 (s, 1H), 6.55 (s, 1H), 5.01-4.81 (m, 1H), 3.91 (s, 3H), 3.56 (s, 3H), 2.68-2.51 (m, 2H), 2.25-2.19 (m, 1H), 1.71-1.65 (m, 1H), 1.19-1.05 (m, 4H).

Example S93: Synthesis of (1S,2S)-N-(2-(4,6-dimethoxypyrimidin-5-yl)-1-(methyl-d3)-1H-pyrrolo[2,3-c]pyridin-5-yl)-2-fluorocyclopropane-1-carboxamide (Compound 93)

Step 1: Synthesis of 4,6-dimethoxy-5-(4,4,5,5-tetramethyl-1,3,2-dioxaborolan-2-yl)pyrimidine

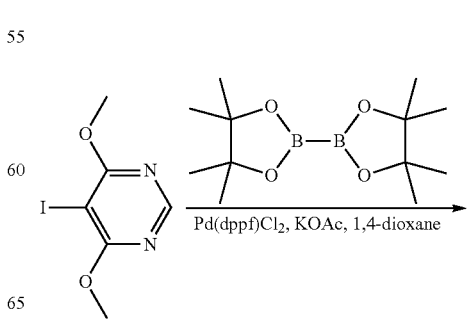

-continued

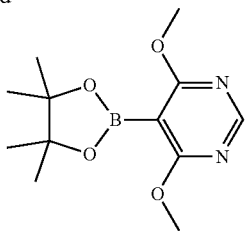

To a solution of 5-iodo-4,6-dimethoxypyrimidine (500.0 mg, 1.88 mmol) in 1,4-dioxane (20.0 mL) was added 4,4,4',4',5,5,5',5'-octamethyl-2,2'-bi(1,3,2-dioxaborolane) (1.4 g, 5.64 mmol), KOAc (553.4 mg, 5.64 mmol) and Pd(dppf)Cl$_2$ (275.0 mg, 0.38 mmol) at room temperature under N$_2$. The resulting mixture was stirred at 80° C. for 4 h under N$_2$. After the reaction was completed, the resulting mixture was concentrated under reduced pressure. The residue was purified by flash column chromatography with petroleum ether/ethyl acetate (70/30, v/v) to afford 4,6-dimethoxy-5-(4,4,5,5-tetramethyl-1,3,2-dioxaborolan-2-yl)pyrimidine (450.0 mg, 89%) as a white solid. LCMS (ESI, m/z): [M+H]$^+$=267.1.

Step 2: Synthesis of 5-chloro-2-(4,6-dimethoxypyrimidin-5yl)-1-(methyl-d$_3$)-1H-pyrrolo[2,3-c]pyridine

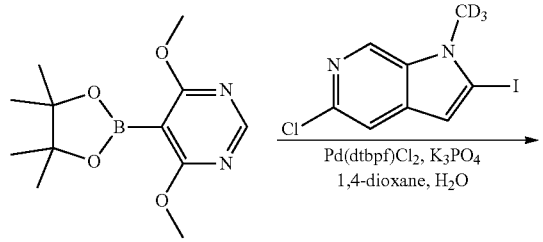

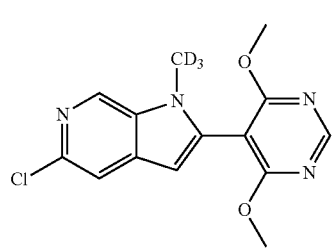

To a solution of 4,6-dimethoxy-5-(4,4,5,5-tetramethyl-1,3,2-dioxaborolan-2-yl)pyrimidine (400.0 mg, 1.50 mmol) in 1,4-dioxane/H$_2$O (20.0/4.0 mL) was added 5-chloro-2-iodo-1-(methyl-d$_3$)-1H-pyrrolo[2,3-c]pyridine (533.1 mg, 1.80 mmol), K$_3$PO$_4$ (957.3 mg, 4.51 mmol) and Pd(dtbpf)Cl$_2$ (374.6 mg, 0.46 mmol) at room temperature under N$_2$. The resulting mixture was stirred at 90° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford 5-chloro-2-(4,6-dimethoxypyrimidin-5-yl)-1-(methyl-d$_3$)-1H-pyrrolo[2,3-c]pyridine (80.0 mg, 17%) as a brown solid. LCMS (ESI, m/z): [M+H]$^+$=308.1.

Step 3: Synthesis of (1S,2S)-N-(2-(4,6-dimethoxypyrimidin-5-yl)-1-(methyl-d$_3$)-1H-pyrrolo[2,3-c]pyridin-5-yl)-2-fluorocyclopropane-1-carboxamide (Compound 93)

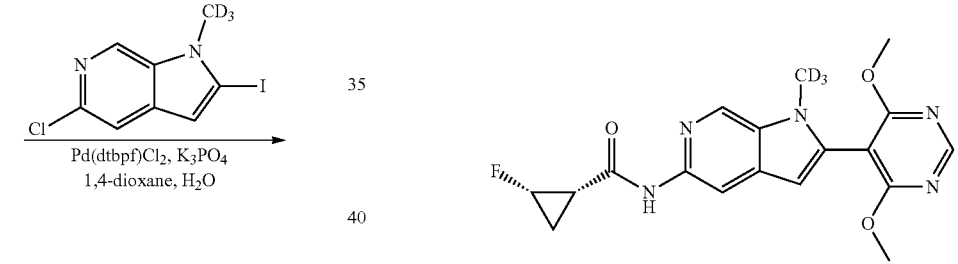

To a solution of 5-chloro-2-(4,6-dimethoxypyrimidin-5-yl)-1-(methyl-d$_3$)-1H-pyrrolo[2,3-c]pyridine (60.0 mg, 0.20 mmol) in 1,4-dioxane (4.0 mL) was added (1S,2S)-2-fluorocyclopropane-1-carboxamide (100.5 mg, 0.98 mmol), K$_2$CO$_3$ (80.8 mg, 0.59 mmol), BrettPhos (20.9 mg, 0.04 mmol) and Brettphos Pd G3 (17.7 mg, 0.02 mmol) at room temperature under N$_2$. The resulting mixture was stirred at 100° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (20/80, v/v) and then purified by reverse phase flash chromatography with CH$_3$CN/H$_2$O (41/59, v/v) to afford (1S,2S)-N-(2-(4,6-dimethoxypyrimidin-5-yl)-1-(methyl-d$_3$)-1H-pyrrolo[2,3-c]pyridin-5-yl)-2-fluorocyclopropane-1-carboxamide (Compound 93) (1.1 mg, 2%) as a white solid. LCMS (ESI, m/z): [M+H]$^+$=375.2. $^1$H NMR (300 MHz, DMSO-d$_6$): δ 10.53 (s, 1H), 8.66-8.62 (m, 2H), 8.19 (s, 1H), 6.50 (d, J=0.9 Hz, 1H), 5.03-4.78 (m, 1H), 3.92 (s, 6H), 2.28-2.18 (m, 1H), 1.72-1.64 (m, 1H), 1.18-1.11 (m, 1H).

Example S94: Synthesis of (1R,2R)-N-[2-(4,6-dimethoxypyrimidin-5-yl)-1-methylpyrrolo[2,3-c]pyridin-5-yl]-2-fluorocyclopropane-1-carboxamide (Compound 94)

Step 1: Synthesis of 5-[5-chloro-1-methylpyrrolo[2,3-c]pyridin-2-yl]-4,6-dimethoxypyrimidine

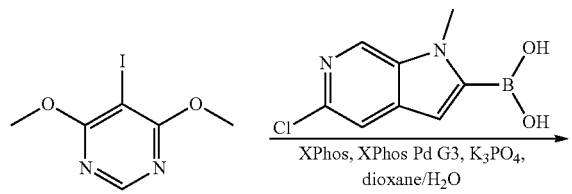

To a solution of 5-iodo-4,6-dimethoxypyrimidine (300.0 mg, 1.13 mmol) in 1,4-dioxane/H$_2$O (20.0 mL/5.0 mL) was added 5-chloro-1-methylpyrrolo[2,3-c]pyridin-2-ylboronic acid (237.3 mg, 1.13 mmol), XPhos (107.5 mg, 0.23 mmol), K$_3$PO$_4$ (718.1 mg, 3.38 mmol) and XPhos Pd G3 (95.5 mg, 0.11 mmol) at room temperature under N$_2$. The resulting mixture was stirred at 60° C. for 2 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (l/1, v/v) to afford 5-{5-chloro-1-methylpyrrolo[2,3-c]pyridin-2-yl}-4,6-dimethoxypyrimidine (250.0 mg, 72%) as a light yellow solid. LCMS (ESI, m/z): [M+H]$^+$=305.1.

Step 2: Synthesis of (1R,2R)-N-[2-(4,6-dimethoxypyrimidin-5-yl)-1-methylpyrrolo[2,3-c]pyridin-5-yl]-2-fluorocyclopropane-1-carboxamide (Compound 94)

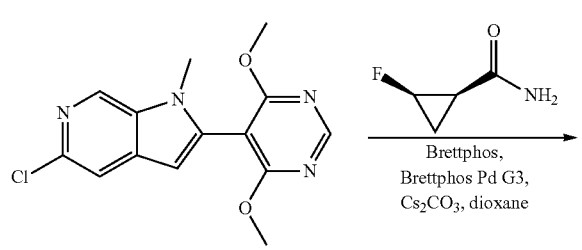

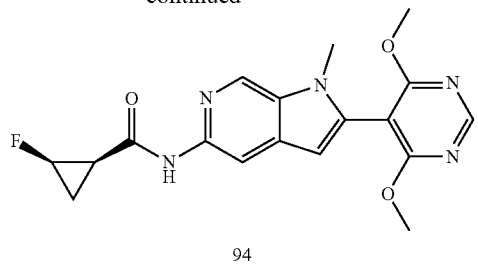

To a solution of 5-{5-chloro-1-methylpyrrolo[2,3-c]pyridin-2-yl}-4,6-dimethoxypyrimidine (220.0 mg, 0.72 mmol) in 1,4-dioxane (8.0 mL) was added (1R,2R)-2-fluorocyclopropane-1-carboxamide (372.2 mg, 3.61 mmol), BrettPhos (77.5 mg, 0.14 mmol), Cs$_2$CO$_3$ (705.7 mg, 2.17 mmol) and BrettPhos Pd G3 (65.4 mg, 0.07 mmol) at room temperature under N$_2$. The resulting mixture was stirred at 100° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/9, v/v) and then purified by Prep-HPLC with the following conditions (Column: YMC-Actus Triart C18 ExRS, 30×150 mm, 5 μm; Mobile Phase A: Water (10 mmol/L NH$_4$HCO$_3$), Mobile Phase B: ACN; Flow rate: 60 mL/min; Gradient: 40% B to 50% B in 8 min; Wave Length: 254 nm) to afford (1R,2R)-N-[2-(4,6-dimethoxypyrimidin-5-yl)-1-methylpyrrolo[2,3-c]pyridin-5-yl]-2-fluorocyclopropane-1-carboxamide (Compound 94) (36.6 mg, 13%) as a white solid. LCMS (ESI, m/z): [M+H]$^+$=372.1. $^1$H NMR (400 MHz, DMSO-d$_6$): δ 10.53 (s, 1H), 8.66 (s, 1H), 8.63 (s, 1H), 8.20 (s, 1H), 6.50 (s, 1H), 5.01-4.80 (m, 1H), 3.93 (s, 6H), 3.58 (s, 3H), 2.22-2.17 (m, 1H), 1.70-1.61 (m, 1H), 1.16-1.09 (m, 1H).

Example S95: Synthesis of (1S,2S)-N-(2-(4,6-bis(methoxy-d3)pyrimidin-5-yl)-1-methyl-1H-pyrrolo[2,3-c]pyridin-5-yl)-2-fluorocyclopropane-1-carboxamide (Compound 95)

Step 1: Synthesis of 5-bromo-4,6-bis(methoxy-d3)pyrimidine

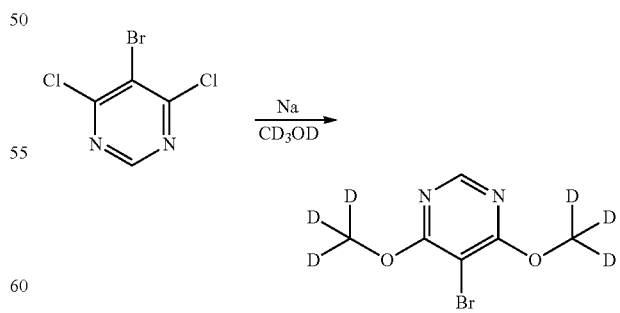

A solution of Na (252.2 mg, 10.97 mmol) in CD$_3$OD (6.0 mL) was stirred at room temperature for 0.5 h. Then 5-bromo-4,6-dichloropyrimidine (500.0 mg, 2.19 mmol) was added to the mixture at room temperature. The resulting mixture was stirred at 40° C. for 16 h. After the reaction was completed, the resulting mixture was quenched with H₂O and extracted with ethyl acetate. The combined organic layer was washed with brine, dried over anhydrous sodium sulfate and filtered. The filtrate was concentrated under reduced pressure to afford 5-bromo-4,6-bis(methoxy-d3)pyrimidine (400.0 mg, crude) as a white solid. LCMS (ESI, m/z): [M+H]⁺=225.0.

Step 2: Synthesis of 2-(4,6-bis(methoxy-d3)pyrimidin-5-vi)-5-chloro-1-methyl-1H-pyrrolo[2,3-c]pyridine

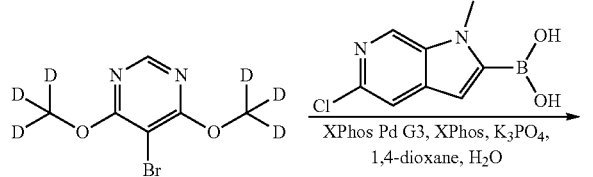

To a solution of 5-bromo-4,6-bis(methoxy-d3)pyrimidine (400.0 mg, 1.78 mmol) in 1,4-dioxane/H₂O (10.0/2.0 mL) was added 5-chloro-1-methylpyrrolo[2,3-c]pyridin-2-ylboronic acid (187.0 mg, 0.89 mmol), K₃PO₄ (566.3 mg, 2.67 mmol), XPhos (169.4 mg, 0.36 mmol) and XPhos Pd G3 (150.4 mg, 0.18 mmol) at room temperature under N₂. The resulting mixture was stirred at 60° C. for 2 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford 2-(4,6-bis(methoxy-d3)pyrimidin-5-yl)-5-chloro-1-methyl-1H-pyrrolo[2,3-c]pyridine (190.0 mg, 34%) as a red solid. LCMS (ESI, m/z): [M+H]⁺=311.1.

Step 3: Synthesis of (1S,2S)-N-(2-(4,6-bis(methoxy-d3)pyrimidin-5-yl)-1-methyl-1H-pyrrolo[2,3-c]pyridin-5-yl)-2-fluorocyclopropane-1-carboxamide (Compound 95)

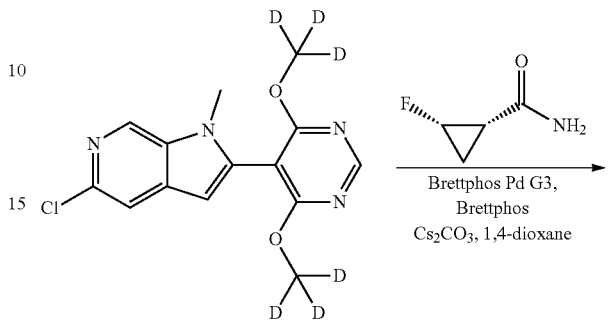

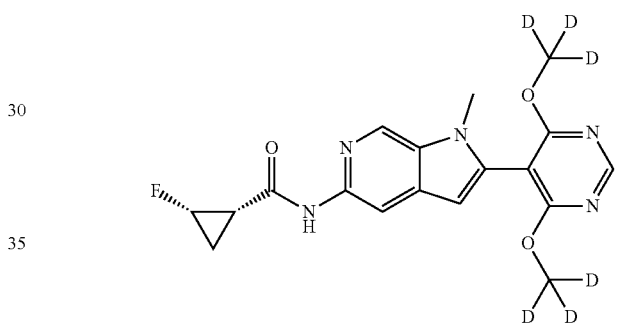

To a solution of 2-(4,6-bis(methoxy-d3)pyrimidin-5-yl)-5-chloro-1-methyl-1H-pyrrolo[2,3-c]pyridine (100.0 mg, 0.32 mmol) in 1,4-dioxane (10.0 mL) was added (1S,2S)-2-fluorocyclopropane-1-carboxamide (165.9 mg, 1.61 mmol), Cs₂CO₃ (314.5 mg, 0.97 mmol), BrettPhos (34.5 mg, 0.06 mmol) and BrettPhos Pd G3 (29.2 mg, 0.03 mmol) at room temperature under N₂. The resulting mixture was stirred at 100° C. for 2 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (40/60, v/v) and then purified by Prep-HPLC with the following conditions (Column: Xselect CSH OBD Column 30×150 mm, 5 um; Mobile Phase A:Water (10 mmol/L NH₄HCO₃), Mobile Phase B: ACN; Flow rate: 60 ml/min; Gradient: 26% B to 35% B in 8 min; 254 nm) to afford (1S,2S)-N-(2-(4,6-bis(methoxy-d3)pyrimidin-5-yl)-1-methyl-1H-pyrrolo[2,3-c]pyridin-5-yl)-2-fluorocyclopropane-1-carboxamide (Compound 95) (10.2 mg, 8%) as a white solid. LCMS (ESI, m/z): [M+H]⁺=378.1. ¹H NMR (400 MHz, DMSO-d₆): δ 10.52 (s, 1H), 8.66-8.63 (m, 2H), 8.20 (s, 1H), 6.50 (s, 1H), 5.01-4.80 (m, 1H), 3.58 (s, 3H), 2.24-2.17 (m, 1H), 1.71-1.61 (m, 1H), 1.24-1.01 (m, 1H).

415

Example S96: Synthesis of (1S,2S)-N-(2-(2-(difluoromethyl)-4,6-dimethoxypyrimidin-5-yl)-1-methyl-1H-pyrrolo[2,3-c]pyridin-5-yl)-2-fluorocyclopropane-1-carboxamide (Compound 96)

Step 1: Synthesis of 2-(difluoromethyl)pyrimidine-4,6-diol

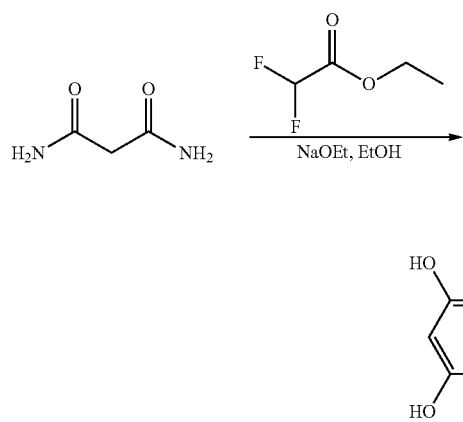

To a solution of malonamide (5.0 g, 48.98 mmol) in EtOH (100.0 mL) was added a solution of NaOEt in EtOH (39.0 mL, 21%) at room temperature. The resulting mixture was stirred at room temperature for 1 h. Then ethyl 2,2-difluoroacetate (7.2 g, 58.28 mmol) was added to the mixture at room temperature. The resulting mixture was stirred at 80° C. for 16 h. After the reaction was completed, the resulting mixture was adjusted to pH=3 with aq. HCl and then extracted with ethyl acetate. The combined organic layer was washed with brine, dried over anhydrous sodium sulfate and filtered. The filtrate was concentrated under reduced pressure. The residue was washed with $CH_2Cl_2$ and then filtered. The solid was collected and dried to afford 2-(difluoromethyl)pyrimidine-4,6-diol (2.0 g, crude) as a brown solid. LCMS (ESI, m/z): [M+H]$^+$=163.0.

Step 2: Synthesis of 5-bromo-2-(difluoromethyl)pyrimidine-4,6-diol

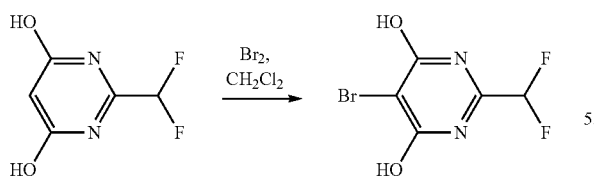

To a solution of 2-(difluoromethyl)pyrimidine-4,6-diol (1.0 g, 6.17 mmol) in $CH_2Cl_2$ (20.0 mL) was added $Br_2$ (2.0 g, 12.33 mmol) at 0° C. under $N_2$. The resulting mixture was stirred at 0° C. for 0.5 h. After the reaction was completed, the resulting mixture was concentrated under reduced pressure to afford 5-bromo-2-(difluoromethyl)pyrimidine-4,6-diol (1.1 g, crude) as a brown solid. LCMS (ESI, m/z): [M+H]$^+$=240.9.

416

Step 3: Synthesis of 5-bromo-2-(difluoromethyl)-4,6-dimethoxypyrimidine

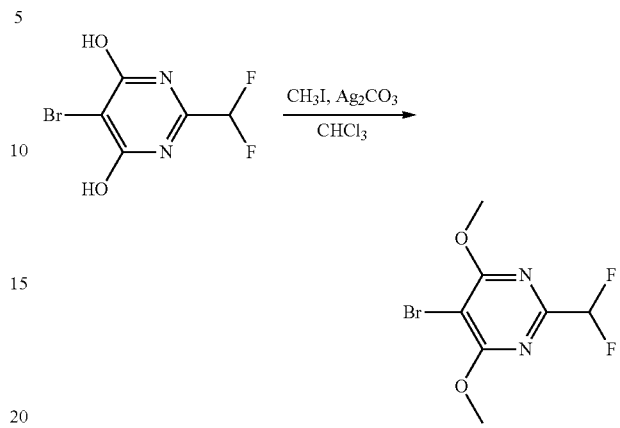

To a solution of 5-bromo-2-(difluoromethyl)pyrimidine-4,6-diol (1.1 g, crude) in $CHCl_3$ (25.0 mL) was added $Ag_2CO_3$ (7.3 g, 26.41 mmol) and $CH_3I$ (3.3 g, 22.91 mmol) at room temperature. The resulting mixture was stirred at room temperature for 16 h. After the reaction was completed, the resulting mixture was filtered. The filtrate was concentrated under reduced pressure. The residue was purified by flash column chromatography with petroleum ether/ethyl acetate (87/13, v/v) to afford 5-bromo-2-(difluoromethyl)-4,6-dimethoxypyrimidine (350.0 mg, 21%) as a yellow solid. LCMS (ESI, m/z): [M+H]$^+$=269.0.

Step 4: Synthesis of 5-chloro-2-(2-(difluoromethyl)-4,6-dimethoxypyrimidin-5-yl)-1-methyl-1H-pyrrolo[2,3-c]pyridine

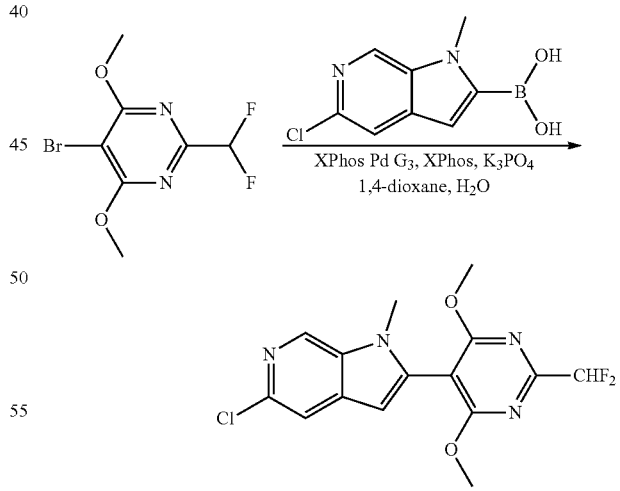

To a solution of 5-bromo-2-(difluoromethyl)-4,6-dimethoxypyrimidine (320.0 mg, 1.19 mmol) in 1,4-dioxane/$H_2O$ (5.0/1.0 mL) was added (5-chloro-1-methyl-1H-pyrrolo[2,3-c]pyridin-2-yl)boronic acid (375.4 mg, 1.78 mmol), $K_3PO_4$ (504.9 mg, 2.38 mmol), XPhos (113.4 mg, 0.24 mmol) and XPhos Pd G3 (101.0 mg, 0.12 mmol) at room temperature under $N_2$. The resulting mixture was stirred at 60° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by silica gel column chromatography with petroleum ether/ethyl acetate (60/40, v/v) to afford 5-chloro-2-(2-(difluoromethyl)-4,6-dimethoxypyrimidin-5-yl)-1-methyl-1H-pyrrolo[2,3-c]pyridine (350.0 mg, 83%) as a light brown solid. LCMS (ESI, m/z): [M+H]⁺=355.1.

Step 5: Synthesis of (1S,2S)-N-(2-(2-(difluoromethyl)-4,6-dimethoxypyrimidin-5-yl)-1-methyl-1H-pyrrolo[2,3-c]pyridin-5-yl)-2-fluorocyclopropane-1-carboxamide (Compound 96)

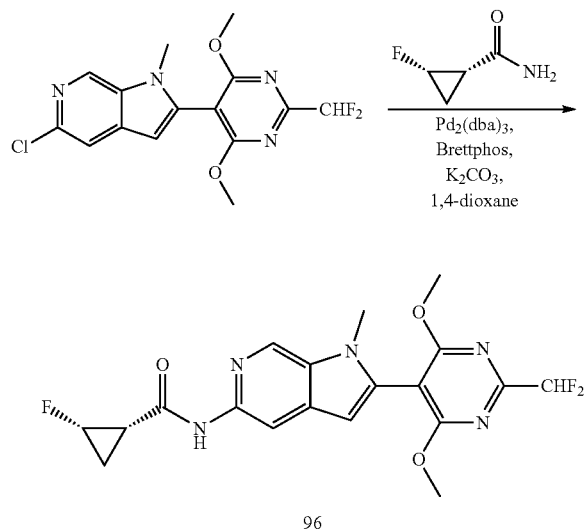

To a solution of 5-chloro-2-(2-(difluoromethyl)-4,6-dimethoxypyrimidin-5-yl)-1-methyl-1H-pyrrolo[2,3-c]pyridine (100.0 mg, 0.28 mmol) in 1,4-dioxane (4.0 mL) was added (1S,2S)-2-fluorocyclopropane-1-carboxamide (145.3 mg, 1.41 mmol), K₂CO₃ (116.9 mg, 0.85 mmol), BrettPhos (30.3 mg, 0.06 mmol) and Pd₂(dba)₃ (25.8 mg, 0.03 mmol) at room temperature. The resulting mixture was stirred at 100° C. for 16 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/CH₃OH (92/8, v/v) and then purified by Prep-HPLC with the following conditions (Column: YMC-Actus Triart C18 ExRS, 30×150 mm, 5 μm; Mobile Phase A: Water (10 mmol/L NH₄HCO₃), Mobile Phase B: ACN; Flow rate: 60 mL/min; Gradient: 40% B to 55% B in 8 min, 254 nm) to afford (1S,2S)-N-(2-(2-(difluoromethyl)-4,6-dimethoxypyrimidin-5-yl)-1-methyl-1H-pyrrolo[2,3-c]pyridin-5-yl)-2-fluorocyclopropane-1-carboxamide (Compound 96) (15.5 mg, 13%) as a white solid. LCMS (ESI, m/z): [M+H]⁺=422.2. ¹H NMR (300 MHz, DMSO-d₆): δ 10.53 (s, 1H), 8.64 (s, 1H), 8.20 (s, 1H), 7.08-6.72 (m, 1H), 6.54 (d, J=0.6 Hz, 1H), 5.02-4.79 (m, 1H), 3.97 (s, 6H), 3.61 (s, 3H), 2.28-2.18 (s, 1H), 1.69-1.62 (m, 1H), 1.17-1.09 (m, 1H).

Example S97: Synthesis of (1R,2R)-N-[2-(2,4-dimethoxypyridin-3-yl)-1-methylpyrrolo[2,3-c]pyridin-5-yl]-2-fluorocyclopropane-1-carboxamide (Compound 97)

Step 1: Synthesis of 3-{5-chloro-1-methylpyrrolo[2,3-c]pyridin-2-yl}-2,4-dimethoxypyridine

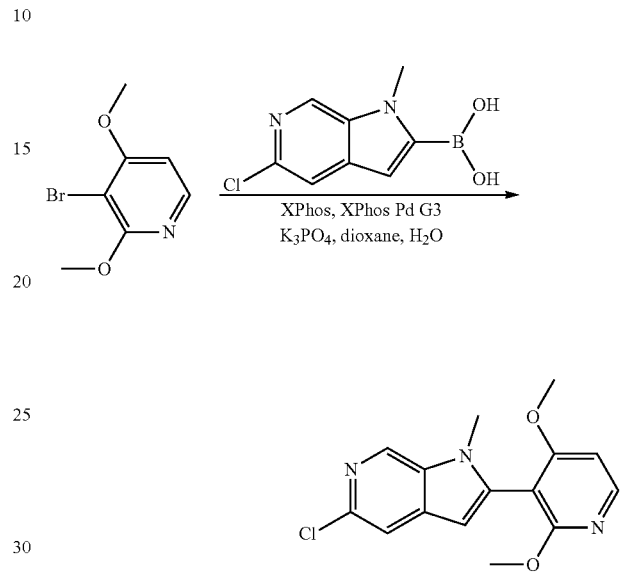

To a solution of 3-bromo-2,4-dimethoxypyridine (300.0 mg, 1.38 mmol) in 1,4-dioxane (75.0 mL)/H₂O (4.0 mL) was added 5-chloro-1-methylpyrrolo[2,3-c]pyridin-2-ylboronic acid (289.5 mg, 1.38 mmol), XPhos (131.2 mg, 0.28 mmol), XPhos Pd G3 (116.5 mg, 0.14 mmol) and K₃PO₄ (876.1 mg, 4.13 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure The residue was purified by flash column chromatography with petroleum ether/ethyl acetate (1/1, v/v) to afford 3-{5-chloro-1-methylpyrrolo[2,3-c]pyridin-2-yl}-2,4-dimethoxypyridine (230.0 mg, 55%) as a brown solid. LCMS (ESI, m/z): [M+H]⁺=304.1.

Step 2: Synthesis of (1R,2R)-N-[2-(2,4-dimethoxypyridin-3-yl)-1-methylpyrrolo[2,3-c]pyridin-5-yl]-2-fluorocyclopropane-1-carboxamide (Compound 97)

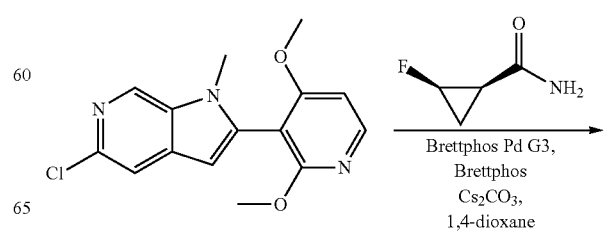

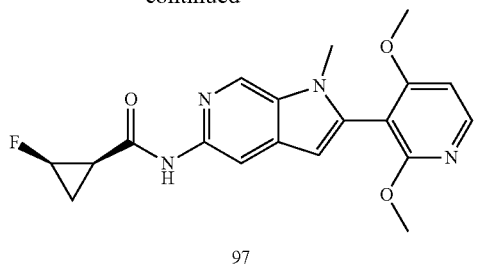

97

To a solution of 3-{5-chloro-1-methylpyrrolo[2,3-c]pyridin-2-yl}-2,4-dimethoxypyridine (200.0 mg, 0.66 mmol) in dioxane (10.0 mL) was added BrettPhos Pd G$_3$ (119.4 mg, 0.13 mmol), (1R,2R)-2-fluorocyclopropane-1-carboxamide (339.4 mg, 3.29 mmol), BrettPhos (35.3 mg, 0.07 mmol) and Cs$_2$CO$_3$ (643.6 mg, 1.98 mmol) at room temperature under N$_2$. The resulting mixture was stirred at 100° C. for 16 h under N$_2$. After the reaction was completed. The resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/6, v/v) and then purified by Prep-HPLC with the following conditions (Column: XBridge Shield RP18 OBD Column, 30×150 mm, 5 μm; Mobile Phase A: Water(10 mmol/L NH$_4$HCO$_3$), Mobile Phase B: ACN; Flow rate: 60 mL/min; Gradient: 20% B to 45% B in 8 min, 45% B; Wave Length: 254 nm) to afford (1R,2R)-N-[2-(2,4-dimethoxypyridin-3-yl)-1-methylpyrrolo[2,3-c]pyridin-5-yl]-2-fluorocyclopropane-1-carboxamide (Compound 97) (11.0 mg, 5%) as a white solid. LCMS (ESI, m/z): [M+H]$^+$=371.2. $^1$H NMR (400 MHz, DMSO-d$_6$): δ 10.53 (s, 1H), 8.60 (s, 1H), 8.26 (d, J=6.0 Hz, 1H), 8.17 (s, 1H), 6.98 (d, J=6.0 Hz, 1H), 6.42 (s, 1H), 5.01-4.81 (m, 1H), 3.82 (s, 6H), 3.54 (s, 3H), 2.22-2.17 (m, 1H), 1.71-1.16 (m, 1H), 1.16-1.08 (m, 1H).

Example S98: Synthesis of (1S,2S)-N-(2-(2,4-dimethoxy-6-methylpyridin-3-yl)-1-methyl-1H-pyrrolo[2,3-c]pyridin-5-yl)-2-fluorocyclopropane-1-carboxamide (Compound 98)

Step 1: Synthesis of 3-bromo-6-methylpyridine-2,4-diol

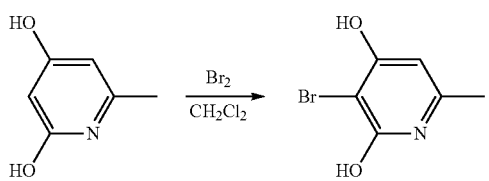

To a solution of 6-methylpyridine-2,4-diol (1.0 g, 7.99 mmol) in CH$_2$Cl$_2$ (20.0 mL) was added dropwise Br$_2$ (1.3 g, 7.99 mmol) at 0° C. under N$_2$. The resulting mixture was stirred at room temperature for 2 h. After the reaction was completed, the reaction was quenched with aq. NaHSO$_3$ at 0° C. The mixture was concentrated under reduced pressure. The residue was purified by flash column chromatography with CH$_2$Cl$_2$/CH$_3$OH (94/6, v/v) to afford 3-bromo-6-methylpyridine-2,4-diol (1.4 g, 85%) as a yellow solid. LCMS (ESI, m/z): [M+H]$^+$=204.0.

Step 2: Synthesis of 3-bromo-2,4-dimethoxy-6-methylpyridine

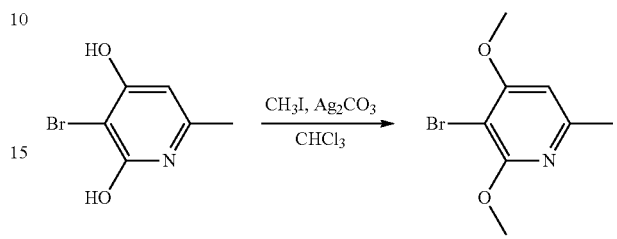

To a solution of 3-bromo-6-methylpyridine-2,4-diol (1.4 g, 6.86 mmol) in CHCl$_3$ (20.0 mL) was added Ag$_2$CO$_3$ (9.5 g, 34.31 mmol) and CH$_3$I (4.9 g, 34.31 mmol) at room temperature. The resulting mixture was stirred at room temperature for 16 h. After the reaction was completed, the resulting mixture was filtered. The filtrate was concentrated under reduced pressure. The residue was purified by flash column chromatography with petroleum ether/ethyl acetate (5/1, v/v) to afford 3-bromo-2,4-dimethoxy-6-methylpyridine (700.0 mg, 43%) as a yellow solid. LCMS (ESI, m/z): [M+H]$^+$=232.0.

Step 3: Synthesis of 5-chloro-2-(2,4-dimethoxy-6-methylpyridin-3-yl)-1-methyl-1H-pyrrolo[2,3-c]pyridine

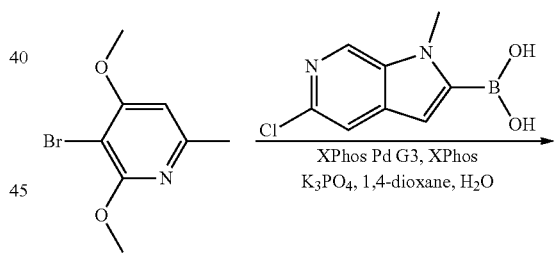

To a solution of 3-bromo-2,4-dimethoxy-6-methylpyridine (400.0 mg, 1.72 mmol) in 1,4-dioxane/H$_2$O (16.0/4.0 mL) was added (5-chloro-1-methyl-1H-pyrrolo[2,3-c]pyridin-2-yl)boronic acid (362.7 mg, 1.72 mmol), K$_3$PO$_4$ (1.1 g, 5.17 mmol), XPhos (164.3 mg, 0.35 mmol) and XPhos Pd G3 (145.9 mg, 0.17 mmol) at room temperature under N$_2$. The resulting mixture was stirred at 60° C. for 2 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 5-chloro-2-(2,4-dimethoxy-6-methylpyridin-3-yl)-1-methyl-1H-pyrrolo[2,3-c]pyridine (270.0 mg, 49%) as a yellow solid. LCMS (ESI, m/z): [M+H]⁺=318.1.

Step 4: Synthesis of (1S,2S)-N-(2-(2,4-dimethoxy-6-methylpyridin-3-yl)-1-methyl-1H-pyrrolo[2,3-c]pyridin-5-yl)-2-fluorocyclopropane-1-carboxamide (Compound 98)

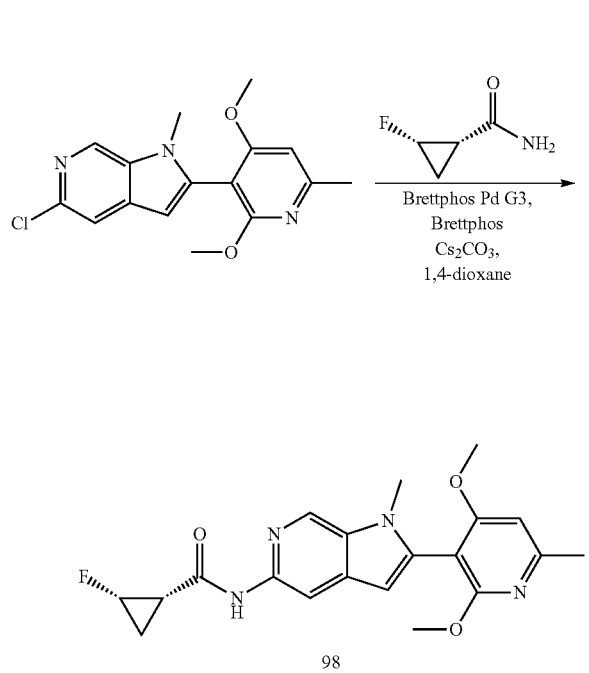

To a solution of 5-chloro-2-(2,4-dimethoxy-6-methylpyridin-3-yl)-1-methyl-1H-pyrrolo[2,3-c]pyridine (270.0 mg, 0.85 mmol) in 1,4-dioxane (10.0 mL) was added (1S,2S)-2-fluorocyclopropane-1-carboxamide (438.0 mg, 4.25 mmol), Cs$_2$CO$_3$ (830.5 mg, 2.55 mmol), Brettphos (91.2 mg, 0.17 mmol) and Brettphos Pd G3 (77.0 mg, 0.09 mmol) at room temperature under N$_2$. The resulting mixture was stirred at 100° C. for 16 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/CH$_3$OH (10/1, v/v) and then purified by Prep-HPLC with the following conditions (Column: XBridge Prep C18 OBD Column, 19×150 mm, 5 um; Mobile Phase A: Water (10 mmol/L NH$_4$HCO$_3$), Mobile Phase B: MeOH—Preparative; Flow rate: 25 mL/min; Gradient: 45% to 65% in 10 min; 254 nm) to afford (1S,2S)-N-(2-(2,4-dimethoxy-6-methylpyridin-3-yl)-1-methyl-1H-pyrrolo[2,3-c]pyridin-5-yl)-2-fluorocyclopropane-1-carboxamide (Compound 98) (18.4 mg, 5%) as a white solid. LCMS (ESI, m/z): [M+H]⁺=385.1. ¹H NMR (400 MHz, DMSO-d$_6$): δ 10.51 (s, 1H), 8.58 (s, 1H), 8.17 (s, 1H), 6.85 (s, 1H), 6.37 (d, J=0.4 Hz, 1H), 5.00-4.80 (m, 1H), 3.80 (s, 6H), 3.52 (s, 3H), 2.47 (s, 3H), 2.22-2.18 (m, 1H), 1.69-1.63 (m, 1H), 1.20-1.09 (m, 1H).

Example S99: Synthesis of (1S,2S)-N-(2-(4,6-dimethoxypyrimidin-5-yl)-1H-pyrrolo[2,3-c]pyridin-5-yl)-2-fluorocyclopropane-1-carboxamide (Compound 99)

Step 1: Synthesis of Tert-butyl (6-chloro-4-((4,6-dimethoxypyrimidin-5-yl)ethynyl)pyridin-3-yl)carbamate

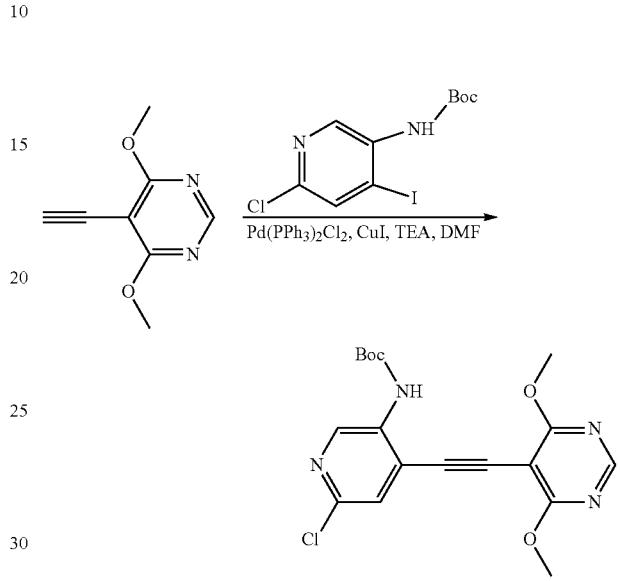

To a solution of 5-ethynyl-4,6-dimethoxypyrimidine (300.0 mg, 1.83 mmol) in DMF (10.0 mL) was added tert-butyl (6-chloro-4-iodopyridin-3-yl)carbamate (647.9 mg, 1.83 mmol), CuI (69.6 mg, 0.37 mmol), TEA (739.7 mg, 7.31 mmol) and Pd(PPh$_3$)$_2$Cl$_2$ (256.5 mg, 0.37 mmol) at room temperature under N$_2$. The resulting mixture was stirred at room temperature for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford tert-butyl (6-chloro-4-((4,6-dimethoxypyrimidin-5-yl)ethynyl)pyridin-3-yl)carbamate (400.0 mg, 56%) as a white solid. LCMS (ESI, m/z): [M+H]⁺=391.1.

Step 2: Synthesis of Tert-butyl 5-chloro-2-(4,6-dimethoxypyrimidin-5-yl)-1H-pyrrolo[2,3-c]pyridine-1-carboxylate

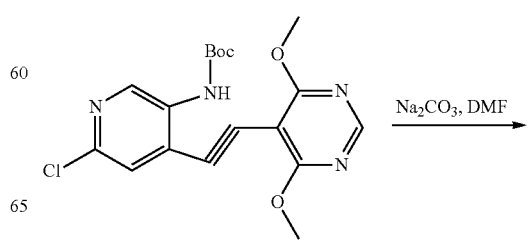

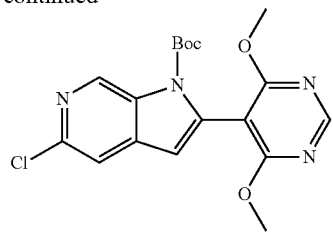

To a solution of tert-butyl (6-chloro-4-((4,6-dimethoxypyrimidin-5-yl)ethynyl)pyridin-3-yl)carbamate (200.0 mg, 0.51 mmol) in DMF (10.0 mL) was added $Na_2CO_3$ (271.2 mg, 2.56 mmol) at room temperature. The resulting mixture was stirred at 80° C. for 4 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (10/3, v/v) to afford tert-butyl 5-chloro-2-(4,6-dimethoxypyrimidin-5-yl)-1H-pyrrolo[2,3-c]pyridine-1-carboxylate (180.0 mg, 88%) as a yellow solid. LCMS (ESI, m/z): $[M+H]^+$=391.1.

Step 3: Synthesis of Tert-butyl 2-(4,6-dimethoxypyrimidin-5-yl)-5-((1S,2S)-2-fluorocyclopropane-1-carboxamido)-1H-pyrrolo[2,3-c]pyridine-1-carboxylate

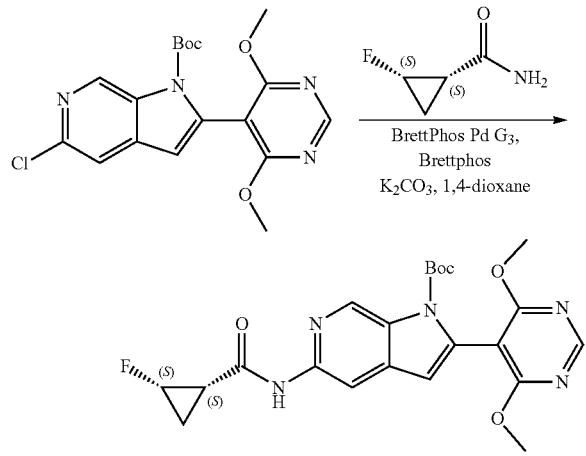

To a solution of tert-butyl 5-chloro-2-(4,6-dimethoxypyrimidin-5-yl)-1H-pyrrolo[2,3-c]pyridine-1-carboxylate (180.0 mg, 0.46 mmol) in 1,4-dioxane (10.0 mL) was added (1S,2S)-2-fluorocyclopropane-1-carboxamide (237.4 mg, 2.31 mmol), $K_2CO_3$ (450.2 mg, 1.38 mmol), BrettPhos (49.4 mg, 0.09 mmol) and BrettPhos Pd G3 (41.8 mg, 0.05 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (70/30, v/v) to afford tert-butyl 2-(4,6-dimethoxypyrimidin-5-yl)-5-((1S,2S)-2-fluorocyclopropane-1-carboxamido)-1H-pyrrolo[2,3-c]pyridine-1-carboxylate (150.0 mg, 71%) as a yellow solid. LCMS (ESI, m/z): $[M+H]^+$=458.2.

Step 4: Synthesis of (1S,2S)-N-(2-(4,6-dimethoxypyrimidin-5-yl)-1H-pyrrolo[2,3-c]pyridin-5-yl)-2-fluorocyclopropane-1-carboxamide (Compound 99)

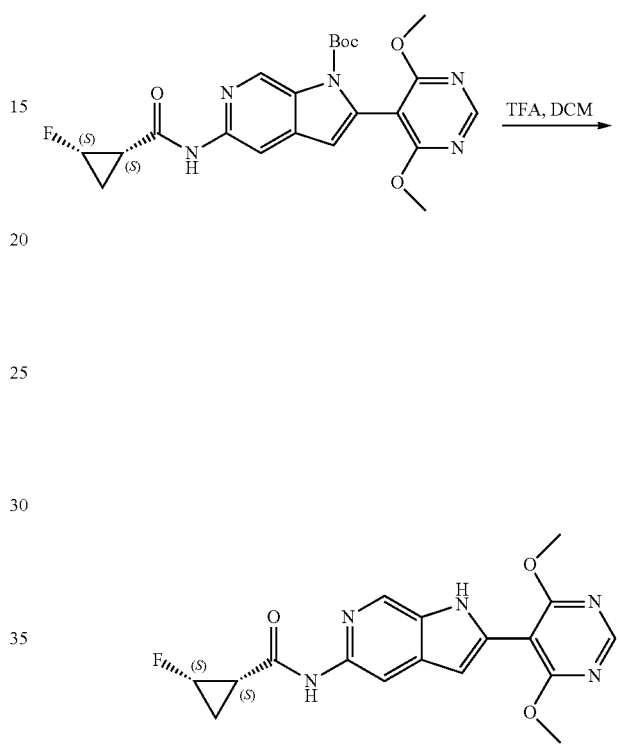

To a solution of tert-butyl 2-(4,6-dimethoxypyrimidin-5-yl)-5-((1S,2S)-2-fluorocyclopropane-1-carboxamido)-1H-pyrrolo[2,3-c]pyridine-1-carboxylate (130.0 mg, 0.29 mmol) in DCM (2.0 mL) was added and TFA (1.0 mL) at room temperature. The resulting mixture was stirred for 2 h at room temperature. After the reaction was completed, the resulting mixture was diluted with $H_2O$. The pH value of the resulting mixture was adjusted to 7 with aq. $NaHCO_3$. The mixture was extracted with ethyl acetate. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A: Water (10 mmol/L $NH_4HCO_3$), Mobile Phase B: ACN; Flow rate: 60 mL/min; Gradient: 29% B to 39% B in 8 min; 254 nm) to afford (1S,2S)-N-(2-(4,6-dimethoxypyrimidin-5-yl)-1H-pyrrolo[2,3-c]pyridin-5-yl)-2-fluorocyclopropane-1-carboxamide (Compound 99) (22.0 mg, 10%) as a white solid. LCMS (ESI, m/z): $[M+H]^+$=358.0. $^1$H NMR (400 MHz, DMSO-$d_6$): δ 11.39 (s, 1H), 10.47 (s, 1H), 8.56 (s, 1H), 8.55 (s, 1H), 8.20 (s, 1H), 6.97 (s, 1H), 5.02-4.79 (m, 1H), 4.08 (s, 6H), 2.30-2.15 (m, 1H), 1.78-1.54 (m, 1H), 1.24-1.02 (m, 1H).

Example S100: Synthesis of (1S,2S)-N-(2-(2-cyclopropyl-4,6-dimethoxypyrimidin-5-yl)-1-methyl-1H-pyrrolo[2,3-c]pyridin-5-yl)-2-fluorocyclopropane-1-carboxamide (Compound 100)

Step 1: Synthesis of 2-cyclopropyl-4,6-dimethoxypyrimidine

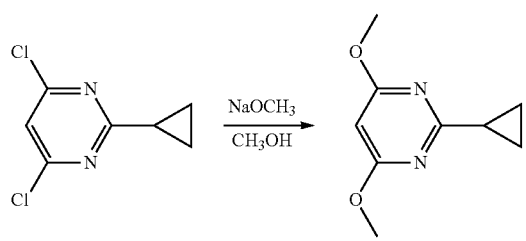

To a solution of 4,6-dichloro-2-cyclopropylpyrimidine (1.0 g, 5.29 mmol) in CH$_3$OH (10.0 mL) was added NaOCH$_3$ (1.4 g, 26.5 mmol) at room temperature. The resulting mixture was stirred at 80° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure to afford 2-cyclopropyl-4,6-dimethoxypyrimidine (900.0 mg, crude) as a yellow oil. LCMS (ESI, m/z): [M+H]$^+$=181.1.

Step 2: Synthesis of 2-cyclopropyl-5-iodo-4,6-dimethoxypyrimidine

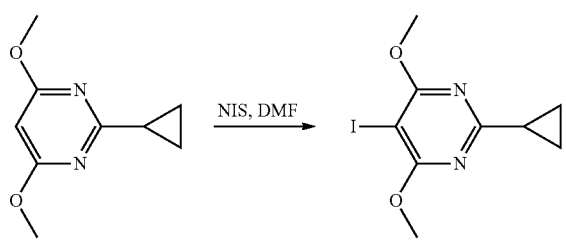

To a solution of 2-cyclopropyl-4,6-dimethoxypyrimidine (900.0 mg, 5.00 mmol) in DMF (10.0 mL) was added NIS (3.4 g, 15.00 mmol) at 0° C. under N$_2$. The resulting mixture was stirred at room temperature for 16 h. After the reaction was completed, the resulting mixture was quenched with aq. NaS$_2$O$_3$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (95/5, v/v) to afford 2-cyclopropyl-5-iodo-4,6-dimethoxypyrimidine (840.0 mg, 55%) as a white solid. LCMS (ESI, m/z): [M+H]$^+$=307.0.

Step 3: Synthesis of 5-chloro-2-(2-cyclopropyl-4,6-dimethoxypyrimidin-5-yl)-1-methyl-1H-pyrrolo[2,3-c]pyridine

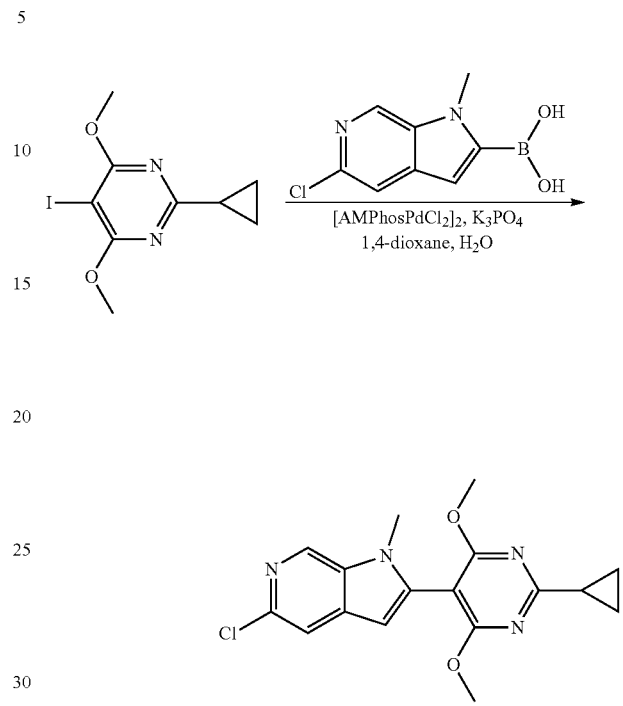

To a solution of 2-cyclopropyl-5-iodo-4,6-dimethoxypyrimidine (400.0 mg, 1.31 mmol) in 1,4-dioxane/H$_2$O (20.0/4.0 mL) was added (5-chloro-1-methyl-1H-pyrrolo[2,3-c]pyridin-2-yl)boronic acid (247.9 mg, 1.31 mmol), K$_3$PO$_4$ (832.1 mg, 3.92 mmol) and [AMPhosPdCl$_2$]$_2$ (92.5 mg, 0.13 mmol) at room temperature under N$_2$. The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (71/29, v/v) to afford 5-chloro-2-(2-cyclopropyl-4,6-dimethoxypyrimidin-5-yl)-1-methyl-1H-pyrrolo[2,3-c]pyridine (130.0 mg, 29%) as a light yellow solid. LCMS (ESI, m/z): [M+H]$^+$=345.1.

Step 4: Synthesis of (1S,2S)-N-(2-(2-cyclopropyl-4,6-dimethoxypyrimidin-5-yl)-1-methyl-1H-pyrrolo[2,3-c]pyridin-5-yl)-2-fluorocyclopropane-1-carboxamide (Compound 100)

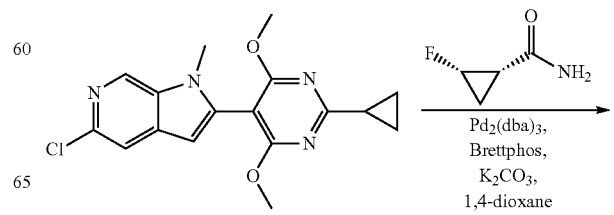

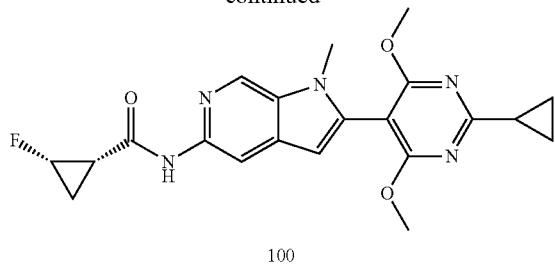

100

To a solution of 5-chloro-2-(2-cyclopropyl-4,6-dimethoxypyrimidin-5-yl)-1-methyl-1H-pyrrolo[2,3-c]pyridine (110.0 mg, 0.32 mmol) in 1,4-dioxane (8.0 mL) was added (1S,2S)-2-fluorocyclopropane-1-carboxamide (164.5 mg, 1.59 mmol), K$_2$CO$_3$ (132.3 mg, 0.96 mmol), BrettPhos (34.3 mg, 0.06 mmol) and Pd$_2$(dba)$_3$ (29.2 mg, 0.03 mmol) at room temperature under N$_2$. The resulting mixture was stirred at 100° C. for 3 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (9/91, v/v) and then purified by Prep-HPLC with the following conditions (Column: YMC-Actus Triart C18 ExRS, 30 mm×150 mm, 5 um; Mobile Phase A: Water (10 mmol/L NH$_4$HCO$_3$). Mobile Phase B: ACN; Flow rate: 60 mL/min; Gradient: 52% B to 62% B in 8 min; 254 nm) to afford (1S,2S)-N-(2-(2-cyclopropyl-4,6-dimethoxypyrimidin-5-yl)-1-methyl-1H-pyrrolo[2,3-c]pyridin-5-yl)-2-fluorocyclopropane-1-carboxamide (Compound 100) (7.7 mg, 6%) as a white solid. LCMS (ESI, m/z): [M+H]$^+$=412.2. $^1$H NMR (400 MHz, DMSO-d$_6$): δ 10.52 (s, 1H), 8.60 (s, 1H), 8.17 (s, 1H), 6.43 (s, 1H), 4.99-4.83 (m, 1H), 3.87 (s, 6H), 3.55 (s, 3H), 2.22-2.10 (m, 2H), 1.69-1.62 (m, 1H), 1.20-1.02 (m, 5H).

Example S101: Synthesis of (1S,2S)-2-fluoro-N-[2-(5-fluoro-2,4-dimethoxy-6-methylpyridin-3-yl)-1-methylpyrrolo[2,3-c]pyridin-5-yl]cyclopropane-1-carboxamide (Compound 101)

Step 1: Synthesis of 3-fluoro-5-iodo-4,6-dimethoxy-2-methylpyridine

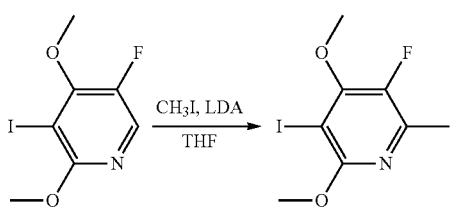

To a solution of 5-fluoro-3-iodo-2,4-dimethoxypyridine (500.0 mg, 1.77 mmol) in THF (40.0 mL) was added dropwise LDA (283.8 mg, 2.65 mmol) at −78° C. under N$_2$. The resulting mixture was stirred at −78° C. for 1 h under N$_2$. Then CH$_3$I (275.8 mg, 1.94 mmol) was added dropwise to the mixture at −78° C. under N$_2$. The resulting mixture was stirred at −78° C. for another 1 h under N$_2$. After the reaction was completed, the reaction mixture was quenched with saturated NH$_4$Cl (aq.). The reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (10/1, v/v) to afford 3-fluoro-5-iodo-4,6-dimethoxy-2-methylpyridine (600.0 mg, 85%) as a white solid. LCMS (ESI, m/z): [M+H]$^+$=298.0.

Step 2: Synthesis of 3-[5-chloro-1-methylpyrrolo[2,3-c]pyridin-2-yl]-5-fluoro-2,4-dimethoxy-6-methylpyridine

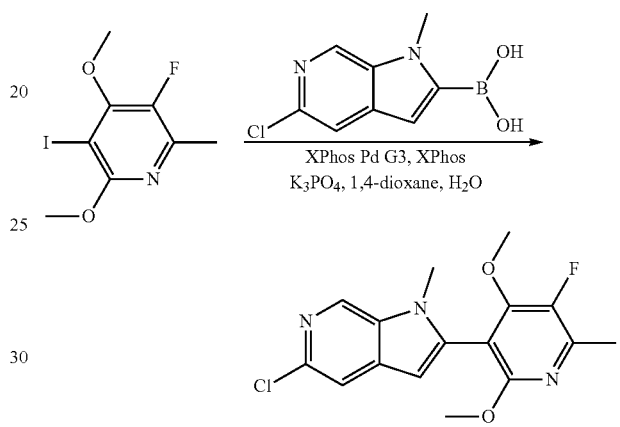

To a solution of 3-fluoro-5-iodo-4,6-dimethoxy-2-methylpyridine (520.0 mg, 1.75 mmol) in dioxane/H$_2$O (20.0 mL/4.0 mL) was added 5-chloro-1-methylpyrrolo[2,3-c]pyridin-2-ylboronic acid (368.3 mg, 1.75 mmol), K$_3$PO$_4$ (1114.7 mg, 5.25 mmol), XPhos Pd G3 (148.2 mg, 0.18 mmol) and X-Phos (166.9 mg, 0.35 mmol) at room temperature under N$_2$. The resulting mixture was stirred at 60° C. for 16 h under N$_2$. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 3-{5-chloro-1-methylpyrrolo[2,3-c]pyridin-2-yl}-5-fluoro-2,4-dimethoxy-6-methylpyridine (200.0 mg, 34%) as a white solid. LCMS (ESI, m/z): [M+H]$^+$=336.1.

Step 3: Synthesis of (1S,2S)-2-fluoro-N-[2-(5-fluoro-2,4-dimethoxy-6-methylpyridin-3-yl)-1-methylpyrrolo[2,3-c]pyridin-5-yl]cyclopropane-1-carboxamide (Compound 101)

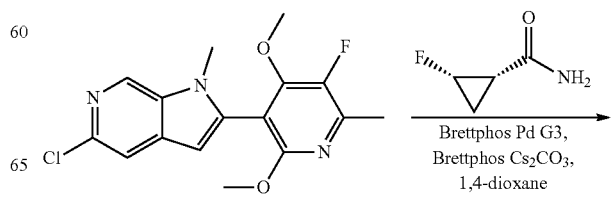

-continued

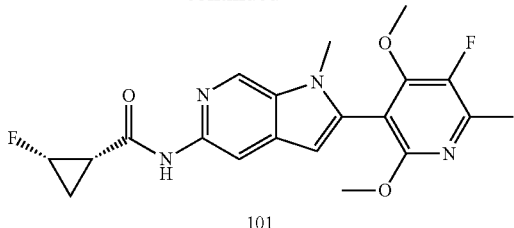

101

To a solution of 3-{5-chloro-1-methylpyrrolo[2,3-c]pyridin-2-yl}-5-fluoro-2,4-dimethoxy-6-methylpyridine (160.0 mg, 0.48 mmol) in 1,4-dioxane (15.0 mL) was added (1S,2S)-2-fluorocyclopropane-1-carboxamide (245.6 mg, 2.39 mmol), BrettPhos (51.2 mg, 0.10 mmol), $Cs_2CO_3$ (465.8 mg, 1.43 mmol) and BrettPhos Pd G3 (43.2 mg, 0.05 mmol) at room temperature under $N_2$. The resulting mixture was stirred at 100° C. for 16 h. After the reaction was completed, the reaction mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/2, v/v) and then purified by Prep-HPLC with the following conditions Column: (XBridge Prep OBD C18 Column. 30×150 mm, 5 um; Mobile Phase A:Water (10 mmol/L $NH_4HCO_3$), Mobile Phase B: ACN; Flow rate: 60 mL/min; Gradient: 45% B to 65% B in 9 min; 254 nm) to afford (1S,2S)-2-fluoro-N-[2-(5-fluoro-2,4-dimethoxy-6-methylpyridin-3-yl)-1-methylpyrrolo[2,3-c]pyridin-5-yl]cyclopropane-1-carboxamide (Compound 101) (8.6 mg, 4%) as a white solid. LCMS (ESI, m/z): $[M+H]^+$=403.1. $^1$H NMR (400 MHz, DMSO-$d_6$): δ 10.61 (s, 1H), 8.74 (s, 1H), 8.26 (s, 1H), 6.88 (d, J=2.8 Hz, 1H), 5.00-4.83 (m, 1H), 4.04 (s, 3H), 4.03 (s, 3H), 3.94 (s, 3H), 2.12-2.13 (m, 1H), 2.08 (s, 3H), 1.69-1.62 (m, 1H), 1.17-1.11 (m, 1H).

Example S102: Synthesis of (1S,2S)-2-fluoro-N-(1-methyl-2-(2,4,6-trimethoxypyrimidin-5-yl)-1H-pyrrolo[2,3-c]pyridin-5-yl)cyclopropane-1-carboxamide (Compound 102)

Step 1: Synthesis of 2,4,6-trimethoxypyrimidine

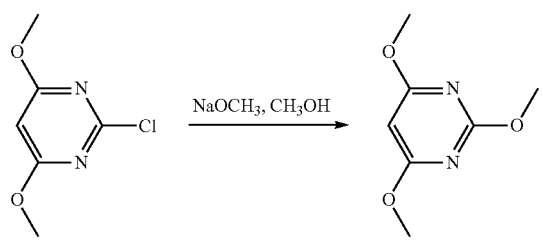

To a solution 2-chloro-4,6-dimethoxypyrimidine (5.0 g, 28.64 mmol) in $CH_3OH$ (100.0 mL) was added $NaOCH_3$ (3.1 g, 57.28 mmol) at room temperature. The resulting mixture was stirred at 40° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure to afford 2,4,6-trimethoxypyrimidine (4.6 g, crude) as a white solid. LCMS (ESI, m/z): $[M+H]^+$=171.1.

Step 2: Synthesis of 5-iodo-2,4,6-trimethoxypyrimidine

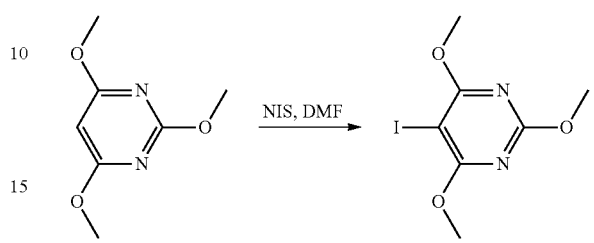

To a solution of 2,4,6-trimethoxypyrimidine (2.0 g, 11.75 mmol) in DMF (40.0 mL) was added NIS (5.3 g, 23.51 mmol) at room temperature. The resulting mixture was stirred at 80° C. for 16 h. After the reaction was completed, the resulting mixture was quenched with aq. $NaHSO_3$, diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (80/20, v/v) to afford 5-iodo-2,4,6-trimethoxypyrimidine (2.4 g, 68%) as a white solid. LCMS (ESI, m/z): $[M+H]^+$=297.0.

Step 3: Synthesis of 5-chloro-1-methyl-2-(2,4,6-trimethoxypyrimidin-5-yl)-1H-pyrrolo[2,3-c]pyridine

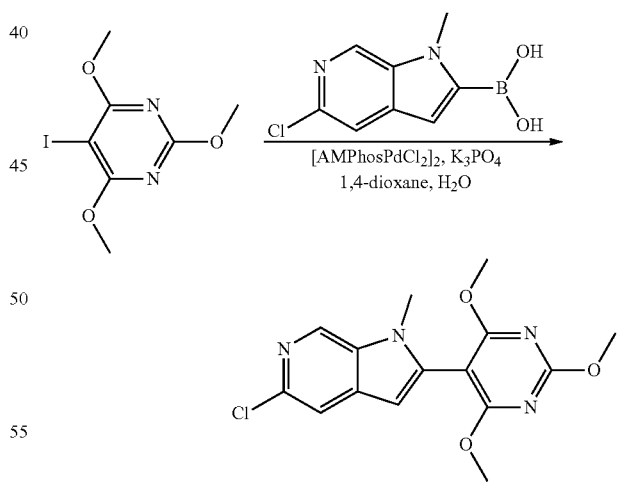

To a solution of 5-iodo-2,4,6-trimethoxypyrimidine (600.0 mg, 1.01 mmol) in 1,4-dioxane/$H_2O$ (20.0/5.0 mL) was added 5-chloro-1-methylpyrrolo[2,3-c]pyridin-2-ylboronic acid (426.4 mg, 1.01 mmol), $K_3PO_4$ (1.3 g, 0.20 mmol) and $[AMPhosPdCl_2]_2$ (143.6 mg, 0.10 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford 5-chloro-1-methyl-2-(2,4,6-trimethoxypyrimidin-5-yl)-1H-pyrrolo[2,3-c]pyridine (380.0 mg, 56%) as a white solid. LCMS (ESI, m/z): [M+H]$^+$=335.1.

Step 4: Synthesis of (1S,2S)-2-fluoro-N-(1-methyl-2-(2,4,6-trimethoxypyrimidin-5-yl)-1H-pyrrolo[2,3-c]pyridin-5-yl)cyclopropane-1-carboxamide (Compound 102)

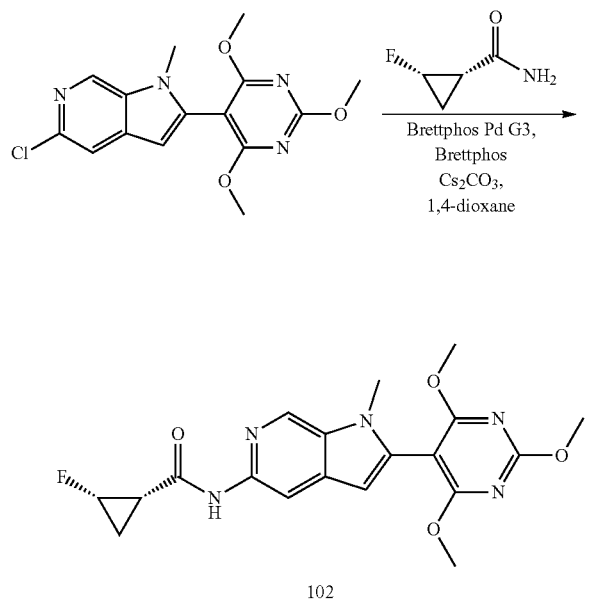

102

To a solution of 5-chloro-1-methyl-2-(2,4,6-trimethoxypyrimidin-5-yl)-1H-pyrrolo[2,3-c]pyridine (300.0 mg, 0.90 mmol) in 1,4-dioxane (5.0 mL) was added (1S,2S)-2-fluorocyclopropane-1-carboxamide (462.0 mg, 4.48 mmol), Cs$_2$CO$_3$ (876.0 mg, 2.69 mmol), BrettPhos (96.2 mg, 0.18 mmol) and BrettPhos Pd G$_3$ (81.2 mg, 0.09 mmol) at room temperature under N$_2$. The resulting mixture was stirred at 100° C. for 2 h under N$_2$. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (83/17, v/v) and then purified by Prep-HPLC with the following conditions (Column: XBridge Shield RP18 OBD Column 19×250 mm, 10 um; Mobile Phase A: Water (10 mmol/L NH$_4$HCO$_3$), Mobile Phase B: MeOH; Flow rate: 25 mL/min; Gradient: 55% B to 60% B in 10 min; 254 nm) to afford (1S,2S)-2-fluoro-N-(1-methyl-2-(2,4,6-trimethoxypyrimidin-5-yl)-1H-pyrrolo[2,3-c]pyridin-5-yl)cyclopropane-1-carboxamide (Compound 102) (13.3 mg, 3%) as a white solid. LCMS (ESI, m/z): [M+H]$^+$=402.4. $^1$H NMR (400 MHz, DMSO-d$_6$): δ 10.50 (s, 1H), 8.59 (s, 1H), 8.17 (s, 1H), 6.42 (s, 1H), 5.00-4.79 (m, 1H), 3.99 (s, 3H), 3.89 (s, 6H), 3.56 (s, 3H), 2.23-2.16 (m, 1H), 1.70-1.59 (m, 1H), 1.20-1.04 (m, 1H).

Example S103: Synthesis of (1S,2S)-N-(2-(2-amino-4,6-dimethoxypyrimidin-5-yl)-1-methyl-1H-pyrrolo[2,3-c]pyridin-5-yl)-2-fluorocyclopropane-1-carboxamide (Compound 103)

Step 1: Synthesis of Tert-butyl N-(tert-butoxycarbonyl)-N-(4,6-dimethoxypyrimidin-2-yl)carbamate

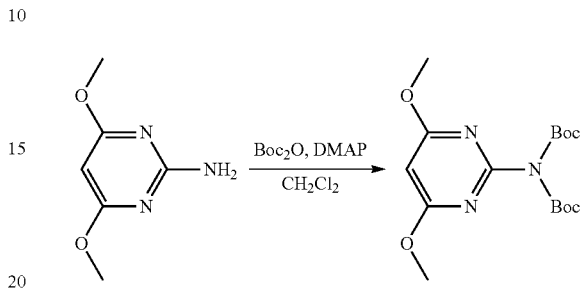

To a solution of 4,6-dimethoxypyrimidin-2-amine (1.0 g, 6.45 mmol) in CH$_2$Cl$_2$ (20.0 mL) was added Boc$_2$O (1.7 g, 7.73 mmol) and DMAP (0.8 g, 6.45 mmol) at room temperature. The resulting mixture was stirred at room temperature for 16 h. After the reaction was completed, the resulting mixture was concentrated under reduced pressure. The residue was purified by flash column chromatography with petroleum ether/ethyl acetate (90/10, v/v) to afford tert-butyl N-(tert-butoxycarbonyl)-N-(4,6-dimethoxypyrimidin-2-yl)carbamate (1.1 g, 48%) as a white solid. LCMS (ESI, m/z): [M+H]$^+$=356.2.

Step 2: Synthesis of Tert-butyl N-(tert-butoxycarbonyl)-N-(5-iodo-4,6-dimethoxypyrimidin-2-yl)carbamate

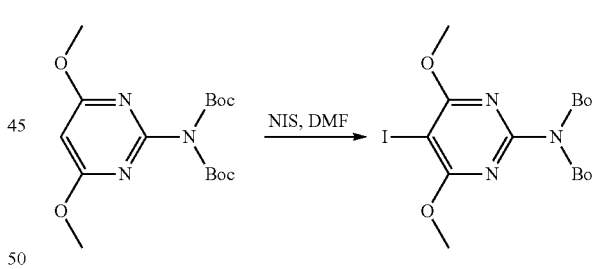

To a solution of tert-butyl N-(tert-butoxycarbonyl)-N-(4,6-dimethoxypyrimidin-2-yl)carbamate (1.0 g, 2.81 mmol) in DMF (20.0 mL) was added NIS (1.3 g, 5.63 mmol) at room temperature. The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (90/10, v/v) to afford tert-butyl N-(tert-butoxycarbonyl)-N-(5-iodo-4,6-dimethoxypyrimidin-2-yl)carbamate (880.0 mg, 65%) as a brown solid. LCMS (ESI, m/z): [M+H]$^+$=482.1.

Step 3: Synthesis of Tert-butyl N-(tert-butoxycarbonyl)-N-(5-(5-chloro-1-methylpyrrolo[2,3-c]pyridin-2-yl)-4,6-dimethoxypyrimidin-2-yl)carbamate

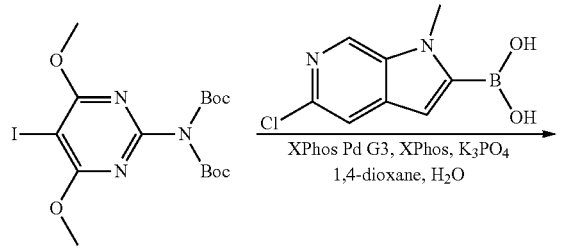

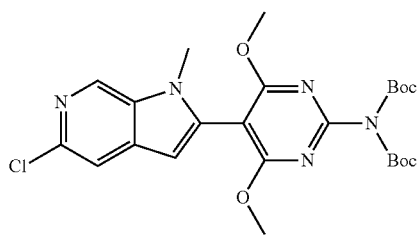

To a solution of tert-butyl N-(tert-butoxycarbonyl)-N-(5-iodo-4,6-dimethoxypyrimidin-2-yl)carbamate (410.0 mg, 0.85 mmol) in 1,4-dioxane/H₂O (10.0/5.0 mL) was added (5-chloro-1-methyl-1H-pyrrolo[2,3-c]pyridin-2-yl)boronic acid (215.1 mg, 1.02 mmol), K₃PO₄ (361.7 mg, 1.70 mmol), XPhos (81.2 mg, 0.17 mmol) and XPhos Pd G₃ (72.1 mg, 0.09 mmol) at room temperature under N₂. The resulting mixture was stirred at 60° C. for 4 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (60/40, v/v) to afford tert-butyl N-(tert-butoxycarbonyl)-N-(5-{5-chloro-1-methylpyrrolo[2,3-c]pyridin-2-yl}-4,6-dimethoxypyrimidin-2-yl)carbamate (320.0 mg, 72%) as a yellow solid. LCMS (ESI, m/z): [M+H]⁺=520.2.

Step 4: Synthesis of Tert-butyl N-(tert-butoxycarbonyl)-N-(5-(5-[(1S,2S)-2-fluorocyclopropaneamido]-1-methylpyrrolo[2,3-c]pyridin-2-yl)-4,6-dimethoxypyrimidin-2-yl)carbamate

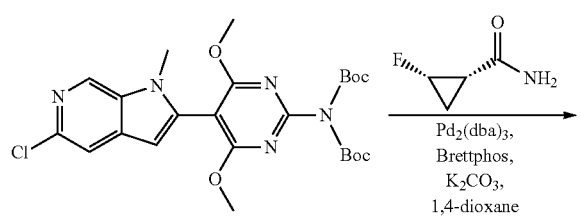

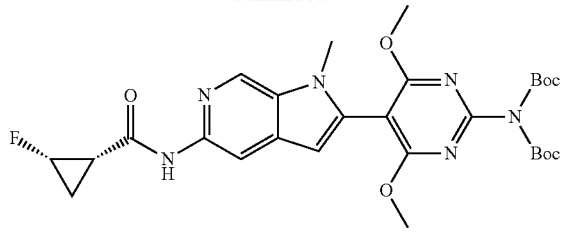

To a solution of tert-butyl N-(tert-butoxycarbonyl)-N-(5-{5-chloro-1-methylpyrrolo[2,3-c]pyridin-2-yl}-4,6-dimethoxypyrimidin-2-yl)carbamate (480.0 mg, 0.92 mmol) in 1,4-dioxane (10.0 mL) was added (1S,2S)-2-fluorocyclopropane-1-carboxamide (175.9 mg, 4.62 mmol), K₂CO₃ (382.7 mg, 2.78 mmol), BrettPhos (99.1 mg, 0.19 mmol) and Pd₂(dba)₃ (84.5 mg, 0.09 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford tert-butyl N-(tert-butoxycarbonyl)-N-(5-{5-[(1S,2S)-2-fluorocyclopropaneamido]-1-methylpyrrolo[2,3-c]pyridin-2-yl}-4,6-dimethoxypyrimidin-2-yl)carbamate (190.0 mg, 35%) as a brown solid. LCMS (ESI, m/z): [M+H]⁺=587.3.

Step 5: Synthesis of (1S,2S)-N-(2-(2-amino-4,6-dimethoxypyrimidin-5-yl)-1-methyl-1H-pyrrolo[2,3-c]pyridin-5-yl)-2-fluorocyclopropane-1-carboxamide (Compound 103)

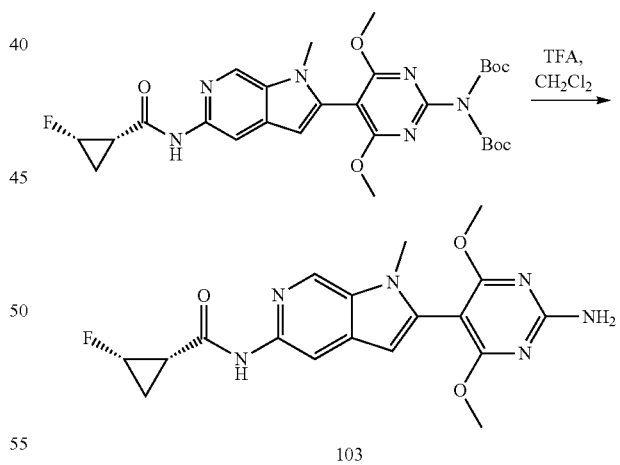

103

To a solution of tert-butyl N-(tert-butoxycarbonyl)-N-(5-{5-[(1S,2S)-2-fluorocyclopropaneamido]-1-methylpyrrolo[2,3-c]pyridin-2-yl}-4,6-dimethoxypyrimidin-2-yl)carbamate (170.0 mg, 0.29 mmol) in CH₂Cl₂ (2.0 mL) was added TFA (2.0 mL) at room temperature. The resulting mixture was stirred at room temperature for 2 h. After the reaction was completed, the resulting mixture was adjusted pH to 7 with aq. NaHCO₃ and then extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Shield RP18 OBD Column, 30×150 mm, 5 μm, Mobile Phase A: Water (10 mmol/L NH₄HCO₃), Mobile Phase B: MeOH—HPLC; Flow rate: 60 mL/min; Gradient: 39% B to 54% B in 8 min, 254 nm) to afford (1S,2S)-N-(2-(2-amino-4,6-dimethoxypyrimidin-5-yl)-1-methyl-1H-pyrrolo[2,3-c]pyridin-5-yl)-2-fluorocyclopropane-1-carboxamide (Compound 103) (23.7 mg, 21%) as a white solid. LCMS (ESI, m/z): [M+H]$^+$=387.3. $^1$H NMR (400 MHz, DMSO-d$_6$): δ 10.46 (s, 1H), 8.53 (s, 1H), 8.13 (s, 1H), 6.95 (s, 2H), 6.31 (s, 1H), 5.21-4.78 (m, 1H), 3.78 (s, 6H), 3.53 (s, 3H), 2.21-2.17 (m, 1H), 1.72-1.60 (m, 1H), 1.19-1.09 (m, 1H).

Example S104: Synthesis of (1S,2S)-N-(2-(2-(dimethylamino)-4,6-dimethoxypyrimidin-5-yl)-1-methyl-1H-pyrrolo[2,3-c]pyridin-5-yl)-2-fluorocyclopropane-1-carboxamide (Compound 104)

Step 1: Synthesis of 5-iodo-4,6-dimethoxypyrimidin-2-amine

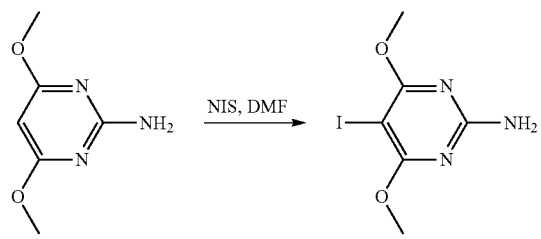

To a solution of 4,6-dimethoxypyrimidin-2-amine (2.0 g, 12.89 mmol) in DMF (40.0 mL) was added NIS (5.8 g, 25.78 mmol) at room temperature. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 5-iodo-4,6-dimethoxypyrimidin-2-amine (1.4 g, 38%) as a white solid. LCMS (ESI, m/z): [M+H]$^+$=282.0.

Step 2: Synthesis of 5-iodo-4,6-dimethoxy-N,N-dimethylpyrimidin-2-amine

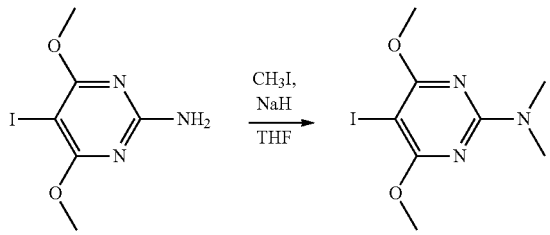

To a solution of 5-iodo-4,6-dimethoxypyrimidin-2-amine (1.3 g, 4.63 mmol) in THF (20.0 mL) was added NaH (666.7 mg, 60%) at 0° C. under N₂. The resulting mixture was stirred at 0° C. for 1 h under N₂. Then CH₃I (1.9 g, 13.88 mmol) was added dropwise to the mixture at 0° C. under N₂. The resulting mixture was stirred at 0° C. for 1 h. After the reaction was completed, the reaction mixture was quenched with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 5-iodo-4,6-dimethoxy-N,N-dimethylpyrimidin-2-amine (1.3 g, 90%) as a white solid. LCMS (ESI, m/z): [M+H]$^+$=310.0.

Step 3: Synthesis of 5-(5-chloro-1-methyl-1H-pyrrolo[2,3-c]pyridin-2-yl)-4,6-dimethoxy-N,N-dimethylpyrimidin-2-amine

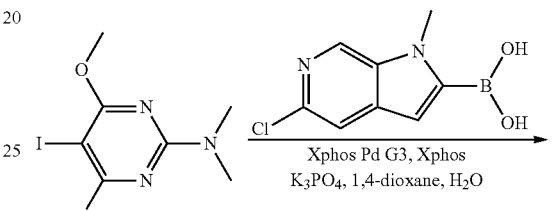

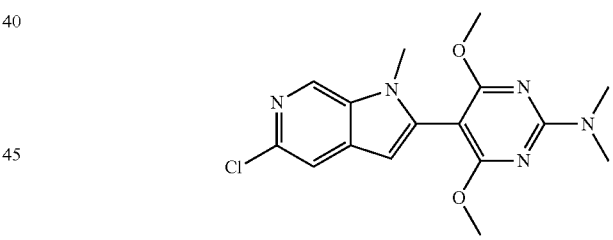

To a solution of 5-iodo-4,6-dimethoxy-N,N-dimethylpyrimidin-2-amine (300.0 mg, 0.97 mmol) in 1,4-dioxane/H₂O (16.0/4.0 mL) was added (5-chloro-1-methyl-1H-pyrrolo[2,3-c]pyridin-2-yl)boronic acid (204.2 mg, 0.97 mmol), K₃PO₄ (618.0 mg, 2.91 mmol), XPhos (92.5 mg, 0.19 mmol) and XPhos Pd G3 (82.2 mg, 0.10 mmol) at room temperature under N₂. The resulting mixture was stirred at 60° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (4/1, v/v) to afford 5-(5-chloro-1-methyl-1H-pyrrolo[2,3-c]pyridin-2-yl)-4,6-dimethoxy-N,N-dimethylpyrimidin-2-amine (320.0 mg, 94%) as a white solid. LCMS (ESI, m/z): [M+H]$^+$=348.1.

Step 4: Synthesis of (1S,2S)-N-(2-(2-(dimethylamino)-4,6-dimethoxypyrimidin-5-yl)-1-methyl-1H-pyrrolo[2,3-c]pyridin-5-yl)-2-fluorocyclopropane-1-carboxamide (Compound 104)

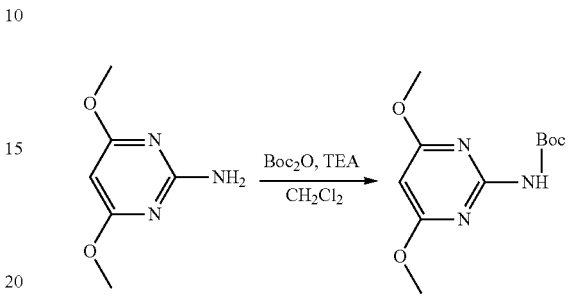

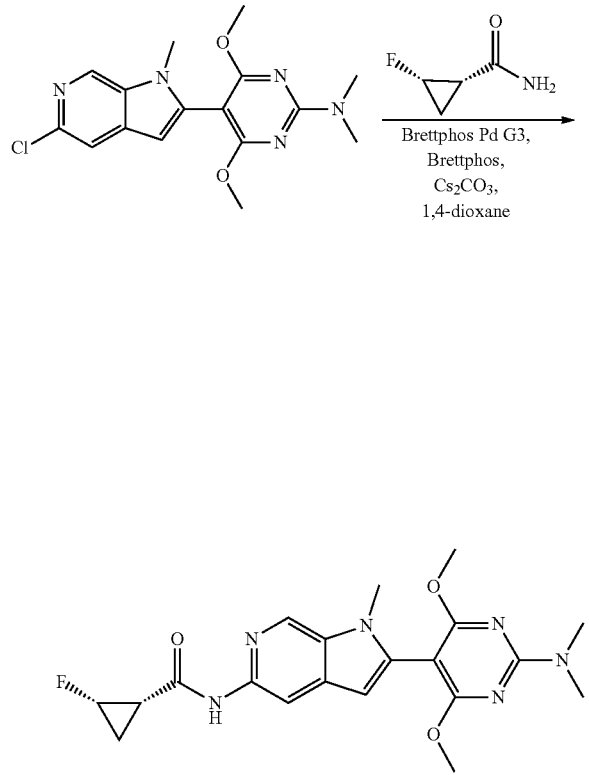

104

To a solution of 5-(5-chloro-1-methyl-1H-pyrrolo[2,3-c]pyridin-2-yl)-4,6-dimethoxy-N,N-dimethylpyrimidin-2-amine (200.0 mg, 0.57 mmol) in 1,4-dioxane (10.0 mL) was added (1S,2S)-2-fluorocyclopropane-1-carboxamide (296.4 mg, 2.88 mmol), Cs$_2$CO$_3$ (562.1 mg, 1.73 mmol), Brettphos (61.7 mg, 0.12 mmol) and Brettphos Pd G3 (52.1 mg, 0.06 mmol) at room temperature under N$_2$. The resulting mixture was stirred at 100° C. for 4 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/CH$_3$OH (10/1, v/v) and then purified by Prep-HPLC with the following conditions (Column: YMC-Actus Triart C18 ExRS, 30 mm×150 mm, 5 um; Mobile Phase A: Water (10 mmol/L NH$_4$HCO$_3$), Mobile Phase B: ACN; Flow rate: 60 mL/min; Gradient: 52% to 64% in 8 min; 254 nm) to afford (1S,2S)-N-(2-(2-(dimethylamino)-4,6-dimethoxypyrimidin-5-yl)-1-methyl-1H-pyrrolo[2,3-c]pyridin-5-yl)-2-fluorocyclopropane-1-carboxamide (Compound 104) (10.4 mg, 4%) as a white solid. LCMS (ESI, m/z): [M+H]$^+$=415.2. $^1$H NMR (400 MHz, DMSO-d$_6$): δ 10.47 (s, 1H), 8.54 (s, 1H), 8.14 (s, 1H), 6.32 (s, 1H), 4.99-4.80 (m, 1H), 3.84 (s, 6H), 3.54 (s, 3H), 3.20 (s, 6H), 2.22-2.18 (m, 1H), 1.68-1.61 (m, 1H), 1.24-1.15 (m, 1H).

Example S105: Synthesis of (1S,2S)-N-(2-(4,6-dimethoxy-2-(methylamino)pyrimidin-5-yl)-1-methyl-1H-pyrrolo[2,3-c]pyridin-5-yl)-2-fluorocyclopropane-1-carboxamide (Compound 105)

Step 1: Synthesis of Tert-butyl (4,6-dimethoxypyrimidin-2-yl)carbamate

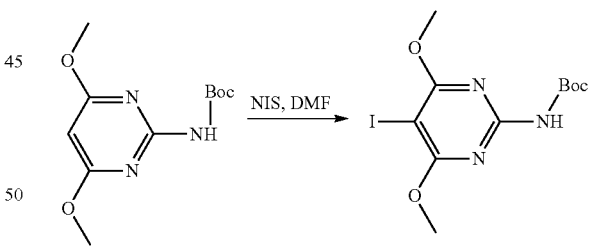

To a solution of 4,6-dimethoxypyrimidin-2-amine (5.0 g, 32.23 mmol) in CH$_2$Cl$_2$ (100 mL) was added Boc$_2$O (14.1 g, 64.45 mmol) and TEA (19.6 g, 193.35 mmol) at room temperature. The resulting mixture was stirred at 40° C. for 16 h. After the reaction was completed, the resulting mixture was diluted with H$_2$O and extracted with CH$_2$Cl$_2$. The combined organic layer was washed with brine, dried over anhydrous sodium sulfate and filtered. The filtrate was concentrated under reduced pressure. The residue was purified by flash column chromatography with petroleum ether/ethyl acetate (91/9, v/v) to afford tert-butyl (4,6-dimethoxypyrimidin-2-yl)carbamate (1.3 g, 22%) as a colorless oil. LCMS (ESI, m/z): [M+H]$^+$=256.1.

Step 2: Synthesis of Tert-butyl (5-iodo-4,6-dimethoxypyrimidin-2-yl)carbamate To a solution of tert-butyl (4,6-dimethoxypyrimidin-2-yl)carbamate (830.0 mg, 3.25 mmol) in DMF (10.0 mL) was added NIS (1.5 g, 6.54 mmol) at room temperature. The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (90/10, v/v) to afford tert-butyl (5-iodo-4,6-dimethoxypyrimidin-2-yl)carbamate (1.2 g, 99%) as a brown oil. LCMS (ESI, m/z): [M+H]$^+$=382.0.

Step 3: Synthesis of Tert-butyl (5-iodo-4,6-dimethoxypyrimidin-2-yl)(methyl)carbamate

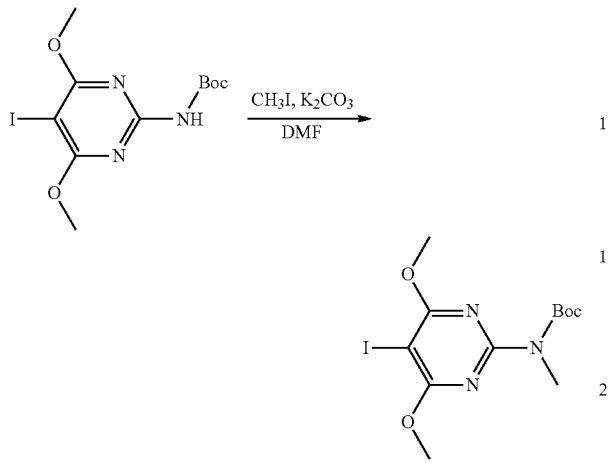

To a solution of tert-butyl (5-iodo-4,6-dimethoxypyrimidin-2-yl)carbamate (1.0 g, 2.62 mmol) in DMF (10.0 mL) was added $K_2CO_3$ (1.1 g, 7.87 mmol) and $CH_3I$ (0.5 g, 3.93 mmol) at room temperature. The resulting mixture was stirred at room temperature for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (90/10, v/v) to afford tert-butyl (5-iodo-4,6-dimethoxypyrimidin-2-yl)(methyl)carbamate (920.0 mg, 89%) as a white solid. LCMS (ESI, m/z): $[M+H]^+$=396.0.

Step 4: Synthesis of Tert-butyl (5-(5-chloro-1-methyl-1H-pyrrolo[2,3-c]pyridin-2-yl)-4,6-dimethoxypyrimidin-2-yl)(methyl)carbamate

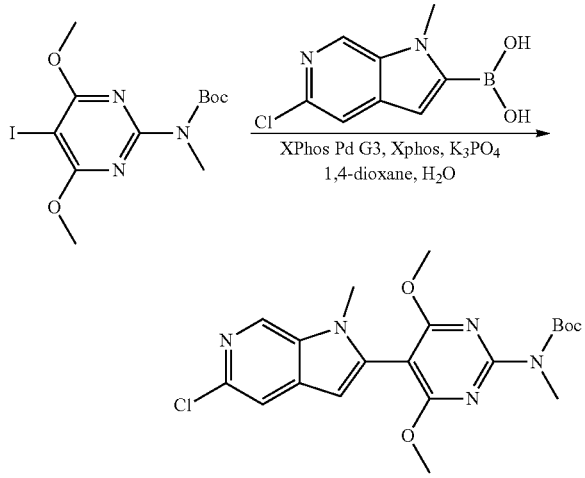

To a solution of tert-butyl (5-iodo-4,6-dimethoxypyrimidin-2-yl)(methyl)carbamate (460.0 mg, 1.16 mmol) in 1,4-dioxane/$H_2O$ (5.0/1.0 mL) was added (5-chloro-1-methyl-1H-pyrrolo[2,3-c]pyridin-2-yl)boronic acid (293.9 mg, 1.40 mmol), $K_3PO_4$ (494.2 mg, 2.33 mmol), XPhos (111.0 mg, 0.23 mmol) and XPhos Pd G3 (82.4 mg, 0.12 mmol) at room temperature under $N_2$. The resulting mixture was stirred at 60° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (86/14, v/v) to afford tert-butyl (5-(5-chloro-1-methyl-1H-pyrrolo[2,3-c]pyridin-2-yl)-4,6-dimethoxypyrimidin-2-yl)(methyl)carbamate (420.0 mg, 83%) as a brown solid. LCMS (ESI, m/z): $[M+H]^+$=434.2.

Step 5: Synthesis of Tert-butyl (5-(5-((1S,2S)-2-fluorocyclopropane-1-carboxamido)-1-methyl-1H-pyrrolo[2,3-c]pyridin-2-yl)-4,6-dimethoxypyrimidin-2-yl)(methyl)carbamate

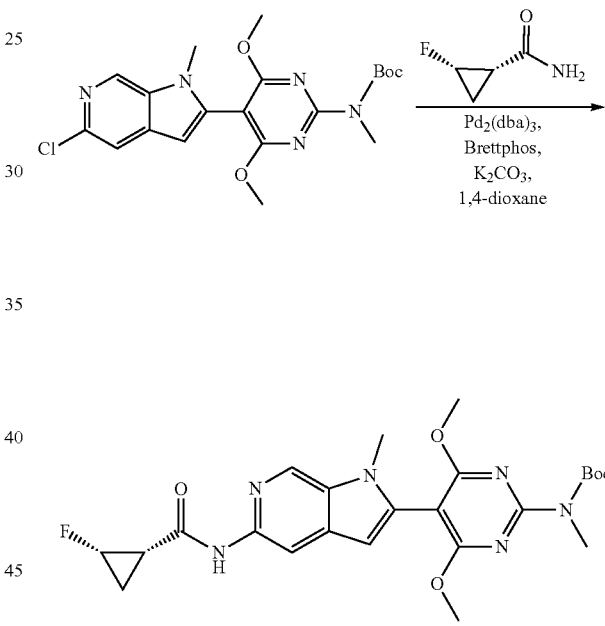

To a solution of tert-butyl (5-(5-chloro-1-methyl-1H-pyrrolo[2,3-c]pyridin-2-yl)-4,6-dimethoxypyrimidin-2-yl)(methyl)carbamate (340.0 mg, 0.78 mmol) in 1,4-dioxane (5.0 mL) was added (1S,2S)-2-fluorocyclopropane-1-carboxamide (403.9 mg, 3.92 mmol), $K_2CO_3$ (324.9 mg, 2.35 mmol), BrettPhos (84.1 mg, 0.16 mmol) and $Pd_2(dba)_3$ (71.8 mg, 0.08 mmol) at room temperature under $N_2$. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (50/50, v/v) to afford tert-butyl (5-(5-(((1S,2S)-2-fluorocyclopropane-1-carboxamido)-1-methyl-1H-pyrrolo[2,3-c]pyridin-2-yl)-4,6-dimethoxypyrimidin-2-yl)(methyl)carbamate (140.0 mg, 76%) as a yellow solid. LCMS (ESI, m/z): $[M+H]^+$=501.2.

Step 6: Synthesis of (1S,2S)-N-(2-(4,6-dimethoxy-2-(methylamino)pyrimidin-5-yl)-1-methyl-1H-pyrrolo[2,3-c]pyridin-5-yl)-2-fluorocyclopropane-1-carboxamide (Compound 105)

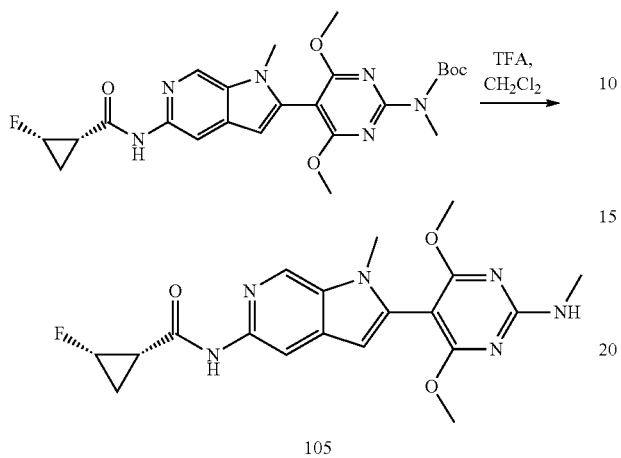

To a solution of tert-butyl (5-(5-(((1S,2S)-2-fluorocyclopropane-1-carboxamido)-1-methyl-1H-pyrrolo[2,3-c]pyridin-2-yl)-4,6-dimethoxypyrimidin-2-yl)(methyl)carbamate (120.0 mg, 0.24 mmol) in CH$_2$Cl$_2$ (2.0 mL) was added TFA (2.0 mL) at room temperature. The resulting mixture was stirred at room temperature for 1 h. After the reaction was completed, the resulting mixture was adjusted pH to 7 with aq. NaHCO$_3$ and then extracted with CH$_2$Cl$_2$. The combined organic layer was washed with brine, dried over anhydrous sodium sulfate and filtered. The filtrate was concentrated under reduced pressure. The residue was purified by Prep-HPLC with the following conditions (Column: Xselect CSH OBD Column 30×150 mm, 5 um; Mobile Phase A: Water (0.1% FA), Mobile Phase B: ACN; Flow rate: 60 mL/min; Gradient: 21% B to 31% B in 9 min, 254 nm) to afford (1S,2S)-N-(2-(4,6-dimethoxy-2-(methylamino)pyrimidin-5-yl)-1-methyl-1H-pyrrolo[2,3-c]pyridin-5-yl)-2-fluorocyclopropane-1-carboxamide (Compound 105) (17.6 mg, 18%) as a white solid. LCMS (ESI, m/z): [M+H]$^+$=401.3. $^1$H NMR (400 MHz, DMSO-d$_6$): δ 10.68 (s, 1H), 8.59 (s, 1H), 8.04 (s, 1H), 7.43 (d, J=4.8 Hz, 1H), 6.40 (s, 1H), 5.04-4.83 (m, 1H), 3.86-3.74 (m, 6H), 3.57 (s, 3H), 2.88 (d, J=4.8 Hz, 3H), 2.27-2.17 (m, 1H), 1.70-1.64 (m, 1H), 1.31-1.11 (m, 1H).

Example S106: Synthesis of (1S,2S)-2-fluoro-N-[2-(4-hydroxy-6-methoxypyrimidin-5-yl)-1-methylpyrrolo[2,3-c]pyridin-5-yl]cyclopropane-1-carboxamide (Compound 106)

Step 1: Synthesis of 4-methoxy-6-[(4-methoxyphenyl)methoxy]pyrimidine

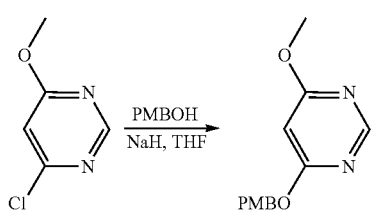

To a solution of PMBOH (955.7 mg, 6.92 mmol) in THF (15.0 mL) was added NaH (830.0 mg, 60%) at 0° C. under N$_2$. The resulting mixture was stirred at 0° C. for 1 h. Then a solution of 4-chloro-6-methoxypyrimidine (1.0 g, 6.92 mmol) in THF (5.0 mL) was added dropwise to the mixture at 0° C. under N$_2$. The resulting mixture was stirred at 0° C. for 1 h. After the reaction was completed, the resulting mixture was quenched with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (86/14, v/v) to afford 4-methoxy-6-[(4-methoxyphenyl)methoxy]pyrimidine (1.0 g, 59%) as a light yellow oil. LCMS (ESI, m/z): [M+H]$^+$=247.1.

Step 2: Synthesis of 5-iodo-4-methoxy-6-[(4-methoxyphenyl)methoxy]pyrimidine

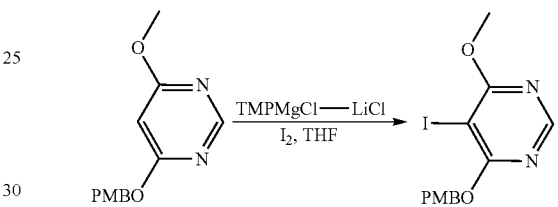

To a solution of 4-methoxy-6-[(4-methoxyphenyl)methoxy]pyrimidine (910.0 mg, 3.70 mmol) in THF (20.0 mL) was added dropwise TMPMgCl-LiCl (7.4 mL, 1 mol/L) at 0° C. under N$_2$. The resulting mixture was stirred at 0° C. for 1 h. Then a solution of I$_2$ (1.9 g, 7.40 mmol) in THF (10.0 mL) was added dropwise to the mixture at 0° C. under N$_2$. The resulting mixture was stirred at 0° C. for 30 min. After the reaction was completed, the resulting mixture was quenched with aq. NH$_4$Cl and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (80/20, v/v) to afford 5-iodo-4-methoxy-6-[(4-methoxyphenyl)methoxy]pyrimidine (880.0 mg, 63%) as a light yellow solid. LCMS (ESI, m/z): [M+H]$^+$=373.0.

Step 3: Synthesis of 5-{5-chloro-1-methylpyrrolo[2,3-c]pyridin-2-yl}-4-methoxy-6-[(4-methoxyphenyl)methoxy]pyrimidine

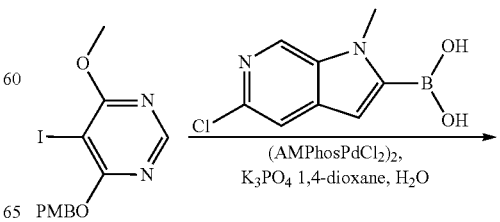

-continued

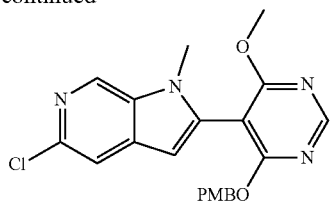

To a solution of 5-iodo-4-methoxy-6-[(4-methoxyphenyl)methoxy]pyrimidine (770.0 mg, 2.07 mmol) in 1,4-dioxane/H₂O (24.0/6.0 mL) was added 5-chloro-1-methylpyrrolo[2,3-c]pyridin-2-ylboronic acid (435.2 mg, 2.07 mmol), K₃PO₄ (1.3 g, 6.21 mmol) and (AMPhosPdCl)₂ (146.4 mg, 0.21 mmol) at room temperature under N₂. The resulting mixture was stirred at 100° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (60/40, v/v) to afford 5-{5-chloro-1-methylpyrrolo[2,3-c]pyridin-2-yl}-4-methoxy-6-[(4-methoxyphenyl)methoxy]pyrimidine (470.0 mg, 55%) as a light yellow solid. LCMS (ESI, m/z): [M+H]⁺=411.1.

Step 4: Synthesis of (1S,2S)-2-fluoro-N-(2-[4-methoxy-6-[(4-methoxyphenyl)methoxy]pyrimidin-5-yl]-1-methylpyrrolo[2,3-c]pyridin-5-yl)cyclopropane-1-carboxamide

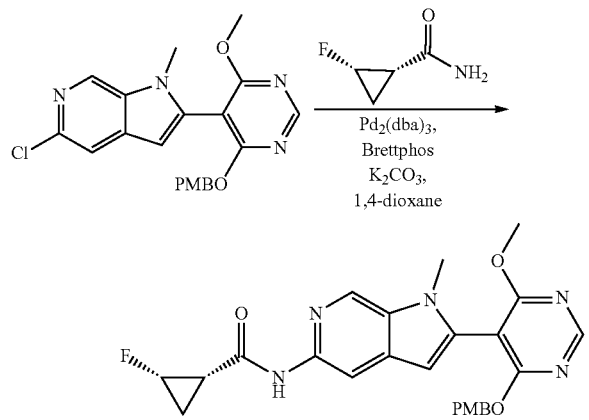

To a solution of 5-{5-chloro-1-methylpyrrolo[2,3-c]pyridin-2-yl}-4-methoxy-6-[(4-methoxyphenyl)methoxy]pyrimidine (390.0 mg, 0.95 mmol) in 1,4-dioxane (20.0 mL) was added (1S,2S)-2-fluorocyclopropane-1-carboxamide (489.3 mg, 4.75 mmol), K₂CO₃ (393.6 mg, 2.85 mmol), BrettPhos (101.9 mg, 0.19 mmol) and Pd₂(dba)₃ (86.92 mg, 0.10 mmol) at room temperature under N₂. The resulting mixture was stirred at 100° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/CH₃OH (97/3, v/v) to afford (1S,2S)-2-fluoro-N-(2-{4-methoxy-6-[(4-methoxyphenyl)methoxy]pyrimidin-5-yl}-1-methylpyrrolo[2,3-c]pyridin-5-yl)cyclopropane-1-carboxamide (290.0 mg, 64%) as a yellow solid. LCMS (ESI, m/z): [M+H]⁺=478.2.

Step 5: Synthesis of (1S,2S)-2-fluoro-N-[2-(4-hydroxy-6-methoxypyrimidin-5-yl)-1-methylpyrrolo[2,3-c]pyridin-5-yl]cyclopropane-1-carboxamide (Compound 106)

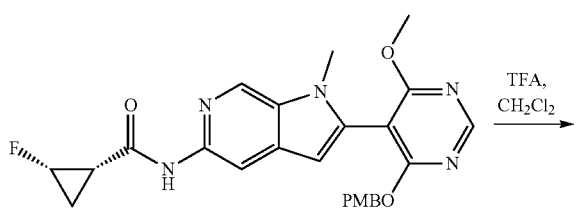

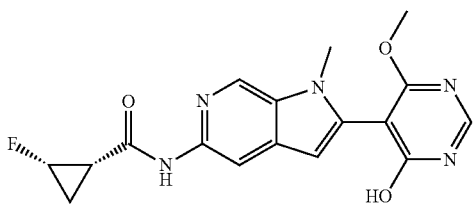

To a solution of (1S,2S)-2-fluoro-N-(2-{4-methoxy-6-[(4-methoxyphenyl)methoxy]pyrimidin-5-yl}-1-methylpyrrolo[2,3-c]pyridin-5-yl)cyclopropane-1-carboxamide (270.0 mg, 0.57 mmol) in CH₂Cl₂ (8.0 mL) was added TFA (2.0 mL) at room temperature. The resulting mixture was stirred at room temperature for 2 h. After the reaction was completed, the mixture was adjusted pH to 7.0 with aq. NaHCO₃. The resulting mixture was extracted with CH₂Cl₂. The combined organic layer was washed with brine, dried over anhydrous sodium sulfate and filtered. The filtrate was concentrated under reduced pressure. The residue was purified by flash column chromatography with CH₂Cl₂/CH₃OH (93/7, v/v) and then purified by Prep-HPLC with the following conditions (Column: XBridge Shield RP18 OBD Column, 30×150 mm, 5 μm; Mobile Phase A: Water (10 mmol/L NH₄HCO₃), Mobile Phase B: ACN; Flow rate: 60 mL/min; Gradient: 10% B to 20% B in 8 min; Wave Length: 254 nm) to afford (1S,2S)-2-fluoro-N-[2-(4-hydroxy-6-methoxypyrimidin-5-yl)-1-methylpyrrolo[2,3-c]pyridin-5-yl]cyclopropane-1-carboxamide (Compound 106) (7.6 mg, 3%) as a white solid. LCMS (ESI, m/z): [M+H]⁺=358.3. ¹H NMR (400 MHz, DMSO-d₆): δ 10.47 (s, 1H), 8.54 (s, 1H), 8.25 (s, 1H), 8.14 (s, 1H), 6.35 (s, 1H), 5.00-4.79 (m, 1H), 3.83 (s, 3H), 3.60 (s, 3H), 2.23-2.16 (m, 1H), 1.70-1.60 (m, 1H), 1.17-1.08 (m, 1H).

Example S107: Synthesis of (1S,2S)-N-[2-(3,5-dimethoxypyridazin-4-yl)-1-methylpyrrolo[2,3-c]pyridin-5-yl]-2-fluorocyclopropane-1-carboxamide (Compound 107)

Step 1: Synthesis of 4,5-dibromo-2-[(4-methoxyphenyl)methyl]pyridazin-3-one

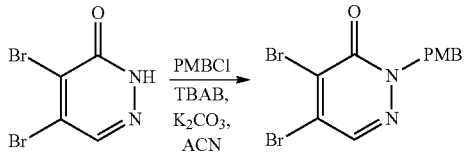

To a solution of 4,5-dibromo-2H-pyridazin-3-one (10.0 g, 39.39 mmol) in ACN (250.0 mL) was added PMBCl (7.4 g, 47.27 mmol), TBAB (1.3 g, 3.94 mmol) and $K_2CO_3$ (16.3 g, 118.17 mmol) at room temperature under $N_2$. The resulting mixture was stirred at 80° C. for 16 h. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 4,5-dibromo-2-[(4-methoxyphenyl)methyl]pyridazin-3-one (8.0 g, 54%) as a yellow solid. LCMS (ESI, m/z): $[M+H]^+=372.9$.

Step 2: Synthesis of 4-bromo-5-methoxy-2-[(4-methoxyphenyl)methyl]pyridazin-3-one

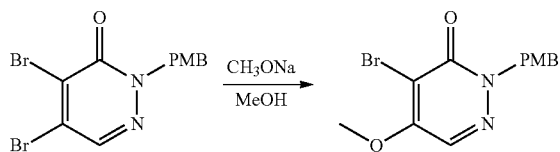

To a solution of 4,5-dibromo-2-[(4-methoxyphenyl)methyl]pyridazin-3-one (2.0 g, 5.35 mmol) in $CH_3OH$ (80.0 mL) was added NaOMe (866.6 mg, 16.04 mmol) at room temperature. The resulting mixture was stirred at 80° C. for 16 h. After the reaction was completed, the reaction mixture was concentrated under reduced pressure. The residue was purified by flash column chromatography with petroleum ether/ethyl acetate (1/1, v/v) to afford 4-bromo-5-methoxy-2-[(4-methoxyphenyl)methyl]pyridazin-3-one (750.0 mg, 43%) as a white solid. LCMS (ESI, m/z): $[M+H]^+=325.0$.

Step 3: Synthesis of 4-bromo-5-methoxy-2H-pyridazin-3-one

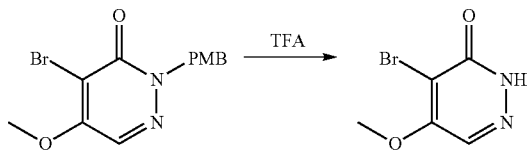

The solution of 4-bromo-5-methoxy-2-[(4-methoxyphenyl)methyl]pyridazin-3-one (730.0 mg, 2.24 mmol) in TFA (10.0 mL) was stirred at 80° C. for 16 h. After the reaction was completed, the reaction mixture was concentrated under reduced pressure to afford 4-bromo-5-methoxy-2H-pyridazin-3-one (300.0 mg, crude) as a green oil. LCMS (ESI, m/z): $[M+H]^+=205.0$.

Step 4: Synthesis of 4-bromo-3,5-dimethoxypyridazine

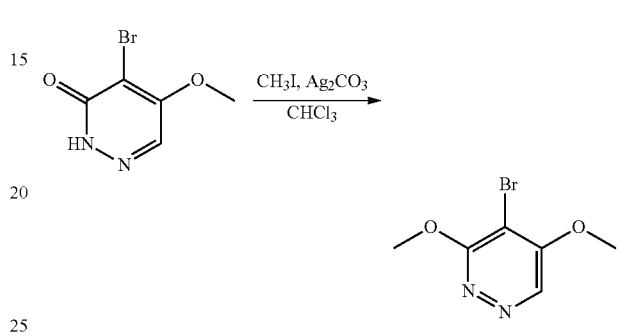

To a solution of 4-bromo-5-methoxy-2H-pyridazin-3-one (2.0 g, 9.76 mmol) in $CHCl_3$ (30.0 mL) was added $Ag_2CO_3$ (10.8 g, 39.02 mmol) and $CH_3I$ (11.1 g, 78.04 mmol) at room temperature. The resulting mixture was stirred at room temperature for 16 h. After the reaction was completed, the resulting mixture was filtered. The filtrate was concentrated under reduced pressure. The residue was purified by reverse phase flash chromatography with $ACN/H_2O$ (1/2, v/v) to afford 4-bromo-3,5-dimethoxypyridazine (100.0 mg, 4%) as a white solid. LCMS (ESI, m/z): $[M+H]^+=219.0$.

Step 5: Synthesis of 4-{5-chloro-1-methylpyrrolo[2,3-c]pyridin-2-yl}-3,5-dimethoxypyridazine

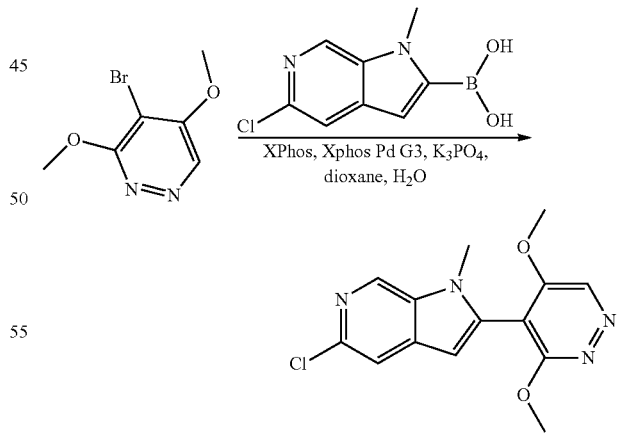

To a solution of 4-bromo-3,5-dimethoxypyridazine (220.0 mg, 1.00 mmol) in $dioxane/H_2O$ (10.0 mL/2.0 mL) was added 5-chloro-1-methylpyrrolo[2,3-c]pyridin-2-ylboronic acid (211.3 mg, 1.00 mmol), XPhos (95.8 mg, 0.20 mmol), $K_3PO_4$ (639.6 mg, 3.01 mmol) and XPhos Pd G3 (85.0 mg, 0.10 mmol) at room temperature under $N_2$. The resulting mixture was stirred at 60° C. for 2 h. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/MeOH (10/1, v/v) to afford 4-{5-chloro-1-methylpyrrolo[2,3-c]pyridin-2-yl}-3,5-dimethoxypyridazine (230.0 mg, 75%) as a yellow oil. LCMS (ESI, m/z): [M+H]$^+$=305.1.

Step 6: Synthesis of (1S,2S)-N-[2-(3,5-dimethoxypyridazin-4-yl)-1-methylpyrrolo[2,3-c]pyridin-5-yl]-2-fluorocyclopropane-1-carboxamide (Compound 107)

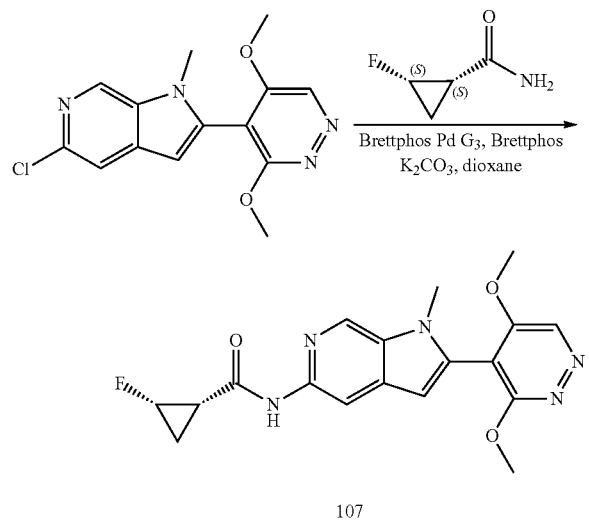

107

To a solution of 4-{5-chloro-1-methylpyrrolo[2,3-c]pyridin-2-yl}-3,5-dimethoxypyridazine (200.0 mg, 0.66 mmol) in 1,4-dioxane (10.0 mL) was added (1S,2S)-2-fluorocyclopropane-1-carboxamide (338.3 mg, 3.28 mmol), BrettPhos (84.4 mg, 0.16 mmol), Cs$_2$CO$_3$ (641.5 mg, 1.97 mmol) and BrettPhos Pd G3 (59.5 mg, 0.07 mmol) at room temperature under N$_2$. The resulting mixture was stirred at 100° C. for 16 h. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/MeOH (10/1, v/v) and then purified by Prep-HPLC with the following conditions Column (XBridge Prep OBD C18 Column, 30×150 mm, 5 μm A:Water (10 mmol/L NH$_4$HCO$_3$), Mobile Phase B: ACN; Flow rate: 60 mL/min; Gradient: 16% B to 36% B in 8 min; 254 nm) to afford (1S,2S)-N-[2-(3,5-dimethoxypyridazin-4-yl)-1-methylpyrrolo[2,3-c]pyridin-5-yl]-2-fluorocyclopropane-1-carboxamide (Compound 107) (15.5 mg, 6%) as a white solid. LCMS (ESI, m/z): [M+H]$^+$=372.1. $^1$H NMR (400 MHz, DMSO-d$_6$): δ 10.56 (s, 1H), 9.19 (s, 1H), 8.66 (s, 1H), 8.22 (s, 1H), 6.55 (s, 1H), 5.00-4.81 (m, 1H), 4.03 (s, 3H), 4.00 (s, 3H), 3.59 (s, 3H), 2.25-2.19 (m, 1H), 1.70-1.60 (m, 1H), 1.21-1.11 (m, 1H).

Example S108: Synthesis of (1S,2S)-2-fluoro-N-(2-(2-hydroxy-4,6-dimethoxypyrimidin-5-yl)-1-methyl-1H-pyrrolo[2,3-c]pyridin-5-yl)cyclopropane-1-carboxamide (Compound 108)

Step 1: Synthesis of 4,6-dimethoxy-2-((4-methoxybenzyl)oxy)pyrimidine

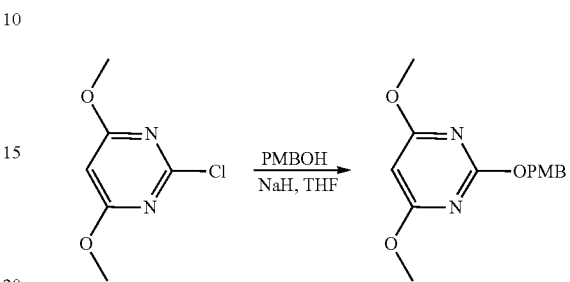

To a solution of (4-methoxyphenyl)methanol (0.8 g, 5.73 mmol) in THF (30.0 mL) was added NaH (0.4 g, 60%) at 0° C. under N$_2$. The resulting mixture was stirred at 0° C. for 30 min. To the above mixture was added 2-chloro-4,6-dimethoxypyrimidine (1.0 g, 5.73 mmol) at 0° C. under N$_2$. The resulting mixture was stirred at 0° C. for 1 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 4,6-dimethoxy-2-((4-methoxybenzyl)oxy)pyrimidine (1.1 g, 72%) as a yellow oil. LCMS (ESI, m/z): [M+H]$^+$=277.1.

Step 2: Synthesis of 5-iodo-4,6-dimethoxy-2-((4-methoxybenzyl)oxy)pyrimidine

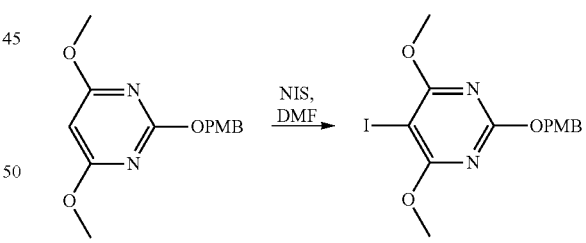

To a solution of 4,6-dimethoxy-2-((4-methoxybenzyl)oxy)pyrimidine (1.1 g, 3.98 mmol) in DMF (30.0 mL) was added NIS (1.8 g, 7.96 mmol) at room temperature. The resulting mixture was stirred at 80° C. for 16 h. After the reaction was completed, the reaction mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with dichloromethane/methanol (10/1, v/v) to afford 5-iodo-4,6-dimethoxy-2-((4-methoxybenzyl)oxy)pyrimidine (1.3 g, 81%) as a yellow solid. LCMS (ESI, m/z): [M+H]$^+$=403.0.

Step 3: Synthesis of 5-chloro-2-(4,6-dimethoxy-2-((4-methoxybenzyl)oxy)pyrimidin-5-yl)-1-methyl-1H-pyrrolo[2,3-c]pyridine

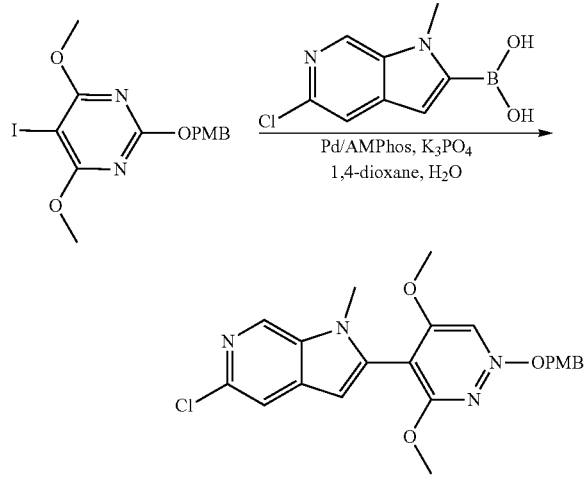

To a solution of 5-iodo-4,6-dimethoxy-2-[(4-methoxyphenyl)methoxy]pyrimidine (1.4 g, 3.36 mmol) in 1,4-dioxane (20.0 mL)/H₂O (5.0 mL) was added 5-chloro-1-methylpyrrolo[2,3-c]pyridin-2-ylboronic acid (706.3 mg, 3.36 mmol), K₃PO₄ (2.1 g, 10.07 mmol) and PdAMPhos (237.7 mg, 0.34 mmol) at room temperature under N₂. The resulting mixture was stirred at 100° C. for 2 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-chloro-2-(4,6-dimethoxy-2-((4-methoxybenzyl)oxy)pyrimidin-5-yl)-1-methyl-1H-pyrrolo[2,3-c]pyridine (1.3 g, 79%) as a yellow solid. LCMS (ESI, m/z): [M+H]⁺=441.1.

Step 4: Synthesis of (1S,2S)-N-(2-{4,6-dimethoxy-2-[(4-methoxyphenyl)methoxy]pyrimidin-5-yl}-1-methylpyrrolo[2,3-c]pyridin-5-yl)-2-fluorocyclopropane-1-carboxamide

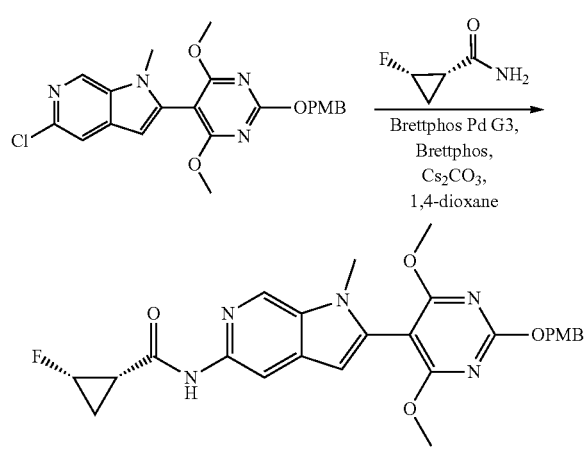

To a solution of 5-{5-chloro-1-methylpyrrolo[2,3-c]pyridin-2-yl}-4,6-dimethoxy-2-[(4-methoxyphenyl)methoxy]pyrimidine (900.0 mg, 2.04 mmol) in 1,4-dioxane (28.0 mL) was added (1S,2S)-2-fluorocyclopropane-1-carboxamide (1.1 g, 10.20 mmol), BrettPhos (219.2 mg, 0.41 mmol), Cs₂CO₃ (2.0 g, 6.12 mmol) and BrettPhos Pd G3 (185.0 mg, 0.20 mmol) at room temperature under N₂. The final reaction mixture was stirred with microwave for 120° C. for 1.5 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford (1S,2S)-N-(2-{4,6-dimethoxy-2-[(4-methoxyphenyl)methoxy]pyrimidin-5-yl}-1-methylpyrrolo[2,3-c]pyridin-5-yl)-2-fluorocyclopropane-1-carboxamide (450.0 mg, 43%) as a yellow solid. LCMS (ESI, m/z): [M+H]⁺=508.2.

Step 5: Synthesis of (1S,2S)-2-fluoro-N-(2-(2-hydroxy-4,6-dimethoxypyrimidin-5-yl)-1-methyl-1H-pyrrolo[2,3-c]pyridin-5-yl)cyclopropane-1-carboxamide (Compound 108)

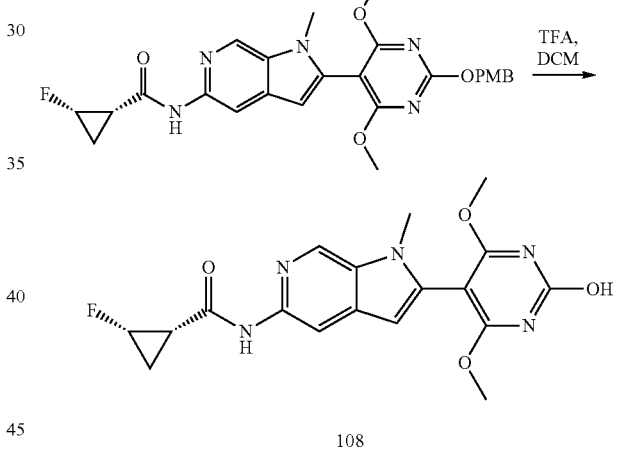

108

To a solution of (1S,2S)-2-fluoro-N-(2-{4-hydroxy-6-methoxy-2-[(4-methoxyphenyl)methoxy]pyrimidin-5-yl}-1-methylpyrrolo[2,3-c]pyridin-5-yl)cyclopropane-1-carboxamide (350.0 mg, 0.71 mmol) in DCM (8.0 mL) was added TFA (2.0 mL) at room temperature. The resulting mixture was stirred at room temperature for 1 h. After the reaction was completed, the resulting mixture was concentrated under reduced pressure. The residue was purified by Prep-HPLC with the following conditions (Column: XBridge Shield RP₁₈ OBD Column, 30×150 mm, 5 µm; Mobile Phase A: Water (10 mmol/L NH₄HCO₃), Mobile Phase B: ACN; Flow rate: 60 mL/min; Gradient: 10% B to 20% B in 8 min; Wave Length: 254 nm) to afford (1S,2S)-2-fluoro-N-(2-(2-hydroxy-4,6-dimethoxypyrimidin-5-yl)-1-methyl-1H-pyrrolo[2,3-c]pyridin-5-yl)cyclopropane-1-carboxamide (Compound 108) (18.3 mg, 6%) as a white solid. LCMS (ESI, m/z): [M+H]⁺=388.2. ¹H NMR (400 MHz, DMSO-d₆): δ 10.43 (s, 1H), 8.50 (s, 1H), 8.11 (s, 1H), 6.27 (s, 1H), 4.98-4.81 (m, 1H), 3.74 (s, 6H), 3.52 (s, 3H), 2.21-2.16 (m, 1H), 1.70-1.61 (m, 1H), 1.16-1.07 (m, 1H).

Example S109: Synthesis of (1S,2S)-2-fluoro-N-(2-(4-methoxy-6-(methylamino)pyrimidin-5-yl)-1-methyl-1H-pyrrolo[2,3-c]pyridin-5-yl)cyclopropane-1-carboxamide (Compound 109)

Step 1: Synthesis of 6-methoxy-N-methylpyrimidin-4-amine

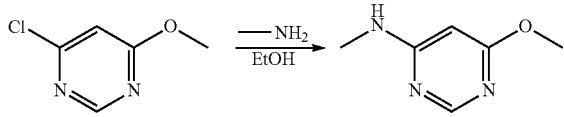

To a solution of 4-chloro-6-methoxypyrimidine (3.0 g, 20.75 mmol) in EtOH (60.0 mL) was added $CH_3NH_2$/EtOH (30.0 mL, 30%) at room temperature. The resulting mixture was stirred at 80° C. for 16 h. After the reaction was completed, the resulting mixture was concentrated under reduced pressure. The residue was purified by flash column chromatography with petroleum ether/ethyl acetate (10/1, v/v) to afford 6-methoxy-N-methylpyrimidin-4-amine (1.2 g, 41%) as a white solid. LCMS (ESI, m/z): [M+H]$^+$=140.1.

Step 2: Synthesis of 5-iodo-6-methoxy-N-methylpyrimidin-4-amine

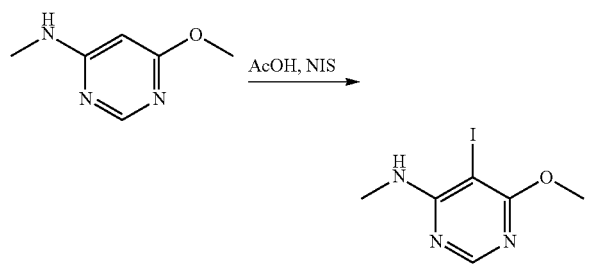

To a solution of 6-methoxy-N-methylpyrimidin-4-amine (1.2 g, 8.62 mmol) in AcOH (20.0 mL) was added NIS (3.8 g, 17.24 mmol) at room temperature. The resulting mixture was stirred at 50° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford 5-iodo-6-methoxy-N-methylpyrimidin-4-amine (1.1 g, 48%) as a yellow solid. LCMS (ESI, m/z): [M+H]$^+$= 266.0.

Step 3: Synthesis of Tert-buty (5-iodo-6-methoxypyrimidin-4-yl)(methyl)carbamate

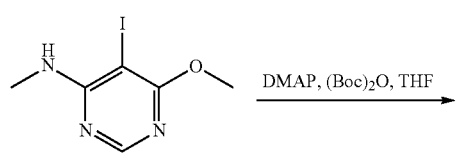

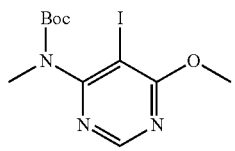

To a solution of 5-iodo-6-methoxy-N-methylpyrimidin-4-amine (1.0 g, 3.77 mmol) in THF (20.0 mL) was added (Boc)$_2$O (1.0 g, 4.53 mmol) and DMAP (0.5 g, 3.77 mmol) at room temperature. The resulting mixture was stirred at 70° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $H_2O/CH_3CN$ (2/3, v/v) to afford tert-butyl (5-iodo-6-methoxypyrimidin-4-yl)(methyl)carbamate (600.0 mg, 43%) as a yellow oil. LCMS (ESI, m/z): [M+H]$^+$= 366.0.

Step 4: Synthesis of Tert-butyl(5-(5-chloro-1-methyl-1H-pyrrolo[2,3-c]pyridin-2-yl)-6-methoxy-pyrimidin-4-yl)(methyl)carbamate

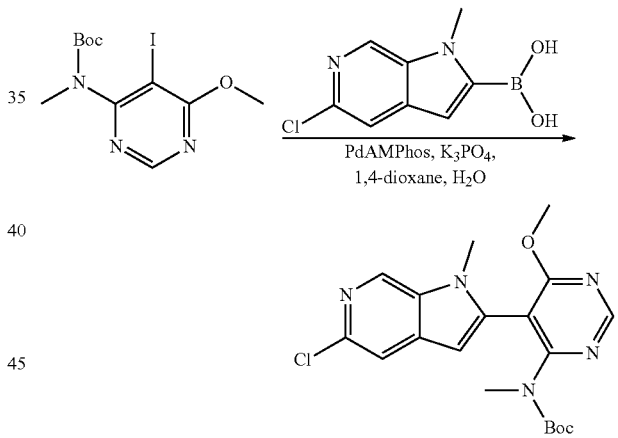

To a solution of tert-butyl (5-iodo-6-methoxypyrimidin-4-yl)(methyl)carbamate (1.8 g, 4.92 mmol) in 1,4-dioxane/$H_2O$ (16.0/4.0 mL) was added (5-chloro-1-methyl-1H-pyrrolo[2,3-c]pyridin-2-yl)boronic acid (1.0 g, 4.92 mmol), PdAMPhos (0.4 g, 0.49 mmol) and $K_3PO_4$ (3.1 g, 14.78 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $H_2O/CH_3CN$ (1/1, v/v) to afford tert-butyl (5-(5-chloro-1-methyl-1H-pyrrolo[2,3-c]pyridin-2-yl)-6-methoxypyrimidin-4-yl)(methyl)carbamate (600.0 mg, 30%) as a yellow solid. LCMS (ESI, m/z): [M+H]$^+$=404.1.

Step 5: Synthesis of Tert-butyl 5-(5-((1S,2S)-2-fluorocyclopropanecarboxamido)-1-methyl-1H-pyrrolo[2,3-c]pyridin-2-yl)-6-methoxypyrimidin-4-yl(methyl)carbamate

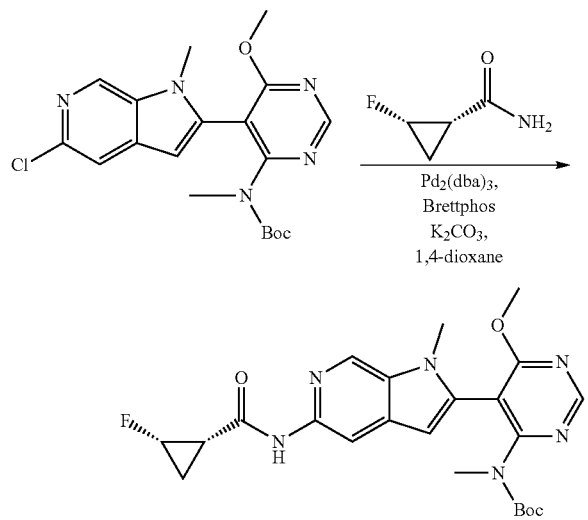

To a solution of tert-butyl (5-(5-chloro-1-methyl-1H-pyrrolo[2,3-c]pyridin-2-yl)-6-methoxypyrimidin-4-yl)(methyl)carbamate (700.0 mg, 1.73 mmol) in 1,4-dioxane (10.0 mL) was added (1S,2S)-2-fluorocyclopropane-1-carboxamide (893.4 mg, 8.66 mmol), Pd$_2$(dba)$_3$ (158.7 mg, 0.17 mmol), Brettphos (186.0 mg, 0.34 mmol) and K$_2$CO$_3$ (718.6 mg, 5.19 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/1, v/v) to afford tert-butyl (5-(5-((1S,2S)-2-fluorocyclopropane-1-carboxamido)-1-methyl-1H-pyrrolo[2,3-c]pyridin-2-yl)-6-methoxypyrimidin-4-yl)(methyl)carbamate (100.0 mg, 12%) as a yellow solid. LCMS (ESI, m/z): [M+H]$^+$=471.2.

Step 6: Synthesis of (1S,2S)-2-fluoro-N-(2-(4-methoxy-6-(methylamino)pyrimidin-5-yl)-1-methyl-1H-pyrrolo[2,3-c]pyridin-5-yl)cyclopropane-1-carboxamide (Compound 109)

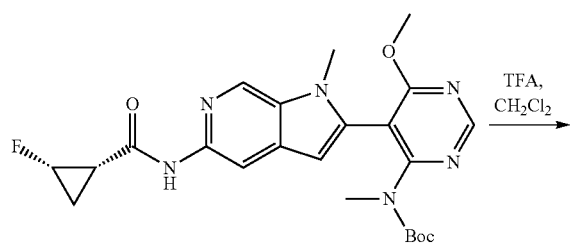

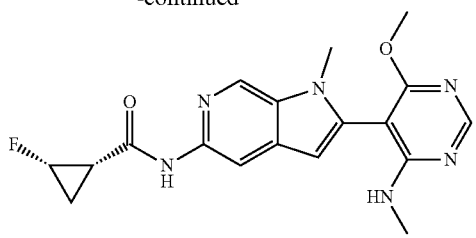

To a solution of tert-butyl (5-(5-((1S,2S)-2-fluorocyclopropane-1-carboxamido)-1-methyl-1H-pyrrolo[2,3-c]pyridin-2-yl)-6-methoxypyrimidin-4-yl)(methyl)carbamate (100.0 mg, 0.21 mmol) in CH$_2$Cl$_2$ (2.0 mL) was added TFA (2.0 mL) at room temperature. The resulting mixture was stirred at room temperature for 3 h. The mixture was concentrated under reduced pressure. The residue was purified by Prep-HPLC with the following conditions (Column: XBridge Prep OBD C18 Column, 30×150 mm, 5 um; Mobile Phase A: Water (10 mmol/L NH$_4$HCO$_3$), Mobile Phase B: ACN; Flow rate: 60 mL/min; Gradient: 24% to 24% in 8 min; 254 nm) to afford (1S,2S)-2-fluoro-N-(2-(4-methoxy-6-(methylamino)pyrimidin-5-yl)-1-methyl-1H-pyrrolo[2,3-c]pyridin-5-yl)cyclopropane-1-carboxamide (Compound 109) (11.5 mg, 11%) as a white solid. LCMS (ESI, m/z): [M+H]$^+$=371.3. $^1$H NMR (400 MHz, DMSO-d$_6$): δ 10.51 (d, J=2.8 Hz, 1H), 8.61 (s, 1H), 8.36 (s, 1H), 8.20 (s, 1H), 6.46 (s, 2H), 4.99-4.82 (m, 1H), 3.80 (s, 3H), 3.53 (s, 3H), 2.78-2.73 (m, 3H), 2.23-2.18 (m, 1H), 1.70-1.61 (m, 1H), 1.15-1.06 (m, 1H).

Example S110: Synthesis of (1S,2S)-N-(2-(4-(cyclopropylamino)-6-methoxypyrimidin-5-yl)-1-methyl-1H-pyrrolo[2,3-c]pyridin-5-yl)-2-fluorocyclopropane-1-carboxamide (Compound 110)

Step 1: Synthesis of 4-chloro-6-methoxypyrimidine

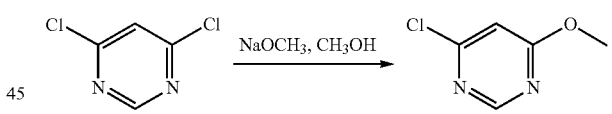

To a solution of 4,6-dichloropyrimidine (5.0 g, 33.56 mmol) in CH$_3$OH (50.0 mL) was added NaOCH$_3$ (1.8 g, 33.56 mmol) at room temperature. The resulting mixture was stirred at 40° C. for 16 h. After the reaction was completed, the resulting mixture was quenched with H$_2$O and extracted with ethyl acetate. The combined organic layer was washed with brine, dried over anhydrous sodium sulfate and filtered. The filtrate was concentrated under reduced pressure to afford 4-chloro-6-methoxypyrimidine (4.0 g, crude) as a white solid. LCMS (ESI, m/z): [M+H]$^+$=145.0.

Step 2: Synthesis of N-cyclopropyl-6-methoxypyrimidin-4-amine

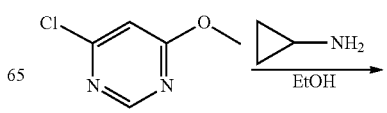

-continued

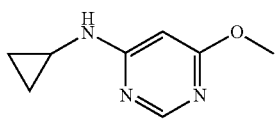

To a solution of 4-chloro-6-methoxypyrimidine (2.0 g, 13.84 mmol) in EtOH (20.0 mL) was added cyclopropanamine (2.37 g, 41.51 mmol) at room temperature. The resulting mixture was stirred at 80° C. for 16 h. After the reaction was completed, the resulting mixture was concentrated under reduced pressure. The residue was purified by flash column chromatography with petroleum ether/ethyl acetate (1/1, v/v) to afford N-cyclopropyl-6-methoxypyrimidin-4-amine (1.3 g, 56%) as a white solid. LCMS (ESI, m/z): [M+H]$^+$=166.1.

Step 3: Synthesis of N-cyclopropyl-5-iodo-6-methoxypyrimidin-4-amine

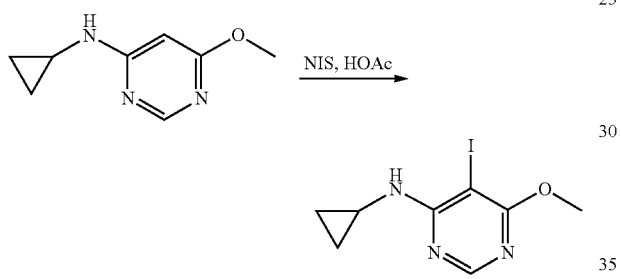

To a solution of N-cyclopropyl-6-methoxypyrimidin-4-amine (500.0 mg, 3.02 mmol) in HOAc (20.0 mL) was added NIS (1.4 g, 6.05 mmol) at room temperature. The resulting mixture was stirred at 50° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford N-cyclopropyl-5-iodo-6-methoxypyrimidin-4-amine (300.0 mg, 34%) as a yellow solid. LCMS (ESI, m/z): [M+H]$^+$=292.0.

Step 4: Synthesis of 5-(5-chloro-1-methyl-1H-pyrrolo[2,3-c]pyridin-2-yl)-N-cyclopropyl-6-methoxypyrimidin-4-amine

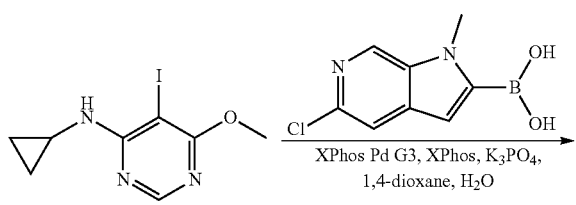

-continued

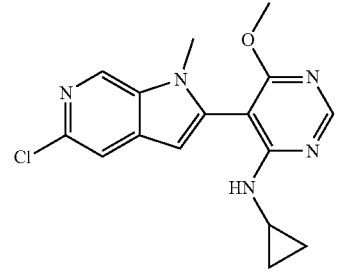

To a solution of N-cyclopropyl-5-iodo-6-methoxypyrimidin-4-amine (220.0 mg, 0.76 mmol) in 1,4-dioxane/H$_2$O (16.0/4.0 mL) was added (5-chloro-1-methyl-1H-pyrrolo[2,3-c]pyridin-2-yl)boronic acid (159.0 mg, 0.76 mmol), K$_3$PO$_4$ (481.3 mg, 2.27 mmol), XPhos (72.1 mg, 0.15 mmol) and XPhos Pd G3 (64.0 mg, 0.08 mmol) at room temperature under N$_2$. The resulting mixture was stirred at 60° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-(5-chloro-1-methyl-1H-pyrrolo[2,3-c]pyridin-2-yl)-N-cyclopropyl-6-methoxypyrimidin-4-amine (240.0 mg, 96%) as a yellow solid. LCMS (ESI, m/z): [M+H]$^+$=330.1.

Step 5: Synthesis of (1S,2S)-N-(2-(4-(cyclopropylamino)-6-methoxypyrimidin-5-yl)-1-methyl-1H-pyrrolo[2,3-c]pyridin-5-yl)-2-fluorocyclopropane-1-carboxamide (Compound 110)

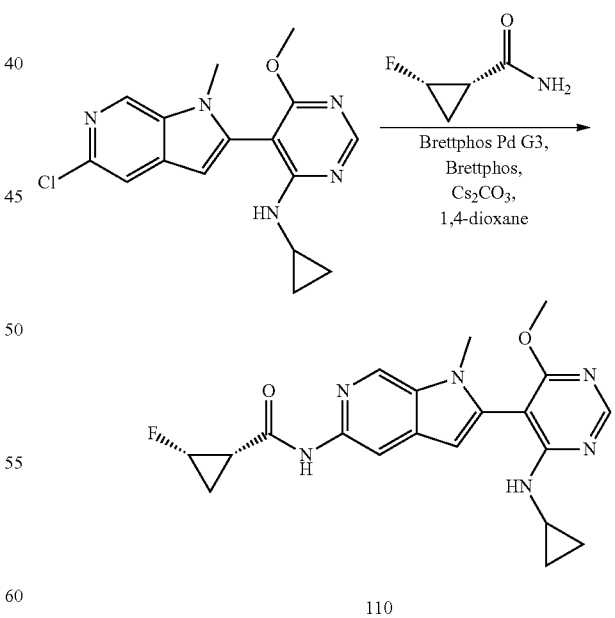

110

To a solution of 5-(5-chloro-1-methyl-1H-pyrrolo[2,3-c]pyridin-2-yl)-N-cyclopropyl-6-methoxypyrimidin-4-amine (160.0 mg, 0.49 mmol) in 1,4-dioxane (10.0 mL) was added (1S,2S)-2-fluorocyclopropane-1-carboxamide (250.1 mg, 0.49 mmol), Cs$_2$CO$_3$ (474.2 mg, 1.46 mmol). Brettphos (52.1 mg, 0.10 mmol) and Brettphos Pd G3 (44.0 mg, 0.05 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/CH$_3$OH (10/1, v/v) and then purified by Prep-HPLC with the following conditions (Column: XBridge Prep OBD C18 Column. 30×150 mm, 5 um; Mobile Phase A: Water (10 mmol/L NH$_4$HCO$_3$), Mobile Phase B: MeOH—HPLC; Flow rate: 60 mL/min; Gradient: 42% to 48% in 8 min; 254 nm) to afford (1S,2S)-N-(2-(4-(cyclopropylamino)-6-methoxypyrimidin-5-yl)-1-methyl-1H-pyrrolo[2,3-c]pyridin-5-yl)-2-fluorocyclopropane-1-carboxamide (Compound 110) (3.4 mg, 1%) as a white solid. LCMS (ESI, m/z): [M+H]$^+$=397.3. $^1$H NMR (300 MHz, DMSO-d$_6$): δ 10.49 (s, 1H), 8.59 (s, 1H), 8.40 (s, 1H), 8.19 (s, 1H), 6.57 (s, 1H), 6.42 (s, 1H), 5.02-4.79 (m, 1H), 3.80 (s, 3H), 3.55 (s, 3H), 2.78-2.73 (m, 1H), 2.22-2.18 (m, 1H), 1.72-1.60 (m, 1H), 1.19-1.03 (m, 1H), 0.67-0.58 (m, 2H), 0.53-0.41 (m, 2H).

Example S111: Synthesis of (1S,2S)-N-(2-(4,6-bis(methoxy-d3)pyrimidin-5-yl)-1-(methyl-d3)-1H-pyrrolo[2,3-c]pyridin-5-yl)-2-fluorocyclopropane-1-carboxamide (Compound 111)

Step 1: Synthesis of 5-bromo-4,6-bis(methoxy-d3)pyrimidine

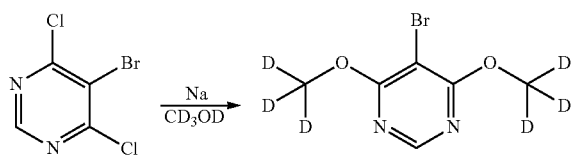

A solution of Na (500.0 mg, 21.94 mmol) in CD$_3$OD (11.0 mL) was stirred at room temperature for 0.5 h. Then 5-bromo-4,6-dichloropyrimidine (1.0 g, 4.39 mmol) was added to the mixture at room temperature. The resulting mixture was stirred at 40° C. for 16 h. After the reaction was completed, the reaction was quenched with H$_2$O and extracted with ethyl acetate. The combined organic layer was washed with brine, dried over anhydrous sodium sulfate and filtered. The filtrate was concentrated under reduced pressure to afford 5-bromo-4,6-bis(methoxy-d3)pyrimidine (980.0 mg, crude) as a white solid. LCMS (ESI, m/z): [M+H]$^+$=225.0.

Step 2: Synthesis of 2-(4,6-bis(methoxy-d3)pyrimidin-5-yl)-5-chloro-1-(methyl-d3)-1H-pyrrolo[2,3-c]pyridine

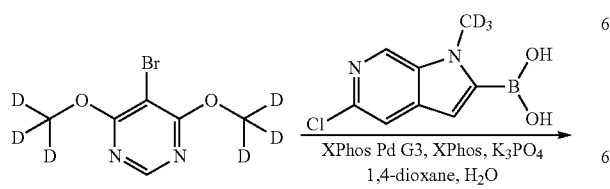

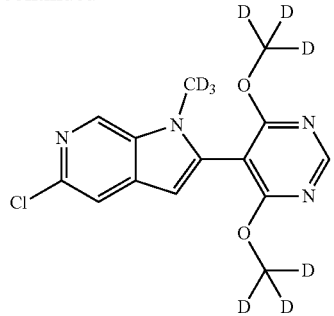

To a solution of 5-bromo-4,6-bis(methoxy-d3)pyrimidine (980.0 mg, 4.38 mmol) in 1,4-dioxane/H$_2$O (10.0/2.0 mL) was added 5-chloro-1-(methyl-d3)-1H-pyrrolo[2,3-c]pyridin-2-ylboronic acid (933.3 mg, 4.38 mmol), K$_3$PO$_4$ (2785.7 mg, 13.14 mmol), XPhos (834.0 mg, 1.75 mmol) and XPhos Pd G3 (741.0 mg, 0.88 mmol) at room temperature under N$_2$. The resulting mixture was stirred at 60° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (47/53, v/v) to afford 2-(4,6-bis(methoxy-d3)pyrimidin-5-yl)-5-chloro-1-(methyl-d3)-1H-pyrrolo[2,3-c]pyridine (310.0 mg, 22%) as a white solid. LCMS (ESI, m/z): [M+H]$^+$=314.1.

Step 3: Synthesis of (1S,2S)-N-(2-(4,6-bis(methoxy-d3)pyrimidin-5-yl)-1-(methyl-d3)-1H-pyrrolo[2,3-c]pyridin-5-yl)-2-fluorocyclopropane-1-carboxamide (Compound 111)

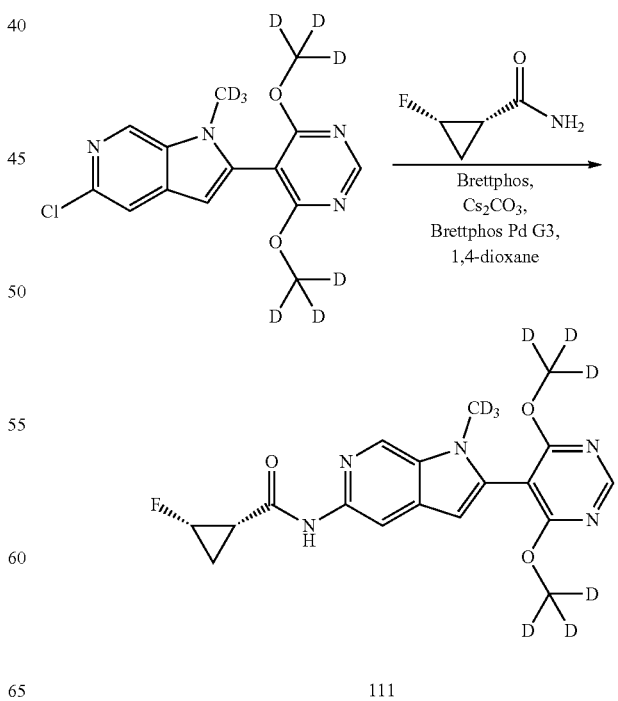

111

To a solution of 2-(4,6-bis(methoxy-d3)pyrimidin-5-yl)-5-chloro-1-(methyl-d3)-1H-pyrrolo[2,3-c]pyridine (120.0 mg, 0.38 mmol) in 1,4-dioxane (10.0 mL) was added (1S,2S)-2-fluorocyclopropane-1-carboxamide (39.4 mg, 0.382 mmol). Cs₂CO₃ (373.8 mg, 1.15 mmol), BrettPhos (82.1 mg, 0.15 mmol) and BrettPhos Pd G3 (69.3 mg, 0.08 mmol) at room temperature under N₂. The resulting mixture was stirred at 100° C. for 3 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (10/90, v/v) and then purified by Prep-HPLC with the following conditions (Column: XBridge Prep OBD C18 Column, 30×150 mm, 5 μm; Mobile Phase A: Water (10 mmol/L NH₄HCO₃). Mobile Phase B: ACN; Flow rate: 60 mL/min; Gradient: 25% B to 35% B in 8 min; Wave Length: 254 nm) to afford (1S,2S)-N-(2-(4,6-bis(methoxy-d3)pyrimidin-5-yl)-1-(methyl-d3)-1H-pyrrolo[2,3-c]pyridin-5-yl)-2-fluorocyclopropane-1-carboxamide (Compound 111) (3.1 mg, 2%) as a white solid. LCMS (ESI, m/z): [M+H]⁺=381.3. ¹H NMR (400 MHz, DMSO-d₆): δ 10.52 (s, 1H), 8.66-8.63 (m, 2H), 8.20 (s, 1H), 6.50 (s, 1H), 5.01-4.80 (m, 1H), 2.23-2.19 (m, 1H), 1.69-1.62 (m, 1H), 1.15-1.09 (m, 1H).

Example S112: Synthesis of (1S,2S)-N-[2-(2-ethylpyridin-3-yl)-1-methylpyrrolo[2,3-c]pyridin-5-yl]-2-fluorocyclopropane-1-carboxamide (Compound 112)

Step 1: Synthesis of 5-chloro-2-(2-ethylpyridin-3-yl)-1-methyl-1H-pyrrolo[2,3-c]pyridine

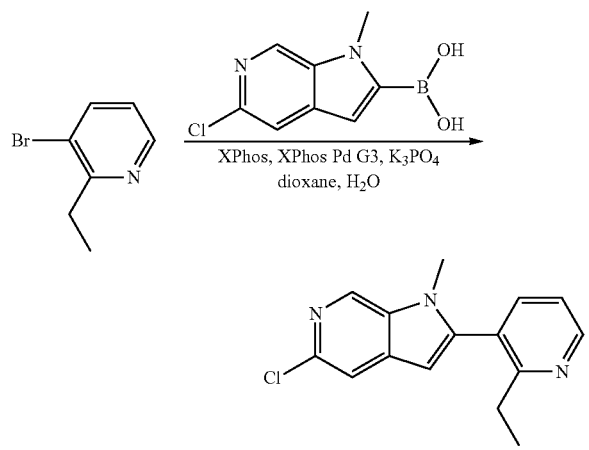

To a solution of 3-bromo-2-ethylpyridine (300.0 mg, 1.61 mmol) in 1,4-dioxane/H₂O (20.0/5.0 mL) was added 5-chloro-1-methylpyrrolo[2,3-c]pyridin-2-ylboronic acid (407.2 mg, 1.93 mmol), XPhos (153.7 mg, 0.32 mmol), K₃PO₄ (1.0 g, 4.84 mmol) and XPhos Pd G3 (136.5 mg, 0.16 mmol) at room temperature under N₂. The resulting mixture was stirred at 80° C. for 4 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/1, v/v) to afford 5-chloro-2-(2-ethylpyridin-3-yl)-1-methyl-1H-pyrrolo[2,3-c]pyridine (400.0 mg, 91%) as a yellow solid. LCMS (ESI, m/z): [M+H]⁺=272.1.

Step 2: Synthesis of (1S,2S)-N-[2-(2-ethylpyridin-3-yl)-1-methylpyrrolo[2,3-c]pyridin-5-yl]-2-fluorocyclopropane-1-carboxamide (Compound 112)

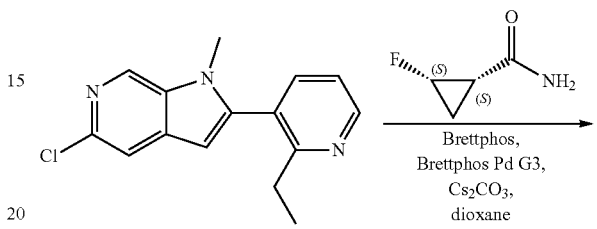

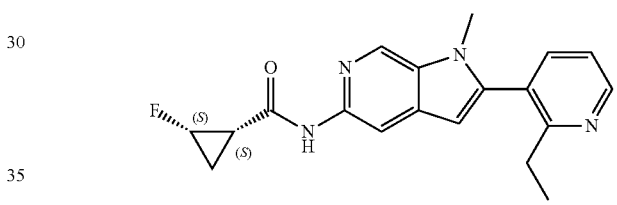

112

To a stirred solution of 3-{5-chloro-1-methylpyrrolo[2,3-c]pyridin-2-yl}-2-ethylpyridine (380.0 mg, 1.41 mmol) in 1,4-dioxane (20.0 mL) was added (1S,2S)-2-fluorocyclopropane-1-carboxamide (726.5 mg, 7.05 mmol), Brettphos (151.3 mg, 0.28 mmol), CS₂CO₃ (1.4 g, 4.23 mmol) and Brettphos Pd G₃ (127.8 mg, 0.14 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (99/1, v/v) and then purified by Prep-HPLC with the following conditions (Column: XBridge Prep OBD C₁₈ Column, 30×150 mm, 5 μm; Mobile Phase A: Water (10 mmol/L NH₄HCO₃), Mobile Phase B: ACN; Flow rate: 60 mL/min; Gradient: 24% B to 34% B in 8 min; 254 nm) to afford (1S,2S)-N-[2-(2-ethylpyridin-3-yl)-1-methylpyrrolo[2,3-c]pyridin-5-yl]-2-fluorocyclopropane-1-carboxamide (Compound 112) (22.7 mg, 4%) as a white solid. LCMS (ESI, m/z): [M+H]⁺=339.1. ¹H NMR (400 MHz, DMSO-d₆): δ 10.58 (s, 1H), 8.80-8.66 (m, 2H), 8.24 (s, 1H), 7.85-7.77 (m, 1H), 7.40 (s, 1H), 6.56 (s, 1H), 5.13-4.83 (m, 1H), 3.58 (s, 3H), 2.65-2.53 (m, 2H), 2.21-2.08 (m, 1H), 1.77-1.63 (m, 1H), 1.24-1.05 (m, 4H).

Example S113: Synthesis of (1S,2S)-2-fluoro-N-[2-(4-methoxy-6-methylpyrimidin-5-yl)-1-methylpyrrolo[2,3-c]pyridin-5-yl]cyclopropane-1-carboxamide (Compound 113)

Step 1: Synthesis of 5-[5-chloro-1-methylpyrrolo[2,3-c]pyridin-2-yl]-4-methoxy-6-methylpyrimidine

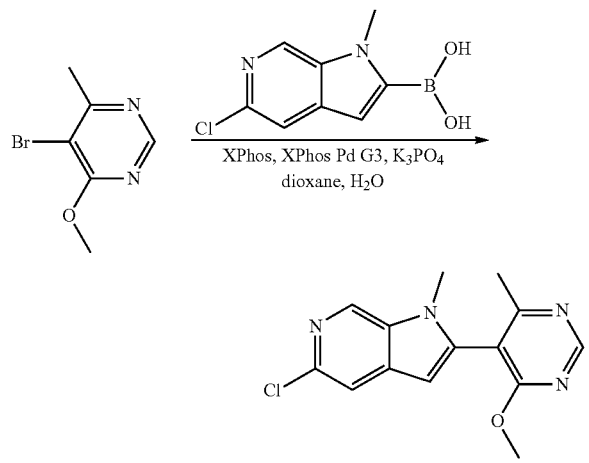

To a solution of 5-bromo-4-methoxy-6-methylpyrimidine (100.0 mg, 0.49 mmol) in dioxane/H₂O (10.0 mL/2.0 mL) was added 5-chloro-1-methylpyrrolo[2,3-c]pyridin-2-ylboronic acid (103.6 mg, 0.49 mmol), XPhos (47.0 mg, 0.10 mmol), K₃PO₄ (313.6 mg, 0.05 mmol) and XPhos Pd G3 (41.7 mg, 0.05 mmol) at room temperature under N₂. The resulting mixture was stirred at 60° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (5/1, v/v) to afford 5-{5-chloro-1-methylpyrrolo[2,3-c]pyridin-2-yl}-4-methoxy-6-methylpyrimidine (120.0 mg, 84%) as a light yellow solid. LCMS (ESI, m/z): [M+H]⁺=289.1.

Step 2: Synthesis of (1S,2S)-2-fluoro-N-[2-(4-methoxy-6-methylpyrimidin-5-yl)-1-methylpyrrolo[2,3-c]pyridin-5-yl]cyclopropane-1-carboxamide (Compound 113)

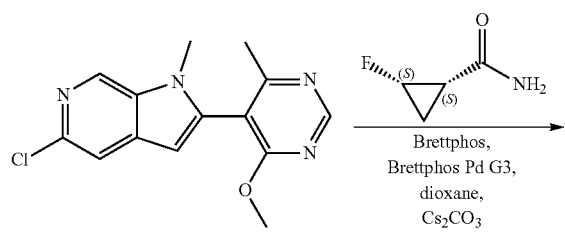

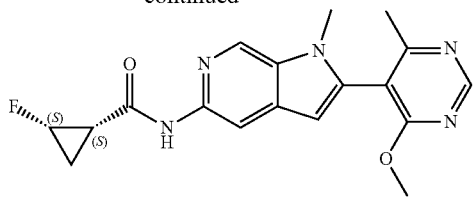

113

To a solution of 5-{5-chloro-1-methylpyrrolo[2,3-c]pyridin-2-yl}-4-methoxy-6-methylpyrimidine (120.0 mg, 0.42 mmol) in dioxane (15.0 mL) was added (1S,2S)-2-fluorocyclopropane-1-carboxamide (214.2 mg, 2.08 mmol), BrettPhos (44.6 mg, 0.08 mmol), Cs₂CO₃ (406.2 mg, 1.25 mmol) and BrettPhos Pd G3 (37.7 mg, 0.04 mmol) at room temperature under N₂. The resulting mixture was stirred at 100° C. for 30 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by reverse phase flash column chromatography with acetonitrile/water (3/2, v/v) and then purified by Prep-HPLC with the following conditions (Column: XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 20% B to 30% B in 8 min; Wave Length: 254 nm) to afford (1S,2S)-2-fluoro-N-[2-(4-methoxy-6-methylpyrimidin-5-yl)-1-methylpyrrolo[2,3-c]pyridin-5-yl]cyclopropane-1-carboxamide (Compound 113) (6.2 mg, 4%) as a white solid. LCMS (ESI, m/z): [M+H]⁺=356.2. ¹H NMR (400 MHz, DMSO-d₆): δ 10.54 (s, 1H), 8.81 (s, 1H), 8.66 (s, 1H), 8.23 (s, 1H), 6.55 (s, 1H), 5.00-4.81 (m, 1H), 3.92 (s, 3H), 3.57 (s, 3H), 2.30 (s, 3H), 2.23-2.19 (m, 1H), 1.71-1.61 (m, 1H), 1.18-1.15 (m, 1H).

Example S114: Synthesis of (1S,2S)-N-[2-(2-ethoxy-4-methylpyridin-3-yl)-1-methylpyrrolo[2,3-c]pyridin-5-yl]-2-fluorocyclopropane-1-carboxamide (Compound 114)

Step 1: Synthesis of 3-bromo-2-ethoxy-4-methylpyridine

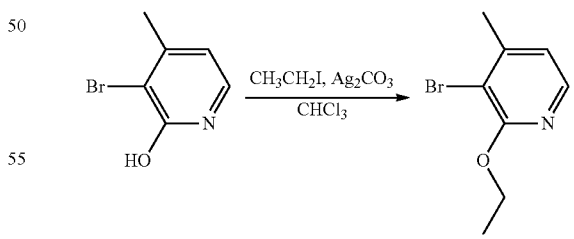

To a solution of 3-bromo-4-methylpyridin-2-ol (2.0 g, 15.96 mmol) in CHCl₃ (60.0 mL) was added iodoethane (5.0 g, 31.91 mmol) and Ag₂CO₃ (6.6 g, 23.93 mmol) at room temperature. The resulting mixture was stirred at room temperature for 4 h. After the reaction was completed, the resulting mixture was filtered. The filtrate was concentrated under reduced pressure. The residue was purified by flash column chromatography with petroleum ether/ethyl acetate (75/25, v/v) to afford 3-bromo-2-ethoxy-4-methylpyridine (485.2 mg, 14%) as a white solid. LCMS (ESI, m/z): [M+H]$^+$=216.0.

Step 2: Synthesis of 3-[5-chloro-1-methylpyrrolo[2,3-c]pyridin-2-yl]-2-ethoxy-4-methylpyridine

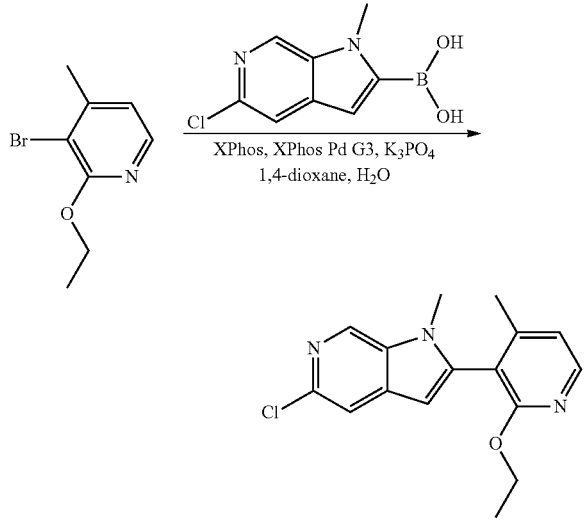

To a solution of 3-bromo-2-ethoxy-4-methylpyridine (385.0 mg, 1.78 mmol) in 1,4-dioxane/H$_2$O (10.0/2.0 mL) was added 5-chloro-1-methylpyrrolo[2,3-c]pyridin-2-ylboronic acid (374.9 mg, 1.78 mmol) K$_3$PO$_4$ (738.8 mg, 5.35 mmol), XPhos (169.9 mg, 0.36 mmol) and XPhos Pd G3 (150.8 mg, 0.18 mmol) at room temperature under N$_2$. The resulting mixture was stirred at 60° C. for 4 h. After the reaction was completed, the reaction was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (25/75, v/v) to afford 3-{5-chloro-1-methylpyrrolo[2,3-c]pyridin-2-yl}-2-ethoxy-4-methylpyridine (274.0 mg, 51%) as a white solid. LCMS (ESI, m/z): [M+H]$^+$=302.1.

Step 3: Synthesis of (1S,2S)-N-[2-(2-ethoxy-4-methylpyridin-3-yl)-1-methylpyrrolo[2,3-c]pyridin-5-yl]2-fluorocyclopropane-1-carboxamide (Compound 114)

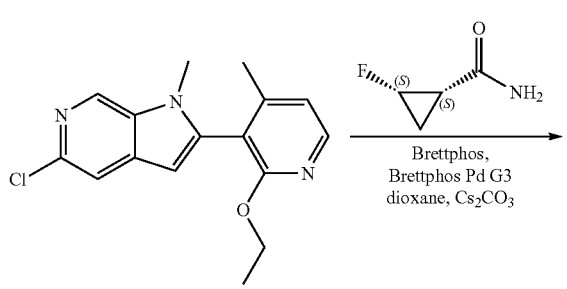

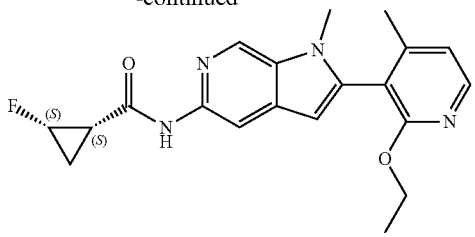

114

To a solution of 3-{5-chloro-1-methylpyrrolo[2,3-c]pyridin-2-yl}-2-ethoxy-4-methylpyridine (190.0 mg, 0.63 mmol) in 1,4-dioxane (4.0 mL) was added Cs$_2$CO$_3$ (615.4 mg, 1.89 mmol), BrettPhos (67.6 mg, 0.13 mmol), (1S,2S)-2-fluorocyclopropane-1-carboxamide (324.6 mg, 3.15 mmol) and BrettPhos Pd G3 (57.1 mg, 0.06 mmol) at room temperature under N$_2$. The final reaction mixture was stirred with microwave at 120° C. for 2 h under N$_2$. After the reaction was completed, the reaction was diluted with H$_2$O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep Phenyl OBD Column, 19×250 mm, 5 um; Mobile Phase A:Water (10 mmol/L NH$_4$HCO$_3$), Mobile Phase B:MeOH; Flow rate: 25 mL/min; Gradient: 58% B to 60% B in 10 min; 254 nm) to afford (1S,2S)-N-[2-(2-ethoxy-4-methylpyridin-3-yl)-1-methylpyrrolo[2,3-c]pyridin-5-yl]-2-fluorocyclopropane-1-carboxamide (Compound 114) (4.0 mg, 2%) as a white solid. LCMS (ESI, m/z): [M+H]$^+$=369.2. $^1$H NMR (400 MHz, DMSO-d$_6$): δ 10.54 (s, 1H), 8.63 (s, 1H), 8.21-8.16 (m, 2H) 7.05 (d, J=5.2 Hz, 1H), 6.45 (s, 1H), 5.00-4.82 (m, 1H), 4.41-4.36 (m, 1H), 4.29-4.24 (m, 1H), 3.54 (s, 3H), 2.32-2.19 (m, 1H), 2.13 (s, 3H), 1.69-1.62 (m, 1H), 1.20-1.11 (m, 4H).

Example S115: Synthesis of (1S,2S)-N-[2-(2-cyclopropoxypyridin-3-yl)-1-methylpyrrolo[2,3-c]pyridin-5-yl]-2-fluorocyclopropane-1-carboxamide (Compound 115)

Step 1: Synthesis of 3-bromo-2-cyclopropoxypyridine

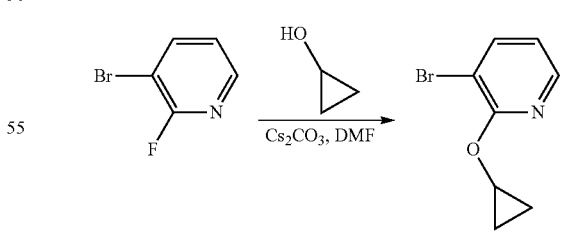

To a solution of 3-bromo-2-fluoropyridine (2.5 g, 14.20 mmol) in DMF (30.0 mL) was added Cs$_2$CO$_3$ (6.9 g, 21.31 mmol) and cyclopropanol (2.5 g, 42.62 mmol) at room temperature. The resulting mixture was stirred at 25° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/1, v/v) to afford 3-bromo-2-cyclopropoxypyridine (2.2 g, 72%) as a colorless oil. LCMS (ESI, m/z): [M+H]$^+$ =214.0.

Step 2: Synthesis of 3-{5-chloro-1-methylpyrrolo[2,3-c]pyridin-2-yl}-2-cyclopropoxypyridine

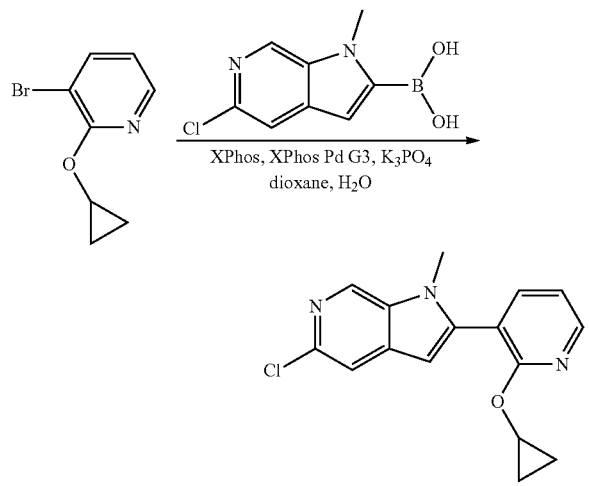

To a solution of 3-bromo-2-cyclopropoxypyridine (1.2 g, 5.60 mmol) in 1,4-dioxane (30.0 mL)/H$_2$O (6.0 mL) was added 5-chloro-1-methylpyrrolo[2,3-c]pyridin-2-ylboronic acid (1.2 g, 5.61 mmol), XPhos (0.5 g, 1.12 mmol), K$_3$PO$_4$ (3.6 g, 16.82 mmol) and XPhos Pd G3 (0.5 g, 0.56 mmol) at room temperature under N$_2$. The resulting mixture was stirred at 80° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/1, v/v) to afford 3-{5-chloro-1-methylpyrrolo[2,3-c]pyridin-2-yl}-2-cyclopropoxypyridine (660.0 mg, 39%) as a yellow oil. LCMS (ESI, m/z): [M+H]$^+$= 300.1.

Step 3: Synthesis of (1S,2S)-N-[2-(2-cyclopropoxypyridin-3-yl)-1-methylpyrrolo[2,3-c]pyridin-5-yl]-2-fluorocyclopropane-1-carboxamide (Compound 115)

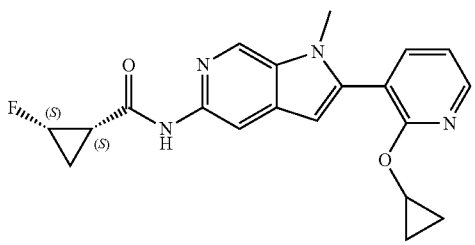

115

To a solution of 3-{5-chloro-1-methylpyrrolo[2,3-c]pyridin-2-yl}-2-cyclopropoxypyridine (500.0 mg, 1.67 mmol) in 1,4-dioxane (20.0 mL) was added (1S,2S)-2-fluorocyclopropane-1-carboxamide (859.8 mg, 8.34 mmol), Brettphos (89.5 mg, 0.17 mmol), Cs$_2$CO$_3$ (1.6 g, 5.00 mmol) and Brettphos Pd G3 (302.4 mg, 0.33 mmol) at room temperature under N$_2$. The resulting mixture was stirred at 100° C. for 16 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/99, v/v) and then purified by Prep-HPLC with the following conditions (Column: XBridge Shield RP$_{18}$ OBD Column, 30×150 mm, 5 μm; Mobile Phase A: Water (10 mmol/L NH$_4$HCO$_3$), Mobile Phase B: ACN; Flow rate: 60 mL/min; Gradient: 32% B to 45% B in 8 min; Wave Length: 254 nm) to afford (1S,2S)-N-[2-(2-cyclopropoxypyridin-3-yl)-1-methylpyrrolo[2,3-c]pyridin-5-yl]-2-fluorocyclopropane-1-carboxamide (Compound 115) (19.3 mg, 3%) as a white solid. LCMS (ESI, m/z): [M+H]$^+$=367.2. $^1$H NMR (300 MHz, DMSO-d$_6$): δ 10.55 (s, 1H), 8.63 (s, 1H), 8.39-8.37 (m, 1H), 8.21 (s, 1H), 7.86-7.84 (m, 1H), 7.23-7.20 (m, 1H), 6.51 (s, 1H), 5.01-4.80 (m, 1H), 4.35-4.32 (m, 1H), 3.60 (s, 3H), 2.23-2.17 (m, 1H), 1.70-1.60 (m, 1H), 1.16-1.11 (m, 1H), 0.79-0.74 (m, 2H), 0.70-0.66 (m, 2H).

Example S116: Synthesis of (1S,2S)-N-[2-(4-cyclopropoxypyridin-3-yl)-1-methylpyrrolo[2,3-c]pyridin-5-yl]-2-fluorocyclopropane-1-carboxamide (Compound 116)

Step 1: Synthesis of 2-(4-cyclopropoxypyridin-3-yl)-1-methylpyrrolo[2,3-c]pyridin-5-amine

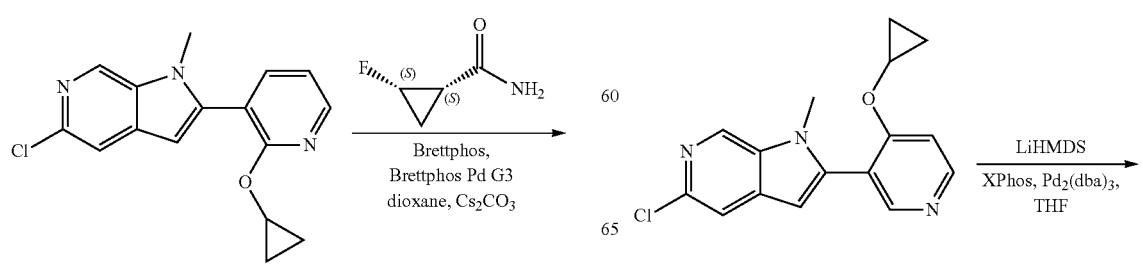

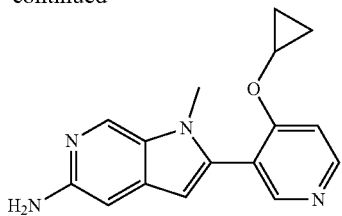

To a solution of 3-{5-chloro-1-methylpyrrolo[2,3-c]pyridin-2-yl}-4-cyclopropoxypyridine (500.0 mg, 1.67 mmol) in THF (15.0 mL) was added XPhos (159.0 mg, 0.10 mmol), Pd₂(dba)₃ (152.7 mg, 0.17 mmol) and LiHMDS (3.3 mL, 1 mol/L) at room temperature under N₂. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by reverse phase flash column chromatography with methylene acetonitrile/water (1/1, v/v) to afford 2-(4-cyclopropoxypyridin-3-yl)-1-methylpyrrolo[2,3-c]pyridin-5-amine (60.0 mg, 12%) as a light brown oil. LCMS (ESI, m/z): [M+H]⁺=281.1.

Step 2: Synthesis of (1S,2S)-N-[2-(4-cyclopropoxypyridin-3-yl)-1-methylpyrrolo[2,3-c]pyridin-5-yl]-2-fluorocyclopropane-1-carboxamide (Compound 116)

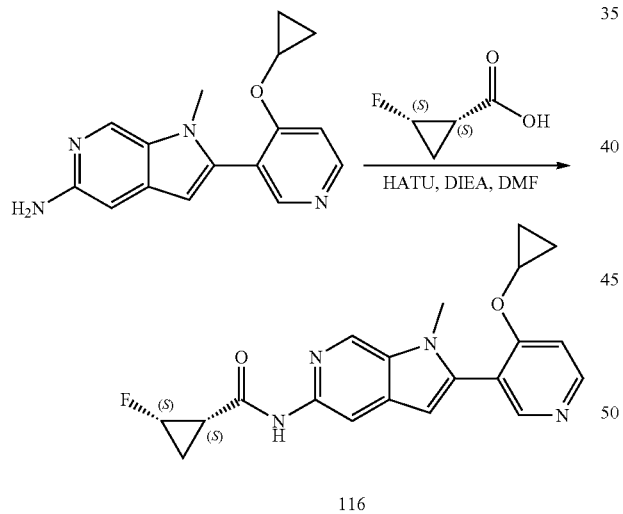

116

To a solution of 2-(4-cyclopropoxypyridin-3-yl)-1-methylpyrrolo[2,3-c]pyridin-5-amine (50.0 mg, 0.18 mmol) in DMF (10.0 mL) was added (1S,2S)-2-fluorocyclopropane-1-carboxylic acid (22.3 mg, 0.21 mmol), DIEA (92.2 mg, 0.71 mmol) and HATU (101.7 mg, 0.27 mmol) at room temperature. The resulting mixture was stirred at room temperature for 1 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by Prep-HPLC with the following conditions (Column: XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 24% B to 34% B in 8 min; Wave Length: 254 nm) to afford (1S,2S)-N-[2-(4-cyclopropoxypyridin-3-yl)-1-methylpyrrolo[2,3-c]pyridin-5-yl]-2-fluorocyclopropane-1-carboxamide (Compound 116) (15.3 mg, 23%) as a white solid. LCMS (ESI, m/z): [M+H]⁺=367.1. H NMR (400 MHz, DMSO-d₆): δ 10.57 (s, 1H), 8.65-8.63 (m, 2H), 8.46 (s, 1H), 8.23 (s, 1H), 7.53 (d, J=5.6 Hz, 1H), 6.53 (s, 1H), 5.01-4.81 (m, 1H), 4.08-4.05 (m, 1H), 3.58 (s, 3H), 2.24-2.17 (m, 1H), 1.70-1.60 (m, 1H), 1.18-1.08 (m, 1H), 0.90-0.81 (m, 2H), 0.78-0.65 (m, 2H).

Example S117: Synthesis of (1S,2S)-N-[2-(3-cyclopropoxypyridin-4-yl)-1-methylpyrrolo[2,3-c]pyridin-5-yl]-2-fluorocyclopropane-1-carboxamide (Compound 117)

Step 1: Synthesis of 4-bromo-3-cyclopropoxypyridine

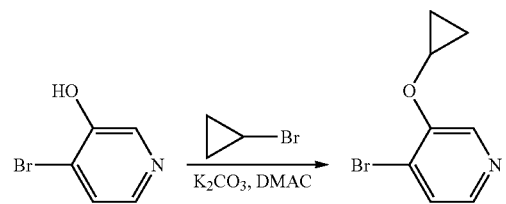

To a solution of 4-bromopyridin-3-ol (1.0 g, 5.75 mmol) in DMAC (20.0 mL) was added bromocyclopropane (2.1 g, 17.24 mmol) and K₂CO₃ (2.4 g, 17.24 mmol) at room temperature. The resulting mixture was stirred at 140° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/MeOH (98/2, v/v) to afford 4-bromo-3-cyclopropoxypyridine (500.0 mg, 40%) as a yellow solid. LCMS (ESI, m/z): [M+H]⁺=214.0.

Step 2: Synthesis of 4-{5-chloro-1-methylpyrrolo[2,3-c]pyridin-2-yl}-3-cyclopropoxypyridine

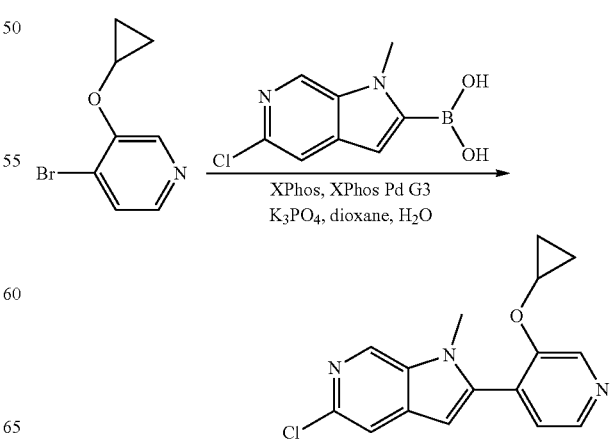

To a solution of 4-bromo-3-cyclopropoxypyridine (280.0 mg, 1.31 mmol) in 1,4-dioxane/H₂O (20.0/4.0 mL) was added 5-chloro-1-methylpyrrolo[2,3-c]pyridin-2-ylboronic acid (330.2 mg, 1.57 mmol), XPhos (124.7 mg, 0.26 mmol), K₃PO₄ (832.9 mg, 3.92 mmol) and XPhos Pd G3 (110.7 mg, 0.13 mmol) at room temperature under N₂. The resulting mixture was stirred at 80° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 4-{5-chloro-1-methylpyrrolo[2,3-c]pyridin-2-yl}-3-cyclopropoxypyridine (260.0 mg, 66%) as a yellow solid. LCMS (ESI, m/z): [M+H]⁺=300.1.

Step 3: Synthesis of (1S,2S)-N-[2-(3-cyclopropoxy-pyridin-4-yl)-1-methylpyrrolo[2,3-c]pyridin-5-yl]-2-fluorocyclopropane-1-carboxamide (Compound 117)

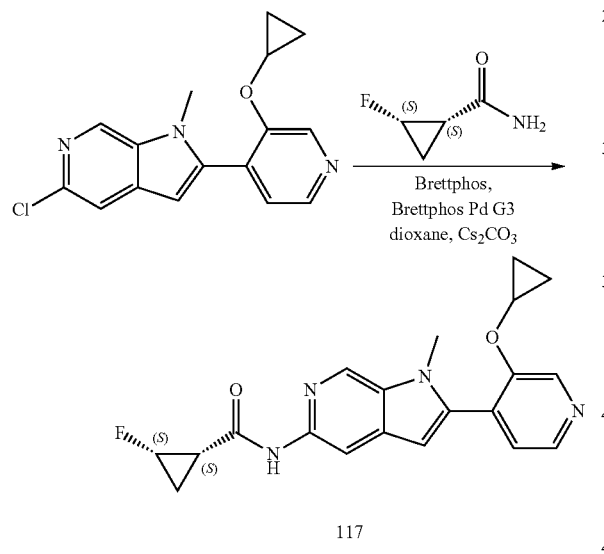

117

To a stirred solution of 4-{5-chloro-1-methylpyrrolo[2,3-c]pyridin-2-yl}-3-cyclopropoxypyridine (230.0 mg, 0.77 mmol) in 1,4-dioxane (20.0 mL) was added (1S,2S)-2-fluorocyclopropane-1-carboxamide (395.5 mg, 3.84 mmol), Brettphos (82.4 mg, 0.15 mmol), K₂CO₃ (318.1 mg, 2.30 mmol) and Brettphos Pd G3 (69.6 mg, 0.08 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/99, v/v) and then purified by Prep-HPLC with the following conditions (Column: XBridge Prep OBD C₁₈ Column, 30×150 mm, 5 μm; Mobile Phase A: Water (10 mmol/L NH₄HCO₃), Mobile Phase B: ACN; Flow rate: 60 mL/min; Gradient: 25% B to 35% B in 8 min; 254 nm) to afford (1S,2S)-N-[2-(3-cyclopropoxypyridin-4-yl)-1-methylpyrrolo[2,3-c]pyridin-5-yl]-2-fluorocyclopropane-1-carboxamide (Compound 117) (7.9 mg, 2%) as a white solid. LCMS (ESI, m/z): [M+H]⁺=367.2. ¹H NMR (400 MHz, DMSO-d₆): δ 10.57 (s, 1H), 8.84 (s, 1H), 8.65 (s, 1H), 8.39 (d, J=4.4 Hz, 1H), 8.23 (s, 1H), 7.44 (d, J=4.8 Hz, 1H), 6.57 (s, 1H), 5.01-4.80 (m, 1H), 4.09-4.07 (m, 1H), 3.62 (s, 3H), 2.23-2.19 (m, 1H), 1.69-1.60 (m, 1H), 1.25-1.12 (m, 1H), 0.90-0.85 (m, 2H), 0.79-0.72 (m, 2H).

Example S118: Synthesis of N-[2-(4,6-dimethoxy-pyrimidin-5-yl)-1-methylpyrrolo[2,3-c]pyridin-5-yl]cyclopropanecarboxamide (Compound 118)

Step 1: Synthesis of 5-[5-chloro-1-methylpyrrolo[2,3-c]pyridin-2-yl]-4,6-dimethoxypyrimidine

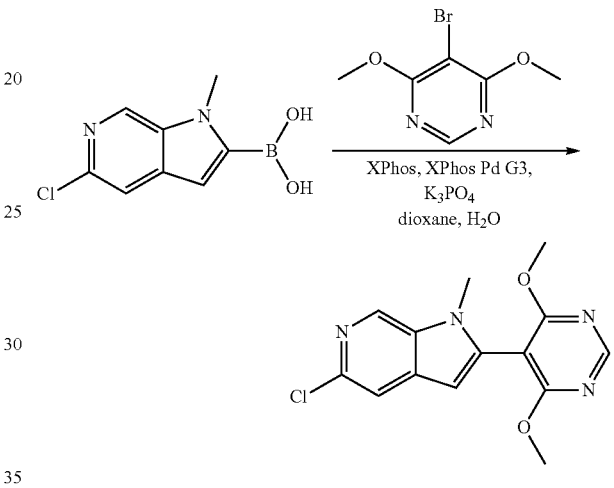

To a stirred solution of 5-chloro-1-methyl-1H-pyrrolo[2,3-c]pyridin-2-ylboronic acid (500.0 mg, 1.64 mmol) in dioxane/H₂O (32.0 mL/6.0 mL) was added K₃PO₄ (1044.8 mg, 4.92 mmol), 5-bromo-4,6-dimethoxypyrimidine (359.4 mg, 1.64 mmol), XPhos (156.4 mg, 0.32 mmol) and XPhos Pd G3 (138.8 mg, 0.16 mmol) at room temperature under N₂. The resulting mixture was stirred at 60° C. for 3 h. After the reaction was completed, the resulting mixture was concentrated under reduced pressure. The residue was purified by flash column chromatography with petroleum ether/ethyl acetate (1/1, v/v) to afford 5-{5-chloro-1-methylpyrrolo[2,3-c]pyridin-2-yl}-4,6-dimethoxypyrimidine (300.0 mg, 25%) as a light yellow solid. LCMS (ESI, m/z): [M+H]⁺=305.1.

Step 2: Synthesis of N-[2-(4,6-dimethoxypyrimidin-5-yl)-1-methylpyrrolo[2,3-c]pyridin-5-yl]cyclopropanecarboxamide (Compound 118)

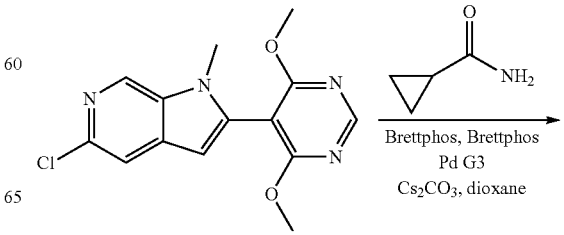

-continued

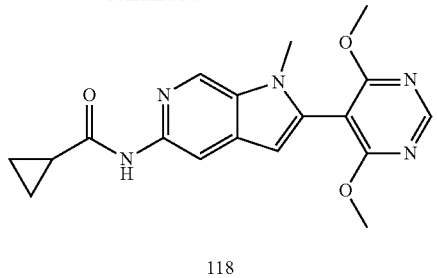

118

To a stirred solution of 5-{5-chloro-1-methylpyrrolo[2,3-c]pyridin-2-yl}-4,6-dimethoxypyrimidine (300 mg, 0.98 mmol) in dioxane (10.0 mL) were added cyclopropanecarboxamide (418.9 mg, 4.92 mmol), K₂CO₃ (408.2 mg, 2.95 mmol), BrettPhos (105.7 mg, 0.20 mmol) and BrettPhos Pd G3 (89.2 mg, 0.10 mmol) at room temperature under N₂. The resulting mixture was stirred at 100° C. for 16 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/EtOAc (1/99, v/v) and then purified by Prep-HPLC with the following conditions (Column: XBridge Shield RP18 OBD Column, 30×150 mm, 5 μm; Mobile Phase A: Water (10 mmol/L NH₄HCO₃), Mobile Phase B: ACN; Flow rate: 60 mL/min; Gradient: 30% B to 44% B in 8 min; Wave Length: 220/254 nm) to afford N-[2-(4,6-dimethoxypyrimidin-5-yl)-1-methylpyrrolo[2,3-c]pyridin-5-yl]cyclopropanecarboxamide (Compound 118) (89.1 mg, 25%) as a white solid. LCMS (ESI, m/z): [M+H]⁺=354.2. ¹H NMR (400 MHz, DMSO-d₆): δ 10.48 (s, 1H), 8.66-8.61 (m, 2H), 8.18 (s, 1H), 6.47 (s, 1H), 3.92 (s, 6H), 3.57 (s, 3H), 2.04-1.98 (m, 1H), 0.84-0.72 (m, 4H).

Example S119: Synthesis of (1S,2S)-N-[2-(2,6-dimethoxyphenyl)-1-methylpyrrolo[2,3-c]pyridin-5-yl]-2-fluorocyclopropane-1-carboxamide (Compound 119)

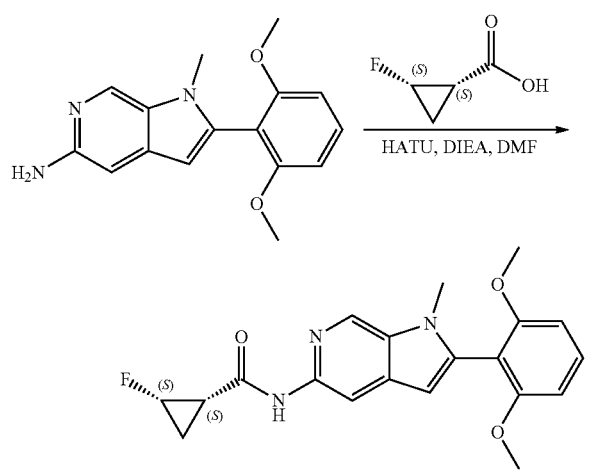

To a solution of 2-(2,6-dimethoxyphenyl)-1-methylpyrrolo[2,3-c]pyridin-5-amine (200.0 mg, 0.71 mmol) in DMF (9.0 mL) was added (1S,2S)-2-fluorocyclopropane-1-carboxylic acid (88.2 mg, 0.85 mmol), DIEA (364.9 mg, 2.82 mmol) and HATU (375.8 mg, 0.99 mmol) at 0° C. under N₂. The resulting mixture was stirred at 0° C. for 1 h. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with CH₂Cl₂/MeOH (10/1, v/v) and then purified by Prep-HPLC with the following conditions (Column: XBridge Shield RP18 OBD Column, 30×150 mm, 5 μm; Mobile Phase A: Water (10 mmol/L NH₄HCO₃), Mobile Phase B: ACN; Flow rate: 60 mL/min; Gradient: 30% B to 80% B in 12 min; Wave Length: 254 nm) to afford (1S,2S)-N-[2-(2,6-dimethoxyphenyl)-1-methylpyrrolo[2,3-c]pyridin-5-yl]-2-fluorocyclopropane-1-carboxamide (Compound 119) (12.6 mg, 4%) as a yellow solid. LCMS (ESI, m/z): [M+H]⁺=370.2. ¹H NMR (400 MHz, DMSO-d₆): δ 10.48 (s, 1H), 8.57 (s, 1H), 8.17 (s, 1H), 7.50-7.45 (m, 1H), 6.82 (d, J=8.4 Hz, 2H), 6.34 (s, 1H), 5.01-4.80 (m, 1H), 3.75 (s, 6H), 3.54 (s, 3H), 2.24-2.15 (m, 1H), 1.71-1.66 (m, 1H), 1.20-1.11 (m, 1H).

Example S120: Synthesis of (1S,2S)-N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide and (1R,2R)-N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide (Compound 120 and Compound 121)

Step 1: Synthesis of 5-chloro-2-(2,4-dimethoxypyridin-3-yl)-1-methyl-1H-pyrrolo[2,3-c]pyridine

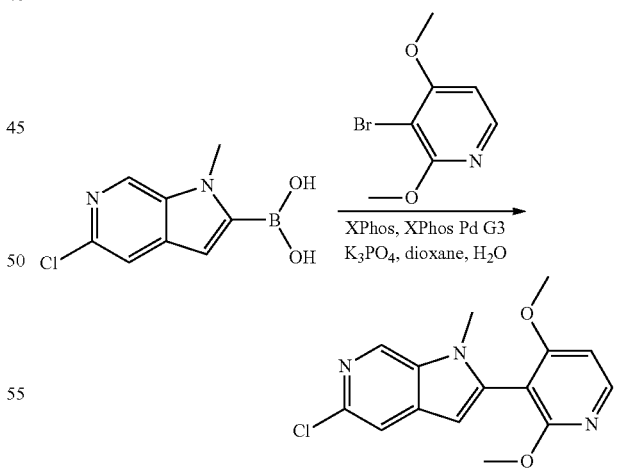

To a solution of (5-chloro-1-methyl-1H-pyrrolo[2,3-c]pyridin-2-yl)boronic acid (1.0 g, 6.75 mmol) in dioxane/H₂O (10.0/1.0 mL) was added 3-bromo-2,4-dimethoxypyridine (1.3 g, 6.75 mmol), XPhos Pd G3 (0.6 g, 0.67 mmol) and XPhos (0.6 g, 1.34 mmol) at room temperature. The resulting mixture was stirred at 80° C. for 12 h under N₂. The resulting mixture was stirred at 80° C. for 12 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 5-chloro-2-(2,4-dimethoxypyridin-3-yl)-1-methyl-1H-pyrrolo[2,3-c]pyridine (750.0 mg, 40%) as a red oil. LCMS (ESI, m/z): [M+H]⁺=304.1.

Step 2: Synthesis of 2-(2,4-dimethoxypyridin-3-yl)-1-methylpyrrolo[2,3-c]pyridin-5-amine

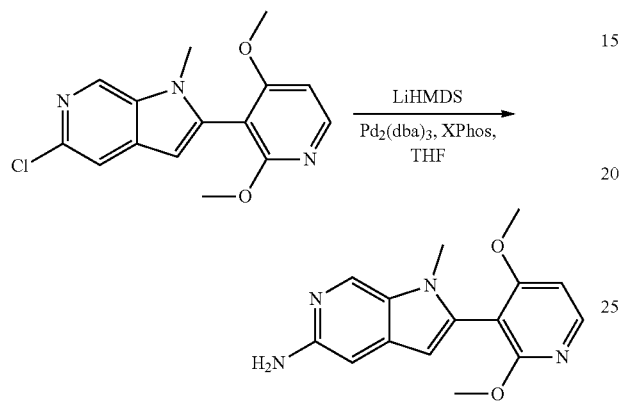

To a solution of 5-chloro-2-(2,4-dimethoxypyridin-3-yl)-1-methyl-1H-pyrrolo[2,3-c]pyridine (1.0 g, 3.29 mmol) in THF (10.0 mL) was added LiHMDS (5.0 mL, 1 mol/L), Pd₂(dba)₃ (0.3 g, 0.33 mmol) and XPhos (0.3 g, 0.66 mmol) at room temperature. The resulting mixture was stirred at 80° C. for 12 h under N₂. After the reaction was completed, the resulting mixture was diluted with H₂O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford 2-(2,4-dimethoxypyridin-3-yl)-1-methylpyrrolo[2,3-c]pyridin-5-amine (700.0 mg, 75%) as a red oil. LCMS (ESI, m/z): [M+H]⁺=285.1.

Step 3: Synthesis of trans-methyl-2-((2-(2,4-dimethoxypyridin-3-yl)-1-methyl-1H-pyrrolo[2,3-c]pyridin-5-yl)carbamoyl)cyclopropane-1-carboxylate

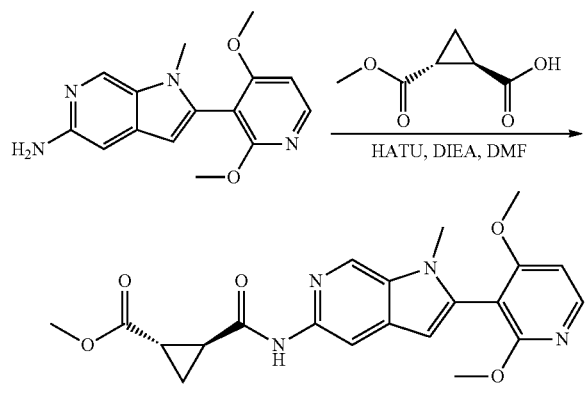

To a solution of trans-2-(methoxycarbonyl)cyclopropane-1-carboxylic acid (344.7 mg, 2.39 mmol) in DMF (5.0 mL) was added DIEA (463.6 mg, 3.58 mmol), HATU (1.4 g, 3.58 mmol) and 2-(2,4-dimethoxypyridin-3-yl)-1-methylpyrrolo[2,3-c]pyridin-5-amine (680.0 mg, 2.39 mmol) at room temperature. The resulting mixture was stirred at room temperature for 2 h. After the reaction was completed, the reaction mixture was diluted with water and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/1, v/v) to afford trans-methyl-2-((2-(2,4-dimethoxypyridin-3-yl)-1-methyl-1H-pyrrolo[2,3-c]pyridin-5-yl)carbamoyl)cyclopropane-1-carboxylate (820.0 mg, 84%) as a yellow oil. LCMS (ESI, m/z): [M+H]⁺=411.2.

Step 4: Synthesis of trans-N-[2-(2,4-dimethoxypyridin-3-yl)-1-methylpyrrolo[2,3-c]pyridin-5-yl]-2-(hydroxymethyl)cyclopropane-1-carboxamide

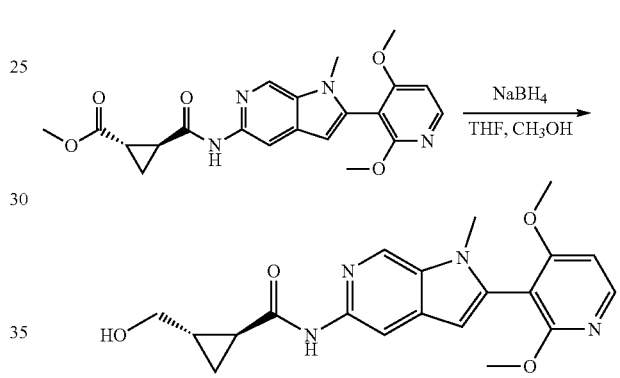

To a solution of trans-methyl-2-((2-(2,4-dimethoxypyridin-3-yl)-1-methyl-1H-pyrrolo[2,3-c]pyridin-5-yl)carbamoyl)cyclopropane-1-carboxylate (820.0 mg, 2.00 mmol) in THF/MeOH (4.0/1.0 mL) was added with NaBH₄ (720.2 mg, 20.00 mmol) at 0° C. The resulting mixture was stirred at 40° C. for 2 h. After the reaction was completed, the reaction was quenched with water and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (1/1, v/v) to afford trans-N-[2-(2,4-dimethoxypyridin-3-yl)-1-methylpyrrolo[2,3-c]pyridin-5-yl]-2-(hydroxymethyl)cyclopropane-1-carboxamide (130.0 mg, 28%) as a red oil. LCMS (ESI, m/z): [M+H]⁺=383.2.

Step 5: Synthesis of trans-N-(2-(2,4-dimethoxypyridin-3-yl)-1-methyl-1H-pyrrolo[2,3-c]pyridin-5-yl)-2-formylcyclopropane-1-carboxamide

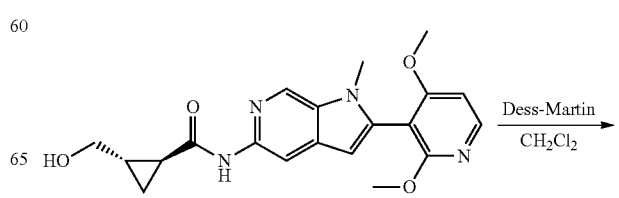

475

-continued

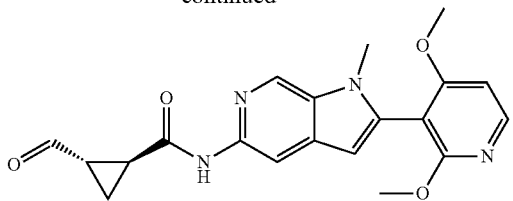

To a solution of trans-N-[2-(2,4-dimethoxypyridin-3-yl)-1-methylpyrrolo[2,3-c]pyridin-5-yl]-2-(hydroxymethyl)cyclopropane-1-carboxamide (200.0 mg, 0.52 mmol) in CH$_2$Cl$_2$ (5.0 mL) was added Dess-Martin (221.8 mg, 0.52 mmol) at 0° C. The resulting mixture was stirred at 0° C. for 3 h. After the reaction was completed, the reaction mixture was quenched with NaHCO$_3$(aq) at room temperature and extracted with DCM. The combined organic layer was washed with brine, dried over anhydrous sodium sulfate and filtered. The filtrate was concentrated under reduced pressure to afford trans-N-(2-(2,4-dimethoxypyridin-3-yl)-1-methyl-1H-pyrrolo[2,3-c]pyridin-5-yl)-2-formylcyclopropane-1-carboxamide (160.0 mg, crude) as a yellow solid. LCMS (ESI, m/z): [M+H]$^+$=381.1.

Step 6: Synthesis of trans-N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide

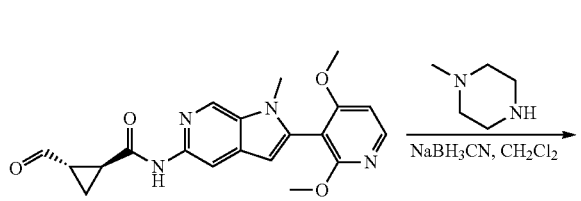

476

-continued

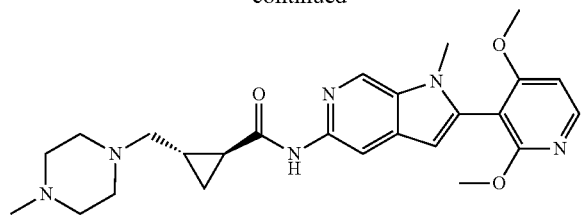

To a solution of trans-N-(2-(2,4-dimethoxypyridin-3-yl)-1-methyl-1H-pyrrolo[2,3-c]pyridin-5-yl)-2-formylcyclopropane-1-carboxamide (130.0 mg, crude) in CH$_2$Cl$_2$ (5.0 mL) was added 1-methylpiperazine (102.7 mg, 1.03 mmol) and NaBH$_3$CN (77.4 mg, 1.23 mmol) at room temperature. The resulting mixture was stirred at room temperature for 2 h. After the reaction was completed, the resulting mixture was diluted with H$_2$O and extracted with CH$_2$Cl$_2$. The combined organic layer was washed with brine, dried over anhydrous sodium sulfate and filtered. The filtrate was concentrated under reduced pressure to afford trans-N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide (100.0 mg, crude) as a yellow solid. LCMS (ESI, m/z): [M+H]$^+$=465.3.

Step 7: Synthesis of (1S,2S)-N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide and (1R,2R)-N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide (Compound 120 and Compound 121)

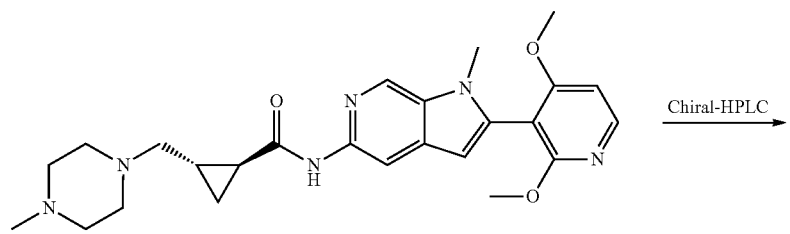

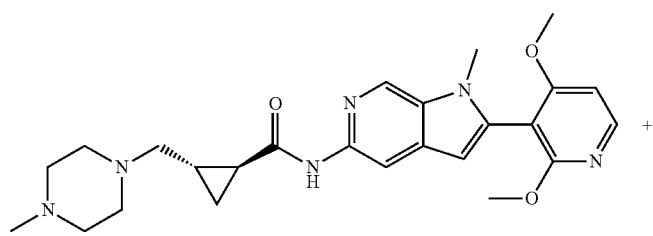

120

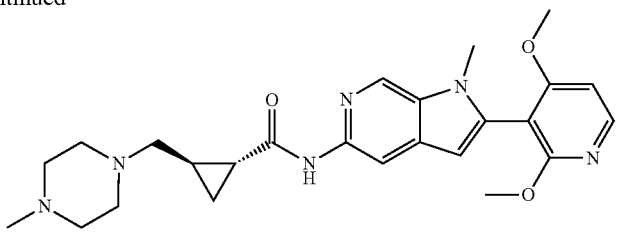

121

The compound trans-N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide (100.0 mg, 0.22 mmol) was separated by Prep-Chiral-HPLC with the following conditions (Column: CHIRAL ART Amylose-SA, 2×25 cm, 5 um; Mobile Phase A: Hex (0.5% 2M NH$_3$-MeOH)-HPLC, Mobile Phase B: MeOH: EtOH=1:1—HPLC; Flow rate: 14 mL/min; Gradient: 80% B to 80% B in 31 min; 254 nm) to afford N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide Enantiomer 1 (12.8 mg, 25%, retention time 1: 22.47 min) as a white solid and N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide Enantiomer 2 (8.9 mg, 19%, retention time 2: 26.92 min) as a white solid. The absolute stereochemistry of Enantiomers 1 and 2 was not assigned. The two enantiomeric structures that could be obtained from chiral separation of the enantiomeric mixture as described above are shown as Compounds 120 and 121 in Table 1.

N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide Enantiomer 1: Retention Time 1: 22.47 min; LCMS (ESI, m/z): [M+H]$^+$=465.3. $^1$H NMR (300 MHz, Methanol-d$_4$): δ 8.51 (s, 1H), 8.22 (d, J=6.0 Hz, 1H), 8.06 (s, 1H), 6.92 (d, J=6.0 Hz, 1H), 6.43 (s, 1H), 3.90 (s, 3H), 3.88 (s, 3H), 3.65 (s, 3H), 2.94-2.71 (m, 6H), 2.68 (s, 3H), 2.65-2.49 (m, 4H), 1.85-1.80 (m, 1H), 1.65-1.60 (m, 1H), 1.42-1.30 (m, 1H), 0.99-0.84 (m, 1H).

N-(2-(2,4-dimethoxypyridin-3-yl)-1-methyl-1H-pyrrolo[2,3-c]pyridin-5-yl)-2-((4-methylpiperazin-1-yl)methyl)cyclopropane-1-carboxamide Enantiomer 2: Retention Time 2: 26.92 min; LCMS (ESI, m/z): [M+H]$^+$=465.3. $^1$H NMR (300 MHz, DMSO-d$_6$): δ 10.43 (s, 1H), 8.58 (s, 1H), 8.25 (d, J=6.0 Hz, 1H), 8.16 (s, 1H), 6.97 (d, J=6.0 Hz, 1H), 6.39 (s, 1H), 3.82 (s, 6H), 3.57 (s, 3H), 2.74-2.60 (m, 2H), 2.55-2.50 (m, 2H), 2.36-2.23 (m, 6H), 2.15 (s, 3H), 1.89-1.83 (m, 1H), 1.45-1.31 (m, 1H), 1.09-0.99 (m, 1H), 0.79-0.64 (m, 1H).

Example S121: Synthesis of Synthesis of (1R,2R)-N-[2-(2,4-dimethoxypyridin-3-yl)-1-methylpyrrolo[2,3-c]pyridin-5-yl]-2-[(dimethylamino)methyl]cyclopropane-1-carboxamide and (1S,2S)-N-[2-(2,4-dimethoxypyridin-3-yl)-1-methylpyrrolo[2,3-c]pyridin-5-yl]-2-[(dimethylamino)methyl]cyclopropane-1-carboxamide (Compound 122 and Compound 123)

Step 1: Synthesis of Trans-N-[2-(2,4-dimethoxypyridin-3-yl)-1-methylpyrrolo[2,3-c]pyridin-5-yl]-2-formylcyclopropane-1-carboxamide

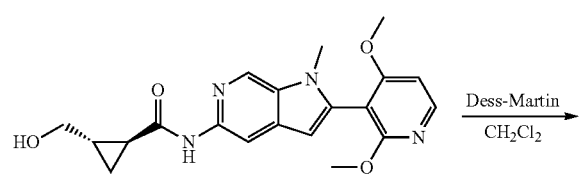

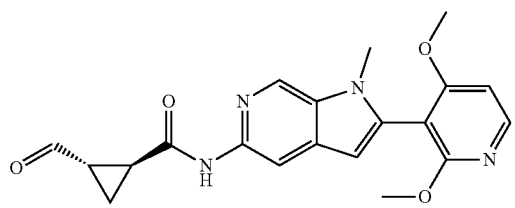

To a solution of trans-N-[2-(2,4-dimethoxypyridin-3-yl)-1-methylpyrrolo[2,3-c]pyridin-5-yl]-2-(hydroxymethyl)cyclopropane-1-carboxamide (290.0 mg, 0.76 mmol) in CH$_2$Cl$_2$ (5.0 mL) was added Dess-Martin (321.6 mg, 0.76 mmol) at 0° C. under N$_2$. The resulting mixture was stirred at room temperature for 1 h. After the reaction was completed, the resulting mixture was diluted with H$_2$O and extracted with CH$_2$Cl$_2$. The combined organic layer was washed with aq. NaHCO$_3$, brine, dried over anhydrous sodium sulfate and filtered. The filtrate was concentrated under reduced pressure to afford trans-N-[2-(2,4-dimethoxypyridin-3-yl)-1-methylpyrrolo[2,3-c]pyridin-5-yl]-2-formylcyclopropane-1-carboxamide (370.0 mg, crude) as a yellow solid. LCMS (ESI, m/z): [M+H]$^+$=381.1.

Step 2: Synthesis of Trans-N-[2-(2,4-dimethoxypyridin-3-yl)-1-methylpyrrolo[2,3-c]pyridin-5-yl]-2-[(dimethylamino)methyl]cyclopropane-1-carboxamide

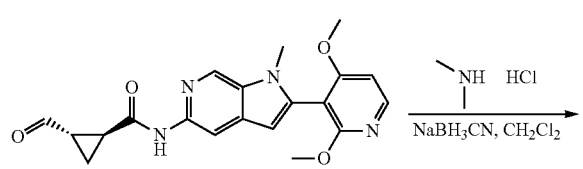

To a solution of trans-N-[2-(2,4-dimethoxypyridin-3-yl)-1-methylpyrrolo[2,3-c]pyridin-5-yl]-2-formylcyclopropane-1-carboxamide (360.0 mg, crude) in $CH_2Cl_2$ (5.0 mL) was added dimethylamine hydrochloride (231.5 mg, 2.84 mmol) and $NaBH_3CN$ (178.4 mg, 2.84 mmol) at room temperature. The resulting mixture was stirred at room temperature for 0.5 h. After the reaction was completed, the resulting mixture was diluted with $H_2O$ and extracted with $CH_2Cl_2$. The combined organic layer was washed with brine, dried over anhydrous sodium sulfate and filtered. The filtrate was concentrated under reduced pressure. The residue was purified by reverse phase flash column chromatography with $ACN/H_2O$ (46/54, v/v) to afford trans-N-[2-(2,4-dimethoxypyridin-3-yl)-1-methylpyrrolo[2,3-c]pyridin-5-yl]-2-[(dimethylamino)methyl]cyclopropane-1-carboxamide (136.8 mg, 38%) as a white solid. LCMS (ESI, m/z): $[M+H]^+=410.2$.

Step 3: Synthesis of (1R,2R)-N-[2-(2,4-dimethoxypyridin-3-yl)-1-methylpyrrolo[2,3-c]pyridin-5-yl]-2-[(dimethylamino)methyl]cyclopropane-1-carboxamide and (1S,2S)-N-[2-(2,4-dimethoxypyridin-3-yl)-1-methylpyrrolo[2,3-c]pyridin-5-yl]-2-[(dimethylamino)methyl]cyclopropane-1-carboxamide (Compound 122 and Compound 123)

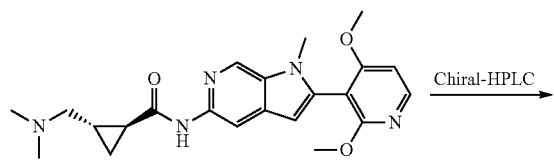

The product trans-N-[2-(2,4-dimethoxypyridin-3-yl)-1-methylpyrrolo[2,3-c]pyridin-5-yl]-2-[(dimethylamino)methyl]cyclopropane-1-carboxamide (136.8 mg, 0.33 mmol) was separated by Prep-Chiral-HPLC with the following conditions (Column: CHIRALPAK IE, 2×25 cm, 5 μm; Mobile Phase A: Hex (0.5% 2M $NH_3$-MeOH)—HPLC, Mobile Phase B: MeOH: EtOH=1:1—HPLC; Flow rate: 15 mL/min; Gradient: 70% B to 70% B in 25 min; Wave Length: 254/220 nm) to afford N-[2-(2,4-dimethoxypyridin-3-yl)-1-methylpyrrolo[2,3-c]pyridin-5-yl]-2-[(dimethylamino)methyl]cyclopropane-1-carboxamide Enantiomer 1 (10.9 mg, 16%) as a white solid and N-[2-(2,4-dimethoxypyridin-3-yl)-1-methylpyrrolo[2,3-c]pyridin-5-yl]-2-[(dimethylamino)methyl]cyclopropane-1-carboxamide Enantiomer 2 (12.8 mg, 18%) as a white solid. The absolute stereochemistry of Enantiomers 1 and 2 was not assigned. The two enantiomeric structures that could be obtained from chiral separation of the enantiomeric mixture as described above are shown as Compounds 122 and 123 in Table 1.

N-[2-(2,4-dimethoxypyridin-3-yl)-1-methylpyrrolo[2,3-c]pyridin-5-yl]-2-[(dimethylamino)methyl]cyclopropane-1-carboxamide Enantiomer 1: Retention Time 1=18.05 min; LCMS (ESI, m/z): $[M+H]^+=410.2$. $^1H$ NMR (400 MHz, DMSO-$d_6$): δ 10.45 (s, 1H), 8.58 (s, 1H), 8.25 (d, J=6.0 Hz, 1H), 8.16 (s, 1H), 6.98 (d, J=6.0 Hz, 1H), 6.36 (s, 1H), 3.82 (s, 6H), 3.53 (s, 3H), 2.34-2.27 (m, 2H), 2.24 (s, 6H), 1.92-1.87 (m, 1H), 1.35-1.31 (m, 1H), 1.07-1.04 (m, 1H), 0.83-0.67 (m, 1H).

N-[2-(2,4-dimethoxypyridin-3-yl)-1-methylpyrrolo[2,3-c]pyridin-5-yl]-2-[(dimethylamino)methyl]cyclopropane-1-carboxamide Enantiomer 2: Retention Time 2=21.18 min; LCMS (ESI, m/z): $[M+H]^+=410.2$. $^1H$ NMR (400 MHz, DMSO-$d_6$): δ 10.44 (s, 1H), 8.58 (s, 1H), 8.25 (d, J=6.0 Hz, 1H), 8.16 (s, 1H), 6.97 (d, J=6.0 Hz, 1H), 6.39 (s, 1H), 3.82 (s, 6H), 3.53 (s, 3H), 2.33-2.18 (m, 8H), 1.88-1.84 (m, 1H), 1.35-1.31 (m, 1H), 1.07-1.04 (m, 1H), 0.73-0.62 (m, 1H).

Example S122: Synthesis of (1S,2S)-N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide and (1R,2R)-N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide (Compound 124 and Compound 125)

Step 1: Synthesis of 5-chloro-2-(4,6-dimethoxypyrimidin-5-yl)-1-methyl-1H-pyrrolo[2,3-c]pyridine

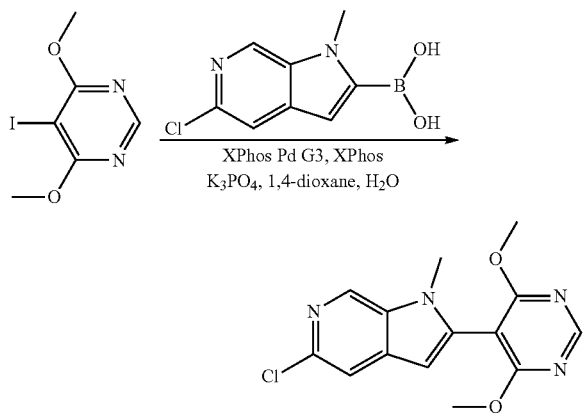

To a solution of 5-iodo-4,6-dimethoxypyrimidine (2.4 g, 9.02 mmol) in 1,4-dioxane/H$_2$O (48.0 mL/12.0 mL) was added (5-chloro-1-methyl-1H-pyrrolo[2,3-c]pyridin-2-yl)boronic acid (1.9 g, 9.02 mmol), K$_3$PO$_4$ (5.7 g, 27.06 mmol), XPhos (860.1 mg, 1.80 mmol) and XPhos Pd G3 (763.6 mg, 0.90 mmol) at room temperature under N$_2$. The resulting mixture was stirred at 60° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/2, v/v) to afford 5-chloro-2-(4,6-dimethoxypyrimidin-5-yl)-1-methyl-1H-pyrrolo[2,3-c]pyridine (2.0 g, 72%) as a yellow solid. LCMS (ESI, m/z): [M+H]$^+$=305.1.

Step 2: Synthesis of 2-(4,6-dimethoxypyrimidin-5-yl)-1-methyl-1H-pyrrolo[2,3-c]pyridin-5-amine

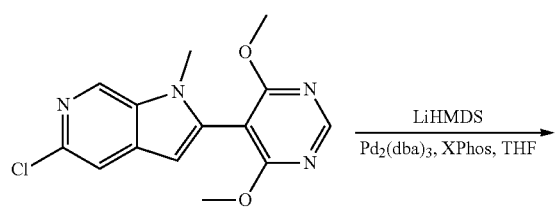

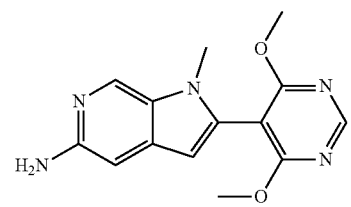

To a solution of 5-chloro-2-(4,6-dimethoxypyrimidin-5-yl)-1-methyl-1H-pyrrolo[2,3-c]pyridine (2.0 g, 6.56 mmol) in THF (30.0 mL) was added LiHMDS (13.1 mL, 2 mol/L), XPhos (625.8 mg, 1.31 mmol) and Pd$_2$(dba)$_3$ (601.0 mg, 0.66 mmol) at room temperature under N$_2$. The resulting mixture was stirred at 60° C. for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/CH$_3$OH (10/1, v/v) to afford 2-(4,6-dimethoxypyrimidin-5-yl)-1-methyl-1H-pyrrolo[2,3-c]pyridin-5-amine (1.8 g, 96%) as a yellow solid. LCMS (ESI, m/z): [M+H]$^+$=286.1.

Step 3: Synthesis of trans-methyl 2-((2-(4,6-dimethoxypyrimidin-5-yl)-1-methyl-1H-pyrrolo[2,3-c]pyridin-5-yl)carbamoyl)cyclopropane-1-carboxylate

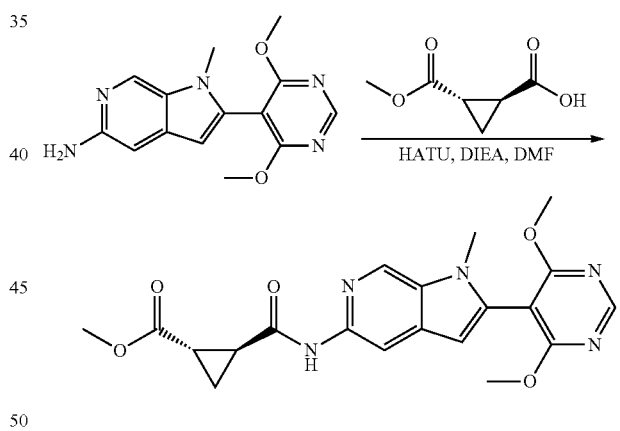

To a solution of 2-(4,6-dimethoxypyrimidin-5-yl)-1-methyl-1H-pyrrolo[2,3-c]pyridin-5-amine (1.8 g, 6.31 mmol) in DMF (20.0 mL) was added trans-2-(methoxycarbonyl)cyclopropane-1-carboxylic acid (1.0 g, 6.94 mmol), DIEA (4.1 g, 31.55 mmol) and HATU (3.6 g, 9.46 mmol) at 0° C. under N$_2$. The resulting mixture was stirred at room temperature for 2 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/CH$_3$OH (10/1, v/v) to afford trans-methyl 2-((2-(4,6-dimethoxypyrimidin-5-yl)-1-methyl-1H-pyrrolo[2,3-c]pyridin-5-yl)carbamoyl)cyclopropane-1-carboxylate (1.1 g, 42%) as a yellow solid. LCMS (ESI, m/z): [M+H]$^+$=412.2.

Step 4: Synthesis of Trans-N-(2-(4,6-dimethoxypyrimidin-5-yl)-1-methyl-1H-pyrrolo[2,3-c]pyridin-5-yl)-2-(hydroxymethyl)cyclopropane-1-carboxamide

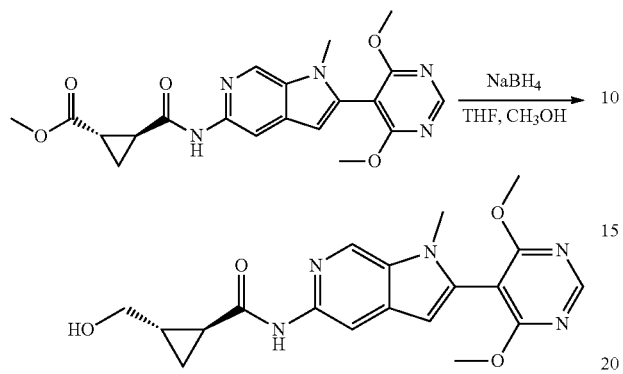

To a solution of trans-methyl 2-((2-(4,6-dimethoxypyrimidin-5-yl)-1-methyl-1H-pyrrolo[2,3-c]pyridin-5-yl)carbamoyl)cyclopropane-1-carboxylate (1.1 g, 2.67 mmol) in THF/CH$_3$OH (90.0/10.0 mL) was added NaBH$_4$ (2.0 g, 53.48 mmol) at room temperature. The resulting mixture was stirred at 40° C. for 4 h. After the reaction was completed, the reaction was quenched with H$_2$O and extracted with ethyl acetate. The combined organic layer was washed with brine, dried over anhydrous sodium sulfate and filtered. The filtrate was concentrated under reduced pressure. The residue was purified by flash column chromatography with CH$_2$Cl$_2$/CH$_3$OH (10/1, v/v) to afford trans-N-(2-(4,6-dimethoxypyrimidin-5-yl)-1-methyl-1H-pyrrolo[2,3-c]pyridin-5-yl)-2-(hydroxymethyl)cyclopropane-1-carboxamide (410.0 mg, 40%) as a yellow solid. LCMS (ESI, m/z): [M+H]$^+$=384.2.

Step 5: Synthesis of Trans-N-(2-(4,6-dimethoxypyrimidin-5-yl)-1-methyl-1H-pyrrolo[2,3-c]pyridin-5-yl)-2-formylcyclopropane-1-carboxamide

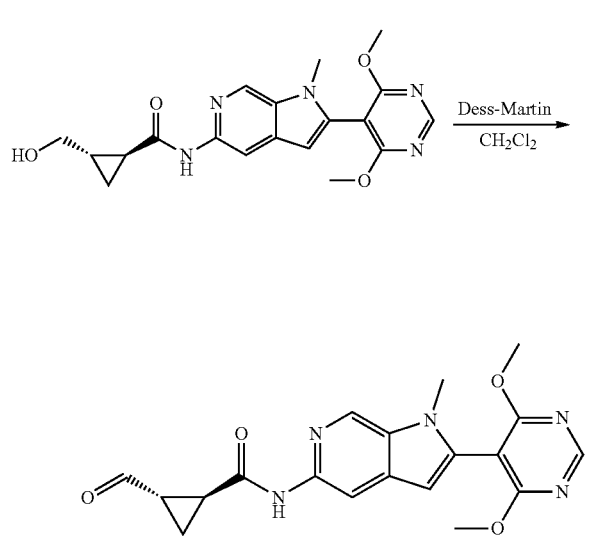

To a solution of trans-N-(2-(4,6-dimethoxypyrimidin-5-yl)-1-methyl-1H-pyrrolo[2,3-c]pyridin-5-yl)-2-(hydroxymethyl)cyclopropane-1-carboxamide (300.0 mg, 0.60 mmol) in CH$_2$Cl$_2$ (30.0 mL) was added Dess-Martin (614.0 mg, 1.45 mmol) at room temperature. The resulting mixture was stirred at room temperature for 1 h. After the reaction was completed, the reaction mixture was diluted with H$_2$O and extracted with CH$_2$Cl$_2$. The combined organic layer was washed with brine, dried over anhydrous sodium sulfate and filtered. The filtrate was concentrated under reduced pressure to afford trans-N-(2-(4,6-dimethoxypyrimidin-5-yl)-1-methyl-1H-pyrrolo[2,3-c]pyridin-5-yl)-2-formylcyclopropane-1-carboxamide (500.0 mg, crude) as a yellow solid. LCMS (ESI, m/z): [M+H]$^+$=382.1.

Step 6: Synthesis of trans-N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide

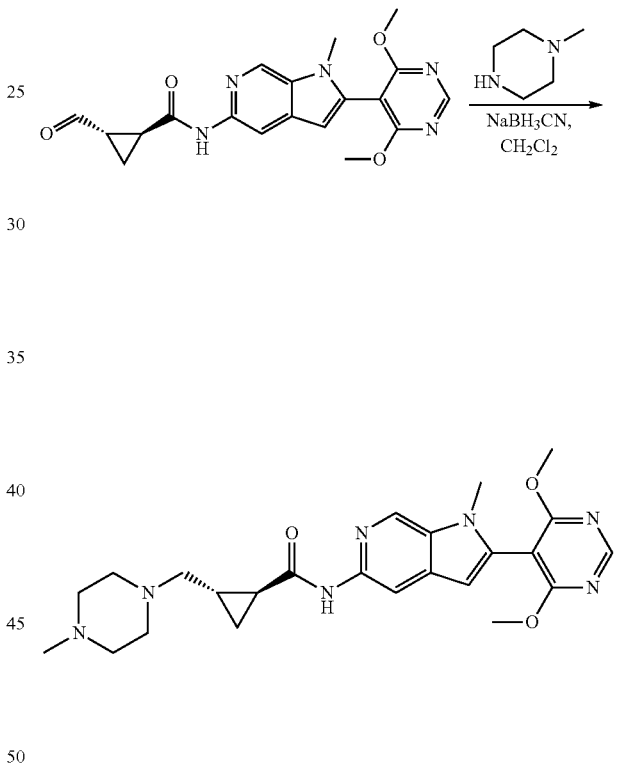

To a solution of trans-N-(2-(4,6-dimethoxypyrimidin-5-yl)-1-methyl-1H-pyrrolo[2,3-c]pyridin-5-yl)-2-formylcyclopropane-1-carboxamide (500.0 mg, crude) in CH$_2$Cl$_2$ (20.0 mL) was added 1-methylpiperazine (394.0 mg, 3.93 mmol) and NaBH$_3$CN (247.2 mg, 3.93 mmol) at room temperature. The resulting mixture was stirred at room temperature for 2 h. After the reaction was completed, the resulting mixture was quenched with CH$_3$OH. The resulting mixture was concentrated under reduced pressure. The residue was purified by flash column chromatography with CH$_2$Cl$_2$/CH$_3$OH (4/1, v/v) to afford trans-N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide (90.0 mg, 14%) as a light yellow solid. LCMS (ESI, m/z): [M+H]$^+$=466.3.

Step 7: Synthesis of (1S,2S)-N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide and (1R,2R)-N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide (Compound 124 and Compound 125)

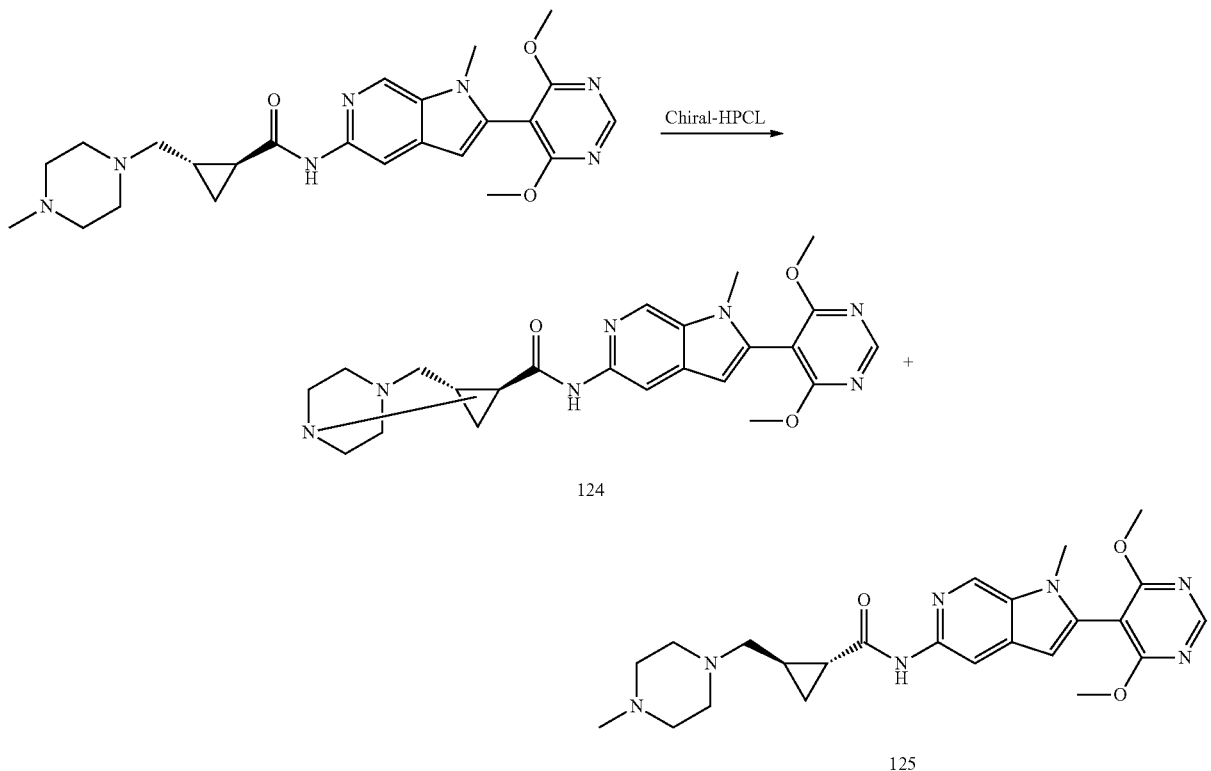

124

125

The product trans-N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide (90.0 mg, 0.19 mmol) was separated by Prep-Chiral-HPLC with the following conditions (Column: CHIRALPAK IG, 2×25 cm, 5 um; Mobile Phase A: Hex: DCM=3:1 (0.5% 2M NH₃-MeOH)—HPLC, Mobile Phase B: EtOH—HPLC; Flow rate: 20 mL/min; Gradient: 30% to 30% in 18.5 min; 220/254 nm) to afford N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide Enantiomer 1 (24.4 mg, 27%) as a white solid and N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide Enantiomer 2 (26.0 mg, 28%) as a white solid. The absolute stereochemistry of Enantiomers 1 and 2 was not assigned. The two enantiomeric structures that could be obtained from chiral separation of the enantiomeric mixture as described above are shown as Compounds 124 and 125 in Table 1.

N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide Enantiomer 1: Retention Time 1=9.11 min; LCMS (ESI, m/z): [M+H]⁺=466.3.
¹H NMR (400 MHz, CD₃OD): δ 8.56-8.52 (m, 2H), 8.09 (s, 1H), 6.49 (s, 1H), 3.99 (s, 6H), 3.62 (s, 3H), 2.78-2.48 (m, 8H), 2.45-2.38 (m, 2H), 2.32 (s, 3H), 1.81-1.77 (m, 1H), 1.60-1.57 (m, 1H), 1.34-1.27 (m, 1H), 0.89-0.81 (m, 1H).
N-(2-(4,6-dimethoxypyrimidin-5-yl)-1-methyl-1H-pyrrolo[2,3-c]pyridin-5-yl)-2-((4-methylpiperazin-1-yl)methyl)cyclopropane-1-carboxamide Enantiomer 2: Retention Time 2=14.50 min; LCMS (ESI, m/z): [M+H]⁺=466.3.
¹H NMR (400 MHz, CD₃OD): δ 8.56-8.52 (m, 2H), 8.09 (s, 1H), 6.49 (s, 1H), 3.99 (s, 6H), 3.62 (s, 3H), 2.75-2.48 (m, 8H), 2.43-2.38 (m, 2H), 2.32 (s, 3H), 1.81-1.77 (m, 1H), 1.60-1.56 (m, 1H), 1.34-1.28 (m, 1H), 0.89-0.81 (m, 1H).

Example S123: Synthesis of (1R,2R)-N-[2-(4,6-dimethoxypyrimidin-5-yl)-1-methylpyrrolo[2,3-c]pyridin-5-yl]-2-[(dimethylamino)methyl]cyclopropane-1-carboxamide and (1S,2S)-N-[2-(4,6-dimethoxypyrimidin-5-yl)-1-methylpyrrolo[2,3-c]pyridin-5-yl]-2-[(dimethylamino)methyl]cyclopropane-1-carboxamide (Compound 126 and Compound 127)

Step 1: Synthesis of Trans-N-(2-(4,6-dimethoxypyrimidin-5-yl)-1-methyl-11H-pyrrolo[2,3-c]pyridin-5-yl)-2-formylcyclopropane-1-carboxamide

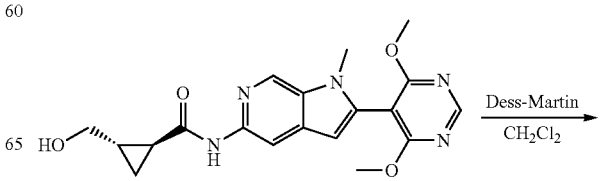

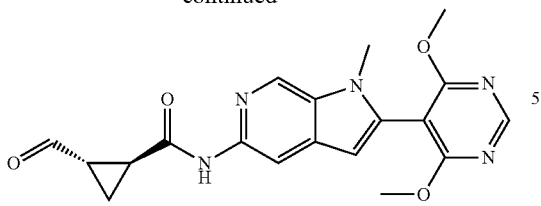

To a solution of trans-N-[2-(4,6-dimethoxypyrimidin-5-yl)-1-methylpyrrolo[2,3-c]pyridin-5-yl]-2-(hydroxymethyl)cyclopropane-1-carboxamide (580.0 mg, 1.51 mmol) in $CH_2Cl_2$ (10.0 mL) was added Dess-Martin (962.4 mg, 2.27 mmol) at room temperature. The resulting mixture was stirred at room temperature for 2 h. After the reaction was completed, the resulting mixture was diluted with $H_2O$ and extracted with $CH_2Cl_2$. The combined organic layer was washed with aq. $NaHCO_3$, brine, dried over anhydrous sodium sulfate and filtered. The filtrate was concentrated under reduced pressure to afford trans-N-(2-(4,6-dimethoxypyrimidin-5-yl)-1-methyl-1H-pyrrolo[2,3-c]pyridin-5-yl)-2-formylcyclopropane-1-carboxamide (700.0 mg, crude) as a light yellow solid. LCMS (ESI, m/z): $[M+H]^+=382.1$.

Step 2: Synthesis of Trans-N-[2-(4,6-dimethoxypyrimidin-5-yl)-1-methylpyrrolo[2,3-c]pyridin-5-yl]-2-[(dimethylamino)methyl]cyclopropane-1-carboxamide

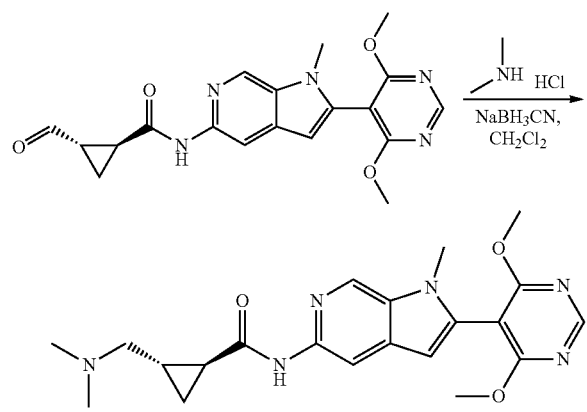

To a solution of trans-N-[2-(4,6-dimethoxypyrimidin-5-yl)-1-methylpyrrolo[2,3-c]pyridin-5-yl]-2-formylcyclopropane-1-carboxamide (700.0 mg, crude) in $CH_2Cl_2$ (15.0 mL) was added dimethylamine hydrochloride (449.0 mg, 5.51 mmol) and $NaBH_3CN$ (346.0 mg, 5.51 mmol) at room temperature. The resulting mixture was stirred at room temperature for 3 h. After the reaction was completed, the resulting mixture was quenched with $H_2O$ and extracted with $CH_2Cl_2$. The combined organic layer was washed with brine, dried over anhydrous sodium sulfate and filtered. The filtrate was concentrated under reduced pressure. The residue was purified by reverse phase flash column chromatography with acetonitrile/water (63/37, v/v) to afford trans-N-[2-(4,6-dimethoxypyrimidin-5-yl)-1-methylpyrrolo[2,3-c]pyridin-5-yl]-2-[(dimethylamino)methyl]cyclopropane-1-carboxamide (150.0 mg, 20%) as a white solid. LCMS (ESI, m/z): $[M+H]^+=411.3$.

Step 3: Synthesis of (1R,2R)-N-[2-(4,6-dimethoxypyrimidin-5-yl)-1-methylpyrrolo[2,3-c]pyridin-5-yl]-2-[(dimethylamino)methyl]cyclopropane-1-carboxamide and (1S,2S)-N-[2-(4,6-dimethoxypyrimidin-5-yl)-1-methylpyrrolo[2,3-c]pyridin-5-yl]-2-[(dimethylamino)methyl]cyclopropane-1-carboxamide (Compound 126 and Compound 127)

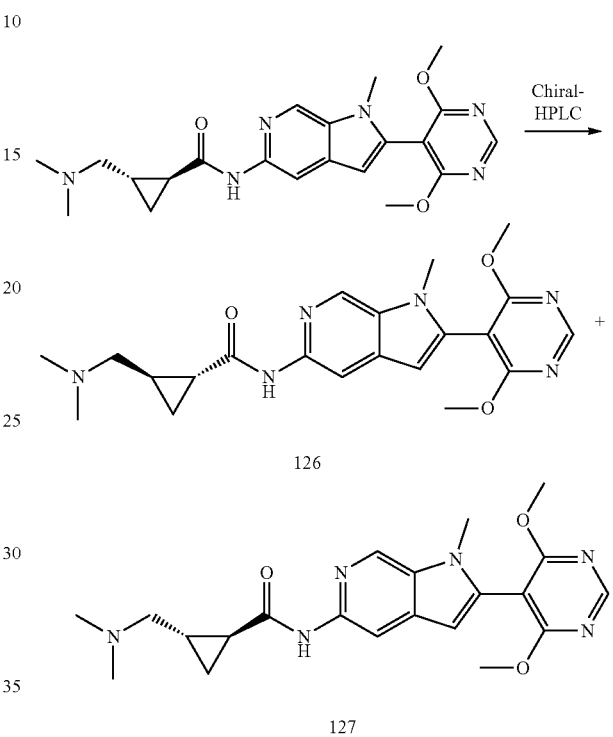

The product of trans-N-[2-(4,6-dimethoxypyrimidin-5-yl)-1-methylpyrrolo[2,3-c]pyridin-5-yl]-2-[(dimethylamino)methyl]cyclopropane-1-carboxamide (150.0 mg, 0.37 mmol) was separated by Prep-Chiral-HPLC with the following conditions (Column: CHIRALPAK IG, 2×25 cm, 5 µm; Mobile Phase A: Hex: DCM=3:1 (0.5% 2M $NH_3$-MeOH)—HPLC, Mobile Phase B: EtOH—HPLC; Flow rate: 20 mL/min; Gradient: 20% B to 20% B in 13 min; Wave Length: 220/254 nm) to afford N-[2-(4,6-dimethoxypyrimidin-5-yl)-1-methylpyrrolo[2,3-c]pyridin-5-yl]-2-[(dimethylamino)methyl]cyclopropane-1-carboxamide Enantiomer 1 (12.1 mg, 16%) as a white solid and N-[2-(4,6-dimethoxypyrimidin-5-yl)-1-methylpyrrolo[2,3-c]pyridin-5-yl]-2-[(dimethylamino)methyl]cyclopropane-1-carboxamide Enantiomer 2 (5.7 mg, 8%) as a white solid. The absolute stereochemistry of Enantiomers 1 and 2 was not assigned. The two enantiomeric structures that could be obtained from chiral separation of the enantiomeric mixture as described above are shown as Compounds 126 and 127 in Table 1.

N-[2-(4,6-dimethoxypyrimidin-5-yl)-1-methylpyrrolo[2,3-c]pyridin-5-yl]-2-[(dimethylamino)methyl]cyclopropane-1-carboxamide Enantiomer 1: Retention Time 1=9.07 min; LCMS (ESI, m/z): $[M+H]^+=411.3$. $^1H$ NMR (400 MHz, DMSO-$d_6$): δ 10.46 (s, 1H), 8.66-8.61 (m, 2H), 8.18 (s, 1H), 6.47 (s, 1H), 3.92 (s, 6H), 3.57 (s, 3H), 2.39-2.22 (m, 8H), 1.91-1.85 (m, 1H), 1.35-1.24 (m, 1H), 1.06-1.01 (m, 1H), 0.75-0.63 (m, 1H).

N-[2-(4,6-dimethoxypyrimidin-5-yl)-1-methylpyrrolo[2,3-c]pyridin-5-yl]-2-[(dimethylamino)methyl]cyclopropane-1-carboxamide Enantiomer 2: Retention Time 2=11.60 min; LCMS (ESI, m/z): [M+H]⁺=411.3. 1H NMR (400 MHz, DMSO-$d_6$): δ 10.46 (s, 1H), 8.66-8.61 (m, 2H), 8.18 (s, 1H), 6.48 (s, 1H), 3.92 (s, 6H), 3.57 (s, 3H), 2.33-2.23 (m, 8H), 1.89-1.87 (m, 1H), 1.35-1.24 (m, 1H), 1.06-1.01 (m, 1H), 0.75-0.63 (m, 1H).

Example S124: Synthesis of (1S,2S)-N-(2-(5-fluoro-2,4-dimethoxypyridin-3-yl)-1-methyl-1H-pyrrolo[2,3-c]pyridin-5-yl)-2-((4-methylpiperazin-1-yl)methyl)cyclopropane-1-carboxamide and (1R,2R)-N-(2-(5-fluoro-2,4-dimethoxypyridin-3-yl)-1-methyl-1H-pyrrolo[2,3-c]pyridin-5-yl)-2-((4-methylpiperazin-1-yl)methyl)cyclopropane-1-carboxamide (Compound 128 and Compound 129)

Step 1: Synthesis of 3-[5-chloro-1-methylpyrrolo[2,3-c]pyridin-2-yl]-5-fluoro-2,4-dimethoxypyridine

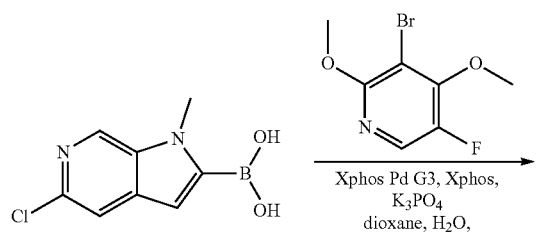

To a solution of 5-chloro-1-methylpyrrolo[2,3-c]pyridin-2-ylboronic acid (1.5 g, 7.13 mmol) in dioxane (30.0 mL)/H₂O (6.0 mL) was added 3-bromo-5-fluoro-2,4-dimethoxypyridine (1.7 g, 7.13 mmol), XPhos (0.7 g, 1.43 mmol), K₃PO₄ (4.5 g, 21.39 mmol) and XPhosPdG₃ (0.6 g, 0.71 mmol) at room temperature. The resulting mixture was stirred at 70° C. for 3 h. After the reaction was completed, the resulting mixture was diluted with water and extracted with ethyl acetate. The combined organic layers were washed with brine, dried over anhydrous sodium sulfate and filtered. The filtrate was concentrated under reduced pressure. The residue was purified by flash column chromatography with petroleum ether/ethyl acetate (1/1, v/v) to afford 3-{5-chloro-1-methylpyrrolo[2,3-c]pyridin-2-yl}-5-fluoro-2,4-dimethoxypyridine (250.0 mg, 32%) as a yellow oil. LCMS (ESI, m/z): [M+H]⁺=322.1.

Step 2: Synthesis of 2-(5-fluoro-2,4-dimethoxypyridin-3-yl)-1-methylpyrrolo[2,3-c]pyridin-5-amine

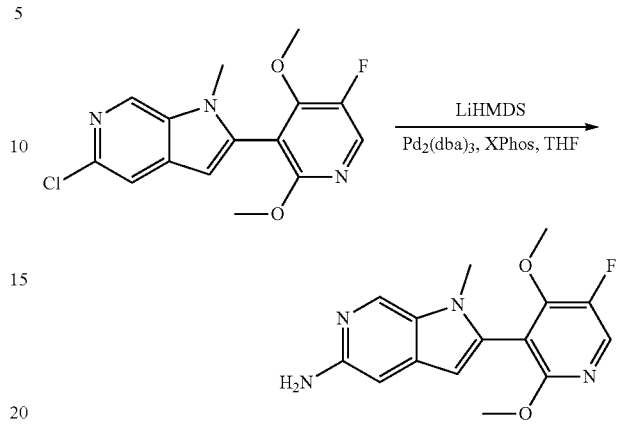

To a solution of 3-(5-chloro-1-methylpyrrolo[2,3-c]pyridin-2-yl)-5-fluoro-2,4-dimethoxypyridine (950.0 mg, 2.95 mmol) in THF (20.0 mL) was added Pd₂(dba)₃ (270.4 mg, 0.30 mmol), XPhos (422.3 mg, 0.89 mmol) and LiHMDS (5.1 mL, 2 mol/L) at room temperature under N₂. The resulting mixture was stirred at 80° C. for 1 h. After the reaction was completed, the resulting mixture was concentrated under reduced pressure. The residue was purified by flash column chromatography with CH₂Cl₂/CH₃OH (20/1, v/v) to afford 2-(5-fluoro-2,4-dimethoxypyridin-3-yl)-1-methylpyrrolo[2,3-c]pyridin-5-amine (430.0 mg, 98%) as a yellow solid. LCMS (ESI, m/z): [M+H]⁺=303.1.

Step 3: Synthesis of Methyl trans-2-[[12-(5-fluoro-2,4-dimethoxypyridin-3-yl)-1-methylpyrrolo[2,3-c]pyridin-5-yl]carbamoyl]cyclopropane-1-carboxylate

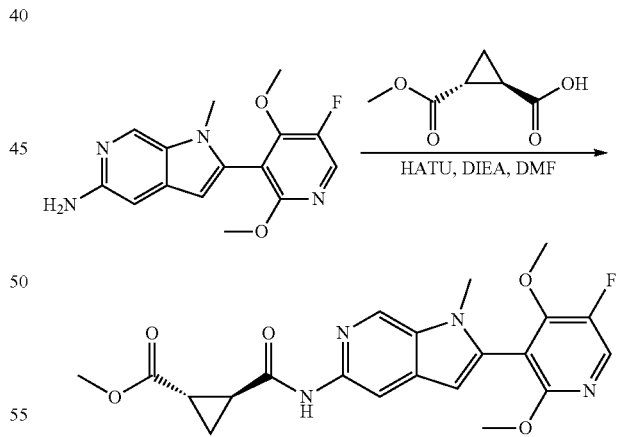

To a solution of 2-(5-fluoro-2,4-dimethoxypyridin-3-yl)-1-methylpyrrolo[2,3-c]pyridin-5-amine (730.0 mg, 2.42 mmol) in DMF (30.0 mL) was added DIEA (1560.5 mg, 12.08 mmol), trans-2-(methoxycarbonyl)cyclopropane-1-carboxylic acid (348.0 mg, 2.40 mmol) and HATU (1101.8 mg, 2.90 mmol) at room temperature. The resulting mixture was stirred at 0° C. for 1 h. After the reaction was completed, the resulting mixture was diluted with water and extracted with ethyl acetate. The combined organic layer was washed with brine, dried over anhydrous sodium sulfate and filtered.

The filtrate was concentrated under reduced pressure. The residue was purified by flash column chromatography with CH₂Cl₂/CH₃OH (10/1, v/v) to afford methyl trans-2-{[2-(5-fluoro-2,4-dimethoxypyridin-3-yl)-1-methylpyrrolo[2,3-c]pyridin-5-yl]carbamoyl}cyclopropane-1-carboxylate (630.0 mg, 60%) as a yellow solid. LCMS (ESI, m/z): [M+H]⁺ =429.1.

Step 4: Synthesis of trans-N-[2-(5-fluoro-2,4-dimethoxypyridin-3-yl)-1-methylpyrrolo[2,3-c]pyridin-5-yl]-2-(hydroxymethyl)cyclopropane-1-carboxamide

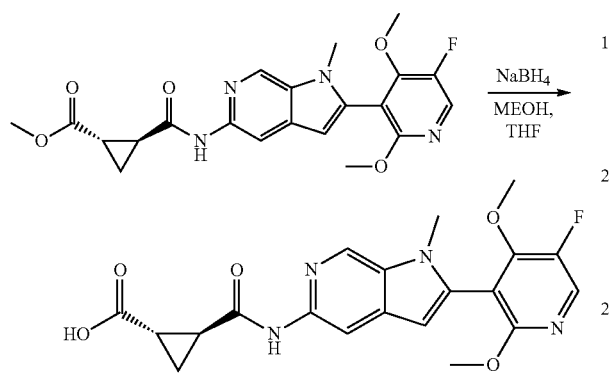

To a solution of methyl trans-2-((2-(5-fluoro-2,4-dimethoxypyridin-3-yl)-1-methyl-1H-pyrrolo[2,3-c]pyridin-5-yl)carbamoyl)cyclopropane-1-carboxylate (580.0 mg, 1.30 mmol) in THF (20.0 mL) was added methanol (20.0 mL) and NaBH₄ (3931.0 mg, 103.92 mmol) at room temperature. The resulting mixture was stirred at room temperature for 1 h. After the reaction was completed, the resulting mixture was diluted with water and extracted with ethyl acetate. The combined organic layer was washed with brine, dried over anhydrous sodium sulfate and filtered. The filtrate was concentrated under reduced pressure. The residue was purified by flash column chromatography with CH₂Cl₂CH₃OH (20/1, v/v) to afford trans-N-[2-(5-fluoro-2,4-dimethoxypyridin-3-yl)-1-methylpyrrolo[2,3-c]pyridin-5-yl]-2-(hydroxymethyl)cyclopropane-1-carboxamide (320.0 mg, 61%) as a white solid. LCMS (ESI, m/z): [M+H]⁺=401.2.

Step 5: Synthesis of trans-N-[2-(5-fluoro-2,4-dimethoxypyridin-3-yl)-1-methylpyrrolo[2,3-c]pyridin-5-yl]-2-formylcyclopropane-1-carboxamide

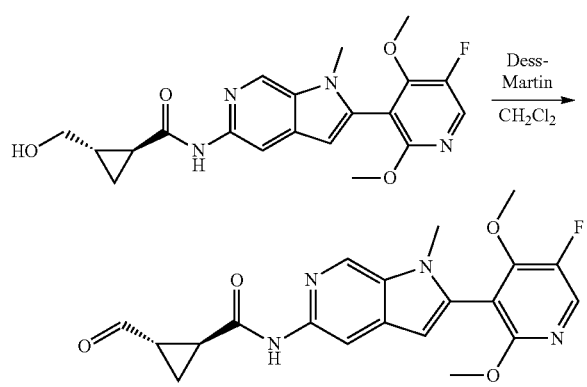

To a solution of trans-N-[2-(5-fluoro-2,4-dimethoxypyridin-3-yl)-1-methylpyrrolo[2,3-c]pyridin-5-yl]-2-(hydroxymethyl)cyclopropane-1-carboxamide (200.0 mg, 0.50 mmol) in CH₂Cl₂ (10.0 mL) was added Dess-Martin (317.8 mg, 0.75 mmol) at 0° C. The resulting mixture was stirred at room temperature for 2 h. After the reaction was completed, the resulting mixture was diluted with water and extracted with CH₂Cl₂. The combined organic layer was washed with brine, dried over anhydrous sodium sulfate and filtered. The filtrate was concentrated under reduced pressure to afford trans-N-[2-(5-fluoro-2,4-dimethoxypyridin-3-yl)-1-methylpyrrolo[2,3-c]pyridin-5-yl]-2-formylcyclopropane-1-carboxamide (190.0 mg, crude) as a yellow solid. LCMS (ESI, m/z): [M+H]⁺=399.1.

Step 6: Synthesis of trans-N-(2-(5-fluoro-2,4-dimethoxypyridin-3-yl)-1-methyl-1H-pyrrolo[2,3-c]pyridin-5-yl)-2-((4-methylpiperazin-1-yl)methyl)cyclopropane-1-carboxamide

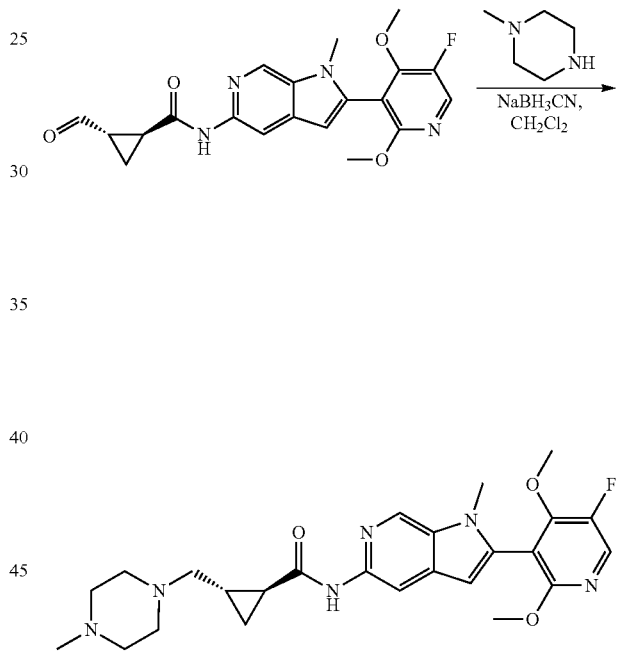

To a solution of trans-N-[2-(5-fluoro-2,4-dimethoxypyridin-3-yl)-1-methylpyrrolo[2,3-c]pyridin-5-yl]-2-formylcyclopropane-1-carboxamide (180.0 mg, crude) in DCM (10.0 mL) was added 1-methylpiperazine (135.8 mg, 1.36 mmol) and NaBH₃CN (85.2 mg, 1.36 mmol) at room temperature. The resulting mixture was stirred at room temperature for 2 h. After the reaction was completed, the resulting mixture was diluted with water and extracted with CH₂Cl₂. The combined organic layer was washed with brine, dried over anhydrous sodium sulfate and filtered. The filtrate was concentrated under reduced pressure. The residue was purified by flash column chromatography with CH₂Cl₂/CH₃OH (10/1, v/v) to afford trans-N-(2-(5-fluoro-2,4-dimethoxypyridin-3-yl)-1-methyl-1H-pyrrolo[2,3-c]pyridin-5-yl)-2-((4-methylpiperazin-1-yl)methyl)cyclopropane-1-carboxamide (90.0 mg, 60%) as a yellow solid. LCMS (ESI, m/z): [M+H]⁺=483.2.

Step 7: Synthesis of (1S,2S)-N-(2-(5-fluoro-2,4-dimethoxypyridin-3-yl)-1-methyl-1H-pyrrolo[2,3-c]pyridin-5-yl)-2-((4-methylpiperazin-1-yl)methyl)cyclopropane-1-carboxamide and (1R,2R)-N-(2-(5-fluoro-2,4-dimethoxypyridin-3-yl)-1-methyl-1H-pyrrolo[2,3-c]pyridin-5-yl)-2-((4-methylpiperazin-1-yl)methyl)cyclopropane-1-carboxamide (Compound 128 and Compound 129)

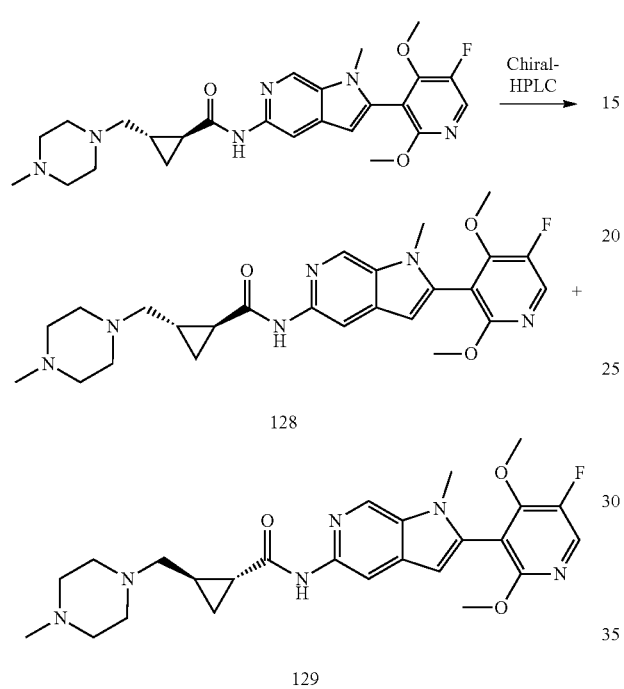

128

129

The product trans-N-(2-(5-fluoro-2,4-dimethoxypyridin-3-yl)-1-methyl-1H-pyrrolo[2,3-c]pyridin-5-yl)-2-((4-methylpiperazin-1-yl)methyl)cyclopropane-1-carboxamide (90.0 mg) was separated by Prep-Chiral-HPLC with the following conditions (Column: XBridge Prep OBD $C_{18}$ Column, 30×150 mm, 5 μm; Mobile Phase A: Water (10.00 mmol/L $NH_4HCO_3$), Mobile Phase B: ACN; Flow rate: 60 mL/min; Gradient: 20% B to 60% B in 8 min; Wave Length: 254 nm) to afford N-[2-(5-fluoro-2,4-dimethoxypyridin-3-yl)-1-methylpyrrolo[2,3-c]pyridin-5-yl]-2-[(4-methylpiperazin-1-yl)methyl]cyclopropane-1-carboxamide Enantiomer 1 (10.0 mg, 4%) as a white solid and N-[2-(5-fluoro-2,4-dimethoxypyridin-3-yl)-1-methylpyrrolo[2,3-c]pyridin-5-yl]-2-[(4-methylpiperazin-1-yl)methyl]cyclopropane-1-carboxamide Enantiomer 2 (21.0 mg, 8%) as a white solid. The absolute stereochemistry of Enantiomers 1 and 2 was not assigned. The two enantiomeric structures that could be obtained from chiral separation of the enantiomeric mixture as described above are shown as Compounds 128 and 129 in Table 1.

N-[2-(5-fluoro-2,4-dimethoxypyridin-3-yl)-1-methylpyrrolo[2,3-c]pyridin-5-yl]-2-[(4-methylpiperazin-1-yl)methyl]cyclopropane-1-carboxamide Enantiomer 1: Retention Time 1=7.10 min; LCMS (ESI, m/z): [M+H]$^+$=483.2. $^1$H NMR (400 MHz, DMSO-d$_6$): δ 10.48 (s, 1H), 8.63 (s, 1H), 8.32 (d, J=3.6 Hz, 1H), 8.19 (s, 1H), 6.49 (s, 1H), 3.87 (s, 3H), 3.81 (s, 3H), 3.59 (s, 3H), 2.46-2.40 (m, 3H), 2.39-2.22 (m, 6H), 2.14 (s, 3H), 1.89-1.82 (m, 1H), 1.39-1.29 (m, 1H), 1.07-0.99 (m, 1H), 0.72-0.65 (m, 1H).

N-[2-(5-fluoro-2,4-dimethoxypyridin-3-yl)-1-methylpyrrolo[2,3-c]pyridin-5-yl]-2-[(4-methylpiperazin-1-yl)methyl]cyclopropane-1-carboxamide Enantiomer 2: Retention Time 2=10.60 min; LCMS (ESI, m/z): [M+H]$^+$=483.2. $^1$H NMR (400 MHz, DMSO-d$_6$): δ 10.48 (s, 1H), 8.63 (s, 1H), 8.32 (d, J=4.0 Hz, 1H), 8.19 (s, 1H), 6.48 (s, 1H), 3.87 (s, 3H), 3.81 (s, 3H), 3.59 (s, 3H), 2.42-2.33 (m, 1H), 2.25 (s, 3H), 1.92-1.86 (m, 1H), 1.39-1.31 (m, 1H), 1.07-1.03 (m, 1H), 0.72-0.68 (m, 1H).

Example S125: Synthesis of (1R,2R)-2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide and (1S,2S)-2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide (Compound 130 and Compound 131)

Step 1: Synthesis of trans-2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide

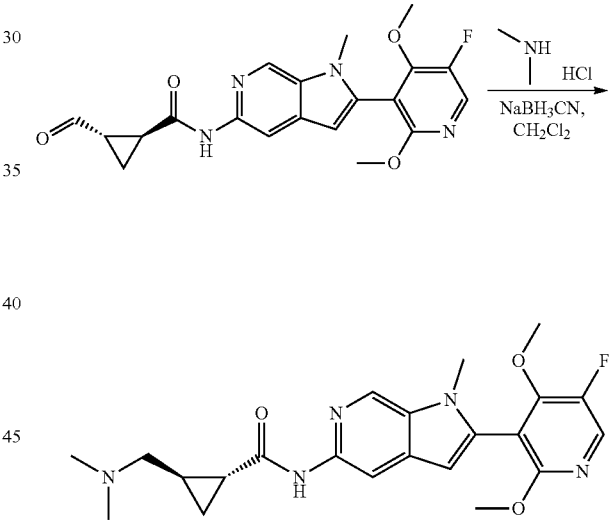

To a solution of trans-N-[2-(5-fluoro-2,4-dimethoxypyridin-3-yl)-1-methylpyrrolo[2,3-c]pyridin-5-yl]-2-formylcyclopropane-1-carboxamide (360.0 mg, 0.90 mmol) in DCM (10.0 mL) was added dimethylamine hydrochloride (221.1 mg, 2.71 mmol) and NaBH$_3$CN (170.4 mg, 2.71 mmol) at room temperature. The resulting mixture was stirred at room temperature for 2 h. After the reaction was completed, the resulting mixture was diluted with H$_2$O and extracted with CH$_2$Cl$_2$. The combined organic layer was washed with brine, dried over anhydrous sodium sulfate and filtered. The filtrate was concentrated under reduced pressure. The residue was purified by reverse phase flash chromatography with CH$_3$OH/H$_2$O (2/1, v/v) to afford trans-2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide (79.0 mg, 20%) as a white solid. LCMS (ESI, m/z): [M+H]$^+$=428.2.

Step 2: Synthesis of (1R,2R)-2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide and (1S,2S)-2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide (Compound 130 and Compound 131)

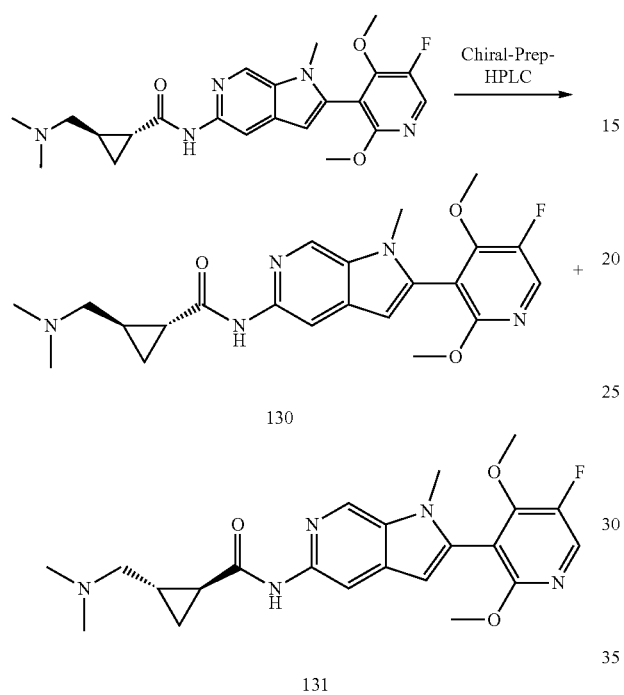

130

131

The product trans-2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide (79.0 mg, 0.19 mmol) was separated by Prep-Chiral-HPLC with the following conditions (Column: CHIRAL ART Cellulose-SC, 2×25 cm, 5 μm; Mobile Phase A: Hex (0.5% 2M NH$_3$-MeOH)—HPLC, Mobile Phase B: MeOH: EtOH=1:1—HPLC; Flow rate: 20 mL/min; Gradient: 25% B to 25% B in 18 min; Wave Length: 220/254 nm) to afford 2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide Enantiomer 1 (16.9 mg, 20%) as a white solid and 2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide Enantiomer 2 (17.8 mg, 21%) as a white solid. The absolute stereochemistry of Enantiomers 1 and 2 was not assigned. The two enantiomeric structures that could be obtained from chiral separation of the enantiomeric mixture as described above are shown as Compounds 130 and 131 in Table 1.

2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide Enantiomer 1: Retention Time 1=14.52 min; LCMS (ESI, m/z): [M+H]$^+$=428.2. $^1$H NMR (400 MHz, DMSO-d$_6$): δ 10.48 (s, 1H), 8.63 (s, 1H), 8.33 (d, J=3.6 Hz, 1H), 8.19 (s, 1H), 6.49 (s, 1H), 3.87 (s, 3H), 3.81 (s, 3H), 3.62 (s, 3H), 2.34-2.27 (m, 2H), 2.23-2.18 (m, 6H), 1.89-1.85 (m, 1H), 1.35-1.29 (m, 1H), 1.07-0.99 (m, 1H), 0.72-0.65 (m, 1H).

2-[(dimethylamino)methyl]-N-[2-(5-fluoro-2,4-dimethoxypyridin-3-yl)-1-methylpyrrolo[2,3-c]pyridin-5-yl]cyclopropane-1-carboxamide Enantiomer 2: Retention Time 2=16.65 min; LCMS (ESI, m/z): [M+H]$^+$=428.2. $^1$H NMR (400 MHz, DMSO-d$_6$): δ 10.48 (s, 1H), 8.63 (s, 1H), 8.33 (d, J=4.0 Hz, 1H), 8.19 (s, 1H), 6.49 (s, 1H), 3.87 (s, 3H), 3.81 (s, 3H), 3.59 (s, 3H), 2.34-2.19 (m, 2H), 2.15 (s, 6H), 1.89-1.85 (m, 1H), 1.35-1.29 (m, 1H), 1.07-0.99 (m, 1H), 0.72-0.65 (m, 1H).

Example S126: Synthesis of (1R,2R)-2-((dimethylamino)methyl)-N-(2-(2-methoxyphenyl)-1-methyl-1H-pyrrolo[2,3-c]pyridin-5-yl)cyclopropane-1-carboxamide and (1S,2S)-2-((dimethylamino)methyl)-N-(2-(2-methoxyphenyl)-1-methyl-1H-pyrrolo[2,3-c]pyridin-5-yl)cyclopropane-1-carboxamide (Compound 132 and Compound 133)

Step 1: Synthesis of 5-chloro-2-(2-methoxyphenyl)-1-methylpyrrolo[2,3-c]pyridine

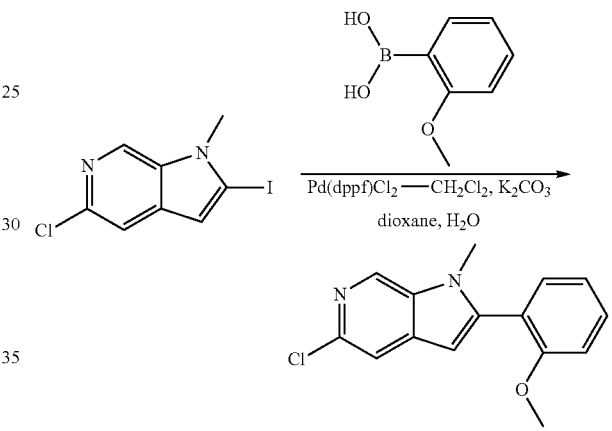

To a solution of 5-chloro-2-iodo-1-methylpyrrolo[2,3-c]pyridine (1.0 g, 3.42 mmol) in dioxane/H$_2$O (40.0 mL/8.0 mL) was added 2-methoxyphenylboronic acid (0.6 g, 4.10 mmol), K$_2$CO$_3$ (1.4 g, 10.26 mmol) and Pd(dppf)Cl$_2$·CH$_2$Cl$_2$ (0.3 g, 0.34 mmol) at room temperature under N$_2$. The resulting mixture was stirred at 80° C. for 2 h. After the reaction was completed, the resulting mixture was diluted with water and extracted with ethyl acetate. The combined organic layers were washed with brine, dried over anhydrous sodium sulfate and filtered. The filtrate was concentrated under reduced pressure. The residue was purified by flash column chromatography with petroleum ether/ethyl acetate (1/1, v/v) to afford 5-chloro-2-(2-methoxyphenyl)-1-methylpyrrolo[2,3-c]pyridine (855.0 mg, 91%) as a light yellow oil: [M+H]$^+$=273.1.

Step 2: Synthesis of 2-(2-methoxyphenyl)-1-methyl-1H-pyrrolo[2,3-c]pyridin-5-amine

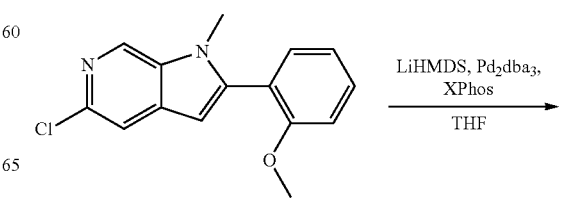

-continued

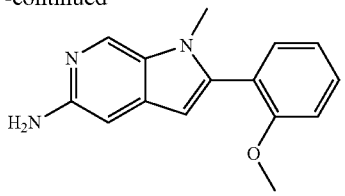

To a solution of 5-chloro-2-(2-methoxyphenyl)-1-methylpyrrolo[2,3-c]pyridine (805.0 mg, 2.95 mmol) in THF (15.0 mL) was added XPhos (281.4 mg, 0.59 mmol), $Pd_2(dba)_3$ (270.3 mg, 0.30 mmol) and LiHMDS (11.8 mL, 1.0 mol/L) at room temperature under $N_2$. The resulting mixture was stirred at 80° C. for 2 h. After the reaction was completed, the reaction mixture was quenched by the addition of sat. $NH_4Cl$ (aq.) at room temperature. The resulting mixture was diluted with water and extracted with ethyl acetate. The combined organic layers were washed with brine, dried over anhydrous sodium sulfate and filtered. The filtrate was concentrated under reduced pressure. The residue was purified by flash column chromatography with petroleum ether/ethyl acetate (1/1, v/v) to afford 2-(2-methoxyphenyl)-1-methyl-1H-pyrrolo[2,3-c]pyridin-5-amine (700.0 mg, 93%) as a brown oil. LCMS (ESI, m/z): $[M+H]^+=254.1$.

Step 3: Synthesis of methyl trans-2-[2-(2-methoxyphenyl)-1-methylpyrrolo[2,3-c]pyridin-5-yl]carbamoyl)cyclopropane-1-carboxylate

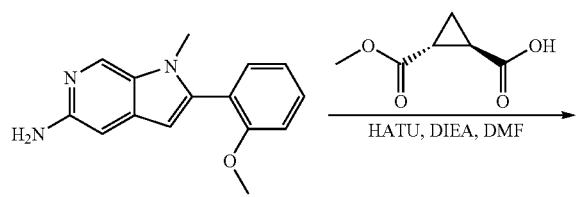

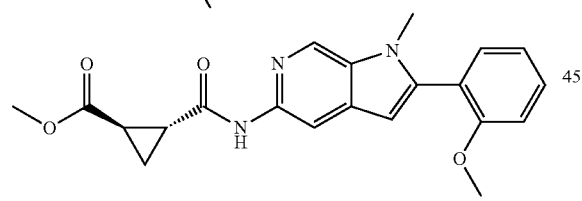

To a solution of 2-(2-methoxyphenyl)-1-methylpyrrolo[2,3-c]pyridin-5-amine (2.6 g, 10.42 mmol) in DMF (10.0 mL) was added DIEA (6.7 g, 52.11 mmol), trans-2-(methoxycarbonyl)cyclopropane-1-carboxylic acid (1.5 g, 10.42 mmol) and HATU (4.8 g, 12.51 mmol) at 0° C. The resulting mixture was stirred at room temperature for 2 h. After the reaction was completed, the resulting mixture was diluted with water and extracted with ethyl acetate. The combined organic layers were washed with brine, dried over anhydrous sodium sulfate and filtered. The filtrate was concentrated under reduced pressure. The residue was purified by reverse phase flash chromatography with acetonitrile/water (50/50, v/v) to afford methyl trans-2-{[2-(2-methoxyphenyl)-1-methylpyrrolo[2,3-c]pyridin-5-yl]carbamoyl}cyclopropane-1-carboxylate (1.0 g, 26%) as a light brown oil. LCMS (ESI, m/z): $[M+H]^+=380.2$.

Step 4: Synthesis of trans-2-(hydroxymethyl)-N-(2-(2-methoxyphenyl)-1-methyl-1H-pyrrolo[2,3-c]pyridin-5-yl)cyclopropane-1-carboxamide

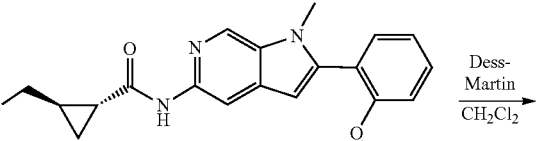

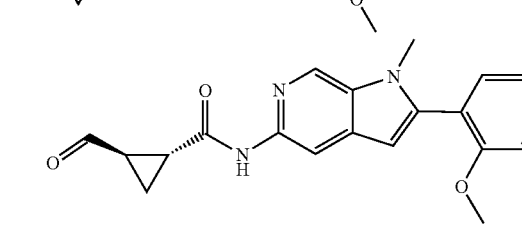

To a solution of methyl trans-2-{[2-(2-methoxyphenyl)-1-methylpyrrolo[2,3-c]pyridin-5-yl]carbamoyl}cyclopropane-1-carboxylate (630.0 mg, 1.66 mmol) in THF/MeOH (12.0 mL/8.0 mL) was added $NaBH_4$ (1.6 g, 41.50 mmol) at room temperature. The resulting mixture was stirred at 40° C. for 0.5 h. After the reaction was completed, the reaction mixture was quenched by the addition of water at room temperature. The resulting mixture was extracted with ethyl acetate. The combined organic layers were washed with brine, dried over anhydrous sodium sulfate and filtered. The filtrate was concentrated under reduced pressure. The residue was purified by reverse phase flash chromatography with acetonitrile/water (50/50, v/v) to afford trans-2-(hydroxymethyl)-N-(2-(2-methoxyphenyl)-1-methyl-1H-pyrrolo[2,3-c]pyridin-5-yl)cyclopropane-1-carboxamide (420.0 mg, 71%) as a yellow solid. LCMS (ESI, m/z): $[M+H]^+=352.2$.

Step 5: Synthesis of trans-2-formyl-N-(2-(2-methoxyphenyl)-1-methyl-1H-pyrrolo[2,3-c]pyridin-5-yl)cyclopropane-1-carboxamide To a solution of trans-2-(hydroxymethyl)-N-[2-(2-methoxyphenyl)-1-methylpyrrolo[2,3-c]pyridin-5-yl]cyclopropane-1-carboxamide (200.0 mg, 0.57 mmol) in $CH_2Cl_2$ (10.0 mL) was added Dess-Martin (362.1 mg, 0.85 mmol) at 0° C. The resulting mixture was stirred at room temperature for 1 h. After the reaction was completed, the resulting mixture was diluted with water and extracted with $CH_2Cl_2$. The combined organic layer was washed with brine, dried over anhydrous sodium sulfate and filtered. The filtrate was concentrated under reduced pressure to afford trans-2-formyl-N-(2-(2-methoxyphenyl)-1-methyl-1H-pyrrolo[2,3-c]pyridin-5-yl)cyclopropane-1-carboxamide (300.0 mg, crude) as a brown oil. LCMS (ESI, m/z): [M+H]$^+$=350.1.

Step 6: Synthesis of trans-2-((dimethylamino)methyl)-N-(2-(2-methoxyphenyl)-1-methyl-1H-pyrrolo[2,3-c]pyridin-5-yl)cyclopropane-1-carboxamide

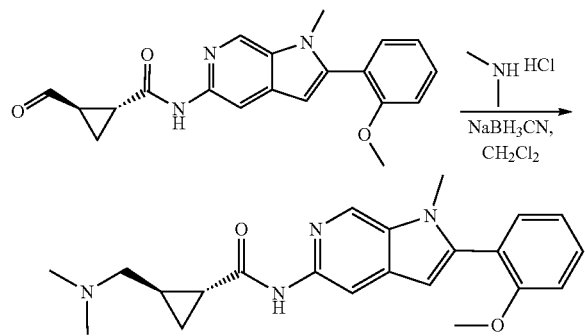

To a solution of trans-2-formyl-N-(2-(2-methoxyphenyl)-1-methyl-1H-pyrrolo[2,3-c]pyridin-5-yl)cyclopropane-1-carboxamide (300.0 mg, crude) in THF (10.0 mL) was added dimethylamine hydrochloride (310.8 mg, 2.65 mmol) and NaBH$_3$CN (166.6 mg, 2.65 mmol) at room temperature. The resulting mixture was stirred at room temperature for 1 h. After the reaction was completed, the reaction mixture was diluted with water and extracted with ethyl acetate. The combined organic layer was washed with brine, dried over anhydrous sodium sulfate and filtered. The filtrate was concentrated under reduced pressure. The residue was purified by reverse phase flash chromatography with acetonitrile/water (50/50, v/v) to afford trans-2-((dimethylamino)methyl)-N-(2-(2-methoxyphenyl)-1-methyl-1H-pyrrolo[2,3-c]pyridin-5-yl)cyclopropane-1-carboxamide (300.0 mg, 89%) as a yellow solid. LCMS (ESI, m/z): [M+H]$^+$=379.2.

Step 7: Synthesis of (1R,2R)-2-((dimethylamino)methyl)-N-(2-(2-methoxyphenyl)-1-methyl-1H-pyrrolo[2,3-c]pyridin-5-yl)cyclopropane-1-carboxamide and (1S,2S)-2-((dimethylamino)methyl)-N-(2-(2-methoxyphenyl)-1-methyl-1H-pyrrolo[2,3-c]pyridin-5-yl)cyclopropane-1-carboxamide (Compound 132 and Compound 133)

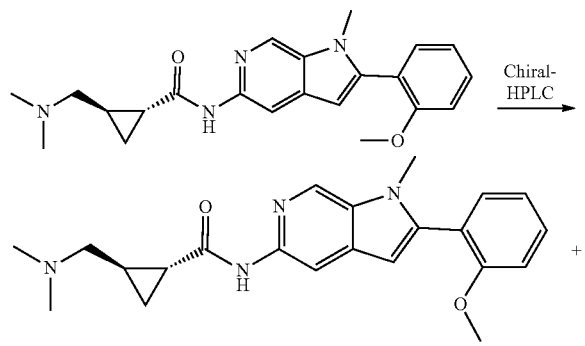

132

The trans-2-((dimethylamino)methyl)-N-(2-(2-methoxyphenyl)-1-methyl-1H-pyrrolo[2,3-c]pyridin-5-yl)cyclopropane-1-carboxamide (90.0 mg, 0.23 mmol) was separated by Prep-Chiral-HPLC with the following conditions (Column: CHIRALPAK IE, 2×25 cm, 5 μm; Mobile Phase A: Hex:DCM=3:1 (0.5% 2M NH$_3$-MeOH)—HPLC, Mobile Phase B: EtOH—HPLC; Flow rate: 18 mL/min; Gradient: 30% B to 30% B in 26 min; Wave Length: 220/254 nm) to afford 2-((dimethylamino)methyl)-N-(2-(2-methoxyphenyl)-1-methyl-1H-pyrrolo[2,3-c]pyridin-5-yl)cyclopropane-1-carboxamide Enantiomer 1 (8.8 mg, 9%) as a white solid and 2-((dimethylamino)methyl)-N-(2-(2-methoxyphenyl)-1-methyl-1H-pyrrolo[2,3-c]pyridin-5-yl)cyclopropane-1-carboxamide Enantiomer 2 (15.1 mg, 16%) as a white solid. The absolute stereochemistry of Enantiomers 1 and 2 was not assigned. The two enantiomeric structures that could be obtained from chiral separation of the enantiomeric mixture as described above are shown as Compounds 132 and 133 in Table 1.

2-((dimethylamino)methyl)-N-(2-(2-methoxyphenyl)-1-methyl-1H-pyrrolo[2,3-c]pyridin-5-yl)cyclopropane-1-carboxamide Enantiomer 1: Retention Time 1: 16.18 min; LCMS (ESI, m/z): [M+H]$^+$=379.2. $^1$H NMR (400 MHz, DMSO-d$_6$): δ 10.46 (s, 1H), 8.59 (s, 1H), 8.20 (s, 1H), 7.55-7.08 (m, 4H), 6.42 (s, 1H), 3.81 (s, 3H), 3.60 (s, 3H), 2.33-2.19 (m, 8H), 1.91-1.85 (m, 1H), 1.37-1.29 (m, 1H), 1.05-0.99 (m, 1H), 0.72-0.65 (m, 1H).

2-((dimethylamino)methyl)-N-(2-(2-methoxyphenyl)-1-methyl-1H-pyrrolo[2,3-c]pyridin-5-yl)cyclopropane-1-carboxamide Enantiomer 2: Retention Time 2: 21.69 min; LCMS (ESI, m/z): [M+H]$^+$=379.2. $^1$H NMR (400 MHz, DMSO-d$_6$): δ 10.47 (s, 1H), 8.59 (s, 1H), 8.19 (s, 1H), 7.55-7.50 (m, 1H), 7.38-7.36 (m, 1H), 7.21 (d, J=8.0 Hz, 1H), 7.12-7.08 (m, 1H), 6.42 (s, 1H), 3.81 (s, 3H), 3.60 (s, 3H), 2.31-2.26 (m, 1H), 2.22-2.17 (m, 7H), 1.89-1.85 (m, 1H), 1.36-1.31 (m, 1H), 1.06-1.04 (m, 1H), 0.72-0.67 (m, 1H).

Example S127: Synthesis of (1R,2R)-N-(2-(2,6-dimethoxyphenyl)-1-methyl-1H-pyrrolo[2,3-c]pyridin-5-yl)-2-((dimethylamino)methyl)cyclopropane-1-carboxamide and (1S,2S)-N-(2-(2,6-dimethoxyphenyl)-1-methyl-1H-pyrrolo[2,3-c]pyridin-5-yl)-2-((dimethylamino)methyl)cyclopropane-1-carboxamide (Compound 134 and Compound 135)

Step 1: Synthesis of methyl trans-2-(chlorocarbonyl)cyclopropane-1-carboxylate

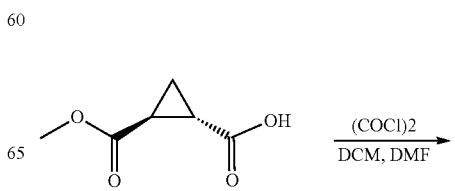

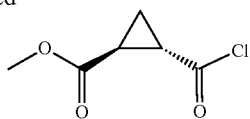

To a solution of trans-2-(methoxycarbonyl)cyclopropane-1-carboxylic acid (2.0 g, 13.00 mmol) in DCM (4.0 mL) was added (COCl)₂ (5.2 g, 41.0 mmol) and DMF (0.1 mL) at 0° C. under N₂. The resulting mixture was stirred at room temperature for 2 h. After the reaction was completed, the resulting mixture was concentrated under reduced pressure to afford methyl trans-2-(chlorocarbonyl)cyclopropane-1-carboxylate (2.1 g, crude) as a yellow oil.

Step 2: Synthesis of methyl trans-2-(dimethylcarbamoyl)cyclopropane-1-carboxylate

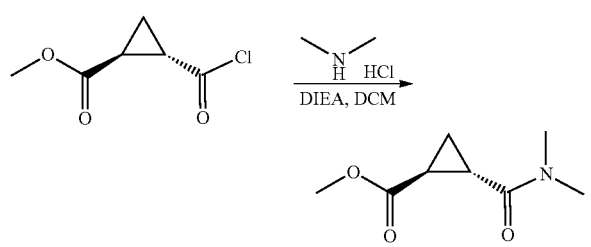

To a solution of methyl trans-2-(chlorocarbonyl)cyclopropane-1-carboxylate (2.0 g, 12.00 mmol) in DCM (20.0 mL) was added DIEA (2.3 g, 18.00 mmol) and dimethylamine hydrochloride (1.4 g, 18.00 mmol) at room temperature. The resulting mixture was stirred at room temperature for 2 h. After the reaction was completed, the resulting mixture was concentrated under reduced pressure. The residue was purified by flash column chromatography with CH₂Cl₂/MeOH (10/1, v/v) to afford methyl trans-2-(dimethylcarbamoyl)cyclopropane-1-carboxylate (1.7 g, 73%) as a yellow oil. LCMS (ESI, m/z): [M+H]⁺=172.1.

Step 3: Synthesis of methyl trans-2-((dimethylamino)methyl)cyclopropane-1-carboxylate

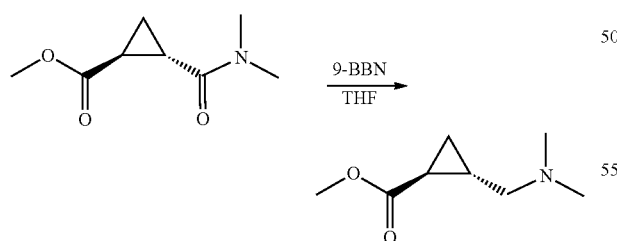

To a solution of methyl trans-2-(dimethylcarbamoyl)cyclopropane-1-carboxylate (1.7 g, 12.00 mmol) in THF (20.0 mL) was added 9-Borabicyclo[3.3.1]nonane (60.1 mL, 0.5 M) at room temperature. The resulting mixture was stirred at 60° C. for 2 h. After the reaction was completed, the resulting mixture was concentrated under reduced pressure. The residue was purified by flash column chromatography with CH₂Cl₂/MeOH (10/1, v/v) to afford methyl trans-2-((dimethylamino)methyl)cyclopropane-1-carboxylate (400.0 mg, 25%) as yellow oil. LCMS (ESI, m/z): [M+H]⁺=158.1.

Step 4: Synthesis of trans-N-(2-(2,6-dimethoxyphenyl)-1-methyl-1H-pyrrolo[2,3-c]pyridin-5-yl)-2-((dimethylamino)methyl)cyclopropane-1-carboxamide To a solution of 2-(2,6-dimethoxyphenyl)-1-methylpyrrolo[2,3-c]pyridin-5-amine (150.0 mg, 0.52 mmol) in THF (4.0 mL) was added methyl trans-2-[(dimethylamino)methyl]cyclopropane-1-carboxylate (33.2 mg, 0.21 mmol) and AlMe₃ (1.0 mL, 2.5 mol/L) at −20° C. The resulting mixture was stirred at 80° C. for 2 h. After the reaction was completed, the resulting mixture was quenched with H₂O and extracted with ethyl acetate. The combined organic layer was washed with brine, dried over anhydrous sodium sulfate and filtered. The filtrate was concentrated under reduced pressure. The residue was purified by reverse phase flash column chromatography with ACN/H₂O (1/1, v/v) to afford trans-N-(2-(2,6-dimethoxyphenyl)-1-methyl-1H-pyrrolo[2,3-c]pyridin-5-yl)-2-((dimethylamino)methyl)cyclopropane-1-carboxamide (95.0 mg, 44%) as yellow solid. LCMS (ESI, m/z): [M+H]⁺=409.2.

Step 5: Synthesis of (1R,2R)-N-(2-(2,6-dimethoxyphenyl)-1-methyl-1-pyrrolo[2,3-c]pyridin-5-yl)-2-((dimethylamino)methyl)cyclopropane-1-carboxamide and (S,2S)-N-(2-(2,6-dimethoxyphenyl)-1-methyl-1H-pyrrolo[2,3-c]pyridin-5-yl)-2-((dimethylamino)methyl)cyclopropane-1-carboxamide (Compound 134 and Compound 135)

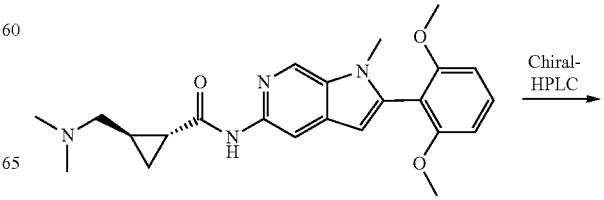

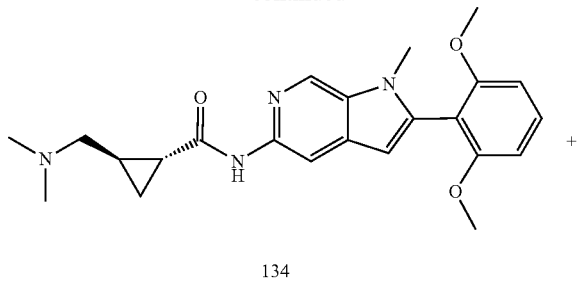

134

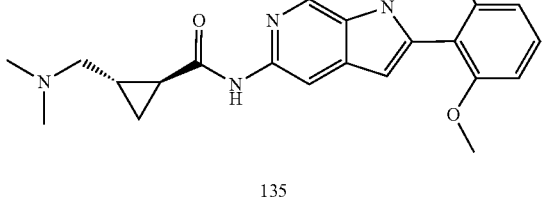

135

The product trans-N-(2-(2,6-dimethoxyphenyl)-1-methyl-1H-pyrrolo[2,3-c]pyridin-5-yl)-2-((dimethylamino)methyl)cyclopropane-1-carboxamide (95.0 mg) was separated by Prep-chiral HPLC with the following conditions (Column: CHIRALPAK IE, 2×25 cm, 5 μm; Mobile Phase A: Hex: DCM=3:1 (0.5% 2M NH₃-MeOH)—HPLC, Mobile Phase B: EtOH—HPLC; Flow rate: 18 mL/min; Gradient: 30% B to 30% B in 20 min; Wave Length: 220/254 nm) to afford N-(2-(2,6-dimethoxyphenyl)-1-methyl-1H-pyrrolo[2,3-c]pyridin-5-yl)-2-((dimethylamino)methyl)cyclopropane-1-carboxamide Enantiomer 1 (17.1 mg, 36%) and N-(2-(2,6-dimethoxyphenyl)-1-methyl-1H-pyrrolo[2,3-c]pyridin-5-yl)-2-((dimethylamino)methyl)cyclopropane-1-carboxamide Enantiomer 2 (18.4 mg, 38%) as a white solid. The absolute stereochemistry of Enantiomers 1 and 2 was not assigned. The two enantiomeric structures that could be obtained from chiral separation of the enantiomeric mixture as described above are shown as Compounds 134 and 135 in Table 1.

N-(2-(2,6-dimethoxyphenyl)-1-methyl-1H-pyrrolo[2,3-c]pyridin-5-yl)-2-((dimethylamino)methyl)cyclopropane-1-carboxamide Enantiomer 1: Retention Time 1=12.79 min; LCMS (ESI, m/z): [M+H]⁺=409.2. ¹H NMR (400 MHz, DMSO-d₆): δ 10.40 (s, 1H), 8.55 (s, 1H), 8.15 (s, 1H), 7.49-7.45 (s, 1H), 6.82 (d, J=8.4 Hz, 2H), 6.32 (s, 1H), 3.72 (s, 6H), 3.50 (s, 3H), 2.37-2.21 (m, 8H), 1.88-1.86 (m, 1H), 1.35-1.31 (m, 1H), 1.06-0.99 (m, 1H), 0.71-0.66 (m, 1H).

N-(2-(2,6-dimethoxyphenyl)-1-methyl-1H-pyrrolo[2,3-c]pyridin-5-yl)-2-((dimethylamino)methyl)cyclopropane-1-carboxamide Enantiomer 2: Retention Time 2=16.18 min; LCMS (ESI, m/z): [M+H]⁺=409.2. ¹H NMR (400 MHz, DMSO-d₆): δ 10.40 (s, 1H), 8.55 (s, 1H), 8.15 (s, 1H), 7.51-7.45 (m, 1H), 6.82 (d, J=8.4 Hz, 2H), 6.32 (s, 1H), 3.72 (s, 6H), 3.53 (s, 3H), 2.33-2.19 (m, 8H), 1.89-1.85 (m, 1H), 1.36-1.32 (m, 1H), 1.06-1.02 (m, 1H), 0.71-0.66 (m, 1H).

Example S128: Synthesis of (1S)-N-[2-(4,6-dimethoxypyrimidin-5-yl)-1-methylpyrrolo[2,3-c]pyridin-5-yl]-2,2-difluorocyclopropane-1-carboxamide and (1R)-N-[2-(4,6-dimethoxypyrimidin-5-yl)-1-methylpyrrolo[2,3-c]pyridin-5-yl]-2,2-difluorocyclopropane-1-carboxamide (Compound 136 and Compound 137)

Step 1: Synthesis of N-[2-(4,6-dimethoxypyrimidin-5-yl)-1-methylpyrrolo[2,3-c]pyridin-5-yl]-2,2-difluorocyclopropane-1-carboxamide

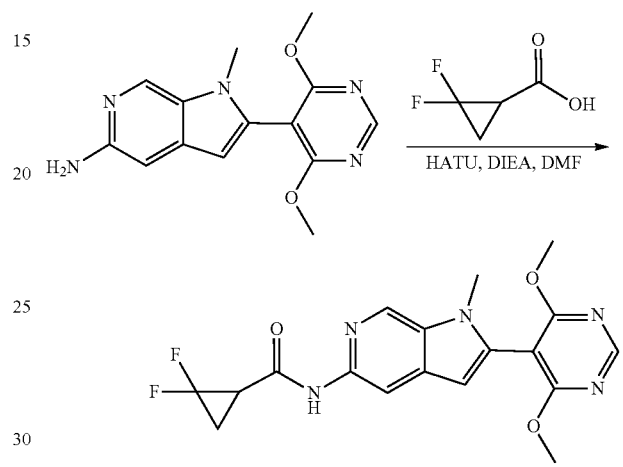

To a solution of 2-(4,6-dimethoxypyrimidin-5-yl)-1-methylpyrrolo[2,3-c]pyridin-5-amine (120.0 mg, 0.42 mmol) in DMF (6.0 mL) was added 2,2-difluorocyclopropane-1-carboxylic acid (77.0 mg, 0.63 mmol), DIEA (271.8 mg, 2.11 mmol) and HATU (191.9 mg, 0.51 mmol) at 0° C. under N₂. The resulting mixture was stirred at room temperature for 1 h. After the reaction was completed, the reaction mixture was diluted with H₂O and extracted with ethyl acetate. The combined organic layer was washed with brine, dried over anhydrous sodium sulfate and filtered. The filtrate was concentrated under reduced pressure. The residue was purified by reverse phase flash chromatography with acetonitrile/water (1/2, v/v) to afford N-[2-(4,6-dimethoxypyrimidin-5-yl)-1-methylpyrrolo[2,3-c]pyridin-5-yl]-2,2-difluorocyclopropane-1-carboxamide (100.0 mg, 61%) as a white solid. LCMS (ESI, m/z): [M+H]⁺=390.1.

Step 2: Synthesis of (1S)-N-[2-(4,6-dimethoxypyrimidin-5-yl)-1-methylpyrrolo[2,3-c]pyridin-5-yl]-2,2-difluorocyclopropane-1-carboxamide and (1R)-N-[2-(4,6-dimethoxypyrimidin-5-yl)-1-methylpyrrolo[2,3-c]pyridin-5-yl]-2,2-difluorocyclopropane-1-carboxamide (Compound 136 and Compound 137)

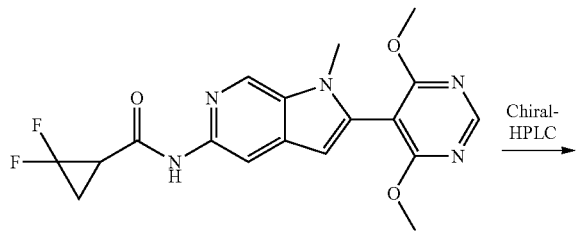

-continued

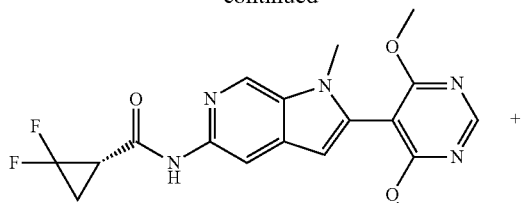

136

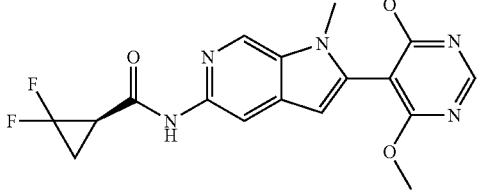

137

The product N-[2-(4,6-dimethoxypyrimidin-5-yl)-1-methylpyrrolo[2,3-c]pyridin-5-yl]-2,2-difluorocyclopropane-1-carboxamide (100.0 mg, 0.26 mmol) was separated by Prep-Chiral-HPLC with the following conditions (Column: CHIRAL ART Cellulose-SB, 3×25 cm, 5 um; Mobile Phase A:Hex:DCM=3:1 (0.5% 2M NH$_3$-MeOH)—HPLC, Mobile Phase B:EtOH—HPLC; Flow rate: 20 mL/min; Gradient: 50% B to 50% B in 7 min; 220/254 nm) to afford N-[2-(4,6-dimethoxypyrimidin-5-yl)-1-methylpyrrolo[2,3-c]pyridin-5-yl]-2,2-difluorocyclopropane-1-carboxamide Enantiomer 1 (28.6 mg, 57%) as a white solid. and N-[2-(4,6-dimethoxypyrimidin-5-yl)-1-methylpyrrolo[2,3-c]pyridin-5-yl]-2,2-difluorocyclopropane-1-carboxamide Enantiomer 2 (14.5 mg, 29%) as a white solid. The absolute stereochemistry of Enantiomers 1 and 2 was not assigned. The two enantiomeric structures that could be obtained from chiral separation of the enantiomeric mixture as described above are shown as Compounds 136 and 137 in Table 1.

N-[2-(4,6-dimethoxypyrimidin-5-yl)-1-methylpyrrolo[2,3-c]pyridin-5-yl]-2,2-difluorocyclopropane-1-carboxamide Enantiomer 1: Retention Time 1=4.69 min; LCMS (ESI, m/z): [M+H]$^+$=390.1. $^1$H NMR (400 MHz, DMSO-d$_6$): δ 10.72 (s, 1H), 8.67-8.65 (m, 2H), 8.18 (s, 1H), 6.52 (s, 1H), 3.93 (s, 6H), 3.59 (s, 3H), 3.04-2.95 (m, 1H), 2.08-1.94 (m, 2H).

N-[2-(4,6-dimethoxypyrimidin-5-yl)-1-methylpyrrolo[2,3-c]pyridin-5-yl]-2,2-difluorocyclopropane-1-carboxamide Enantiomer 2: Retention Time 2=5.92 min; LCMS (ESI, m/z): [M+H]$^+$=390.1. $^1$H NMR (400 MHz, DMSO-d$_6$): δ 10.72 (s, 1H), 8.67-8.65 (m, 2H), 8.18 (s, 1H), 6.52 (s, 1H), 3.93 (s, 6H), 3.59 (s, 3H), 3.04-2.95 (m, 1H), 2.08-1.94 (m, 2H).

Example S129: Synthesis of (1S,2S)-N-[2-(2,4-dimethoxypyridin-3-yl)-1-methylpyrrolo[2,3-c]pyridin-5-yl]-2-(piperazin-1-ylmethyl)cyclopropane-1-carboxamide and (1R,2R)-N-[2-(2,4-dimethoxypyridin-3-yl)-1-methylpyrrolo[2,3-c]pyridin-5-yl]-2-(piperazin-1-ylmethyl)cyclopropane-1-carboxamide (Compound 138 and Compound 139)

Step 1: Synthesis of Trans-N-(2-(2,4-dimethoxypyridin-3-yl)-1-methyl-1H-pyrrolo[2,3-c]pyridin-5-yl)-2-(piperazin-1-ylmethyl)cyclopropane-1-carboxamide

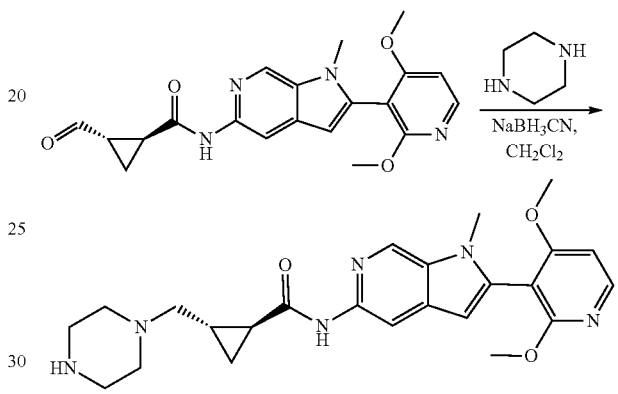

To a solution of trans-N-[2-(2,4-dimethoxypyridin-3-yl)-1-methylpyrrolo[2,3-c]pyridin-5-yl]-2-formylcyclopropane-1-carboxamide (1.6 g, 4.20 mmol) in CH$_2$Cl$_2$ (20.0 mL) was added piperazine (720.0 mg, 8.41 mmol) and NaBH$_3$CN (400.0 mg, 6.31 mmol) at room temperature. The resulting mixture was stirred at room temperature for 0.5 h. After the reaction was completed, the resulting mixture was diluted with H$_2$O and extracted with CH$_2$Cl$_2$. The combined organic layer was washed with brine, dried over anhydrous sodium sulfate and filtered. The filtrate was concentrated under reduced pressure. The residue was purified by reverse phase flash column chromatography with ACN/H$_2$O (46/54, v/v) to afford trans-N-(2-(2,4-dimethoxypyridin-3-yl)-1-methyl-1H-pyrrolo[2,3-c]pyridin-5-yl)-2-(piperazin-1-ylmethyl)cyclopropane-1-carboxamide (100.0 mg, 5%) as a white solid. LCMS (ESI, m/z): [M+H]$^+$=451.2.

Step 2: Synthesis of (1S,2S)-N-[2-(2,4-dimethoxypyridin-3-yl)-1-methylpyrrolo[2,3-c]pyridin-5-yl]-2-(piperazin-1-ylmethyl)cyclopropane-1-carboxamide and (1R,2R)-N-[2-(2,4-dimethoxypyridin-3-yl)-1-methylpyrrolo[2,3-c]pyridin-5-yl]-2-(piperazin-1-ylmethyl)cyclopropane-1-carboxamide (Compound 138 and Compound 139)

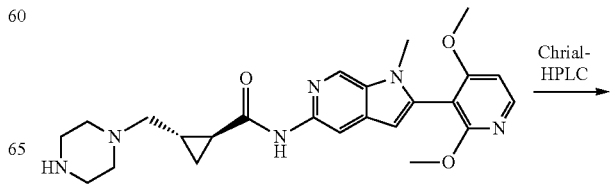

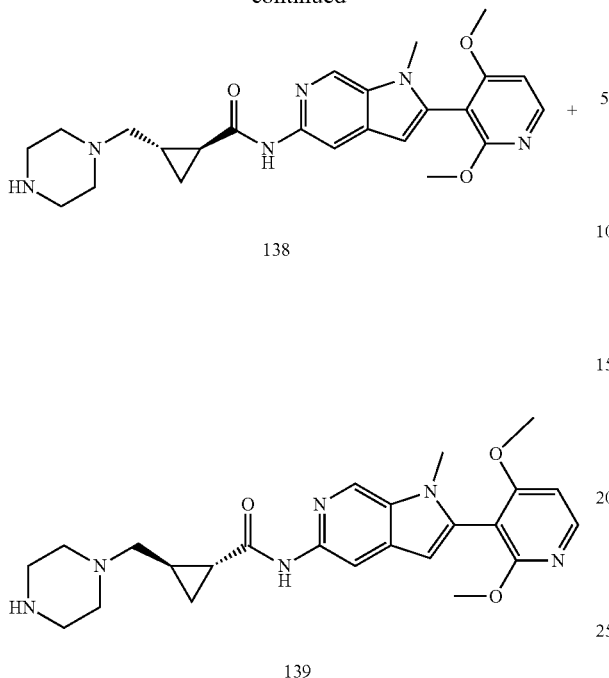

138

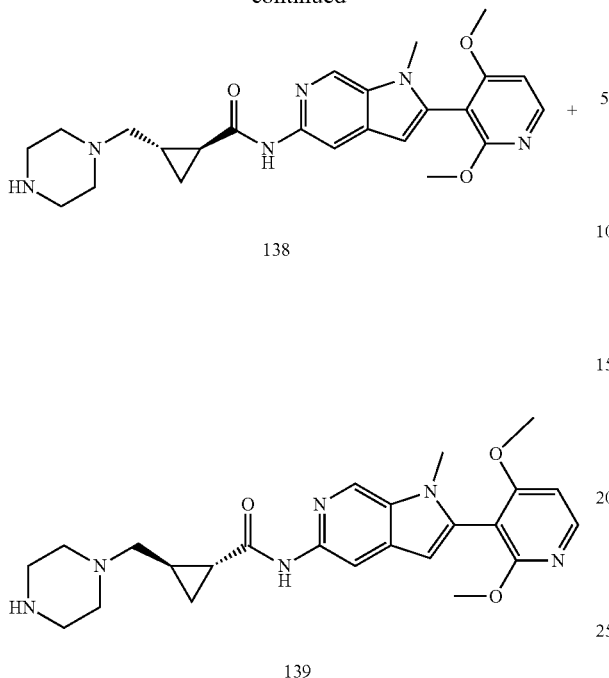

139

The product trans-N-(2-(2,4-dimethoxypyridin-3-yl)-1-methyl-1H-pyrrolo[2,3-c]pyridin-5-yl)-2-(piperazin-1-ylmethyl)cyclopropane-1-carboxamide (100.0 mg, 0.22 mmol) was separated by Prep-Chiral-HPLC with the following conditions (Column: CHIRALPAK 1G, 2×25 cm, 5 μm; Mobile Phase A: Hex (0.5% 2M $NH_3$-MeOH)—HPLC, Mobile Phase B: MeOH: EtOH=1:1—HPLC; Flow rate: 15 mL/min; Gradient: 70% B to 70% B in 33 min; Wave Length: 220/254 nm) to afford N-[2-(2,4-dimethoxypyridin-3-yl)-1-methylpyrrolo[2,3-c]pyridin-5-yl]-2-(piperazin-1-ylmethyl)cyclopropane-1-carboxamide Enantiomer 1 (31.2 mg, 62%) as a white solid and N-[2-(2,4-dimethoxypyridin-3-yl)-1-methylpyrrolo[2,3-c]pyridin-5-yl]-2-(piperazin-1-ylmethyl)cyclopropane-1-carboxamide Enantiomer 2 (26.2 mg, 52%) as a white solid. The absolute stereochemistry of Enantiomers 1 and 2 was not assigned. The two enantiomeric structures that could be obtained from chiral separation of the enantiomeric mixture as described above are shown as Compounds 138 and 139 in Table 1.

N-[2-(2,4-dimethoxypyridin-3-yl)-1-methylpyrrolo[2,3-c]pyridin-5-yl]-2-(piperazin-1-ylmethyl)cyclopropane-1-carboxamide Enantiomer 1: Retention Time 1(min): 21.52; LCMS (ESI, m/z): $[M+H]^+$=451.3. $^1$H NMR (400 MHz, DMSO-$d_6$): δ 10.42 (s, 1H), 8.58 (s, 1H), 8.25 (d, J=6.0 Hz, 1H), 8.16 (s, 1H), 6.97 (d, J=6.0 Hz, 1H), 6.39 (s, 1H), 3.82 (s, 6H), 3.53 (s, 3H), 2.85-2.61 (m, 4H), 2.36-2.31 (m, 4H), 2.28-2.20 (m, 2H), 1.88-1.83 (m, 1H), 1.37-1.32 (m, 1H), 1.06-0.96 (m, 1H), 0.82-0.72 (m, 1H).

N-[2-(2,4-dimethoxypyridin-3-yl)-1-methylpyrrolo[2,3-c]pyridin-5-yl]-2-(piperazin-1-ylmethyl)cyclopropane-1-carboxamide Enantiomer 2: Retention Time 2(min): 27.11; LCMS (ESI, m/z): $[M+H]^+$=451.3. $^1$H NMR (400 MHz, DMSO-$d_6$): δ 10.42 (s, 1H), 8.58 (s, 1H), 8.25 (d, J=6.0 Hz, 1H), 8.16 (s, 1H), 6.97 (d, J=6.0 Hz, 1H), 6.39 (s, 1H), 3.82 (s, 6H), 3.53 (s, 3H), 2.84-2.68 (m, 4H), 2.42-2.32 (m, 4H), 2.31-2.28 (m, 2H), 1.88-1.84 (m, 1H), 1.37-1.28 (m, 1H), 1.06-0.99 (m, 1H), 0.75-0.66 (m, 1H).

Example S130: Synthesis of (1S,2S)-N-[2-(2-cyclopropoxy-5-fluoropyridin-3-yl)-1-methylpyrrolo[2,3-c]pyridin-5-yl]-2-fluorocyclopropane-1-carboxamide (Compound 140)

Step 1: Synthesis of 3-bromo-2-cyclopropoxy-5-fluoropyridine

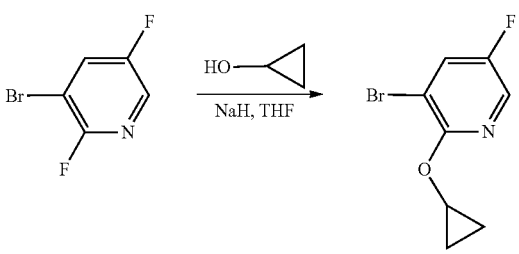

To a solution of cyclopropanol (389.2 mg, 6.70 mmol) in THF (20.0 mL) was added NaH (1.2 g, 60%) at 0° C. under $N_2$. The resulting mixture was stirred at room temperature for 30 min under $N_2$. Then 3-bromo-2,5-difluoropyridine (1.0 g, 5.15 mmol) was added to the mixture at room temperature under $N_2$. The resulting mixture was stirred at room temperature for 2 h. After the reaction was completed, the reaction mixture was quenched with $H_2O$ and extracted with ethyl acetate. The combined organic layer was washed with brine, dried over anhydrous sodium sulfate and filtered. The filtrate was concentrated under reduced pressure to afford 3-bromo-2-cyclopropoxy-5-fluoropyridine (500.0 mg, crude) as a yellow oil. LCMS (ESI, m/z): $[M+H]^+$= 232.0.

Step 2: Synthesis of 3-[5-chloro-1-methylpyrrolo[2,3-c]pyridin-2-yl]-2-cyclopropoxy-5-fluoropyridine

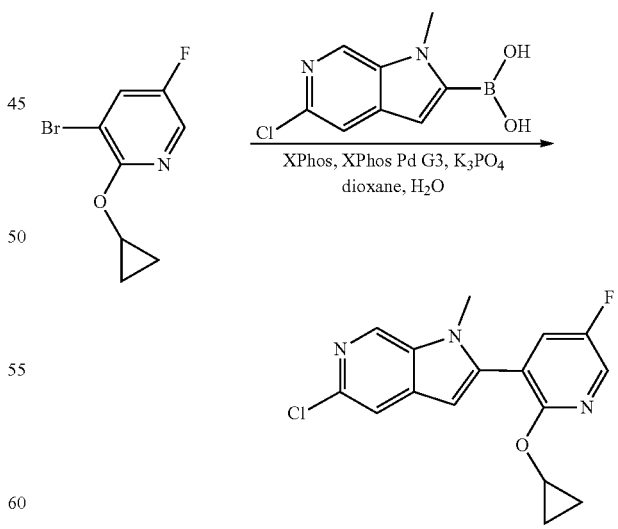

To a solution of 3-bromo-2-cyclopropoxy-5-fluoropyridine (500.0 mg, crude) in 1,4-dioxane (10.0 mL)/$H_2O$ (2.0 mL) was added (5-chloro-1-methyl-1H-pyrrolo[2,3-c]pyridin-2-yl)boronic acid (453.4 mg, 2.15 mmol), XPhos (205.4 mg, 0.43 mmol), $K_3PO_4$ (1.4 g, 6.46 mmol) and XPhos Pd G3 (182.4 mg, 0.21 mmol) at room temperature under $N_2$. The resulting mixture was stirred at 80° C. for 4 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (7/3, v/v) to afford 3-{5-chloro-1-methylpyrrolo[2,3-c]pyridin-2-yl}-2-cyclopropoxy-5-fluoropyridine (300.0 mg, 43%) as a yellow solid. LCMS (ESI, m/z): $[M+H]^+=318.1$.

Step 3: Synthesis of (1S,2S)-N-[2-(2-cyclopropoxy-5-fluoropyridin-3-vi)-1-methylpyrrolo[2,3-c]pyridin-5-yl]-2-fluorocyclopropane-1-carboxamide (Compound 140)

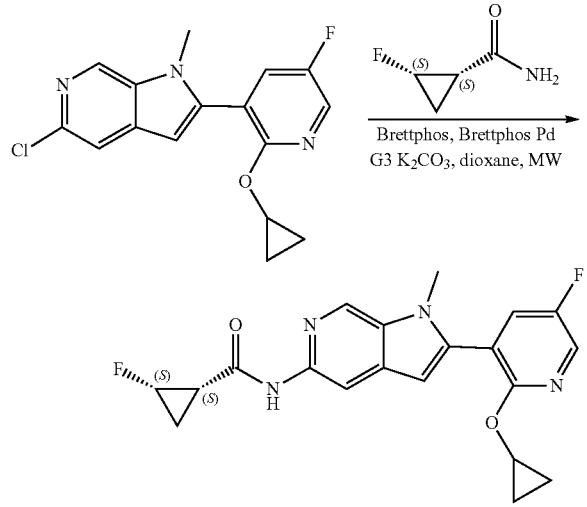

To a stirred solution of 3-{5-chloro-1-methylpyrrolo[2,3-c]pyridin-2-yl}-2-cyclopropoxy-5-fluoropyridine (300.0 mg, 0.94 mmol) in 1,4-dioxane (10.0 mL) was added (1S,2S)-2-fluorocyclopropane-1-carboxamide (292.0 mg, 2.83 mmol), BrettPhos (101.7 mg, 0.19 mmol), $K_2CO_3$ (391.5 mg, 2.83 mmol) and BrettPhos Pd G3 (85.6 mg, 0.09 mmol) at room temperature under $N_2$. The reaction mixture was stirred with microwave at 120° C. for 1.5 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (3/1, v/v) and then purified by Prep-HPLC with the following conditions (Column: XBridge Shield $RP_{18}$ OBD Column, 30×150 mm, 5 μm; Mobile Phase A: Water (10 mmol/L $NH_4HCO_3$), Mobile Phase B: ACN; Flow rate: 60 mL/min; Gradient: 31% B to 51% B in 10 min; Wave Length: 254 nm) to afford (1S,2S)-N-[2-(2-cyclopropoxy-5-fluoropyridin-3-yl)-1-methylpyrrolo[2,3-c]pyridin-5-yl]-2-fluorocyclopropane-1-carboxamide (Compound 140) (11.6 mg, 3%) as a white solid. LCMS (ESI, m/z): $[M+H]^+=385.1$. $^1H$ NMR (400 MHz, DMSO-$d_6$): δ 10.55 (s, 1H), 8.65 (s, 1H), 8.39 (d, J=3.2 Hz, 1H), 8.22 (s, 1H), 7.92-7.89 (m, 1H), 6.58 (s, 1H), 5.00-4.81 (m, 1H), 4.31-4.27 (m, 1H), 3.63 (s, 3H), 2.23-2.19 (m, 1H), 1.70-1.62 (m, 1H), 1.17-1.11 (m, 1H), 0.79-0.71 (m, 2H), 0.68-0.64 (m, 2H).

Example S131: Synthesis of (1S,2S)-2-fluoro-N-[2-(4-methoxy-2-methylpyrimidin-5-yl)-1-methylpyrrolo[2,3-c]pyridin-5-yl]cyclopropane-1-carboxamide (Compound 141)

Step 1: Synthesis of 5-bromo-4-methoxy-2-methylpyrimidine

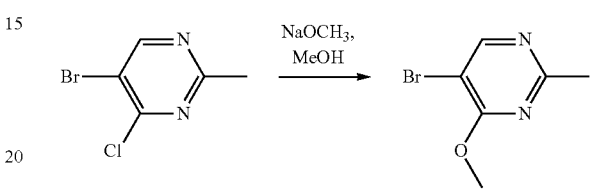

To a solution of 5-bromo-4-chloro-2-methylpyrimidine (950.0 mg, 4.58 mmol) in methanol (20.0 mL) was added $NaOCH_3$ (741.8 mg, 13.74 mmol) at 0° C. The resulting mixture was stirred at 0° C. for 2 h. After the reaction was completed, the reaction mixture was diluted with water and extracted with ethyl acetate. The combined organic layer was washed with brine, dried over anhydrous sodium sulfate and filtered. The filtrate was concentrated under reduced pressure to afford 5-bromo-4-methoxy-2-methylpyrimidine (890.0 mg, crude) as a brown oil. LCMS (ESI, m/z): $[M+H]^+=203.1$.

Step 2: Synthesis of 5-{5-chloro-1-methylpyrrolo[2,3-c]pyridin-2-yl}-4-methoxy-2-methylpyrimidine

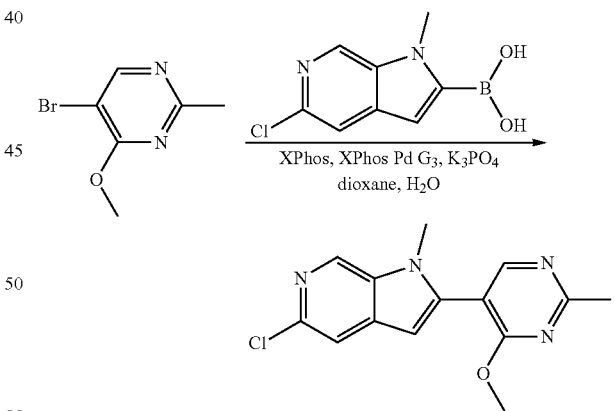

To a solution of 5-bromo-4-methoxy-2-methylpyrimidine (300.0 mg, crude) in dioxane/$H_2O$ (10.0 mL/2.0 mL) was added 5-chloro-1-methylpyrrolo[2,3-c]pyridin-2-ylboronic acid (310.9 mg, 1.48 mmol), XPhos (140.9 mg, 0.30 mmol), $K_3PO_4$ (940.9 mg, 4.43 mmol) and XPhos Pd G3 (125.1 mg, 0.15 mmol) at room temperature under $N_2$. The resulting mixture was stirred at 60° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced

Step 3: Synthesis of (1S,2S)-2-fluoro-N-[2-(4-methoxy-2-methylpyrimidin-5-yl)-1-methylpyrrolo[2,3-c]pyridin-5-yl]cyclopropane-1-carboxamide (Compound 141)

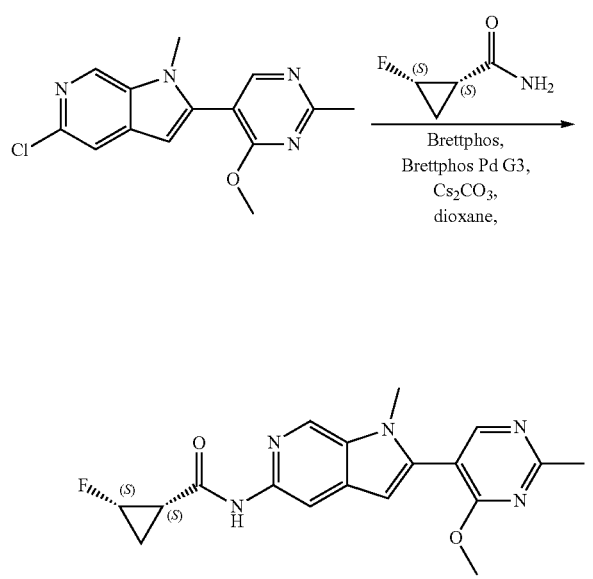

141

To a solution of 5-{5-chloro-1-methylpyrrolo[2,3-c]pyridin-2-yl}-4-methoxy-2-methylpyrimidine (150.0 mg, 0.52 mmol) in dioxane (15.0 mL) was added (1S,2S)-2-fluorocyclopropane-1-carboxamide (267.8 mg, 2.60 mmol), BrettPhos (55.7 mg, 0.10 mmol), $Cs_2CO_3$ (507.8 mg, 1.56 mmol) and BrettPhos Pd G3 (47.1 mg, 0.05 mmol) at room temperature under $N_2$. The reaction mixture was stirred with microwave at 120° C. for 1.5 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with acetonitrile/water (1/2, v/v) and then purified by Prep-HPLC with the following conditions (Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 20% B to 45% B in 8 min; Wave Length: 254 nm) to afford (1S,2S)-2-fluoro-N-[2-(4-methoxy-2-methylpyrimidin-5-yl)-1-methylpyrrolo[2,3-c]pyridin-5-yl]cyclopropane-1-carboxamide (Compound 141) (6.7 mg, 3%) as a white solid. LCMS (ESI, m/z): [M+H]$^+$=356.1. $^1$H NMR (400 MHz, DMSO-d$_6$): δ 10.66 (s, 1H), 8.68 (s, 1H), 8.54 (s, 1H), 8.19 (s, 1H), 6.63 (s, 1H), 5.00-4.84 (m, 1H), 3.99 (s, 3H), 3.67 (s, 3H), 2.64 (s, 3H), 2.25-2.19 (m, 1H), 1.69-1.63 (m, 1H), 1.16-1.09 (m, 1H).

Example S132: Synthesis of (1S,2S)-N-[2-(4-ethyl-2-methoxypyridin-3-yl)-1-methylpyrrolo[2,3-c]pyridin-5-yl]-2-fluorocyclopropane-1-carboxamide (Compound 142)

Step 1: Synthesis of 4-chloro-2-methoxy-3-nitropyridine

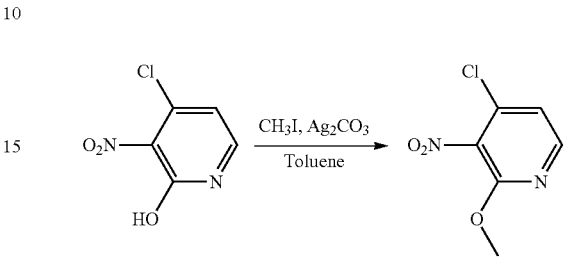

To a solution of 4-chloro-3-nitropyridin-2-ol (10.0 g, 57.30 mmol) in toluene (200.0 mL) was added $Ag_2CO_3$ (23.7 g, 85.94 mmol) and $CH_3I$ (16.3 g, 114.58 mmol) at room temperature. The resulting mixture was stirred at 80° C. for 2 h. After the reaction was completed, the resulting mixture was filtered. The filtrate was concentrated under reduced pressure to afford 4-chloro-2-methoxy-3-nitropyridine (7.4 g, crude) as a white solid. LCMS (ESI, m/z): [M+H]$^+$=189.0.

Step 2: Synthesis of 4-ethenyl-2-methoxy-3-nitropyridine

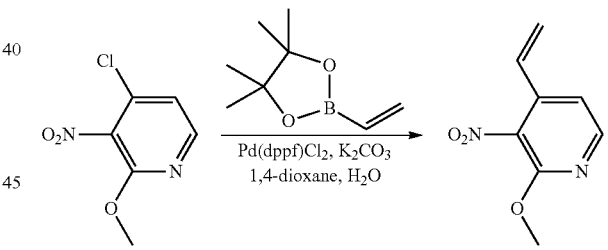

To a solution of 4-chloro-2-methoxy-3-nitropyridine (4.4 g, 23.12 mmol) in dioxane/$H_2O$ (50.0 mL/10.0 mL) was added 2-ethenyl-4,4,5,5-tetramethyl-1,3,2-dioxaborolane (10.7 g, 69.36 mmol), $K_2CO_3$ (9.6 g, 69.36 mmol) and Pd(dppf)Cl$_2$ (1.7 g, 2.31 mmol) at room temperature under $N_2$. The resulting mixture was stirred at 80° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (85/15, v/v) to afford 4-ethenyl-2-methoxy-3-nitropyridine (1.1 g, 27%) as a white solid. LCMS (ESI, m/z): [M+H]$^+$=181.1.

Step 3: Synthesis of 4-ethyl-2-methoxypyridin-3-amine

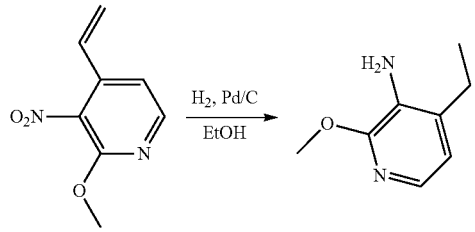

To a solution of 4-ethenyl-2-methoxy-3-nitropyridine (1.0 g, 5.55 mmol) in EtOH (30.0 mL) was added Pd/C (300.0 mg, dry) at room temperature under $N_2$. The resulting mixture was stirred at room temperature for 16 h under $H_2$. After the reaction was completed, the resulting mixture was filtered. The filtrate was concentrated under reduced pressure to afford 4-ethyl-2-methoxypyridin-3-amine (800.0 mg, crude) as a brown oil. LCMS (ESI, m/z): $[M+H]^+=153.1$.

Step 4: Synthesis of 3-bromo-4-ethyl-2-methoxypyridine

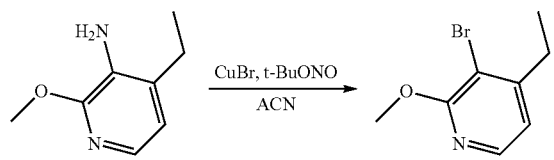

To a solution of 4-ethyl-2-methoxypyridin-3-amine (800.0 mg, 5.26 mmol) in ACN (30.0 mL) was added CuBr (904.8 mg, 6.31 mmol) at room temperature. Then t-BuONO (813.1 mg, 7.88 mmol) was added dropwise to the mixture at 0° C. under $N_2$. The resulting mixture was stirred at 80° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure to afford 3-bromo-4-ethyl-2-methoxypyridine (1.0 g, crude) as a brown oil. LCMS (ESI, m/z): $[M+H]^+=216.1$.

Step 5: Synthesis of 3-{5-chloro-1-methylpyrrolo[2,3-c]pyridin-2-yl}-4-ethyl-2-methoxypyridine

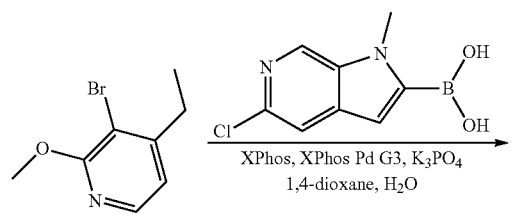

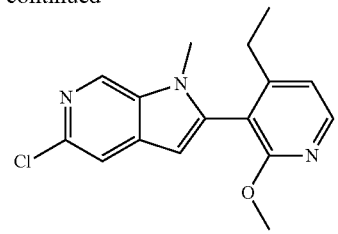

To a solution of 3-bromo-4-ethyl-2-methoxypyridine (500.0 mg, 2.31 mmol) in dioxane/$H_2O$ (10.0 mL/2.0 mL) was added 5-chloro-1-methylpyrrolo[2,3-c]pyridin-2-ylboronic acid (486.9 mg, 2.31 mmol), XPhos (220.6 mg, 0.46 mmol), $K_3PO_4$ (1.5 g, 6.94 mmol) and XPhos Pd G3 (195.9 mg, 0.23 mmol) at room temperature under $N_2$. The resulting mixture was stirred at 60° C. for 4 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (76124, v/v) to afford 3-{5-chloro-1-methylpyrrolo[2,3-c]pyridin-2-yl}-4-ethyl-2-methoxypyridine (197.0 mg, 28%) as a brown oil. LCMS (ESI, m/z): $[M+H]^+=302.1$.

Step 6: Synthesis of (1S,2S)-N-[2-(4-ethyl-2-methoxypyridin-3-yl)-1-methylpyrrolo[2,3-c]pyridin-5-yl]-2-fluorocyclopropane-1-carboxamide (Compound 142)

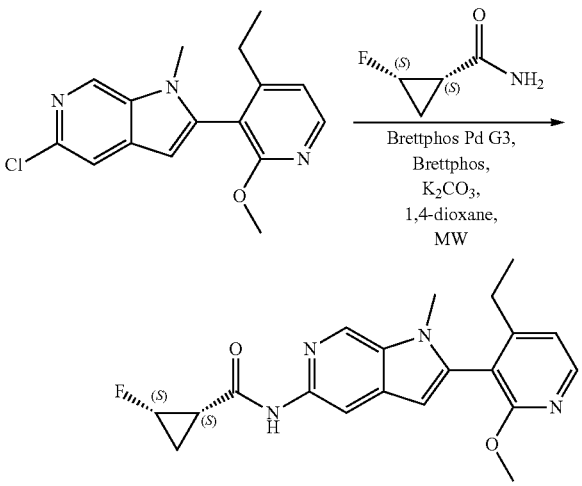

142

To a solution of 3-{5-chloro-1-methylpyrrolo[2,3-c]pyridin-2-yl}-4-ethyl-2-methoxypyridine (177.0 mg, 0.62 mmol) in dioxane (15.0 mL) was added (1S,2S)-2-fluorocyclopropane-1-carboxamide (302.4 mg, 2.94 mmol), BrettPhos (63.0 mg, 0.12 mmol), $Cs_2CO_3$ (573.3 mg, 1.76 mmol) and BrettPhos Pd G3 (53.2 mg, 0.06 mmol) at room temperature under $N_2$. The reaction mixture was stirred with microwave at 120° C. for 1.5 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) and then purified by Prep-HPLC with the following conditions (Column: XBridge Shield RP$_{18}$ OBD Column, 19×250 mm, 10 μm; Mobile Phase A: Water (10 mmol/L NH$_4$HCO$_3$), Mobile Phase B: ACN; Flow rate: 25 mL/min; Gradient: 55% B to 65% B in 8 min; Wave Length: 254 nm) to afford (1S,2S)-N-[2-(4-ethyl-2-methoxypyridin-3-yl)-1-methylpyrrolo[2,3-c]pyridin-5-yl]-2-fluorocyclopropane-1-carboxamide (Compound 142) (5.2 mg, 2%) as a white solid. LCMS (ESI, m/z): [M+H]$^+$=369.3. 1 H NMR (400 MHz, DMSO-d$_6$): δ 10.51 (s, 1H), 8.62 (s, 1H), 8.24-8.20 (m, 2H), 7.11 (d, J=5.2 Hz, 1H), 6.46 (s, 1H), 5.00-4.80 (m, 1H), 3.81 (s, 3H), 3.50-3.42 (m, 3H), 2.38-2.32 (m, 1H), 2.22-2.18 (m, 1H), 1.71-1.64 (m, 1H), 1.20-1.10 (m, 1H), 1.07-0.98 (m, 3H).

Example S133: Synthesis of (1S,2S)-N-[2-(2-ethoxy-5-fluoropyridin-3-yl)-1-methylpyrrolo[2,3-c]pyridin-5-yl]-2-fluorocyclopropane-1-carboxamide (Compound 143)

Step 1: Synthesis of 3-bromo-2-ethoxy-5-fluoropyridine

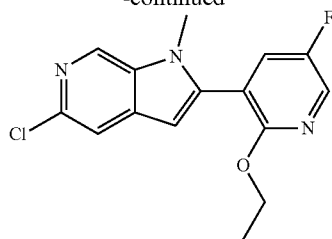

To a solution of 3-bromo-5-fluoropyridin-2-ol (1.0 g, 5.21 mmol) in toluene (30.0 mL) was added ethyl iodide (1.6 g, 10.42 mmol) and Ag$_2$CO$_3$ (2.2 g, 7.81 mmol) at room temperature. The resulting mixture was stirred at 80° C. for 16 h. After the reaction was completed, the resulting mixture was filtered. The filtrate was concentrated under reduced pressure. The residue was purified by flash column chromatography with petroleum ether/ethyl acetate (89/11, v/v) to afford 3-bromo-2-ethoxy-5-fluoropyridine (875.0 mg, 76%) as a white solid. LCMS (ESI, m/z): [M+H]$^+$=220.0.

Step 2: Synthesis of 3-{5-chloro-1-methylpyrrolo[2,3-c]pyridin-2-yl}-2-ethoxy-5-fluoropyridine

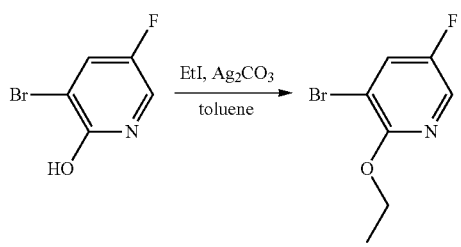

To a solution of 3-bromo-2-ethoxy-5-fluoropyridine (700.0 mg, 3.18 mmol) in dioxane/H$_2$O (10.0 mL/2.0 mL) was added 5-chloro-1-methylpyrrolo[2,3-c]pyridin-2-ylboronic acid (669.4 mg, 0.64 mmol), XPhos (303.3 mg, 0.64 mmol), K$_3$PO$_4$ (2.03 g, 9.54 mmol) and XPhos Pd G3 (269.3 mg, 0.32 mmol) at room temperature under N$_2$. The resulting mixture was stirred at 100° C. for 4 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (72/28, v/v) to afford 3-{5-chloro-1-methylpyrrolo[2,3-c]pyridin-2-yl}-2-ethoxy-5-fluoropyridine (309.0 mg, 31%) as a white solid. LCMS (ESI, m/z): [M+H]$^+$=306.1.

Step 3: Synthesis of (1S,2S)-N-[2-(2-ethoxy-5-fluoropyridin-3-yl)-1-methylpyrrolo[2,3-c]pyridin-5-yl]-2-fluorocyclopropane-1-carboxamide (Compound 143)

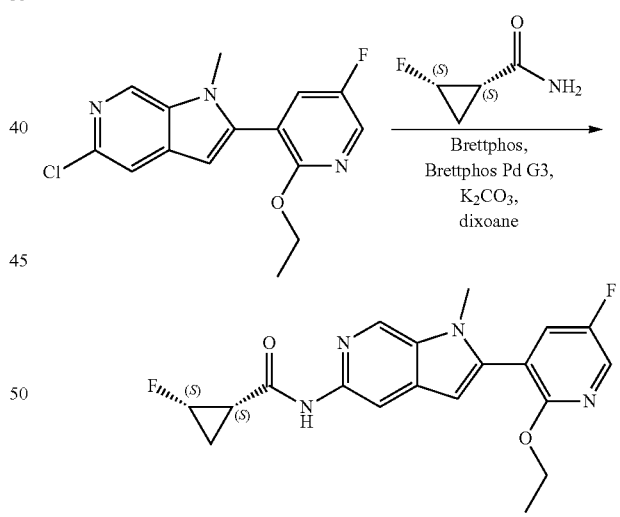

143

To a solution of 3-{5-chloro-1-methylpyrrolo[2,3-c]pyridin-2-yl}-2-ethoxy-5-fluoropyridine (280.0 mg, 0.92 mmol) in dioxane (15.0 mL) was added (1S,2S)-2-fluorocyclopropane-1-carboxamide (472.1 mg, 4.58 mmol), BrettPhos (98.3 mg, 0.18 mmol), Cs$_2$CO$_3$ (859.2 mg, 2.75 mmol) and BrettPhos Pd G$_3$ (83.0 mg, 0.09 mmol) at room temperature under N$_2$. The resulting mixture was stirred at 100° C. for 4 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (15/85, v/v) and then purified by Prep-HPLC with the following conditions (Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 38% B to 48% B in 8 min; Wave Length: 254 nm) to afford (1S,2S)-N-[2-(2-ethoxy-5-fluoropyridin-3-yl)-1-methylpyrrolo[2,3-c]pyridin-5-yl]-2-fluorocyclopropane-1-carboxamide (Compound 143) (14.4 mg, 4%) as a white solid. LCMS (ESI, m/z): [M+H]$^+$=373.2. $^1$H NMR (400 MHz, DMSO-d$_6$): δ 10.66 (s, 1H), 8.67 (s, 1H), 8.33 (d, J=4.4 Hz, 1H), 8.23 (s, 1H), 7.91-7.88 (m, 1H), 6.60 (s, 1H), 5.01-4.81 (m, 1H), 4.41-4.36 (m, 2H), 3.70 (s, 3H), 2.25-2.18 (m, 1H), 1.71-1.61 (m, 1H), 1.30-1.26 (m, 3H), 1.18-1.10 (m, 1H).

Example S134: Synthesis of (1S,2S)-N-(2-(4,6-bis(methoxy-d3)pyrimidin-5-yl)-1H-pyrrolo[2,3-c]pyridin-5-yl)-2-fluorocyclopropane-1-carboxamide (Compound 144)

Step 1: Synthesis of 5-bromo-4,6-bis(methoxy-d$_3$)pyrimidine

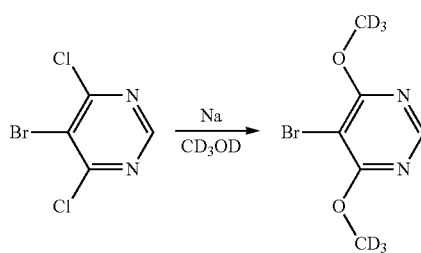

The solution of Na (500.0 mg, 21.75 mmol) in CD$_3$OD (11.0 mL) was stirred at room temperature for 0.5 h. Then 5-bromo-4,6-dichloropyrimidine (1.0 g, 4.39 mmol) was added to the mixture at room temperature. The resulting mixture was stirred at 40° C. for 16 h. After the reaction was completed, the reaction mixture was quenched by the addition of water and extracted with ethyl acetate. The combined organic layer was washed with brine, dried over anhydrous sodium sulfate and filtered. The filtrate was concentrated under reduced pressure to afford 5-bromo-4,6-bis(methoxy-d3)pyrimidine (830.0 mg, crude) as a white solid. LCMS (ESI, m/z): [M+H]$^+$=225.0.

Step 2: Synthesis of 4,6-bis(methoxy-d3)-5-(4,4,5,5-tetramethyl-1,3,2-dioxaborolan-2-yl)pyrimidine

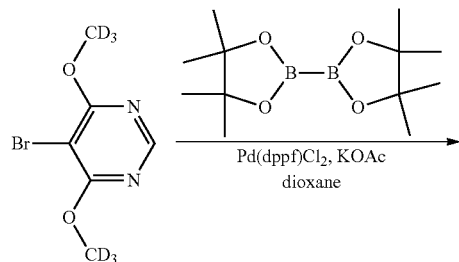

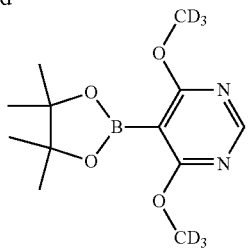

To a solution of 5-bromo-4,6-bis(methoxy-d3)pyrimidine (770.0 mg, 3.42 mmol) in dioxane (25.0 mL) was added bis(pinacolato)diboron (2.6 g, 10.26 mmol), KOAc (1.0 g, 10.26 mmol) and Pd(dppf)Cl$_2$ (250.0 mg, 0.34 mmol) at room temperature under N$_2$. The resulting mixture was stirred at 80° C. for 16 h. After the reaction was completed, the resulting mixture was concentrated under reduced pressure. The residue was purified by flash column chromatography with petroleum ether/ethyl acetate (1/1, v/v) to afford 4,6-bis(methoxy-d3)-5-(4,4,5,5-tetramethyl-1,3,2-dioxaborolan-2-yl)pyrimidine (570.0 mg, 61%) as a yellow solid. LCMS (ESI, m/z): [M+H]$^+$=273.2.

Step 3: Synthesis of tert-butyl 5-(bis(4-methoxybenzyl)amino)-2-(4,6-bis(methoxy-d3)pyrimidin-5-yl)-1H-pyrrolo[2,3-c]pyridine-1-carboxylate

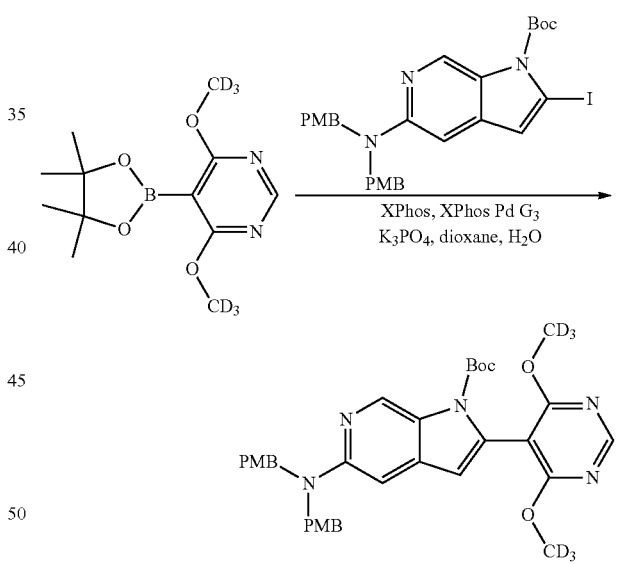

To a solution of 4,6-bis(methoxy-d3)-5-(4,4,5,5-tetramethyl-1,3,2-dioxaborolan-2-yl)pyrimidine (560.0 mg, 2.06 mmol) in dioxane/H$_2$O (20.0 mL/2.0 mL) was added tert-butyl 5-{bis[(4-methoxyphenyl)methyl]amino}-2-iodopyrrolo[2,3-c]pyridine-1-carboxylate (1.2 g, 2.06 mmol), K$_3$PO$_4$ (1.3 g, 6.17 mmol), XPhos (196.2 mg, 0.41 mmol) and XPhos Pd G$_3$ (174.2 mg, 0.21 mmol) at room temperature under N$_2$. The resulting mixture was stirred at 80° C. for 4 h. After the reaction was completed, the resulting mixture was diluted with H$_2$O and extracted with ethyl acetate. The combined organic layer was washed with brine, dried over anhydrous sodium sulfate and filtered. The filtrate was concentrated under reduced pressure. The residue was purified by flash column chromatography with petroleum ether/ ethyl acetate (1/2, v/v) to afford tert-butyl 5-(bis(4-methoxybenzyl)amino)-2-(4,6-bis(methoxy-d3)pyrimidin-5-yl)-1H-pyrrolo[2,3-c]pyridine-1-carboxylate (410.0 mg, 32%) as a yellow solid. LCMS (ESI, n/z): [M+H]+=618.3.

Step 4: Synthesis of 2-(4,6-bis(methoxy-d3)pyrimidin-5-yl)-1H pyrrolo[2,3-c]pyridin-5-amine

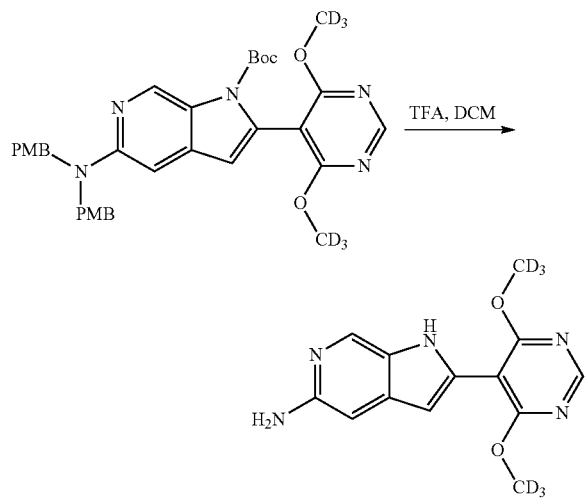

To a solution of tert-butyl 5-(bis(4-methoxybenzyl)amino)-2-(4,6-bis(methoxy-d3)pyrimidin-5-yl)-1H-pyrrolo[2,3-c]pyridine-1-carboxylate (390.0 mg, 0.63 mmol) in DCM (10.0 mL) was added TFA (10.0 mL) at room temperature. The resulting mixture was stirred at room temperature for 1 h. After the reaction was completed, the reaction mixture was concentrated under reduced pressure. The pH value of the residue was adjusted to 8 with aq. NaHCO₃. The resulting mixture was extracted with CH₂Cl₂. The combined organic layers was washed with brine, dried over anhydrous sodium sulfate and filtered. The filtrate was concentrated under reduced pressure. The residue was purified by flash column chromatography with petroleum ether/ethyl acetate (1/2, v/v) to afford 2-(4,6-bis(methoxy-d3)pyrimidin-5-yl)-1H-pyrrolo[2,3-c]pyridin-5-amine (310.0 mg, 88%) as an off-white solid. LCMS (ESI, m/z): [M+H]+=278.1.

Step 5: Synthesis of (1S,2S)-N-(2-(4,6-bis(methoxy-d3)pyrimidin-5-yl)-1H-pyrrolo[2,3-c]pyridin-5-yl)-2-fluorocyclopropane-1-carboxamide (Compound 144)

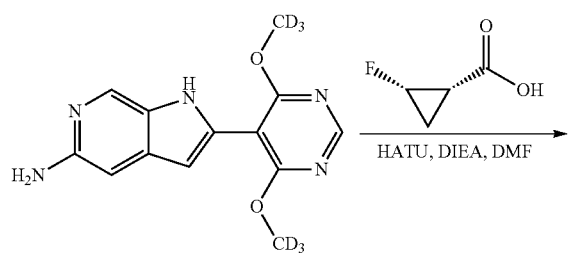

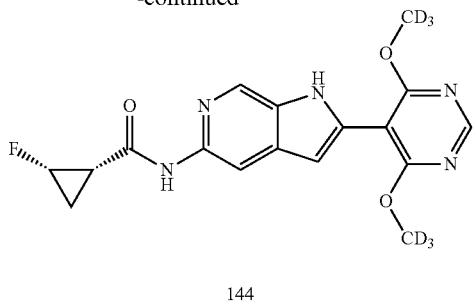

144

To a solution of 2-(4,6-bis(methoxy-d3)pyrimidin-5-yl)-1H-pyrrolo[2,3-c]pyridin-5-amine (300.0 mg, 1.08 mmol) in DMF (10.0 mL) was added (1S,2S)-2-fluorocyclopropane-1-carboxylic acid (135.1 mg, 1.30 mmol), DIEA (559.3 mg, 4.33 mmol) and HATU (575.9 mg, 1.52 mmol) at room temperature. The resulting mixture was stirred at room temperature for 1 h. After the reaction was completed, the resulting mixture was diluted with H₂O and extracted with CH₂Cl₂. The combined organic layer was washed with brine, dried over anhydrous sodium sulfate and filtered. The filtrate was concentrated under reduced pressure. The residue was purified by flash column chromatography with petroleum ether/ethyl acetate (1/99, v/v) and then purified by Prep-HPLC with the following conditions (Column: XBridge Prep OBD C18 Column, 30×150 mm, 5 µm; Mobile Phase A: Water (10 mmol/L NH₄HCO₃), Mobile Phase B: ACN; Flow rate: 60 mL/min; Gradient: 26% B to 36% B in 8 min; Wave Length: 254 nm) to afford (1S,2S)-N-(2-(4,6-bis(methoxy-d3)pyrimidin-5-yl)-1H-pyrrolo[2,3-c]pyridin-5-yl)-2-fluorocyclopropane-1-carboxamide (Compound 144) (16.6 mg, 4%) as a white solid. LCMS (ESI, m/z): [M+H]+=364.2. ¹H NMR (400 MHz, DMSO-d₆): δ 11.37 (s, 1H), 10.44 (s, 1H), 8.56-8.54 (m, 2H), 8.19 (s, 1H), 6.96 (d, J=1.6 Hz, 1H), 5.00-4.80 (m, 1H), 2.23-2.16 (m, 1H), 1.71-1.62 (m, 1H), 1.21-1.08 (m, 1H).

Example S135: Synthesis of (1S,2S)-2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide and (1R,2R)-2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide (Compound 145 and Compound 146)

Step 1: Synthesis of Tert-butyl 3-[trans-2-(methoxycarbonyl)cyclopropanecarbonyl]-3,6-diazabicyclo[3.1.1]heptane-6-carboxylate

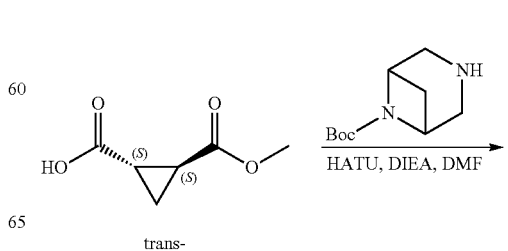

trans-

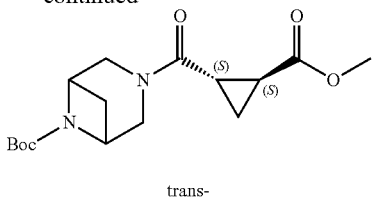

trans-

To a solution of trans-2-(methoxycarbonyl)cyclopropane-1-carboxylic acid (1.0 g, 6.94 mmol) in DMF (10.0 mL) was added DIEA (4.5 g, 34.69 mmol), tert-butyl 3,6-diazabicyclo[3.1.1]heptane-6-carboxylate (1.7 g, 8.33 mmol) and HATU (4.0 g, 10.41 mmol) at 0° C. under $N_2$. The resulting mixture was stirred at room temperature for 1 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $H_2O/CH_3CN$ (50/50, v/v) to afford tert-butyl 3-[trans-2-(methoxycarbonyl)cyclopropanecarbonyl]-3,6-diazabicyclo[3.1.1]heptane-6-carboxylate (2.0 g, 88%) as a yellow solid. LCMS (ESI, m/z): $[M+H]^+=$ 325.2.

Step 2: Synthesis of tert-butyl 3-{[trans-2-(methoxycarbonyl)cyclopropyl]methyl}-3,6-diazabicyclo[3.1.1]heptane-6-carboxylate

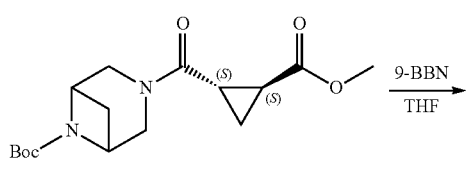

trans-

To a solution of tert-butyl 3-[trans-2-(methoxycarbonyl)cyclopropanecarbonyl]-3,6-diazabicyclo[3.1.1]heptane-6-carboxylate (750.0 mg, 2.31 mmol) in THF (8.0 mL) was added 9-borabicyclo[3.3.1]nonane (18.5 ml, 0.5 mol/L) at room temperature. The resulting mixture was stirred at 60° C. for 2 h. After the reaction was completed, the mixture was concentrated under reduced pressure. The residue was purified by reverse phase flash column chromatography with $H_2O/CH_3CN$ (50/50, v/v) to afford tert-butyl 3-{[trans-2-(methoxycarbonyl)cyclopropyl]methyl}-3,6-diazabicyclo[3.1.1]heptane-6-carboxylate (450.0 mg, 62%) as a yellow solid. LCMS (ESI, m/z): $[M+H]^+=311.2$.

Step 3: Synthesis of 2-(2,4-dimethoxypyridin-3-yl)-1-methylpyrrolo[2,3-c]pyridin-5-amine

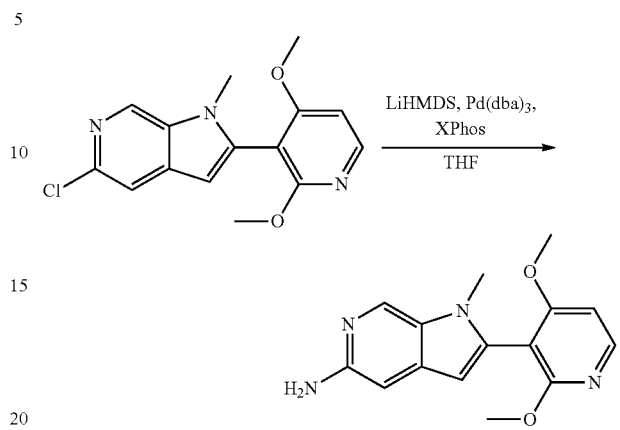

To a solution of 3-{5-chloro-1-methylpyrrolo[2,3-c]pyridin-2-yl}-2,4-dimethoxypyridine (1.9 g, 6.26 mmol) in THF (20.0 mL) was added $Pd_2(dba)_3$ (572.8 mg, 0.63 mmol), XPhos (596.4 mg, 1.25 mmol) and LiHMDS (12.5 mL, 1 mol/L) at room temperature. The resulting mixture was stirred at 60° C. for 1 h. After the reaction was completed, the resulting mixture was quench with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2/CH_3OH$ (90/10, v/v) to afford 2-(2,4-dimethoxypyridin-3-yl)-1-methylpyrrolo[2,3-c]pyridin-5-amine (1.9 g, 96%) as a yellow solid. LCMS (ESI, m/z): $[M+H]^+=285.1$.

Step 4: Synthesis of tert-butyl 3-{[trans-2-{[2-(2,4-dimethoxypyridin-3-yl)-1-methylpyrrolo[2,3-c]pyridin-5-yl]carbamoyl}cyclopropyl]methyl}-3,6-diazabicyclo[3.1.1]heptane-6-carboxylate

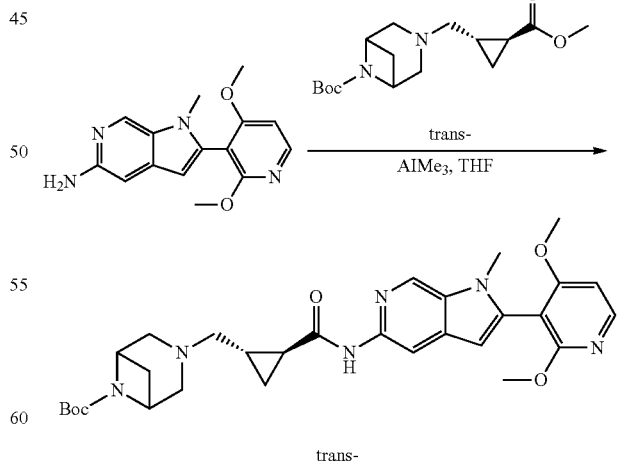

trans-

To a solution of 2-(2,4-dimethoxypyridin-3-yl)-1-methylpyrrolo[2,3-c]pyridin-5-amine (122.0 mg, 0.43 mmol) in THF (3.0 mL) was added tert-butyl 3-{[trans-2-(methoxycarbonyl)cyclopropyl]methyl}-3,6-diazabicyclo[3.1.1]heptane-6-carboxylate (199.8 mg, 0.64 mmol) and AlMe$_3$ (1.1 mL, 2 mol/L) at 0° C. under N$_2$. The resulting mixture was stirred at 80° C. for 3 h. After the reaction was completed, the resulting mixture was quench with CH$_3$OH at 0° C. and then concentrated under reduced pressure. The residue was purified by reverse phase flash column chromatography with H$_2$O/CH$_3$CN (20/80, v/v) to afford tert-butyl 3-{[trans-2-{[2-(2,4-dimethoxypyridin-3-yl)-1-methylpyrrolo[2,3-c]pyridin-5-yl]carbamoyl}cyclopropyl]methyl}-3,6-diazabicyclo[3.1.1]heptane-6-carboxylate (160.0 mg, 66%) as a white solid. LCMS (ESI, m/z): [M+H]$^+$=563.3.

Step 5: Synthesis of Trans-2-(3,6-diaza-bicyclo[3.1.1]heptan-3-ylmethyl)-N-(2-(2,4-dimethoxypyridin-3-yl)-1-methyl-1H-pyrrolo[2,3-c]pyridin-5-yl)cyclopropanecarboxamide

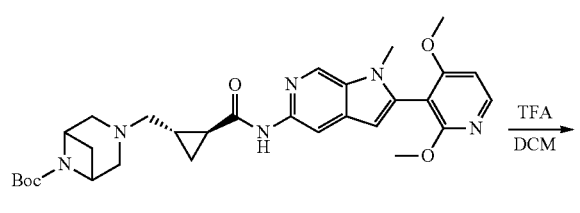

trans-

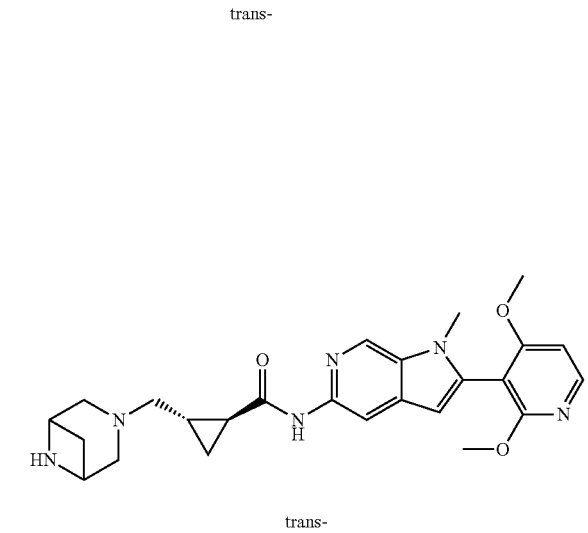

trans-

To a solution of tert-butyl 3-{[trans-2-{[2-(2,4-dimethoxypyridin-3-yl)-1-methylpyrrolo[2,3-c]pyridin-5-yl]carbamoyl}cyclopropyl]methyl}-3,6-diazabicyclo[3.1.1]heptane-6-carboxylate (150.0 mg, 0.27 mmol) in DCM (2.0 mL) was added TFA (2.0 mL) at room temperature. The resulting mixture was stirred at room temperature for 0.5 h. After the reaction was completed, the mixture was adjust pH to 7.0 with aq. NaHCO$_3$. The resulting mixture was extracted with CH$_2$Cl$_2$. The combined organic layer was washed with brine, dried over anhydrous sodium sulfate and filtered. The filtrate was concentrated under reduced pressure. The residue was purified by reverse phase lash column chromatography with H$_2$O/CH$_3$CN (50/50, v/v) to afford trans-2-(3,6-diaza-bicyclo[3.1.1]heptan-3-ylmethyl)-N-(2-(2,4-dimethoxypyridin-3-yl)-1-methyl-1H-pyrrolo[2,3-c]pyridin-5-yl)cyclopropanecarboxamide (60.0 mg, 48%) as a white solid LCMS (ESI, m/z): [M+H]$^+$=463.2.

Step 6: Synthesis of (1S,2S)-2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide and (1R,2R)-2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide (Compound 145 and Compound 146)

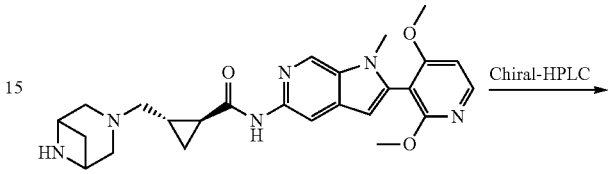

trans-

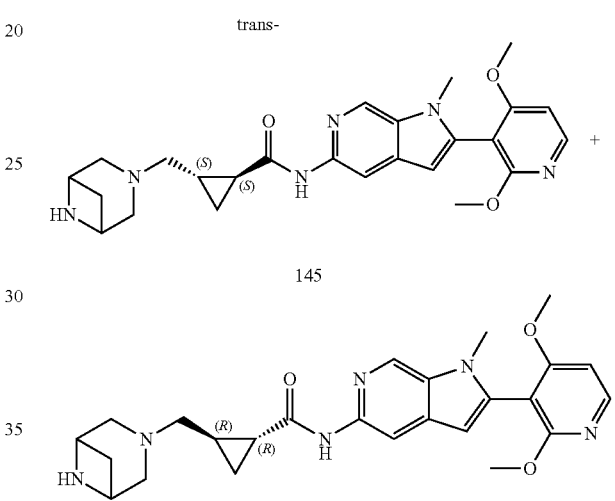

The racemic mixture of trans-2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide (60.0 mg, 0.12 mmol) was separated by Prep-Chiral-HPLC with the following conditions (Column: CHIRAL ART Cellulose-SC, 2×25 cm, 5 μm; Mobile Phase A: Hex (0.3% i-PrNH$_2$)—HPLC, Mobile Phase B: MeOH: EtOH=1:1—HPLC; Flow rate: 20 mL/min; Gradient: 60% B in 12 min; Wave Length: 220/254 nm; RT1(min): 9.17; RT2(min): 10.88) to afford (1S,2S)-2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide Enantiomer 1 (RT1: 9.17 min, 12.1 mg, 40%) as a white solid and (1R,2R)-2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide Enantiomer 2 (RT2: 10.88 mi, 12.2 mg, 40%) as a white solid. The absolute stereochemistry of Enantiomers 1 and 2 was not assigned. The two enantiomeric structures that could be obtained from chiral separation of the enantiomeric mixture as described above are shown as Compounds 145 and 146 in Table 2.

2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide Enantiomer 2: RT1(min): 9.17; LCMS (ESI, m/z): [M+H]$^+$=463.3. $^1$H NMR (400

MHz, DMSO-$d_6$): δ 10.45 (s, 1H), 8.58 (s, 1H), 8.25 (d, J=6.0 Hz, 1H), 8.17 (s, 1H), 6.97 (d, J=6.4 Hz, 1H), 6.39 (s, 1H), 3.82 (s, 6H), 3.64 (d, J=5.2 Hz, 3H), 3.53 (s, 4H), 3.40-3.32 (m, 2H), 3.15-3.12 (m, 2H), 2.34-2.30 (m, 1H), 1.93-1.88 (m, 2H), 1.41-1.38 (m, 1H), 1.09-1.04 (m, 1H), 0.74-0.70 (m, 1H).

2-{3,6-diazabicyclo[3.1.1]heptan-3-ylmethyl}-N-[2-(2,4-dimethoxypyridin-3-yl)-1-methylpyrrolo[2,3-c]pyridin-5-yl]cyclopropane-1-carboxamide Enantiomer 2: RT2(min): 10.88; LCMS (ESI, m/z): [M+H]$^+$=463.3. $^1$H NMR (400 MHz, DMSO-$d_6$): δ 10.43 (s, 1H), 8.58 (s, 1H), 8.25 (d, J=6.0 Hz, 1H), 8.17 (s, 1H), 6.97 (d, J=6.4 Hz, 1H), 6.39 (s, 1H), 3.82 (s, 6H), 3.60-3.53 (m, 7H), 3.13-3.10 (m, 2H), 2.74-2.65 (m, 2H), 2.34-2.25 (m, 1H), 1.92-1.84 (m, 2H), 1.42-1.37 (m, 1H), 1.08-1.04 (m, 1H), 0.74-0.69 (m, 1H).

Example S136: Synthesis of Trans-2-((3,8-diazabicyclo[3.2.1]octan-8-yl)methyl)-N-(2-(2,4-dimethoxypyridin-3-yl)-1-methyl-1H-pyrrolo[2,3-c]pyridin-5-yl)cyclopropane-1-carboxamide (Compound 147)

Step 1: Synthesis of tert-butyl 8-((trans)-2-(methoxycarbonyl)cyclopropane-1-carbonyl)-3,8-diazabicyclo[3.2.1]octane-3-carboxylate

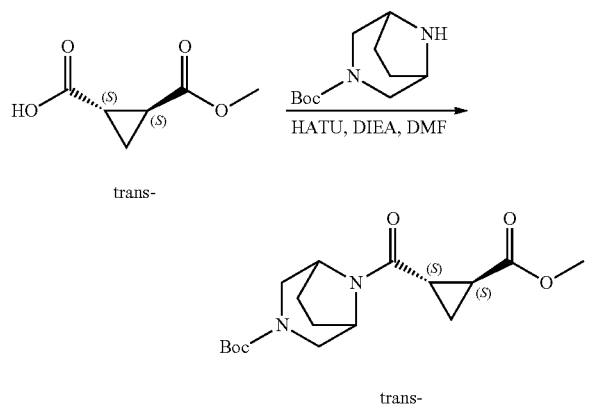

To a solution of trans-2-(methoxycarbonyl)cyclopropane-1-carboxylic acid (500.0 mg, 3.47 mmol) in DMF (5.0 mL) was added DIEA (2241.8 mg, 17.35 mmol), tert-butyl 3,8-diazabicyclo[3.2.1]octane-3-carboxylate (883.9 mg, 4.16 mmol) and HATU (1978.6 mg, 5.20 mmol) at 0° C. under N$_2$. The resulting mixture was stirred at 0° C. for 2 h under N$_2$. After the reaction was completed, the mixture was purified by reverse phase flash column chromatography with CH$_3$CN/H$_2$O (40/60, v/v) to afford tert-butyl 8-((trans)-2-(methoxycarbonyl)cyclopropane-1-carbonyl)-3,8-diazabicyclo[3.2.1]octane-3-carboxylate (1.1 g, 93%) as a brown oil. LCMS (ESI, m/z): [M+H]$^+$=339.2.

Step 2: Synthesis of tert-butyl 8-(((trans)-2-(methoxycarbonyl)cyclopropyl)methyl)-3,8-diazabicyclo[3.2.1]octane-3-carboxylate

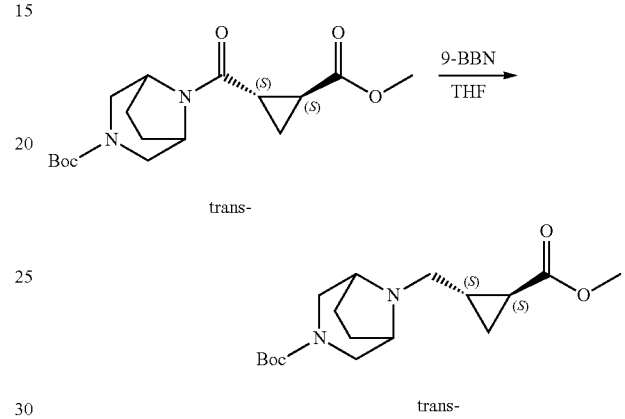

To a solution of tert-butyl 8-((trans)-2-(methoxycarbonyl)cyclopropane-1-carbonyl)-3,8-diazabicyclo[3.2.1]octane-3-carboxylate (500.0 mg, 1.48 mmol) in THF (5.0 mL) was added 9-borabicyclo[3.3.1]nonane (11.8 mL, 0.5 mol/L) at room temperature. The resulting mixture was stirred at 60° C. for 2 h. After the reaction was completed, the resulting mixture was concentrated under reduced pressure. The residue was purified by flash column chromatography with petroleum ether/ethyl acetate (50/50, v/v) to afford tert-butyl 8-(((trans)-2-(methoxycarbonyl)cyclopropyl)methyl)-3,8-diazabicyclo[3.2.1]octane-3-carboxylate (327.0 mg, 68%) as a yellow solid. LCMS (ESI, m/z): [M+H]$^+$=325.2.

Step 3: Synthesis of tert-butyl 8-(((trans)-2-((2-(2,4-dimethoxypyridin-3-yl)-1-methyl-1H-pyrrolo[2,3-c]pyridin-5-yl)carbamoyl)cyclopropyl)methyl)-3,8-diazabicyclo[3.2.1]octane-3-carboxylate

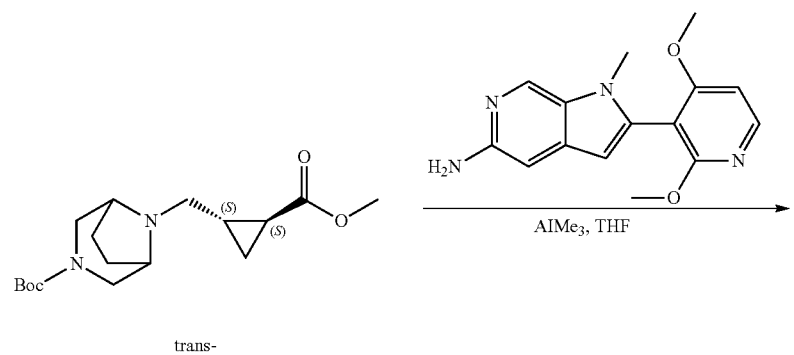

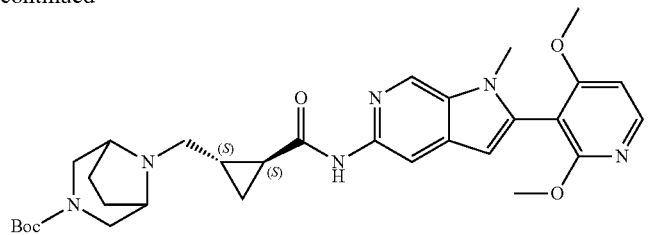

trans-

To a solution of tert-butyl 8-(((trans)-2-(methoxycarbonyl)cyclopropyl)methyl)-3,8-diazabicyclo[3.2.1]octane-3-carboxylate (240.0 mg, 0.74 mmol) in THF (5.0 mL) was added 2-(2,4-dimethoxypyridin-3-yl)-1-methyl-1H-pyrrolo[2,3-c]pyridin-5-amine (69.9 mg, 0.25 mmol) at room temperature. Then AlMe₃ (1.2 mL, 2 mol/L) was added to mixture at 0° C. The resulting mixture was stirred at 80° C. for 3 h. After the reaction was completed, the reaction mixture was quenched by MeOH at room temperature. The mixture was filtered. The filtrate was concentrated under reduced pressure. The residue was purified by reverse phase flash chromatography with CH₃CN/H₂O (56/44, v/v) to afford tert-butyl 8-(((trans)-2-((2-(2,4-dimethoxypyridin-3-yl)-1-methyl-1H-pyrrolo[2,3-c]pyridin-5-yl)carbamoyl)cyclopropyl)methyl)-3,8-diazabicyclo[3.2.1]octane-3-carboxylate (77.0 mg, 54%) as a brown oil. LCMS (ESI, m/z): [M+H]⁺=577.3.

Step 4: Synthesis of Trans-2-((3,8-diazabicyclo[3.2.1]octan-8-yl)methyl)-N-(2-(2,4-dimethoxypyridin-3-vi)-1-methyl-1H-pyrrolo[2,3-c]pyridin-5-yl)cyclopropane-1-carboxamide

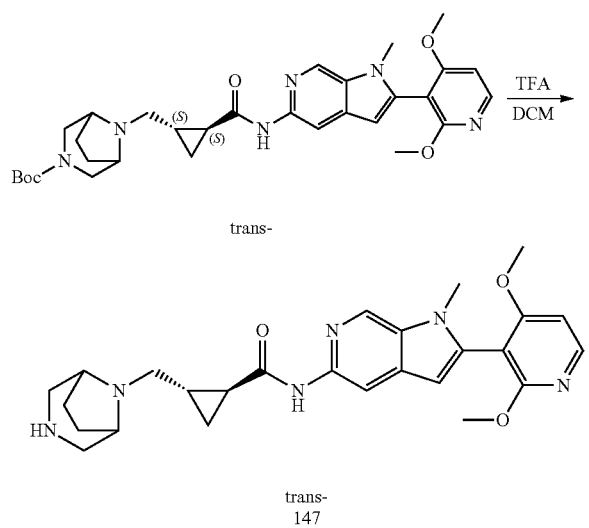

trans-
147

To a solution of tert-butyl 8-(((trans)-2-((2-(2,4-dimethoxypyridin-3-yl)-1-methyl-1H-pyrrolo[2,3-c]pyridin-5-yl)carbamoyl)cyclopropyl)methyl)-3,8-diazabicyclo[3.2.1]octane-3-carboxylate (77.0 mg, 0.13 mmol) in DCM (2.0 mL) was added TFA (2.0 mL) at room temperature. The resulting mixture was stirred at room temperature for 30 min. After the reaction was completed, the reaction mixture was concentrated under reduced pressure. The pH value of the residue was adjusted to 7 with aq·NaHCO₃. The resulting mixture was extracted with CH₂Cl₂. The combined organic layer was washed with brine, dried over anhydrous sodium sulfate and filtered. The filtrate was concentrated under reduced pressure. The residue was purified by reverse phase flash chromatography with CH₃CN/H₂O (99/1, v/v) and then purified by Prep-HPLC with the following conditions: (Column: XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 19% B to 29% B in 8 min; Wave Length: 254 nm) to afford trans-2-((3,8-diazabicyclo[3.2.1]octan-8-yl)methyl)-N-(2-(2,4-dimethoxypyridin-3-yl)-1-methyl-1H-pyrrolo[2,3-c]pyridin-5-yl)cyclopropane-1-carboxamide (Compound 147) (5.2 mg, 8%) as a white solid. LCMS (ESI, m/z): [M+H]⁺=477.3. ¹H NMR (400 MHz, DMSO-d₆): δ 10.44 (s, 1H), 8.58 (s, 1H), 8.25 (d, J=6.0 Hz, 1H), 8.17 (s, 1H), 6.97 (d, J=6.0 Hz, 1H), 6.39 (s, 1H), 3.82 (s, 6H), 3.53 (s, 3H), 3.10-3.05 (m, 2H), 2.89-2.68 (m, 2H), 2.44-2.39 (m, 1H), 2.33-2.17 (m. 2H), 1.89-1.86 (m, 1H), 1.83-1.73 (m, 2H), 1.68-1.63 (m, 2H), 1.62-1.50 (m, 1H), 1.49-1.31 (m, 1H), 1.01-0.97 (m, 1H), 0.71-0.67 (m, 1H).

Biological Examples

K562 and HL60 Cell Proliferation Assay

K562 and HL60 cells, cultured in Iscove's Modified Dulbecco's Media (IMDM) supplemented with 10% FBS, were harvested at 50-80% confluency and plated at 2,000 cells per well (K562) or 1,500 cells per well (HL60) in 384-well tissue culture plates. A subset of wells contained media only (low control, LC). Compounds were serially diluted in DMSO, 40 nL of compound or DMSO only (high control, HC) were added to each well using an Echo 550 liquid handler (Labcyte). The plates were placed in a 37° C. incubator with 5% CO₂ for 72 hours. Cell viability was measured using a CellTiter-Glo luminescent cell viability assay (Promega), which allows for relative quantification of metabolically active cells by luminescence-based measurements of intracellular ATP concentrations. Briefly, plates were removed from the incubator and equilibrated for 15 minutes at room temperature prior to the addition of 40 μL of CellTiter-Glo reagent. Plates were then incubated for 30 minutes at room temperature. Luminescence was measured using an EnSpire plate reader (Perkin Elmer). As noted above, luminescence values from wells with DMSO only or media without cells were used as high and low controls (HC and LC), respectively. Normalized percent viability was calculated as follows: percent viability=100×(Lum$_{sample}$−

$Lum_{LC}/(Lum_{HC}-Lum_{LC})$. $IC_{50}$ values were calculated using the XLFit software and are shown in Table 2.

TABLE 2

| Cmpd No. | Cell Line ($IC_{50}$, nM) | |
|---|---|---|
| | K562 | HL60 |
| 2 | 109 | 202 |
| 3 | 127 | 209 |
| 7 | 37.8 | 60.9 |
| 8 | 95.6 | 59.1 |
| 11 | 0.421 | 182 |
| 12 | 317 | 4220 |
| 22 | 179 | 958 |
| 23 | 631 | 1690 |
| 24 | 122 | 794 |
| 25 | 91.7 | 523 |
| 26 | 174 | 2930 |
| 27 | 112 | 761 |
| 28 | 30.4 | 233 |
| 29 | 258 | 800 |
| 30 | 245 | 320 |
| 31 | 143 | 514 |
| 32 | 182 | 5120 |
| 34 | 208 | 3840 |
| 35 | 123 | 4150 |
| 36 | 105 | 3630 |
| 38 | 27.5 | 1350 |
| 39 | 33.6 | 3780 |
| 43 | 317 | >10.0E+03 |
| 44 | 368 | >10.0E+03 |
| 47 | 1360 | >10.0E+03 |
| 48 | 85.8 | 808 |
| 52 | 109 | 1200 |
| 53 | 90.9 | >10.0E+03 |
| 54 | 51.1 | 957 |
| 56 | 240 | 6200 |
| 57 | 128 | 4270 |
| 59 | 120 | 1460 |
| 60 | 718 | 6490 |
| 61 | 576 | 4860 |
| 64 | 139 | 1610 |
| 65 | 217 | >10.0E+03 |
| 66 | 100 | 1750 |
| 67 | 207 | 5280 |
| 70 | 193 | 1030 |
| 72 | 38.7 | 3130 |
| 73 | 3710 | >10.0E+03 |
| 74 | 44.7 | 59.6 |
| 75 | 11.6 | 682 |
| 76 | 200 | 6240 |
| 79 | 329 | >10.0E+03 |
| 80 | 1610 | >10.0E+03 |
| 81 | 40.4 | >10.0E+03 |
| 82 | 125 | >10.0E+03 |
| 83 | 160 | >10.0E+03 |
| 85 | 16.5 | 1710 |
| 86 | 700 | >10.0E+03 |
| 87 | 78.5 | >10.0E+03 |
| 88 | 166 | 5150 |
| 89 | 153 | 2110 |
| 90 | 6.01 | 548 |
| 92 | 227 | >10.0E+03 |
| 94 | 79.4 | 9640 |
| 95 | 47.8 | 3550 |
| 97 | 91.5 | 3320 |
| 98 | 63 | 605 |
| 99 | 396 | >10.0E+03 |
| 100 | 66.2 | |
| 101 | 456 | |
| 103 | 17.7 | 385 |
| 104 | | 240 |
| 105 | 60.9 | 199 |
| 106 | >10.0E+03 | >10.0E+03 |
| 107 | 40.5 | 2550 |
| 108 | 736 | >10.0E+03 |
| 111 | 23 | |
| 112 | 1780 | >10.0E+03 |
| 113 | 314 | >10.0E+03 |
| 114 | 257 | >10.0E+03 |
| 115 | 80.8 | 1550 |
| 116 | 256 | 9310 |
| 117 | 141 | 4180 |
| 118 | 71.4 | 929 |
| 119 | 9.35 | 159 |
| 120 | 47.6 | >10.0E+03 |
| 121 | 99.1 | >10.0E+03 |
| 122 | 117 | >10.0E+03 |
| 123 | 106 | 1770 |
| 124 | 41.4 | >10.0E+03 |
| 125 | 113 | >10.0E+03 |
| 128 | 28.6 | >10.0E+03 |
| 129 | 85.5 | >10.0E+03 |
| 130 | 108 | >10.0E+03 |
| 132 | 165 | |
| 133 | 181 | |
| 134 | 53.1 | |
| 135 | 27.9 | |
| 136 | 98.8 | 1200 |
| 137 | 37 | 148 |
| 140 | 291 | >10.0E+03 |
| 141 | 381 | >10.0E+03 |
| 142 | 59.3 | 1690 |
| 143 | 289 | 9800 |
| 144 | 1070 | >10.0E+03 |
| 147 | 152 | |

Luminescence-Based ABL Kinase Assay (300 µM ATP)

Kinase activity of ABL1 was measured using the ADP-Glo system (Promega), which measures formation of ADP using a luminescence-based method. Compounds were serially diluted in DMSO. 20 nL of compound or DMSO only (high control, HC) were added to a 384-well plate (OptiPlate-384. PerkinElmer) using an Echo550 liquid handler (Labcyte). 15 µL of kinase solution (10 mM $MgCl_2$, 0.01% Brij-35, 2 mM DTT, 0.05% BSA, 1 mM EGTA, 50 mM HEPES pH 7.5, and 3.325 nM ABL1 [Carna Biosciences]) were added to each well of the 384-well plate containing the compounds. No enzyme control wells were included (low control, LC). The plate was incubated at room temperature for 30 minutes. 5 µL of a second solution containing 10 mM $MgCl_2$, 0.01% Brij-35, 2 mM DTT, 0.05% BSA, 1 mM EGTA, 50 mM HEPES pH 7.5, 6 µM Peptide 2 (Perkin Elmer, Cat No 760346), and 1.2 mM ATP were added to each well to start the kinase reaction. The plate was incubated for 90 minutes at room temperature. 20 µL of ADP-Glo reagent (Promega) were then added to each well and the plate was incubated for 40 minutes at room temperature. 40 µL of kinase detection reagent (Promega) was added to each well and the plate was incubated for an additional 45 minutes at room temperature. During this step, ADP was converted to ATP, a substrate for luciferase, to produce luminescence signal. Luminescence was measured on an Envision plate reader (Perkin Elmer). Luminescence signal positively correlates with kinase activity. The percent kinase activity was calculated as follows: percent kinase activity=$100\times(Lum_{sample}-Lum_{LC})/(Lum_{HC}-Lum_{LC})$. As noted above, DMSO only and no enzyme wells were used as high and low controls, respectively. IC50 values were calculated using the XLFit software.

$IC_{50}$ data obtained using the screening procedures described above for certain compounds disclosed herein are listed in Table 3.

TABLE 3

| Cmpd No. | ABL1 Kinase, IC$_{50}$ (nM) | ABL1 (T315I) |
|---|---|---|
| 2 | 25.4 | 17.7 |
| 4 | 817 | 599 |
| 7 | 9.22 | 6.59 |
| 11 | 13.8 | 38.6 |
| 13 | 567 | 300 |
| 14 | 29.6 | 124 |
| 15 | 103 | 101 |
| 16 | 184 | 545 |
| 17 | 59.7 | 160 |
| 18 | 743 | 336 |
| 19 | 263 | 68.3 |
| 20 | >10.0E+03 | 999 |
| 23 | 119 | 79.5 |
| 24 | 9.33 | 8.34 |
| 25 | 10.9 | 10.8 |
| 26 | 30.3 | 8.99 |
| 27 | 40.7 | 1.85 |
| 28 | 9.95 | 19.8 |
| 29 | 52 | 22.2 |
| 30 | 119 | 139 |
| 31 | 10.7 | 9.48 |
| 32 | 28.6 | 83.1 |
| 33 | 59.5 | 183 |
| 34 | 40.8 | 124 |
| 35 | 39.7 | 79.6 |
| 36 | 6.33 | 308 |
| 37 | 35.4 | 551 |
| 38 | 11.3 | 23.9 |
| 39 | 36 | 71.8 |
| 40 | 113 | 145 |
| 41 | 324 | 212 |
| 43 | 50.2 | 24.7 |
| 44 | 74.5 | 36 |
| 45 | 220 | 17.9 |
| 47 | 244 | 548 |
| 48 | 31.7 | 4.48 |
| 50 | 294 | 681 |
| 51 | 88.6 | 64.1 |
| 52 | 51.3 | 4.23 |
| 53 | 82.4 | 8.3 |
| 54 | 51.9 | 6.51 |
| 55 | 71.3 | 7.24 |
| 56 | 198 | 141 |
| 57 | 111 | 83.7 |
| 59 | 40.2 | 40.7 |
| 60 | 191 | 193 |
| 61 | 207 | 308 |
| 63 | 1430 | 2670 |
| 63 | 1350 | 4510 |
| 64 | 32.5 | 47.8 |
| 65 | 49.2 | 47.6 |
| 66 | 25.4 | 68 |
| 67 | 126 | 513 |
| 68 | 109 | 431 |
| 69 | 20.4 | 62.9 |
| 70 | 87.4 | 316 |
| 71 | 105 | 716 |
| 72 | 37.1 | 54.7 |
| 73 | 519 | 315 |
| 74 | 19.6 | 30.2 |
| 75 | 8.65 | 13.6 |
| 76 | 46.7 | 55.4 |
| 77 | 95.9 | 148 |
| 78 | 183 | 411 |
| 79 | 79.2 | 77 |
| 80 | 155 | 193 |
| 81 | 17.2 | 23.5 |
| 82 | 31.6 | 88.1 |
| 83 | 106 | 230 |
| 84 | 44.5 | 164 |
| 85 | 4.33 | 147 |
| 86 | 200 | 2930 |
| 87 | 35 | 76.6 |
| 88 | 409 | 459 |
| 89 | 76.6 | 15 |
| 90 | 2.26 | 22.2 |
| 91 | 388 | 399 |
| 92 | 494 | 1650 |
| 94 | 57.4 | 127 |
| 95 | 12.7 | 43.5 |
| 96 | 40.4 | 207 |
| 97 | 36.6 | 76.4 |
| 98 | 11.6 | 38.8 |
| 99 | 111 | >10.0E+03 |
| 100 | 49.2 | 233 |
| 101 | 153 | 2330 |
| 102 | 123 | 412 |
| 103 | 3.98 | 7.85 |
| 104 | 526 | 786 |
| 105 | 71.4 | 79 |
| 106 | 1690 | >10.0E+03 |
| 107 | 17.4 | 94.6 |
| 108 | 6.32 | 12.4 |
| 109 | 60.2 | 203 |
| 110 | 280 | 357 |
| 112 | 1320 | 564 |
| 113 | 84.4 | 366 |
| 114 | 77 | 546 |
| 115 | 18.5 | 469 |
| 116 | 66.9 | 1190 |
| 117 | 43.3 | 662 |
| 118 | 35.3 | 108 |
| 119 | 2.38 | 1.76 |
| 120 | 27.1 | 39.8 |
| 121 | 88.8 | 87.9 |
| 122 | 53.4 | 52.8 |
| 123 | 59.4 | 80.6 |
| 124 | 14.9 | 56.7 |
| 125 | 48.3 | 107 |
| 126 | 169 | 295 |
| 127 | 147 | 502 |
| 128 | 13.4 | 12.9 |
| 129 | 33.4 | 34.6 |
| 130 | 37.3 | 58.1 |
| 131 | 78.3 | 78.3 |
| 132 | 59.4 | 75.1 |
| 133 | 73.5 | 85.9 |
| 138 | 12.8 | 24.4 |
| 139 | 48.6 | 85.9 |
| 140 | 95.8 | |
| 141 | 316 | 1990 |
| 142 | 18.6 | 17.5 |
| 143 | 74.9 | 299 |
| Example 135, Enantiomer 1 | 30 | 66.7 |
| Example 135, Enantiomer 2 | 10.6 | 26 |
| 147 | 24.4 | 41.8 | pCRKL ELISA Assay:

K562 or Ba/F3 ABL T315I cells (2.0*10$^5$ cells/100 µl/well) were seeded in 96 well (Corning, cat #3799). Compounds were dissolved in DMSO, serially diluted in DMSO and then were added, mixed, and incubated for 90 minutes at 37° C., 5% CO$_2$. Following the 90-minute incubation, plates were centrifuged for 5 min at 3000 RPM and supernatant was removed from each well. Cells were washed 3 times with 150 µl PBS prior to addition of 100 µl cell RIPA lysis buffer (Boston BioProducts, cat #BP-115D) supplied with 1× complete ULTRA cocktail inhibitor (Roche, 05892791001) and 1× PhosSTOP Phosphatase Inhibitor Cocktail Tablets (Roche, 04906837001). Cells were incubated with lysis buffer for 1 hour at 4° C. prior to storage at −80C.

A capture antibody able to detect phosphorylated and non-phosphorylated CRKL (R&D Systems, cat #AF5127)

was added to Meso Scale Discovery (MSD) standard bind plates (MSD, cat #L15XA-3) at 5 ug/mL and incubated at 4° C. overnight. The next day, plates were washed with PBS+ 0.05% Tween20 (PBST) and 150 μl of 5% BSA blocking solution was added for 1 hour at room temperature with shaking. Plates were washed with PBST. Lysates were thawed and 30 μl of lysate was added to the MSD plates and incubated for 2 hours at room temperature with shaking. MSD plates were washed with PBST and 30 μl of a detection antibody that binds phosphorylated pCRKL (R&D Systems, cat #MAB6910) was added at 1 ug/mL to each well. Plates were incubated for 1 hour at room temperature with shaking. Plates were washed with PBST prior to addition of 30 μl of a sulfo tagged goat anti mouse detection antibody (MSD cat #R32AC-1). Plates were incubated for 1 hour at room temperature with shaking. Plates were washed with PBST prior to addition of 150 ul of 1×MSD read buffer T (MSD, cat #R92TC-2). Electrochemiluminescence (ECLU) was read on an MSD plate reader (Meso Scale Discovery). The remaining activity by calculated as follows: % Relative activity=100× (ELCU$_{sample}$−ECLU$_{LC}$)/(ECLU$_{HC}$−ECLU$_{LC}$). The low and high controls (LC/HC) are generated from lysate from wells without cells or with cells treated with 0.1% DMSO, respectively. IC50 values were calculated using XLFit software using a nonlinear regression model with a sigmoidal dose response and are shown in Table 4 and Table 5 below.

TABLE 4

| Cmpd No. | pCRKL ELISA, Cell Line IC$_{50}$ (nM) K562 |
|---|---|
| 26 | 303 |
| 27 | 553 |
| 31 | 83.2 |
| 32 | 189 |
| 35 | 241 |
| 38 | 73.2 |
| 39 | 96.4 |
| 52 | 416 |
| 53 | 574 |
| 54 | 151 |
| 72 | 137 |
| 75 | 45.3 |
| 76 | 326 |
| 79 | 594 |
| 90 | 29.8 |
| 95 | 66.3 |
| 98 | 99.4 |
| 103 | 35.5 |
| 120 | 108 |
| 128 | 61.75 |
| 138 | 254 |

TABLE 5

| Compound No. | pCRKL ELISA, Cell Line IC$_{50}$ (nM) Ba/F3 ABL1 (T315I) |
|---|---|
| 35 | 329 |
| 38 | 248 |
| 39 | 263 |
| 72 | 1140 |
| 75 | 93.2 |
| 76 | 194 |
| 98 | 253 |
| 103 | 172 |
| 128 | 171 |

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed:

1. A compound of formula (I-A):

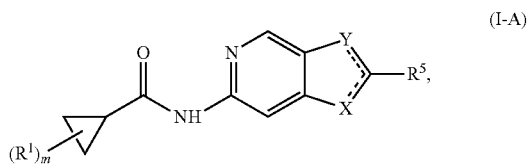

or a pharmaceutically acceptable salt thereof, wherein:
X is NR$^{3'}$ or CR$^3$,
Y is NR$^2$ or CR$^4$,
wherein when X is NR$^{3'}$, then Y is CR$^4$, Y has a double bond to CR$^5$, and X has a single bond to CR$^5$; or when X is CR$^3$, then Y is NR$^2$, Y has a single bond to CR$^5$, and X has a double bond to CR$^5$;
m is an integer from 0 to 3;
each R$^1$ is independently -D, —F, C$_1$-C$_3$ alkyl, C$_1$-C$_3$ alkylene-NR$^7$R$^8$, C$_1$-C$_3$ alkylene-NR$^7$R$^{8'}$, C$_1$-C$_3$ alkylene-OH, C$_1$-C$_3$ alkylene-CN, C$_1$-C$_2$ alkylene-(C$_3$-C$_6$ cycloalkylene)-(C$_0$-C$_2$ alkylene)-NR$^7$R$^8$, C$_1$-C$_2$ alkylene-(C$_3$-C$_6$ cycloalkylene)-(C$_0$-C$_2$ alkylene)-NR$^7$R$^{8'}$, C$_1$-C$_2$ alkylene-(C$_3$-C$_6$ cycloalkylene)-(C$_0$-C$_2$ alkylene)-OH, C$_1$-C$_2$ alkylene-(4 to 8-membered heterocycloalkylene)-(C$_0$-C$_2$ alkylene)-NR$^7$R$^8$, C$_1$-C$_2$ alkylene-(4 to 8-membered heterocycloalkylene)-(C$_0$-C$_2$ alkylene)-NR$^7$R$^{8'}$, C$_1$-C$_2$ alkylene-(C$_3$-C$_7$ heterocycloalkylene)-(C$_0$-C$_2$ alkylene)-NR$^7$R$^8$, or C$_1$-C$_2$ alkylene-(C$_3$-C$_7$ heterocycloalkylene)-(C$_0$-C$_2$ alkylene)-NR$^7$R$^{8'}$, wherein the alkyl, alkylene, cycloalkylene, and heterocycloalkylene moieties in R$^1$ are optionally substituted with 1-3 fluorine atoms and/or 1-6 deuterium atoms, and wherein each heterocyclic nitrogen atom, if present, is independently optionally substituted with C$_1$-C$_3$ alkyl, C$_3$-C$_6$ cycloalkyl, C$_2$-C$_3$ haloalkyl, C$_2$-C$_3$ alkylene-CN, or C$_2$-C$_3$ heteroalkyl;
R$^2$ is C$_1$-C$_3$ alkyl or C$_3$-C$_6$ cycloalkyl, wherein said C$_1$-C$_3$ alkyl is optionally substituted with 1-3 fluorine atoms and/or 1-6 deuterium atoms;
R$^3$ is —H, C$_3$-C$_6$ cycloalkyl, halogen, or —CN;
R$^{3'}$ is —H, —C$_3$-C$_6$ cycloalkyl, or —CN;
R$^4$ is —H, C$_1$-C$_3$ alkyl, or halogen, wherein said C$_1$-C$_3$ alkyl is optionally substituted with 1-3 fluorine atoms and/or 1-6 deuterium atoms;
R$^5$ is C$_6$-C$_{14}$ aryl optionally substituted with 1-5 R$^9$ groups;
each R$^7$ is independently —H, C$_1$-C$_6$ alkyl, C$_3$-C$_6$ cycloalkyl, C$_1$-C$_6$ haloalkyl, C$_1$-C$_6$ alkylene-CN, or C$_1$-C$_6$ heteroalkyl;
each R$^8$ is independently —H, C$_1$-C$_6$ alkyl, C$_3$-C$_6$ cycloalkyl, C$_1$-C$_6$ haloalkyl, C$_1$-C$_6$ alkylene-CN, or C$_1$-C$_6$ heteroalkyl;
each pair of R$^7$ and R$^{8'}$ taken together with the nitrogen atom to which they are attached independently form a 3- to 8-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —$OR^{10}$, —$NR^7R^8$, $C_1$-$C_3$ alkyl, $C_1$-$C_3$ haloalkyl, $C_3$-$C_6$ cycloalkyl, —CN, $S(O)_nC_1$-$C_3$ alkyl, or $S(O)_nC_3$-$C_6$ cycloalkyl, wherein n is an integer from 0 to 2; and each $R^{10}$ is independently —H, $C_1$-$C_3$ alkyl, $C_1$-$C_3$ haloalkyl, or $C_3$-$C_6$ cycloalkyl, wherein said $C_1$-$C_3$ alkyl is optionally substituted with hydroxyl, $C_1$-$C_3$ alkoxy, and/or 1-6 deuterium atoms.

2. The compound of claim 1, or a pharmaceutically acceptable salt thereof, wherein the compound of formula (I) is a compound of formula (I-A-i) or formula (I-A-ii):

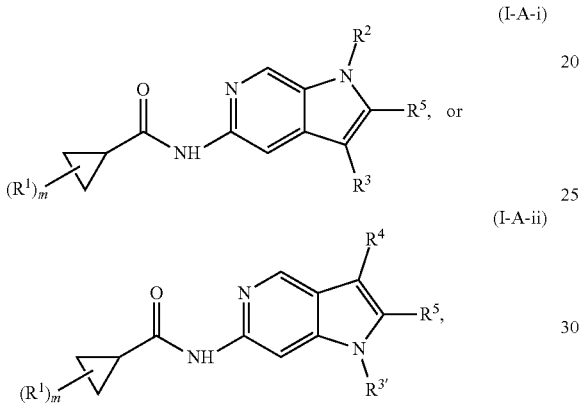

wherein
m is an integer 0 or 2;
each $R^1$ is independently —F, $C_1$-$C_3$ alkyl, $C_1$-$C_3$ alkylene-$NR^7R^8$, $C_1$-$C_3$ alkylene-$NR^{7'}R^{8'}$, $C_1$-$C_3$ alkylene-OH, $C_1$-$C_3$ alkylene-CN, $C_1$-$C_2$ alkylene-($C_3$-$C_6$ cycloalkylene)-($C_0$-$C_2$ alkylene)-$NR^7R^8$, $C_1$-$C_3$ alkylene-CN, $C_1$-$C_2$ alkylene-($C_3$-$C_6$ cycloalkylene)-($C_0$-$C_2$ alkylene)-$NR^{7'}R^{8'}$, $C_1$-$C_2$ alkylene-($C_3$-$C_6$ cycloalkylene)-($C_0$-$C_2$ alkylene)-OH, $C_1$-$C_2$ alkylene-($C_4$-$C_6$ heterocycloalkylene)-($C_0$-$C_2$ alkylene)-$NR^7R^8$, or $C_1$-$C_2$ alkylene-($C_4$-$C_6$ heterocycloalkylene)-($C_0$-$C_2$ alkylene)-$NR^{7'}R^{8'}$, wherein the alkyl, alkylene, cycloalkylene, and heterocycloalkylene in $R^1$ are optionally substituted with 1-3 fluorine atoms and/or 1-6 deuterium atoms, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;
$R^2$ is —$CH_3$, $CD_3$, —$CHF_2$, or —$CH_2CH_3$;
$R^3$ is —H, $C_3$-cycloalkyl, halogen, or —CN;
$R^{3'}$ is —H, $C_3$-cycloalkyl, or —CN;
$R^4$ is —H, —$CH_3$, —$CD_3$, —$CHF_2$, —$CH_2CH_3$, or halogen;
$R^5$ is $C_6$-$C_{14}$ aryl optionally substituted with 1-5 $R^9$ groups;
each $R^7$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;
each $R^8$ is independently —H, $C_1$-$C_3$ alkyl, $C_3$-$C_6$ cycloalkyl, $C_2$-$C_3$ haloalkyl, $C_2$-$C_3$ alkyl-CN, or $C_2$-$C_3$ heteroalkyl;
each pair of $R^{7'}$ and $R^{8'}$ taken together with the nitrogen atom to which they are attached independently form a 4-to-6-membered heterocyclic ring, wherein the heterocyclic ring optionally contains an additional 1-2 heteroatoms selected from the group consisting of N, O, and S, and wherein each heterocyclic nitrogen atom, if present, is independently optionally substituted with $C_1$-$C_3$ alkyl, $C_3$-$C_6$ cycloalkyl, $C_2$-$C_3$ haloalkyl, $C_2$-$C_3$ alkylene-CN, or $C_2$-$C_3$ heteroalkyl;

each $R^9$ is independently halogen, —$OR^{10}$, $C_1$-$C_3$ alkyl, —$CF_2H$, —$CF_3$, $C_3$-$C_6$ cycloalkyl, or —CN, and each $R^{10}$ is independently —H, $C_1$-$C_3$ alkyl, —$CD_3$, —$CF_2H$, —$CF_3$, or $C_3$-$C_6$ cycloalkyl, wherein said $C_1$-$C_3$ alkyl is optionally substituted with hydroxyl and/or $C_1$-$C_3$ alkoxy and/or 1-6 deuterium atoms.

3. The compound of claim 1, or a pharmaceutically acceptable salt thereof, wherein
each $R^1$ is independently —F, $C_1$-$C_3$ alkylene-$NR^{7'}R^{8'}$, or $C_1$-$C_3$ alkylene-OH; and
wherein each pair of $R^{7'}$ and $R^{8'}$ of $R^1$ taken together with the nitrogen atom to which they are attached independently form a 4-to-6-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by —H or $C_1$-$C_3$ alkyl.

4. The compound of claim 1, or a pharmaceutically acceptable salt thereof, wherein $R^5$ is phenyl optionally substituted with 1-3 $R^9$ groups.

5. The compound of claim 1, or a pharmaceutically acceptable salt thereof, wherein
$R^2$ is —$CH_3$, —$CD_3$, or —$CH_2CH_3$;
$R^3$ is —H, —F, —$CH_3$, or —CN;
$R^{3'}$ is —H; and
$R^4$ is —H, —F or —$CH_3$.

6. The compound of claim 1, or a pharmaceutically acceptable salt thereof, wherein
each $R^9$ is independently —F, —Cl, —$OR^{10}$, —$CH_3$, or —CN, and
each $R^{10}$ is independently —H, —$CH_3$, —$CD_3$, or —$CH_2CH_3$, wherein said-$CH_3$ or said —$CH_2CH_3$ is optionally substituted with hydroxyl and/or —$OCH_3$.

7. The compound of claim 1, or a pharmaceutically acceptable salt thereof, wherein the compound of formula (I) is a compound of formula (I-A-i) or formula (I-A-ii):

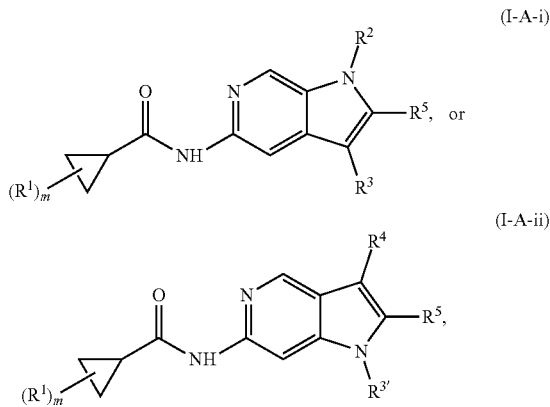

wherein
m is an integer 0 or 1;
R is —F, $C_1$-$C_3$ alkylene-$NR^{7'}R^{8'}$, or $C_1$-$C_3$ alkylene-OH;

$R^2$ is —$CH_3$, —$CD_3$, or —$CH_2CH_3$;
R is —H, —F, —$CH_3$, or —CN;
$R^{3'}$ is —H;
$R^4$ is —H, —F or —$CH_3$;
$R^5$ is phenyl optionally substituted with 1-3 $R^9$ groups;
each pair of $R^{7'}$ and $R^{8'}$ taken together with the nitrogen atom to which they are attached independently form a 4-to-6-membered heterocyclic ring, wherein the heterocyclic ring optionally contains an additional 1-2 heteroatoms selected from the group consisting of N and O, and wherein the nitrogen atom of any primary or secondary amine present in the heterocyclic ring is optionally substituted by —H or $C_1$-$C_3$ alkyl;
each $R^9$ is independently —F, —$C_1$, —$OR^{10}$, —$CH_3$, or —CN, and
each $R^{10}$ is independently —H, —$CH_3$, —$CD_3$, or —$CH_2CH_3$, wherein said-$CH_3$ or said-$CH_2CH_3$ is optionally substituted with hydroxyl and/or —$OCH_3$.

8. The compound of claim 1, or a pharmaceutically acceptable salt thereof, wherein
each $R^9$ is independently —F, —$OR^{10}$, or —$CH_3$, and
each $R^{10}$ is independently —H, —$CH_3$, —$CD_3$, —$CF_2H$, or —$CF_3$.

9. The compound of claim 1, or a pharmaceutically acceptable salt thereof, wherein
$R^2$ is —$CH_3$;
$R^3$ is —H;
$R^{3'}$ is —H; and
$R^4$ is —H or —$CH_3$.

10. A compound, or a pharmaceutically acceptable salt thereof, selected from the group consisting of:

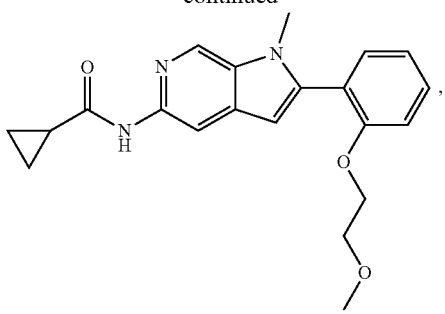

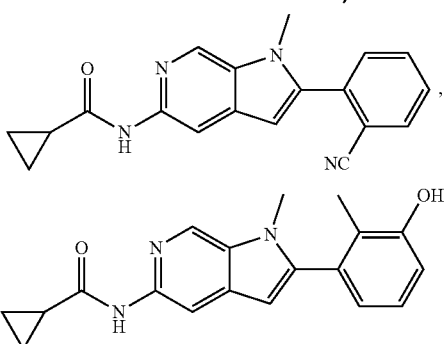

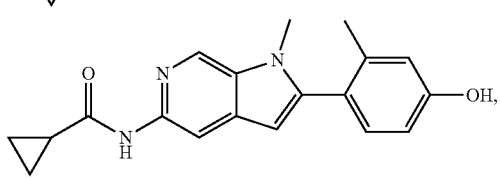

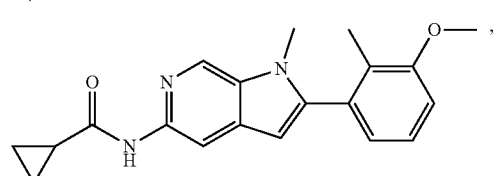

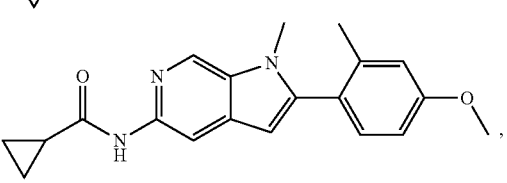

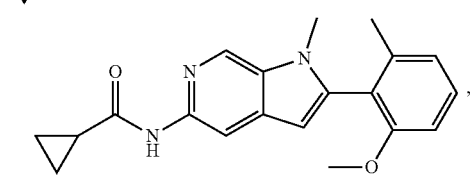

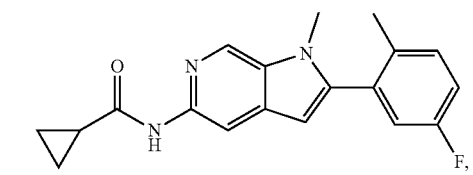

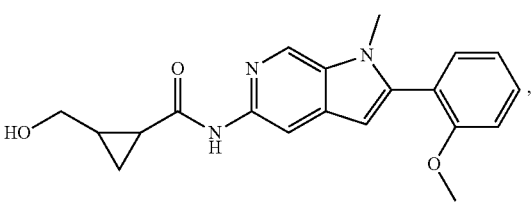

539
-continued
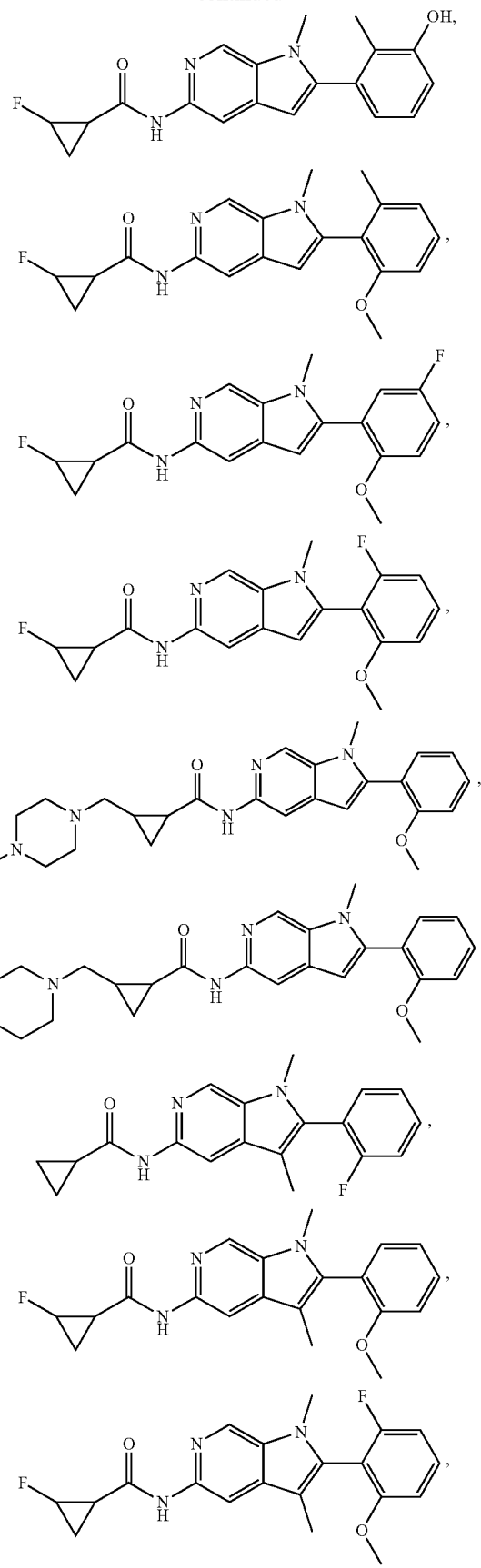
540
-continued
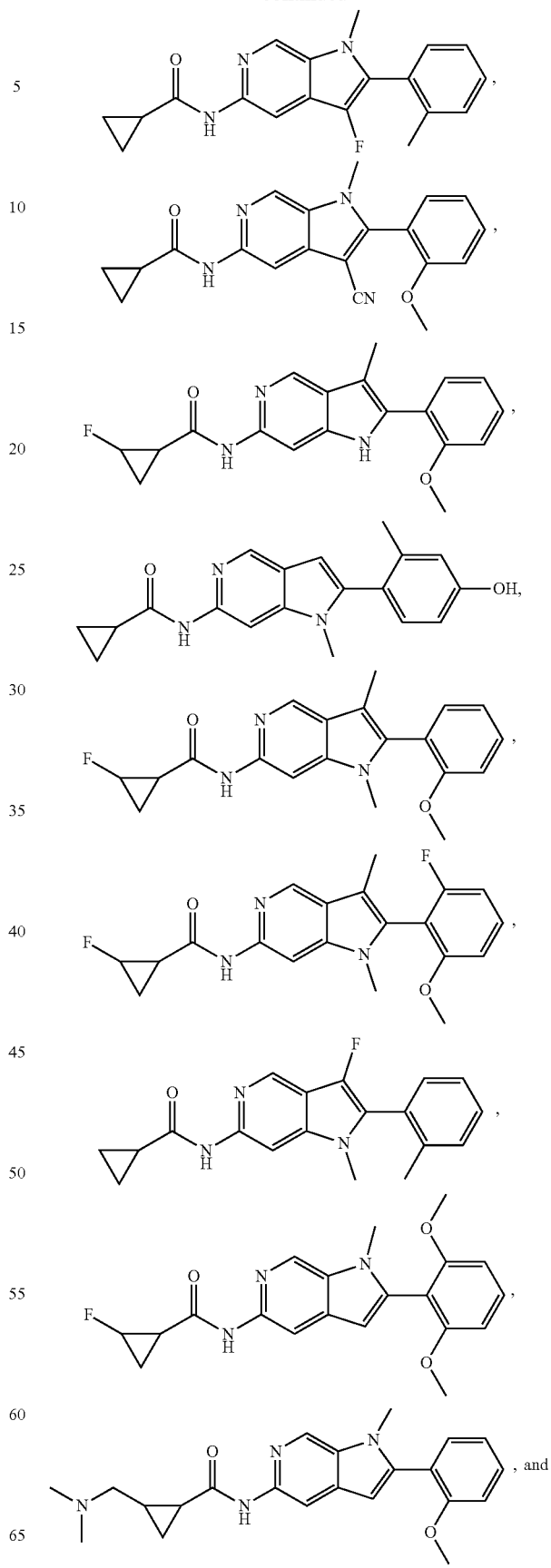

-continued

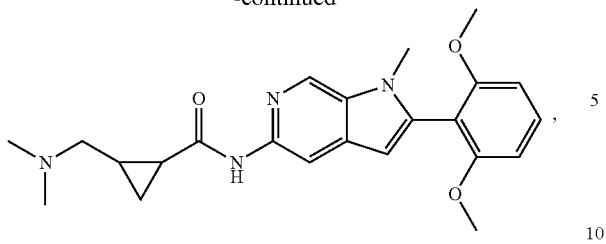, 5 and pharmaceutically acceptable salt of any of the foregoing.

11. A pharmaceutical composition comprising the compound of claim 1, or a pharmaceutically acceptable salt thereof, and one or more pharmaceutically acceptable excipients.

12. A method of inhibiting Bcr-Abl enzymatic activity in a cell, comprising exposing the cell to an effective amount of the compound of claim 1, or a pharmaceutically acceptable salt thereof.

13. A method of treating chronic myeloid leukemia (CML), acute myeloid leukemia (AML), acute lymphoblastic leukemia (ALL), or a mixed phenotype acute leukemia, in a human in need thereof, comprising administering to the human an effective amount of the compound of claim 1, or a pharmaceutically acceptable salt thereof.

14. The method of claim 13, wherein the leukemia is refractory leukemia.

* * * * *